(12) United States Patent
Brawn et al.

(10) Patent No.: US 12,251,283 B2
(45) Date of Patent: Mar. 18, 2025

(54) INTRA-ORAL LIGHT-THERAPY APPARATUSES AND METHODS FOR THEIR USE

(71) Applicant: Biolux Group SA, Anières (CH)

(72) Inventors: Peter Brawn, Vancouver (CA); Ryan Bredin, Breton (CA); Timothy G. Shaughnessy, Marietta, GA (US); Kevin Strange, Victoria (CA); Paul Mathews, Langley, WA (US); Robert Marsanyi, Clinton, WA (US)

(73) Assignee: Biolux Group SA (CH)

( * ) Notice: Subject to any disclaimer, the term of this patent is extended or adjusted under 35 U.S.C. 154(b) by 0 days.

(21) Appl. No.: 16/935,847

(22) Filed: Jul. 22, 2020

(65) Prior Publication Data

US 2021/0068936 A1   Mar. 11, 2021

Related U.S. Application Data

(63) Continuation of application No. 15/858,533, filed on Dec. 29, 2017, now Pat. No. 10,729,524, which is a
(Continued)

(51) Int. Cl.
*A61C 19/06* (2006.01)
*A61C 7/08* (2006.01)
(Continued)

(52) U.S. Cl.
CPC .............. *A61C 19/06* (2013.01); *A61C 7/08* (2013.01); *A61C 19/006* (2013.01);
(Continued)

(58) Field of Classification Search
CPC ..... A61C 19/06; A61C 19/003; A61C 19/063; A61C 19/066; A61C 7/008; A61C 7/006;
(Continued)

(56) References Cited

U.S. PATENT DOCUMENTS

| 2,635,175 A | 4/1953 | Wilson |
| 2,884,926 A | 5/1959 | Grasso |

(Continued)

FOREIGN PATENT DOCUMENTS

| CA | 2212010 | 8/1996 |
| CA | 2439882 | 9/2002 |

(Continued)

OTHER PUBLICATIONS

Supplementary European Search Report for European Application No. 06710427, mailed Apr. 1, 2008, 6 pages.
(Continued)

*Primary Examiner* — Edward Moran
(74) *Attorney, Agent, or Firm* — Levine Bagade Han LLP

(57) ABSTRACT

In some embodiments, an apparatus comprises a housing, an emitter, and an electronic circuit. The housing is configured to fit within a patient's mouth. The emitter is at least partially encased within the housing. The emitter is configured to emit an effective amount of light to the alveolar soft tissue when the housing is disposed within the mouth. The electronic circuit is operatively coupled to the emitter. The electronic circuit is configured to control the emitter when the housing is disposed within the mouth and the apparatus is in use during orthodontic treatment. The apparatus and its use for regulating tooth movement or maintaining or improving oral tissue health are disclosed herein.

27 Claims, 80 Drawing Sheets

Related U.S. Application Data continuation of application No. 15/676,422, filed on Aug. 14, 2017, now abandoned, which is a continuation of application No. 14/521,121, filed on Oct. 22, 2014, now Pat. No. 9,730,780.

(60) Provisional application No. 62/045,439, filed on Sep. 3, 2014, provisional application No. 61/984,667, filed on Apr. 25, 2014, provisional application No. 61/894,404, filed on Oct. 22, 2013.

(51) Int. Cl.
*A61C 19/00* (2006.01)
*A61N 5/06* (2006.01)

(52) U.S. Cl.
CPC ............ *A61C 2203/00* (2013.01); *A61N 5/06* (2013.01); *A61N 2005/0606* (2013.01); *A61N 2005/0632* (2013.01); *A61N 2005/0651* (2013.01)

(58) Field of Classification Search
CPC . A61C 19/006; A61N 2005/0606; A61N 5/06
See application file for complete search history.

(56) References Cited

U.S. PATENT DOCUMENTS

| | | | |
|---|---|---|---|
| 3,516,411 A | 6/1970 | Adler |
| 3,971,387 A | 7/1976 | Mantell |
| 4,244,373 A | 1/1981 | Nachman |
| 4,273,535 A | 6/1981 | Yamamoto et al. |
| 4,368,040 A | 1/1983 | Weissman |
| 4,457,707 A | 7/1984 | Smiley et al. |
| 4,628,931 A | 12/1986 | Barrett |
| 4,736,745 A | 4/1988 | Gluckman |
| 4,836,203 A | 6/1989 | Muller et al. |
| 4,840,174 A | 6/1989 | Gluckman |
| 4,852,549 A | 8/1989 | Mori |
| 4,877,401 A | 10/1989 | Higuchi et al. |
| 4,930,504 A | 6/1990 | Diamantopoulos et al. |
| 4,983,381 A | 1/1991 | Torres Zaragoza |
| 5,137,530 A | 8/1992 | Sand |
| 5,259,380 A | 11/1993 | Mendes et al. |
| 5,358,503 A | 10/1994 | Bertwell et al. |
| 5,365,624 A | 11/1994 | Berns |
| 5,405,368 A | 4/1995 | Eckhouse |
| 5,421,727 A | 6/1995 | Stevens et al. |
| 5,429,501 A | 7/1995 | Farzin-Nia et al. |
| 5,445,608 A | 8/1995 | Chen et al. |
| 5,487,662 A | 1/1996 | Kipke et al. |
| 5,500,009 A | 3/1996 | Mendes et al. |
| 5,549,660 A | 8/1996 | Mendes et al. |
| 5,601,619 A | 2/1997 | Drechsler |
| 5,611,793 A | 3/1997 | Wilson et al. |
| 5,616,140 A | 4/1997 | Prescott |
| 5,660,461 A | 8/1997 | Ignatius et al. |
| 5,683,436 A | 11/1997 | Mendes et al. |
| 5,709,645 A | 1/1998 | Siever |
| 5,766,233 A | 6/1998 | Thiberg |
| 5,814,039 A | 9/1998 | Prescott |
| 5,913,883 A | 6/1999 | Alexander et al. |
| 5,951,141 A | 9/1999 | Bradley |
| 5,989,245 A | 11/1999 | Prescott |
| 6,053,936 A | 4/2000 | Koyama et al. |
| 6,063,108 A | 5/2000 | Salansky et al. |
| 6,077,073 A | 6/2000 | Jacob |
| 6,096,066 A | 8/2000 | Chen et al. |
| 6,156,028 A | 12/2000 | Prescott |
| 6,210,162 B1 | 4/2001 | Chishti et al. |
| 6,217,325 B1 | 4/2001 | Chishti et al. |
| 6,251,127 B1 | 6/2001 | Biel |
| 6,283,956 B1 | 9/2001 | McDaniel |
| 6,290,714 B1 | 9/2001 | Streeter |
| 6,319,273 B1 | 11/2001 | Chen et al. |
| 6,328,732 B1 | 12/2001 | Donitzky et al. |
| 6,366,802 B1 | 4/2002 | Haber et al. |
| 6,398,548 B1 | 6/2002 | Muhammad et al. |
| 6,413,267 B1 | 7/2002 | Dumoulin-White et al. |
| 6,418,345 B1 | 7/2002 | Tepper et al. |
| 6,450,170 B1 | 9/2002 | Friedman |
| 6,454,791 B1 | 9/2002 | Prescott |
| 6,471,716 B1 | 10/2002 | Pecukonis |
| 6,494,900 B1 | 12/2002 | Salansky et al. |
| 6,514,075 B1 | 2/2003 | Jacob |
| 6,524,101 B1 | 2/2003 | Phan et al. |
| 6,524,329 B1 | 2/2003 | Benedict |
| 6,537,305 B1 | 3/2003 | Thiberg |
| 6,554,611 B2 | 4/2003 | Chishti et al. |
| 6,602,275 B1 | 8/2003 | Sullivan |
| 6,613,001 B1 | 9/2003 | Dworkin |
| 6,616,447 B1 | 9/2003 | Rizoiu et al. |
| 6,626,666 B2 | 9/2003 | Chishti et al. |
| 6,629,840 B2 | 10/2003 | Chishti et al. |
| 6,629,971 B2 | 10/2003 | McDaniel |
| 6,645,230 B2 | 11/2003 | Whitehurst |
| 6,648,639 B2 | 11/2003 | Mao |
| 6,648,904 B2 | 11/2003 | Altshuler et al. |
| 6,663,659 B2 | 12/2003 | McDaniel |
| 6,676,655 B2 | 1/2004 | McDaniel |
| 6,678,562 B1 | 1/2004 | Tepper et al. |
| 6,699,037 B2 | 3/2004 | Chishti et al. |
| 6,722,880 B2 | 4/2004 | Chishti et al. |
| 6,743,249 B1 | 6/2004 | Alden |
| 6,746,473 B2 | 6/2004 | Shanks et al. |
| 6,832,912 B2 | 12/2004 | Mao |
| 6,860,896 B2 | 3/2005 | Leber et al. |
| 6,896,693 B2 | 5/2005 | Sullivan |
| 6,941,952 B1 | 9/2005 | Rush, III |
| 6,942,658 B1 | 9/2005 | Rizoiu et al. |
| 6,974,224 B2 | 12/2005 | Thomas-Benedict |
| 6,976,841 B1 | 12/2005 | Osterwalder |
| 6,986,782 B2 | 1/2006 | Chen et al. |
| 7,018,395 B2 | 3/2006 | Chen |
| 7,029,276 B2 | 4/2006 | Mao |
| 7,060,061 B2 | 6/2006 | Altshuler et al. |
| 7,070,611 B2 | 7/2006 | Biel |
| 7,081,128 B2 | 7/2006 | Hart et al. |
| 7,084,389 B2 | 8/2006 | Spector |
| 7,100,615 B1 | 9/2006 | Kert |
| 7,101,384 B2 | 9/2006 | Benedict |
| 7,134,874 B2 | 11/2006 | Chishti et al. |
| 7,144,249 B2 | 12/2006 | Rizoiu et al. |
| 7,163,400 B2 | 1/2007 | Cozean et al. |
| 7,184,614 B2 | 2/2007 | Slatkine |
| 7,201,577 B2 | 4/2007 | Levine |
| 7,223,270 B2 | 5/2007 | Altshuler et al. |
| 7,223,281 B2 | 5/2007 | Altshuler et al. |
| 7,244,253 B2 | 7/2007 | Neev |
| 7,306,620 B2 | 12/2007 | Cumbie |
| 7,314,372 B2 | 1/2008 | Belfor et al. |
| 7,329,273 B2 | 2/2008 | Altshuler et al. |
| 7,329,274 B2 | 2/2008 | Altshuler et al. |
| 7,335,025 B2 | 2/2008 | Levine |
| 7,354,448 B2 | 4/2008 | Altshuler et al. |
| 7,374,569 B2 | 5/2008 | Whatcott et al. |
| 7,422,598 B2 | 9/2008 | Altshuler et al. |
| D582,559 S | 12/2008 | Khawaled et al. |
| 7,474,307 B2 | 1/2009 | Chishti et al. |
| 7,513,906 B2 | 4/2009 | Passy et al. |
| 7,597,497 B2 | 10/2009 | Evine |
| 7,751,895 B2 | 7/2010 | Jones et al. |
| 7,775,795 B2 | 8/2010 | Khawaled et al. |
| 7,798,149 B2 | 9/2010 | Haduong |
| D636,074 S | 4/2011 | Levine |
| 8,021,148 B2 | 9/2011 | Goodson et al. |
| 8,029,278 B1 | 10/2011 | Levine |
| 8,105,079 B2 | 1/2012 | Farrell |
| 8,105,080 B2 | 1/2012 | Chishti et al. |
| D661,806 S | 6/2012 | Khawaled et al. |
| 8,214,958 B2 | 7/2012 | Pinyayev et al. |
| 8,215,954 B2 | 7/2012 | Levine |
| 8,236,036 B1 | 8/2012 | Frost |
| 8,240,312 B2 | 8/2012 | Feuerstein et al. |

(56) References Cited

U.S. PATENT DOCUMENTS

| | | |
|---|---|---|
| 8,241,035 B2 | 8/2012 | Jones et al. |
| 8,262,306 B2 | 9/2012 | Levine |
| 8,262,390 B1 | 9/2012 | Levine |
| 8,267,609 B2 | 9/2012 | Levine |
| 8,308,784 B2 | 11/2012 | Streeter et al. |
| 8,341,791 B2 | 1/2013 | Iwahori |
| 8,371,853 B2 | 2/2013 | Levine |
| 8,459,987 B2 | 6/2013 | Farrell |
| 8,485,818 B2 | 7/2013 | Boutoussov et al. |
| 8,500,446 B2 | 8/2013 | Lowe |
| 8,562,340 B2 | 10/2013 | Chishti et al. |
| 8,591,227 B2 | 11/2013 | Levine |
| 8,636,506 B2 | 1/2014 | Pavlin |
| 8,771,149 B2 | 7/2014 | Rahman et al. |
| 8,900,282 B2 | 12/2014 | Brawn |
| 8,920,163 B2 | 12/2014 | Farrell |
| 8,939,762 B2 | 1/2015 | Lowe |
| 9,028,250 B2 | 5/2015 | Spaulding et al. |
| 9,242,118 B2 | 1/2016 | Brawn |
| 9,308,389 B2 | 4/2016 | Brawn |
| 9,370,405 B2 | 6/2016 | Lowe |
| 9,370,406 B2 | 6/2016 | Lowe |
| 9,655,691 B2 | 5/2017 | Li et al. |
| 9,726,435 B2 | 8/2017 | Dahm |
| 9,730,780 B2 | 8/2017 | Brawn et al. |
| 9,889,315 B2 | 2/2018 | Demarest et al. |
| 9,974,630 B2 | 5/2018 | Heacock et al. |
| 10,111,729 B1* | 10/2018 | Lowe ............. A61C 7/008 |
| 10,729,524 B2 | 8/2020 | Brawn et al. |
| 2002/0161418 A1 | 10/2002 | Wilkens et al. |
| 2002/0165583 A1 | 11/2002 | Tepper et al. |
| 2002/0198575 A1 | 12/2002 | Sullivan |
| 2003/0004499 A1 | 1/2003 | McDaneil |
| 2003/0009205 A1 | 1/2003 | Biel |
| 2003/0125782 A1 | 7/2003 | Streeter |
| 2003/0130709 A1 | 7/2003 | Haber et al. |
| 2003/0153903 A1 | 8/2003 | Kumagi et al. |
| 2003/0167080 A1 | 9/2003 | Hart et al. |
| 2003/0186193 A1 | 10/2003 | Comfort |
| 2004/0034341 A1 | 2/2004 | Altshuler et al. |
| 2004/0043349 A1 | 3/2004 | Liao |
| 2004/0044384 A1 | 3/2004 | Eber et al. |
| 2004/0093042 A1 | 5/2004 | Altshuler et al. |
| 2004/0093047 A1 | 5/2004 | Lach |
| 2004/0127961 A1 | 7/2004 | Whitehurst |
| 2004/0147984 A1 | 7/2004 | Altshuler et al. |
| 2004/0152038 A1 | 8/2004 | Kumagai et al. |
| 2004/0156743 A1 | 8/2004 | Bornstein |
| 2004/0193235 A1* | 9/2004 | Altshuler ............. A61N 5/0603 607/88 |
| 2004/0199227 A1 | 10/2004 | Altshuler et al. |
| 2004/0230259 A1 | 11/2004 | Di Matteo |
| 2004/0239892 A1 | 12/2004 | Cok et al. |
| 2004/0248059 A1 | 12/2004 | Katsuda et al. |
| 2005/0004631 A1 | 1/2005 | Benedict |
| 2005/0015121 A1 | 1/2005 | Molina |
| 2005/0053898 A1 | 3/2005 | Ghosh |
| 2005/0059153 A1 | 3/2005 | George et al. |
| 2005/0070977 A1 | 3/2005 | Molina |
| 2005/0080404 A1 | 4/2005 | Jones et al. |
| 2005/0158687 A1 | 7/2005 | Dahm |
| 2005/0181333 A1 | 8/2005 | Karazivan et al. |
| 2005/0202363 A1 | 9/2005 | Osterwalder |
| 2005/0203592 A1 | 9/2005 | Teichert |
| 2005/0221251 A1 | 10/2005 | Soukos et al. |
| 2005/0244769 A1 | 11/2005 | Keles et al. |
| 2005/0260534 A1 | 11/2005 | Belfor et al. |
| 2005/0266370 A1* | 12/2005 | Suzuki ............. A61C 19/063 433/29 |
| 2005/0278003 A1 | 12/2005 | Feldman |
| 2005/0279949 A1 | 12/2005 | Oldham et al. |
| 2005/0282102 A1 | 12/2005 | Kert |
| 2006/0009823 A1 | 1/2006 | Richardson et al. |
| 2006/0061986 A1 | 3/2006 | Kuo et al. |
| 2006/0084024 A1 | 4/2006 | Farrell |
| 2006/0085052 A1 | 4/2006 | Feuerstein et al. |
| 2006/0166157 A1 | 7/2006 | Rahman et al. |
| 2006/0194164 A1 | 8/2006 | Altshuler et al. |
| 2006/0200212 A1 | 9/2006 | Brawn |
| 2006/0217787 A1 | 9/2006 | Olson et al. |
| 2006/0222600 A1 | 10/2006 | Pinyayev |
| 2006/0223032 A1 | 10/2006 | Fried et al. |
| 2006/0228158 A1 | 10/2006 | Levine et al. |
| 2006/0241726 A1 | 10/2006 | Whitehurst |
| 2006/0269896 A1 | 11/2006 | Liu et al. |
| 2007/0009856 A1* | 1/2007 | Jones ............. A61C 19/063 433/215 |
| 2007/0105212 A1 | 5/2007 | Oldham et al. |
| 2007/0110683 A1 | 5/2007 | Levine et al. |
| 2007/0121786 A1 | 5/2007 | Okawa et al. |
| 2007/0129776 A1 | 6/2007 | Robins et al. |
| 2007/0166666 A1 | 7/2007 | Levine |
| 2007/0183988 A1 | 8/2007 | Prosise et al. |
| 2007/0185553 A1 | 8/2007 | Kennedy |
| 2007/0207436 A1 | 9/2007 | Tan et al. |
| 2007/0208289 A1 | 9/2007 | Walther et al. |
| 2007/0208395 A1 | 9/2007 | Leclerc et al. |
| 2007/0208404 A1 | 9/2007 | Jones et al. |
| 2007/0219605 A1 | 9/2007 | Yaroslavsky et al. |
| 2007/0248930 A1 | 10/2007 | Brawn |
| 2007/0254256 A1 | 11/2007 | Farrell |
| 2007/0255356 A1 | 11/2007 | Rose et al. |
| 2007/0259310 A1 | 11/2007 | Goodson et al. |
| 2007/0265605 A1 | 11/2007 | Vaynberg et al. |
| 2008/0008978 A1 | 1/2008 | Conrad et al. |
| 2008/0032252 A1 | 2/2008 | Hayman et al. |
| 2008/0032253 A1 | 2/2008 | Montgomery et al. |
| 2008/0051858 A1 | 2/2008 | Haber et al. |
| 2008/0077199 A1 | 3/2008 | Shefi et al. |
| 2008/0113313 A1 | 5/2008 | Khouri |
| 2008/0214530 A1 | 9/2008 | Colles |
| 2008/0227046 A1 | 9/2008 | Lowe et al. |
| 2008/0227047 A1 | 9/2008 | Lowe et al. |
| 2008/0233541 A1 | 9/2008 | de Vreese et al. |
| 2008/0254401 A1 | 10/2008 | Yazdi |
| 2008/0255498 A1 | 10/2008 | Houle |
| 2008/0269579 A1 | 10/2008 | Schiebler |
| 2008/0273163 A1 | 11/2008 | Sasaki |
| 2009/0011380 A1 | 1/2009 | Wang |
| 2009/0029311 A1 | 1/2009 | Chan |
| 2009/0210032 A1 | 8/2009 | Beiski et al. |
| 2009/0240310 A1 | 9/2009 | Kennedy |
| 2009/0254154 A1 | 10/2009 | De Taboada et al. |
| 2009/0317770 A1 | 12/2009 | Gatzemeyer et al. |
| 2009/0323370 A1 | 12/2009 | Koo |
| 2010/0040993 A1 | 2/2010 | Karazivan et al. |
| 2010/0055634 A1 | 3/2010 | Spaulding et al. |
| 2010/0086891 A1 | 4/2010 | Jun |
| 2010/0094190 A1 | 4/2010 | Walther et al. |
| 2010/0100160 A1 | 4/2010 | Edman et al. |
| 2010/0121417 A1 | 5/2010 | Hamada et al. |
| 2010/0151406 A1 | 6/2010 | Boutoussov et al. |
| 2010/0151407 A1 | 6/2010 | Rizoiu et al. |
| 2010/0211136 A1 | 8/2010 | Da Taboada et al. |
| 2010/0217358 A1 | 8/2010 | Hebert et al. |
| 2010/0220472 A1 | 9/2010 | Dahm |
| 2010/0305668 A1 | 12/2010 | Brawn |
| 2010/0318161 A1 | 12/2010 | Brawn |
| 2010/0330539 A1 | 12/2010 | Glover et al. |
| 2010/0331928 A1 | 12/2010 | Dunning et al. |
| 2011/0041269 A1 | 2/2011 | Iwahori |
| 2011/0091835 A1 | 4/2011 | Levine |
| 2011/0104631 A1 | 5/2011 | Levine |
| 2011/0104633 A1 | 5/2011 | Levine |
| 2011/0136070 A1 | 6/2011 | Rubin et al. |
| 2011/0136071 A1 | 6/2011 | Levens |
| 2011/0144410 A1 | 6/2011 | Kennedy |
| 2011/0144566 A1 | 6/2011 | Dacey et al. |
| 2011/0159549 A1 | 6/2011 | Oldham et al. |
| 2011/0179851 A1 | 7/2011 | Mack et al. |
| 2011/0183296 A1 | 7/2011 | Levine |
| 2012/0009539 A1 | 1/2012 | Goodson et al. |
| 2012/0040300 A1 | 2/2012 | Levens et al. |
| 2012/0094246 A1 | 4/2012 | Pavlin |

(56) References Cited

U.S. PATENT DOCUMENTS

| | | | |
|---|---|---|---|
| 2012/0148975 A1 | 6/2012 | Brawn | |
| 2012/0148976 A1 | 6/2012 | Brawn | |
| 2012/0172679 A1 | 7/2012 | Logan et al. | |
| 2012/0183919 A1 | 7/2012 | Levine | |
| 2012/0196243 A1 | 8/2012 | Farrell | |
| 2012/0322018 A1 | 12/2012 | Lowe | |
| 2013/0034859 A1 | 2/2013 | Boege et al. | |
| 2013/0059263 A1 | 3/2013 | Lowe et al. | |
| 2013/0144364 A1 | 6/2013 | Wagenaar et al. | |
| 2013/0184693 A1 | 7/2013 | Neev | |
| 2013/0196284 A1 | 8/2013 | Brawn | |
| 2013/0253286 A1 | 9/2013 | Fridman | |
| 2013/0253620 A1 | 9/2013 | Brawn | |
| 2013/0280671 A1 | 10/2013 | Brawn et al. | |
| 2013/0289674 A1 | 10/2013 | Brawn | |
| 2013/0331640 A1 | 12/2013 | Nabat et al. | |
| 2014/0072932 A1 | 3/2014 | Brawn et al. | |
| 2014/0080082 A1 | 3/2014 | Lowe | |
| 2014/0087333 A1 | 3/2014 | DiVito et al. | |
| 2014/0121731 A1 | 5/2014 | Brawn | |
| 2014/0147802 A1 | 5/2014 | Naldoni | |
| 2014/0272761 A1 | 9/2014 | Lowe et al. | |
| 2014/0272770 A1* | 9/2014 | Hurley | A61N 5/0603 433/29 |
| 2015/0079533 A1 | 3/2015 | Lowe | |
| 2015/0079536 A1 | 3/2015 | Brawn | |
| 2015/0112697 A1 | 4/2015 | Bradley | |
| 2015/0140502 A1 | 5/2015 | Brawn et al. | |
| 2015/0164618 A1 | 6/2015 | Heacock et al. | |
| 2015/0169845 A1 | 6/2015 | Bradley | |
| 2015/0173856 A1 | 6/2015 | Lowe et al. | |
| 2016/0096037 A1 | 4/2016 | Brawn | |
| 2016/0184054 A1 | 6/2016 | Lowe | |
| 2017/0080249 A1 | 3/2017 | Brawn et al. | |
| 2017/0173358 A1 | 6/2017 | Demarest et al. | |
| 2017/0173359 A1 | 6/2017 | Brawn | |
| 2017/0312538 A1 | 11/2017 | Brawn et al. | |
| 2018/0014924 A1 | 1/2018 | Brawn et al. | |
| 2018/0117356 A1 | 5/2018 | Brawn et al. | |
| 2018/0140406 A1 | 5/2018 | Brawn et al. | |
| 2018/0140864 A1 | 5/2018 | Brawn | |
| 2018/0177570 A1 | 6/2018 | Alauddin et al. | |
| 2018/0304092 A1 | 10/2018 | Kothari et al. | |
| 2019/0046297 A1 | 2/2019 | Kopelman et al. | |
| 2019/0083202 A1 | 3/2019 | Brawn et al. | |
| 2019/0117994 A1 | 4/2019 | Brawn | |
| 2019/0201711 A1 | 7/2019 | Brawn et al. | |
| 2019/0209857 A1 | 7/2019 | Brawn et al. | |
| 2019/0299022 A1 | 10/2019 | Brawn | |
| 2020/0016426 A1 | 1/2020 | Brawn | |
| 2020/0023191 A1 | 1/2020 | Brawn | |

FOREIGN PATENT DOCUMENTS

| | | | |
|---|---|---|---|
| CA | 2448385 | 11/2002 | |
| CA | 2505559 | 5/2004 | |
| CA | 2515695 | 10/2004 | |
| CA | 2598189 | 8/2006 | |
| CA | 2726322 | 9/2011 | |
| CA | 2829973 | 5/2013 | |
| CA | 2813215 | 12/2013 | |
| CN | 87107026 | 4/1988 | |
| CN | 103126774 | 5/2016 | |
| CN | 107468499 A * | 12/2017 | |
| EP | 2110159 | 10/2009 | |
| EP | 1853347 B1 | 4/2012 | |
| GB | 2203649 | 10/1988 | |
| GB | 2212010 | 7/1989 | |
| GB | 2335363 | 9/1999 | |
| GB | 2360461 | 9/2001 | |
| GB | 2376891 | 12/2002 | |
| GB | 2416311 | 1/2006 | |
| JP | 2000-070292 | 3/2000 | |
| JP | 2004-202189 | 7/2004 | |
| JP | 2011-194220 | 10/2011 | |
| RU | 2133630 | 7/1999 | |
| WO | WO 95/010243 | 4/1995 | |
| WO | WO 97/37723 | 10/1997 | |
| WO | WO 98/06456 | 2/1998 | |
| WO | WO 98/38933 | 9/1998 | |
| WO | WO 2002/024052 | 3/2002 | |
| WO | WO 2002/062419 | 8/2002 | |
| WO | WO 2004/075985 | 9/2004 | |
| WO | WO 2005/015291 | 2/2005 | |
| WO | WO 2005/062710 | 7/2005 | |
| WO | WO 2005/107637 | 11/2005 | |
| WO | WO 2006/028461 | 3/2006 | |
| WO | WO 2006/052682 | 5/2006 | |
| WO | WO 2006/087633 | 8/2006 | |
| WO | WO 2006/098719 | 9/2006 | |
| WO | WO 2006/115765 | 11/2006 | |
| WO | WO 2006/128021 | 11/2006 | |
| WO | WO 2007/007335 | 1/2007 | |
| WO | WO 2007/007336 | 1/2007 | |
| WO | WO 2007/014217 | 2/2007 | |
| WO | WO 2007/025244 | 3/2007 | |
| WO | WO 2007/047892 | 4/2007 | |
| WO | WO 2007/062251 | 5/2007 | |
| WO | WO 2007/085776 | 8/2007 | |
| WO | WO 2007/092368 | 8/2007 | |
| WO | WO 2007/109245 | 9/2007 | |
| WO | WO 2007/121760 | 11/2007 | |
| WO | WO-2007121760 A1 * | 11/2007 | A61C 17/20 |
| WO | WO 2008/001388 | 1/2008 | |
| WO | WO 2008/092660 | 8/2008 | |
| WO | WO 2008/114255 | 9/2008 | |
| WO | WO 2008/124918 | 10/2008 | |
| WO | WO 2009/000075 | 12/2008 | |
| WO | WO 2009/023968 | 2/2009 | |
| WO | WO 2009/072108 | 6/2009 | |
| WO | WO 2009/123965 | 10/2009 | |
| WO | WO 2009/158297 | 12/2009 | |
| WO | WO 2010/093632 | 8/2010 | |
| WO | WO 2010/098761 | 9/2010 | |
| WO | WO 2010/108080 | 9/2010 | |
| WO | WO 2010/142013 | 12/2010 | |
| WO | WO 2010/142031 | 12/2010 | |
| WO | WO 2011/056260 | 5/2011 | |
| WO | WO 2011/134071 | 11/2011 | |
| WO | WO 2012/001639 | 1/2012 | |
| WO | WO 2012/048423 | 4/2012 | |
| WO | WO 2012/075584 | 6/2012 | |
| WO | WO 2013/075246 | 5/2013 | |
| WO | WO 2013/155366 | 10/2013 | |
| WO | WO 2013/155632 | 10/2013 | |
| WO | WO 2015/058284 | 4/2015 | |
| WO | WO 2016/168939 | 10/2016 | |
| WO | WO 2017/044931 | 3/2017 | |

OTHER PUBLICATIONS

Office Action for U.S. Appl. No. 11/355,583, mailed Jul. 17, 2009, 12 pages.

Office Action for U.S. Appl. No. 11/355,583, mailed Jan. 20, 2010, 10 pages.

Office Action for U.S. Appl. No. 11/355,583, mailed Oct. 5, 2011, 14 pages.

Office Action for U.S. Appl. No. 11/355,583, mailed May 29, 2012, 10 pages.

International Search Report and Written Opinion for International Application No. PCT/IB2006/000358, mailed Jun. 20, 2006, 10 pages.

Supplementary European Search Report for European Application No. 08772845, mailed Mar. 21, 2014, 7 pages.

Office Action for U.S. Appl. No. 11/767,302, mailed Nov. 15, 2011, 16 pages.

Office Action for U.S. Appl. No. 11/767,302, mailed Mar. 11, 2010, 18 pages.

Office Action for U.S. Appl. No. 11/767,302, mailed Oct. 8, 2009, 20 pages.

(56) References Cited

OTHER PUBLICATIONS

Office Action for U.S. Appl. No. 11/767,302, mailed May 29, 2012, 13 pages.
International Search Report and Written Opinion for International Application No. PCT/CA2008/001188, mailed Sep. 26, 2008, 7 pages.
European Search Report for European Application No. 12163646, mailed Aug. 24, 2012, 5 pages.
Office Action for U.S. Appl. No. 12/820,070, mailed Feb. 20, 2013, 10 pages.
Office Action for U.S. Appl. No. 12/820,070, mailed Jan. 29, 2014, 11 pages.
Reply and Amendment Under 37 CFR 1.111 for U.S. Appl. No. 12/820,070, filed Aug. 20, 2013, 9 pages.
Declaration of Peter R. Brawn, D.D.S., Under 37 CFR 1.132, for U.S. Appl. No. 12/820,070, executed Aug. 20, 2013, 7 pages.
Office Action for U.S. Appl. No. 12/834,601, mailed Mar. 13, 2013, 13 pages.
Office Action for U.S. Appl. No. 13/895,327, mailed Feb. 4, 2014, 5 pages.
Office Action for U.S. Appl. No. 13/895,330, mailed Mar. 24, 2014, 5 pages.
Office Action for U.S. Appl. No. 14/147,210, mailed Jun. 29, 2016, 11 pages.
Office Action for U.S. Appl. No. 14/554,404, mailed Jun. 18, 2015, 5 pages.
International Search Report and Written Opinion for International Application No. PCT/CA2009/000808, mailed Mar. 4, 2010, 11 pages.
Office Action for U.S. Appl. No. 13/313,830, mailed Dec. 17, 2012, 22 pages.
Office Action for U.S. Appl. No. 13/313,830, mailed Oct. 28, 2013, 16 pages.
Office Action for U.S. Appl. No. 13/313,830, mailed Feb. 11, 2015, 19 pages.
Office Action for U.S. Appl. No. 13/313,830, mailed Dec. 11, 2015, 23 pages.
Office Action for U.S. Appl. No. 13/313,830, mailed Jan. 10, 2017, 21 pages.
International Search Report and Written Opinion for International Application No. PCT/CA2010/000877, mailed Oct. 20, 2010, 9 pages.
Supplementary European Search Report for European Application No. 11831892, mailed Mar. 4, 2014, 6 pages.
Office Action for U.S. Appl. No. 13/826,383, mailed Sep. 5, 2013, 10 pages.
Office Action for U.S. Appl. No. 13/826,383, mailed Mar. 26, 2014, 11 pages.
Office Action for U.S. Appl. No. 13/826,383, mailed Feb. 25, 2016, 14 pages.
Office Action for U.S. Appl. No. 13/826,383, mailed Sep. 9, 2016, 18 pages.
International Search Report and Written Opinion for International Application No. PCT/CA2011/050639, mailed Feb. 20, 2012, 13 pages.
Office Action for U.S. Appl. No. 15/454,763, mailed Jun. 4, 2018, 14 pages.
Office Action for U.S. Appl. No. 15/856,831, mailed May 30, 2018, 11 pages.
Supplementary European Search Report for European Application No. 11846346.2, mailed Jun. 17, 2014, 5 pages.
Office Action for U.S. Appl. No. 13/314,006, mailed Aug. 28, 2013, 19 pages.
Office Action for U.S. Appl. No. 13/314,006, mailed Jul. 8, 2014, 25 pages.
International Search Report and Written Opinion for International Application No. PCT/CA2011/050755, mailed Apr. 4, 2012, 14 pages.
Office Action for U.S. Appl. No. 14/965,786, mailed Feb. 2, 2018, 10 pages.
Supplementary European Search Report for European Application No. 13779083.8, mailed Mar. 14, 2016, 7 pages.
International Search Report and Written Opinion for International Application No. PCT/CA2013/050302, mailed Jul. 19, 2013, 9 pages.
European Search Report for European Application No. 17171423.1, mailed Nov. 24, 2017, 5 pages.
Office Action for U.S. Appl. No. 13/827,541, mailed Mar. 27, 2015, 17 pages.
Office Action for U.S. Appl. No. 13/827,541, mailed Dec. 31, 2015, 16 pages.
Office Action for U.S. Appl. No. 13/827,541, mailed Aug. 11, 2016, 17 pages.
Office Action for U.S. Appl. No. 13/827,541, mailed May 17, 2017, 20 pages.
Office Action for U.S. Appl. No. 13/827,541, mailed Aug. 27, 2018, 22 pages.
Office Action for U.S. Appl. No. 13/827,541, mailed Dec. 14, 2017, 20 pages.
Third-Party Submission Under 37 CFR 1.290 for U.S. Appl. No. 13/866,831, filed Apr. 23, 2014, 48 pages.
Office Action for U.S. Appl. No. 13/866,831, mailed Aug. 5, 2016, 16 pages.
Office Action for U.S. Appl. No. 15/858,373, mailed Apr. 10, 2018, 15 pages.
Supplementary European Search Report for European Application No. 14855209.4, mailed Apr. 3, 2017, 6 pages.
Office Action for U.S. Appl. No. 14/521,121, mailed Jul. 13, 2016, 13 pages.
International Search Report and Written Opinion for International Application No. PCT/CA2014/000760, mailed Feb. 5, 2015, 10 pages.
International Preliminary Report on Patentability for International Application No. PCT/CA2014/000760, dated Apr. 26, 2016, 7 pages.
Office Action for U.S. Appl. No. 15/676,422, mailed Aug. 2, 2018, 17 pages.
Office Action for U.S. Appl. No. 15/858,533, mailed Aug. 2, 2018, 15 pages.
Office Action for U.S. Appl. No. 15/136,127, mailed Sep. 4, 2018, 15 pages.
International Search Report and Written Opinion for International Application No. PCT/CA2016/050471, mailed Jul. 6, 2016, 11 pages.
"DioBeam 830", pamphlet, CMS-Dental, Copenhagen, Denmark (2009), 8 pages.
"Diode laser for low level laser therapy", pamphlet, Model CTL-1106MX, Centre of Laser Technology, Laser Instruments Ltd., Warsaw, Poland (2009), 1 page.
"Hand-held therapy laser", pamphlet, Model CTL-1106MA, Centrum Techniki Laserowej, Laserinstruments Sp. zo.o, Warsaw, Poland (2009), 1 page.
"Lab pen Med Laser", pamphlet, Dr. Hinz Dental (2009), 1 page.
"Medx Phototherapy Series," pamphlet, Laser Light Canada (2006), 1 page.
"The Home Unit" pamphlet, Laser Light Canada (2009), 1 page.
"TheraLASE Therapeutic Laser Treatment," pamphlet, Theralase Inc. (2009), 2 pages.
ASA Laser Therapy Company. Retrieved from the Internet: Nov. 16, 2009. <http://www.asalaser.com/uk/laser_therapy-34.html>, 2 pages.
SpectraMedics. Retrieved from the Internet: Nov. 16, 2009. <http://www.spectramedics.com/>, 3 pages.
Acumed Ltda. Retrieved from the Internet: Nov. 16, 2009. <http://www.acumed.cl/productos.php>, 10 pages.
AIIE-BEEP. Retrieved from the Internet: Dec. 8, 2009. <http://www.aile-beep.com/index.php/en/>, 4 pages.
Apollo Physical Therapy Products LLC, Apollo 2009 Laser Products. Retrieved from the Internet: Nov. 16, 2009. <http://www.apollopt.com/products.htm>, 4 pages.
Avicenna Laser Technology, Inc. Retrieved from the Internet: Nov. 16, 2009. <http://www.avicennalaser.com/>, 1 page.
Biolase Technology, Inc.. Retrieved from the Internet: Nov. 16, 2009. <http://www.biolase.com/>, 3 pages.

(56) References Cited

OTHER PUBLICATIONS

CMS Dental ApS. Retrieved from the Internet: Nov. 16, 2009. <http://www.cmsdental.com/>, 2 pages.
Laserinstruments Ltd., Centre of Laser Technology. Retrieved from the Internet: Nov. 16, 2009. <http://www.ctl.com.pl/english/eindex2.html>, 1 page.
Velkommen til Easy-Laser Technology Aps, Service Division. Retrieved from the Internet: Nov. 16, 2009. <http://www.easy-laser.dk/startside.html>, 4 pages.
Erchonia. Retrieved from the Internet: Nov. 16, 2009. <http://www.erchonia.com/>, 5 pages.
GentleWaves. Retrieved from the Internet: Nov. 16, 2009. <http://www.gentlewaves.com/index.asp>, 3 pages.
GMS Green Medical Systems. Retrieved from the Internet: Nov. 16, 2009. <http://www.greenmed.co.jp/body/index-E.htm>, 2 pages.
IRRADIA. Retrieved from the Internet: Nov. 16, 2009. <http://www.irradia.com/>, 2 pages.
RJ-Laser, Germany. Retrieved from the Internet: Nov. 16, 2009. <http://www.rj-medical.de/>, 4 pages.
Laserex. Retrieved from the Internet: Nov. 16, 2009. <http://www.laserex.net/>, 2 pages.
Laser Therapeutics, Inc. Retrieved from the Internet: Nov. 16, 2009. <http://www.laserhealthsystems.com/>, 2 pages.
Light for Health Limited. Retrieved from the Internet: Dec. 10, 2009. <http://www.lightforhealth.co.uk/>, 1 page.
MediCom Inc. Retrieved from the Internet: Nov. 16, 2009. <http://www.medicom.cz/en/index.php>, 2 pages.
MedSolution. Retrieved from the Internet: Nov. 16, 2009. <http://www.medsolution.de/>, 3 pages.
MedX Health. Retrieved from the Internet: Nov. 16, 2009. <http://www.medxhealth.com/>, 2 pages.
Meridian Co., Ltd. Retrieved from the Internet: Nov. 16, 2009. <http://www.meridian.co.kr/>, 3 pages.
MKW Lasersysteme. Retrieved from the Internet: Nov. 16, 2009. <http://www.mkw-laser.de/MKW-Site_NEU/Sites/en/index.html>, 2 pages.
MM Optics Ltda. Retrieved from the Internet: Nov. 16, 2009. <http://www.mmo.com.br/index_eng.asp>, 4 pages.
Omega Laser Systems. Retrieved from the Internet: Nov. 16, 2009. <http://www.omegalaser.co.uk/>, 2 pages.
Petrolaser Company. Retrieved from the Internet: Nov. 16, 2009. <http://www.petrolaser.spb.ru/indexe.htm>, 2 pages.
RianCorp Pty Ltd. Retrieved from the Internet: Nov. 16, 2009. <http://www.riancorp.com/>, 3 pages.
ScalarWave Lasers. Retrieved from the Internet: Nov. 16, 2009. <http://www.scalarwavelasers.com/>, 4 pages.
SKF Services, Ltd. Retrieved from the Internet: Nov. 16, 2009. <http://www.skfservices.com/>, 3 pages.
Laseuropa Kft. Retrieved from the Internet: Nov. 16, 2009. <http://www.softlaser.hu/company.php>, 1 page.
Theralase Corporate. Retrieved from the Internet: Nov. 16, 2009. <http://www.theralase.com/>, 2 pages.
THOR Laser. Retrieved from the Internet: Nov. 16, 2009. <http://www.thorlaser.com/>, 3 pages.
Motifolio Inc., Periodontium Illustrations, [Online], Retrieved from the Internet: <http://www.motifolio.com/1041132.html>, Jun. 28, 2018, 1 page.
Abi-Ramia, L. B. P. et al., "Effects of low-level laser therapy and orthodontic tooth movement on dental pulps in rats," Angle Orthod., 80(1):116-122 (2010).
Aboul-Ela, S. M. et al., "Miniscrew implant-supported maxillary canine retraction with and without corticotomy-facilitated orthodontics," Am. J. Orthod. Dentofacial Orthop., 139(2):252-259 (2011).
Abtahi, M. et al., "The effect of low level laser on condylar growth during mandibular advancement in rabbits," Head & Face Medicine, 8(4):1-5 (2012).
Ad, N. et al., "Impact of low level laser irradiation on infarct size in the rat following myocardial infarction," International Journal of Cardiology, 80(2-3):109-116 (2001).

Agaiby, A. D. et al., "Laser modulation of angiogenic factor production by T-lymphocytes," Lasers Surg Med., 26(4):357-363 (2000) (Abstract).
Aihara, N. et al., "Low-energy irradiation stimulates formation of osteoclast-like cells via RANK expression in vitro," Lasers Med. Sci., 21(1):24-33 (2006).
Ajdukovic, Z. et al., "Repair of bone tissue affected by osteoporosis with hydroxyapatite-Poly-L-lactide (HAp-PLLA) with and without blood plasma," Journal of Biomaterials Applications, 20(2):179-190 (2005).
Akin, E. et al., "Effects of nitric oxide in orthodontic tooth movement in rats," Am. J. Orthod. Dentofacial Orthop., 126(5):608-614 (2004).
Albrecht-Buehler, G., "Changes of cell behavior by near-infrared signals," Cell Motility and the Cytoskeleton, 32(4):299-304 (1995).
Alexandratou, E. et al., "Human fibroblast alterations induced by low power laser irradiation at the single cell level using confocal microscopy," Photochem. Photobiol. Sci., 1(8):547-552 (2002).
Almeida-Lopes, L. et al., "Comparison of the low level laser therapy effects on cultured human gingival fibroblasts proliferation using different irradiance and same fluence," Lasers in Surgery and Medicine, 29(2):179-184 (2001).
Altan, B. A. et al., "Metrical and histological investigation of the effects of low-level laser therapy on orthodontic tooth movement," Lasers Med. Sci., 27(1):131-140 (2012) (Published online: Oct. 31, 2010).
Alves, J. B. et al., "Local delivery of EGF-liposome mediated bone modeling in orthodontic tooth movement by increasing RANKL expression," Life Sciences, 85(19-20):693-699 (2009).
Aoki, A. et al., "Lasers in nonsurgical periodontal therapy," Periodontology 2000, 36:59-97 (2004).
Artes-Ribas, M. et al., "Analgesic effect of a low-level laser therapy (830 nm) in early orthodontic treatment," Lasers Med. Sci., 28:335-341 (2013).
Bakr, A. et al., "Osteogenesis in the glenoid fossa in response to mandibular advancement," American Journal of Orthodontics and Dentofacial Orthopedics, 119(4):390-400 (2001).
Baloul, S. S. et al., "Mechanism of action and morphologic changes in the alveolar bone in response to selective alveolar decortication-facilitated tooth movement," Am. J. Orthod. Dentofacial Orthop., 139(4, Suppl. 1):S83-S101 (2011).
Barushka, O. et al., "Effect of low-energy laser (He—Ne) irradiation on the process of bone repair in the rat tibia," Bone, 16(1):47-55 (1995).
Bath-Balogh, M. et al., Illustrated Dental Embryology, Histology and Anatomy, 3d ed. (2011), pp. 293, 297 and 300.
Bath-Balogh, M. et al., Unit I, Review of Dental Structures, Illustrated Dental Embryology, Histology and Anatomy, 3rd ed. (2011), p. 14.
Bibikova, A. et al., "Enhancement of angiogenesis in regenerating gastrocnemius muscle of the toad (*Bufo viridis*) by low-energy laser irradiation," Anat. Embryol (Berl), 190(6):597-602 (1994).
Biolux Research, "OrthoPulse Light Accelerated Orthodontics," Clinical and Scientific Dossier, Jun. 2015, 42 pages, Retrieved from the Internet: http://www.orthopulse.com/pdf/dossier.pdf.
Bischoff-Ferrari, H. A. et al., "Fracture prevention with vitamin D supplementation: a meta-analysis of randomized controlled trials," JAMA, 293(18):2257-2264 (2005).
Blaya, D. S. et al., "Histologic study of the effect of laser therapy on bone repair," J. Contemp. Dent. Pract., 9(6):41-48 (2008).
Bouquot, J. et al., "Combined new technologies to improve dental implant success—quantitative ultrasound evaluation of NIR-LED photobiomodulation," Abstracts of the 2008 Annual Meeting of the American Academy of Oral Medicine, p. e6 (2008).
Bouquot, J. E. et al., "Combined new technologies to improve dental implant success and quantitative ultrasound evaluation of NIR-LED photobiomodulation," Proceedings of Light-Activated Tissue Regeneration and Therapy Conference, Waynant, R. and Tata, D.B. (eds.), Springer Science+Business Media, LLC, pp. 191-206 (2008).
Brawn, P. R. et al., "Histologic comparison of light emitting diode phototherapy-treated hydroxyapatite-grafted extraction sockets: a same-mouth case study," Implant Dentistry, 16(2):204-207 (2007).

(56) References Cited

OTHER PUBLICATIONS

Brawn, P. et al., "Accelerated implant stability after LED photobiomodulation treatment," EAO Barcelona (2007), 2 pages.
Brawn, P. et al., "Accelerated implant stability after LED photobiomodulation," J. Dent. Res., 87(Spec Iss B):2021 (2008), IADR 86th General Session & Exhibition Poster Presentation, Toronto, Ontario, Canada, 3 pages.
Brudvik, P. et al., "Multi-nucleated cells remove the main hyalinized tissue and start resorption of adjacent root surfaces," Eur J Orthod., 16(4):265-273 (1994).
Brudvik, P. et al., "Root resorption beneath the main hyalinized zone," Eur J Orthod., 16(4):249-263 (1994).
Brudvik, P. et al., "The initial phase of orthodontic root resorption incident to local compression of the periodontal ligament," Eur J Orthod., 15(4):249-263 (1993).
Burcu, K-A, "The effects of Nd: YAG laser on maxillary canine distalization rate," Turkish Journal of Orthodontics, 22:16-25 (2009).
Byrnes, K. R. et al., "Light promotes regeneration and functional recovery and alters the immune response after spinal cord injury," Lasers in Surgery and Medicine, 36(3):171-185 (2005).
Carvalho-Lobato, P. et al., "Tooth movement in orthodontic treatment with low-level laser therapy: a systematic review of human and animal studies," Photomed. Laser Surg., 32(5):302-309 (2014).
Chamber's 21st Century Dictionary, Definition of Orthodontics, Chambers Harrap, retrieved from the internet on Oct. 17, 2013, retrieved from: http://www.credoreference.com/entry/chambdict/orthodontics (2001).
Chung, H. et al., "The nuts and bolts of low-level laser (light) therapy," Ann. Biomed. Eng., 40(2):516-533 (2012), NIH-PA Author Manuscript.
Clokie, C., et al., "The effects of the helium-neon laser on post-surgical discomfort: a pilot study," Journal of the Canadian Dental Association, 57(7):584-586 (1991).
Cobb, C. M., "Lasers in periodontics: a review of the literature," Journal of Periodontology, 77(4):545-564 (2006).
Collins, M. K. et al., "The local use of vitamin D to increase the rate of orthodontic tooth movement," Am J. Orthod. Dentofac. Orthop., 94(4):278-284 (1988).
Coombe, A. R. et al., "The effects of low level laser irradiation on osteoblastic cells," Clin. Orthod. Res., 4(1):3-14 (2001).
Cruz, D. R. et al., "Effects of low-intensity laser therapy on the orthodontic movement velocity of human teeth: a preliminary study," Lasers in Surgery and Medicine, 35(2):117-120 (2004).
Da Silva, R. V. et al., "Repair of bone defects treated with autogenous bone graft and low-power laser," Journal of Craniofacial Surgery, 17(2):297-301 (2006).
Demir, H. et al., "Comparison of the effects of laser, ultrasound, and combined laser/ultrasound treatments in experimental tendon healing," Lasers in Surgery and Medicine, 35(1):84-89 (2004).
DiBiase, A. T. et al., "Effects of supplemental vibrational force on space closure, treatment duration, and occlusal outcome: A multicenter randomized clinical trial," American Journal of Orthodontics and Dentofacial Orthopedics, vol. 153, Issue 4 (Apr. 2018), pp. 469-480.
Dietz, P. et al., "Very Low-Cost Sensing and Communication Using Bidirectional LEDs," UbiComp 2003, Seattle, Washington, Oct. 12-15, 2003, Mitsubishi Electric Research Laboratories, Inc., TR2003-35 Jul. 2003, Retrieved from the Internet on Oct. 27, 2017: <URL: < http://www.merl.com/publications/docs/TR2003-35.pdf>, 19 pages.
Dorland's Illustrated Medical Dictionary, 29th Edition, W.B. Saunders Company, p. 1851 (2000).
Dortbudak, O. et al., "Effect of low-power laser irradiation on bony implant sites," Clin Oral Impl. Res., 13(3):288-292 (2002).
Dortbudak, O. et al., "Biostimulation of bone marrow cells with a diode soft laser," Clinical Oral Implants Research, 11(6):540-545 (2000).
Doshi-Mehta, G. et al., "Efficacy of low-intensity laser therapy in reducing treatment time and orthodontic pain: A clinical investigation," Am J Orthod Dentofacial Orthop 2012;141(3):289-97.

Eells, J. T. et al., "Mitochondrial signal transduction in accelerated wound and retinal healing by near-infrared light therapy," Mitochondrion, 4(5-6):559-567 (2004).
Eells, J. T. et al., "Therapeutic photobiomodulation for methanol-induced retinal toxicity," PNAS, 100(6):3439-3444 (2003).
Ekizer, A. et al., "Effect of LED-mediated-photobiomodulation therapy on orthodontic tooth movement and root resorption in rats," Lasers Med. Sci., 30(2):779-785 (2015) (Published online: Aug. 29, 2013).
Ekizer, A. et al., "Light-emitting diode photobiomodulation: effect on bone formation in orthopedically expanded suture in rats-early bone changes," Lasers Med. Sci., 28(5):1263-1270 (2013) (Published online: Nov. 9, 2012).
El-Bialy, T. et al., "The effect of light-emitting diode and laser on mandibular growth in rats," Angle Orthod., 85(2):233-238 (2015).
El-Bialy, T. et al., "Growth modification of the mandible with ultrasound in baboons: A preliminary report," American Journal of Orthodontics and Dentofacial Orthopedics, 130(4):435.e7-435.e14 (2006).
El-Bialy, T. et al., "Growth modification of the rabbit mandible using therapeutic ultrasound: Is it possible to enhance functional appliance results?," Angle Orthodontist, 73(6):631-639 (2003).
El Sayed, S. O. et al., "Effect of laser pulse repetition rate and pulse duration on mast cell no and degranulation," Lasers in Surgery and Medicine, 19(4):433-437 (1996).
Enwemeka, C. S., "Laser biostimulation of healing wounds: specific effects and mechanisms of action," The Journal of Orthopaedic and Sports Physical Therapy, 9(10):333-338 (1988).
Featherstone, J. D. B. et al., "Laser effects on dental hard tissues," Adv. Dent. Res., 1(1):21-26 (1987).
Fikackova, H. et al., "Effectiveness of low-level laser therapy in temporomandibular joint disorders: A placebo-controlled study," Photomedicine and Laser Surgery, 25(4):297-303 (2007).
Fleming, P. S. et al., "Self-ligating appliances: evolution or revolution?," Australian Orthodontic Journal, 24(1):41-49 (2008).
Frost, H. M., "Wolff's Law and bone's structural adaptations to mechanical usage: an overview for clinicians," The Angle Orthodontist, 64(3):175-188 (1994).
Fujita, S. et al., "Low-energy laser stimulates tooth movement velocity via expression of RANK and RANKL," Orthod Craniofac Res, 11(3):143-155 (2008).
Fujiyama, K. et al., "Clinical effect of $CO_2$ laser in reducing pain in orthodontics," Angle Orthodontist, 78(2):299-303 (2008).
Ghamsari, S. M. et al., "Evaluation of low level laser therapy on primary healing of experimentally induced full thickness teat wounds in dairy cattle," Vet Surg., 26(2):114-120 (1997) (Abstract).
Gorur, I. et al., "Low-level laser therapy effects in traumatized permanent teeth with extrusive luxation in an orthodontic patient," Angle Orthod., 80(5):968-974 (2010).
Goulart, C. S. et al., "Photoradiation and orthodontic movement: experimental study with canines," Photomedicine and Laser Surgery, 24(2):192-196 (2006).
Gruppo, R. et al., "The pathophysiology of alveolar osteonecrosis of the jaw: anticardiolipin antibodies, thrombophilia, and hypofibrinolysis", J. Lab. Clin. Med., 127(5):481-488 (1996).
Guo, J. et al., "Visible red and infrared light alters gene expression in human marrow stromal fibroblast cells," Orthod. Craniofac. Res., 18(1):50-61 (2015).
Guzzardella, G. A. et al., "Laser stimulation on bone defect healing: an in vitro study," Lasers Med. Sci., 17(3):216-220 (2002).
Hamblin, M. R. et al., "Mechanisms of low level light therapy," Proc. of SPIE, vol. 6140, pp. 614001-1-614001-12 (2006).
Han, X. L. et al., "Expression of osteocalcin during surgically assisted rapid orthodontic tooth movement in beagle dogs," J. Oral Maxillofac. Surg., 66(12):2467-2475 (2008).
Hashimoto, F. et al., "Administration of osteocalcin accelerates orthodontic tooth movement induced by a closed coil spring in rats," European Journal of Orthodontics, 23(5):535-545 (2001).
Hashimoto, H., "Effect of micro-pulsed electricity on experimental tooth movement," The Journal of Japan Orthodontic Society, 49(4):352-361 (1990).

(56) References Cited

OTHER PUBLICATIONS

Hawkins, D. et al., "Effect of multiple exposures of low-level laser therapy on the cellular responses of wounded human skin fibroblasts," Photomedicine and Laser Surgery, 24(6):705-714 (2006).
Hita-Carrillo, C. et al., "Tooth-implant connection: A bibliographic review," Med. Oral Patol. Oral Cir. Bucal. Mar. 2010. 1;15 (2):e387-e394.
Hou, Y. et al., "Effects of IL-1 on experimental tooth movement in rabbits," Chin. J. Stomatol., 32(1):46-48 (1997) (with English Abstract).
Houreld, N. N. et al., "Irradiation at 830 nm stimulates nitric oxide production and inhibits pro-inflammatory cytokines in diabetic wounded fibroblast cells," Lasers in Surgery and Medicine, 42(6):494-502 (2010).
Hsieh, F. Y. et al., "Sample-size calculations for the Cox proportional hazards regression model with nonbinary covariates," Controlled Clinical Trials, 21(6):552-560 (2000).
Huang, T. H. et al., "Low-level laser effects on simulated orthodontic tension side periodontal ligament cells," Photomedicine and Laser Surgery, 31(2):72-77 (2013).
Iglesias-Linares, A. et al., "Corticotomy-assisted orthodontic enhancement by bone morphogenetic protein-2 administration," J. Oral Maxillofac. Surg., 70(2):e124-e132 (2012).
Iscan, D. et al., "Photobiostimulation of Gingival Fibroblast and Vascular Endothelial Cell Proliferation," Presented in Annual Meeting of Turkish Society of Orthodontics, Ankara, Turkey, Abstract (Oct. 26-30, 2014).
Iseri, H. et al., "Rapid canine retraction and orthodontic treatment with dentoalveolar distraction osteogenesis," Am. J. Orthod. Dentofacial Orthop., 127(5):533-541 (2005).
Jiang, R.-P. et al., "Root resorption before and after orthodontic treatment: a clinical study of contributory factors," Eur J Orthod., doi:10.1093/ejo/cjpl165 (2010), 5 pages.
Kaipatur, N. et al., "Effect of infrared radiation on mandible condylar growth in rats," IADR General Session, Miami, FL, 1 page, (2009).
Kang, N. et al., "Effect of alveolar surgery-aided rapid orthodontic tooth movement on bone formation," J. Sichuan Univ. (Med. Sci. Edi.), 37(2):254-257 (2006) (with English Abstract).
Kanzaki, H. et al., "Local RANKL gene transfer to the periodontal tissue accelerates orthodontic tooth movement," Gene Therapy, 13(8):678-685 (2006).
Karu, T. I. et al., "Exact action spectra for cellular responses relevant to phototherapy," Photomedicine and Laser Surgery, 23(4):355-361 (2005).
Karu, T. I. et al., "Absorption measurements of a cell monolayer relevant to phototherapy: reduction of cytochrome c oxidase under near IR radiation," Journal of Photochemistry and Photobiology B: Biology B1, 81(2):98-106 (2005).
Karu, T. I. et al., "Absorption measurements of cell monolayers relevant to mechanisms of laser phototherapy: reduction or oxidation of cytochrome c oxidase under laser radiation at 632.8nm," Photomedicine and Laser Surgery, 26(6):593-599 (2008).
Katchooi, M. et al., "Effect of supplemental vibration on orthodontic treatment with aligners: A randomized trial," American Journal of Orthodontics and Dentofacial Orthopedics, vol. 153, Issue 3 (Mar. 2018), pp. 336-346.
Kau, C. H., "A radiographic analysis of tooth morphology following the use of a novel cyclical force device in orthondontics," Head & Face Medicine, 7:14 (2011), 5 pages.
Kau, C. H., Biotechnology in Orthodontics, Dentistry, 2(5):e108 (2012).
Kau, C. H., "Orthodontics in the 21st century: a view from across the pond," Journal of Orthodontics, 39(2):75-76 (2012).
Kau, C. H. et al., "Photobiomodulation accelerates orthodontic alignment in the early phase of treatment," Progress in Orthodontics, 14:30 (2013), 9 pages.
Kau, C. H., "Creation of the virtual patient for the study of facial morphology," Facial Plast. Surg. Clin. N. Am., 19(4):615-622 (2011).

Kawakami, M. et al., "Local injection of 1,25-dihydroxyvitamin D3 enhanced bone formation for tooth stabilization after experimental tooth movement in rats," J Bone Miner Metab., 22(6):541-546 (2004).
Kawakami, M., "Effects of local application of 1,25 (OH)2D3 on experimental tooth movement in rats," Osaka Daigaku Shigaku Zasshi, 35(1):128-146 (1990) (English-language abstract).
Kawasaki, K. et al., "Effects of low-energy laser irradiation on bone remodeling during experimental tooth movement in rats," Lasers in Surgery and Medicine, 26(3):282-291 (2000).
Khadra, M. et al., "Effect of laser therapy on attachment, proliferation and differentiation of human osteoblast-like cells cultured in titanium implant material," Biomaterials, 26(17):3503-3509 (2005).
Khadra, M. et al., "Low-level laser therapy stimulates bone-implant interaction: an experimental study in rabbits," Clin. Oral Implants Res., 15(3):325-332 (2004).
Khadra, M. et al., "The effect of low level laser irradiation on implant-tissue interaction. In vivo and in vitro studies," Swed. Dent. J. Suppl., 172:1-63 (2005) (Abstract).
Khadra, M. et al., "Determining optimal dose of laser therapy for attachment and proliferation of human oral fibroblasts cultured on titanium implant material," Journal of Biomedical Materials Research, 73A(1):55-62 (2005).
Khadra, M. et al., "Enhancement of bone formation in rat calvarial bond defects using low-level laser therapy," Oral Surg. Oral Med. Oral Pathol. Oral Radial. Endod., 97(6):693-700 (2004).
Khadra, M. et al., "Laser therapy accelerates initial attachment and subsequent behaviour of human oral fibroblasts cultured on titanium implant material: a scanning electron microscopic and histomorphometric analysis," Clin. Oral Impl. Res., 16(2):168-175 (2005).
Kim, S-J et al., "Effects of low-level laser therapy after corticision on tooth movement and paradental remodeling," Lasers in Surgery and Medicine, 41(7):524-533 (2009).
Kim, Y-D et al., "Low-level laser irradiation facilitates fibronectin and collagen type I turnover during tooth movement in rats," Lasers Med. Sci., Springer-Verlag London Ltd. (2008), 7 pages.
Kim, Y. D. et al., "Low-level laser irradiation facilitates fibronectin and collagen type I turnover during tooth movement in rats," Lasers Med Sci., 25(1):25-31 (2010) (Published online: Jul. 4, 2008).
Kim, H. J. et al., "The Src family kinase, Lyn, suppresses osteoclastogenesis in vitro and in vivo," Proc Natl Acad Sci USA, 106(7):2325-2330 (2009).
Kreisler, M. et al., "Effect of low-level GaAlAs laser irradiation on the proliferation rate of human periodontal ligament fibroblasts: an in vitro study," J Clin Periodontol, 30(4):353-358 (2003) (Abstract).
Kreisler, M. et al., "Low level 809-nm diode laser-induced in vitro stimulation of the proliferation of human gingival fibroblasts," Lasers in Surgery and Medicine, 30(5):365-369 (2002).
Krishnan, V. et al., "Cellular, molecular, and tissue-level reactions to orthodontic force," Am. J. Orthod. Dentofacial Orthop., 129(4):469e.1-460e.32 (2006).
Krishnan, V. et al., "On a path to unfolding the biological mechanisms of orthodontic tooth movement.," Journal of Dental Research, 88(7):597-608 (2009).
Kucerova, H. et al., "Low-level laser therapy after molar extraction," Journal of Clinical Laser Medicine & Surgery, 18(6):309-315 (2000).
Kujawa, J. et al., "Effect of low-intensity (3.75-25 J/cm$^2$) near-infrared (810 nm) laser radiation on red blood cell ATPase activities and membrane structure," Journal of Clinical Laser Medicine & Surgery, 22(2):111-117 (2004).
Kvam, E., "Scanning electron microscopy of tissue changes on the pressure surface of human premolars following tooth movement," Scand. J. Dent. Res., 80(5):357-368 (1972).
Kwong-Hing, A. et al., "Accelerated implant stability in indirect sinus lifts with bone grafts using LED phototherapy," Shenzhen (2006), 1 page.
Lai, M. et al., "An evaluation of two-phase treatment with the herbst appliance and preadjusted edgewise therapy," Semin. Orthod., 4(1):46-58 (1998).
Lane, N., "Power games," Nature, 443(7114):901-903 (2006).

(56) References Cited

OTHER PUBLICATIONS

Le, A. et al., "Human Osteoblast Response to photobiomodulation," Presented at IADR 2014 General Session, Boston, MA, Abstract Final ID: 3448 (2014).
Leiker, B. J. et al., "The effects of exogenous prostaglandins on orthodontic tooth movement in rats," Am. J. Orthod. Dentofac. Orthop., 108(4):380-388 (1995).
Lim, H-M et al., "A clinical investigation of the efficacy of low level laser therapy in reducing orthodontic postadjustment pain," Am. J. Orthod. Dentofacial Orthop., 108(6):614-622 (1995).
Limpanichkul, W. et al., "Effects of low-level laser therapy on the rate of orthodontic tooth movement," Orthod. Craniofacial Res., 9(1):38-43 (2006).
Little, R. M., "The irregularity index: A quantitative score of mandibular anterior alignment," Am. J. Orthod., 68(5):554-563 (1975).
Lopes, C. B. et al., "Infrared laser light reduces loading time of dental implants: a Raman spectroscopic study," Photomedicine and Laser Surgery, 23(1):27-31 (2005).
Lu, H. et al., "Effect of sensitized lymphocytes on rabbit calvarial osteoblasts," Natl. Med. J. China, 81(7):429-431 (2001) (with English Abstract).
Luger, E. J. et al. "Effect of low-power laser irradiation on the mechanical properties of bone fracture healing in rats," Lasers in Surgery and Medicine, 22(2):97-102 (1998).
Lv, T. et al., "Biologic response of rapid tooth movement with periodontal ligament distraction," Am. J. Orthod. Dentofacial Orthop., 136(3):401-411 (2009).
Maegawa, Y. et al., "Effects of near-infrared low-level laser irradiation on microcirculation," Lasers in Surgery and Medicine, 27(5):427-437 (2000).
Marques, M. M. et al., "Effect of low-power laser irradiation on protein synthesis and ultrastructure of human gingival fibroblasts," Lasers in Surgery and Medicine, 34(3):260-265 (2004).
Mathews, D. P. et al., "Managing treatment for the orthodontic patients with periodontal problems," Seminars in Orthodontics, 3(1):21-38 (1997).
Meguro, D. et al., "Laser irradiation inhibition of open gingival embrasure space after orthodontic treatment," Aust Orthod J., 18(1):53-63 (2002).
Melsen, B., "Tissue reaction to orthodontic tooth movement—a new paradigm," Eur J Orthod., 23(6):671-681 (2001).
Mendez, T. M. et al., "Dose and wavelength of laser light have influence on the repair of cutaneous wounds," J Clin Laser Med Surg, 22(1):19-25 (2004) (Abstract).
Merli, L., "Effect of low-intensity laser irradiation on the process of bone repair," Photomedicine and Laser Surgery, 23(2):212-215 (2005).
Merriam-Webster, Incorporated, "Definition of the term sensor," Merriam-Webster's Collegiate Dictionary, Eleventh Edition, p. 1133 (2012).
Miles, P. et al., "Assessment of the rate of premolar extraction space closure in the maxillary arch with the AcceleDent Aura appliance vs no appliance in adolescents: A single-blind randomized clinical trial," American Journal of Orthodontics and Dentofacial Orthopedics, vol. 153, Issue 1 (Jan. 2018), pp. 8-14.
Miloro, M. et al., "Low-level laser effect on mandibular distraction osteogenesis," J. Oral Maxillofac. Surg., 65(2):168-176 (2007).
Moher, D. et al., "CONSORT 2010 Explanation and Elaboration: Updated guidelines for reporting parallel group randomised trial," BMJ, 340:c869 (2010), 28 pages.
Mognato, M. et al., "Cell growth modulation of human cells irradiated in vitro with low-level laser therapy," Photomed. Laser Surg., 22(6):523-526 (2004).
Moriyama, E. H. et al., "Dentin evaluation after Nd: YAG laser irradiation using short and long pulses," Journal of Clinical Laser Medicine & Surgery, 22(1):43-50 (2004).
Moriyama, Y. et al., "In vivo effects of low level laser therapy on inducible nitric oxide synthase," Lasers in Surgery and Medicine, 41(3):227-231 (2009).

Mosby's Dental Dictionary, Definition of Orthodontics, Elsevier Health Sciences, retrieved from the internet on Oct. 17, 2013, retrieved from: http://www.credoreference.com/entry/ehsdent/orthodontics (2008).
Murphy, K. G. et al., "Periodontal accelerated osteogenic orthodontics: a description of the surgical technique," J. Oral Maxillofac. Surg., 67(10):2160-2166 (2009).
Nicolau, R. A. et al., "Effect of low-power GaAlAs laser (660 nm) on bone structure and cell activity: an experimental animal study," Lasers Med. Sci., 18(2):89-94 (2003).
New Oxford American Dictionary, Definition of Promote, Third Edition, Oxford University Press, Oxford, New York, p. 1398 (2010).
Nimeri, G. et al., "The effect of photobiomodulation on root resorption during orthodontic treatment," Clinical, Cosmetic and Investigational Dentistry, 6:1-8 (2014).
Ninomiya, T. et al., "High-intensity pulsed laser irradiation accelerates bone formation in metaphyseal trabecular bone in rat femur," J. Bone Miner Metab., 21(2):67-73 (2003).
Ninomiya, T. et al., "Increase of bone vol. by a nanosecond pulsed laser irradiation is caused by a decreased osteoclast number and an activated osteoblasts," Bone, 40(1):140-148 (2007).
Nishimura, M. et al., "Periodontal tissue activation by vibration: intermittent stimulation by resonance vibration accelerates experimental tooth movement in rats," Am J Orthod Dentofacial Orthop., 133(4):572-583 (2008).
Nissan, J. et al., "Effect of low intensity laser irradiation on surgically created bony defects in rats," Journal of Oral Rehabilitation, 33(8):619-624 (2006).
O'Brien, K. et al., "Effectiveness of treatment for Class II malocclusion with the Herbst or Twin-block appliances: A randomized, controlled trial," Am. J. Orthod. Dentofacial Orthop., 124(2):128-137 (2003).
Ojima, K. et al., "Invisalign treatment accelerated by photobiomodulation," JCO, Inc., The Cutting Edge, vol. L, No. 5, pp. 309-317 (May 2016).
Ontiveros, J. C. et al., "Clinical evaluation of a chairside whitening lamp and bleaching efficacy," #1081, The University of Texas, Dental Branch at Houston (2008). Retrieved from the Internet on Oct. 14, 2009. <http://www.discusdental.com/files/University%20of%20Texas.pdf>, 1 page.
Oron, U. et al., "Ga—As (808 nm) laser irradiation enhances ATP production in human neuronal cells in culture," Photomedicine and Laser Surgery, 25(3):180-182 (2007).
Owman-Moll, P. et al., "The effects of a four-fold increased orthodontic force magnitude on tooth movement and root resorptions. An intra-individual study in adolescents," Eur J Orthod., 18(3):287-294 (1996).
Ozawa, Y. et al., "Low-energy laser irradiation stimulates bone nodule formation at early stages of cell culture in rat calvarial cells," Bone, 22(4):347-354 (1998) (Abstract).
Ozawa, Y. et al., "Low-energy laser irradiation stimulates bone nodule formation at early stages of cell culture in rat calvarial cells," Bone, 22(4):347-354 (1998).
Ozkan, N. et al., "Investigation of the supplementary effect of GaAs laser therapy on the rehabilitation of human digital flexor tendons," Journal of Clinical Laser Medicine & Surgery, 22(2):105-110 (2004).
Paetyangkul, A. et al., "Physical properties of root cementum: Part 14. The amount of root resorption after force application for 12 weeks on maxillary and mandibular premolars: a microcomputed-tomography study," Am J Orthod Dentofacial Orthop., 136(4):492.e1-492.e9 (2009).
Pancherz, H. et al., "Dentofacial orthopedics in relation to somatic maturation: An analysis of 70 consecutive cases treated with the Herbst appliance," American Journal of Orthodontics, 88(4):273-287 (1985).
Pancherz, H. et al., "Amount and direction of temporomandibular joint growth changes in Herbst treatment: a cephalometric long-term investigation," Angle Orthod., 73(5):493-501 (2003).
Pancherz, H. et al., "Occlusal changes during and after Herbst treatment: a cephalometric investigation," European Journal of Orthodontics, 8(4):215-228 (1986).

(56) References Cited

OTHER PUBLICATIONS

Pandis, N. et al., "External apical root resorption in patients treated with conventional and self-ligating brackets," American Journal of Orthodontics and Dentofacial Orthopedics, 134(5):646-651 (2008).
Pereira, A. N. et al., "Effect of low-power laser irradiation on cell growth and procollagen synthesis of cultured fibroblasts," Lasers in Surgery and Medicine, 31(4):263-267 (2002).
Pinheiro, A. L. et al., "Effect of 830-nm laser light on the repair of bone defects grafted with inorganic bovine bone and decalcified cortical osseus membrane," J Clin Laser Med Surg., 21(5):301-306 (2003) (Abstract).
Pinheiro, A. L. B. et al., "Photoengineering of bone repair processes," Photomedicine and Laser Surgery, 24(2):169-178 (2006).
Pope, N. J. et al., "Wavelength dependence of intracellular nitric oxide levels in hTERT-RPE cells in vitro", Proc. SPIE 10477, Mechanisms of Photobiomodulation Therapy XIII, 104770J (Feb. 8, 2018), 16 pages.
Pourzarandian, A. et al., "Effect of low-level Er: YAG laser irradiation on cultured human gingival fibroblasts," J. Periodontal, 76(2):187-193 (2005).
Pretel, H. et al., "Effect of low-level laser therapy on bone repair: Histological study in rats," Lasers Surg. Med, 39(10):788-796 (2007).
Proffit, W. R. et al., Excerpts from Chapters 14-17 In: Contemporary Orthodontics, Fourth Edition, Mosby-Elsevier 2007, pp. 551, 577, 602 and 617, 8 pages.
Proffit, W. R. et al., Excerpts from Chapter 8, The Biologic Basis of Orthodontic Therapy, In: Contemporary Orthodontics, Fifth Edition, Elsevier (2013), pp. 293-295, 6 pages.
Raghoebar, G. M. et al., "Does platelet-rich plasma promote remodeling of autologous bone grafts used for augmentation of the maxillary sinus floor?," Clin. Oral Impl. Res., 16(3):349-356 (2005).
Ren, A. et al., "Rapid orthodontic tooth movement aided by alveolar surgery in beagles," Am. J. Orthod. Dentofacial Orthop., 131(2):160.e1-160.e10 (2007).
Ren, Y. et al., "The rat as a model for orthodontic tooth movement—a critical review and a proposed solution," European Journal of Orthodontics, 26(5):483-490 (2004).
Renno, A. C. M. et al., "Effects of 830-nm Laser, used in two doses, on biomechanical properties of osteopenic rat femora," Photomedicine and Laser Surgery, 24(2):202-206 (2006).
Renno, A. C. M. et al., "The effects of infrared-830 nm laser on exercised osteopenic rats," Lasers Med. Sci., 21(4):202-207 (2006).
Ross, G. et al., "Photobiomodulation: An Invaluable Tool for All Dental Specialties," J. Laser Den., 17(3):117-124 (2009).
Rossouw, P. E., Chapter 7 in Orthodontics, "Orthodontic Appliances," Pocket Dentistry (online), Retrieved from the Internet on Oct. 27, 2017: URL: <https://pocketdentistry.com/7-orthodontic-appliances/>, Jan. 1, 2015, 6 pages.
Ruf, S. et al., "Temporomandibular joint growth adaptation in Herbst treatment: a prospective magnetic resonance imaging and cephalometric roentgenographic study," European Journal of Orthodontics, 20(4):375-388 (1998).
Rygh, P., "Ultrastructural cellular reactions in pressure zones of rat molar periodontium incident to orthodontic tooth movement," Acta Odontol Scand., 30(5):575-593 (1972).
Rygh, P., "Ultrastructural vascular changes in pressure zones of rat molar periodontium incident to orthodontic movement," Scand J Dent Res., 80(4):307-321 (1972).
Saito, S. et al., "Stimulatory effects of low-power laser irradiation on bone regeneration in midpalatal suture during expansion in the rat," Am J. Orthod. Dentofac. Orthop., 111(5):525-532 (1997).
Samara, S. A. et al., "Velocity of orthodontic active space closure with and without photobiomodulation therapy: a single-center, cluster randomized clinical trial," Lasers in Dental Science (Feb. 20, 2018) (https://doi.org/10.1007/s41547-018-0026-3), 10 pages.
Samoilova, K. A. et al., "Role of Nitric Oxide in the Visible Light-Induced Rapid Increase of Human Skin Microcirculation at the Local and Systemic Level: I. Diabetic Patients," Photomedicine and Laser Surgery, 26(5):433-442 (2008).

Samoilova, K. A. et al., "Role of Nitric Oxide in the Visible Light-Induced Rapid Increase of Human Skin Microcirculation at the Local and Systemic Levels: II. Healthy Volunteers," Photomedicine and Laser Surgery, 26(5):443-449 (2008).
Schindl, A. et al., "Direct stimulatory effect of low-intensity 670 nm laser irradiation on human endothelial cell proliferation," Br J Dermatol, 148(2):334-336 (2003) (Abstract).
Scott, P. et al., "Alignment efficiency of Damon3 self-ligating and conventional orthodontic bracket systems: a randomized clinical trial," American Journal of Orthodontics and Dentofacial Orthopedics, 134(4):470.e1-470.e8 (2008).
Schulz, K. F. et al., "CONSORT 2010 Statement: Updated guidelines for reporting parallel group randomized trials," Annals of Internal Medicine, 152(11):726-732 (2010).
Schulz, K. F. et al., "CONSORT 2010 Statement: Updated guidelines for reporting parallel group randomised trials," PLoS Medicine, 7(3): e1000251. doi:10.1371/journal.pmed.1000251 (2010), 7 pages.
Sebaoun, J. D. et al., "Modeling of trabecular bone and lamina dura following selective alveolar decortication in rats," J. Periodontol., 79(9):1679-1688 (2008).
Seifi, M. et al., "Effects of two types of low-level laser wave lengths (850 and 630 nm) on the orthodontic tooth movements in rabbits," Lasers Med. Sci., 22(4):261-264 (2007).
Seifi, M. et al., "The effect of 904 nm low level laser on condylar growth in rats," Laser Med Sci, 25(1):61-65 (2010).
Shankland, W. E., et al., "Medullary and odontogenic disease in the painful jaw: clinicopathologic review of 500 consecutive lesions," Journal of Craniomandibular Practice, 20(4):295-303 (2002).
Shaughnessy, T. G., "Long-Distance Orthodontic Treatment with Adjunctive Light Therapy," JCO, Inc., The Cutting Edge, vol. XLIX, No. 12, pp. 757-769 (Dec. 2015).
Shaughnessy, T. et al., "Intraoral photobiomodulation-induced orthodontic tooth alignment: a preliminary study," BMC Oral Health, 16:3 (2016), 9 pages.
Shimotoyodome, A. et al., "Improvement of macromolecular clearance via lymph flow in hamster gingiva by low-power carbon dioxide laser-irradiation," Lasers in Surgery and Medicine, 29(5):442-447 (2001).
Shirazi, M. et al., "The role of nitric oxide in orthodontic tooth movement in rats," Angle Orthod., 72(3):211-215 (2002).
Silva, A. N. et al., "Computerized morphometric assessment of the effect of low-level laser therapy on bone repair: an experimental animal study," Journal of Clinical Laser Medicine & Surgery, 20(2):83-87 (2002).
Sousa, M., "Influence of low-intensity laser on the rate of orthodontic movement," http://ibict.metodista.br/tedeSimplificado/tde_busca/arquivo.php?codArquivo=1145 (2008) (English Abstract).
Sousa, M. et al., "Influence of low-level laser on the speed of orthodontic movement," Photomedicine and Laser Surgery, 29(3):191-196 (2011).
Specialty Appliances Inc., Herbst Appliance Reference Manual, 1998 (available online http://www.specialtyappliances.com/files/pdfs/herbst_reference_manual.pdf), 12 pages.
Stadler, I. et al., "In vitro effects of low-level laser irradiation of 660 nm on peripheral blood lymphocytes," Lasers in Surgery and Medicine, 27(3):255-261 (2000).
Stein, A. et al., "Low-level laser irradiation promotes proliferation and differentiation of human osteoblasts in vitro," Photomedicine and Laser Surgery, 23(2):161-166 (2005).
Stephens, B. J., "How much 'useful' radiation does the sun deliver? Very Expensive Sunlight," Laser Therapy Products LLC (d/b/a K-Laser), K-Laser USA, URL: <http://www.k-laserusa.com/how-much-useful-radiation-does-the-sun-deliver/(retrieved on Dec. 7, 2012)>, (2012), 3 pages.
Stolik, S. et al., "Measurement of the penetration depths of red and near infrared light In human "ex vivo" tissues," J. Photochem. Photobiol. B, 57(2-3):90-93 (2000).
Sun, X. et al., "Effects of low energy laser on tooth movement and remodeling of alveolar bone in rabbits," School of Stomatology, Jilin University, 19(5):290-293 (2001) (English Abstract).

(56) References Cited

OTHER PUBLICATIONS

Takano-Yamamoto, T. et al., "Effect of age on the rate of tooth movement in combination with local use of 1,25(OH)$_2$D$_3$ and mechanical force in the rat," J. Dent. Res., 71(8):1487-1492 (1992).
Takano-Yamamoto, T. et al., "The effect of local application of 1,25-Dihydroxycholecalciferol on osteoclast numbers in orthodontically treated rats," J. Dent. Res., 71(1):53-59 (1992).
Takeda, Y., "Irradiation effect of low energy laser on alveolar bone after tooth extraction: experimental study in rats," International Journal of Oral Maxillofacial Surgery, 17(6):388-391 (1988).
Trelles, M. A. et al., "Red light-emitting diode (LED) therapy accelerates wound healing post-blepharoplasty and periocular laser ablative resurfacing," Journal of Cosmetic and Laser Therapy, 8(1):39-42 (2006).
Tuby, H. et al., "Low-level laser irradiation (LLLI) promotes proliferation of mesenchymal and cardiac stem cells in culture," Lasers Surg Med., 39(4):373-378 (2007).
Tuby, H. et al., "Long-term safety of low-level laser therapy at different power densities and single or multiple applications to the bone marrow in mice," Photomed. Laser Surg., 31(6):269-273 (2013).
Turhani, D. et al., "Pain relief by single low-level laser irradiation in orthodontic patients undergoing fixed appliance therapy," Am J Orthod Dentofacial Orthop., 130(3):371-377 (2006).
Ueda, Y. et al., "Effects of pulse frequency of low-level laser therapy (LLLT) on bone nodule formation in rat calvarial cells," J Clin Laser Med Surg., 21(5):271-277 (2003) (Abstract).
Ueda, Y. et al., "Pulse irradiation of low-power laser stimulates bone nodule formation," J Oral Sci., 43(1):55-60 (2001) (Abstract).
Uysal, T. et al., "Resonance frequency analysis of orthodontic miniscrews subjected to light-emitting diode photobiomodulation therapy," Eur. J. Orthod., 34(1):44-51 (2012) (Advance Access Publication: Dec. 27, 2010).
Verna, C. et al., "The rate and the type of orthodontic tooth movement is influenced by bone turnover in a rat model," European Journal of Orthodontics, 22(4):343-352 (2000).
Vinck, E. M. et al., "Increased fibroblast proliferation induced by light emitting diode and low power laser irradiation," Lasers Med. Sci., 18(2):95-99 (2003).
Wahab, R. M. A. et al., "Comparison of self- and conventional-ligating brackets in the alignment stage," European Journal of Orthodontics, doi:10.1093/ejo/cjq179 (2011), 6 pages.
Walsh, L. J., "The current status of low level laser therapy in dentistry. Part 1. Soft tissue applications," Australian Dental Journal, 42(4):247-254 (1997).
Walsh, L. J., "The current status of low level laser therapy in dentistry. Part 2. Hard tissue applications," Australian Dental Journal, 42(5):302-306 (1997).
Wang, X. et al., "Interplay between up-regulation of cytochrome-c-oxidase and hemoglobin oxygenation induced by near-infrared laser," Sci. Rep. 6, 30540; doi: 10.1038/srep30540 (2016).
Wataha, J. C. et al., "Blue light differentially modulates cell survival and growth," J. Dent. Res., 83(2):104-108 (2004).
Waynant, R. W. et al. (eds.), "Proceedings of Light Activated Tissue Regeneration and Therapy Conference," Lecture Notes in Electrical Engineering, Springer (2008), 32 pages.
Weber, J. B. B. et al., "Laser therapy improves healing of bone defects submitted to autologus bone graft," Photomedicine and Laser Surgery, 24(1):38-44 (2006).
Weltman, B. et al., "Root resorption associated with orthodontic tooth movement: a systematic review," Am J Orthod Dentofacial Orthop., 137(4):462-476 (2010).
Whelan, H. T. et al., "Effect of NASA light-emitting diode irradiation on molecular changes for wound healing in diabetic mice," J. Clin. Laser Med. Surg., 21(2):67-74 (2003).
Whelan, H. T. et al., "Effect of NASA light-emitting diode irradiation on wound healing," J. Clin. Laser Med. Surg., 19(6):305-314 (2001).
Wiechmann, D. et al., "Control of mandibular incisors with the combined Herbst and completely customized lingual appliance—a pilot study," Head & Face Medicine, 6:3 (2010), 4 pages.
Wilcko, M. T. et al., "Full-thickness flap/subepithelial connective tissue grafting with Intramarrow penetrations: three case reports of lingual root coverage," Int. J. Periodontics Restorative Dent., 25(6):561-569 (2005).
Wilcko, W. M. et al., "Rapid orthodontics with alveolar reshaping: two case reports of decrowding," Int. J. Periodontics Restorative Dent., 21(1):9-19 (2001).
Wong-Riley, M. T. et al., "Photobiomodulation directly benefits primary neurons functionally inactivated by toxins: role of cytochrome c oxidase", The Journal of Biological Chemistry, 280(6):4761-4771 (2005).
Wong-Riley, M. T. et al., "Light-emitting diode treatment reverses the effect of TTX on cytochrome oxidase in neurons," NeuroReport, 12(14):3033-3037 (2001).
Yaakobi, T. et al., "Promotion of bone repair in the cortical bone of the tibia in rats by low energy laser (He—Ne) irradiation," Calcif Tissue Int., 59(4):297-300 (1996) (Abstract).
Yamada, K., "Biological effects of low power laser irradiation on clonal osteoblastic cells (MC3T3-E1)," J. Japan Orthop. Assoc., 65(9):787-799 (1991).
Yamaguchi, M. et al., "Low-energy laser irradiation facilitates the velocity of tooth movement and the expressions of matrix metalloproteinase-9, cathepsin K, and alpha(v) beta(3) integrin in rats," Eur. J. Orthod., 32(2):131-139 (2010).
Yamaguchi, M. et al., "Low-energy laser irradiation stimulates the tooth movement velocity via expression of M-CSF and c-fms," Orthodontic Waves, 66(4):139-148 (2007).
Yamasaki, K. et al., "Prostaglandin as a mediator of bone resorption induced by experimental tooth movement in rats," J. Dent. Res., 59(10):1635-1642 (1980).
Yen, S. et al., "Deregulation of specific sets of genes detected by microarray analysis of marrow stromal fibroblast cells stimulated by IR and VR light," Journal of Oral and Maxillofacial Surgery, 70(9, Supplement 2):e28 (2012).
Ying, R. et al., "Pretreatment with near-infrared light via light-emitting diode provides added benefit against rotenone- and MPP$^+$-induced neurotoxicity," Brain Research, 1243:167-173 (2008).
Yoshida, T. et al., "Low-energy laser irradiation accelerates the velocity of tooth movement via stimulation of the alveolar bone remodeling," Orthodontics & Craniofacial Research, 12(4):289-298 (2009).
Youssef, M. et al., "The effect of low-level laser therapy during orthodontic movement: a preliminary study," Lasers Med. Sci., 23(1):27-33 (2008).
Zhang, H. et al., "Low level laser irradiation precondition to create friendly milieu of infarcted myocardium and enhance early survival of transplanted bone marrow cells," J. Cell Mol. Med., 14(7):1975-1987 (2010).
Zhang, R. et al., "Near infrared light protects cardiomyocytes from hypoxia and reoxygenation injury by a nitric oxide dependent mechanism," J. Mol. Cell Cardiol., 46(1):4-14 (2009), NIH-PA Author Manuscript.
Zhu, X. et al., "A study on expression of basic fibroblast growth factors in periodontal tissue following orthodontic tooth movement associated with low power laser irradiation," Department of Orthodontics, School for Stomatology, Jilin University, 20(3):166-168 (2002) (English Abstract).
Zou, J., "Impact of photobiomodulation on orthodontic treatment of teeth with reduced periodontal support," Boston Latin School, Class of 2016, Department of Applied Oral Sciences, The Forsyth Institute, Cambridge, MA, Presented on Sep. 22, 2015, 1 page.
Office Action for U.S. Appl. No. 15/651,852, mailed Jan. 24, 2019, 13 pages.
Office Action for U.S. Appl. No. 15/858,373, mailed Dec. 26, 2018, 21 pages.
Office Action for U.S. Appl. No. 15/858,533, mailed Dec. 17, 2018, 11 pages.
International Search Report and Written Opinion for International Application No. PCT/CA2018/051169, mailed Dec. 17, 2018, 10 pages.

(56) References Cited

OTHER PUBLICATIONS

Office Action for U.S. Appl. No. 15/676,422, mailed Feb. 8, 2019, 12 pages.

Office Action for U.S. Appl. No. 15/856,831, mailed Apr. 26, 2019, 14 pages.

Hailan, F. et al. (eds.), "Guidance for Stomatology," Textbook of Stomatology, 2nd Edition, Peking University, Beijing Medical University, China Union Medical College, United Press (2002), 10 pages.

Office Action for U.S. Appl. No. 15/858,533, mailed Jul. 25, 2019, 12 pages.

Costa da Mota, A. C. et al., "Effect of photodynamic therapy for the treatment of halitosis in adolescents—a controlled, microbiological, clinical trial," Journal of Biophotonics, vol. 9, Issue 11-12, Dec. 2016, pp. 1337-1343.

De Paula Eduardo, C. et al., "Laser phototherapy in the treatment of periodontal disease. A review," Lasers in Medical Science, vol. 25, Issue 6, Nov. 2010, pp. 781-792.

Ekizer, A. et al., "Light emitting diode mediated photobiomodulation therapy improves orthodontic tooth movement and miniscrew stability: A randomized controlled clinical trial," Lasers in Surgery and Medicine, vol. 48, Issue 10, Dec. 2016, pp. 936-943.

Esper, M. A. L. R. et al., "The effect of two phototherapy protocols on pain control in orthodontic procedure—a preliminary clinical study," Lasers in Medical Science, vol. 26, Issue 5, Sep. 2011, pp. 657-663.

Garcia-Delaney, C. et al., "Evaluation of the effectiveness of the photobiomodulation in the treatment of dentin hypersensitivity after basic therapy. A randomized clinical trial," J. Clin. Exp. Dent., vol. 9, Issue 5, May 2017, pp. e694-e702.

Khosraviani, F. et al., "Therapeutic effect of laser on pediatric oral soft tissue problems: a systematic literature review." Lasers in Medical Science, 2019, vol. 34, pp. 1735-1746, https://doi.org/10.1007/s10103-019-02834-0.

Kulkarni, S. et al., "Efficacy of photobiomodulation on accelerating bone healing after tooth extraction: a systematic review," Lasers in Medical Science, vol. 34, Issue 4, Jun. 2019, pp. 685-692.

Lang-Bicudo, L. et al., "LED Phototherapy to Prevent Mucositis: A Case Report," Photomedicine and Laser Surgery, vol. 26, No. 6, Dec. 2008, pp. 609-613.

Lins de Sousa, D. et al., "Effect of Twice-Daily Blue Light Treatment on Matrix-Rich Biofilm Development," PLoS ONE, 10(7):e0131941 (Jul. 2015).

Lizarelli, R. F. Z. et al., "Dentin hypersensitivity clinical study comparing LILT and LEDT keeping the same irradiation parameters," Laser Methods in Chemistry, vol. 7, Issue 11, Nov. 2010, pp. 805-811.

Oxford Pocket American Dictionary of Current English, Oxford University Press, Oxford, New York, p. 614 (2002).

Pejcic, A. et al., "The Effects of Low Level Laser Irradiation on Gingival Inflammation," Photomedicine and Laser Surgery, vol. 28, No. 1, Feb. 2010, pp. 69-74.

Rosa, C. B. et al., "Laser and LED phototherapy on midpalatal suture after rapid maxilla expansion: Raman and histological analysis," Lasers in Medical Science, vol. 32, Issue 2, Feb. 2017, pp. 263-274.

Stein, S. et al., "Influence of Photobiomodulation Therapy on Gingivitis Induced by Multi-Bracket Appliances: A Split-Mouth Randomized Controlled Trial," Photomedicine and Laser Surgery, vol. 36, No. 8, Aug. 2018, pp. 399-405.

Wang, Y. et al., "Antimicrobial blue light inactivation of pathogenic microbes: state of the art," Drug. Resist. Update, Nov. 2017, 33-35:1-22. doi:10.1016/j.drup.2017.10.002.

Yang, H. et al., "Comparative Study of 660 and 830 nm Photobiomodulation in Promoting Orthodontic Tooth Movement," Photobiomodulation, Photomedicine, and Laser Surgery, vol. 37, No. 6, Jun. 2019, pp. 349-355.

Office Action for U.S. Appl. No. 16/230,752, mailed Jun. 12, 2020, 13 pages.

Office Action for U.S. Appl. No. 15/651,852, mailed May 15, 2020, 7 pages.

Office Action for U.S. Appl. No. 16/135,842, mailed Oct. 15, 2020, 14 pages.

Declaration of Non-Establishment of International Search Report and Written Opinion for International Application No. PCT/US2019/063197, mailed Feb. 10, 2020, 9 pages.

Prototype Shipments List, Oct. 2, 2014 (redacted), 1 page.

\* cited by examiner

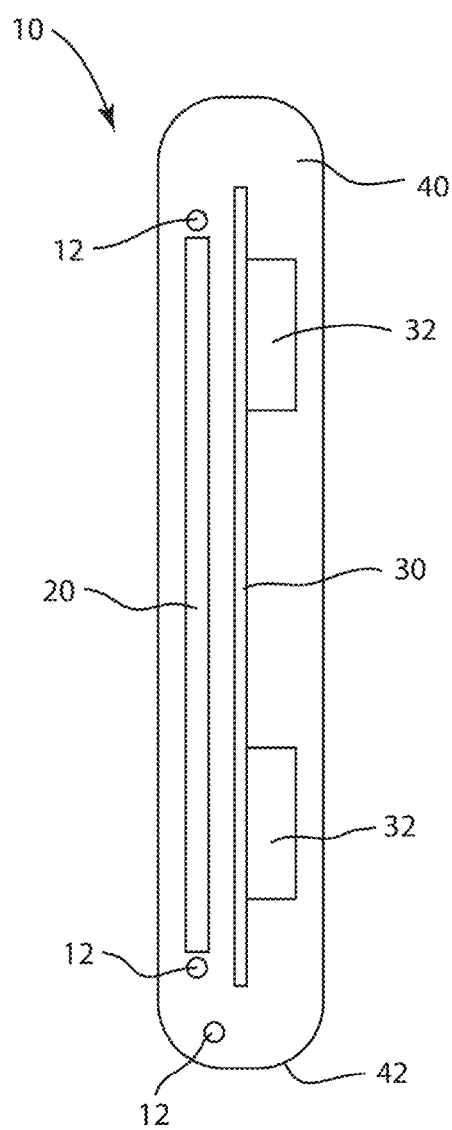
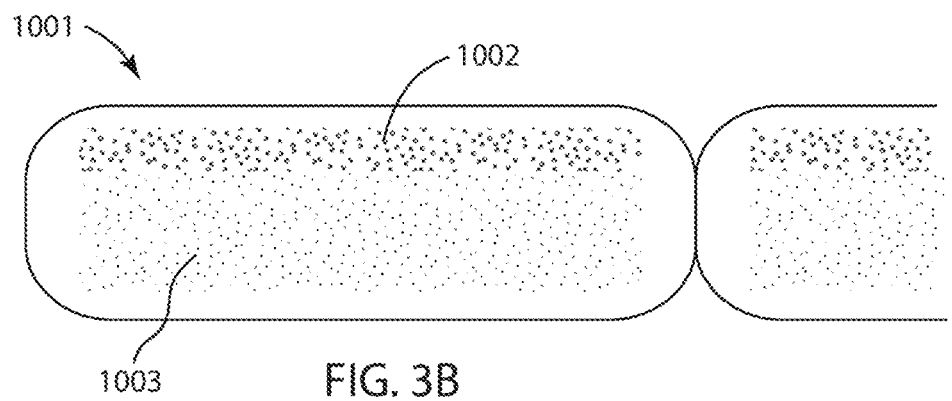
FIG. 3A
FIG. 3B

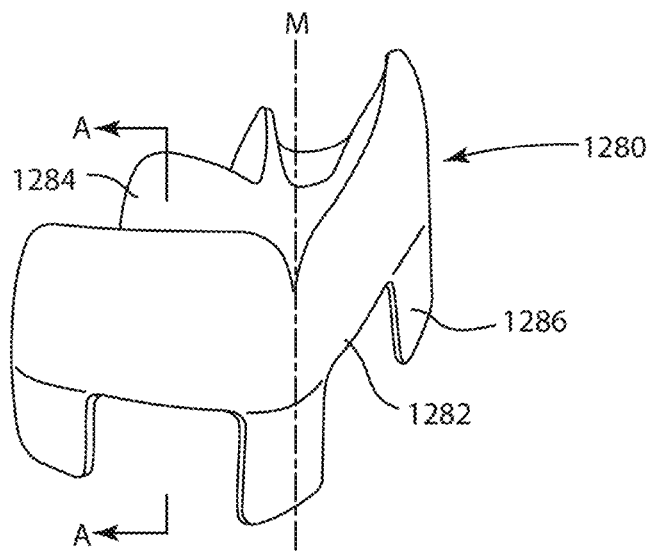
FIG. 20
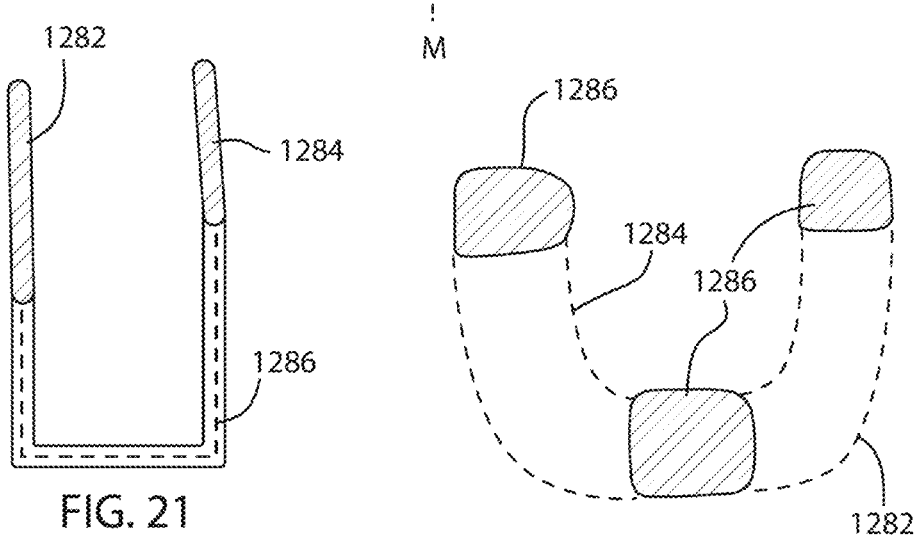
FIG. 21
FIG. 22
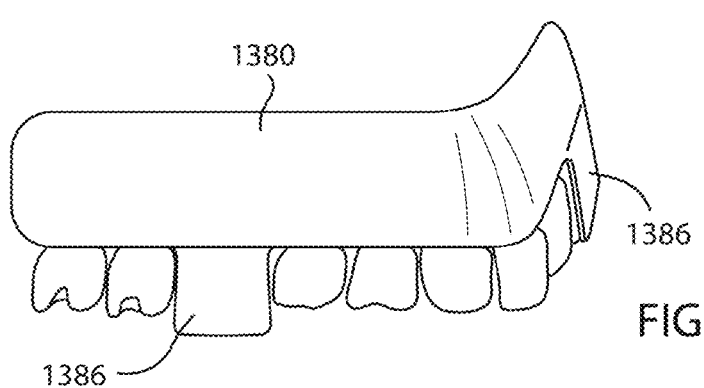
FIG. 23

4100

```
┌─────────────────────────────────────────────────────────────────────┐
│ Receiving a first indication associated with contact between an     │──── 4110
│ orthodontic appliance and a tissue within an oral cavity of a patient│
└─────────────────────────────────────────────────────────────────────┘
                                  │
┌─────────────────────────────────────────────────────────────────────┐
│ Optionally, receiving a second indication associated with contact    │──── 4120
│ between a second orthodontic appliance and the tissue within the     │
│ oral cavity of the patient                                           │
└─────────────────────────────────────────────────────────────────────┘
                                  │
┌─────────────────────────────────────────────────────────────────────┐
│ Determining a treatment period associated with each orthodontic      │──── 4130
│ appliance from a plurality of orthodontic appliances based on the    │
│ first indication and, optionally, the second indication              │
└─────────────────────────────────────────────────────────────────────┘
                                  │
┌─────────────────────────────────────────────────────────────────────┐
│ Producing a first signal associated with the treatment period        │──── 4140
└─────────────────────────────────────────────────────────────────────┘
                                  │
┌─────────────────────────────────────────────────────────────────────┐
│ Optionally, determining a total treatment duration associated with   │──── 4150
│ the plurality of orthodontic appliances based on at least the first  │
│ indication                                                           │
└─────────────────────────────────────────────────────────────────────┘
                                  │
┌─────────────────────────────────────────────────────────────────────┐
│ Optionally, producing a second signal associated with the total      │──── 4160
│ treatment duration                                                   │
└─────────────────────────────────────────────────────────────────────┘
```

| \multicolumn{4}{c}{Control Group Individual Patient Data} ||||
| Patient Identification No. | Tooth No. | Total Space T1 (mm) | Total Space T2 (mm) | Space Closure Time (days) |
| --- | --- | --- | --- | --- |
| 1 | 24 | 2.92 | 2.25 | 188 |
| 2 | 14 | 7.56 | 2.1 | 140 |
| 2 | 24 | 7.59 | 2.17 | 140 |
| 3 | 25 | 3.3 | 0.97 | 315 |
| 4 | 45 | 5.08 | 0.89 | 189 |
| 5 | 35 | 5.52 | 0.5 | 220 |
| 5 | 45 | 5.29 | 0.39 | 220 |
| 6 | 14 | 3.85 | 0 | 71 |
| 6 | 24 | 3.32 | 0 | 71 |
| 6 | 34 | 6.53 | 2.22 | 126 |
| 6 | 44 | 4.78 | 1.26 | 126 |
| 7 | 14 | 5.56 | 1.42 | 75 |
| 7 | 24 | 5.33 | 0.99 | 75 |
| 8 | 45 | 5.58 | 2.27 | 186 |
| 10 | 14 | 5.34 | 1.33 | 176 |
| 10 | 44 | 3.48 | 1.15 | 160 |
| 11 | 35 | 4.1 | 0.57 | 82 |
| 11 | 45 | 2.44 | 1.05 | 42 |
| 12 | 24 | 3.05 | 1 | 127 |
| 13 | 34 | 7.21 | 1.26 | 259 |
| 13 | 44 | 5.23 | 1 | 200 |
| 14 | 14 | 6.79 | 0.52 | 155 |
| 14 | 24 | 5.49 | 1.44 | 196 |
| 14 | 35 | 6.21 | 1.07 | 224 |
| 14 | 45 | 4.82 | 0.96 | 128 |
| 15 | 14 | 6.2 | 1.49 | 207 |
| 15 | 24 | 7.24 | 1.86 | 207 |
| 15 | 35 | 7.68 | 2.77 | 207 |
| 15 | 45 | 6.34 | 1.73 | 207 |
| 16 | 14 | 4.77 | 0.73 | 158 |
| 16 | 24 | 6.23 | 1.6 | 221 |
| 16 | 34 | 2.73 | 0.76 | 112 |
| 16 | 44 | 4.83 | 0.88 | 158 |

FIG. 114A

| Control Group Individual Patient Data (continued) | | | | |
|---|---|---|---|---|
| Patient Identification No. | Tooth No. | Total Space T1 (mm) | Total Space T2 (mm) | Space Closure Time (days) |
| 18 | 35 | 7.38 | 1.99 | 122 |
| | 45 | 4.9 | 0.84 | 98 |
| 20 | 14 | 3.19 | 1.46 | 58 |
| | 34 | 3.28 | 1.55 | 58 |
| | 44 | 3 | 1.31 | 44 |
| 22 | 14 | 7.35 | 2.28 | 128 |
| | 35 | 5.18 | 1.84 | 169 |
| | 45 | 5.93 | 2.05 | 169 |
| 24 | 14 | 7.85 | 4.59 | 230 |
| | 24 | 7.68 | 2.49 | 230 |
| | 34 | 6.52 | 1.96 | 230 |
| | 44 | 6.45 | 3.03 | 230 |
| 28 | 14 | 5.84 | 3.33 | 179 |
| | 24 | 6.98 | 1.8 | 179 |
| | 34 | 5.28 | 2.99 | 179 |
| | 44 | 5.9 | 2.47 | 179 |
| 29 | 14 | 6.65 | 2.9 | 155 |
| | 24 | 7.52 | 5.01 | 155 |
| 30 | 14 | 5.9 | 1.73 | 70 |
| | 35 | 4.85 | 2.41 | 101 |
| | 45 | 5.18 | 2.58 | 101 |

FIG. 114B

| Intra-Oral Group Individual Patient Data ||||
| Patient Identification No. | Tooth No. | Total Space T1 (mm) | Total Space T2 (mm) | Space Closure Time (days) |
|---|---|---|---|---|
| 32 | 14 | 1.9 | 0 | 43 |
| | 24 | 5.28 | 1.13 | 84 |
| | 34 | 2.89 | 0.37 | 84 |
| | 44 | 3.81 | 0.84 | 84 |
| 33 | 15 | 3.96 | 0.43 | 166 |
| | 25 | 4.25 | 1.14 | 166 |
| 34 | 14 | 5.31 | 1.54 | 71 |
| | 24 | 3.56 | 1.76 | 71 |
| | 35 | 5.38 | 0.96 | 138 |
| | 45 | 5.69 | 2.78 | 138 |
| 36 | 34 | 4.5 | 2.28 | 81 |
| | 44 | 6.11 | 2.02 | 137 |
| 37 | 14 | 6.17 | 1.54 | 153 |
| | 24 | 5.58 | 1.29 | 90 |
| | 45 | 4.91 | 0.94 | 90 |
| 38 | 24 | 3.71 | 1.21 | 109 |
| | 44 | 3.93 | 1.59 | 109 |
| 39 | 14 | 6.1 | 3.24 | 137 |
| | 24 | 4.88 | 1.47 | 137 |
| | 35 | 3.67 | 0.5 | 137 |
| | 45 | 4.6 | 1.58 | 137 |
| 40 | 14 | 2.865 | 0.8 | 28 |
| | 24 | 4.82 | 1.45 | 45 |
| | 35 | 7.13 | 1.91 | 112 |
| | 45 | 6.54 | 2.03 | 112 |
| 41 | 14 | 2.87 | 0.4 | 112 |
| 43 | 15 | 6.68 | 0.95 | 166 |
| | 25 | 7.8 | 1.73 | 166 |
| | 35 | 8.51 | 2.48 | 207 |
| | 45 | 7.51 | 0.79 | 207 |
| 44 | 34 | 4.29 | 2.26 | 116 |
| | 44 | 6.07 | 3.27 | 116 |
| 45 | 25 | 4.69 | 1.58 | 114 |
| | 35 | 4.83 | 1.85 | 185 |
| 46 | 15 | 4.22 | 0.83 | 112 |
| | 25 | 5.83 | 1.5 | 112 |
| | 34 | 4.91 | 1.29 | 112 |
| | 44 | 5.5 | 1.23 | 112 |
| 47 | 14 | 6.93 | 2.57 | 56 |
| | 24 | 7.8 | 2.57 | 56 |
| | 35 | 7.2 | 1.45 | 125 |
| | 45 | 6.93 | 0.5 | 125 |

FIG. 115A

| \multicolumn{5}{c}{Intra-Oral Group Individual Patient Data (continued)} |
|---|---|---|---|---|
| Patient Identification No. | Tooth No. | Total Space T1 (mm) | Total Space T2 (mm) | Space Closure Time (days) |
| 48 | 14 | 6.93 | 1.23 | 168 |
|  | 24 | 6.23 | 2.75 | 84 |
|  | 35 | 7.28 | 1.56 | 183 |
|  | 45 | 6.04 | 1.72 | 140 |
| 49 | 34 | 5.13 | 1.23 | 70 |
|  | 44 | 3.84 | 1.116 | 70 |
| 51 | 14 | 2.7 | 1.21 | 28 |
|  | 24 | 5.76 | 2.76 | 42 |
|  | 34 | 5.74 | 1.74 | 96 |
|  | 44 | 3.81 | 1.07 | 72 |
| 52 | 35 | 4.17 | 2.98 | 84 |
|  | 45 | 6.25 | 3.87 | 84 |
| 53 | 15 | 7.42 | 2.82 | 238 |
|  | 25 | 7.15 | 3.87 | 238 |
|  | 35 | 7.82 | 4.42 | 238 |
|  | 45 | 7.58 | 2.38 | 238 |
| 55 | 14 | 6.23 | 2.22 | 84 |
|  | 24 | 5.14 | 1.43 | 84 |
|  | 45 | 4.83 | 1.38 | 84 |
| 56 | 35 | 7.48 | 1.49 | 111 |
|  | 45 | 8.53 | 2.84 | 111 |
| 59 | 35 | 5.71 | 4.39 | 56 |
|  | 45 | 4.36 | 2.92 | 56 |
| 60 | 14 | 6.38 | 2.83 | 187 |
|  | 24 | 6.77 | 3.87 | 187 |

FIG. 115B

INTRA-ORAL LIGHT-THERAPY APPARATUSES AND METHODS FOR THEIR USE

CROSS REFERENCE TO RELATED APPLICATIONS

This application is a continuation of U.S. patent application Ser. No. 15/858,533, entitled "Intra-Oral Light-Therapy Apparatuses and Methods for Their Use," filed on Dec. 29, 2017, which is a continuation of U.S. patent application Ser. No. 15/676,422, entitled "Intra-Oral Light-Therapy Apparatuses and Methods for Their Use," filed on Aug. 14, 2017, which is a continuation of U.S. patent application Ser. No. 14/521,121, entitled "Intra-Oral Light-Therapy Apparatuses and Methods for Their Use," filed on Oct. 22, 2014, (now U.S. Pat. No. 9,730,780), which claims the benefit of U.S. Provisional Application Nos. 61/894,404, filed Oct. 22, 2013, 61/984,667, filed Apr. 25, 2014, and 62/045,439, filed Sep. 3, 2014, the disclosure of each of which is incorporated by reference herein in its entirety.

BACKGROUND

The invention relates generally to intra-oral light therapy apparatuses and methods for using the same, including methods for regulating and/or facilitating orthodontic tooth movement.

Orthodontics involves the movement of teeth through bone. By applying pressure to a tooth, bone can be broken down at a leading edge of the tooth to facilitate tooth movement. New bone is then created at a trailing edge of the tooth. Bone is resorbed in (e.g., broken down) in areas of pressure between a tooth root and periodontium, and bone is deposited (created) in areas of tension between a tooth root and periodontium. Pressure can cause resorption and tension can cause deposition regardless of where they occur along a tooth root surface. Movement of teeth through bone is slow based on the speed of the remodeling process while teeth are undergoing conventional orthodontic treatment, thereby necessitating treatments of long duration in order to achieve the desired tooth position. Tooth movement in adults is slower than tooth movement in adolescents. Long-term orthodontic treatment can have an increased risk of root resorption, gingival inflammation and dental caries. Moreover, movement of teeth through bone can be uneven, as teeth might "tip" due to the force applied, i.e., the crown of the tooth can move in the desired direction more quickly than the root of the tooth, resulting in tipped movement of the tooth. When teeth move "bodily" through the bone, i.e., in a more or less perpendicular orientation relative to the bone, the teeth move without tipped movement or with only a low degree of tipped movement.

Methods for increasing the rate of tooth movement without damage to the tooth and periodontium have been sought. For example, acceleration of tooth movement can be achieved by the local injection of prostaglandin, the active form of vitamin D3, and osteocalcin around the alveolar socket. These substances might increase the rate of tooth movement, but might also cause side effects such as local pain and discomfort for a patient during the process of injection. An alternative strategy for increasing the rate of tooth movement is to improve bone regeneration. For example, light therapy has been found to be effective in the treatment of bone disorders and the biostimulation of bone and soft tissue, and can be effective in accelerating alveolar bone regeneration. Light can stimulate a variety of biological activities in cells and tissues that are compromised in function, for example, by stimulating cytochrome C oxidase or nitric oxide synthase.

Known phototherapy or light therapy treatments are typically administered by a dentist, orthodontist, physician or therapist who directs light from a hand-held light emitting apparatus at an affected area. Known light emitting apparatuses can be difficult to position consistently over the affected area. Thus, known methods for light therapy are often administered by a practitioner in a clinical setting. This also allows for the practitioner to manually address compliance and safety concerns. For example, by performing the light therapy in a clinical setting, the practitioner can supervise a patient's compliance with a prescribed light therapy treatment program. Even with such manual supervision, however, the likelihood still exists that a patient may skip a scheduled or prescribed treatment session or fail to maintain a log documenting the therapeutic sessions. Thus, the practitioner prescribing the treatment program may be unable to accurately assess whether the patient is benefitting from use of the light emitting apparatus.

Additionally, the use of known devices for light therapy can present other complications and/or risks associated with emitting light when not being directed to the affected area. For example, light directed to a different part of the patient's anatomy (e.g., the eyes) potentially may be harmful. Moreover, the temperature of a light emitting apparatus may exceed a desired temperature threshold, thus subjecting the patient to potential harm. More particularly, various regulations and/or industry standards have been promulgated to address safety concerns, including concerns related to excessive temperature, for light emitting apparatuses. For example, the International Electrotechnical Commission ("IEC") has promulgated Standards No. 60601, which sets forth general basic safety and performance requirements for medical electrical equipment. More specifically, IEC Standards No. 60601-2-57 sets forth safety and performance requirements for light source equipment intended for therapeutic and other uses, and IEC Standards No. 60601-1-11 sets forth requirements for medical electrical equipment and systems used in the home environment. In another example, the IEC has promulgated Standards No. 62471, which addresses the photobiological safety of lamps and lamp systems. The compliance with these, and any other applicable standards, can present challenges for known methods and systems for light therapy.

Additionally, intra-oral light therapy typically involves repeated treatments over at least several days. Accordingly, known methods for intra-oral light therapy involves patients undergoing the light therapy to make multiple visits to a practitioner's office or clinic in order to complete a therapy regimen. Such repeated visits can be time consuming or expensive Furthermore, in a recent study, more than 65% of the subjects in North America were shown to be deficient vitamin D serum levels. In these vitamin D-deficient subjects, bone metabolism and remodeling can be adversely affected.

Thus, a need exists for methods and apparatuses that are useful for increasing the velocity (or rate) or improving the quality of tooth movement through bone in response to orthodontic treatment, to decrease treatment times for patients without undesirable side effects or pain. There is also a need for methods and apparatuses that can be used to achieve a desired mode or quality of movement of teeth through the bone, e.g., bodily movement of teeth through bone, using intra-orally administered light therapy that permits tooth movement to be modulated at a desired specific location or locations within a patient's mouth without undue difficulty. A need also exits for methods and apparatuses that can be used to administer light therapy in a home environment that monitor patient compliance with a prescribed treatment program. A need further exists for methods and apparatuses configured to address patient safety concerns associated with self-administration of light therapy in a home environment, including ensuring compliance of the apparatuses with applicable safety and performance regulations and/or standards.

Additionally, some known orthodontic treatment regimens include wearing each of a set of orthodontic appliances, such as custom-made aligners, in a predetermined sequence, each for a period of time. Known methods for treatment using such aligners often specify a fixed time period during (e.g., six days) during which each aligner should be worn. Known methods do not provide a method for employing a time period that is associated with the specific patient (i.e., that takes into account the patient's specific rate of tooth movement). Moreover, known methods for treatment using aligners do not include light therapy. Thus, a need exists for improved methods and apparatus for determining a period of time during which an orthodontic appliance should be worn.

SUMMARY

The invention provides light therapy apparatuses comprising: a mouthpiece disposable within a mouth of a subject, the mouthpiece comprising: a bite tray; a first inner flange and a second inner flange coupled to a first side of the bite tray, the first inner flange and the second inner flange each comprising a plurality of light emitters; and an outer flange coupled to a second side of the bite tray, the outer flange comprising a plurality of light emitters, wherein the first inner flange and the second inner flange are independently deflectable.

The apparatuses are useful for regulating tooth movement or for maintaining or improving oral tissue health.

The system is useful for administering light therapy to alveolar soft tissue of a patient.

BRIEF DESCRIPTION OF THE DRAWINGS

FIG. 3A is a sectional view of the apparatus of FIG. 1, taken along line X-X.

FIG. 3B is a side view of a portion of an intra-oral light-therapy apparatus according to an embodiment of the invention.

FIG. 20 is a perspective view of an intra-oral light-therapy apparatus according to an embodiment of the invention.

FIG. 21 is a sectional view of the apparatus of FIG. 20 taken along line A-A.

FIG. 22 is a bottom view of the apparatus of FIG. 20.

FIG. 23 is a side view of an intra-oral light-therapy apparatus according to an embodiment of the invention in use within an oral cavity.

FIG. 112 is a flow chart of a method according to an embodiment.

FIG. 113 is an image of a sample display screen of an external electronic device according to an embodiment.

FIGS. 114A, 114B and 115A, 115B are tables of individual patient data during a space closure phase of orthodontic treatment for study group participants.

DETAILED DESCRIPTION

Figure 1:
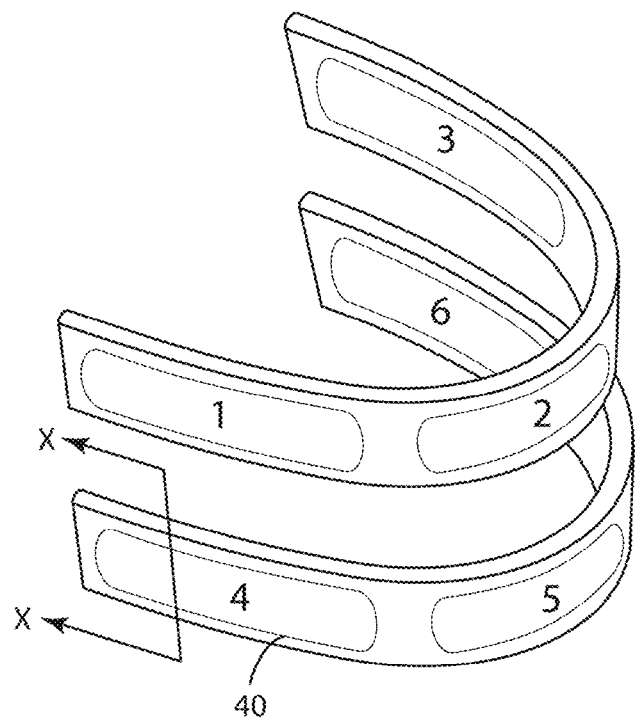
FIGS. 1 and 2 are perspective views of intra-oral light-therapy apparatuses according to an embodiment of the invention.

The term "about" as used herein in connection with a referenced numeric indication means the referenced numeric indication plus or minus up to 10% of that referenced numeric indication. For example, the language "about 50" units means from 45 units to 55 units.

The verb "surround" as used herein means to be within about one (1) centimeter of a target object. For example, oral tissue that surrounds a tooth is within about 1 cm of the tooth. In some embodiments, the methods disclosed herein are useful for preventing or minimizing inflammation that is within about 1 cm of a tooth.

The term "patient" as used herein refers to any living subject that can receive medical, including orthodontic, treatment. A patient can be, for example, a mammal such as a human. The patient can be an adult patient or a child patient. In some embodiments, the patient can be a living subject that receives light treatment, e.g., light administered to the patient intra-orally using an intra-oral apparatus described herein.

The term "root area" as used herein refers to a portion of a patient's anatomy that includes the anatomic length and width of a tooth root, as well as at least a portion of peripheral tissue that facilitates attachment of the tooth to the alveolar bone within which the tooth sits. The peripheral tissue can include the periodontal ligament and the boney socket in which the periodontal ligament is disposed and which surround the tooth. The root area can include tissue extending from the gum line to a depth of about 10 mm to about 22 mm, depending on the type of tooth. The root area can also include an area within a particular distance (e.g., within about 0.1 cm to about 3 cm) of the root area of each tooth, unless the context clearly indicates otherwise. The dimensions of a root area can vary depending on the particular subject tooth. References to the root area herein can include at least a portion of the root area or the entirety of the root area, unless the context clearly indicates otherwise.

As used herein, the term "flexibility" relates to an object's resistance to deflection, deformation, and/or displacement by an applied force. For example, a mouthpiece or oral structure with greater flexibility is less resistant to deflection, deformation, and/or displacement when exposed to a force than a mouthpiece or oral structure with lower flexibility. Similarly stated, a mouthpiece with higher stiffness can be characterized as being more rigid (or less flexible) than a mouthpiece with lower stiffness. In some embodiments, the flexibility and/or deformability of an object can be characterized by the object's linear flexibility and/or deformability. Linear flexibility and/or deformability can be characterized in terms of the amount of force applied to the object and the resulting distance through which a first portion of the object deflects, deforms, and/or displaces with respect to a second portion of the object.

Flexibility is an extensive property of the object being described, and thus is dependent upon the material from which the object is formed and certain physical characteristics of the object (e.g., shape and boundary conditions). For example, the flexibility of an object can be increased or decreased by selectively including in the object a material having a desired modulus of elasticity. The modulus of elasticity is an intensive property of the constituent material and describes an object's tendency to elastically (i.e., non-permanently) deform in response to an applied force. A material having a high modulus of elasticity will not deflect as much as a material having a low modulus of elasticity in the presence of an equally applied force. Thus, the flexibility of the object can be increased, for example, by introducing into the object and/or constructing the object of a material having a low modulus of elasticity. In another example, the flexibility of the object can be increased or decreased by changing the flexural modulus of a material of which the object is constructed. Flexural modulus is used to describe the ratio of the applied stress on an object in flexure to the corresponding strain in the outermost portions of the object. The flexural modulus, rather than the modulus of elasticity, is used to characterize certain materials, for example plastics, that do not have material properties that are substantially linear over a range of conditions. An object with a first flexural modulus is less elastic and has a greater strain on the outermost portions of the object than an object with a second flexural modulus lower than the first flexural modulus. Thus, the flexibility of an object can be increased by including in the object a material having a low flexural modulus.

The flexibility of an object can also be increased or decreased by changing a physical characteristic of the object, such as the shape or cross-sectional area of the object. For example, an object having a length and a cross-sectional area may have a greater flexibility than an object having an identical length but a greater cross-sectional area. Thus, the flexibility and/or stiffness of the object can be increased by increasing and/or changing the shape of the cross-sectional area of the object.

The term "transparent" as used herein relates to an object's ability to transmit light therethrough. The transparency of an object is directly related to the absence of (or very low amounts of) scattering of light within the object. An object is said to be "substantially transparent" if the object allows visible light to be transmitted therethrough such that another objects can be distinctly seen through the subject object. In another embodiment, an object is said to be "substantially transparent" if the object permits transmission of at least sixty percent of incident light in a visible range through a portion of the object, as measured by any applicable test, such as ASTM D-1746, ASTM D-1003 or the like. In yet other embodiments, an object is said to be "substantially transparent" if the object permits transmission of at least seventy percent of incident light in a visible range through a portion of the object. In yet other embodiments, an object is said to be "substantially transparent" if the object permits transmission of at least eighty percent of incident light in a visible range through a portion of the object. In yet other embodiments, an object is said to be "substantially transparent" if the object permits transmission of at least ninety percent of incident light in a visible range through a portion of the object. In yet other embodiments, an object is said to be "substantially transparent" if the object permits transmission of at least ninety-five percent of incident light in a visible range through a portion of the object. In yet other embodiments, an object is said to be "substantially transparent" if the object permits transmission of at least ninety-nine percent of incident light in a visible range through a portion of the object.

Intra-Oral Light Treatment Apparatuses

Some embodiments described herein relate to exposing the alveolar soft tissue, e.g., the alveolar mucosa, to light (e.g., having an intensity from about 10 to about 200 $mW/cm^2$). Administering the light can modify the rate of tooth movement, increase the rate of healing, or provide one or more other orthodontic benefits. For example, administering light to an extraction site can increase the rate of healing and slow the movement of a tooth into the site. Some embodiments described herein include an intra-oral light-therapy apparatus configured to administer light to one or more portions of the patient's alveolar soft tissue. Such an apparatus can be used prior to, during or subsequent to orthodontic treatment and/or prior to, during or subsequent to oral surgery. In some embodiments, as disclosed herein, an apparatus can be used to administer light to a patient for 1 minute to 60 minutes per day. In other embodiments, the apparatus can contact a patient's oral mucosa for minutes, hours, day, weeks, months, or years, and one or more of the apparatus's emitters can irradiate light during at least some time during that period.

In some embodiments, an apparatus is configured to conform to the alveolar soft tissue of any human patient; in other embodiments, an apparatus can be configured to conform to the alveolar soft tissue of a specific human patient. For example, the apparatus can be configured to conform to any human patient's, or to a specific human patient's, particular dental geometry, for example, using information obtained from CT scans (e.g., cone beam CT scans), models of the patient's jaw, intra-oral digital scanned models, and/or photographs of the patient's jaw. More specifically, the placement of LEDs within an apparatus to be positioned within the patient's mouth can be custom designed, using CAD/CAM design applications, for example, based on information obtained from one or more of the foregoing methods. In other embodiments, a standardized apparatus can be selected from a set of apparatuses configured to conform generally to human patients' oral anatomical features. In some such embodiments, the standardized apparatus can be adjusted to conform to a specific human patient's features.

In some embodiments, an apparatus is configured to deflect, bend and/or deform to conform to the oral anatomy of a patient. For example, in some embodiments, an apparatus includes a mouthpiece configured to transition between a first configuration when the mouthpiece is outside of the patient's mouth and a second configuration when the mouthpiece is inside of the patient's mouth. Further, in some embodiments, an apparatus includes a mouthpiece and a light emitter. In some embodiments, the mouthpiece is configured to fit within a patient's mouth and includes a bite tray and a flange coupled to the bite tray. In some embodiments, an inner face of the flange forms a first angle with an upper surface of the bite tray, for example, when the mouthpiece is outside of the patient's mouth. In some embodiments the flange is deflectable with respect to the bite tray such that a second angle is formed between the inner face of the flange and the upper surface of the bite tray when the mouthpiece is disposed within the patient's mouth. In some embodiments, the light emitter is disposed within the flange and is configured to emit light to the patient's oral tissue when the mouthpiece is disposed within the mouth.

In some embodiments, a method for regulating tooth movement comprises disposing a mouthpiece of a light-therapy device into a patient's mouth. In some embodiments, the mouthpiece includes one or more of a bite tray, a flange, and a light emitter. In some embodiments, the flange is coupled to the bite tray and optionally includes the light emitter therein. In some embodiments, the flange is configured to move with respect to the bite tray during the disposing such that an angle between an inner face of the flange and an upper surface of the bite tray has a first value before the disposing and a second value after the disposing. In some embodiments, the method further comprises administering to the patient in need thereof an effective amount of light from the light emitter.

In some embodiments, the apparatus is configured to administer light therapy based on a customized dosage, e.g., a dosage that is customized for a particular patient. Younger patients may have less dense bone than older patients. Density of the patient's bone can be measured, for example, using computed tomography (CT), in one embodiment, cone beam CT, prior to light therapy administration. In some embodiments, the patient's bone density can be measured by irradiating the patient's teeth and measuring the amount of light that penetrates the teeth (e.g., using an apparatus similar to or such as that depicted in FIG. 18A.) Once the patient's bone density is determined, an optimal dosage of light can be determined for achieving the desired tooth movement.

In some embodiments, the apparatus can include a bite pad to improve patient comfort when the apparatus is in contact with the patient's alveolar soft tissue and/or for positioning of the apparatus in a patient's mouth.

In some embodiments, the apparatus can be used in conjunction with an appliance that exerts a force on the patient's teeth and/or on muscular tissue such as buccal and labial cheeks, tongue, etc. In some embodiments, the apparatus of the invention is used in conjunction with more than one appliance that exerts a force on the patient. Exerting one or more forces to the gum region and intra-orally administering light to a patient's alveolar soft tissue can increase the rate of tooth movement, increase the rate of healing of oral tissue and provide other orthodontic benefits. In some embodiments, one or more of the forces exerted is a heavy force. In some embodiments, one or more of the appliances exerting a force is a functional appliance. Heavy forces and functional appliances are disclosed herein.

In other embodiments, the apparatus can be used in conjunction with an orthodontic appliance.

In some embodiments, a method for orthodontic treatment comprises disposing a mouthpiece of a light-therapy device into a patient's mouth. The mouthpiece includes a bite tray, a flange, and a light emitter. In some embodiments, the flange is coupled to the bite tray and optionally includes the light emitter therein. In some embodiments, the flange is configured to move with respect to the bite tray during the disposing such that an angle between an inner face of the flange and an upper surface of the bite tray has a first value before the disposing and a second value after the disposing. In some embodiments, the method further comprises administering to the patient an effective amount of light from the light emitter.

In some embodiments, the apparatus can be used in conjunction with an appliance or other suitable conveyance that is configured to deliver vitamin D to the patient. Vitamin D treatment raises the vitamin D blood serum levels of the patient and, when combined with intra-oral light treatment, can increase the rate of tooth movement, increase the rate of healing of oral tissue and provide other orthodontic benefits. Vitamin D treatment is disclosed herein.

In some embodiments, the apparatus of this invention can be used in conjunction with one or more appliances that exert a force on the patient's oral tissue, such as a patient's tooth, or with an appliance (or other suitable conveyance) that is configured to deliver vitamin D to the patient. In this manner, the patient receives light treatment and vitamin D treatment and also has forces exerted, for example, on one or more teeth.

In some embodiments, an apparatus is configured to detect and/or send a signal when a mouthpiece is disposed within a patient's mouth. In this manner, the apparatus can initiate and/or control delivery of any of the methods of light therapy disclosed herein. For example, in some embodiments, a light-therapy apparatus includes one or more of a mouthpiece, a bill and an electronics assembly. In some embodiments, the mouthpiece is configured to be disposed within a mouth of a patient, and includes a series of light emitters therein. In some embodiments, the series of light emitters is configured to emit light to alveolar soft tissue of the patient. In some embodiments, the bill is coupled to an anterior end of the mouthpiece, and is configured to be disposed externally to the mouth when the mouthpiece is disposed within the mouth. In some embodiments, the least a portion of the electronics assembly is disposed within the bill. In some embodiments, the electronics assembly is configured to control operation of the light emitters. In some embodiments, the electronics assembly is further configured to send a first signal to cause a first light emitter to emit light. In some embodiments, the electronics assembly is configured to receive a second signal from a second light emitter, the second signal associated with the light emitted from the first light emitter. The electronics assembly is configured to detect when the mouthpiece is disposed within the mouth based on the second signal.

Figure 2:
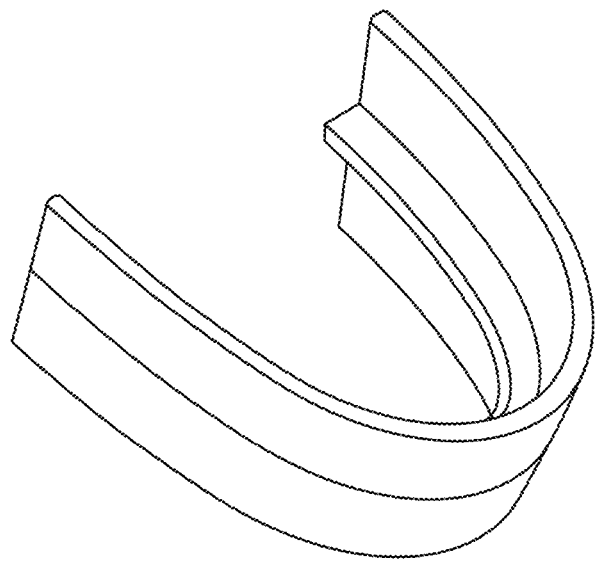

FIGS. 1 and 2 are schematic diagrams of intra-oral light-therapy apparatuses of the invention. As shown in FIG. 1, the apparatus includes panels 1, 2, 3, 4, 5, and 6. Panels 1, 2, and 3 are configured to be disposed near the root area of one or more teeth of the upper jaw. In some embodiments, panels 1, 2, and 3 can be configured to be disposed adjacent to the upper buccal alveolar soft tissue. For example, in one embodiment, the panels 1, 2, and 3 are in contact with the upper buccal alveolar soft tissue; whereas, in other embodiments, the panels 1, 2, and 3 are not in contact with the upper buccal alveolar soft tissue but are within a certain distance (e.g., within 0.1 cm to 3 cm) of the upper buccal alveolar soft tissue. The alveolar soft tissue can include, for example, the alveolar mucosa. In other embodiments, panels 1, 2, and 3 can be configured to be disposed adjacent to the upper lingual alveolar soft tissue. For example, in one embodiment, the panels 1, 2, and 3 are in contact with the upper lingual alveolar soft tissue; whereas, in other embodiments, the panels 1, 2, and 3 are not in contact with the upper lingual alveolar soft tissue but are within a certain distance (e.g., within 0.1 cm to 3 cm) of the upper lingual alveolar soft tissue. Similarly stated, in some embodiments, panels 1, 2, and/or 3 can be configured to be disposed posterior to the maxillary root area, while in other embodiments, panels 1, 2, and/or 3 can be configured to be disposed anterior to the maxillary root area. Similarly, panels 4, 5, and/or 6 can be configured to be disposed adjacent to anterior and/or posterior mandibular root area.

In other embodiments, the panels (or other portions of the apparatus) can be disposed at any of the various regions or areas described herein. For example, although in some embodiments, the panels are described herein as being in contact with or within a certain distance (e.g., within 0.1 cm to 3 cm) of the upper buccal or lingual alveolar soft tissue, in other embodiments, the panels are configured to be in contact with and/or within a certain distance (e.g., within 0.1 cm to 3 cm) of the lower buccal or lingual alveolar soft tissue. In still other embodiments, an apparatus can include a plurality of panels of which at least a first portion are configured to be in contact with or within a certain distance (e.g., within 0.1 cm to 3 cm) of the upper buccal or lingual alveolar soft tissue, and of which at least a second portion is configured to be in contact with or within a certain distance (e.g., within 0.1 cm to 3 cm) of the lower buccal or lingual alveolar soft tissue when the first portion is in contact with or within the certain distance of the upper alveolar soft tissue.

In some embodiments, an apparatus is configured to be disposed only adjacent to the maxillary or mandibular root area. For example, in one embodiment, the apparatus is in contact with the maxillary or mandibular root area; whereas, in other embodiments, the apparatus is not in contact with the maxillary or mandibular root area but is within a certain distance (e.g., within 0.1 cm to 3 cm) of the maxillary or mandibular root area. Similarly stated, although FIG. 1 depicts an apparatus including an upper portion and a lower portion, in other embodiments, the apparatus has only an upper portion or only a lower portion. Although the apparatus is shown with six panels, in other embodiments, the apparatus can have one or more panels. For example, a single panel can be configured to cover at least a portion of the maxillary and/or mandibular root area or the entirety. In other embodiments, one or more panels can be disposed adjacent to the root area of each tooth. For example, in one embodiment, one or more panels are in contact with the root area of each tooth; whereas, in other embodiments, one or more panels are not in contact with the root area of each tooth but are within a certain distance (e.g., within 0.1 cm to 3 cm) of the root area of each tooth.

Although in some embodiments the panels described herein cover at least some of the anatomical dimensions (e.g., length) of most tooth roots, variation in soft tissue and boney architecture of individual patients may prevent the panel from covering the apical extent of some tooth roots. In such cases, apical portions of the teeth may receive lower energy density. In some embodiments, however, the panels include an embedded LED array that is configured to direct light in the direction of such apical portion(s) or is configured to otherwise increase the intensity in the apical portions of the panels.

In some embodiments, such as the embodiment depicted in FIG. 2, the apparatus is configured to wrap over the teeth, such that a first portion of the apparatus is disposed adjacent to the anterior root area and a second portion of the apparatus is disposed adjacent to the posterior root area. In such embodiments, the apparatus is relieved over the anatomical crowns in order to provide freedom of tooth movement when the apparatus is in operation. For example, in one embodiment, the first portion of the apparatus is in contact with the anterior root area and/or the second portion of the apparatus is in contact with the posterior root area; whereas, in other embodiments, the first portion of the apparatus is not in contact with the anterior root area and/or the second portion of the apparatus is not in contact with the posterior root area but the first portion and/or the second portion of the apparatus is/are within a certain distance (e.g., within 0.1 cm to 3 cm) of the anterior root area or posterior root area, respectively.

FIG. 3A depicts a cross section of the apparatus of FIG. 1 taken along line X-X. The apparatus 10 can include one or more wires 12, a reflective backing 20, a circuit 30, and one or more emitters 32, encased in the panel 40. In some embodiments, the one or more emitters 32 can be partially encased within the panel 40 such that at least a portion of the one or more emitters 32 are exposed and can contact, for example, the alveolar soft tissue of the patient when the apparatus is in the patient's mouth. The panel 40 can be constructed of a substantially transparent, flexible, and/or soft polymer, such as a silicone. In other embodiments, the panel 40 can be a rigid plastic, such as an acrylic. The panel 40 can be shaped to cover a specific region of the patient's mouth when the apparatus is worn by the patient. For example, the panel 40 can have a width and a length effective to cover at least four of the patient's tooth roots. A portion of the panel 42 can have a rounded and/or teardrop shape to provide for patient comfort and to allow the apparatus to adapt to the flange area. The portion of the panel 42 can have any shape that does not include sharp or acute edges as such edges would irritate or be uncomfortable in the depth of the vestibule of the patient's mouth.

In some embodiments, the panel 40 is at least partially encased in the apparatus, which can have a shape similar to a mouth guard or to a clear dental aligner and can be constructed of any material suitable for use in the mouth. In this manner, the components encased in the panel 40 are also at least partially encased in the apparatus. In some embodiments, the panel 40 is fully encased in the apparatus. The panel 40 and components encased therein can be fluidically sealed within the apparatus so that saliva or another fluid cannot contact the panel 40. Sealing the panel 40 in this manner can provide safety benefits, extend the life of the intra-oral apparatus, and/or require less maintenance. For example, if the panel 40 is not fluidically sealed within the apparatus, then the apparatus may require frequent maintenance to clean fluids and other buildup from the panel 40.

The emitters 32 can be any suitable device that is operable to emit light. The emitters 32 can be, for example, light emitting diodes (LEDs). In some embodiments, the emitters 32 are optical fibers (or portions thereof) that emit light. In some embodiments, the emitters 32 are devices that are connected to and receive light input from one or more optical fibers. The panel 40 can include any combination of the LED and optical fiber emitters disclosed herein. In some embodiments, the emitters 32 can emit monochromatic light having a wavelength of about 620 nm. In other embodiments, the emitters 32 can emit monochromatic light having a wavelength of about 850 nm. In yet other embodiments, the emitters 32 can be configured to emit a light having a wavelength ranging from about 600 nm to about 1200 nm, emit light at more than one wavelength, progress through a range of wavelengths, and/or emit a broad spectrum light or any suitable wavelength or wavelengths. The emitters 32 can be configured to emit light having any wavelength or characteristic described herein. Such wavelengths and characteristics of light are described in more detail herein.

The emitters 32 can be positioned and arranged within the panel 40 in any suitable manner. The emitters 32 can be arranged, for example, so that they cover and irradiate light to a specific region of the mouth when the apparatus is worn by the patient. In one example, each emitter 32 is positioned over and irradiates light to a different tooth root. In another example, the emitters 32 are grouped together into sets so that one set of emitters is positioned over and irradiates light to a first region of the patient's mouth (e.g., a tooth root) while another set of emitters is positioned over and irradiates light to a second, different region of the patient's mouth (e.g., another tooth root). In this manner, the apparatus and the emitters 32 within each corresponding panel 40 can be customized for a specific patient so that particular needs of the orthodontic treatment are met. As noted herein, the panels, and thus the emitters 32, can be in contact with or within a certain distance of the alveolar soft tissue or tooth root. A light dose emitted by the emitters 32 can be more effective for regulating tooth movement the closer the emitters 32 are to the alveolar soft tissue or tooth root, due to a loss of energy that can occur over a distance between the emitters 32 and the tissue or root. In some embodiments, however, the power density of light emitted by emitters 32 can be maximized by positioning the emitters 32 in contact with and/or within the certain distance of the tissue or root, as described herein.

In some embodiments, as shown in FIG. 3B, a light emitting array 1001 has a first portion 1002 and a second portion 1003. The first portion 1002 of the light emitting array 1001 is configured to include a greater density of light emitters than a density of light emitters in the second portion 1003. In some embodiments, the first portion 1002 of the light emitting array 1001 includes a tighter weave on a portion of a light mat. The first portion 1002 of the light emitting array 1001 (or light mat) can be disposed at an apical portion of the array. The increased power density at the apex resulting from the tighter weave of the light mat permits a shorter extension to a flange as the increased power at least partially compensates for a shorter extension.

Referring again to FIG. 3A, the circuit 30 can be, for example, a flexible circuit. In some embodiments, the circuit 30 includes a controller (not shown) operable to control the operation of one or more emitters 32. In other embodiments, the circuit 30 can be coupled to a controller, such as an intra-oral or extra-oral controller. In some embodiments, the controller can independently control each of the one or more emitters 32. For example, using the circuit 30, the controller can collectively and/or individually control the on/off state, the intensity, the frequency, the pulse, the duty factor, and/or any other suitable parameter of the one or more emitters 32. Any one of these parameters can be changed while the apparatus is in use. By powering on one or more of the emitters 32, the controller enables the one or more emitters 32 to emit light and thereby accelerate bone remodeling and/or tooth movement. By powering off one or more of the emitters 32, the controller minimizes the movement of the teeth in the area, as bone remodeling will not have been accelerated by the light. In some embodiments, one or more emitters 32 within panel 40 can be on while one or more other emitters 32 within panel 40 are off. In some embodiments, when the apparatus is in use, one or more emitters 32 can start in the on state and then, at some later time, switch to the off state. By increasing or decreasing the intensity of the light, the controller can increase or decrease the dosage of light to the patient. A dosage of light is based on intensity and time so, in some instances, increasing the intensity of the light allows a decrease in the amount of time that the light needs to be administered to the patient. As a practical matter, there is a biological threshold of both minimum time and intensity in order to produce a therapeutic result. The controller can operate the emitters 32 at or above this threshold. In some embodiments, the intensity of light emitted from one or more emitters 32 within the panel 40 can be increased while the intensity of light emitted from one or more other emitters 32 within the panel 40 is decreased. This increase and decrease can occur, for example, while the apparatus is in use.

The controller can control the frequency and duty factor so that higher peak intensities can be achieved. High peak intensities can be useful in thicker tissues and/or when dosages of light need to be administered at greater depths. In some embodiments, a first emitter within the panel 40 can be disposed adjacent to and targeting a bone region that is deeper beneath the alveolar soft tissue than the bone region that a second emitter within the panel 40 is targeting. In these embodiments, the controller can program or control the first emitter so that it emits light having a higher peak intensity than the second emitter. Controlling the duty factor can also protect the emitters from overheating. For example, the controller can operate one or more emitters 32 at a 25% duty factor and at a frequency of 100 Hz such that the emitters 32 are ON for $\frac{1}{400}$th of a second and then OFF for $\frac{3}{400}$ths of a second. The OFF time would allow the emitters 32 to cool down, thereby avoiding any potential performance degradation associated with higher temperatures.

As disclosed herein, the controller can individually and selectively control the various light emission characteristics of each emitter 32 within the panel 40 and, as a result, each emitter 32 can operate independently of the other emitters 32 within the panel 40. Specifically, each emitter 32 within the panel 40 can emit light having different characteristics, if needed. The panel 40, therefore, can irradiate light at more than one wavelength or otherwise irradiate light having multiple different characteristics. In other embodiments, the controller can collectively control the various light emission characteristics of the emitters 32 within the panel 40. In some instances, all of the emitters 32 within the panel 40 are controlled so that they emit light having the same characteristics. These emitters 32, however, can be operated and controlled independently of emitters within other panels of the apparatus. For example, the emitters 32 can emit light having a wavelength of 850 nm while the emitters within another panel (e.g., panel 3 shown in FIG. 1) emit light having a wavelength of 650 nm. Emitted light characteristics, therefore, can vary from panel to panel within the apparatus. In other instances, the emitters 32 within the panel 40 can form groups and the emitters within each group are collectively controlled. For example, the panel 40 can include two groups of emitters 32: the first group of emitters can emit light at a first wavelength and the second group of emitters can emit light at a second, different wavelength. The panel 40, and the emitters 32 therein, can be customized for a specific patient so that an effective amount or dosage of light is administered to the patient and specific regions within the mouth are targeted. This customization can be useful when, for example, one region of the mouth undergoes a different light treatment than another region of the mouth.

In some embodiments, the apparatus can include an internal power source, such as a battery (not shown). In other embodiments, the apparatus can include a port, such that the circuit 30 can be coupled to an external power source.

In some embodiments, the circuit 30 can include one or more sensors (not shown) to detect the temperature of the apparatus, the patient's alveolar soft tissue and/or the patient's root area. For example, a thermistor or similar temperature measuring device can be placed in the circuitry 30 to monitor the temperature of the emitters 32 (e.g., an LED array) and panel 40 as well as measure the temperature inside the patient's mouth. This information can serve as a method of obtaining temperature-related information as well as monitoring patient compliance. When the circuits are placed in the mouth (i.e., circuit 30 and the circuits from the remaining panels of the apparatus) and when the apparatus emits light, the temperature of the emitters will rise from pre-treatment ambient temperature closer to normal body temperature. By monitoring the change in temperature, the controller can monitor the period of time that the emitters 32 are in the mouth, based on the period of time the temperature is elevated and close to body temperature. Alternatively, as described in more detail with reference to FIGS. 18A-18C, a photodetector can be placed in the circuit 30 and/or with the emitters 32 to measure the reflectance of light from the alveolar soft tissue. This configuration can serve as a method of monitoring patient compliance and also serve as a failsafe mechanism to ensure that the emitters 32 do not operate unless the apparatus is within the mouth of the patient.

The reflective backing 20 can be a metallic foil or other suitable reflective material operable to cause the light emitted by the emitters 20 to be directed in a desired direction, in one embodiment, substantially one direction, e.g., within about 1 to about 10 degrees of a specific direction. For example, the reflective backing 20 can define the back of the apparatus, such that the light is directed towards the alveolar soft tissue or root area of the patient (e.g., the region beneath the alveolar soft tissue that includes bone and roots).

The wires 12 can be super-elastic wires operable to cause the apparatus to conform to the alveolar soft tissue and/or gingiva. In some embodiments, the wires 12 can produce a relatively large orthodontic and/or orthopedic force, such as a force operable to urge one or more teeth to move. The force can be, for example, from about 10 to about 1000 grams of force. In some embodiments, the force is a heavy force. In other embodiments, the apparatus can be a portion of and/or be coupled to a separate intra-oral apparatus, such as orthodontic braces, retainers and/or any other suitable functional appliance. In some such embodiments, the separate intra-oral apparatus can produce a force in conjunction with or in lieu of the wires 12 producing a force.

Figure 4:
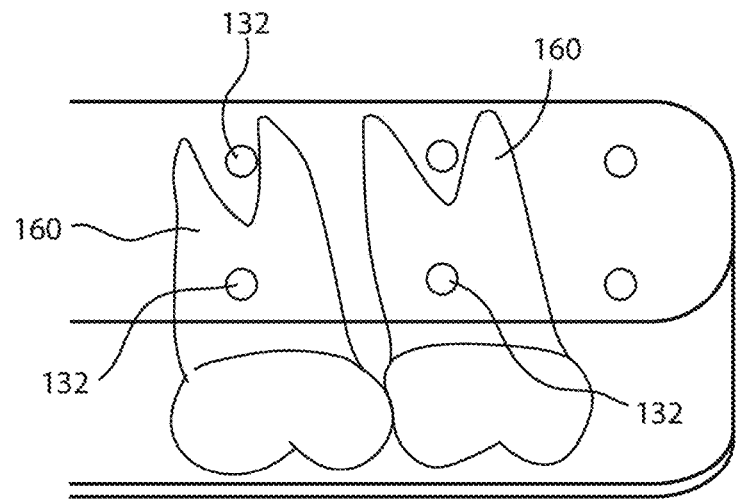
FIGS. 4-8 are schematic diagrams of intra-oral light-therapy apparatuses according to an embodiment of the invention.
Figure 5:
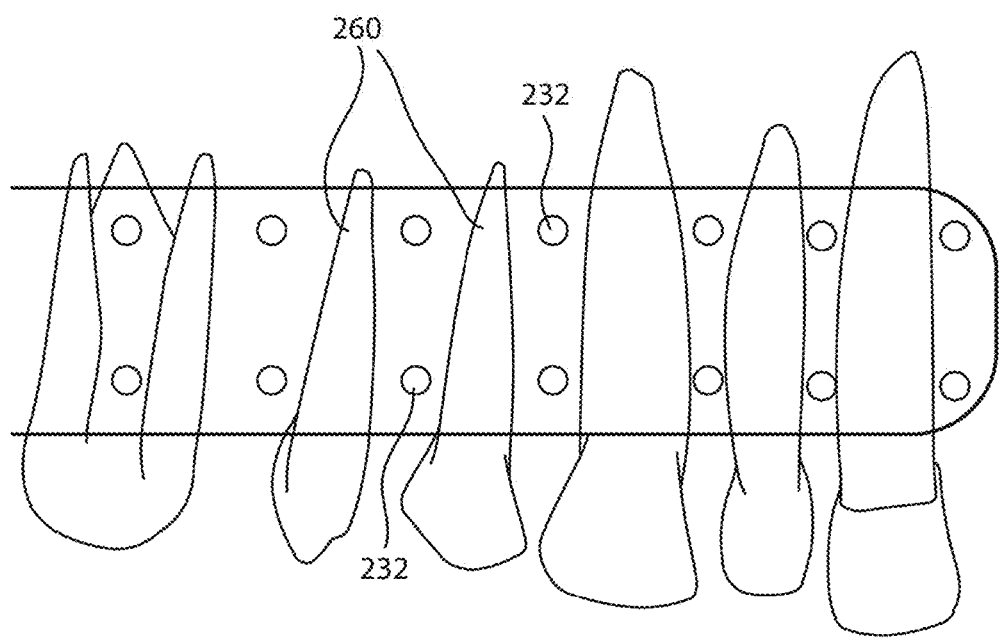
Figure 6:
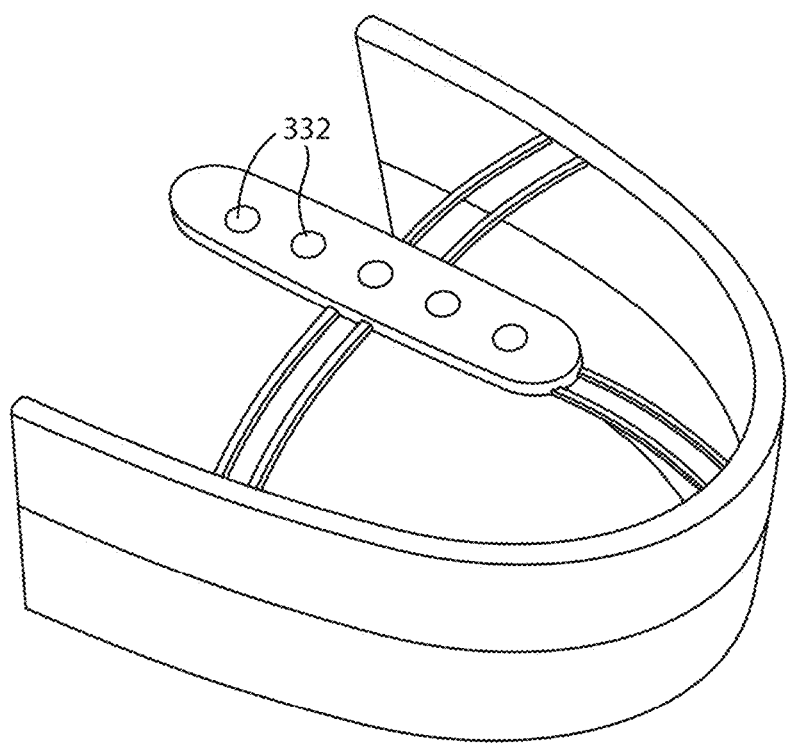

FIGS. 4-6 are schematic diagrams of an apparatus of the invention. As shown in FIG. 4, in some embodiments, one or more emitters 132 can be disposed over the roots of one or more teeth 160. In other embodiments, as shown in FIG. 5, one or more emitters 232 can be disposed between the roots of one or more teeth 260. In such embodiments, a mask can be applied to the apparatus and/or the root area of each tooth 260 to prevent the root area of the teeth 260 from being exposed to the light. As is disclosed herein, the mask blocks the light irradiated from the one or more emitters 132 so that little or none of the light reaches the area covered by the mask. The mask can be a tooth mask. The mask can be opaque and/or reflective. In some embodiments, the mask includes an adhesive surface so that the mask can be placed and adhered to an outer surface of the apparatus at a location where light is desired to be blocked. In some embodiments, the mask is in the form of a sticker. The adhesive surface of the mask can contact and/or cover one or more panels (or a portion thereof). In some embodiments, the opposing outer surface of the mask (or a portion thereof) can contact the alveolar soft tissue (e.g., the alveolar mucosa) when the mask is adhered to the apparatus and the apparatus is in the patient's mouth. In some embodiments, more than one mask can be applied to the apparatus and/or the root area of each tooth 260 to prevent the root area of the teeth 260 from being exposed to the light. In some such embodiments, more than one type of mask can be applied. For example, both an opaque mask and a reflective mask can be applied to the apparatus.

In other embodiments, as shown in FIG. 6, one or more emitters 332 can be operable to illuminate the maxillary suture, for example, the midline of the maxillary suture. In some embodiments, the one or more emitters 332 emit light directed towards the maxillary suture before, during, and/or after an orthopedic force is exerted on the maxillary suture. The orthopedic force can be exerted by an orthodontic appliance, such as, for example, a Rapid Maxillary Expansion (RME) appliance. A RME appliance can exert orthopedic forces on the patient's molars to open up and expand the maxillary suture for skeletal expansion of the upper jaw (as opposed to an orthodontic expansion where only the teeth move). Light therapy can be used in these embodiments to accelerate the rate at which the maxillary bone grows and the gaps caused by the skeletal expansion are filled. In some embodiments, the present methods are useful for accelerating the fill of bone and/or decreasing the potential for relapse or narrowing of the maxillary arch after orthodontic appliance removal. In some embodiments, the one or more emitters 332 emit light directed towards the midline of the palate such that boney regeneration is simulated through light therapy. In some embodiments, the apparatus shown in FIG. 6 is customized to fit around the RME appliance or other like fixed orthodontic expander. In some embodiments, the apparatus shown in FIG. 6 includes the one or more emitter 332 that illuminate the maxillary suture as well as one or more other emitters that illuminate the alveolar soft tissue.

The emitters 132, 232 and/or 332 can operate in a manner similar to the emitters 32 depicted in FIG. 3A.

Figure 7:
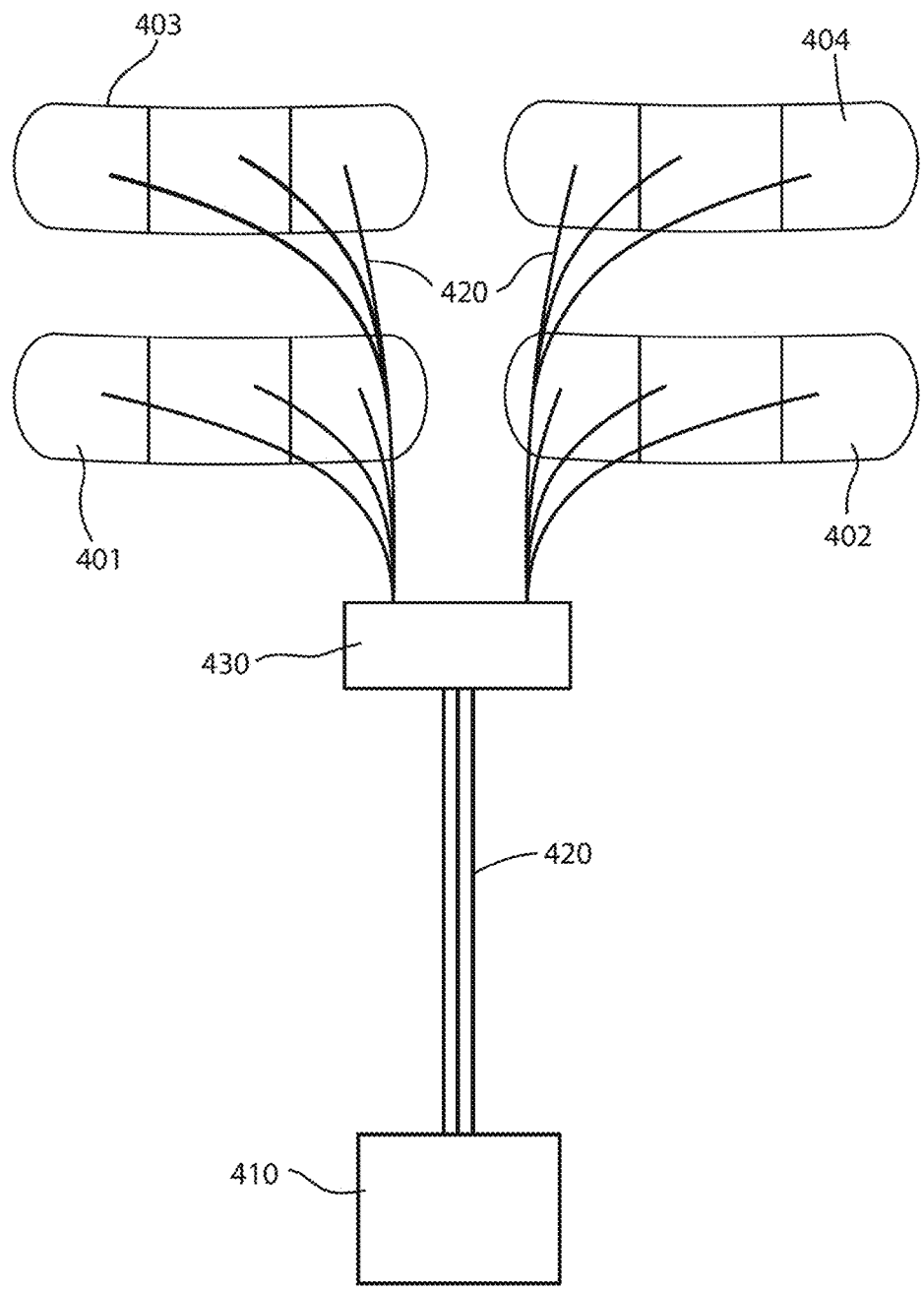

FIG. 7 is a schematic diagram of an apparatus, according to an embodiment. The apparatus includes four panels 401, 402, 403, 404, a light source 410, one or more optical fiber cables 420, and a controller 430. The panels 401, 402, 403, and/or 404 can be configured to be disposed adjacent to the root area of the upper and/or lower jaw. For example, in one embodiment, the panels 401, 402, 403, and/or 404 are in contact with the root area of the upper and/or lower jaw; whereas, in other embodiments, the panels 401, 402, 403, and/or 404 are not in contact with the root area of the upper and/or lower jaw but are within a certain distance (e.g., within 0.1 cm to 3 cm) of the root area of the upper and/or lower jaw. Such configurations can eliminate the need to place electronics in the oral cavity.

The light source 410 can be operable to emit light. For example, in some embodiments, the light source 410 can output monochromatic light. For example, the light source 410 can be a laser, an LED, and/or any other suitable light source. The light source 410 can be configured to emit a light having a wavelength ranging from about 600 nm to about 1200 nm, emit light output at more than one wavelength, progress through a range of wavelengths, and/or emit a broad spectrum light output or any suitable wavelength or wavelengths. The light source 410 can output light with any wavelength or characteristic described herein.

The light can be conveyed from the light source 410 to the controller 430 via one or more optical fibers 420. The controller 430 can be, for example, an optical switch. The controller 430 can be operable to selectively transmit light from the light source 410 to the panels 401, 402, 403, and/or 404 via one or more optical fibers 420. For example, the controller 430 can collectively and/or individually control the on/off state, the intensity, the frequency, the pulse, the duty factor, and/or any other suitable parameters of the light that is delivered to the panels 401, 402, 403, and/or 404. The controller 430 can operate similar to the controller depicted in FIG. 3A.

In some embodiments, more than one optical fiber 420 can be directed to each panel. The optical fiber can terminate adjacent to (e.g., within 0.1 cm to 3 cm) or at the root area, similar to the apparatuses shown and described with reference to FIGS. 4 and 5. Thus, each optical fiber can direct light from the light source 410 to the root area. By providing more than one fiber 420, light from the source 410 can be directed and/or controlled to illuminate a specific portion of the root area. In this way, the controller 430 can selectively apply light to the root area of one or more teeth, similar to the emitters 32, 132 and/or 232 as shown and described herein with reference to FIGS. 3, 4 and 5.

Figure 8:
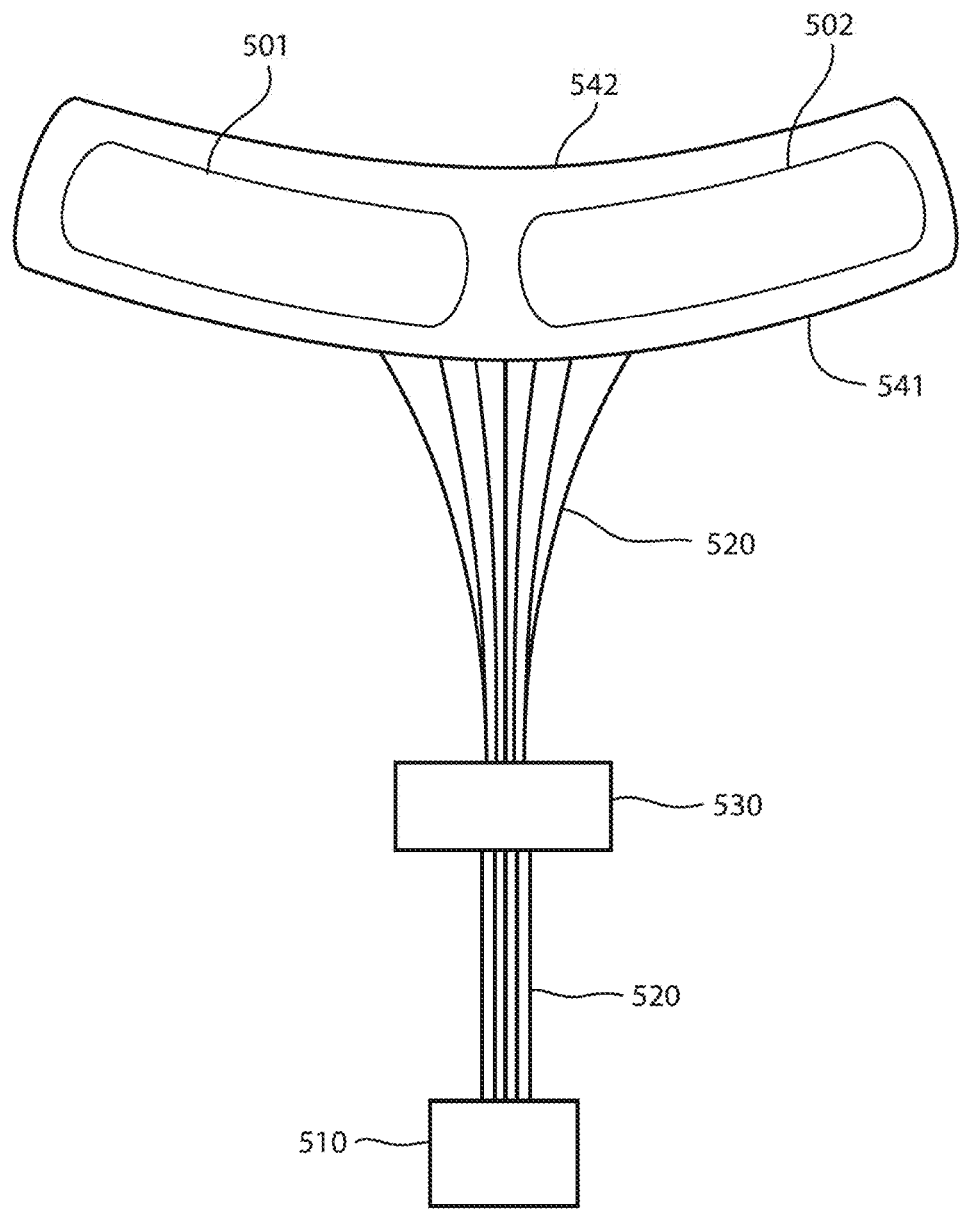

FIG. 8 is a schematic diagram of an apparatus, according to an embodiment. The apparatus includes two panels 501, 502, a light source 510, an optical fiber ribbon 520, and a controller 530. The panels 501 and 502 can be configured to be disposed adjacent to the root area of the upper jaw as well as the root area of the lower jaw. As is disclosed herein, the panels 501 and 502, for example, can first be disposed adjacent to the root area of the upper jaw; then, after orthodontic treatment of the upper jaw is complete, the panels 501 and 502 can be removed from the upper jaw and placed on the lower jaw such that they are disposed adjacent to the root area of the lower jaw. In one embodiment, the panels 501, 502 are in contact with the root area of the upper and/or lower jaw; whereas, in other embodiments, the panels 501, 502 are not in contact with the root area of the upper and/or lower jaw but are within a certain distance (e.g., within 0.1 cm to 3 cm) of the root area of the upper and/or lower jaw. Such configurations can eliminate the need to place electronics in the oral cavity.

The panels 501, 502 can define an upper portion 542. The cross-section of the upper portion 542 can be rounded and/or teardrop shaped (similar to the portion of the panel 42 depicted in FIG. 3A) to provide for patient comfort and to allow the apparatus to adapt to the flange area of the upper and lower jaw. For example, as is disclosed herein, the apparatus can be worn on the upper jaw so that the upper portion 542 of the panels 501, 502 adapt to the upper flange area; then, the apparatus can be removed from the upper jaw, flipped upside down, and then installed on the lower jaw such that the upper portion 542 is now disposed in the lower flange area. In this manner, the upper portion 542 of the panels 501, 502 is configured to fit and adapt to both the upper and lower flange area of the patient's mouth. In some embodiments, the panels 501, 502 can also define a lower portion 541 that has a rounded and/or teardrop shaped cross-section so that, for example, the apparatus can be removed from the upper jaw and installed on the lower jaw without having to flip the apparatus. Here, the lower portion 541, as opposed to the upper portion 542, is disposed and configured to fit in the lower flange area.

The portions 541, 542 of the panels 501, 502 can have any shape that does not include sharp or acute edges as such edges would irritate or be uncomfortable in the depth of the vestibule of the patient's mouth. In some embodiments, the portions 541 and/or 542 have a shape or cross-sectional shape that disperses forces and minimizes pressure points which would cause discomfort for the patient. In some embodiments, the portions 541 and/or 542 have a thicker cross-section than the remaining portions of the panels 501, 502. In this manner, the portions 541 and/or 542 can deflect the delicate mucosal soft tissue and allow full extension of the flanges with little or no discomfort to the patient. More specifically, the portions 541 and/or 542 can deflect buccal tissue away from the alveolus.

The light source 510 can be operable to emit light in the same manner as the light source 410 in reference to FIG. 7. The light can be conveyed from the light source 510 to the controller 530 via the optical fiber ribbon 520. The controller 530 can be operable to selectively transmit light from the light source 510 to the panels 501 and/or 502 via the optical fiber ribbon 520 in the same manner as the controller 430 in reference to FIG. 7. For example, the controller 530 can collectively and/or individually control the on/off state, the intensity, the frequency, the pulse, the duty factor, and/or any other suitable parameters of the light that is delivered to the panels 501 and/or 502.

The optical fiber ribbon 520 can be coupled to the apparatus, as shown in FIG. 8, such that one or more optical fibers of the ribbon 520 are electrically connected and/or directed to each panel 501, 502. For example, one or more of the optical fibers in the ribbon 520 can terminate adjacent to (e.g., within 0.1 cm to 3 cm) or at the root area, similar to the apparatuses shown and described with reference to FIGS. 4 and 5. Thus, each optical fiber of the ribbon 520 can direct light from the light source 510 to the root area in the same manner as the optical fibers 420 in reference to FIG. 7. The optical fibers of the ribbon 520 can be configured to optically couple the panels 501, 502 together. The optical fiber ribbon 520 can have one or more optical fibers for example, in one or more bundles, therein. For example, the ribbon 520 can have anywhere from 1 fiber to 500 fibers for each panel 501, 502 depending on the specific light emission technology or pattern used for the treatment. The optical fiber ribbon 520 can have any suitable shape and/or size such that the ribbon can comfortably extend from the apparatus to outside the patient's mouth. The ribbon 520 can, for example, have a width of about 0.5 cm to about 1.0 cm. Although the apparatus of FIG. 8 is illustrated and described as having a single ribbon that electrically couples to both panels 501 and 502, in other embodiments, the apparatus includes more than one ribbon. For example, in one embodiment, the apparatus includes two ribbons. In some embodiments, one ribbon can be electrically connected to the panel 501 and the other ribbon can be separately electrically connected to the panel 502. In some embodiments, the ribbon 520 is a woven fiber-optic fabric. More specifically, the ribbon 520 in this embodiment can be comprised of one or more optical fibers that are woven into a fabric. In some embodiments, light from the woven fiber optic fabric is emitted at about 90 degrees or is emitted perpendicular to the plane of the fabric. An example of a woven fiber optic fabric that can be used with the apparatus of FIG. 8 is LightMat®, which is commercially available from Lumitex, Inc. (http://www.lumitex.com/).

As disclosed herein, the apparatus in FIG. 8 can be installed on either the upper or lower jaw. In some embodiments, the apparatus in FIG. 8 is installed during orthodontic treatment. For example, at the outset of the treatment, the apparatus can be installed on the upper jaw such that the upper portion 542 of the apparatus is disposed in the upper flange area. Then, at a later time during the treatment, the patient can remove the apparatus from the upper jaw and install the apparatus on the lower jaw for the remainder of the treatment. In one embodiment, the apparatus can be installed on the lower jaw such that the lower portion 541 of the apparatus is disposed within the lower flange area. In this embodiment, the apparatus remains right-side up. In another embodiment, however, the apparatus can be installed on the lower jaw such that the upper portion 542 of the apparatus is disposed within the lower flange area. In other words, after the patient removes the apparatus from his or her upper jaw, he or she rotates the apparatus 180 degrees so that it is upside down and then installs the apparatus on the lower jaw. The upper portion 542, in this embodiment, fits both the upper and lower flange area.

In some embodiments, the apparatus includes an electronic device, such as a position sensor, that can determine the position or orientation of the apparatus relative to the patient's mouth. More specifically, in embodiments where the apparatus is turned upside down (e.g., rotated 180 degrees) for installment on the lower jaw, the apparatus can include an electronic device that determines the apparatus's position or orientation in a patient's oral cavity during an orthodontic treatment. For example, the sensor can determine whether the apparatus is being worn on the upper jaw or on the lower jaw. Such an electronic device can be useful in monitoring compliance during orthodontic treatment. In some embodiments, the electronic device can be one or more switches, sensors, and/or the like.

Figure 37:
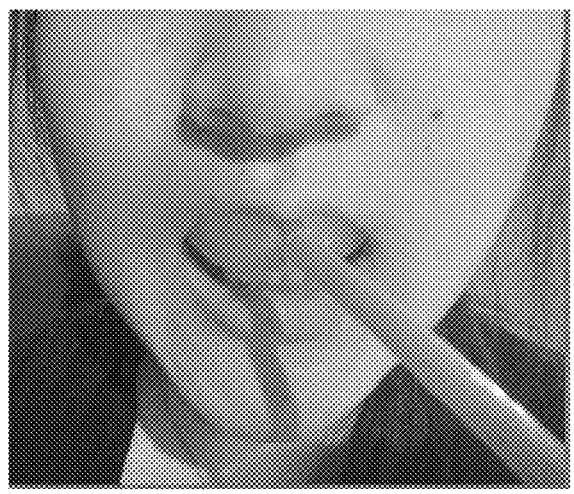
FIG. 37 is an image of the apparatus of FIGS. 30-36 disposed in the oral cavity of and in use by a patient.

Any of the apparatus illustrated and described herein with reference to FIGS. 1-8 can have any number of panels, which can operate and function in any manner described herein. Although not necessarily illustrated, in some embodiments, the panels can be coupled together and/or encapsulated within one or more units. For example, the panels 403 and 404 in FIG. 7 can be coupled together and/or encapsulated in a single unit, similar to a mouth guard that fits the upper teeth. The panels 401 and 402 can likewise be coupled together and/or encapsulated within a single unit, similar to a mouth guard that fits the lower teeth. Example of mouth guards including light emitting panels are shown in FIGS. 30-37 and FIGS. 43-50. It should be noted that although the mouth guard is shown in FIG. 37 positioned with respect to the upper teeth of the patient, the mouth guard is also configured to be positioned with respect to the lower teeth of the patient. In another example, the panels 403 and 404 can be coupled together such at least a portion of the panel 403 overlaps a portion of the panel 404. The panel 403 in this example can emit light at the same wavelength as or at a wavelength different from the panel 404. Furthermore, power output and light treatment intensity can be increased by the layering or overlapping of one or more panels.

In some embodiments, any of the intra-oral apparatuses described herein can include a handheld controller that houses one or more of a microprocessor, menu-driven software and an LCD screen. The controller can be programmed to calculate and/or monitor one or more light therapy sessions and their duration. A user interface can display session information to the patient so that, for example, the patient is aware of the number of sessions completed and the time remaining in each session. The controller can use any suitable power supply including, for example, a UL-certified power supply. In some embodiments, the intra-oral apparatus can include four treatment arrays, each of which can include a flexible printed circuit board and a set of LEDs mounted to a contoured heat sink and infrared-transmissible lens, in one embodiment, a plastic lens, and having conductive cables that attach to the controller.

Figure 9:
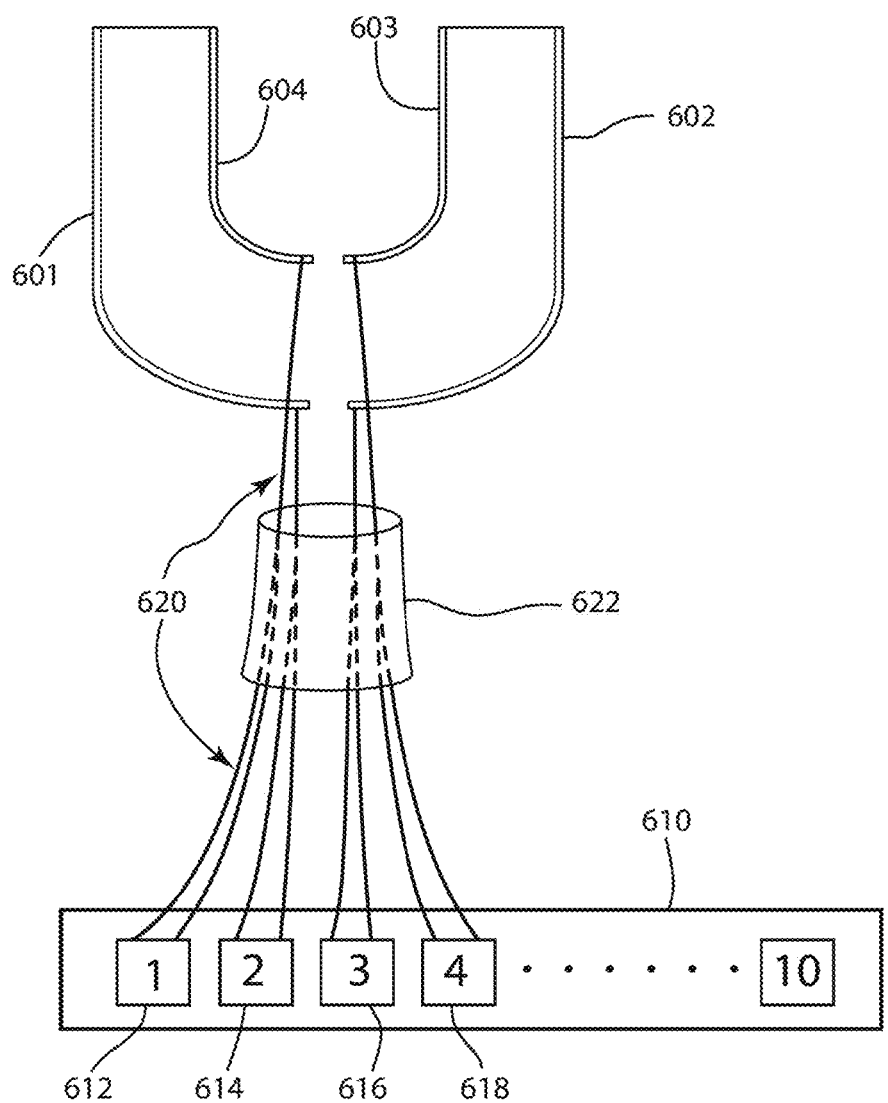
FIG. 9 is a schematic diagram of an intra-oral light-therapy apparatus according to an embodiment of the invention.

FIG. 9 is a schematic diagram of an apparatus, according to an embodiment. The apparatus can be configured for intra-oral light therapy of a patient. The apparatus includes four panels 601, 602, a light source 610, and optical fibers 620. The panels 601, 602, 603 and 604 can be configured to be disposed adjacent to the root area of the upper jaw as well as the root area of the lower jaw, for example, in a similar manner as described herein in reference to FIGS.1-8. More specifically, panels 601 and 602 can be disposed adjacent to the anterior root area of the upper jaw (or lower jaw), and panels 603 and 604 can be disposed adjacent to the posterior root area of the upper jaw (or lower jaw). In other words, the panels 601, 602, 603, 604 can be configured to be disposed anterior (for panels 601, 602) and posterior (for panels 603, 604) to each of the maxillary root area and the mandibular root area. In this manner, in use, the panels 601, 602 can be configured to emit light in a direction towards the panels 603,604, and panels 603, 604 can be configured to emit light in a direction towards the panels 601, 602. The panels 601, 602, 603 and 604, for example, can first be disposed adjacent to the respective anterior or posterior root area of the upper jaw; then, after orthodontic treatment of the upper jaw is complete, the panels 601, 602, 603 and 604 can be removed from the upper jaw and placed on the lower jaw such that they are disposed adjacent to the respective anterior or posterior root area of the lower jaw. In one embodiment, the panels 601, 602, 603 and 604 are in contact with the root area of the upper and/or lower jaw; whereas, in other embodiments, the panels 601, 602, 603 and 604 are not in contact with the root area of the upper and/or lower jaw but are within a certain distance (e.g., within 0.1 cm to 3 cm) of the root area of the upper and/or lower jaw. In some embodiments, the panels 601, 602 can be configured to be disposed adjacent to (e.g., in contact with or within a certain distance of) the upper and/or lower buccal lingual alveolar soft tissue and panels 603, 604 can be configured to be disposed adjacent to the upper and/or lower lingual alveolar soft tissue. Such configurations can eliminate the need to place electronics in the oral cavity.

The panels can be similar in one or more respects or identical to any panel described herein, including, for example, those described in reference to FIGS. 1-8. Each panel 601, 602, 603, 604 is associated with a bundle of optical fibers 620 that extend to the light source 610. More specifically, each panel 601, 602, 603, 604 is associated with an emitter 632 of the light source 610 via a bundle of optical fibers 620. In this manner, each panel 601, 602, 603, 604, and any housing (not shown in FIG. 9) to which the respective panel is coupled, is optically coupled to the emitter 632 of the light source 610.

The light source 610 can be operable to emit light in the same manner as the light source 410 in reference to FIG. 7 and/or light source 510 in reference to FIG. 8. The light source 610 can include, for example, one, two three, four or more (e.g., ten) LEDs (including, for example, the LEDs 612, 614, 616, 618 shown in FIG. 9). At least a portion of the light source 610, for example, including the LEDs 612, 614, 616, 618, can be disposed in an external housing of the apparatus, at least a portion of which is configured to be disposed extraorally when the panels 601, 602, 603, 604 are disposed in the oral cavity adjacent the root area as described herein. For example, the external housing of the apparatus can be extended through an opening formed by the patient's lips when the panels 601, 602, 603, 604 are disposed in the oral cavity adjacent the root area as described herein.

Figure 10:
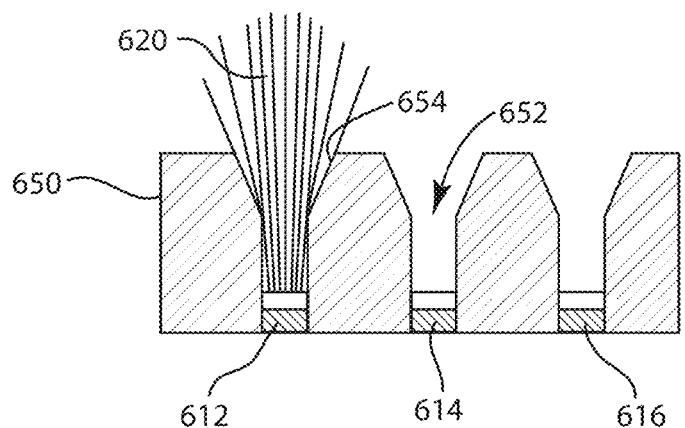
FIG. 10 is a sectional view of a portion of the apparatus of FIG. 9.
Figure 11:
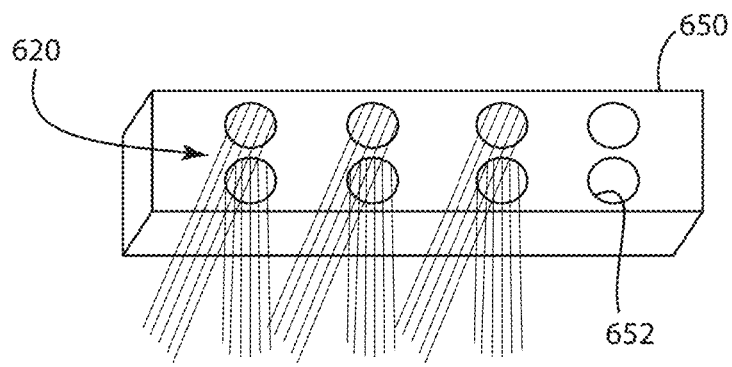
FIG. 11 is a top perspective view of a portion of the apparatus of FIG. 9.
Figure 12:
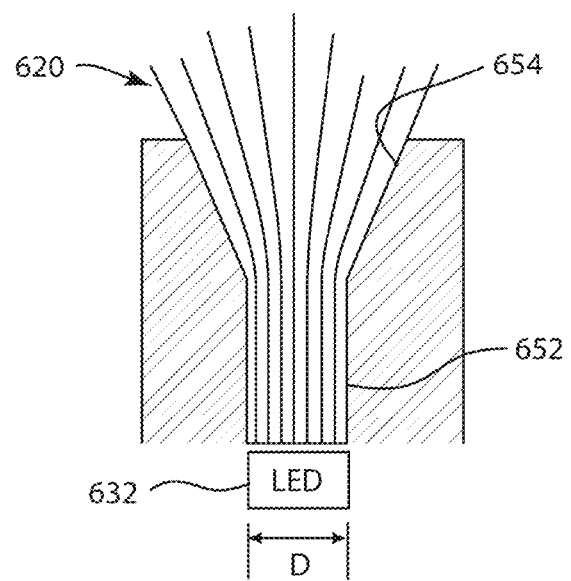
FIG. 12 is a sectional view of a portion of the apparatus of FIG. 9.

The apparatus can include a manifold 650 defining one or more openings 652 therethrough. Each opening 652 of the manifold 650 can include a tapered surface portion 654 such that at least a portion of the opening 652 is funnel-shaped. A bundle of optical fibers 620 extending between the light source 610 (e.g., one of the LEDs 612, 614, 616, 618) and one of the panels (e.g., panel 601) can be disposed through the opening 652 of the manifold 650. As illustrated in FIG. 10, ends of the optical fibers 620 in the bundle are seated over, or adjacent, the LED 612. For example, in some embodiments, ends of the optical fibers 620 in the bundle are seated over an LED package (e.g., LED package 632, shown in FIG. 12, which can include, for example, LED 612) or other suitable light source. At least one of the portion of the opening 652 of the manifold 650 proximate to the LED package (or other emitter) 632, or the LED package (or other emitter) 632, can have a diameter equal to or narrower than a diameter of the optical fiber bundle. For example, as shown in FIG. 12, each of the optical fiber bundle 620 and the manifold 650 opening 652 proximate to the LED package 632 has a diameter D. The use of the funnel-shaped manifold allows for organization of the optical fibers 620 into groups of smaller bundles, thereby eliminating any need for bulky on-board ferrules. Such organization of the optical fibers 620 via the manifold 650 also provides for addressing of an individual panel 601, 602, 603, 604, as described in more detail herein.

The light can be conveyed from the LEDs (e.g., LED 612, 614, 616, 618) of the light source 610 to the panels 601, 602, 603 and/or 604 via the optical fibers 620. For example, a controller (not shown in FIG. 9) can collectively and/or individually control the on/off state, the intensity, the frequency, the pulse, the duty factor, and/or any other suitable parameters of the light that is delivered to the panels 601, 602, 603 and/or 604.

The optical fibers 620 can be coupled to the apparatus, as shown in FIG. 9, such that bundles of optical fibers 620 are electrically connected and/or directed to each panel 601, 602, 603, 604. For example, the optical fibers 620 can be coupled such that proximal ends of the optical fibers 620 are coupled, or are otherwise adjacent, at least one of the light source 610 and the manifold 650 and such that distal ends of the optical fibers 620 are coupled, or are otherwise adjacent, to one or more panels 601, 602, 603 and/or 604. One or more of the optical fibers 620 (i.e., the distal end of one or more of the optical fibers) can terminate adjacent to (e.g., within 0.1 cm to 3 cm) or at the root area, similar to the apparatuses shown and described with reference to FIGS. 4 and 5. Thus, each optical fiber 620 can direct light from the light source 610 to the root area in the same manner as the optical fibers 420 in reference to FIG. 7. The optical fibers 620 can be configured to optically couple the panels 601, 602, 603 and/or 604 together. The optical fibers 620 can be bundled in any suitable number of fibers. For example, each panel 601, 602, 603 and/or 604 can be associated with a bundle of anywhere from 1 fiber to 500 fibers depending on the specific light emission technology or pattern used for the treatment. The optical fibers 620 can have any suitable shape and/or size such that the fibers can comfortably extend from the panel to the light source 610 disposed outside the patient's mouth. The optical fibers 620 can, for example, have a collective width of about 0.5 cm to about 1.0 cm. A collar 622 can be disposed about one or more of the bundles of optical fibers 620 to maintain fiber bundles together. The apparatus shown in FIGS. 9-12 can be installed on either the upper or lower jaw, for example, during orthodontic treatment.

Figure 13:
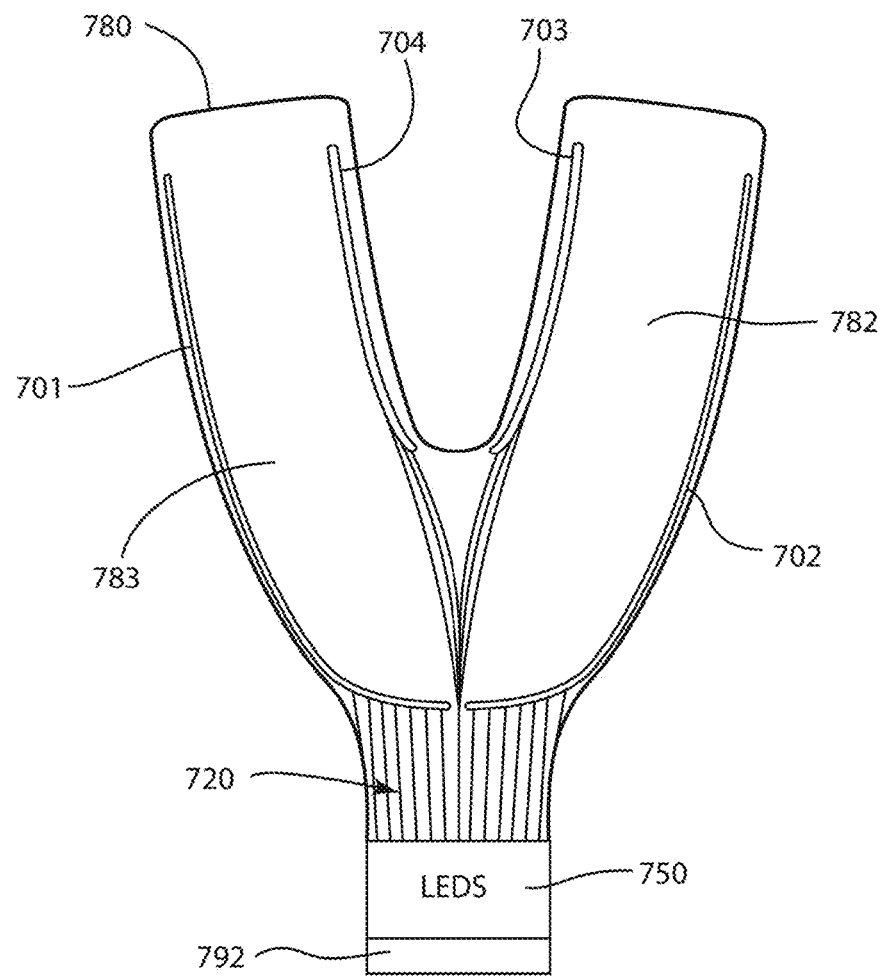
FIG. 13 is a schematic diagram of an intra-oral light-therapy apparatus according to an embodiment of the invention.

FIG. 13 is a schematic diagram of an apparatus, according to an embodiment. The apparatus can be configured for intra-oral light therapy of a patient. The apparatus can be similar in one or more respects or identical to other intra-oral light-therapy apparatuses described herein, including, for example, the apparatus described herein with reference to FIGS. 9-12. The apparatus includes an intra-oral housing 780 and an external housing 790 that extends from a front portion of the intra-oral housing such that at least a portion of the housing is disposed extraorally when the intra-oral housing is disposed within the oral cavity.

The intra-oral housing 780 includes one or more panels 701, 702, 703, 704. The panels 701, 702, 703, 704 can include light emitting arrays, fiber mats, organic LEDs ("OLEDs"), or any suitable combination of the foregoing. The panels 701, 702, 703, 704 can be configured to be disposed within the patient's oral cavity in any manner described herein with reference to panels 601, 602, 603, 604.

The intra-oral housing 780 can be connected between the panels 701, 702 configured to be positioned adjacent the anterior root area of the jaw (or the buccal alveolar soft tissue) and the panels 703, 704 configured to be positioned adjacent the posterior root area of the jaw (or the lingual alveolar soft tissue). In some embodiments, the intra-oral housing 780 includes a lower portion configured to extend between a lower portion (not shown in FIG. 13) of the panel 701 and a lower portion (not shown in FIG. 13) of the panel 704, and similarly between a lower portion (not shown in FIG. 13) of the panel 702 and a lower portion (not shown in FIG. 13) of the panel 703. In this manner, the intra-oral housing 780 can include recessed portions 782, 783 defined by the lower portion of the intra-oral housing and an upper portion of the intra-oral housing including the panels 701, 702, 703, 704. The recessed portions 782, 783 can be configured to receive, or be disposed about, at least a portion of the patient's dentition. More specifically, the recessed portions 782, 783 are configured to have a depth sufficient to receive at least a portion of the patient's dentition in the lower portion of the intra-oral housing such that the upper portion of the intra-oral housing including the panels 701, 702, 703, 704 is disposed adjacent and/or in contact with the alveolar soft tissue or the root area of the upper and/or lower jaw.

Optical fibers 720 extend between the panels 701, 702, 703, 704 and a light source (not shown in FIG. 13) disposed in the external housing 790 (e.g., at a front portion of the external housing configured to remain outside the oral cavity when the apparatus is in use) such that one or more optical fibers are electrically connected and/or directed to each panel 701, 702, 703, 704. For example, one or more of the optical fibers 720 can terminate adjacent to (e.g., within 0.1 cm to 3 cm) or at the root area, similar to the apparatuses shown and described with reference to FIGS. 4 and 7. Thus, each optical fiber 720 can direct light from the light source to the root area in the same manner as the optical fibers 420 described in reference to FIG. 7. The optical fibers 720 can be configured to optically couple any combination of the panels 701, 702, 703, 704 together. The apparatus can have any suitable number of optical fibers. For example, the apparatus can have anywhere from 1 fiber to 500 fibers for each panel 701, 702, 703, 704 depending on the specific light emission technology or pattern used for the treatment. The optical fibers 720 can be connected to the light source by a manifold 750. The manifold can be similar in one or more respects or identical to the manifold 650 described with respect to FIGS. 10-12, and thus is not described in detail herein.

The light source can be similar in one or more respects or identical to the light source 610 described herein with reference to FIGS. 9-12, and thus is not described in detail herein. The light source can be operable to emit light. For example, in some embodiments, the light source can output monochromatic light. For example, the light source can be or include one or more of a laser, an LED, and/or any other suitable light source. The light source can be configured to emit a light having a wavelength ranging from about 600 nm to about 1200 nm, or at any wavelength or wavelength range disclosed herein; emit light output at more than one wavelength; progress through a range of wavelengths; and/or emit a broad spectrum light output or any suitable wavelength or wavelengths. The light source can output light with any wavelength or characteristic described herein.

Figure 14:
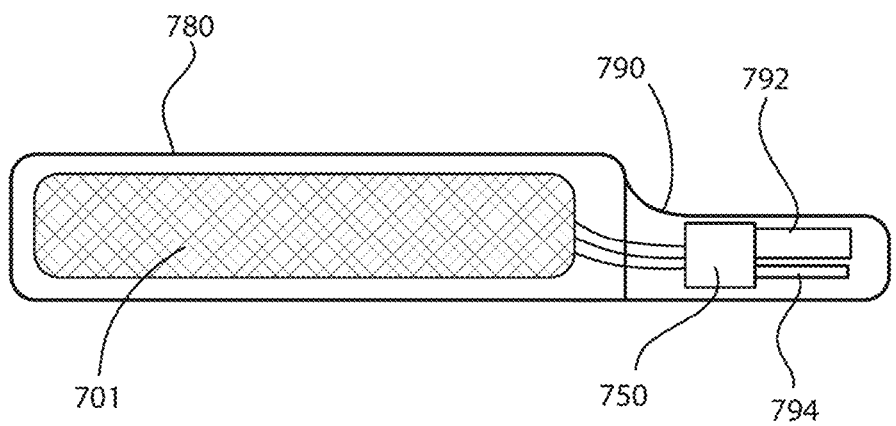
FIG. 14 is a side view of the apparatus of FIG. 13.

The external housing 790 includes a power source 792 and an electronic circuit 794, as shown in FIG. 14. The power source 792 can be a battery, including, for example, a rechargeable battery. The electronic circuit 794 can include a circuit board. The electronic circuit 794 and any associated electronics can be configured to control the apparatus, i.e., during an orthodontic treatment. For example, the electronic circuit is configured to control at least one of an operational state of the light source and/or optical fibers 720, a wavelength, an intensity, a frequency, or a duration of light emission. Because the apparatus does not require any physical connection to external components during the treatment (e.g., does not require connection to an external light source, external controller, or external power source), the apparatus can be characterized as being self-contained.

The apparatus can be configured to determine whether the apparatus is in an upright or upside down (e.g., rotated 180 degrees) position or orientation (i.e., whether the apparatus is oriented with respect to the upper jaw or the lower jaw). For example, in some embodiments, the external housing 790 includes at least one of a position sensor, a gyroscope and an accelerometer. The gyroscope and/or the accelerometer can be include one or more sensors configured to determine the position (or orientation) of the apparatus.

Figure 15:
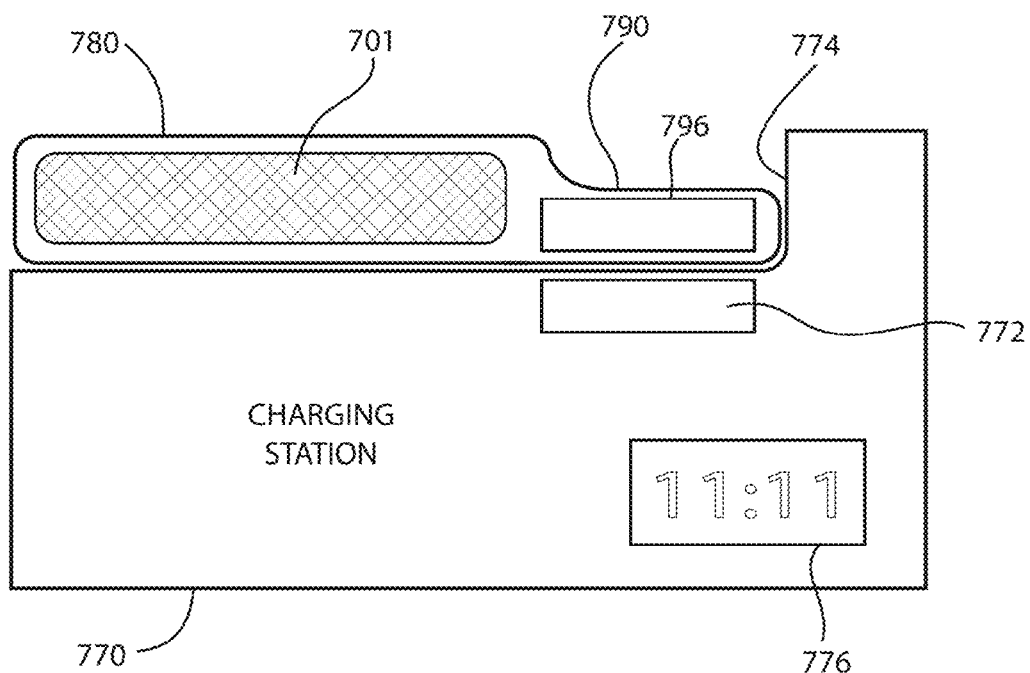
FIG. 15 is a side view of the apparatus of FIG. 13 and a charging station.

In some embodiments, the apparatus is included in a system that also includes a charging station 770, as shown in FIG. 15. The charging station 770 defines a receiving portion 774 configured to receive at least a portion of the apparatus (e.g., at least a portion of the intra-oral housing 780 and/or the external housing 790), a connection assembly 772, and a display 776. The connection assembly 772 is configured to facilitate charging (or recharging) of the power source 792 disposed in the external housing 790. In some embodiments, the connection assembly 772 provides for a physical or wired connection for coupling to a connection assembly 796 of the apparatus to facilitate charging of the power source 792. For example, the connection assembly 772 can include a socket disposed on one of the apparatus or the charging station 770 and a corresponding plug disposed on the other of the apparatus or the charging station. In some embodiments, the connection assembly 772 is configured for wirelessly charging the power source 792. For example, the connection assembly 772 can be configured to inductively charge the power source 792. The display 776 of the charging station 770 is configured to display information associated with the apparatus and/or the charging station. For example, the display 776 can be configured to display information related to a status or amount of the charge of the power source 792, parameters associated with a treatment protocol, and/or instructions for using one of the charging station 770 or the apparatus. In some embodiments, the charging station 770 is configured for uni-directional or bi-directional communication with the apparatus. In this manner, information associated with the treatment protocol and/or treatment history (e.g., patient usage or compliance with the prescribed treatment protocol), including updates including any changes to the treatment protocol and/or treatment history since the most recent information transfer between the apparatus and the charging station.

Figure 16:
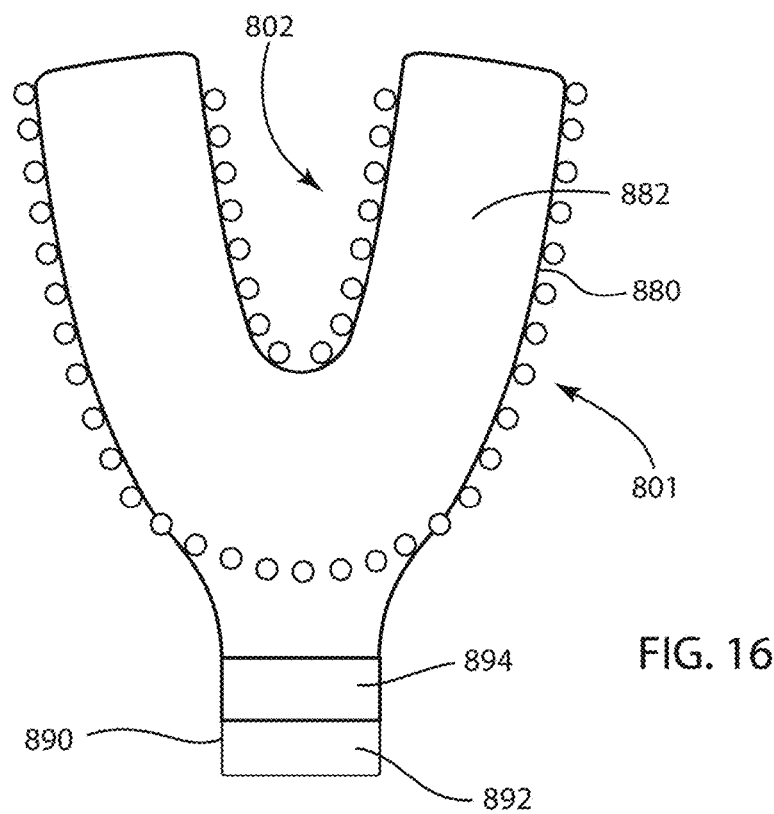
FIGS. 16 and 17 are schematic diagrams of intra-oral light-therapy apparatuses according to an embodiment of the invention.

FIG. 16 is a schematic illustration of an apparatus, according to an embodiment. The apparatus can be configured for intra-oral light therapy of a patient. The apparatus can be similar in one or more respects, and include components similar in one or more respects, or identical, to the apparatus and associated components described herein, including those described herein with reference to FIGS. 13-15. For example, the apparatus includes an intra-oral housing 880 and an external housing 890. The intra-oral housing 880 is configured to be disposed in an oral cavity. The external housing 890 is extended from a front of the intra-oral housing 880 such that at least a portion of the external housing can extend through an opening formed by the patient's lips and such that at least a portion of the external housing is outside of the oral cavity when the intra-oral housing is disposed in the oral cavity.

The intra-oral housing 880 can be configured to be positioned within the oral cavity in any suitable manner described herein. The intra-oral housing 880 includes a first light emitting array 801 configured to be disposed adjacent the anterior root area of an upper and/or lower jaw (and/or the buccal alveolar soft tissue) and a second light emitting array 802 configured to be disposed adjacent the lingual root area of an upper and/or lower jaw (and/or the lingual alveolar soft tissue). For example, from a top view, as schematically shown in FIG. 16, the intra-oral housing 880 can have a shape similar to the shape of a U or a horseshoe. Thus, said another way, the first light emitting array 801 is disposed on an outer portion of the U-shape of the intra-oral housing 880, and the second light emitting array 802 is disposed on an inner portion of the U-shape of the intra-oral housing. In this manner, in use, the light emitting arrays 801, 802 can be configured to emit light in a direction towards the light emitting arrays 803,804, and light emitting arrays 803, 804 can be configured to emit light in a direction towards the light emitting arrays 801, 802.

The light emitting arrays 801, 802 are at least partially embedded in a material of which the intra-oral housing 880 is constructed. The intra-oral housing 880 can be constructed of any suitable material, including, for example, silicone or another soft, e.g., malleable, material. For example, the light emitting arrays 801, 802 can include LEDs, OLEDs, light emitting semiconductors, or any suitable combination thereof, at least partially embedded in the material of which the intra-oral housing 880 is constructed. In some embodiments, the light emitting arrays 801, 802 are fully embedded in the intra-oral housing 880 material.

The intra-oral housing 880 can define a recessed portion 882 in a similar manner as that described with respect to recessed portion 782 in reference to FIG. 13, and thus the recessed portion 782 is not described in detail herein.

The external housing 890 includes a power source 892, electronic circuit 894, and an orientation-sensing mechanism (not shown in FIG. 16). In this manner, the apparatus can be characterized as being self-contained. The power source 892 (e.g., a battery) is configured to provide power to the light emitting arrays 801, 802 via the electronic circuit

894. The electronic circuit 894 can be configured to control the apparatus, e.g., during an orthodontic treatment. The orientation-sensing mechanism is configured to determine a position or orientation of the apparatus, e.g., whether the apparatus is upright for positioning with respect to the upper jaw or upside down for positioning with respect to the lower jaw. The orientation-sensing mechanism can include at least one of a position sensor, a gyroscope (e.g., a semi-gyroscope) and an accelerometer.

The apparatus can be configured to be used with a charging station, such as charging station 770, in a similar manner as the apparatus described herein with reference to FIGS. 13-15.

Figure 17:
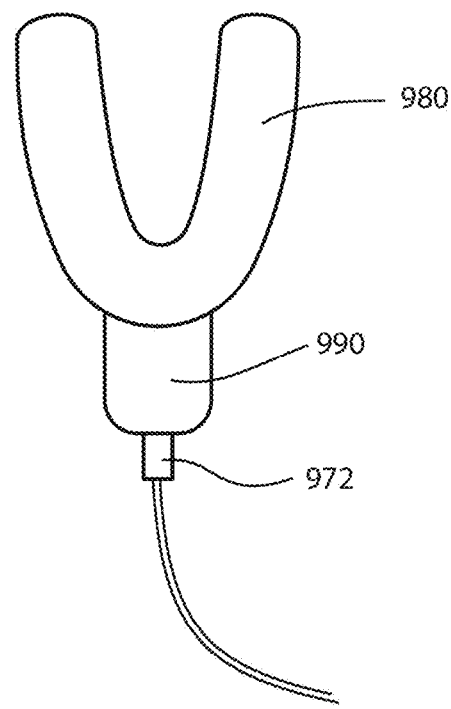

Although the apparatuses described with respect to FIGS. 13-16 have been described as being configured for use with a charging station (e.g., charging station 770), in other embodiments, a self-contained apparatus can be differently configured for charging the power source and/or controlling the emission of light by the apparatus. For example, referring to FIG. 17, an apparatus includes an intra-oral housing 980 configured to be disposed in an oral cavity and an external housing 990 configured to extend through an opening formed by the patient's lips such that at least a portion of the external housing is outside of the oral cavity when the intra-oral housing is disposed in the oral cavity. The intra-oral housing 980 can be similar in one or more respects, and can include components that are similar or identical to those of any intra-oral housing or apparatus for intra-oral light therapy described herein. The external housing 990 can be similar in one or more respects, and can include components that are similar or identical to those of external housings 790 and 890 described herein.

A power source (not shown in FIG. 17) in the external housing 990 is configured to be charged via a connector 972 (e.g., a USB mini- or microplug). The apparatus can be electronically linked, or paired, with an external electronic device, such as a mobile phone, including smartphones (e.g., an iPhone® or an Android™ based device). The apparatus can be configured for at least one of wireless uni-directional or wireless bi-directional communication with the external electronic device, such as via a Bluetooth® or other wireless connection. For example, the apparatus can be configured to transmit to the external electronic device information associated with patient usage and/or treatment protocol compliance, and can be configured to receive from the external electronic device information associated with a medical, e.g., an orthodontic, treatment. An application loaded onto the external electronic device can be used to monitor and control the orthodontic treatment using the apparatus and/or to record and review patient usage history and/or prescribed treatment protocol compliance history.

Figure 18A:
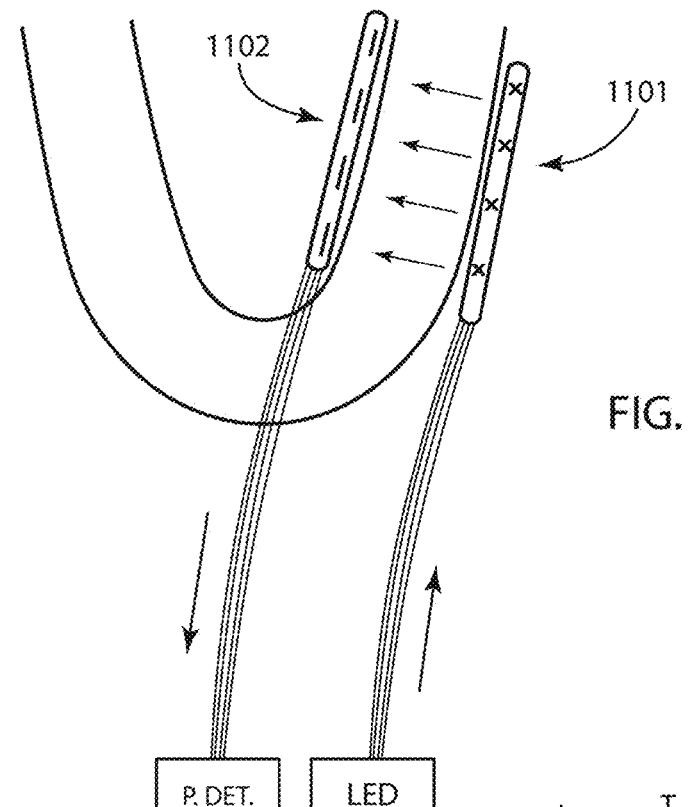
FIG. 18A is a top view of a portion of an intra-oral light-therapy apparatus according to an embodiment of the invention.

In some embodiments, an apparatus according to an embodiment is configured to detect an amount of light, e.g., its intensity or duration that is irradiated at, absorbed by or reflected by a patient's periodontia (e.g., a portion of the root area of the upper and/or lower jaw and/or the alveolar soft tissue) by the apparatus. In this manner, for example, an apparatus according to an embodiment can be configured to assess patient compliance with a prescribed orthodontic treatment protocol, as described herein. Referring to FIG. 18A, an apparatus according to an embodiment can include a light emitting array 1101, which can be similar or identical to any light emitting array described herein, and one or more photodetectors 1102. In some embodiments, the light emitting array 1101 includes one or more emitters operable to illuminate a region of or associated with a portion of the root area of the upper and/or lower jaw and/or the alveolar soft tissue. At least a portion of the photodetectors 1102, such as one or more sensors of the photodetectors, are configured to be positioned within the oral cavity to detect the transmission or reflectance of light (i.e., photons) emitted by the light emitting array 1101 from the alveolar soft tissue (and associated alveolus). For example, the photodetectors 1102, or a sensor thereof, can be positioned on a palatial surface within the oral cavity, and can be in electrical communication with a portion of the photodetector disposed outside of the oral cavity. Detection of the light transmission by the photodetectors 1102 during an orthodontic treatment activates the photodetectors every few seconds. The apparatus can be configured to power off if no light attenuation is detected by the photodetectors within a predetermined period of time. The apparatus can be configured to store a record of the history of light detection and of the apparatus being powered off because of a lack of detection. Such usage information can be used to determine whether the patient is compliant with a prescribed orthodontic treatment protocol. This configuration can also serve as a failsafe mechanism to ensure that the light emitting array 1101 does not operate unless the apparatus is within the mouth of the patient. This configuration can also be used to obtain information about a patient's bone density, where the information can be used to customize a dosage of light therapy to be administered to a patient, as described herein. The foregoing compliance assessment mechanism can be included in, or otherwise incorporated into, any apparatus for intra-oral light therapy described herein.

Figure 18B:
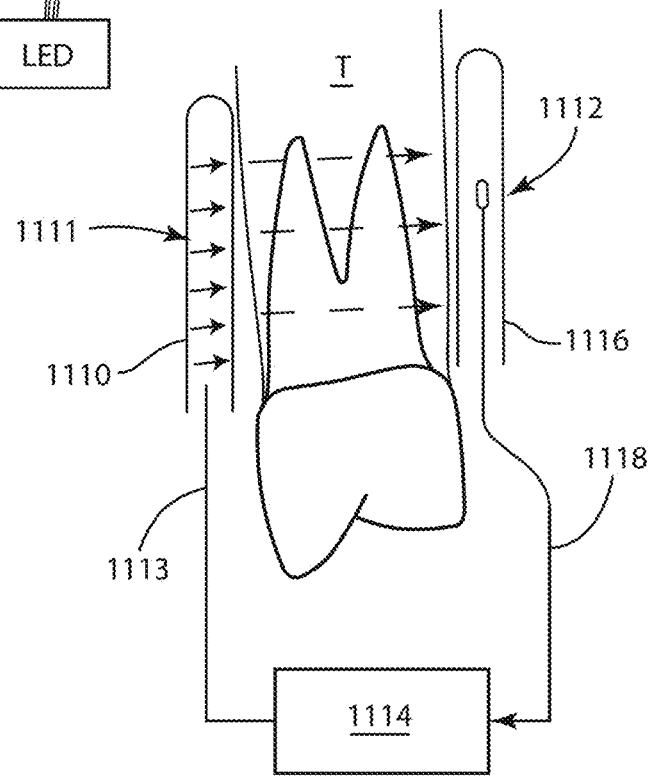
FIG. 18B is a front view of a portion of an intra-oral light-therapy apparatus according to an embodiment of the invention.

In another example, referring to FIG. 18B, an apparatus according to an embodiment is configured to detect an amount of light, e.g., its intensity or duration, that is irradiated at, absorbed by or reflected by a patient's periodontia (e.g., a portion of the root area of the upper and/or lower jaw and/or the alveolar soft tissue) by the apparatus. For example, the apparatus can be configured to determine an energy density that is irradiated at, absorbed by or reflected by the root area from an amount or dosage of light to which the root area was exposed. The apparatus is also configured to determine whether an amount of light being emitted by the apparatus should be adjusted based on the detected amount, intensity and/or duration of light (or energy density) is irradiated at, absorbed by or reflected by the patient's periodontia, as described herein.

In some embodiments, the apparatus includes a mouthpiece having a first flange 1110 and a second flange 1116. The first flange 1110 includes one or a plurality of light emitters 1111, and is configured to be disposed adjacent the buccal side of a first portion of the root area of the upper and/or lower jaw and/or the alveolar soft tissue (generally designated as tissue T) when the mouthpiece is disposed within the patient's oral cavity. In some embodiments, the one or plurality of light emitters 1111 can be at least partially or wholly enclosed in the first flange. In some embodiments, the one or plurality of light emitters 1111 is disposed on a surface of the first flange. The one or plurality of light emitters 1111 are positioned such that light emitted therefrom is directed to the first portion of the root area of the upper and/or lower jaw and/or the alveolar soft tissue. The one or plurality of light emitters 1111 is configured to be in electrical communication with a controller 1114, such as via pathway 1113. In this manner, the controller 1114 can control parameters (e.g., duration, intensity, and wavelength) affecting the emission of light by the one or plurality of light emitters 1111.

The second flange 1116 of the mouthpiece includes one or more photodetectors 1112, and is configured to be disposed adjacent the palatial or lingual side of a second portion, opposite to the first portion, of the root area of the upper and/or lower jaw and/or the alveolar soft tissue when the mouthpiece is disposed within the patient's oral cavity (and the first flange is disposed adjacent the buccal side of the first portion of the root area of the upper and/or lower jaw and/or the alveolar soft tissue). The photodetector 1112 can be at least partially or wholly enclosed within the second flange 1116. The photodetector 1112 is configured to receive light passed through the root area of the upper and/or lower jaw and/or the alveolar soft tissue between the first portion and the second portion. The photodetector 1112 is configured to be in electrical communication with the controller 1114, such as via pathway 1118. The photodetector 1112 is configured to convey information associated with the light received by the photodetector 1112 to the controller 1114. For example, the photodetector 1112 can convey information to the controller 1114 associated with the intensity of light received.

The controller 1114 is configured to execute an algorithm for determining whether a parameter of light emission by the one or plurality of light emitters 1111 should be adjusted, for example, to achieve a target light transmission through the patient's tissue. For example, the controller 1114 can execute the algorithm based on the information associated with the light received by the photodetector 1112 and conveyed to the controller 1114, as well as one or more known parameters (e.g., duration, intensity, and wavelength) associated with the light emission by the one or plurality of light emitters 1111. The controller 1114 can be configured to adjust one or more parameters of light emission by the one or plurality of light emitters 1111 based on the foregoing determination. The parameters of light emission that can be adjusted, or otherwise controlled, by the controller 1114 include an intensity of light emitted by the one or plurality of emitters 1111, a duration of emission of light by the one or plurality of light emitters 1111, one or more wavelengths of light, or one or more of the intensity, duration, and wavelength.

In some embodiments, the controller 1114 is configured to determine whether the mouthpiece of the apparatus is positioned with respect to (e.g., adjacent) the maxilla or mandible root areas. For example, the controller 1114 can cause the one or plurality of light emitters 1111 to emit light at a known intensity, duration, or wavelength. The controller 1114 can then receive information from the photodetector 1112 associated with the transmission of light through the root area, and then determine whether the light was transmitted through the maxillary root area or the mandibular root area based on the received information. In other words, the controller 1114 can determine whether the mouthpiece was positioned with respect to the maxilla if the light transmission received by the photodetector 1112 is within a first value range, or whether the mouthpiece was positioned with respect to the mandible if the light transmission received by the photodetector 1112 is within a second value range.

In some embodiments, the apparatus is configured to be calibrated prior to or at the beginning of a prescribed treatment regime with respect to each of the mandible and maxilla. In this manner, the mouthpiece is positioned with respect to the maxilla, then light is emitted by the one or plurality of light emitters 1111 and an energy density based on the light transmitted through the maxillary root area is detected by the photodetector 1112. With respect to the maxilla, the value of light transmission or reflectance (as the case may be), referred to herein as the $I_{ratio}$, can be calculated as follows, with $I_{delivery}$ being the value (e.g., intensity measured in mW/cm$^2$) of light emitted by the emitter and $I_{transmission}$ being the value (e.g., intensity measured in mW/cm$^2$) of light received by the photodetector:

$$\frac{I_{delivery(max)} \text{ mW/cm}^2}{I_{transmission(max)} \text{ mW/cm}^2} = \gamma_{1\,max} \text{ mW/cm}^2$$

Similarly, with respect to the mandible, the $I_{ratio}$ can be calculated as follows:

$$\frac{I_{delivery(mnd)} \text{ mW/cm}^2}{I_{transmission(mnd)} \text{ mW/cm}^2} = \gamma_{1\,mnd} \text{ mW/cm}^2$$

The $I_{ratio}$ can be, for example, based at least in part on photon power density. The controller 1114 can be configured to store an $I_{ratio}$ value (i.e., the $\gamma_{1max}$ and/or $\gamma_{1mnd}$). In this manner, the apparatus can reference the stored values to determine whether the mouthpiece is optimally positioned with respect to the maxilla or mandible. In a similar manner as described herein with reference to FIG. 18A, the apparatus can be configured to monitor patient compliance throughout the duration of an orthodontic treatment regime. In use, each $I_{ratio}$ value can be adjusted based on a patient's range of tolerance according to the following calculation: $\gamma_1 \pm \%$ range of tolerance. In some embodiments, the controller 1114 is configured to adjust the $I_{delivery}$ to achieve a desired $I_{transmission}$, such as by selectively changing (e.g., increasing or decreasing) the $I_{delivery}$ intensity.

Although the $I_{ratio}$ is described herein as being measured in mW/cm$^2$, in some embodiments, the $I_{ratio}$ can be measured using a different unit of measurement commensurate with a desired lighting parameter, or characteristic. For example, the $I_{ratio}$ can be measured with respect to light wavelength (in, e.g., nanometers). In this manner, the controller 1114 can be configured to, for example, analyze the cellular photo-absorption state as represented by changes in wavelengths absorbed and/or transmitted by chromophores in the patient's tissue.

Referring to FIG. 18C, an apparatus according to an embodiment is configured to control an amount, intensity, wavelength and/or duration of light emitted towards a portion of the root area of the upper and/or lower jaw and/or the alveolar soft tissue and to detect an amount, intensity, wavelength and/or duration of light passed through the root area of the upper and/or lower jaw and/or the alveolar soft tissue. The apparatus can be similar in many respects, or identical to, or include components similar in many respects, or identical, to components of, any other apparatus described herein, such as, for example, apparatus described herein with reference to FIGS. 18A and 18B. In some embodiments, the apparatus includes a mouthpiece having a first flange 1120 configured to be disposed on the buccal side of the root area and a second flange 1126 configured to be disposed on the palatial or lingual side of the root area.

One or more light emitters (e.g., a plurality of light emitters) 1121 are disposed in the first flange 1120. The one or more light emitters 1121 includes individually addressable (or controllable) sections 1123. Parameters affecting the emission of light (e.g., intensity, duration and/or wavelength) by a section of the one or more light emitters 1121 can be controlled separately from and independently of a different section of the one or more light emitters. Stated another way, the intensity, duration, and/or wavelength of light emitted by the one or more light emitters 1121 can vary among the various sections 1123 of the one or more light emitters. The second flange 1126 includes one or more photodetectors (e.g., a plurality of photodetectors 1122). The plurality of photodetectors 1122 can include two or more discrete photodetectors 1124. In some embodiments, the one or more photodetectors 1122 includes a number of photodetectors 1124 equal to the number of sections 1123 in the one or more light emitters 1121. In this manner, each photodetector 1124 can be configured to receive light that was emitted by a corresponding section 1123 of the one or more light emitters 1121 and that passed through the root area between the section 1123 and the photodetector 1124. In this manner, light emission by each section of the one or more light emitters 1121 can be adjusted to accommodate variations in treatment goals for and/or anatomy of different patients, whose alveolar dimensions can vary. These adjustments can be based at least in part on the light received by the corresponding photodetector 1124.

In some embodiments, an apparatus including photodetectors for sensing light transmission or reflectance, such as the apparatus described herein with reference to FIGS. 18A-18C, is configured to perform an initial calibration. For example, in some embodiments, to calibrate the apparatus, the patient places the apparatus in the upper arch of the oral cavity. The apparatus registers its orientation (i.e., upright or upside down) using an internal orientation-sensing mechanism (e.g., a gyroscope). A light source, such as one or more LEDs, is activated. One or more optical fibers act as receivers and photodetectors at their distal ends, which are configured to determine photon, or light, transmission or reflectance. Activation of the light source and determination of the light transmission or reflectance by the receiver/photodetector fibers is repeated, such as for two or three times. An average value of light transmission or reflectance is calculated, and the calculated average value is used as a threshold or range during the orthodontic treatment. If the amount of light detected becomes inconsistent with the threshold or range, then the apparatus deactivates to stop the orthodontic treatment.

In some embodiments, an apparatus includes an intra-oral housing that is contoured to complement curvature and/or other physical attributes of a patient's tissue within the patient's oral cavity. For example, referring to FIGS. 20-22, an apparatus according to an embodiment includes an intra-oral housing 1280 including a front portion 1282 configured to be disposed adjacent buccal alveolar soft tissue of a patient and a rear portion 1284 configured to be disposed adjacent lingual alveolar soft tissue of the patient. A midline M divides left and right sides (also referred to herein as wings or flanges) of the front and rear portions 1282, 1284, respectively, of the intra-oral housing 1280. In some embodiments, a height of the left and or right side is configured to correspond to a length including an average incisor root length and a length of the premolars. A portion of the side that is configured to be adjacent the canine teeth can be slightly under-extended compared to, or shorter than, a different (e.g., incisor) portion of the side. A first light emitting array or mat (not shown in FIGS. 20-22) configured to be disposed adjacent the buccal alveolar soft tissue, for example, can have a length substantially equal to a width of two molar teeth. A second, corresponding light emitting array or mat configured to be disposed on the palatial side of the teeth, adjacent the lingual alveolar soft tissue for example, can have a similar length as the first light emitting array. The intra-oral housing 1280 can include a palatial portion or wing 1288, which can be configured to move vertically with respect to the first and second sides, e.g., up against the upper hard palate.

The intra-oral housing 1280 includes one or more distinct segments 1286 that each include a first portion extending (e.g., downwardly) from a lower surface of the front portion 1282 of the intra-oral housing, a second portion extending (e.g., downwardly) from a lower surface of the rear portion 1284 of the intra-oral housing, and a third portion extending (e.g., horizontally) between ends of the first portion and the second portion of the segment 1286. In this manner, the segments 1286 (also referred to as bite pads) are configured to be disposed about at least a portion of crowns of one or more teeth adjacent each segment when the intra-oral housing 1280 is disposed in the oral cavity as described herein. The segments 1286 are laterally spaced apart from each other with respect to the front portion 1282 of the intra-oral housing 1280. In this manner, when the intra-oral housing 1280 is disposed in the oral cavity as described herein, the segments 1286, or bite pads, are disposed about the crowns of fewer than all teeth. In some embodiments, a first number of the patient's teeth are covered by the segments 1286 and a second number, greater than the first number, are not covered by the segments. For example, each segment 1286 can have a sufficient height, width, and/or depth for being disposed about the crowns of one or two teeth. In use, the patient can bite down on the segments 1286 during the orthodontic treatment, such as to maintain a position of the intra-oral housing 1280 within the oral cavity. Use of the segments, or bite pads, described herein also serves to reduce bulk associated with the surface area of the apparatus, and thus provides enhanced patient comfort.

The segments 1286 can be constructed of a material similar or identical to or different than that of the front and rear portions 1282, 1284 of the intra-oral housing 1280. For example, the front and rear portions 1282, 1284 of the intra-oral housing 1280 can be constructed of a soft, e.g., malleable, material such as silicone, and the segments 1286 can be constructed of a harder, less malleable material, e.g., silicone, that is overmolded with a soft material, such as the soft silicone.

In the embodiment illustrated in FIGS. 20-22, the intra-oral housing 1280 includes three bite pad segments. The first segment is extended from the lower surfaces of the front and rear portions 1282, 1284 along the midline M. The second and third segments are extended from the lower surfaces of the front and rear portions 1282, 1284 at ends of the left and right sides of the intra-oral housing 1280 opposite the midline M. In other embodiments, however, the segments can extend from a different location along the lower surfaces of the front and rear portions 1282, 1284. For example, as shown in FIG. 23, an apparatus can include an intra-oral housing 1380 including a segment extending from the lower surfaces of front and rear portions of the intra-oral housing at a midline (not shown in FIG. 23) defined by the intra-oral housing, and one or more segments extending from the lower surfaces of the front and rear portions of the intra-oral housing from one or more locations between the midline and left and right ends, respectively, of the intra-oral housing opposite the midline.

Figure 24:
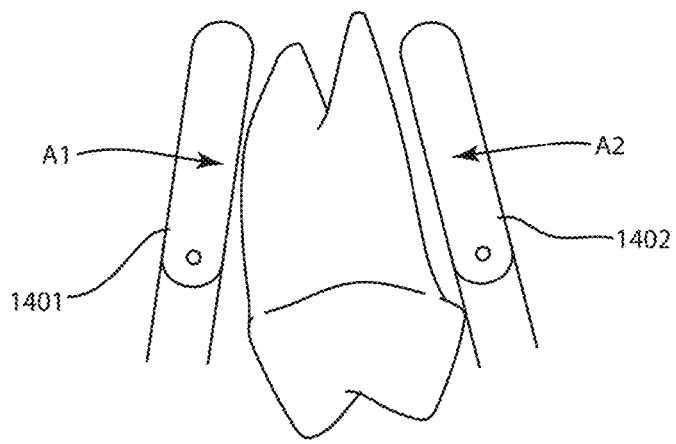
FIGS. 24 and 25 are side and front views, respectively, of portions of intra-oral light-therapy apparatuses according to embodiments of the invention.

In some embodiments, at least a portion of an apparatus is biased towards a portion of the patient's body, which can, for example, help maintain the position of the apparatus with respect to a patient's oral cavity. As shown in FIG. 24, an apparatus can include a first portion 1401 configured to be disposed adjacent a root area of the jaw between the root area and the buccal mucosa, and a second portion 1402 configured to be disposed adjacent the palatial side of the root area of the jaw. The first portion 1401 is biased in a first direction towards the root area, and the second portion 1402 is biased in a second, opposite direction towards the root area. More specifically, the first portion 1401 is spring-loaded such that a free end of the first portion is moved toward and/or can apply a pressure upon the root area in the first direction, indicated by arrow A1, and the second portion 1402 is spring-loaded such that a free end of the second portion is moved toward and/or can apply a pressure upon the root area in the second direction, indicated by arrow A2. In some embodiments, the pressure applied by the first portion 1401 and/or the second portion 1402 is sufficient to displace at least a portion of the patient's tissue. The first and second portions 1401, 1402 can be configured to pivot at a joint disposed adjacent the root area, e.g., immediately above the crown of the tooth.

Figure 25:
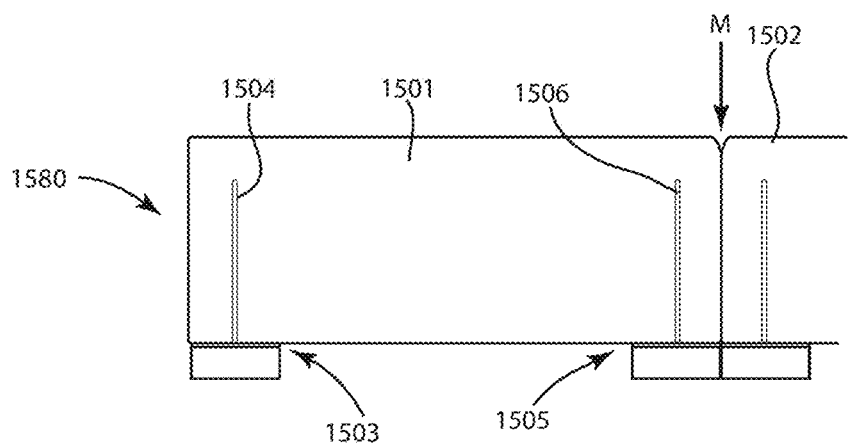

In another example, as shown in FIG. 25, an apparatus can include an intra-oral housing 1580 having a right flange 1501 and a left flange 1502 divided by a midline M. The right flange 1501 and left flange 1502 are each configured to be disposed adjacent a root area of the jaw. The right flange 1501 is biased in a first direction towards the root area. The right flange 1501 is coupled to the apparatus by one or more hinges (e.g., two hinges 1503, 1505, as shown in FIG. 25) and includes one or more wires (e.g., two nitinol or other super-elastic wires, each associated with a respective hinge, as shown in FIG. 25) embedded within the right flange 1501 of the intra-oral housing 1580. For example, the hinges 1503, 1505 can move about a horizontal axis and the nitinol wires 1504, 1506 can be embedded in a silicone of the intra-oral housing 1580 along an axis substantially normal to the horizontal axis of the hinges. The wires 1504, 1506 are configured to be biased towards the root area. As such, the wires 1504, 1506 push against an apical portion of the right flange and cause the right flange 1501 to push against the tissue of the root area. The left flange 1502 can be configured similarly to the right flange 1501. In some embodiments, the hinges 1503, 1505 and/or wires 1504, 1506 can produce a relatively large orthodontic and/or orthopedic force, such as a force operable to urge one or more teeth to move.

Figure 26:
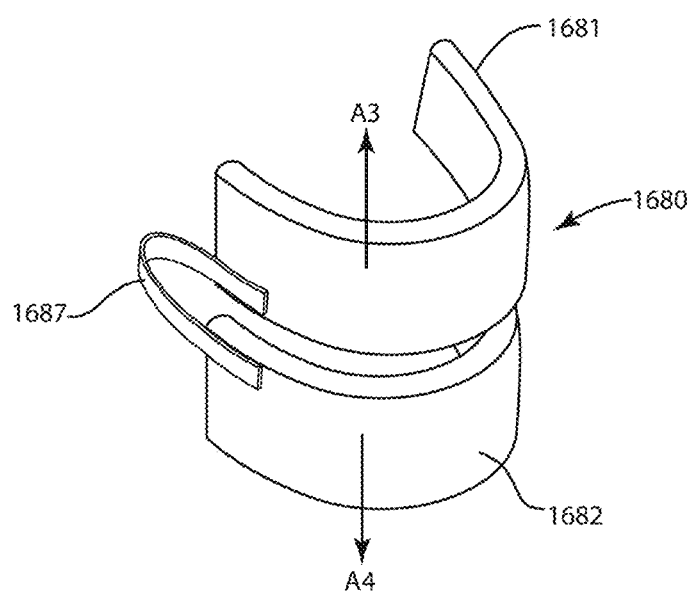
FIG. 26 is perspective view of an intra-oral light-therapy apparatus according to an embodiment of the invention.

In another example, an apparatus according to an embodiment is illustrated in FIG. 26. The apparatus includes an intra-oral housing 1680 having an upper portion 1681 extended between a first end and a second end, and a lower portion 1682 extended between a first end and a second end. The upper and lower portions 1681, 1682 are each configured to be disposed adjacent a root area within an oral cavity. The upper and lower portions 1681, 1682 have a curvature configured to substantially correspond to a curvature of a patient's dentition (e.g., are U or horseshoe shaped). The first end of the upper portion 1681 is coupled to the first end of the lower portion 1682 by a shape retaining member 1687. The shape retaining member 1687 can include, for example, a curved stiff plastic material having shape memory characteristics. The shape retaining member 1687 is biased towards an open configuration in which the first end of the upper portion 1681 is moved in a first direction, indicated by arrow A3, away from the first end of the lower portion 1682 of the intra-oral housing 1680, and the first end of the lower portion 1682 is moved in a second, opposite direction, indicated by arrow A4, away from the first end portion of the upper portion 1681 of the intra-oral housing 1680. The second end of the upper portion 1681 is coupled to the second end of the lower portion 1682 by a similar shape retaining member 1687. As such, the second end of the upper portion 1681 and second end of the lower portion 1682 are biased away from each other towards the open configuration. In this manner, the upper and lower portions 1681, 1682 of the intra-oral housing 1680 are configured to remain adjacent their respective root portions when the patient jaws are opened. The biasing force exerted by the shape retaining member 1687 is sufficient to move the seating of at least a portion of the upper portion 1681 and/or lower portion 1682 toward a depth of the patient's cheek/alveolus vestibule; such force alone, however, may be insufficient to cause the jaw of the patient to open.

Figure 27:
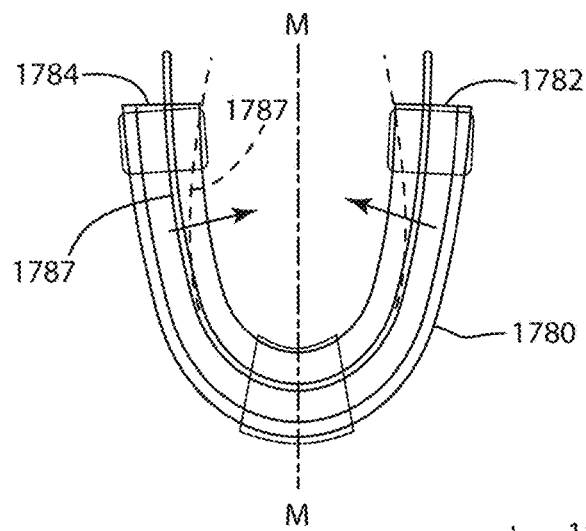
FIGS. 27-29 are top views of intra-oral light-therapy apparatuses according to embodiments of the invention.

A portion of an apparatus according to an embodiment is illustrated in FIG. 27. The apparatus includes a substantially U or horseshoe shaped intra-oral housing. The intra-oral housing can be constructed of a soft silicone. A wire 1787 (e.g., nitinol or other super-elastic wire), or other shape retaining member, is embedded in the intra-oral housing. A first end of the wire is disposed at a first end 1782 of the intra-oral housing 1780, and a second end of the wire is disposed at a second, opposite, end 1784 of the intra-oral housing. The first and second ends of the wire are inwardly biased such that the first end of the intra-oral housing and second end of the intra-oral housing are (or can be) moved in a direction towards each other. In other words, the wire is biased to move from an open position in which the first and second ends 1782, 1784 of the intra-oral housing 1780 are disposed a first distance from a midline M of the intra-oral housing, as shown by the solid line in FIG. 27, to a closed position in which the first and second ends 1782, 1784 are disposed a second distance less than the first distance from the midline M of the intra-oral housing, as shown by the dashed line in FIG. 27. In this manner, the wire causes a portion of the intra-oral housing (e.g., left and right portions and/or light emitting panels) to apply a gentle pressure on the buccal side of the root area towards a lingual or palatial side of the root area. Also in this manner, the intra-oral housing 1780 is configured to cause displacement of a portion of oral soft tissue over the tooth root.

Figure 28:
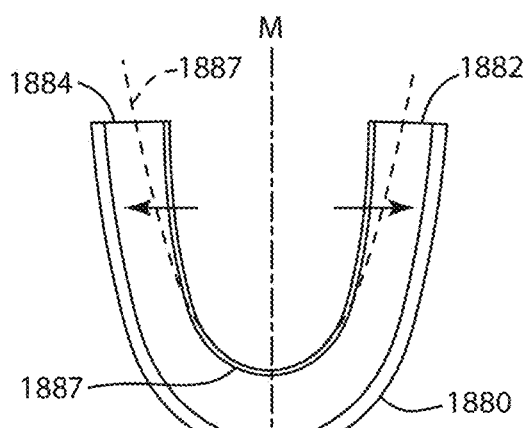

In some embodiments, as shown in FIG. 28, an apparatus can include an intra-oral housing 1880 having a wire 1887 (e.g., nitinol or other super-elastic wire), or other shape retaining member, configured to bias first and second ends 1882, 1884, respectively, of the intra-oral housing 1880 away from each other, e.g., in a direction opposite to that shown and described with reference to FIG. 27. In other words, the wire 1887 is biased to move from a closed position in which the first and second ends 1882, 1884 are disposed a first distance from a midline M of the intra-oral housing as shown by the solid line in FIG. 28 to an open position in which the first and second ends 1882, 1884 are disposed a second distance greater than the first distance from the midline M of the intra-oral housing as shown by the dashed line in FIG. 28. In this manner, the wire is configured to cause a portion of the intra-oral housing (e.g., left and right portions and/or light emitting panels, not shown in FIG. 28) to apply a gentle pressure on the lingual or palatial side of the root area towards, or in the direction of, the buccal side of the root area. Also in this manner, the intra-oral housing 1880 is configured to cause displacement of a portion of oral soft tissue over the tooth root.

Figure 29:
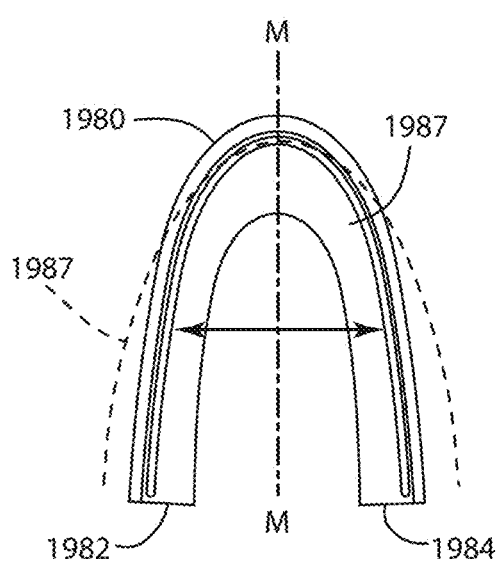
Figure 30:
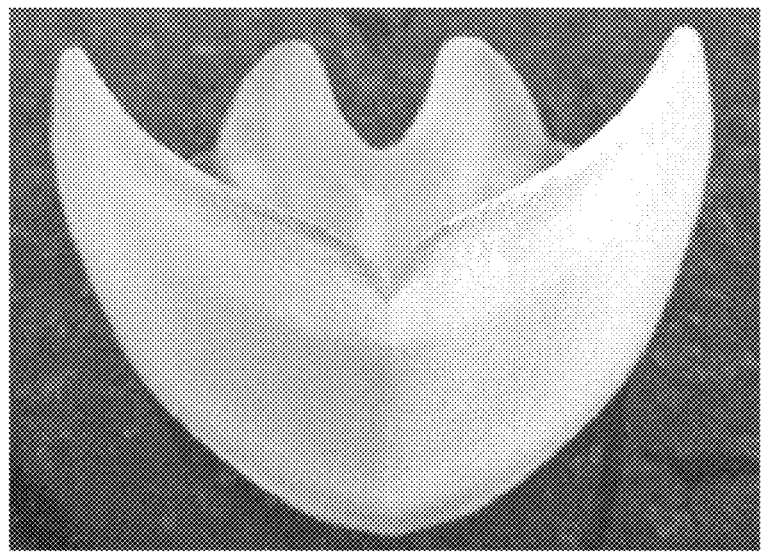
FIGS. 30-33 are perspective views of an intra-oral light-therapy apparatus according to an embodiment of the invention.
Figure 31:
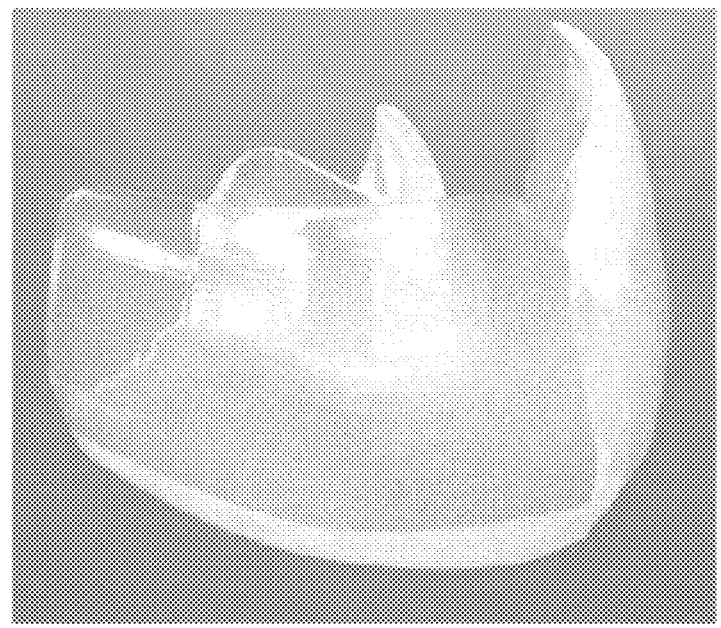
Figure 32:
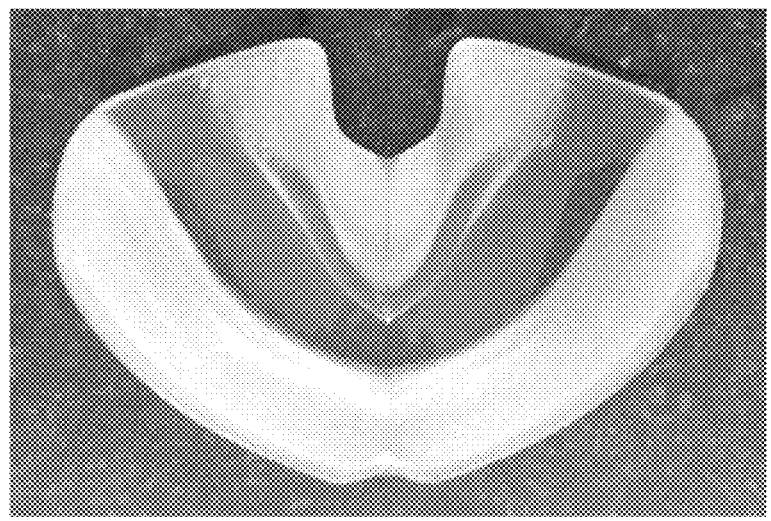
Figure 33:
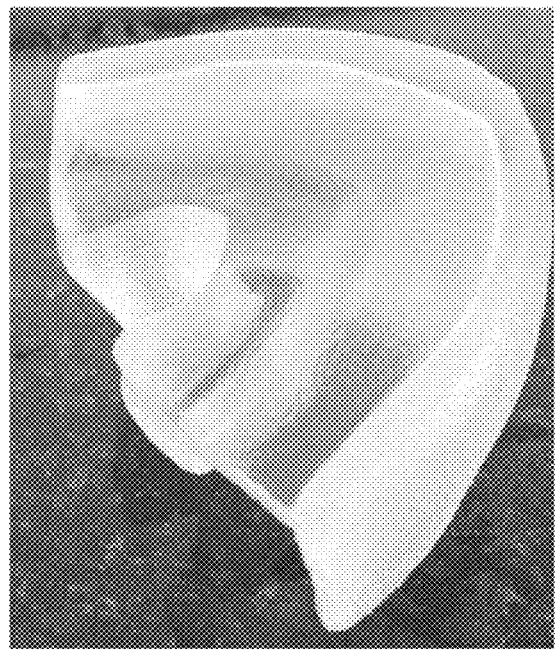
Figure 34:
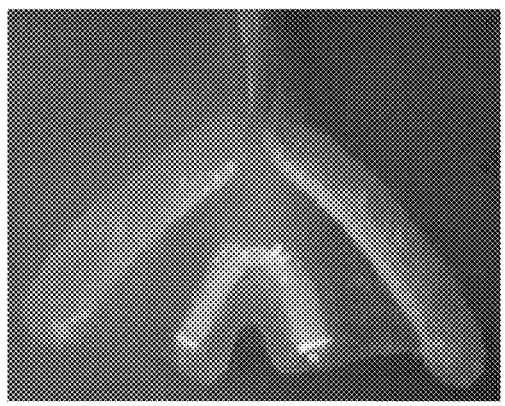
FIGS. 34 and 35 are top and rear views, respectively, of the apparatus of FIGS. 30-33 in a powered (i.e., "on") operational state.
Figure 35:
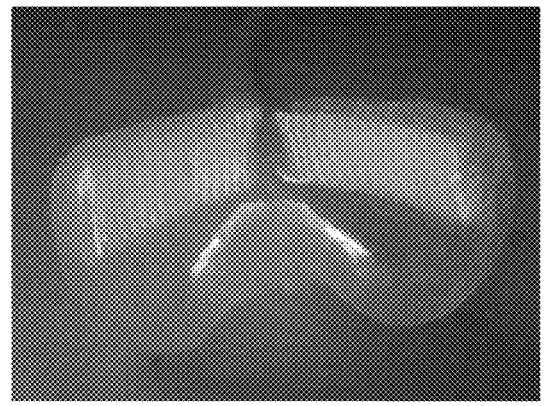
Figure 36:
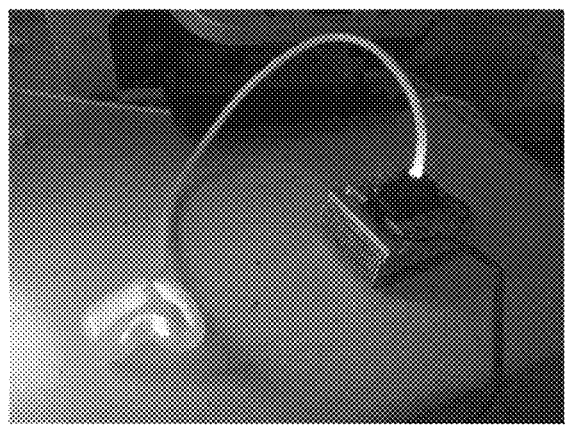
FIG. 36 is a perspective view of the apparatus of FIGS. 34 and 35 coupled to an electronic device.

The wire 1887 can be disposed within the intra-oral housing 1880 in any suitable position. For example, as shown in FIG. 28, the wire 1887 can be positioned adjacent an inner curvature of the intra-oral housing 1880. In other embodiments, however, a wire 1987 can be positioned adjacent an outer curvature of an intra-oral housing 1980, as shown in FIG. 29. The wire 1987 can be similar in many respects to wire 1887, for example, in that the wire 1987 can be configured to bias first and second ends 1982, 1984, respectively, of the intra-oral housing 1980 away from each other, e.g., in a direction opposite to that shown and described with reference to FIG. 27 and similar to that shown and described with reference to FIG. 28. In other words, the wire 1987 is biased to move from a closed position (as shown by the solid line in FIG. 29) to an open position (as shown by the dashed line in FIG. 28) in a similar manner as described herein with reference to FIG. 28. Thus, the wire 1987 is configured to cause a portion of the intra-oral housing 1980 to apply a gentle laterally, and outwardly, directly pressure on the lingual or palatial side of the root area.

Although the apparatuses depicted in FIGS. 27 and 28 are described as including a wire (e.g., a nitinol wire) as the shape retaining member, in other embodiments, a different shape retaining member (or biasing member) can be included in the apparatus. For example, the shape retaining member can include an overmolded plastic insert.

Figure 43:
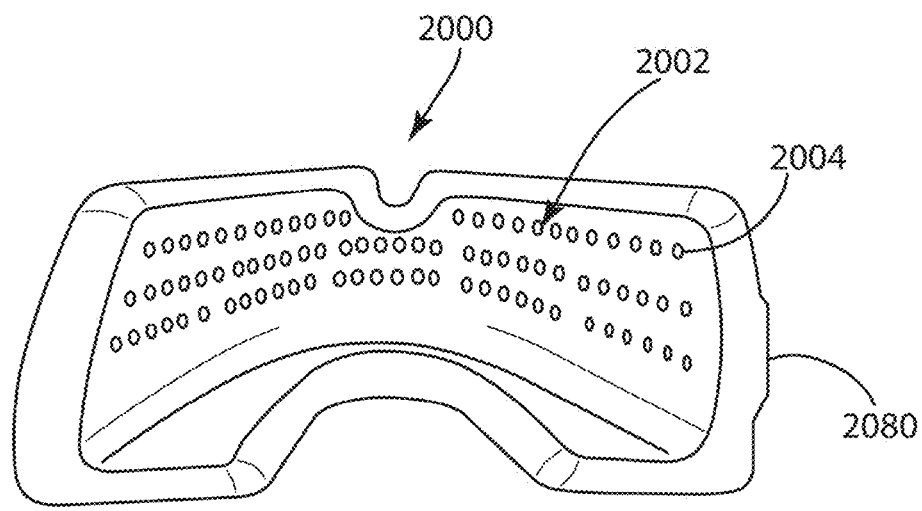
FIG. 43 is a rear view of an intra-oral apparatus according to an embodiment of the invention.
Figure 44:
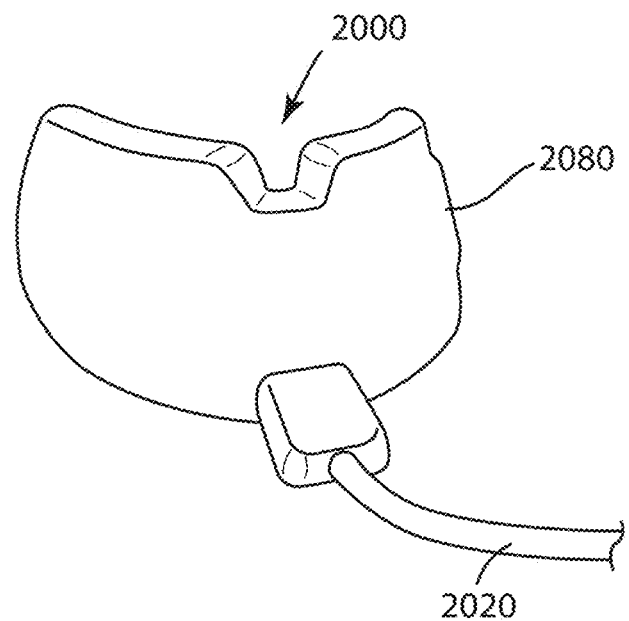
FIG. 44 is a front view of the intra-oral apparatus of FIG. 43.
Figure 45:
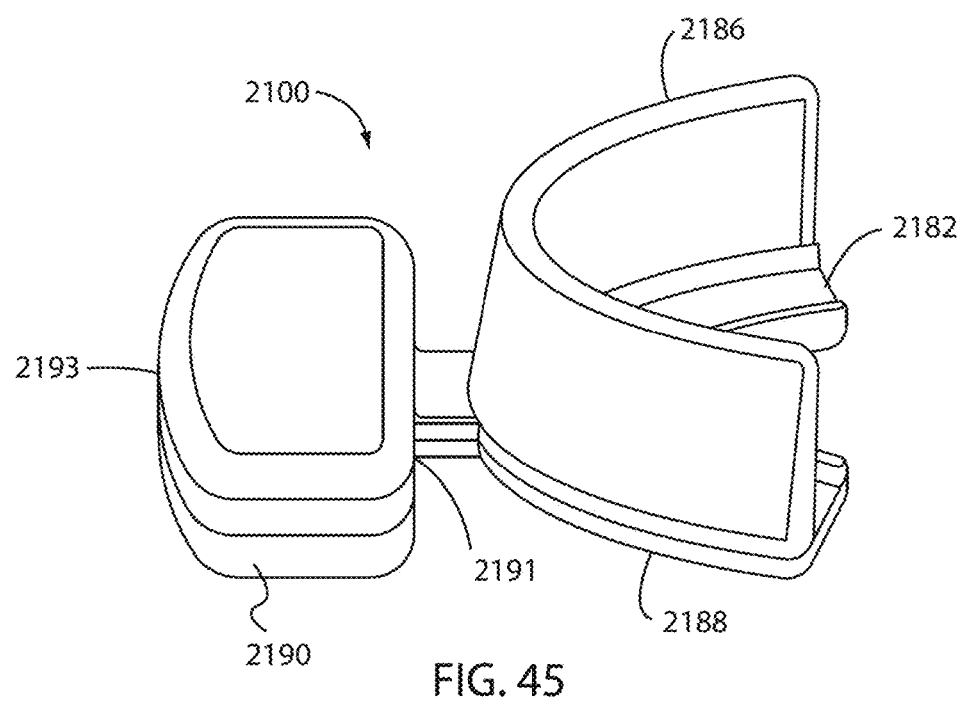
FIGS. 45 and 46 are side and top views of an intra-oral apparatus according to an embodiment of the invention.

An intra-oral apparatus 2000 according to an embodiment of the invention is illustrated in FIGS. 43 and 44. The apparatus 2000 can be the same as or similar in many respects to, or include components the same as or similar in many respects to, the intra-oral apparatuses described herein. The intra-oral apparatus 2000 includes an intra-oral housing 2080 configured to be disposed in an oral cavity of a patient. In some embodiments, the intra-oral housing 2080 is configured to be positioned within the oral cavity of the patient with respect to the upper jaw, the lower jaw, or each of the upper and lower jaws. The intra-oral housing 2080 includes at least one light emitting panel 2002. The light emitting panel 2002 can include one or more light emitters 2004, such as LEDs. The intra-oral apparatus 2000 can be configured to irradiate light in any suitable manner described herein. In some embodiments, for example, the intra-oral apparatus 2000 can be configured to irradiate light at a density of about 60 mW/cm$^2$.

Although the light emitting panel 2002 is illustrated as including the one or more light emitters 2004 in three parallel rows, in other embodiments, the one or more light emitters can be differently positioned with respect to the light emitting panel and/or the intra-oral housing (e.g., in one or more vertical rows, one or more diagonal rows, a random pattern, or any other suitable configuration). In some embodiments, the light emitting panel 2002 is at least partially enclosed within the intra-oral housing 2080. For example, the light emitting panel 2002 can be embedded within the intra-oral housing 2080. The intra-oral housing 2080 can be constructed of any suitable material, including, for example, a soft silicone material. The intra-oral housing 2080 is configured to be electrically coupled to an electronic device, such as a controller (not shown in FIGS. 43-44) as described herein. As shown in FIG. 44, the intra-oral housing 2080 can be coupled to the electronic device by a tether 2020.

The intra-oral apparatus 2000 can be configured for use in an orthodontic treatment, including any such treatment described herein. In some embodiments, for example, the intra-oral apparatus 2000 is used to irradiate at least a portion of the patient's upper jaw for about 3 minutes, the patient's lower jaw for about 3 minutes, or each of the patient's upper and lower jaws for about 3 minutes.

An intra-oral apparatus 2100 according to an embodiment of the invention is illustrated in FIGS. 45-50. The apparatus 2100 can be the same as or similar in many respects to, or include components the same as or similar in many respects to, the intra-oral apparatuses described herein. The intra-oral apparatus 2100 includes an intra-oral housing 2180 configured to be disposed in an oral cavity (e.g., in the mouth) of a patient and an extra-oral housing 2190 (also referred to herein as a "bill") coupled to the intra-oral housing 2180. The extra-oral housing 2190 is coupled to a front portion of the intra-oral housing 2180. For example, the extra-oral housing 2190 can be coupled to the intra-oral housing 2180 by a protrusion 2188. In this manner, the protrusion 2188 is extended through the opening of the patient's mouth, e.g., through the opening between the patient's lips, such that at least a portion of the extra-oral housing 2190 is disposed exterior to the oral cavity of the patient when the intra-oral housing 2180 is disposed within the oral cavity of the patient. Also in this manner, the extra-oral housing 2190, or bill, can be supported with respect to the patient's mouth by the intra-oral housing 2180 and/or the protrusion 2188 when the intra-oral housing 2180 is disposed within the patient's mouth. The extra-oral housing 2190 is configured to at least partially enclose one or more electronic components of the apparatus 2100, as described in more detail herein.

The intra-oral apparatus 2100 is configured to be useful for light therapy with respect to each of the upper jaw and the lower jaw of the patient. In other words, the intra-oral apparatus 2100 can be configured to administer light therapy with respect to the patient's upper jaw when the apparatus is in an upright position, and can be configured to administer light therapy with respect to the patient's lower jaw when the apparatus is in an inverted position. As such, the intra-oral housing 2180 can be configured to be disposed within the patient's oral cavity with respect to each of the upper and lower jaws of the patient. It should be noted that although the intra-oral apparatus 2100 and intra-oral housing 2180 are described as being in the upright position when configured to be oriented with respect to the upper jaw and in the inverted position when configured to be oriented with respect to the lower jaw, in other embodiments, the intra-oral apparatus 2100 and the intra-oral housing 2180 are in the upright position when configured to be oriented with respect to the lower jaw of the patient, and in the inverted position when configured to be oriented with respect to the upper jaw of the patient.

The intra-oral apparatus 2100 can be configured to determine the orientation of the apparatus. Said another way, the intra-oral apparatus 2100 can be configured to determine if the intra-oral housing 2180 is oriented in the upright or inverted position. For example, the intra-oral apparatus 2100 includes a gyroscope (not shown in FIG. 47) configured to determine if the intra-oral housing 2180 is oriented in the upright or inverted position. The gyroscope is disposed within, or otherwise coupled to, the extra-oral housing 2190 of the apparatus 2100.

Figure 47:
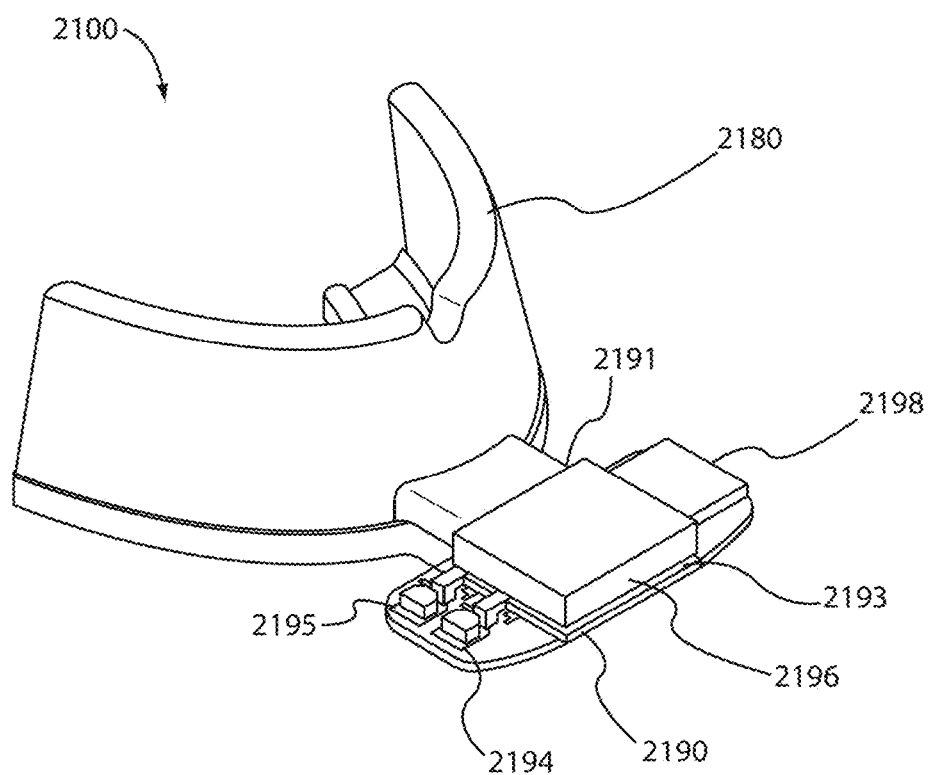
FIG. 47 is a perspective view of a portion of the intra-oral apparatus of FIG. 45.
Figure 48A:
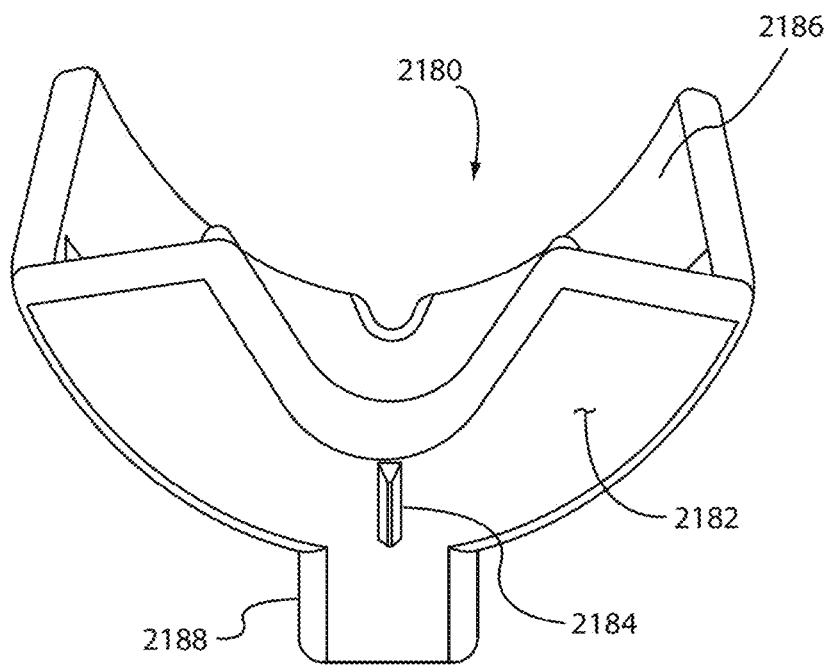
FIGS. 48A and 48B are bottom-rear and top-rear perspective views of a portion of the intra-oral apparatus of FIG. 45.
Figure 48B:
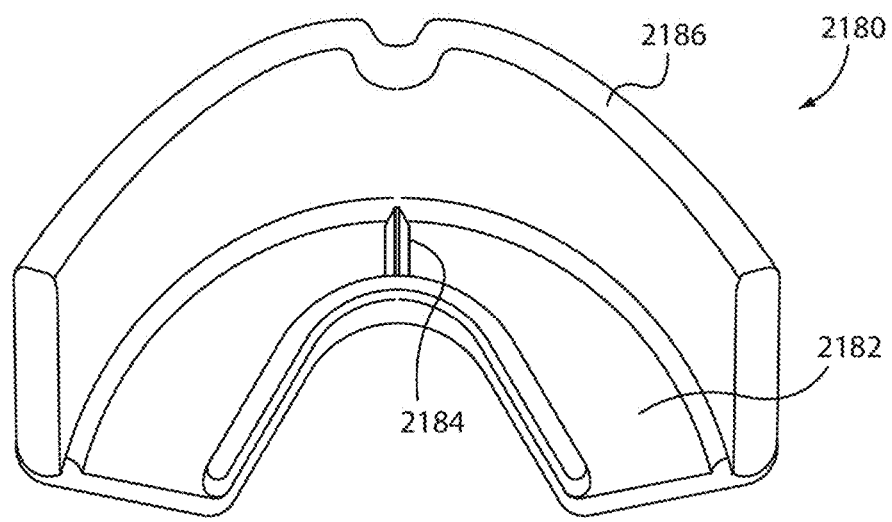

The apparatus 2100 includes at least one battery, or other suitable power source. For example, as shown in FIG. 47, a first battery 2194 and a second battery 2195 are coupled to the extra-oral housing 2190 of the apparatus 2100. For example, the batteries 2194, 2195 can be disposed in the extra-oral housing 2190. Each battery 2194, 2195 can be configured to provide power to one or more light-emitting panels (schematically illustrated in FIG. 52) disposed within the intra-oral housing 2180, as described in more detail herein. The first battery 2194 can include, for example, a rechargeable lithium ion battery. The second battery 2195 can be configured for inductive charging. For example, the second battery 2195 can include a Qi-based charging coil.

A microprocessor 2196 is coupled to the extra-oral housing 2190 of the apparatus 2100. The microprocessor 2196 can be disposed in the extra-oral housing 2190. The microprocessor 2196 is configured to store information related to the patient's use of the intra-oral apparatus 2100. For example, the microprocessor 2196 can be configured to store information associated with the patient's treatment program and use of the apparatus 2100 during the treatment program, including, for example, a schedule of one or more treatment sessions included in the treatment program, an orientation of the apparatus 2100 during a treatment session, a duration of a treatment session, and a duration between a treatment session and one or more previous treatment sessions. The microprocessor 2196 can also be configured to determine whether the patient's usage of the intra-oral apparatus 2100 is in compliance with the patient's treatment program. In other words, the microprocessor 2196 can be configured to determine whether a patient's history of use (including, for example, a number of treatment sessions applied to the upper and/or lower jaw of the patient, duration of the treatment sessions, whether any treatment session was interrupted, and the like) complies with a schedule of treatment sessions specified by the patient's treatment program, including identifying any deviation from the treatment program. The microprocessor's 2196 determination regarding patient compliance can be based, at least in part, on information received from the proximity detector. For example, the proximity detector can be configured to be activated when the device is placed fully into the patient's mouth. The microprocessor 2196 can be configured to transmit information associated with the patient's usage and/or compliance of the apparatus 2100 with an external device. For example, in some embodiments, the microprocessor 2196 is configured to transmit the usage and/or compliance information to the external device (e.g., a mobile phone, personal digital assistant, computer, portable electronic device, or the like) via Bluetooth® or another suitable wireless mechanism. For example, as shown in FIG. 47, a Bluetooth® communication module 2198 can be disposed within the extra-oral housing 2190.

The extra-oral housing 2190 includes a communication mechanism (not shown in FIG. 47) configured to provide indicia of the status of a treatment session. The term "indicia," is used herein as including the singular ("indicium") or the plural ("indicia"), unless the context clearly indicates otherwise. The indicia can include one or more of an audible indicia (e.g., a tone, beep, announcement, or the like), a tactile indicia (e.g., a vibration or the like), or a visual indicia (e.g., a light, a displayed message, or the like). More specifically, for example, the extra-oral housing 2190 includes a light indicia that is configured to indicate a status, or stage, of the treatment session. The light indicia is configured to display no light during a first stage of the treatment session, a blinking or pulsed light during a second stage of the treatment session, and/or a solid light during a third stage of the treatment session. The light indicia can be, for example, configured to display a solid light for a first predetermined duration (e.g., 2 minutes and 30 seconds, 2 minutes and 45 seconds, or 2 minutes and 10 seconds) upon initiation of the treatment session. The light indicia can be configured to display the blinking or pulsed light for a second predetermined duration (e.g., 10, 15 or 30 seconds) following the first predetermined duration as a signal to the patient that the treatment session is nearing its end. The light indicia can be configured to display no light when a treatment session is ended (e.g., after 3 minutes from initiation of the treatment session) and the apparatus 2100 is not irradiating light.

In some embodiments, the extra-oral housing 2190 has a sufficient length (e.g., between a first end 2191 of the extra-oral housing engaged with the intra-oral housing 2080 and a second, opposite, end 2193 of the extra-oral housing (i.e., the end of the extra-oral housing farthest from the patient's oral cavity when the intra-oral housing is disposed in the patient's oral cavity)) such that at least a portion of the extra-oral housing is visible to the patient when the intra-oral housing is disposed in the patient's oral cavity. In other words, at least a portion of the extra-oral housing 2190, e.g., including the second end 2193 of the extra-oral housing, is within the patient's line of sight when the intra-oral housing 2180 is disposed with the patient's oral cavity. In this manner, the light indicia can be coupled to the extra-oral housing 2190 in a manner such that the light indicia is within the patient's line of sight during the treatment session.

As noted herein, the intra-oral housing 2180 is configured to be positioned within the oral cavity of the patient with respect to the upper jaw, the lower jaw, or is invertible for positioning with respect to each of the upper and lower jaws. The intra-oral housing 2180 can be similar in one or more respects, and include components similar in one or more respects, or identical, to the intra-oral housings described herein, including, for example, the intra-oral housings described herein with reference to FIGS. 13-15 and 43-44. Accordingly, the intra-oral housing 2180 is not described in detail.

The intra-oral housing 2180 includes a lower portion 2182 and an upper portion 2186. The lower portion 2182 has a first plane, and the upper portion 2186 has a second plane different than the first plane. For example, the upper portion 2186 can be substantially vertical, and the lower portion 2182 can be substantially horizontal when the intra-oral housing 2180 is disposed within the patient's oral cavity for a treatment session. In this manner, the upper portion 2186 can be disposed adjacent a portion of a side of the patient's teeth and/or adjacent the alveolar mucosa and the lower portion 2182 can be disposed adjacent an occlusal surface of the patient's teeth. For example, the lower portion 2182 can be configured as a bite pad for the patient to bite down upon during a treatment session.

Figure 46:
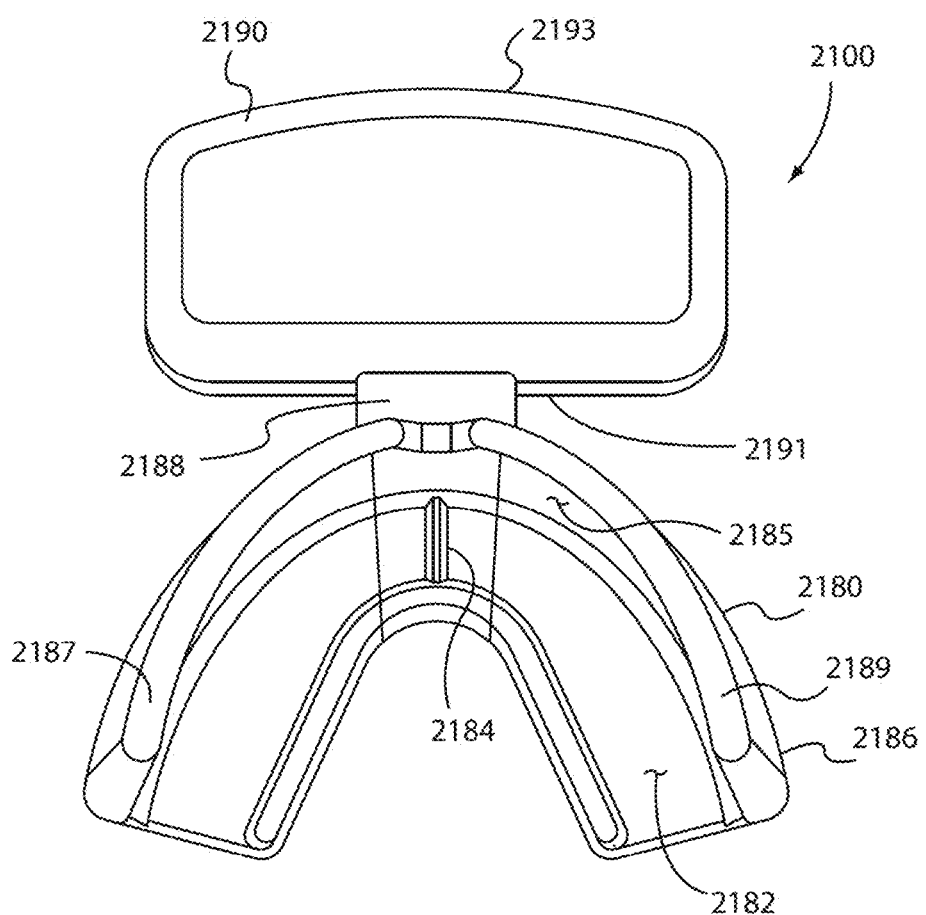

As shown in FIG. 46, the lower portion 2182 of the intra-oral housing 2180 includes a ridge 2184. The ridge 2184 is disposed along a midline of the intra-oral housing 2180 and is elevated with respect to the first plane of the lower portion 2182. The ridge 2184 facilitates positioning of the intra-oral housing 2180 within the patient's oral cavity by the patient when the intra-oral housing 2180 is disposed within the patient's oral cavity. For example, the intra-oral housing 2180 is configured to be positioned within the patient's oral cavity such that the ridge 2184 is disposed between the patient's front central incisors. Proprioception of the patient related to the teeth and periodontium would permit sensory feedback to the patient regarding the position of the ridge 2184 of the intra-oral housing 2180. In this manner, the ridge 2184 facilitates centering of the intra-oral housing 2180 within the oral cavity, thus promoting symmetry of a light therapy treatment on the alveolus, or other oral tissue, on both sides of the patient's mouth. In other words, in order to promote the symmetrical administration of light therapy to the root area, the intra-oral housing 2180 can be positioned with the midline of the intra-oral housing 2180 seated along the sagittal plane or within (i.e., plus or minus) 5 degrees of the sagittal plane, and the ridge 2184 can facilitate such obtaining such a position.

The upper portion 2186 includes a first (or left) flange 2187 and a second (or right) flange 2189. The flanges 2187, 2189 are each configured to apically displace oral soft tissue. More specifically, the flanges 2187, 2189 are each configured to displace buccal tissue away from the patient's alveolus. In some embodiments, an inner face 2185 of the upper portion 2186 can be spaced apart from the patient's alveolar tissue when the intra-oral housing 2180 is disposed within the patient's mouth and the flanges 2187, 2189 are displacing the buccal tissue. In some embodiments, at least a portion of the inner face 2185 of the upper portion 2186 can contact the patient's alveolar tissue when the intra-oral housing 2180 is disposed within the patient's mouth and the flanges 2187, 2189 are displacing the buccal tissue.

The intra-oral housing 2180 can be constructed of any suitable material, including, for example, an elastomeric material (e.g., a soft silicone). More specifically, in some embodiments, the intra-oral housing can be fabricated from medical-grade injection molded highly flexible silicone. The ridge 2184 can be constructed of the same material as the intra-oral housing 2180, or at least the same material as the lower portion 2182 of the intra-oral housing 2180. In this manner, when a patient bites together with the upper and lower jaw, the lower portion 2182 of the intra-oral housing 2180, including the ridge 2184, may deform slightly from pressure exerted by an occlusal surface of the patient's teeth. Nonetheless, the ridge 2184 is of sufficient dimensions that the patient should be aware of its position, despite any slight deformation of the lower portion 2182 and/or ridge 2184.

Figure 52:
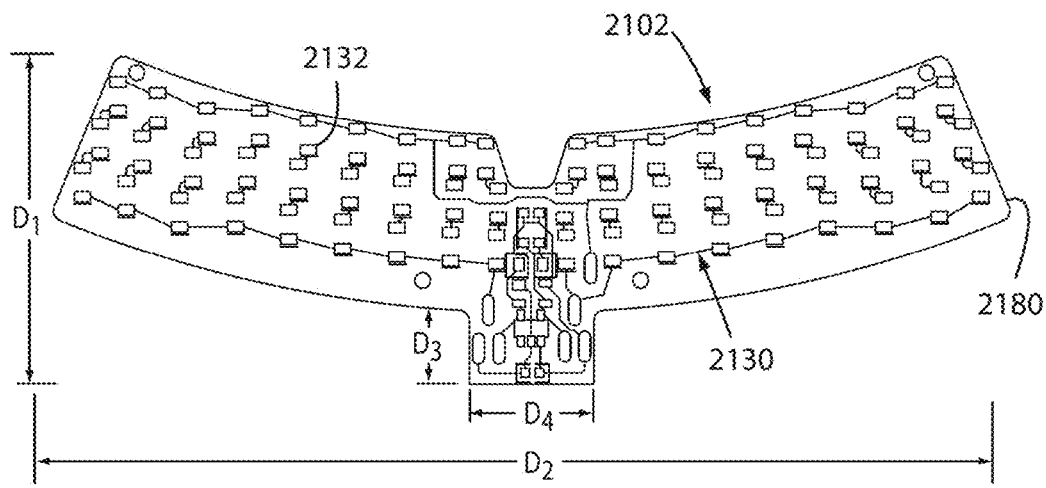
FIG. 52 is a schematic illustration of a portion of the intra-oral apparatus of FIG. 45.

The intra-oral housing 2180 includes at least one light emitting panel 2102 (the circuitry 2130 of which is schematically illustrated in FIG. 52). The light emitting panel 2102 can include one or more light emitters 2132, such as a plurality of LEDs, and a flexible circuit 2130. The intra-oral apparatus 2100 can be configured to irradiate light in any suitable manner described herein to irradiate the alveolus and/or root area of the patient. The LEDs, or other suitable light emitter(s), can be included in the light emitting panel 2102 in any suitable configuration, including in any configuration described herein. In some embodiments, the light emitting panel 2102 is at least partially enclosed within the intra-oral housing 2180. For example, the light emitting panel can be embedded within the intra-oral housing 2180 (e.g., in the inner face 2185 of the upper portion 2186 of the intra-oral housing 2180. As noted herein, the intra-oral housing 2180 can be constructed of a soft silicone material. In this manner, the light emitting panel, and thus any LED or light emitter included in the panel, can be embedded in the silicone material such that the light emitting panel is prevented from engaging a portion of the patient's oral tissue when the intra-oral housing 2180 is disposed within the patient's oral cavity. The light emitting panel 2102 can have any suitable dimensions for being coupled to, or embedded in, the upper portion 2186 of the intra-oral housing 2180. For example, as shown in FIG. 52, the light emitting panel 2102 can have a height $D_1$ and a width $D_2$ greater than the height $D_1$. In some embodiments, for example, the panel 2102 has a height of about 31.9 mm and a width of about 92.5 mm. A portion of the height $D_1$ of the panel 2102 can include a lower protrusion that extends downwardly from left and right flanges 2187, 2189 of the intra-oral housing 2180. The protrusion can have a height $D_3$ and a width $D_4$. In some embodiments, for example, the protrusion has a height of about 6.9 mm and a width of about 12 mm. Although specific examples of the dimensions of the panel 2102 are provided, such dimensions are presented by way of example only, and not limitation.

The intra-oral housing 2180 can be configured to be disposed within the patient's oral cavity such that an outer surface of the intra-oral housing 2180 is spaced apart from the alveolar soft tissue of the patient. In this manner, the intra-oral housing 2180 is configured to be spaced apart from (i.e., not touch) the alveolar soft tissue of the patient during the treatment session. In some embodiments, for example, at least a portion of the intra-oral housing 2180 can be configured to be disposed over at least a portion of the patient's teeth. A first portion of the intra-oral housing 2180 is disposed about the portion of the patient's teeth and a second portion of the intra-oral housing 2180 is disposed proximate to and spaced apart from the alveolar soft tissue when the intra-oral housing 2180 is disposed in the patient's mouth.

In some embodiments, at least a portion (e.g., the first portion) of the intra-oral housing 2180 is configured to snap onto, or otherwise snugly fit, at least a portion of the patient's teeth when the intra-oral housing 2180 is disposed in the patient's mouth for the treatment session. For example, at least a portion of the intra-oral housing 2180 can be biased in a manner similar to that described herein with reference to FIGS. 24 and/or 25. In some embodiments, the intra-oral housing 2180 can include one or more retractors configured to facilitate opening of the patient's mouth. In some embodiments, at least a portion of the intra-oral housing 2180 can be configured to contact at least a portion of the alveolar soft tissue when the intra-oral housing 1280 is disposed within the patient's mouth for the treatment session. In some embodiments, at least a portion of the intra-oral housing 2180 is configured to not contact, but be within a certain distance (e.g., within 0.1 cm to 3 cm) of the alveolar soft tissue when the intra-oral housing 2180 is disposed within the patient's mouth for the treatment session.

Figure 49:
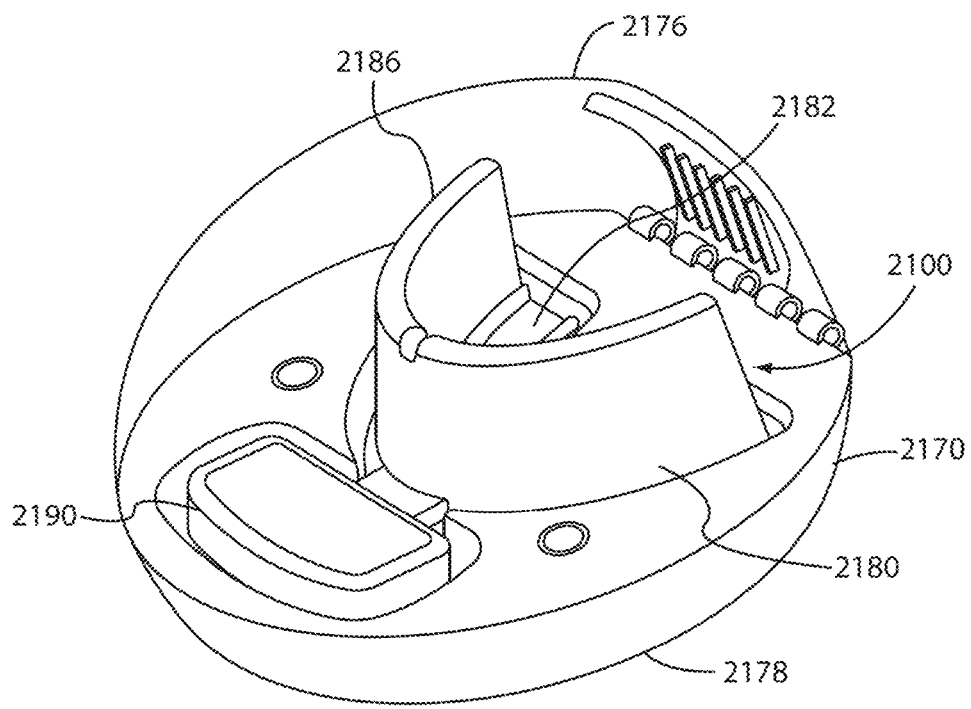
FIGS. 49 and 50 are perspective and front views of the intra-oral apparatus of FIG. 45 and an external station according to an embodiment of the invention.
Figure 50:
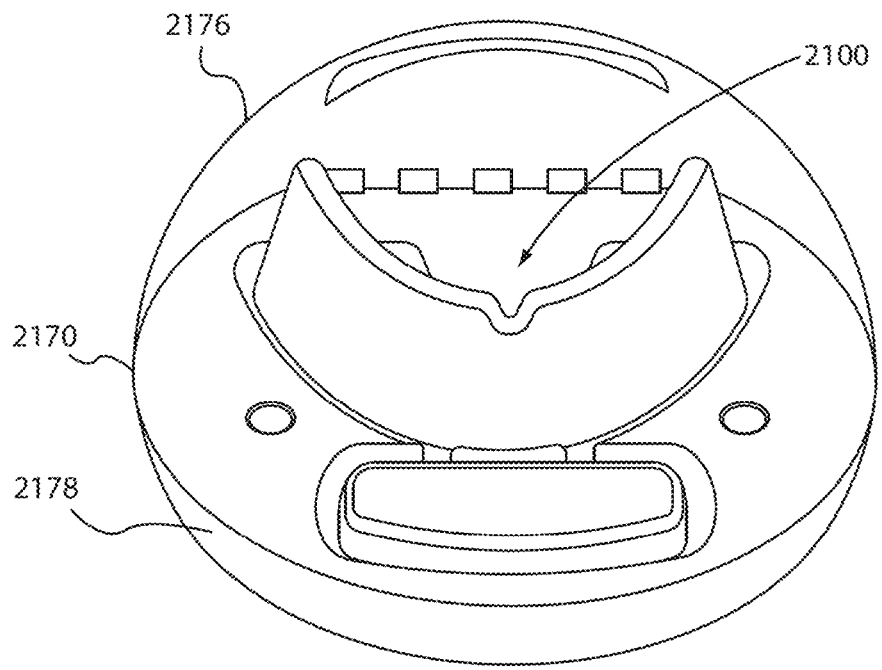
Figure 51:
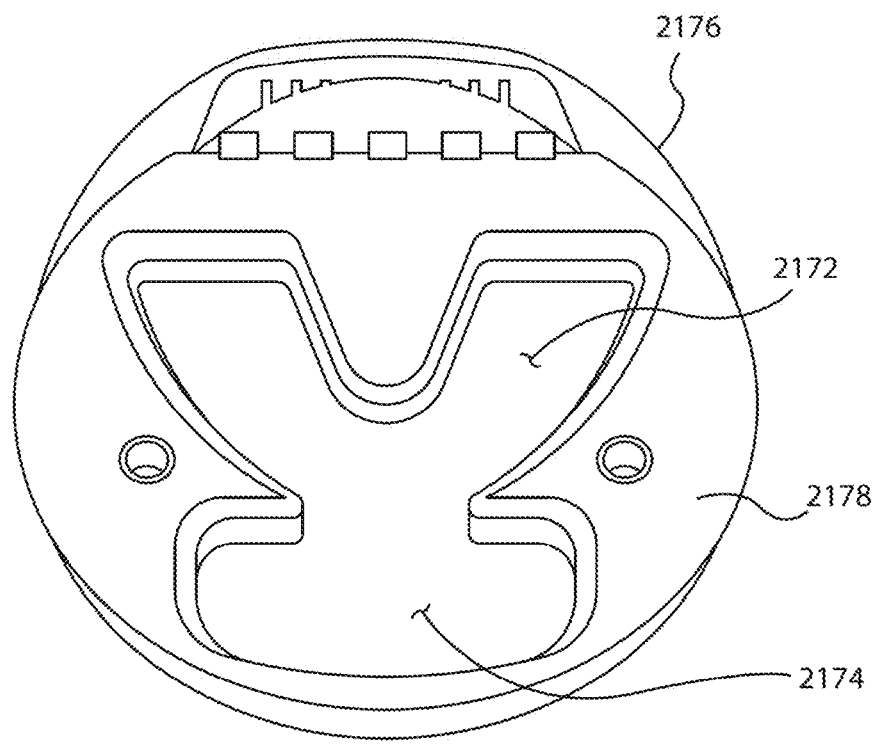
FIG. 51 is a front view of the external station of FIG. 49.

Referring to FIGS. 49-51, the extra-oral housing 2190 can be configured to be disposed on or otherwise coupled to an external station 2170, for example, when the apparatus 2100 is not in use by the patient. The external station 2170 can be, for example a carrying case, charging caddy or station, or the like, or a combination of the foregoing.

The station 2170 includes a base 2178 and a lid 2176 and defines a cavity formed by and between the base 2178 and the lid 2176 when the lid is in a closed position (as shown in FIGS. 49-51). The lid 2176 can be coupled to the base 2178 using any suitable coupling mechanism, for example, using a hinge as shown in FIGS. 49-51. In this manner, the lid 2176 is conveniently moveable between its closed position and an open position (not shown). The base 2178 can define a first recess 2172 configured to receive at least a portion of the intra-oral housing 2180 and a second recess 2174 configured to receive at least a portion of the extra-oral housing 2190. A perimeter of the first recess 2172 can, for example, complement the contour of the intra-oral housing 2180. A perimeter of the second recess 2174 can, for example, complement the contour of the extra-oral housing 2190.

The external station 2170 can be configured to charge the apparatus 2100 when the apparatus 2100 is disposed on or otherwise coupled to the station. In this manner, the battery 2194 can be recharged when the extra-oral housing 2190 is coupled to the charging station. In some embodiments, for example, the station 2170 is configured to inductively charge the apparatus 2100, e.g., by inductively charging the second battery 2195, described herein. In some embodiments, the second end 2193 of the extra-oral housing 2190 includes a connector (not shown in FIGS. 45-51) configured to be coupled to a complementary or mating connector (not shown in FIGS. 45-51) of the external station 2170.

The intra-oral apparatus 2100 can be configured to determine when the intra-oral housing 2180 is disposed within the patient's mouth (i.e., in a manner suitable for the treatment session). In some embodiments, for example, the intra-oral apparatus 2100 includes a sensor (not shown in FIGS. 45-49) configured to detect reflection of light off of a patient's oral soft tissue. The sensor can be, for example, a proximity detector included, or embedded, in the flexible circuit 2130. Such a proximity detector can, for example, include any suitable capacitance detection device. The light emitting panel 2102 can be configured to blink or pulse the LEDs included therein, for example, upon removal of the apparatus 2100 from the external station 2170 based, for example, on feedback from the proximity detector. The LEDs can be configured to blink or pulse at a predetermined rate.

At least a portion of light emitted from the pulsing or blinking LEDs towards the oral soft tissue of the patient's mouth is reflected to the intra-oral housing 2180 and is thereby detected by a sensor or other light reflectance detection mechanism (generally referred to as a "reflectance sensor;" not shown in FIGS. 45-49). The reflectance sensor is configured to evaluate the functionality of a portion of the light emitting array 2102 coupled to the left side of the intra-oral housing 2180 and a portion of the light emitting array 2102 coupled to the right side of the intra-oral housing 2180. In this manner, the reflectance sensor facilitates detection of any faulty operation of the apparatus 2100 with respect to each of the left and right sides of the intra-oral housing 2180 before operation of the apparatus 2100 with respect to the patient. Suitable reflectance thresholds can be established to measure reflectance in order to determine that the LEDs of the light emitting array 2102 are operating properly. The apparatus 2100 can be configured to initiate irradiation of the oral tissue (i.e., begin a treatment session) when the reflectance sensor detects the light reflection off of the oral soft tissue. In some embodiments, the reflectance sensor is configured to transmit a signal to the microprocessor 2196 to initiate the treatment session when the reflectance sensor detects light reflection (e.g., at or above a predetermined threshold) from the oral soft tissue.

The intra-oral apparatus 2100 can be configured for use in an orthodontic treatment, including any treatment described herein. In some embodiments, for example, the intra-oral apparatus 2100 is useful to irradiate at least a portion of the patient's upper jaw for about 3 minutes, the patient's lower jaw for about 3 minutes, or each of the patient's upper and lower jaws for about 3 minutes. More specifically, in one treatment program, the intra-oral apparatus 2100 is useful to administer a light-therapy treatment session in which the oral tissue associated with each of the upper arch of the patient's mouth and the lower arch of the patient's mouth (or vice versa) are consecutively irradiated for 3 minutes per day, for a total treatment session of 6 minutes per day.

During the treatment session, for example, the apparatus 2100 is configured to administer the light therapy using 12 Joules/cm$^2$. In some embodiments, the 12 Joules/cm$^2$ is administered at an intensity of 150 mW/cm$^2$ for the three minutes duration. As such, the LEDs tend to remain under a thermal threshold of about 41 degrees Celsius in contact with, or within the certain distance of, oral tissue (and thus under a maximum limit of 43 degrees Celsius). In some embodiments, the 12 Joules/cm$^2$ can be administered at a higher intensity, such as at an intensity of about 600 mW/cm$^2$ for about 20 seconds or about 1 W/cm$^2$ for about 12 seconds. In other embodiments, the light is administered at an intensity of about 60-12 mW/cm$^2$.

The light is emitted at a wavelength of 850 nm during the treatment session. In some embodiments, the light is emitted at a wavelength of 850 nm (±5 nm) during the treatment session. In other words, LEDs can emit light at a blend of wavelengths, and not at a single wavelength like a laser. The peak light emission wavelength ($\lambda_{max}$) by the LEDs is 855 nm. The treatment sessions can be administered for any suitable period, including, but not limited to, a period of four to twelve months. Such a treatment program can, for example, reduce the duration of an average period a patient is expected to need to use an orthodontic appliance (e.g., braces) to achieve a desired orthodontic result from two years to six months. The foregoing treatment program and/or any treatment program described herein can reduce a duration of an orthodontic treatment administered without light therapy, as described herein, by about 50 percent to about 75 percent.

Figure 53:
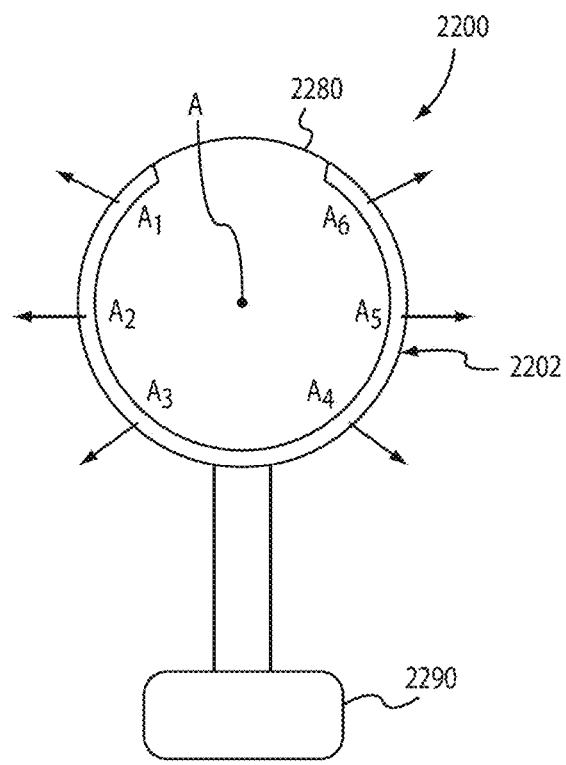
FIG. 53 is a top view of an intra-oral apparatus according to an embodiment of the invention.

Although the intra-oral housing (e.g., intra-oral housing 780, 880, 980, 1280, 1680, 1780, 1880, 1980, 2080, 2180) have been illustrated and described herein as having an arch shape similar to at least one of the upper or lower arch of a patient's teeth, in other embodiments, an light therapy apparatus can include an intra-oral housing having another suitable configuration. For example, referring to FIG. 53, an intra-oral apparatus 2200 configured to administer light therapy to a patient's oral tissue (e.g., the oral mucosa and/or root area) includes an intra-oral housing 2280 and an extra-oral housing 2290 coupled to the intra-oral housing. The extra-oral housing can be similar in many respects, or identical, to the extra-oral housing 2190 described herein with reference to FIGS. 45-47, and is therefore not described in detail herein. Although the intra-oral housing 2280 is shown and described as being coupled to the extra-oral housing 2290, in other embodiments, the intra-oral housing 2280 can be configured to be electrically coupled to a separate electronic device (e.g., via fiber optic cable(s), or other electronic tether as shown and described with respect to FIG. 44) configured to perform the functions of the components of the extra-oral housing 2290.

The intra-oral housing 2280 includes a light emitting array 2202. The light emitting array 2202 can be the same as or similar in many respects to a light emitting array described herein, and thus is not described in detail with respect to FIG. 53. The intra-oral housing 2280 can be configured to be received in the oral cavity such that a light emitting array 2202 is wholly disposed on the lingual side of the upper and/or lower arches of the patient's teeth. The intra-oral housing 2280 can define a substantially circular perimeter. For example, the intra-oral housing 2280 can be spherical, disc shaped, or the like. For descriptive purposes, the intra-oral housing 2280 can have a shape and can be disposed within a patient's mouth similar to a lollipop. In this manner, the light emitting array 2202 can be disposed adjacent the perimeter of the intra-oral housing 2280 such that the light emitting array 2202 emits light towards the patient's oral tissue (e.g., the oral mucosa and/or the root area) in a direction radiating from a central axis A, as shown by the arrows $A_1, A_2, A_3, A_4, A_5$ and $A_6$, in FIG. 53. In some embodiments, at least a portion of the intra-oral housing 2280 can be configured to contact at least a portion of the alveolar soft tissue when the intra-oral housing 2280 is disposed within the patient's mouth. In some embodiments, at least a portion of the intra-oral housing 2280 is configured to not contact, but be within a certain distance (e.g., within 0.1 cm to 3 cm) of, the alveolar soft tissue when the intra-oral housing 2280 is disposed within the patient's mouth.

Figure 54:
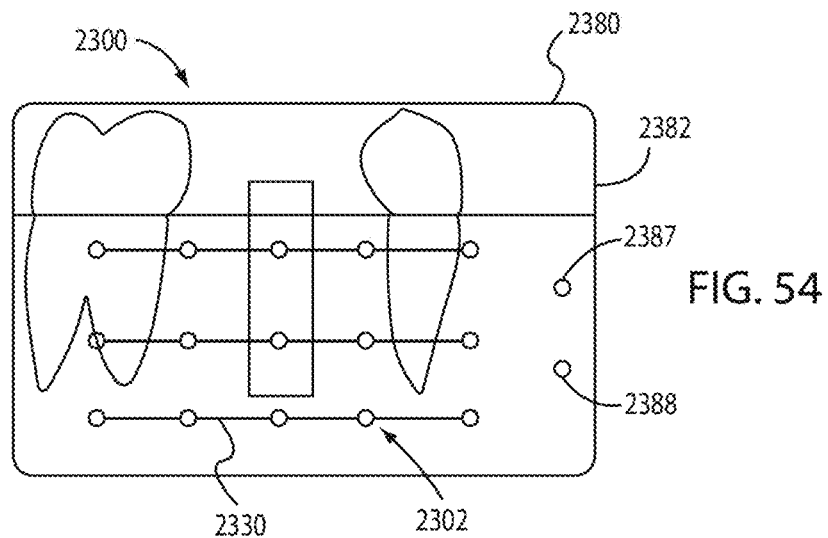
FIG. 54 is a side view of a portion of an intra-oral apparatus according to an embodiment of the invention.
Figure 55:
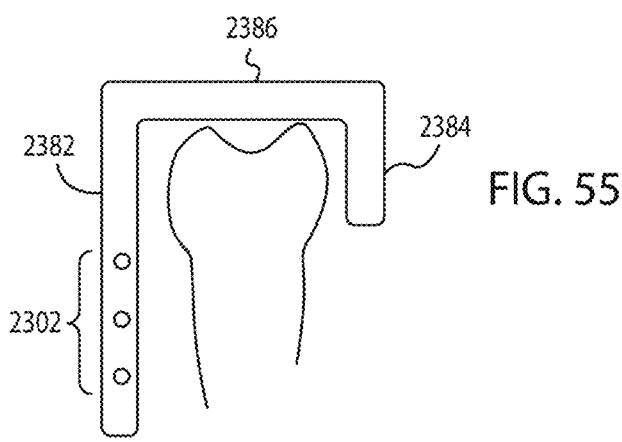
FIGS. 55 and 56 are end and perspective views of the intra-oral apparatus of FIG. 54.
Figure 56:
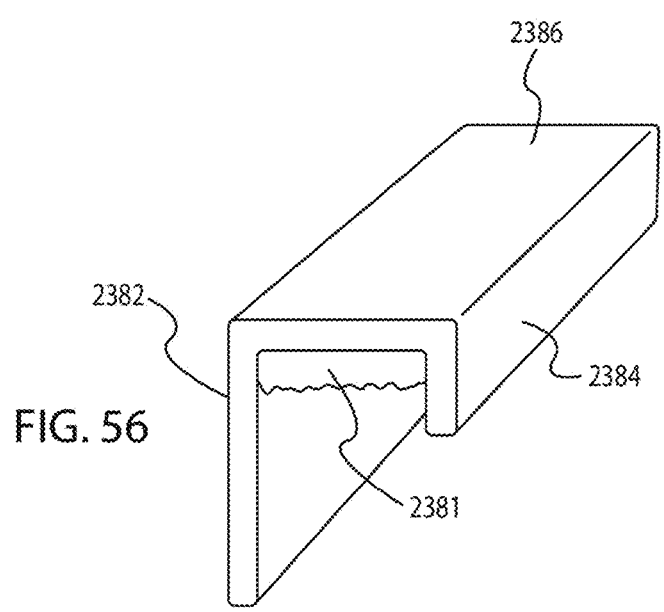

Although the intra-oral apparatus have been illustrated and described herein as being configured to administer light therapy to the upper and/or lower arch of a patient's teeth, in some embodiments, an intra-oral apparatus is configured to administer light therapy to a portion or section of the patient's oral mucosa (e.g., the alveolus). For example, referring to FIG. 54, in some embodiments, an apparatus 2300 is configured to administer light therapy to three or four teeth of the patient, to a quadrant of the patient's teeth, or to one arch of the patient's teeth. Such an intra-oral apparatus can be beneficial in the case of implantology and/or oral surgery.

The apparatus 2300 includes an intra-oral housing 2380 configured to be disposed within the oral cavity of the patient. The intra-oral housing 2380 defines a first segment 2382, a second segment 2384 and a third segment 2386 coupling the first segment and the second segment. When the intra-oral housing 2380 is disposed within the patient's oral cavity for a treatment session, the first segment 2382 of the intra-oral housing is configured to be disposed (e.g., vertically) between the patient's teeth and the patient's buccal mucosa, the second segment 2384 is configured to be disposed (e.g., vertically) on the lingual side of the crown of the patient's teeth, and the third segment 2386 is configured to be disposed (e.g., horizontally) adjacent and/or on the occlusal surface of the patient's teeth. The second segment 2384 has a sufficient height (i.e., measured in a direction from the occlusal surface to the root area) to inhibit tipping of the intra-oral housing 2380 towards the patient's cheek.

In some embodiments, a layer 2381 of moldable material is disposed on an occlusal-facing surface of the third segment 2386 of the intra-oral housing 2380. A moldable impression of the designated teeth can be made using the layer 2381, thus facilitating placement of the intra-oral housing 2380 when the housing is later re-inserted into the oral cavity by the patient (e.g., for a subsequent treatment session).

A flexible circuit 2330 is disposed within the first segment 2382 of the intra-oral housing 2380. The flexible circuit 2330 includes a light emitting array 2302 configured to administer light therapy, in any manner described herein, to the patient's teeth. For example, the flexible circuit 2330 can include a light emitting array 2302 including 15 LEDs, or 15 LEDs per tooth that will be subjected to light therapy. The light emitting array 2302 can includes LEDs configured to administer, or emit, light within the range of 600 to 1200 nm. The flexible circuit 2330 of the intra-oral housing 2380 includes a sensor 2387. The sensor 2387 can be the same as or similar in many respect to the sensor shown and described herein with reference to FIG. 3A. The sensor 2387 can be configured to detect the temperature of the apparatus 2300, the patient's alveolar soft tissue and/or the patient's root area. For example, a thermistor or similar temperature measuring device can be placed in the circuit 2330 to monitor the temperature of the light emitting array 2302, as well as measure the temperature inside the patient's mouth. This information can serve as a method of obtaining temperature-related information as well as monitoring patient compliance. When the intra-oral housing 2380, and thus the circuit 2330, is placed in the mouth and when the apparatus 2300 emits light, the temperature of the light emitting array 2302 will rise from pre-treatment ambient temperature to closer to normal body temperature. By monitoring the change in temperature, a controller 2314, described in more detail herein, can monitor the period of time that the light emitting array 2302 is in the oral cavity, based on the period of time the temperature is elevated and close to body temperature.

In some embodiments, the circuit 2330 includes a sensor (or proximity detector) that is configured to detect contact of, or a proximity within a certain distance (e.g., within 0.1 cm to 3 cm) of, the first segment and/or light emitted by the light emitting array 2302 with the patient's oral mucosa and/or root area. In this manner, the controller 2314 can detect that the intra-oral housing 2380 is disposed within the patient's oral cavity, and therefore can determine that a treatment session can be initiated.

Figure 57:
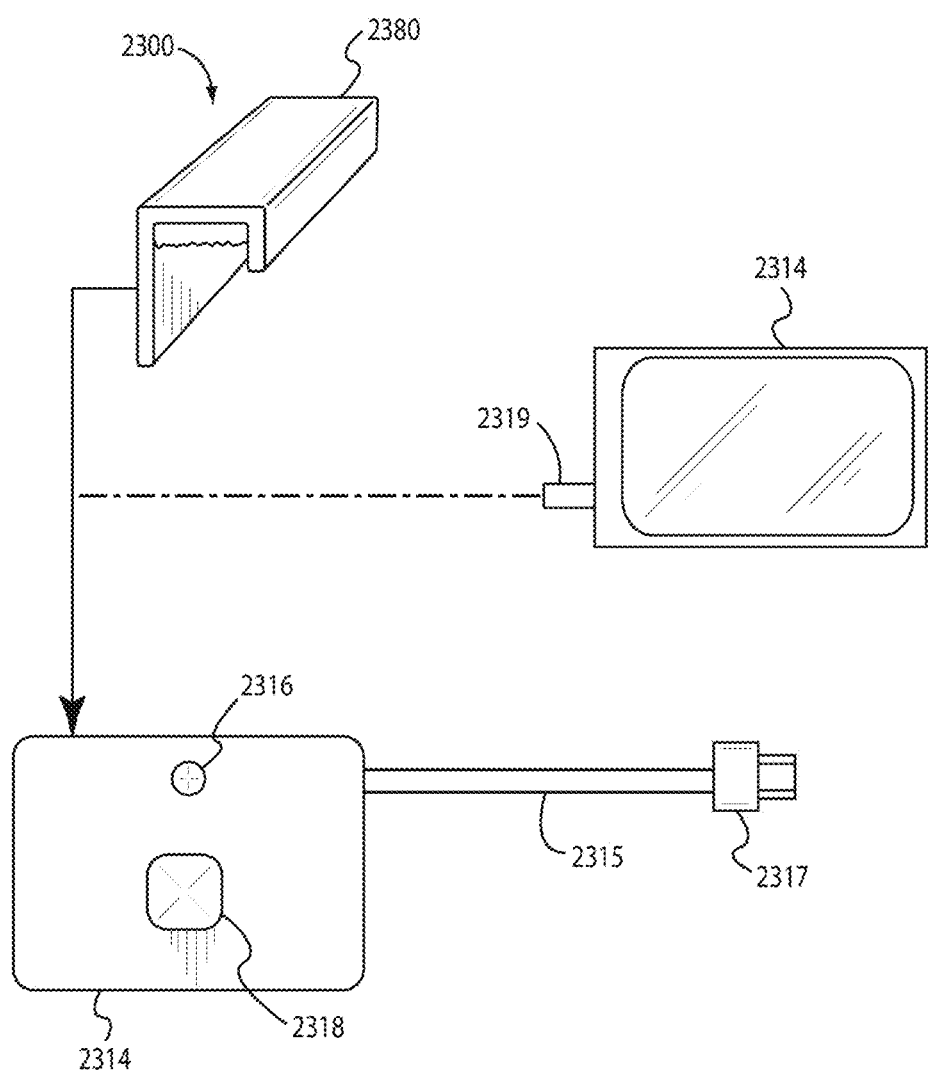
FIG. 57 is a schematic illustration of a system including the intra-oral apparatus of FIG. 54 according to an embodiment of the invention.
Figure 58:
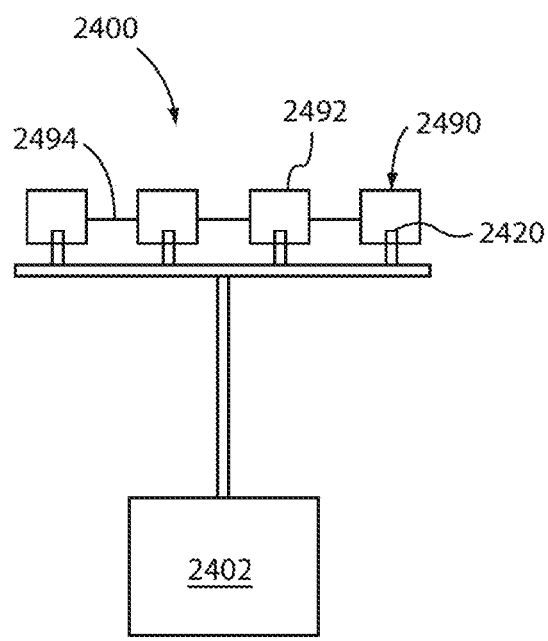
FIG. 58 is a schematic illustration of an intra-oral apparatus according to an embodiment of the invention.

Referring to FIG. 57, the intra-oral housing 2380 is configured to be coupled to an external electronic device, e.g., via a wired or wireless connection. The external electronic device can be configured to provide or convey power to the intra-oral housing 2380, for example, for operation of the light emitting array 2302 during a treatment session. The external electronic device can also be configured to control operation of the light-emitting array 2302.

In some embodiments, the external electronic device is a controller 2314. The intra-oral housing 2380 can be removably coupleable to the controller 2314. In some embodiments, the intra-oral housing 2380 is disposable and the controller 2314 is reusable. In this manner, the intra-oral housing 2380 can be disposed of after a predetermined number of uses and/or after a predetermined period of time, and a second intra-oral housing (not shown) can optionally be used with the controller 2314. The controller 2314 can be electrically coupled to a charger 2317, such as a medical grade USB charger, via a cable 2315, such as a USB cable.

The controller 2314 can be similar in many respects or identical to any controller (e.g., controller 430, 1114) described herein. The controller 2314 can also include many components the same as or similar to those disposed within the extra-oral housing 2190 of apparatus 2100. For example, the controller 2314 can include a microprocessor. Because the microprocessor can be the same as or similar in many respects to any microprocessor described herein (e.g., microprocessor 2196), it is not described in detail herein. The controller 2314 can be preconfigured with a treatment protocol. The controller 2314 includes a button 2318 for initiating a treatment session. The button 2318 can also be configured to, for example, pause or stop a treatment session.

The controller 2314 includes an LED indicator 2316 that can be configured to provide an indicia to the patient of the status of the controller, the intra-oral housing 2380, and/or the treatment program. The LED indicator 2316 can be similar or identical, for example, to the communication mechanism of extra-oral housing 2190, described herein, in that it is configured to indicate a status, or stage, of the treatment session. In some embodiments, the LED indicator 2316 is configured to display no light during a first stage of the treatment session, a blinking or pulsed light during a second stage of the treatment session, and/or a solid light during a third stage of the treatment session. The LED indicator 2316 can be, for example, configured to display a solid light for a first predetermined duration (e.g., 2 minutes and 30 seconds, 2 minutes and 45 seconds, or 2 minutes and 10 seconds) upon initiation of the treatment session. The LED indicator 2316 can be configured to display the blinking or pulsed light for a second predetermined duration (e.g., 10, 15 or 30 seconds) following the first predetermined duration as a signal to the patient that the treatment session is nearing its end. The LED indicator 2316 can be configured to display no light when a treatment session is ended (e.g., after 3 minutes from initiation of the treatment session) and the apparatus 2100 is not irradiating light to the patient.

In some embodiments, the external electronic device 2314 is a personal electronic device such as a mobile phone (e.g., a smartphone, such as an iPhone®, a tablet, such as an iPad®), a personal digital assistant, or the like. The intra-oral housing 2380 can be coupled to the device 2314 using a connector 2319. In an embodiment in which the device 2390 includes, for example, a smartphone, the smartphone can be configured to perform any operation or function that the controller is configured to perform. For example, the device 2314 can be configured to provide power to the intra-oral housing 2380. In another example, the device 2314 can include an application configured to provide an interface for the patient, control the light-emitting array 2302, and/or record usage information (e.g., compliance information) for subsequent accessing of the information by the patient and/or a physician.

In some embodiments, a system includes a first portion configured to administer light therapy to a patient, as described herein, for a first time period, and a second portion configured to administer light therapy to the patient, as described herein, for a second time period different than the first time period. For example, in some embodiments, the system includes a plurality of apparatus (or intra-oral housings), such that at least a portion of each apparatus is configured to be disposed within the patient's mouth. Each apparatus of the plurality can include any apparatus or intra-oral housing described herein. For example, the system includes a first intra-oral apparatus and a second intra-oral apparatus distinct from the first intra-oral apparatus. The first apparatus is configured to begin administering light therapy to a patient at a first time period beginning at $T_0$. $T_0$ represents the start of a phototherapy session (e.g., corresponding to a date the patient is assigned the first apparatus and/or starts daily usage of the first apparatus). For at least some patients, $T_0$ can also represent the day of maxillary bonding and/or the start of an orthodontic treatment. The start of orthodontic treatment can include, for example, the day a conventional fixed orthodontic brackets and wires are installed on the patient's teeth. The first apparatus can be selected based on a position or configuration of the patient's teeth prior to administration of the light therapy. The first apparatus is configured to administer light at a first wavelength, such as, but not limited to, about 850 nm.

The second apparatus is configured to administer light therapy to a patient at a second time period beginning at $T_{>0}$, subsequent to $T_0$. In some embodiments, the second apparatus is optimally configured to administer light therapy to the patient based on a position of the patient's teeth after administration of at least a portion of the light therapy. For example, the second apparatus can include a light emitting array differently configured from a light emitting array of the first apparatus. The second apparatus can be configured to administer light at a second wavelength different than the first wavelength, such as, but not limited to, about 620 nm. In this manner, the second apparatus can be selected based, at least in part, on tooth movement that occurred during the light therapy administered in conjunction with the first apparatus and during a time period between $T_0$ and $T_{>0}$. For example, the first apparatus can be used by the patient at start of the light therapy program and for the first time period, and the second apparatus can be used by the patient beginning about three months after the beginning of the light therapy program and for the second time period. The system can include any suitable number of apparatus, such as two, three, four or more apparatus configured to administer the light therapy. For example, the system can include the first apparatus configured to administer the light therapy beginning at $T_0$, the second apparatus configured to administer light therapy beginning at $T_1$, and a third apparatus configured to administer light therapy beginning at $T_2$.

In another example, the system can include an apparatus having a first light emitting array (e.g., the first portion) and a second light emitting array (e.g., the second portion). The first light emitting array can be configured to administer light at a first wavelength, such as, but not limited to, about 850 nm. The second light emitting array can be configured to administer light at a second wavelength different than the first wavelength, such as, but not limited to, about 620 nm. The first light emitting array and the second light emitting array can be included in a single intra-oral housing. The system, which includes a first portion configured to emit light at the first wavelength for the first time period and at the second wavelength for the second time period, is beneficial at least because it permits a transition during a light therapy program from a higher light wavelength to a lower light wavelength that can help start to increase bone mineralization in the patient's treated area. Such an increase in bone mineralization can facilitate ensuring a more stable result of the moved teeth following an orthodontic treatment.

In some embodiments, the light therapy apparatus described herein are configured for use in conjunction with a functional dental appliance, as described in more detail herein. In other embodiments, a light therapy apparatus is integrally formed with a functional appliance configured to exert a force on the teeth of a patient, such as a functional appliance described in more detail herein. For example, referring to FIG. 57, a system 2400 according to an embodiment is configured to regulate tooth movement. The system 2400 includes one or more light emitters (e.g., fiber optical cable(s)) 2420 and an orthodontic bracket system 2490. The light emitters 2420 can be the same as or similar to any light emitter described herein, including, but not limited to, optical fiber cables 420 depicted in FIG. 7. The light emitters 2420 are coupled to the bracket system 2490. For example, the light emitters 2420 can be coupled to one or more brackets 2492 of the bracket system 2490, to one or more wires 2494 of the bracket system 2490, or any combination of the foregoing. In this manner, a separate intra-oral housing is not needed to maintain a position of the light emitters 2420 with respect to the patient's tooth, root area and/or oral mucosa. The light emitters 2420 are coupleable to a light source 2402. The light source 2402 can be any suitable light source, including any light source described herein (such as light source 402 depicted in FIG. 7).

A light therapy system according to an embodiment is illustrated in FIGS. 62-91. The system includes a light therapy apparatus 2500 (see, e.g., FIGS. 62-75) and an external station 2580 (see, e.g., FIGS. 87-91). The light therapy apparatus 2500 is configured to irradiate light in any suitable manner described herein, including, for example, to irradiate the alveolus and/or root area of the patient. Similarly stated, the light therapy apparatus 2500 is configured to administer light therapy to a patient's teeth and/or oral mucosa. More specifically, the light therapy apparatus 2500 is configured to administer light to the patient's teeth and/or oral mucosa sufficient to accelerate orthodontic movement of the patient's teeth and to reduce the overall treatment time for the patient when undergoing orthodontic treatment. The light therapy apparatus 2500 is configured to be used in conjunction with traditional orthodontic treatment with an orthodontic appliance, such as brackets and wires, or aligners. The light therapy apparatus 2500 can be the same as or similar in many respects to, or include components the same as or similar in many respects to, the intra-oral apparatuses described herein, including, for example, apparatus 2100. The light therapy apparatus 2500 is configured to be disposed in or on the external station 2580 when the apparatus is not in use for a light therapy treatment session, as described in more detail herein.

The light therapy apparatus 2500 includes an intra-oral housing 2510 (also referred to herein as a "mouthpiece") configured to be disposed in an oral cavity (e.g., in the mouth, not shown in FIGS. 62 and 63) of a patient and an extra-oral housing 2560 (also referred to herein as a "bill") configured to be coupled to the mouthpiece 2510 and disposed externally to the patient's mouth when the mouthpiece 2510 is disposed within the patient's mouth.

Figure 62:
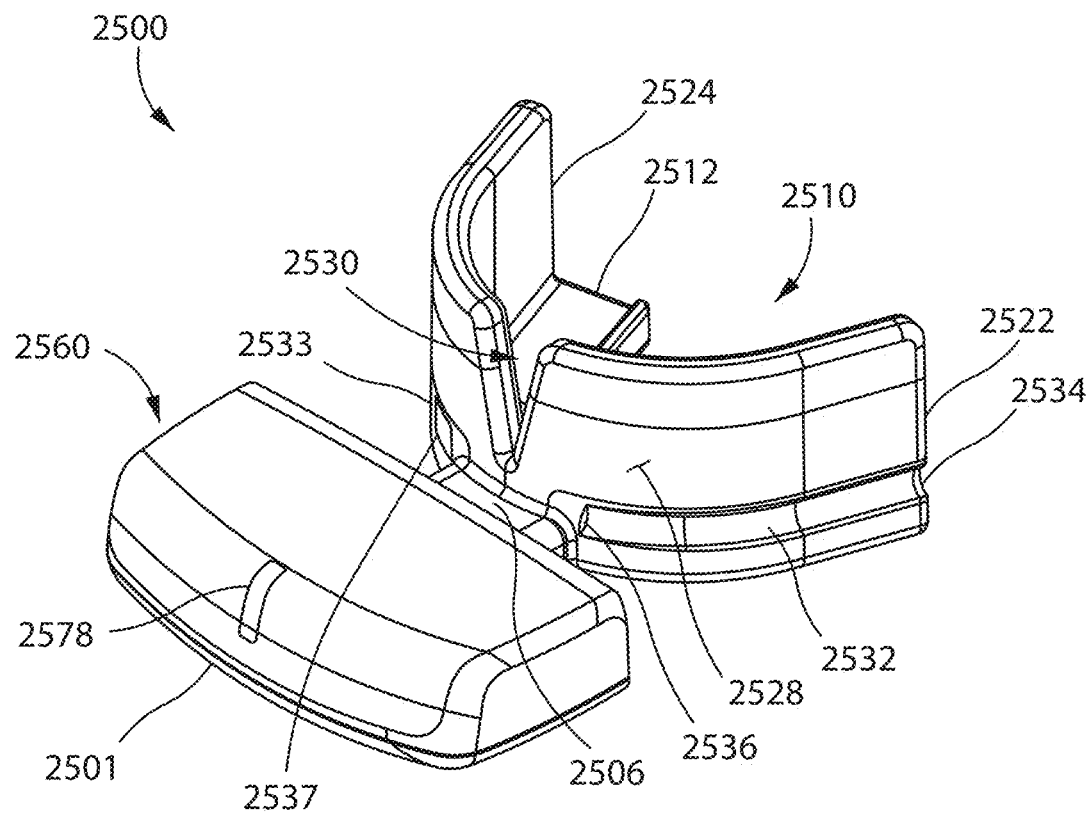
FIGS. 62 and 63 are perspective views of a light therapy apparatus according to an embodiment.
Figure 63:
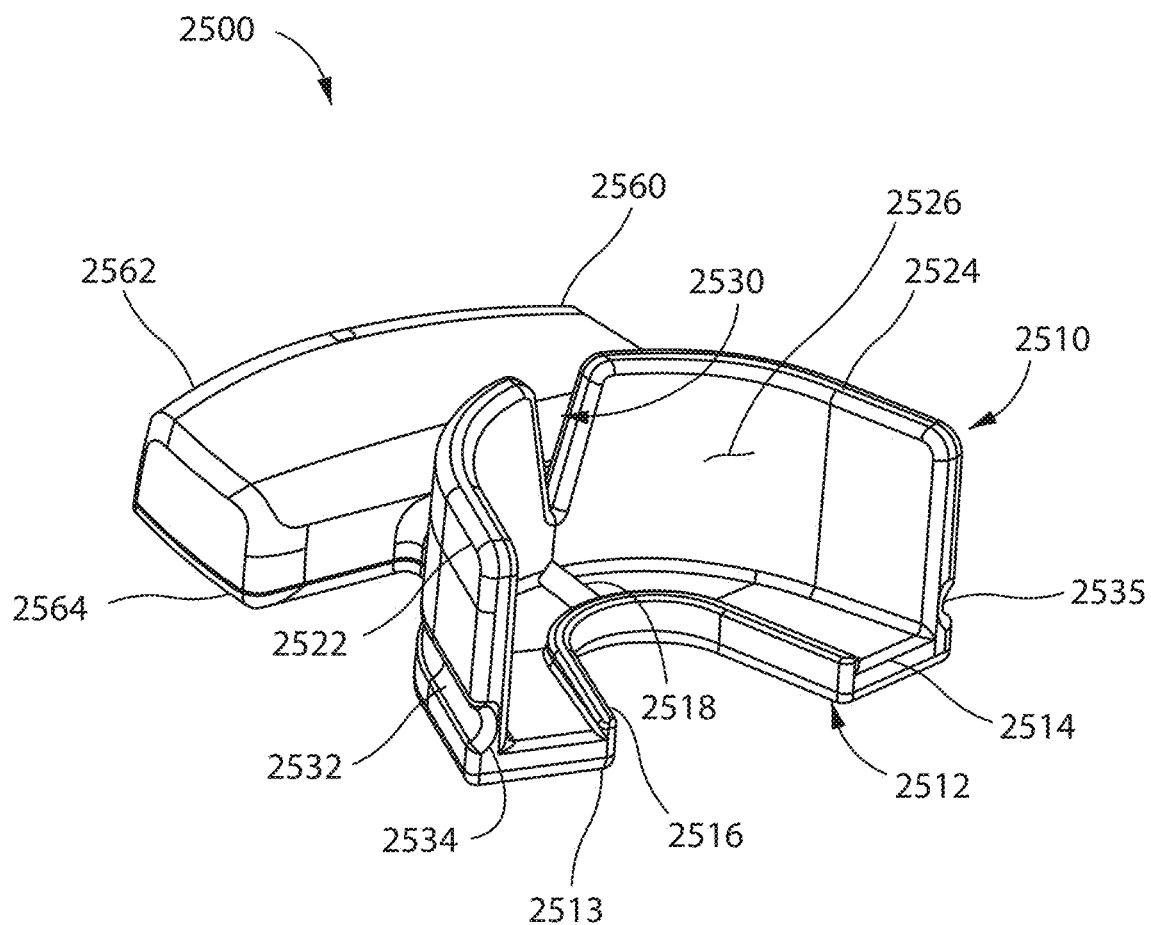
Figure 66:
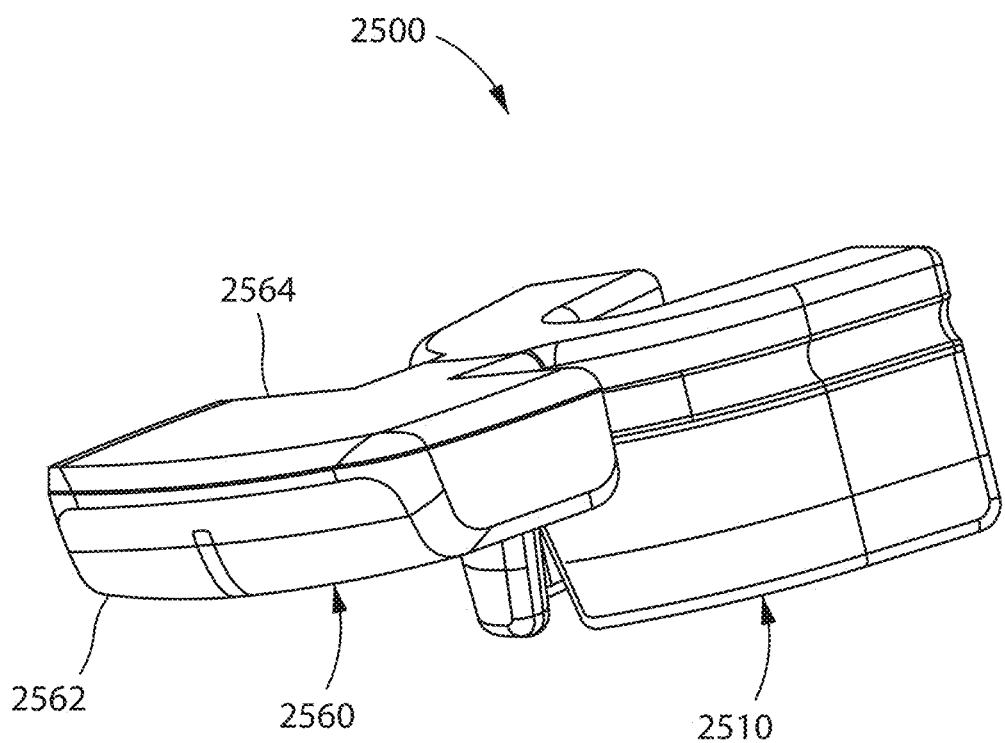
FIG. 66 is a perspective view of the light therapy apparatus of FIG. 62 in an inverted position.
Figure 67:
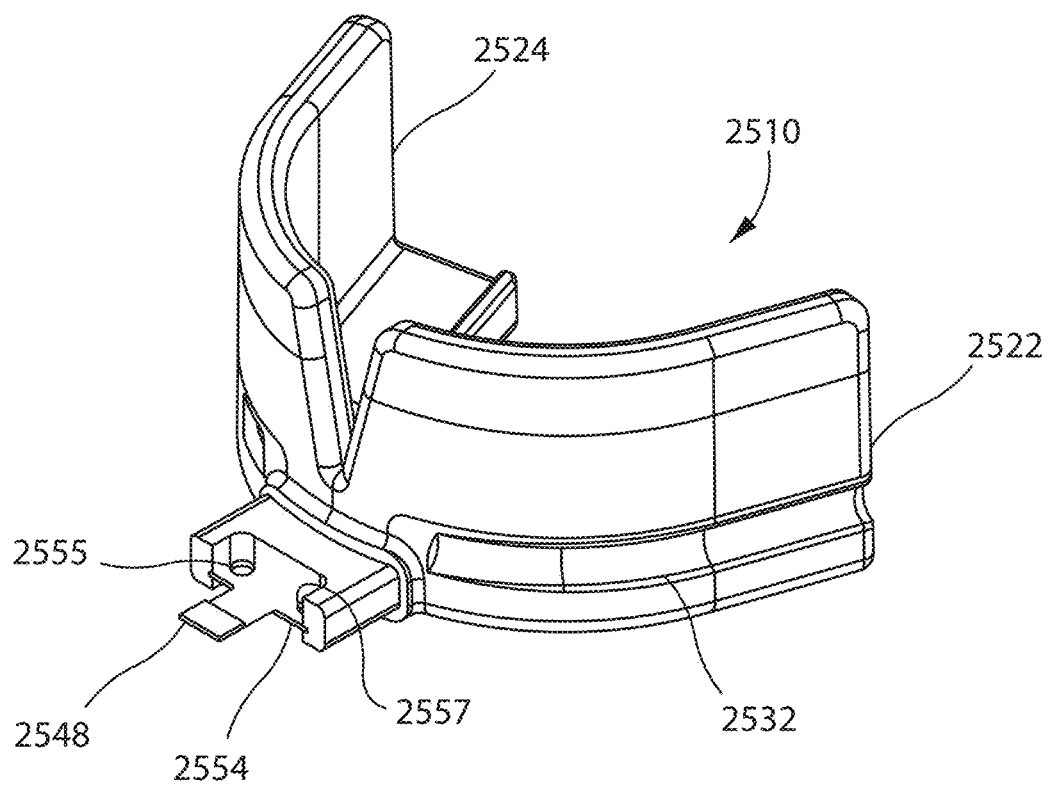
FIG. 67 is a perspective view of a portion of the light therapy apparatus of FIG. 62.

The light therapy apparatus 2500 is configured to be useful for light therapy with the upper jaw and/or the lower jaw of the patient. In other words, the light therapy apparatus 2500 can be configured to administer light therapy with respect to the patient's upper jaw when the apparatus is in an upright position (e.g., as shown in FIG. 62), and can be configured to administer light therapy with respect to the patient's lower jaw when the apparatus is in an inverted position (e.g., as shown in FIG. 66). As such, the mouthpiece 2510 is configured to be disposed within the patient's oral cavity with respect to each of the upper and lower jaws of the patient. Similarly stated, the mouthpiece 2510 is configured matingly adapt to both the upper jaw and the lower jaw, as described herein, thus eliminating the need for a separate mouthpiece for each jaw. It should be noted that although the light therapy apparatus 2500 generally, and the mouthpiece 2510 specifically, may be described as being in the upright position when configured to be oriented with respect to the upper jaw and in the inverted position when configured to be oriented with respect to the lower jaw, in other embodiments, the light therapy apparatus 2500 and the mouthpiece 2510 are in the upright position when configured to be oriented with respect to the lower jaw of the patient, and in the inverted position when configured to be oriented with respect to the upper jaw of the patient.

Figure 64A:
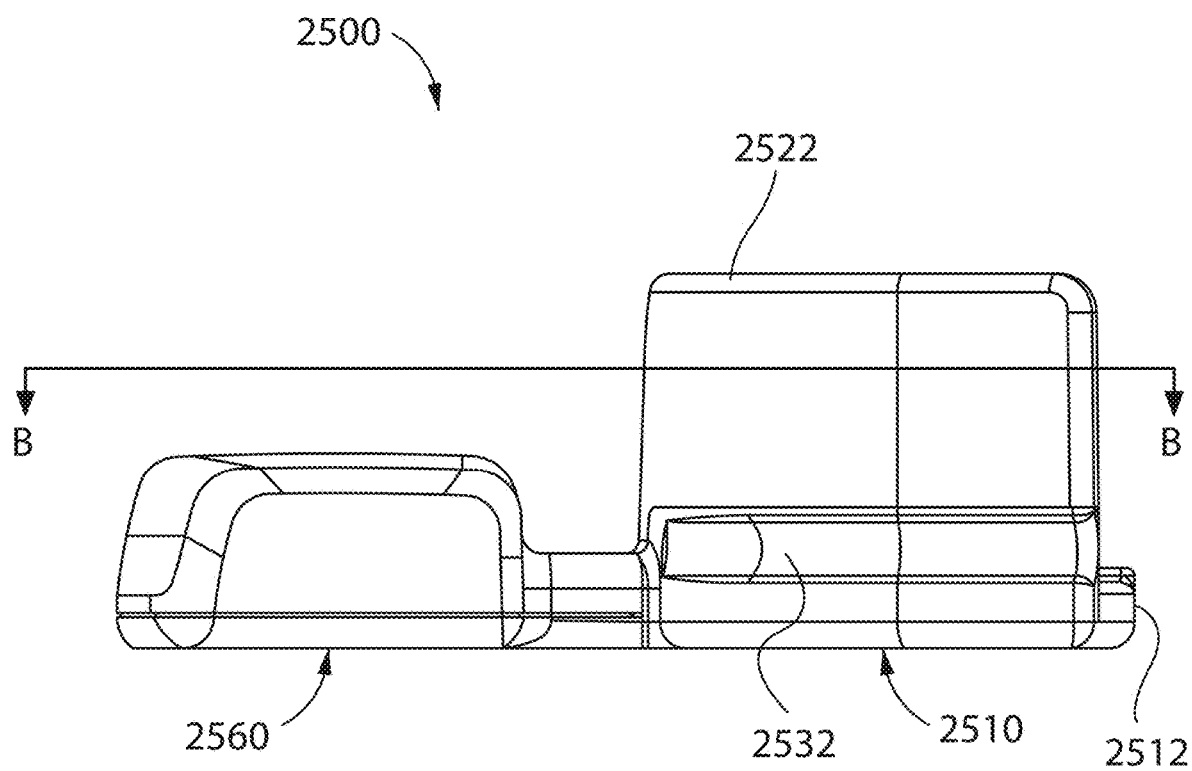
FIG. 64A is a right side view of the light therapy apparatus of FIG. 62. The left side view of the light therapy apparatus of FIG. 62 is a mirror image to the right side view.

The mouthpiece 2510 can be similar in one or more respects, and include components similar in one or more respects, or identical, to the intra-oral housings described herein, including, for example, the intra-oral housings or mouthpieces described herein with reference to FIGS. 13-15, 43-44 and 45-50. The mouthpiece 2510 includes a bite tray 2512, flanges 2522, 2524, a light array 2542 (see, e.g., FIG. 72), and a support plate 2554 (see, e.g., FIG. 72). The bite tray 2512 is configured to receive at least a portion of the patient's teeth of the upper and/or lower jaw. As such, the bite tray 2512 is generally U-shaped, as shown in FIG. 64. The bite tray 2512 is configured to facilitate proper positioning of the mouthpiece 2510 within the patient's mouth. The bite tray 2512 generally includes the lower portion of the mouthpiece 2510. The bite tray 2512 includes a bite pad 2514 with an inner perimeter (or side wall) 2515 and an outer perimeter (or side wall) 2517. Flanges 2522, 2524, described in more detail herein, generally define an upper portion of the mouthpiece 2510 and are coupled to the outer perimeter 2517 of the bite pad 2514. An inner ridge 2516 is coupled to or otherwise formed on the inner perimeter 2515 of the bite pad 2514. The flanges 2522, 2524 of the mouthpiece 2510 and the inner ridge 2516 each extend and/or protrude from the bite pad 2514 in a first direction. As such, when the mouthpiece 2510 is disposed within the patient's mouth, the bite tray 2512 is positioned within the mouth such that the bite pad 2514 is adjacent the occlusal surface of one or more teeth, the flanges 2522, 2524 are disposed between the one or more teeth and buccal tissue, and the inner ridge 2516 is disposed between the one or more teeth and the tongue. Similarly stated, the bite tray is configured such that when the mouthpiece 2510 is disposed within a mouth, a least a portion of one or more teeth are positioned between the flanges 2522, 2524 and the inner ridge 2516.

The bite tray 2512 can have any thickness suitable for receiving a bite force thereon. In some embodiments, the bite pad 2514 can have a constant thickness. In other embodiments, the thickness of the bite pad 2514 can vary spatially. For example, the bite tray 2512, and more specifically, the bite pad 2514, can have a first thickness at an anterior end portion of the bite tray, and a second thickness greater than the first thickness at a posterior end portion of the bite tray. Similarly stated, in some embodiments, the thickness of the bite pad 2514 increases along the length of the bite pad 2514 between a first (anterior) portion of the bite pad 2514 and a second (posterior) portion of the bite pad. For example, in some embodiments, a thickness of the bite pad 2514 at an anterior portion is between about 5 mm and about 25 mm, and a thickness of the bite pad 2514 at a posterior portion is between about 7 mm and about 27 mm. The increased thickness of the first portion of the bite pad 2514 forces most of the contact between the patient's teeth and the mouthpiece 2510 to be between the posterior teeth (e.g., the molars) and the thicker, second portion of the bite pad 2514. Similarly stated, any pressure exerted by the teeth on the bite tray 2512 will be more concentrated on the thicker portion of the bite pad 2514. Having the greater bite force at the posterior portion of the bite tray 2512 improves patient comfort and helps to avoid damage to the mouthpiece 2510 that may otherwise be caused by the patient's sharper anterior teeth.

Additionally, the increased contact interface between the bite tray 2512 and the posterior teeth also provides for a more universal patient fit, because positional variability of the posterior teeth is often less than that of the anterior teeth. Similarly stated, this arrangement produces a more repeatable (treatment-to-treatment and patient-to-patient) fit because the position of a patient's posterior teeth often varies less amongst different patients' anatomies than the position of the anterior teeth and incisors. In some embodiments, the bite pad 2514 is constructed (i.e., is constructed from a material and/or has a sufficient thickness) to withstand a biting force of up to about 340 N. In some embodiments, the bite pad 2514 has shear and/or fatigue strength to withstand 50 N of force repeatedly applied to the bite tray 2514.

Figure 64B:
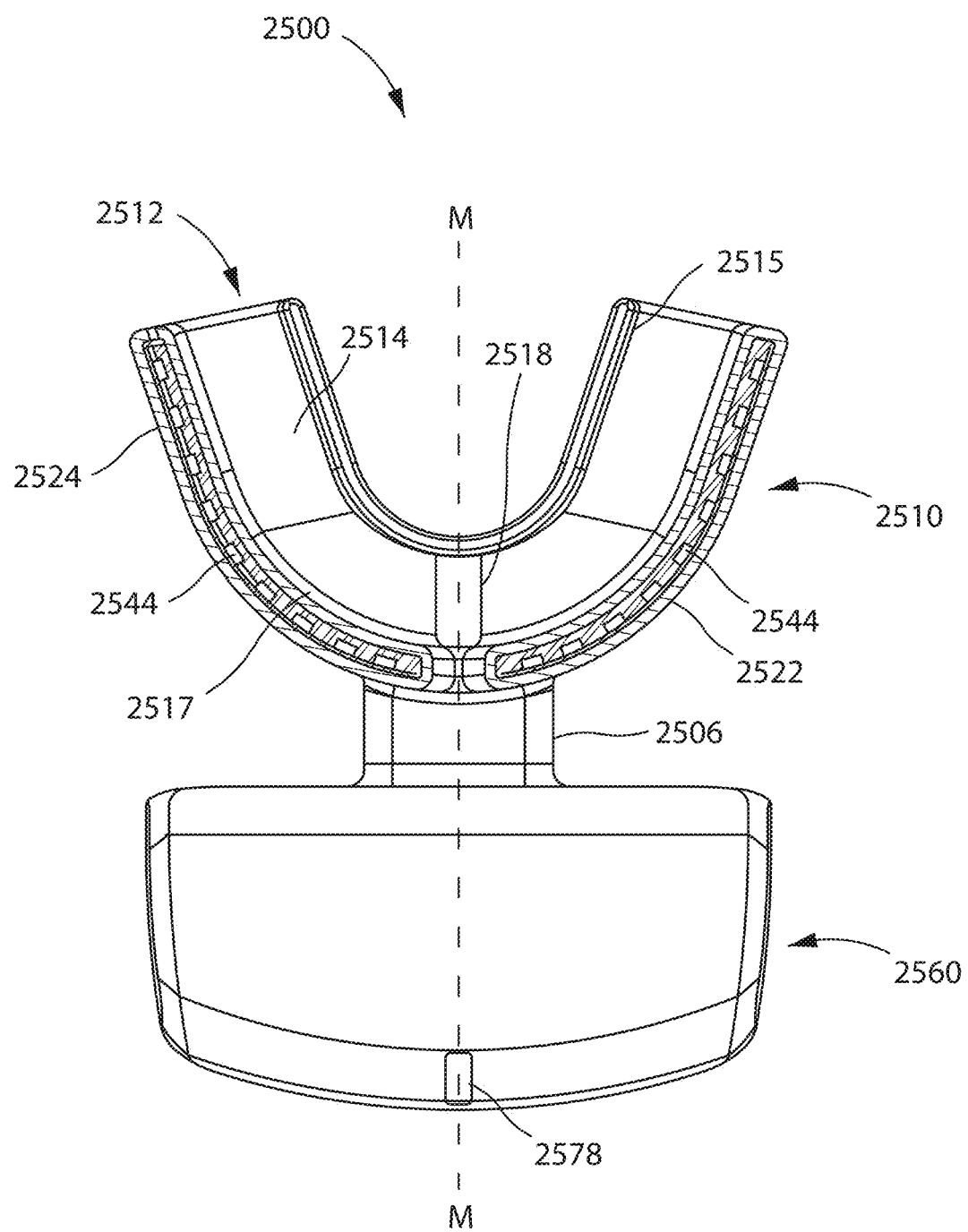
FIG. 64B is a cross-sectional view of the apparatus of FIG. 64A, taken along line B-B in FIG. 64A.
Figure 65:
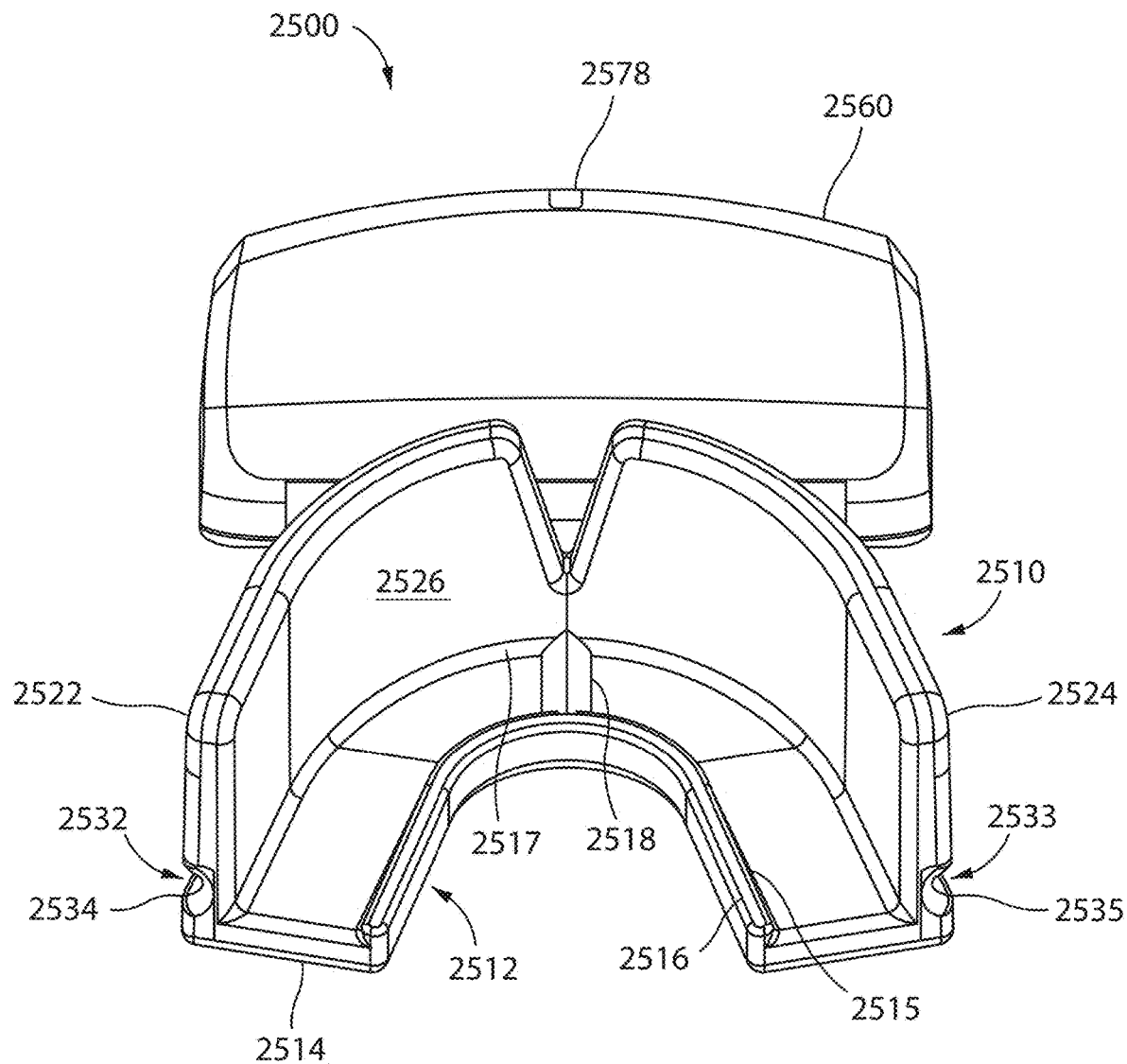
FIG. 65 is a rear perspective view of the light therapy apparatus of FIG. 62.

As shown in FIG. 65, an upper surface of the bite pad 2514 includes a ridge 2518. The ridge 2518 is disposed along a midline M of the mouthpiece 2510 and is elevated with respect to the upper surface of the bite tray 2512 and/or bite pad 2514. The ridge 2518 can extend between the inner perimeter 2515 of the bite pad 2514 and the outer perimeter 2517 of the bite pad 2514, as best shown in FIG. 64B. The ridge 2518 facilitates positioning of the mouthpiece 2510 within the patient's oral cavity. For example, the mouthpiece 2510 is configured to be positioned within the patient's oral cavity such that the ridge 2518 is disposed between the patient's front central incisors (on either the upper jaw or the lower jaw). Proprioception of the patient related to the teeth and periodontium can produce sensory feedback to the patient regarding the position of the ridge 2518 of the mouthpiece 2510.

In this manner, the ridge 2518 facilitates centering of the mouthpiece 2510 within the oral cavity, thus promoting symmetry of a light therapy treatment on the alveolus, or other oral tissue, on both sides of the patient's mouth. In other words, in order to promote the symmetrical administration of light therapy to the root area, the mouthpiece 2510 can be positioned with the midline M of the mouthpiece 2510 seated along the sagittal plane or within (i.e., plus or minus) 5 degrees of the sagittal plane, and the ridge 2518 can facilitate such positioning in use. The ridge 2518 can have any suitable shape, including, for example, the shape of an inverted V as shown in FIG. 65, such that the point of the V can be disposed between the patient's front central incisors.

As noted above, the upper portion of the mouthpiece 2510 includes a first (or left) flange 2522 and a second (or right) flange 2524. The upper portion (i.e., the flanges 2522, 2524) of the mouthpiece 2510 is disposed transversely with respect to the bite plate 2514. The flanges 2522, 2524 are configured to be disposed, when the mouthpiece 2510 is disposed within the patient's mouth such that the bite tray is adjacent an occlusal surface of the patient's teeth, adjacent a portion of a side of the patient's teeth and/or adjacent the alveolar mucosa. In this manner, the light array 2542, enclosed in the flanges 2522, 2524, as described in more detail herein, can be used to administer light to the patient's teeth and/or alveolar mucosa.

The flanges 2522, 2524 collectively contain the light array 2542, and are each configured to be disposed between the buccal tissue and the alveolus. Thus, in use, the flanges 2522 and 2524 displace oral soft tissue to maintain the desired position of the light array 2542 relative to the anatomy of the patient. More specifically, the flanges 2522, 2524 are each configured to displace buccal tissue away from the patient's alveolus. In some embodiments, an inner face 2526 of the flanges 2522, 2524 can be spaced apart from the patient's alveolar tissue when the mouthpiece 2510 is disposed within the patient's mouth and the flanges 2522, 2524 are displacing the buccal tissue. In some embodiments, at least a portion of the inner face 2526 of the flanges 2522, 2524 can contact the patient's alveolar tissue when the mouthpiece 2510 is disposed within the patient's mouth and the flanges 2522, 2524 are displacing the buccal tissue.

The flanges 2522, 2524 of the mouthpiece 2510 are configured to be flexible and/or deformable. Similarly stated, the flanges 2522, 2524 are constructed from a material and have geometrical dimensions and/or configurations to provide the desired flexibility, as described herein. Moreover, each of the first and second flanges 2522, 2524 are independently deflectable, movable and/or deformable with respect to the mouthpiece 2510 and/or each other. In this manner, the mouthpiece 2510 can be easily disposed within the oral cavity for a variety of different patients having a variety of different anatomical structures, as described herein.

Figure 68:
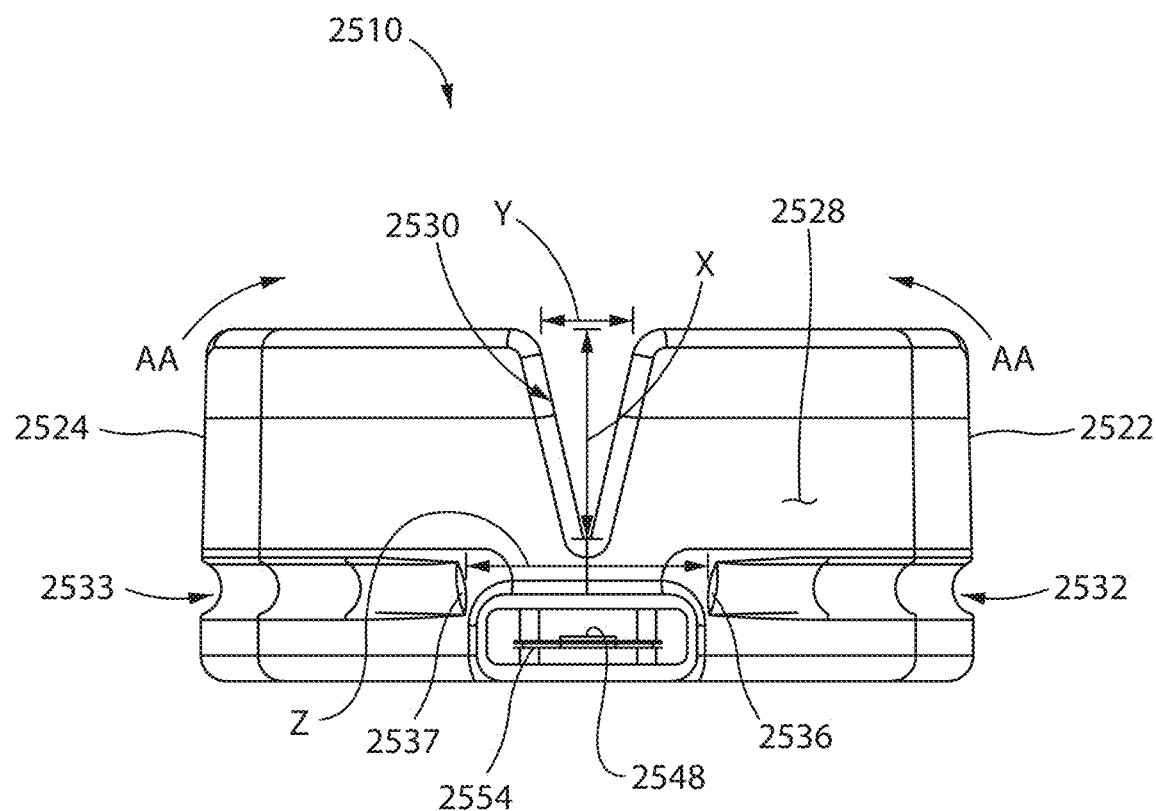
FIG. 68 is a front view of the portion of the light therapy apparatus of FIG. 67.
Figure 69:
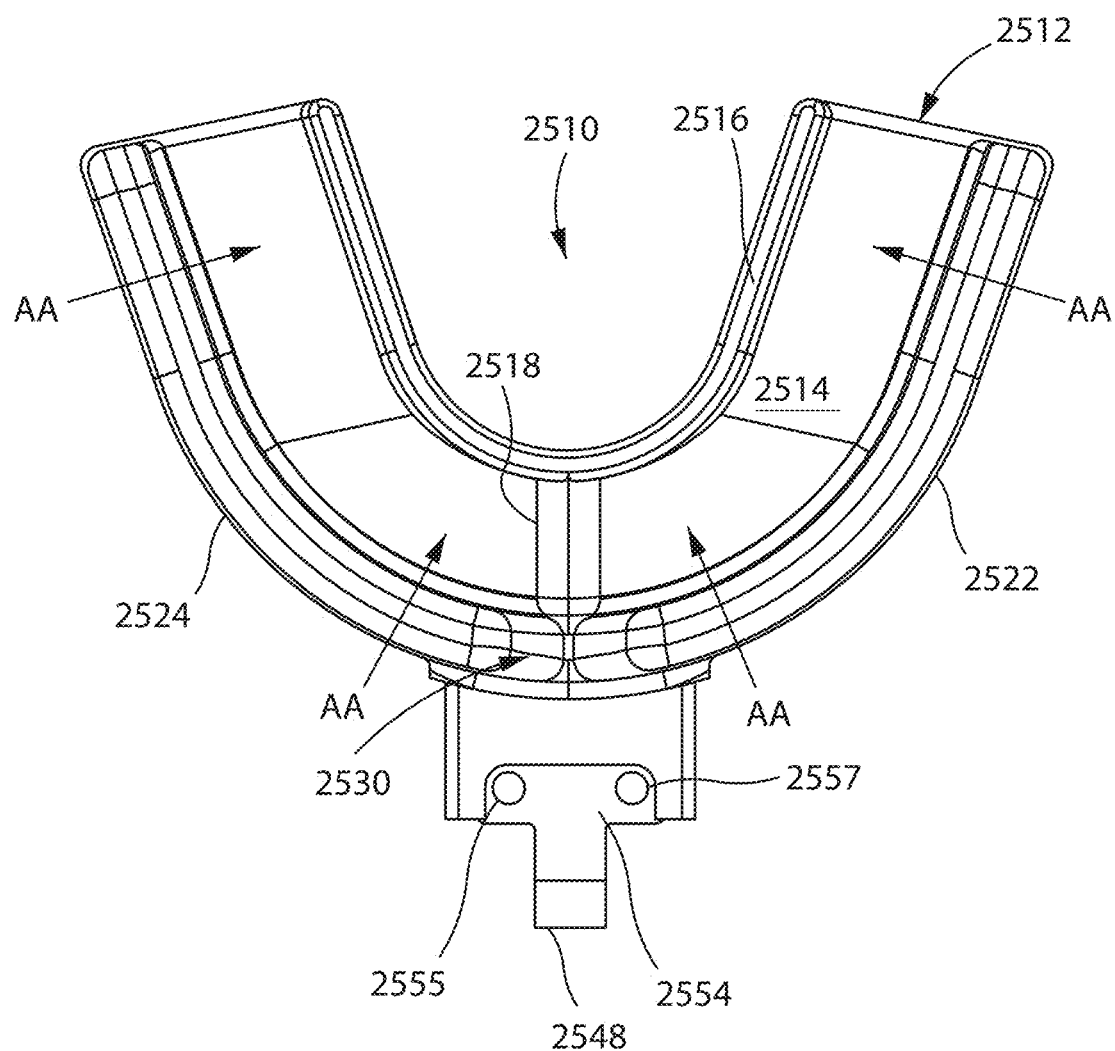
FIG. 69 is a top view of the portion of the light therapy apparatus of FIG. 67.
Figure 70:
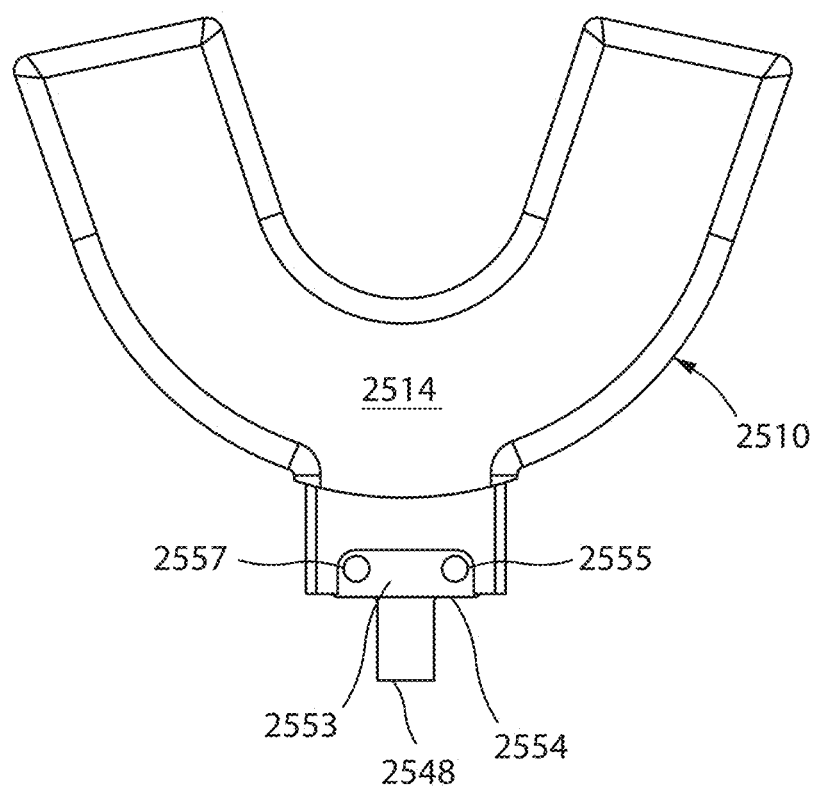
FIG. 70 is a bottom view of the portion of the light therapy apparatus of FIG. 67.

For example, the mouthpiece 2510 includes certain geometric features (e.g., stress concentration risers, areas having a desired bending moment of inertia, etc.) to produce the desired flexibility, deformability and durability in connection with the material(s) from which the mouthpiece 2510 is constructed. As shown, the mouthpiece 2510 defines a notch 2530 and grooves 2532, 2533 configured to permit, or otherwise increase the ability of, the flanges 2522, 2524 to deflect inwardly towards the teeth, gums, jaw, or the like, as shown by the arrows AA in FIG. 68. As shown in FIG. 68, the mouthpiece 2510 defines the notch 2530 at the midline M (see, e.g., FIG. 64B) of the mouthpiece 2510 and between upper portions of the first flange 2522 and the second flange 2524. The notch 2530 is configured to permit the independent and/or inward deflection of each of the first flange 2522 and the second flange 2524, for example, in response to pressure from the patient's lip or inner cheek. In particular, the flanges 2522, 2524 are each configured to deflect inwardly with respect to the bite pad 2514. Similarly stated, when the mouthpiece 2510 is outside of the mouth in an undeformed state (i.e., a first configuration), the first flange 2522 and the second flange 2524 are each approximately perpendicular to the bite pad 2514. When the mouthpiece 2510 is disposed inside the mouth, the upper portion of the mouthpiece 2510 and/or the flanges 2522, 2524 are sufficiently flexible such that an angle formed between each flange 2522, 2524 and the bite pad 2514 (a "flange angle") is acute. This "tipping in" allows the flanges 2522, 2524 to conform to the interior surfaces of the mouth, thereby promoting the desired alignment of the light array 2542 relative to the bone and/or teeth.

As shown in FIG. 68, the notch 2530 can be V-shaped, and has a depth X and a width Y at the widest point of the notch. The width Y is at the upper end of the notch adjacent the free end of the flanges 2522, 2524 opposite the bite tray 2512, and is less than the depth X of the notch. The edge of each flange 2522, 2524 that forms a respective side of the notch 2530 tapers towards the point of the V, which point can be substantially aligned with an upper edge of the grooves 2532, 2533. Similarly stated, the portion of the mouthpiece 2510 that defines a lower boundary of the notch 2530 is aligned, in a horizontal plane, with an upper edge of the portion of the mouthpiece 2510 that defines the grooves 2532, 2533. In other embodiments, however, the portion of the mouthpiece 2510 that defines a lower boundary of the notch 2530 can be in any suitable location relative to the grooves 2532, 2533 (e.g., either above or below the grooves).

The mouthpiece 2510 defines at least one groove 2533, 2534 defined by a lower outer (or front) surface of each of the first and second flanges 2522, 2524. For example, as shown in FIG. 68, the mouthpiece 2510 includes a first groove 2532 and a second groove 2533, each defined by the outer or front surface 2528 of the mouthpiece 2510. In particular, each groove is disposed at a height between the bite pad 2514 and a lower edge of the flexible circuit board 2546 (see, e.g., FIG. 71). Said another way, the grooves 2532, 2533 can be defined by a base portion of each of the first and second flanges 2522, 2524. The grooves 2532, 2533 each extend about the outer surface 2528 of the mouthpiece 2510 between the posterior end portion of the mouthpiece 2510 and an anterior end portion of the mouthpiece 2510, such that a first end 2534, 2535 of each groove 2532, 2533, respectively, is at or proximate to the posterior end portion of the mouthpiece 2510 and a second end 2536, 2537 of each groove 2532, 2533, respectively, is at or proximate to the anterior end of the mouthpiece 2510.

As shown in FIG. 68, the second ends 2536, 2537 of the grooves 2532, 2533 can be spaced apart. In other words, the second ends 2536, 2537 of the grooves 2532, 2533 do not necessarily meet at the anterior end of the mouthpiece 2510. Similarly stated, the grooves 2532, 2533 are noncontiguous and/or do not share a common boundary. For example, the second ends 2536, 2537 of the grooves 2532, 2533 can be spaced apart by a width of a bridge 2506 extending from the front of the mouthpiece 2510. In another example, as shown in FIG. 68, the second ends 2536, 2537 of the grooves 2532, 2533 can be spaced apart by a distance Z (which can be at least as great as the width Y of the notch 2530). The grooves 2532, 2533 can have any suitable shape, including, for example, that of a semi-circle or U-shape. The grooves 2532, 2533 produce a hinge-like structure (i.e., a "living hinge") about which the flanges 2522, 2524 can rotate, bend and/or deflect. In this manner, the grooves 2532, 2533 and the notch 2530 collectively permit the flanges 2522, 2524 to deflect inwardly, for example, in response to pressure from the patient's lip or inner cheek.

As such, the grooves 2532, 2533 and the notch 2530 collectively facilitate the transition of the mouthpiece 2510 between a first configuration and a second configuration. When the mouthpiece 2510 is in the first configuration, the angle formed between each flange 2522, 2524 and the bite pad 2514 (the "flange angle") has a first value. When the mouthpiece 2510 is in the second configuration, the flange angle has a second value that is different from the first value. In particular, the mouthpiece 2510 can be moved to the second configuration when disposed within the patient's mouth. In some embodiments, the second value is less than the first value (i.e., the flanges 2522, 2524 "tip" inward when the mouthpiece 2510 is inserted into the mouth). In some embodiments, the flange angle is approximately 90 degrees when the mouthpiece is in the first configuration and is acute when the mouthpiece is in the second configuration. In some embodiments, the flange angle is about 80 degrees (e.g., the flanges 2522, 2524 tip inward by about 10 degrees) when the mouthpiece is in the second configuration. In other embodiments, the flange angle is between about 75 degrees and about 80 degrees (e.g., the flanges 2522, 2524 tip inward by between about 10 degrees and 15 degrees). In yet other embodiments, the flange angle is approximately 85 degrees, 75 degrees, 70 degrees, or 65 degrees (e.g., the flanges 2522, 2524 tip inward by about 5 degrees, 15 degrees, about 20 degrees and about 25 degrees, respectively) when the mouthpiece is in the second configuration.

The flexibility of the mouthpiece 2510, and of the flanges 2522, 2544 in particular, provides significant advantages. For example, in contrast to mouthpieces constructed of a hard plastic and/or with a permanent set (or shape), the current arrangement allows for easier insertion and better conformance to the oral tissue of the patient. The flexibility of the mouthpiece 2510 also accommodates variation in patient anatomy (whether between two different patients or for the same patient as that patient's anatomy changes over time). For example, some patients have a pronounced overbite and may need more or less than a 10 degree inward deflection (or "tip-in"). In such instances, the mouthpiece 2510 can conform to the internal structure and/or anatomy within the patient's mouth. As another example, as the orthodontia for a patient works over time, the patient's dental anatomy will change. Accordingly, the mouthpiece 2510 can conform to the internal structure and/or anatomy within the patient's mouth to accommodate such change without requiring new mouthpiece moldings or the like. Finally, the flexible design of the mouthpiece 2510 provides greater comfort for the patient than would be provided by mouthpieces constructed of a hard plastic.

Additionally, the flexible nature of the mouthpiece 2510 and/or the flanges 2522, 2524 provides manufacturing benefits. In particular, fabrication and/or molding of a mouthpiece having an acute angle between the bite surface and the side surface of the flange (i.e., the internal angle of the flange or the "flange angle") can be difficult. The design of the mouthpiece 2510, however, allows for the molding and/or fabrication to be performed with a flange angle of approximately ninety degrees (or greater), while allowing for an in-use flange angle that is acute (e.g., when the mouthpiece 2510 is in the second configuration, as described herein).

Figure 71:
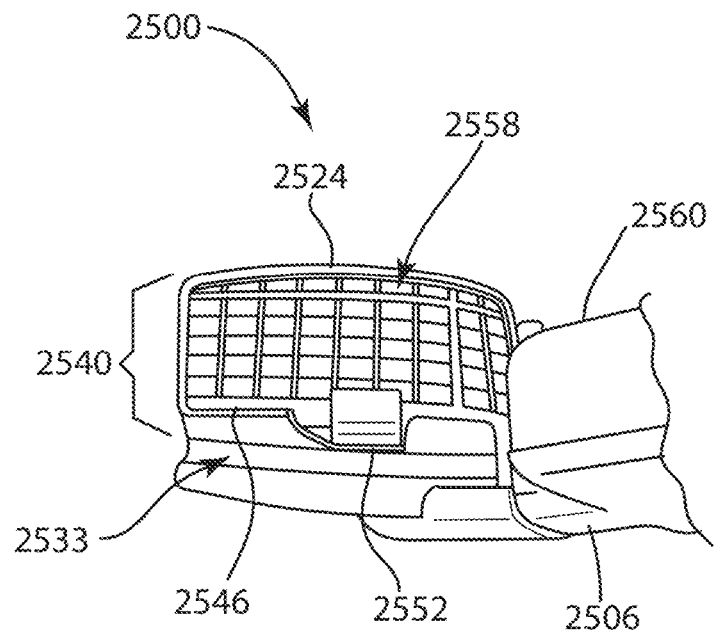
FIG. 71 is a perspective view of a portion of the light therapy apparatus of FIG. 62.
Figure 72:
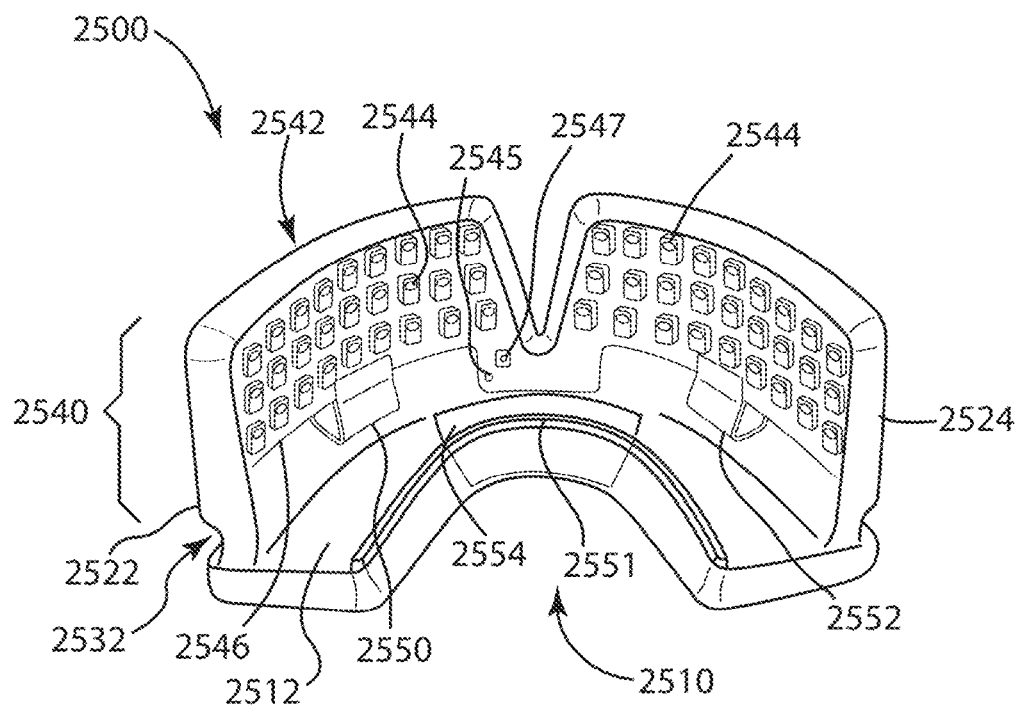
FIG. 72 is a rear view of the light therapy apparatus of FIG. 62.
Figure 73:
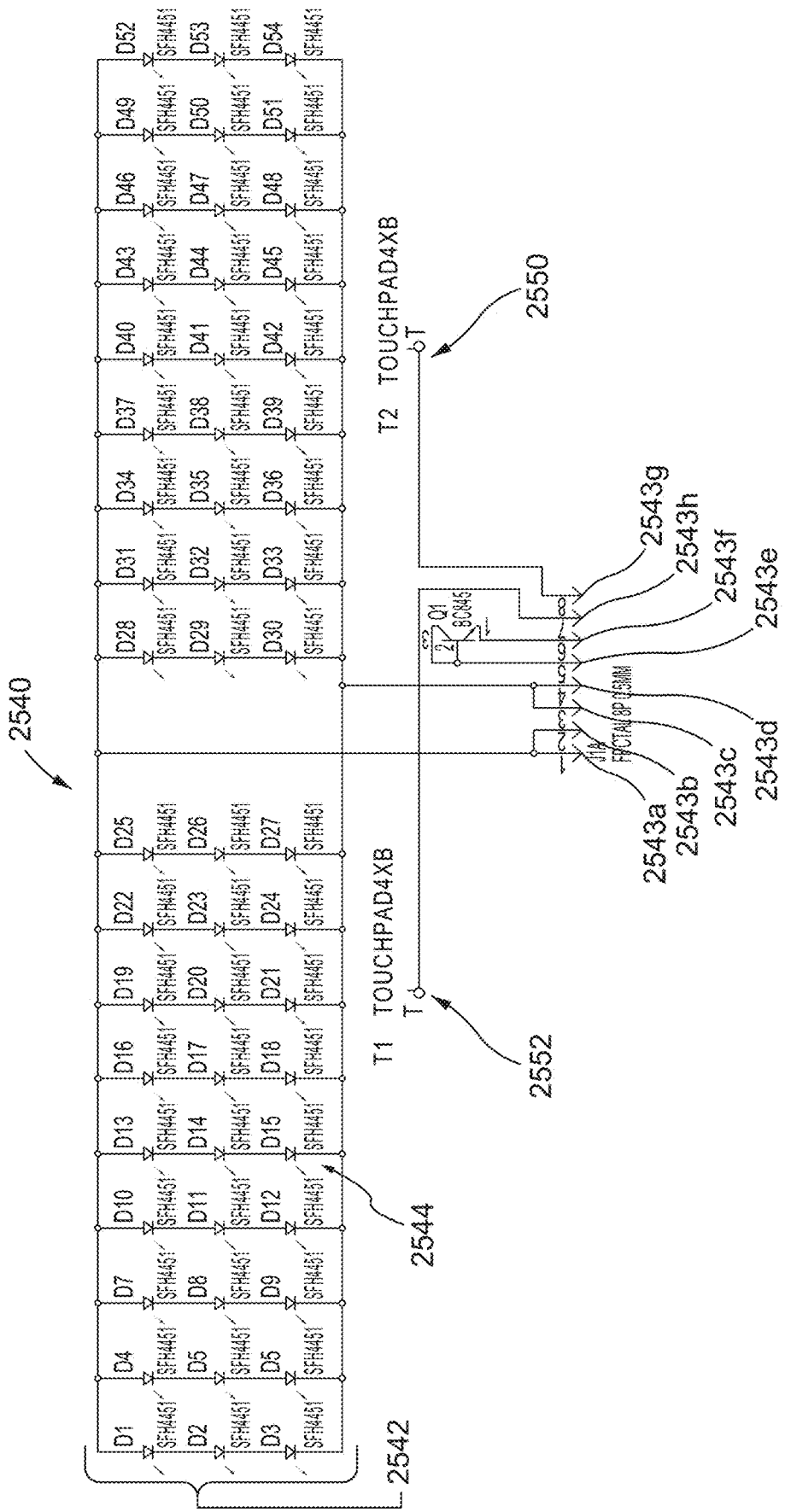
FIG. 73 is a schematic view of a portion of the light therapy apparatus of FIG. 62.
Figure 74A:
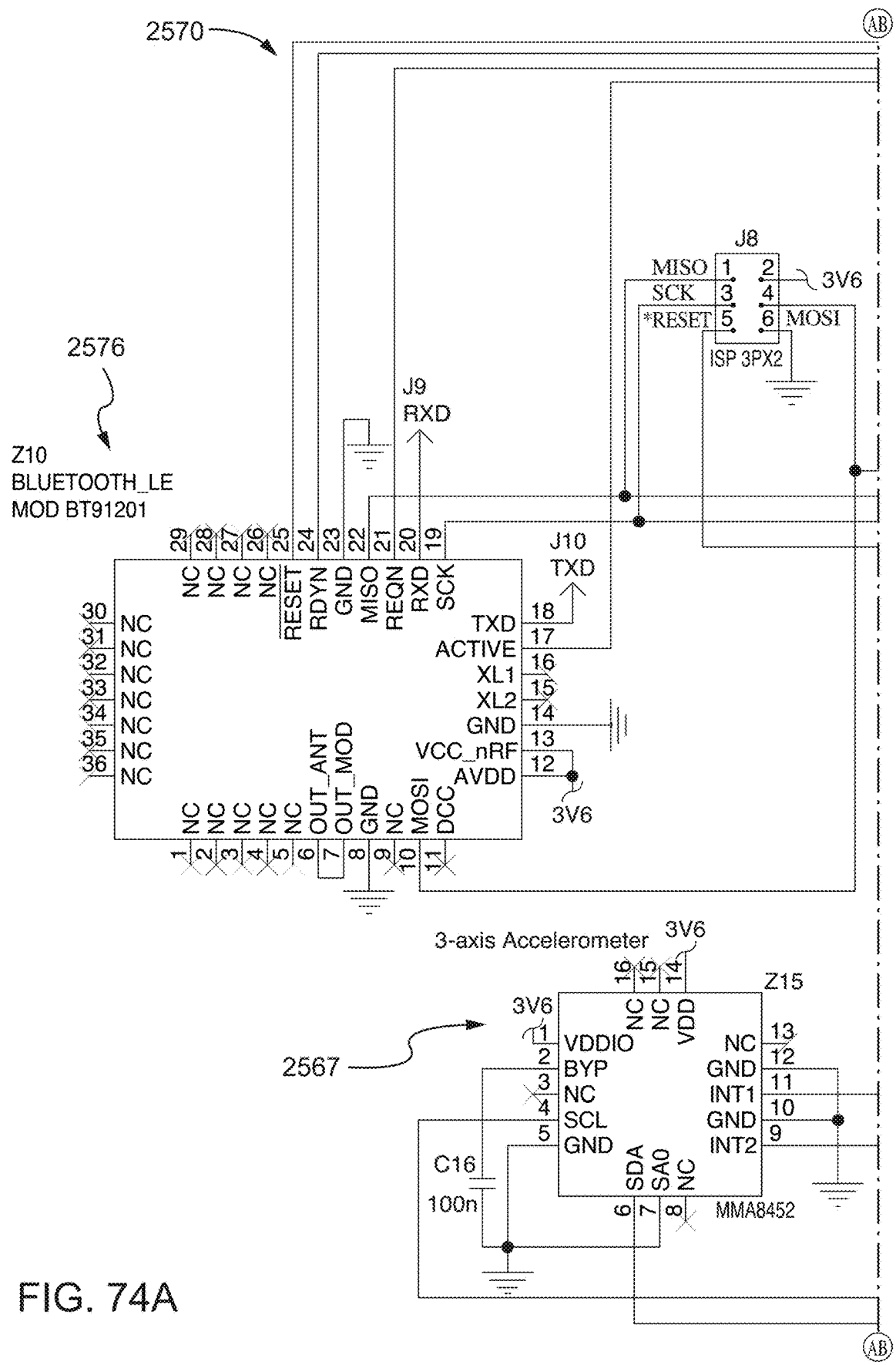
FIGS. 74A-74F collectively are an electrical schematic of a portion of the light therapy apparatus of FIG. 62.
Figure 74B:
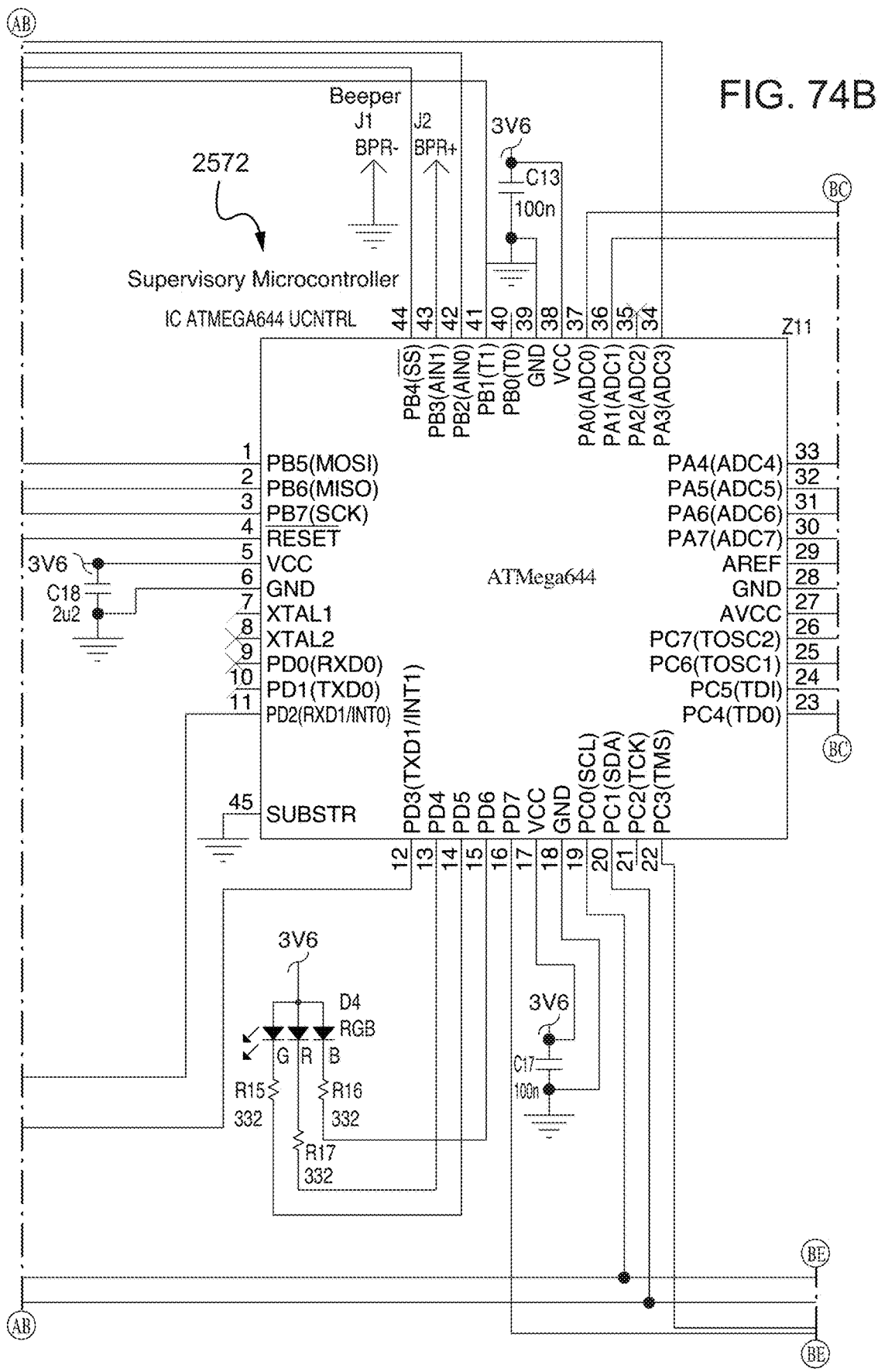
Figure 74C:
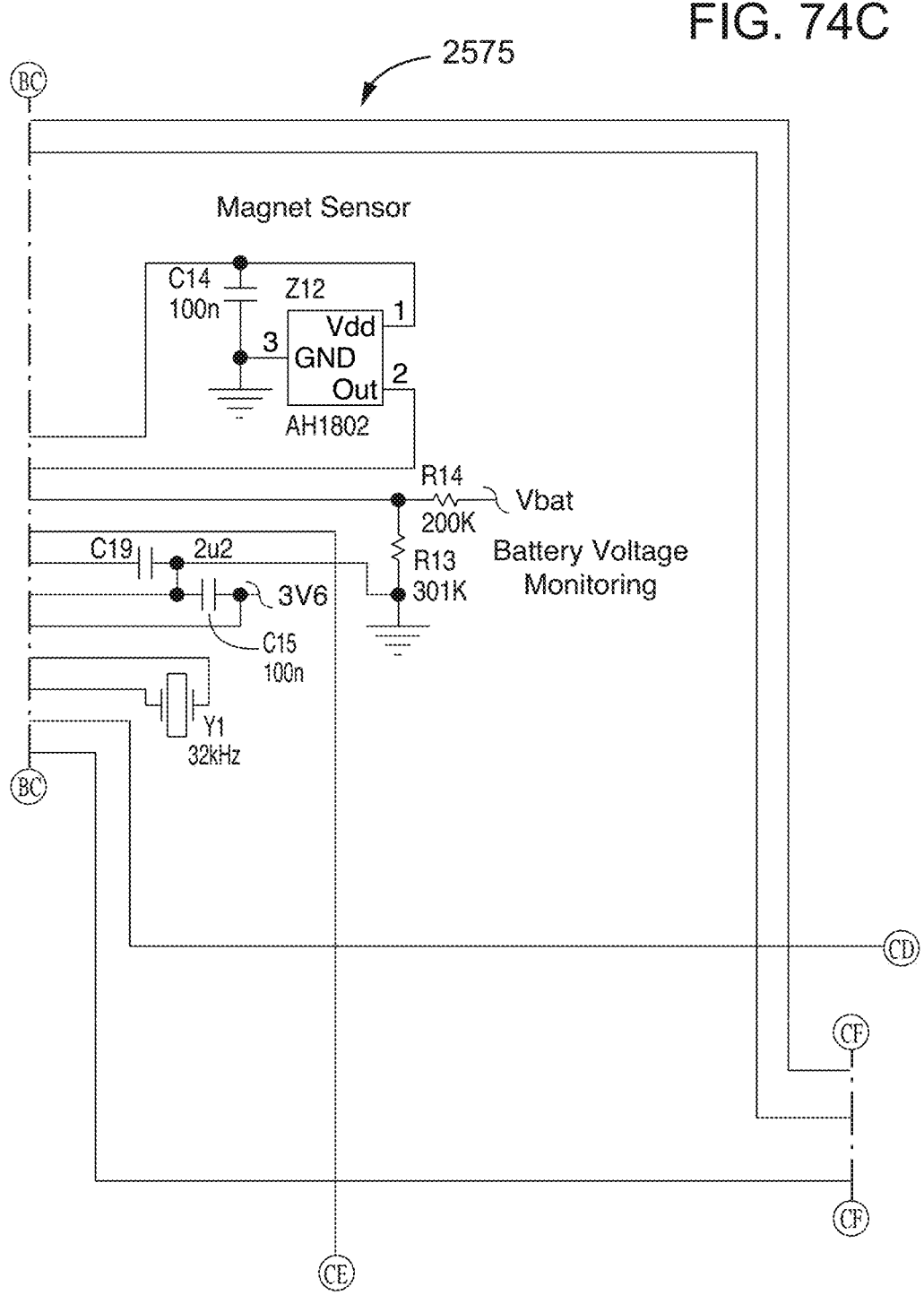
Figure 74D:
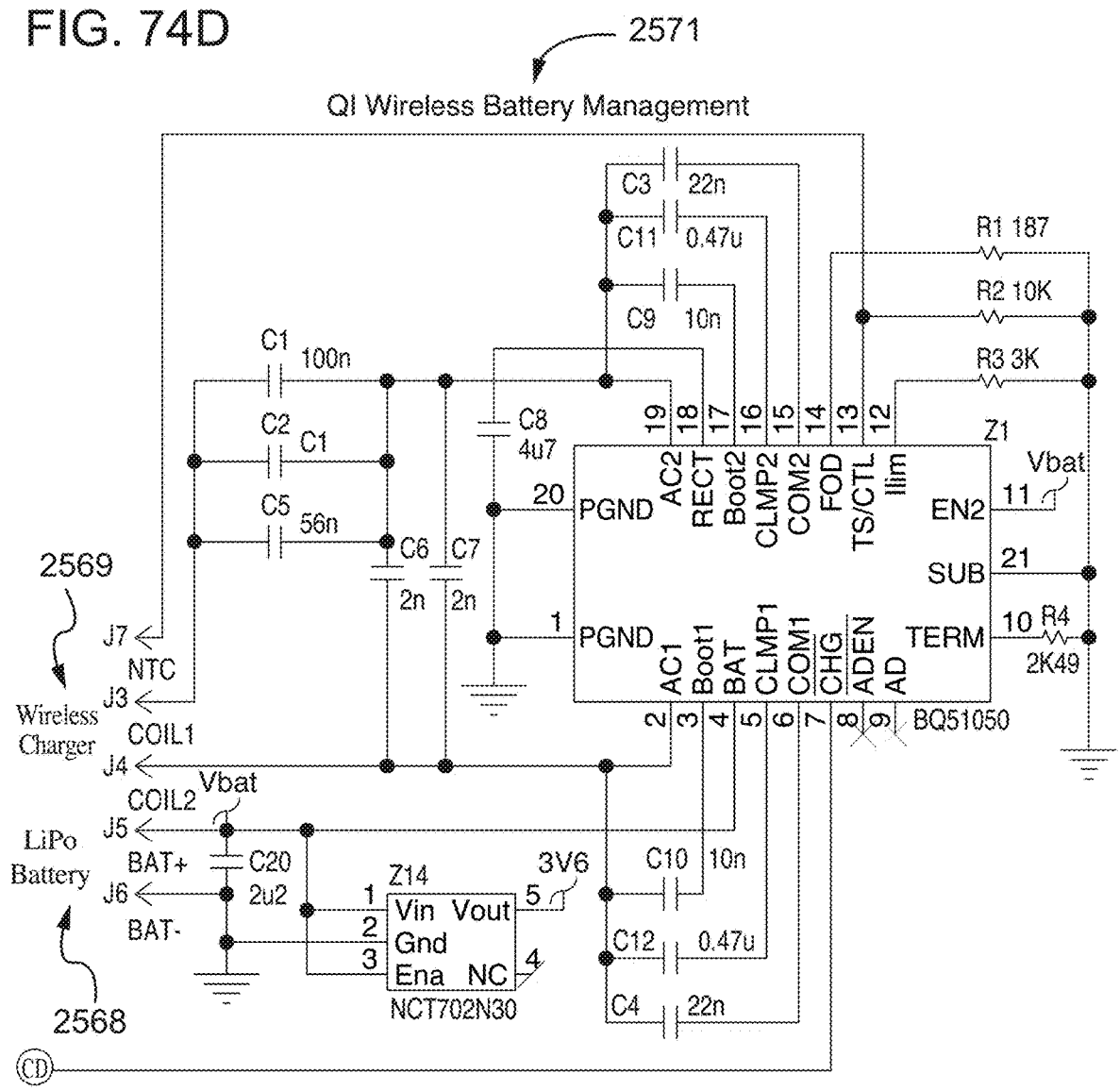
Figure 74E:
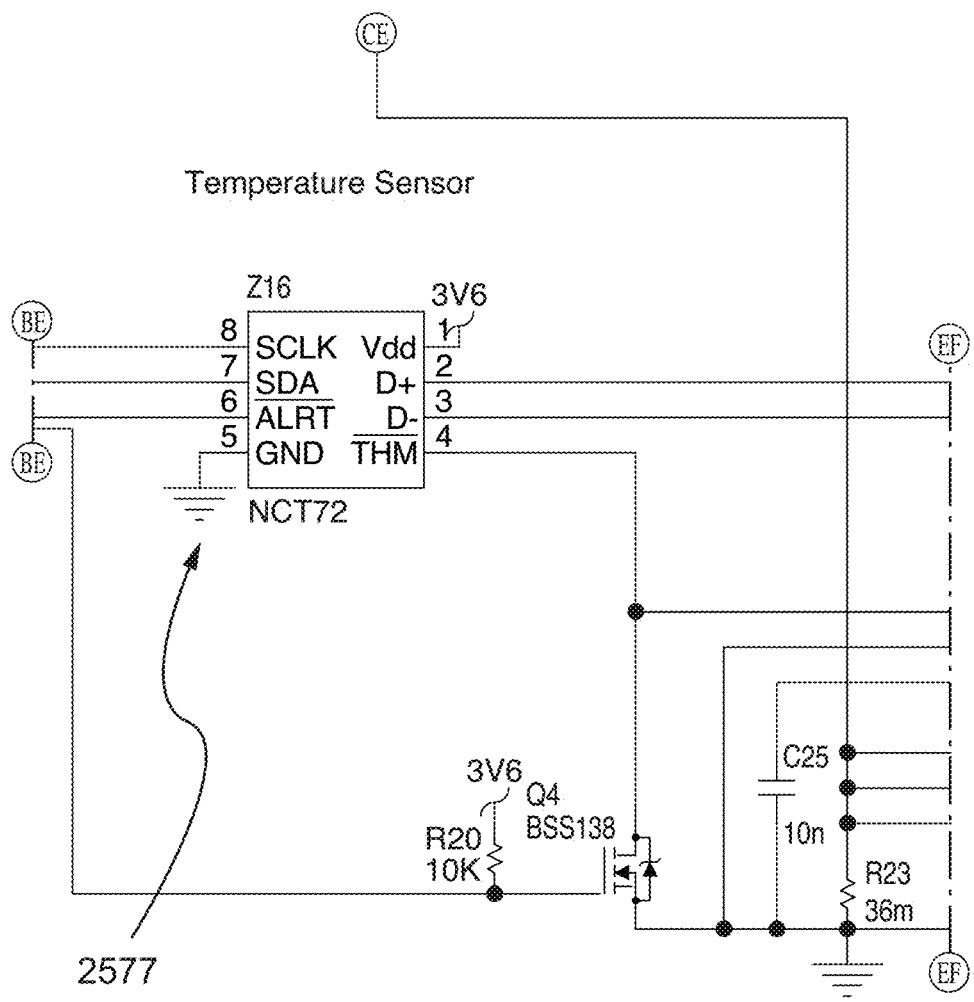
Figure 74F:
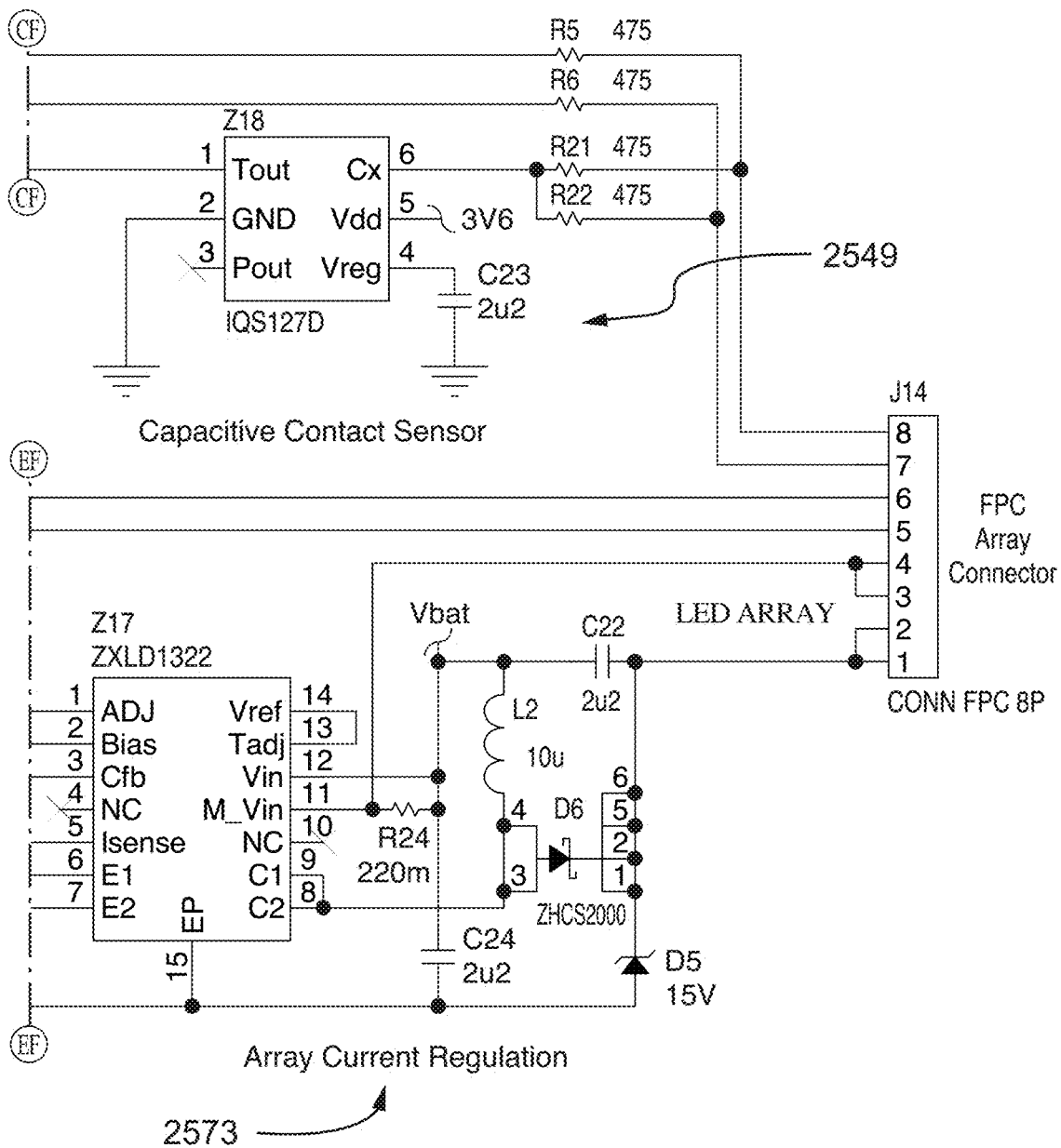
Figure 75:
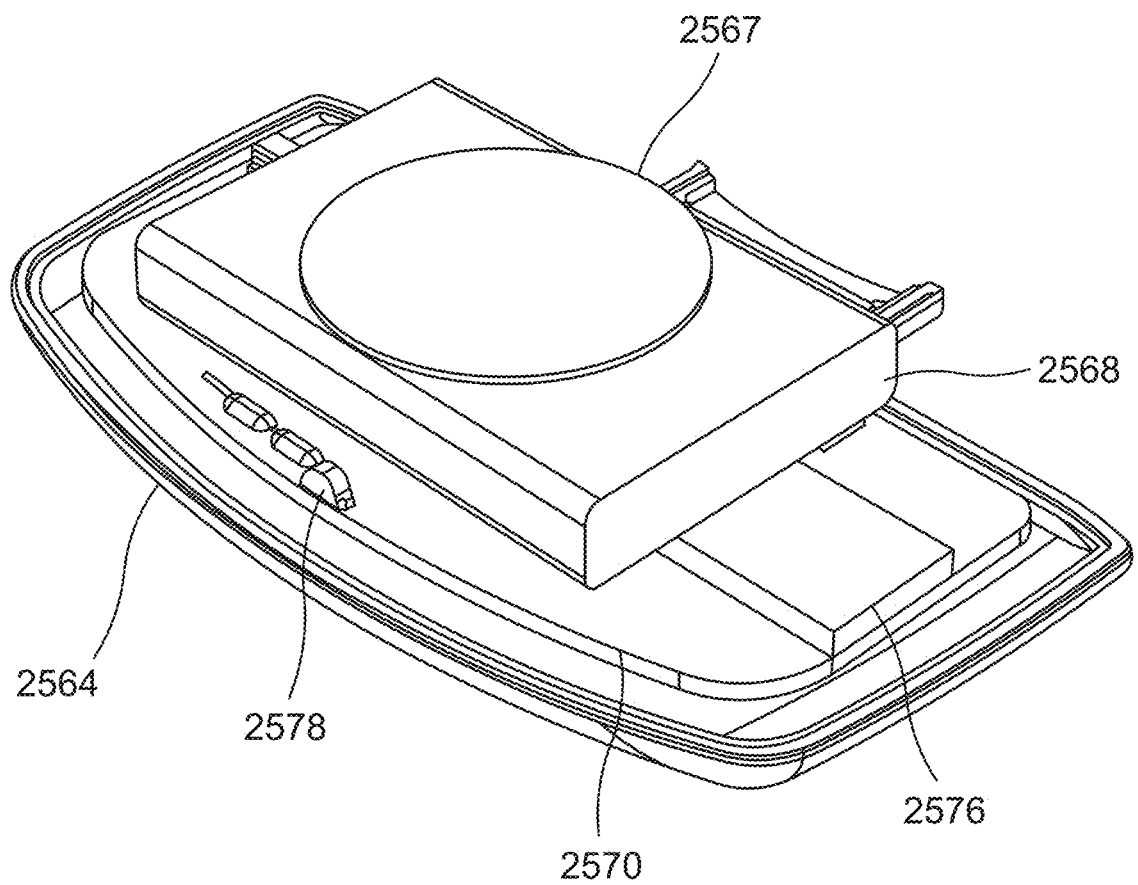
FIG. 75 is a perspective view of a portion of the light therapy apparatus of FIG. 62.

The mouthpiece 2510 of the light therapy apparatus 2500 includes an electronics assembly 2540, generally shown in FIGS. 71 and 72, and schematically in FIG. 73. In some embodiments, at least one or more portions of the mouthpiece 2510 are constructed from a substantially transparent material (e.g., silicone) such that one or more components embedded within the mouthpiece 2510 are visible through the mouthpiece 2510. Thus, for purposes of illustration, portions of the mouthpiece 2510, including portions of the first flange 2522, the second flange 2524 and the bite tray 2512 are shown as being transparent in FIGS. 71 and 72 to show portions of the electronics assembly 2540 and the support plate 2554 disposed therein. The electronics assembly 2540 is configured to cooperatively function with the electronics board 2570 disposed within the bill 2560 to produce the light therapy as described herein. As shown, the electronics assembly 2540 of the mouthpiece 2510 is disposed primarily in the first flange 2522 and the second flange 2524. The electronics assembly 2540 includes a light array 2542, a flexible circuit board 2546, a pair of capacitance sensors 2549, and one or more heat transfer tiles 2558. FIG. 73 schematically illustrates at least a portion of the electronics assembly 2540 of the mouthpiece 2510, according to some embodiments. The light array 2542 includes one or more light emitters 2544, such as a plurality of LEDs (only one light emitter 2544 in each flange is identified in FIG. 72). The light emitters 2544 are electrically and/or physically coupled to the flexible circuit board 2546 (see also, FIG. 64B). The flexible circuit board 2546 electrically couples the light emitters 2544 to electronic circuitry in the bill 2560, such as via pathways 2543a, 2543b, 2543c, 2543d (see, e.g., FIG. 73). In this manner, the light emitters 2544 can receive power and/or a signal to produce the desired light, as described herein.

Referring to FIG. 72, the light emitters 2544 are disposed on a first, palatial (or lingual) side of the flexible circuit board 2546. In this manner, the light emitters 2544 are configured to emit light toward a patient's teeth and/or adjacent oral tissue when the mouthpiece 2510 is disposed within the patient's mouth. The light emitters 2544 can be configured to emit light at any suitable intensity, wavelength and/or frequency described herein. For example, in some embodiments, the light emitters 2544 can be configured to emit light in the infrared or near infrared wavelength range. For example, in some embodiments, the light emitters 2544 are configured to emit light at a wavelength of about 850 nm. In some embodiments, the light emitters 2544 are configured to emit light at a wavelength of 850 nm±5 nm. The light emitters 2544 can be configured to emit light sufficient deliver light energy to the patient's bone to facilitate and/or perform any of the methods described herein. The light emitters 2544 can be configured to emit light at less than 150 mW/cm$^2$.

The light emitters 2544 can be disposed on the flexible circuit board 2546 and/or within the flanges 2522, 2524 in any suitable configuration, including any configuration described herein. For example, in some embodiments, the light emitters 2544 are LEDs coupled to the flexible circuit board 2546 in two or more parallel rows and/or columns. As schematically shown in FIG. 73, the light array 2542 can include about 54 light emitters 2544, or LEDs, with about 27 light emitters embedded in the first flange 2522 and about 27 light emitters 2544 embedded in the second flange 2524. The 27 light emitters 2544 can be arranged in any suitable configuration, including for example in nine evenly spaced columns with three spaced apart LEDs per column. The flexible circuit board 2546 and light emitters 2544 can have any suitable dimensions for being coupled to, or embedded in, the flanges 2522, 2524 of the mouthpiece 2510. Although the light emitters 2544 are shown as being evenly spaced within the first flange 2522 and the second flange 2524, in other embodiments, the light emitters can be unevenly spaced within the first flange 2522 and/or the second flange 2524. For example, in some embodiments, a mouthpiece can include a series of light emitters that are spaced apart by a first amount near the anterior portion of the mouthpiece and a second, different amount near the posterior portion of the mouthpiece.

As shown in FIG. 71, the one or more heat transfer tiles 2558 are disposed on a second, or buccal, side of the flexible circuit board 2546 of the mouthpiece 2510. The tiles can be constructed of any suitable conductive material (e.g., copper, aluminum or the like) and are configured to promote heat transfer away from the light therapy apparatus 2500 and/or the light emitters 2544 and to the patient's buccal tissue. Similarly stated, in use, the copper tiles 2558 can transfer heat from the apparatus 2500 to the patient's cheek, where the patient's naturally occurring circulatory system will draw the heat away from the cheek area. In this manner, the tiles 2558 can facilitate the compliance with applicable temperature regulations and industry standards (e.g., IEC 60601, IEC 60601-2-57, IEC 60601-1-11, EN 62471, etc., described herein) during light therapy administration.

The tiles 2558 can be operatively coupled to the light emitters 2544 in any suitable manner. In some embodiments, the flexible circuit board 2546 has a layer on its second side that includes the one or more heat transfer tiles 2558. The tiles 2558 are spaced apart from each other, and thus may be characterized as being discrete. The discrete nature of the tiles 2558 enhances, or at least does not lessen, the flexibility of the flanges 2522, 2524 of the mouthpiece 2510. In other embodiments, however, the tiles 2558 need not be discrete elements.

In some embodiments, at least a portion of the flexible circuit board 2546 is disposed within the bridge 2506 of the light therapy apparatus 2500. For example, the flexible circuit board 2546 can include a tab portion 2548 disposed in the bridge 2506. The tab portion 2548 of the flexible circuit board 2546 is configured to electrically couple the electronics assembly 2540 of the mouthpiece 2510 with electronic components, described in more detail herein, disposed in the bill 2560. In this manner, the electronic components disposed in the bill 2560 can control operation of the apparatus 2500, and emission of light using the light array 2542, as described in more detail herein.

The mouthpiece 2510 can be constructed of any suitable material, including, for example, an elastomeric material (e.g., a soft silicone). The terms hardness (or softness, as applicable), strength and/or resistance to deformation are used herein to denote a number of related properties associated with the mouthpiece 2510. For example, the terms may be used to refer to specific material properties, such as the yield strength, the modulus of elasticity, the modulus of rigidity, the hardness and/or the elongation percentage. The hardness of a material or the mouthpiece 2510 may be characterized as its "durometer," in reference to the apparatus used to measure the hardness of the types of material used to form mouthpieces.

In some embodiments, the mouthpiece 2510 can be fabricated from medical-grade injection-molded, highly flexible and very low durometer silicone. For example, during manufacture of the mouthpiece 2510, the silicone can be overmolded onto at least a portion of the electronics assembly 2540 of the mouthpiece 2510, including one or more of the flexible circuit board 2546, light emitters 2544, and the copper tiles 2558. In this manner, the portion of the electronics assembly 2540, such as one or more of the flexible circuit board 2546, light emitters 2544, and the copper tiles 2558, are fully encapsulated or embedded within the molded silicone. In this manner, the electronics can be protected for repeated applications within the mouth. In some embodiments, the silicone can be have a hardness (or softness) of about 22 Shore A. Although soft, the silicone is tear resistant, a desirable characteristic because of the sharpness of a patient's teeth (and the anterior teeth in particular). Moreover, the silicone is hydrophobic, and therefore will not absorb water. Suitable silicones include those offered by Bluestar Silicones, East Brunswick, NJ under the name Silbione®, including Silbione® LSR 4305, Silbione® LSR 4310, Silbione® LSR 4325, and Silbione® LSR 4325 PEX (www.bluestarsilicones.com).

In some embodiments, the silicone and/or portions of the mouthpiece 2510 are substantially transparent, such that one or more components embedded within the silicone are visible through the silicone. Moreover, in this manner, the mouthpiece 2510 can provide suitable optical properties for allowing the light produced and/or conveyed by the light emitters 2544 to pass through the mouthpiece 2510 to the desired target tissue. In some embodiments, the mouthpiece 2510 and/or the flanges 2522, 2524 can include one or more components configured to filter, focus and/or otherwise act upon the light produced by the light emitters 2544. In other embodiments, the mouthpiece 2510 can include air gaps between the light emitters 2544 and the surface of the flanges 2522, 2524 to facilitate focusing of the light. As shown in FIG. 64B, however, the mouthpiece 2510 is constructed such that the light emitters 2544 are fully encapsulated or embedded within the molded silicone such that no space or air gap exists between the silicone material and the portion of the electronics assembly 2540. Similarly stated, the mouthpiece 2510 is devoid of an air gap between the light emitters 2544 and the material of the mouthpiece 2510, thus no air gap lensing is needed to produce the desired optical properties of the light produced by the light emitters 2544.

The ridge 2518 can be constructed of the same material as the mouthpiece 2510, or at least the same material as the bite tray 2512 of the mouthpiece 2510. In this manner, when a patient bites together with the upper and lower jaw, the bite tray 2512 of the mouthpiece 2510, including the ridge 2518, may deform slightly from pressure exerted by an occlusal surface of the patient's teeth. Nonetheless, the ridge 2518 is of sufficient dimensions that the patient should be aware of its position, despite any slight deformation of the bite tray 2512 and/or ridge 2518.

The extra-oral housing, or bill, 2560 is coupled to a front portion of the mouthpiece 2510 by the bridge 2506. In this manner, the bill 2560 is disposed exterior to the oral cavity of the patient when the mouthpiece 2510 is disposed within the oral cavity of the patient. Also in this manner, the bill 2560 can be supported with respect to the patient's mouth by the mouthpiece 2510 and/or the bridge 2506 when the mouthpiece 2510 is disposed within the patient's mouth.

The apparatus 2500 can include a support plate 2554. The support plate 2554 is configured to provide structural support to the silicone material of the mouthpiece 2510. The support plate 2554 is configured to help support the bill 2560 with respect to the mouthpiece 2510, for example, when the mouthpiece 2510 is disposed within the patient's mouth. The support plate 2554 has a proximal portion 2551 (see, e.g., FIG. 72) and a distal portion 2553 (see, e.g., FIG. 70). The proximal portion 2551 of the support plate 2554 is coupled to and/or within the mouthpiece 2510. For example, the proximal portion 2551 of the support plate 2554 can be embedded in the silicone material of the bite pad 2514. The support plate 2554 can be substantially planar, and the proximal portion 2551 of the support plate 2554 can be disposed within the mouthpiece 2510 such that the support plate is substantially parallel to the upper surface of the bite pad 2514. At least a portion of the support plate 2554 is disposed in the bridge 2506. The distal portion 2553 of the support plate 2554 is configured to couple the mouthpiece 2510 and the bill 2560. For example, the distal portion 2553 of the support plate 2554 can define two apertures 2555, 2557 each configured to receive a protrusion, or guide pin, (not shown in FIGS. 70 and 72) of the bill 2560. In some embodiments, at least the distal portion 2553 of the support plate 2554 defining the apertures 2555, 2557 is exposed with respect to (or is not disposed within) the material of the mouthpiece 2510.

The bill 2560 of the light therapy apparatus 2500 includes a first, or top, portion 2562 and a second, or bottom, portion 2564 and forms a cavity (not shown) therebetween. Although the bill 2560, in combination with the bridge 2506, is shown in FIGS. 62-66 as generally having a T-shape, in other embodiments, the bill 2560 can have any suitable shape. The bill 2560 is configured to at least partially enclose one or more electronic components of the apparatus 2500, as described in more detail herein, which components can be disposed in the cavity of the bill 2560.

The apparatus 2500 includes at least one battery, or other suitable power source. For example, a battery 2568 is disposed in the cavity of the bill 2560. The battery 2568 can be electrically coupled to and to provide power to one or more electronic components of the bill 2560, including, for example, one or more of an electronics board 2570, a microcontroller 2572, a system clock, a wireless transmitter 2576, and other electronic components of the bill 2560. The battery 2568 is configured to provide power to the electronics assembly 2540 of the mouthpiece 2510. More specifically, the battery 2568 is configured to provide power to the light array 2542 to enable the light emitters 2544 to irradiate light during a treatment session. The battery 2568 can include, for example, a rechargeable lithium ion battery. In some embodiments, the battery is a lithium-ion polymer battery, also referred to as a lithium polymer or LIPO battery. In some embodiments, the battery 2568 is disposed within the cavity of the bill 2560 between an accelerometer 2567 and the electronics board 2570.

In some embodiments, the apparatus 2500 is configured to wirelessly charge, or recharge, the battery 2568. For example, an induction receiver coil 2569 can be disposed in the cavity of the bill 2560. The induction receiver coil 2569 is configured for inductively charging the battery 2568, as described in more detail herein. The induction receiver coil 2569 can include, for example, a Qi-based charging coil.

The electronics board 2570 is disposed in the bill 2560 of the apparatus 2500. The electronics board 2570 is electrically coupled to the flexible circuit board 2546 of the mouthpiece 2510 (e.g., via the tab portion 2548 of the flexible circuit board 2546), thereby electrically coupling electronic components of the bill 2560 with the electronic assembly 2540 of the mouthpiece 2510. Electronic circuitry within the bill 2560 electrically couples the electronics board 2570, the microcontroller 2572, the system clock, the wireless transmitter 2576, one or more switches, and other electronic components of the bill 2560.

The light therapy apparatus 2500 is configured to detect movement of the apparatus. More specifically, the apparatus 2500 is configured to detect when the apparatus is moved in any one of three axes or dimensions (also referred to herein as three-dimensional movement). Referring to FIGS. 74A-74F, in some embodiments, the apparatus 2500 includes an accelerometer 2567 disposed within the cavity of the bill 2560. The accelerometer 2567 can be, for example, a piezoelectric sensor. The accelerometer 2567 can be coupled to the bill 2560 (e.g., to the first portion 2562 of the bill) by any suitable coupling mechanism, including, but not limited to, an adhesive, such as double-sided tape. The accelerometer 2567 is electrically coupled to the electronics board 2570. In some embodiments, two electronic leads or wires (not shown in FIGS. 74A-74F or 75) couple the accelerometer 2567 and the electronics board 2570. The accelerometer 2567 is configured to detect three-dimensional, or three-axis, movement of the light therapy apparatus 2500.

The accelerometer 2567 can be configured to send an electrical signal to a microcontroller 2572 of the apparatus 2500 when the three-dimensional movement is detected. The microcontroller 2572 is disposed in the cavity of the bill 2560. The microcontroller 2572 is in electrical communication with the accelerometer 2567, and is configured to receive the electrical signal from the accelerometer 2567. The detected movement of the apparatus 2500 can be used to control the light emissions and/or other aspects of the performance of the device. For example, in some embodiments, when the microcontroller 2572 detects movement of the apparatus 2500, the microcontroller 2572 can move the apparatus 2500 from a "sleep" state (in which the light emitters 2544 are prevented from being actuated) to a "wake" state (in which the light emitters 2544 are enabled).

In some embodiments, the light therapy apparatus 2500 can be configured to determine the orientation of the apparatus. Said another way, the light therapy apparatus 2500 can be configured to determine if the mouthpiece 2510 is oriented in the upright or inverted position. For example, in some embodiments, the accelerometer 2567 is configured to determine if the apparatus 2500 is oriented in the upright or inverted position. The accelerometer 2567 is configured to send a signal associated with the orientation of the apparatus 2500 to the microcontroller 2572. In this manner, the electronics board 2570 and/or the microcontroller 2572 can adjust and/or control the operation of the device 2500 as a function of the orientation of the mouthpiece 2510, as described herein.

Electronic circuitry disposed in the bill 2560 of the apparatus 2500 includes a switch 2575 (also referred to herein as a magnet switch or sensor, schematically illustrated in FIGS. 74A-74F) that is moveable from a first position (or configuration) to a second position (or configuration). More specifically, the switch 2575 is configured to move from its first position to its second position when the switch is activated by a magnet located within a close proximity to the switch. When the switch 2575 is in its second position, the apparatus 2500 is maintained in its sleep state, even if movement is detected by the accelerometer 2567. In some embodiments, the external station 2580 includes the magnet 2596 (see e.g., FIG. 90) configured to activate the switch 2575. In this manner, when the apparatus 2500 is disposed on the external station 2580, the magnet 2596 of the external station 2580 causes the switch to move from its first position to its second position, thereby preventing the apparatus 2500 from moving to its wake state from its sleep state, regardless of whether the accelerometer 2567 detects movement of the apparatus. This helps to prevent inadvertent waking and/or activation of the apparatus 2500, as may otherwise occur if the external station 2580 is moved with the apparatus 2500 disposed therein (e.g., for transport). The microcontroller 2572 is configured to determine whether the switch 2575 is in its first position or its second position. In this manner, the microcontroller 2572 is configured to determine whether the apparatus 2500 is disposed on the external station 2580.

The light therapy apparatus 2500 can also be configured to determine whether the mouthpiece 2510 is disposed within the patient's mouth (i.e., in a manner suitable for the treatment session). In this manner, the apparatus 2500 can be configured to only irradiate light for the treatment session when the apparatus 2500 has determined that the mouthpiece 2510 is disposed in the patient's mouth. In some embodiments, for example, the light therapy apparatus 2500 includes a capacitance detection system configured to detect a capacitance change when the mouthpiece 2580 is disposed within the patient's mouth. Referring to FIGS. 71-73 and 74A-74F, the capacitance detection system can include a capacitance sensor 2549 (see, e.g., FIGS. 74A-74F) disposed in the bill 2560 and configured to be in electrical communication with a first capacitance electrode 2550 and a second capacitance electrode 2552, each coupled to the flexible circuit board 2546 of the mouthpiece 2510. The flexible circuit board 2546 is configured to electrically couple the electrodes 2550, 2552 to the capacitance sensor 2549 in the bill 2560, such as via pathways 2543a-b and 2543c-d, respectively.

At least a portion of the sensors 2550, 2552 can be embedded in the flanges 2522, 2524 of the mouthpiece 2510, for example, in a similar manner as discussed herein with respect to the light array 2542. The electrodes 2550, 2552 are spaced apart on the flexible circuit board 2546. In some embodiments, the electrodes 2550, 2552 are disposed at opposing locations with respect to the flexible circuit board 2546, as shown in FIG. 72, such that the first electrode 2550 is beneath the portion of the light array 2542 embedded in the first flange 2522 and the second electrode 2552 is beneath the portion of the light array 2542 embedded in the second flange 2524. In this manner, the apparatus 2500 is configured to detect a capacitance change bilaterally. In some embodiments, each electrode 2550, 2552 is extended posteriorly within the patient's mouth, thus providing for more "horizontal" contact with the patient's oral tissue for more robust sensing of the capacitance change.

The electrodes 2550, 2552 are configured to be disposed in close proximity to the patient's buccal tissue, which has a high capacitance, when the mouthpiece 2510 is disposed within the patient's mouth in preparation for treatment. The patient's saliva or wet buccal tissue can activate the capacitance of each electrode 2550, 2552. The apparatus 2500 is configured to irradiate light only after a predetermined capacitance change has been registered. Said another way, the apparatus 2500, and the microcontroller 2572 more specifically, is configured to turn on the light emitters 2544 only after the predetermined capacitance change has been registered. The capacitance change is registered by the microcontroller 2572, which is configured to execute an algorithm to register the change in capacitance, when (1) the capacitance change threshold is detected by the capacitance sensor 2549 with respect to each electrode 2550, 2552 (i.e., bilaterally), and/or (2) the capacitance change is detected for a predetermined duration (e.g., for at least 2 seconds). When the microcontroller 2572 registers the capacitance change, a switch (also referred to herein as the "capacitance switch," not shown in FIGS. 74A-74F, but generally included in the capacitance sensor 2549 components) in the bill 2560 and in electrical communication with the microcontroller 2572 is moved from a first position in which the light emitters 2544 are off, to a second position, in which the light emitters 2544 are on, thereby moving the apparatus 2500 to an active state in which the light emitters 2544 are irradiating light.

Because bilateral capacitance change is required to move the switch to its second position, the incidence of false positives that may result from the use of only one electrode is limited. In other embodiments, however, a light therapy apparatus can include only a single capacitance electrode. In yet other embodiments, a light therapy apparatus can include any other suitable detection mechanism for determining when the mouthpiece 2510 is positioned with the mouth.

Also, the capacitance detection system of the light therapy apparatus 2500 improves patient safety and/or compliance. For example, the light emitters 2544 can be configured to emit infrared light, so it is desirable to prevent emission of the light until the mouthpiece 2510 is properly disposed within the patient's mouth (e.g., to avoid the possibility of emitting radiation that could be harmful to the eyes). The arrangement of the capacitance sensor also eliminates the need for a manual "on/off" switch on the bill 2560. Such manual switches are prone to user error. For example, the patient may accidentally turn the light emitters off when the patient intended to begin a light therapy treatment session, as the patient may not readily discern whether the light emitters are off or on.

In some embodiments, the apparatus 2500 is configured to detect reflection of light off of a patient's oral soft tissue. The light emitters 2544 can be configured to emit light, such as in a blinking or pulsing manner. The light emitters 2544 can be configured to blink or pulse at a predetermined rate. At least a portion of light emitted from the pulsing or blinking light emitters 2544 towards the oral soft tissue of the patient's mouth is reflected to the mouthpiece 2510 and is thereby detected by a sensor or other light reflectance detection mechanism (generally referred to as a "reflectance sensor;" not shown in FIGS. 62-75). The reflectance sensor is configured to evaluate the functionality of a portion of the light array 2542 coupled to the first flange 2522 of the mouthpiece 2510 and a portion of the light array 2542 coupled to the second flange 2524 of the mouthpiece 2510. In this manner, the reflectance sensor facilitates detection of any faulty operation of the apparatus 2500 with respect to each of the flanges 2522, 2544 of the mouthpiece 2510 before operation of the apparatus 2500 with respect to the patient. Suitable reflectance thresholds can be established to measure reflectance in order to determine that the light emitters 2544 of the light array 2542 are operating properly. The apparatus 2500 can be configured to initiate irradiation of the oral tissue (i.e., begin a treatment session) when the reflectance sensor detects the light reflection off of the oral soft tissue and/or when the capacitance detection system detects a threshold capacitance change. In some embodiments, at least one of the reflectance sensor or the capacitance detection system is configured to transmit a signal to the microcontroller 2572 in the bill 2560 to initiate the treatment session when the reflectance sensor detects light reflection (e.g., at or above a predetermined threshold) from the oral soft tissue or when the capacitance sensor 2549 detects the threshold capacitance change.

The reflectance sensor can also be configured to track the patient's compliance with a treatment program. For example, the reflectance sensor can be configured to transmit a signal to the microcontroller 2572 each time the reflectance sensor detects the light reflection at a suitable reflectance threshold, which indicates that the mouthpiece 2510 was disposed in the patient's mouth. In this manner, the microcontroller 2572 can track the occurrences of when the patient placed the mouthpiece into the patient's mouth based on the signal transmitted by the reflectance sensor.

In addition to controlling the operation of the device 2500 based on movement and/or positioning within the mouth, the microcontroller 2572 can also control the operation of the device 2500 and/or the light emitters 2544 based on the temperature of various regions of the device and/or the anatomy of the patient. In particular, as discussed herein, regulatory requirements and/or industry standards may set limits on the temperature of a medical device in the mouth of a patient. The light therapy apparatus 2500 is configured to ensure the apparatus complies with an applicable regulatory requirement and/or industry standard. A temperature sensor 2577 (schematically shown in FIGS. 74A-74F), such as a thermocouple, is disposed in the bill 2560 and is configured to be in communication with the microcontroller 2572. The temperature sensor 2577 is coupled to one or more contacts 2545, 2547, disposed on the flexible circuit board 2546 of the mouthpiece 2510. As schematically shown in FIGS. 73 and 74A-74F, the contacts 2545, 2547 can be coupled to the temperature sensor 2577 via pathways 2543*e*, 2543*f*.

The temperature sensor 2577 is configured to measure the temperature of the mouthpiece 2510 (e.g., via the contacts 2545, 2547) during a light therapy treatment session. The temperature sensor is configured to transmit an electrical signal associated with the measured temperature to the microcontroller 2572, or the like). In some embodiments, the position of the temperature sensor, or its contacts 2545, 2547, with respect to the flexible circuit board 2546 may vary from a position set forth in a regulation or industry standard. As such, the apparatus 2500 can be configured to execute a temperature algorithm (e.g., via the microcontroller 2572) that is configured to correct and/or adjust the temperature as measured by the temperature sensor based on the difference between the sensor's actual position and the position set forth in the regulation or standard, thereby calculating an adjusted temperature used to control the operation of the light therapy apparatus 2500.

In some embodiments, the light therapy apparatus 2500 is configured to temporarily cease light irradiation when a first predetermined temperature threshold is met or exceeded by at least one of the measured temperature or the adjusted temperature. The first predetermined temperature threshold can be a temperature sufficiently high to cause discomfort to the patient, but less than the regulatory (or industry standard) limit. In use, when the first predetermined temperature is met or exceeded, the light emitters 2544 are turned off, and the treatment session is paused. For example, the treatment session can be paused for a cooling period to permit the apparatus' 2500 temperature to drop to at least a predetermined temperature, or to a temperature lower than the first predetermined temperature threshold. For example, during a three minute treatment session, the cooling period can be about 20 seconds or about 30 seconds. If the temperature of the apparatus 2500 is sufficiently reduced, the light emitters 2544 are turned on (e.g., via the microcontroller 2572) and the treatment session is resumed.

In some embodiments, the light therapy apparatus 2500 is configured to cease light irradiation when a second predetermined temperature threshold, greater than the first predetermined temperature threshold, is met or exceeded by at least one of the measured temperature or the adjusted temperature. The second predetermined temperature threshold can be a temperature equivalent to the regulatory (or industry standard) limit. In some embodiments, the second predetermined temperature threshold is within the range of about 45 degrees Celsius to about 55 degrees Celsius. In some embodiments, the second predetermined temperature threshold is about 48 degrees Celsius. If the second predetermined temperature threshold is met or exceeded, the light emitters 2544 are turned off, and the treatment session is ended. In such embodiments, the apparatus 2500 does not automatically resume the treatment program when the second predetermined temperature threshold is met or exceeded by at least one of the measured of adjusted temperature of the apparatus 2500.

The light therapy apparatus 2500 is configured to track a patient's compliance with a prescribed treatment program of light therapy treatment sessions. As such the apparatus 2500 is configured to store data associate with the patient's history of usage of the apparatus 2500. The apparatus 2500 can be configured to store data including one or more of (1) a total number of light therapy treatment sessions initiated and/or completed using the apparatus, (2) a total number of days the apparatus was used to administer light therapy treatment sessions, (3) whether the apparatus was used to administer light therapy to the upper or lower jaw (e.g., per treatment session), (4) a duration that light was administered by the apparatus for a particular date and time (e.g., if the patient completed less than a full treatment session, the apparatus can store the duration that light was administered), and (5) the date and time that light was administered using the apparatus 2500, or any combination of the foregoing.

The microcontroller 2572 is configured to transmit the stored data (i.e., the patient compliance information) to an external device. For example, the light therapy apparatus 2500 can be configured to transmit the patient compliance information to a mobile phone, personal digital assistant, computer, portable electronic device, the external station 2580, or the like. The apparatus 2500 can include a transmitter 2576 disposed in the bill 2560. In some embodiments, the transmitter 2576 is a wireless transmitter 2576 configured to wirelessly transmit data to the external device. The wireless transmitter 2576 can be configured to transmit the data via Bluetooth® or another suitable wireless mechanism and/or protocol. In some embodiments, the apparatus 2500 is configured for one-way transmission of data to the external device, e.g., via the transmitter 2576. In other embodiments, however, the transmitter is a transceiver, and therefore is configured for bi-directional communication of data with the external device.

As discussed herein, the light therapy apparatus 2500 can have any suitable number of operational states or statuses. For example, in some embodiments, the light therapy apparatus 2500 can have a sleep state and a wake state. In the sleep state, the apparatus 2500 is prevented from irradiating light for a light therapy treatment session. The apparatus 2500 can be in a low power state during its sleep state, such that there is minimal electrical activity. Even in the sleep state, however, certain electronic components may continue to operate, such as a system clock (not shown). Additionally, in the sleep state, the apparatus 2500 can have a charge status or a communication status. In the charge status, the battery 2568 of the apparatus 2500 is being charged (or recharged), but the apparatus 2500 remains asleep. In the charge status, the wireless transmitter 2576, or other radio mechanism, of the apparatus 2500 is configured to wirelessly transmit information (e.g., patient compliance data) to the external device, however the apparatus remains in its sleep state.

In the wake state, the apparatus 2500 can be configured to have a ready status, an error status, a waiting status, an advertise status, an active status, a cooling status, a paused status, and a done status, or any combination thereof. In some embodiments, the apparatus 2500 is configured to be in its communication status when in the wake state instead of, or in addition to, when the apparatus is in the sleep state.

In the ready status, the apparatus 2500 is ready to begin irradiating light for the treatment session, but has not begun irradiating light. For example, in the ready status, the apparatus may be configured to begin the light therapy treatment session upon confirmation that the mouthpiece 2510 is properly disposed within the patient's mouth. In the error status, the apparatus 2500 has detected an error and is prevented from irradiating light for the treatment session. Like in the ready status, the apparatus 2500 in the waiting status is ready to begin irradiating light for the treatment session, but has not begun irradiating light. The apparatus 2500 is configured to enter the waiting status subsequent to the ready status, as described in more detail herein. In the advertise status, the apparatus 2500 is configured to produce an alert to the patient that the device is ready for use in the treatment session. In the active status, the apparatus 2500 is irradiating light for the treatment session. In the cooling status, light irradiation from the apparatus 2500 is interrupted, or paused, for a predetermined period to permit the apparatus to cool down. In the paused status, light administration is temporarily ceased for a non-temperature related reason. In the done status, the apparatus 2500 has completed irradiating light for the treatment session, and therefore ceases light administration. In the communication status, the apparatus 2500 is configured to communicate with an external device.

Figure 76:
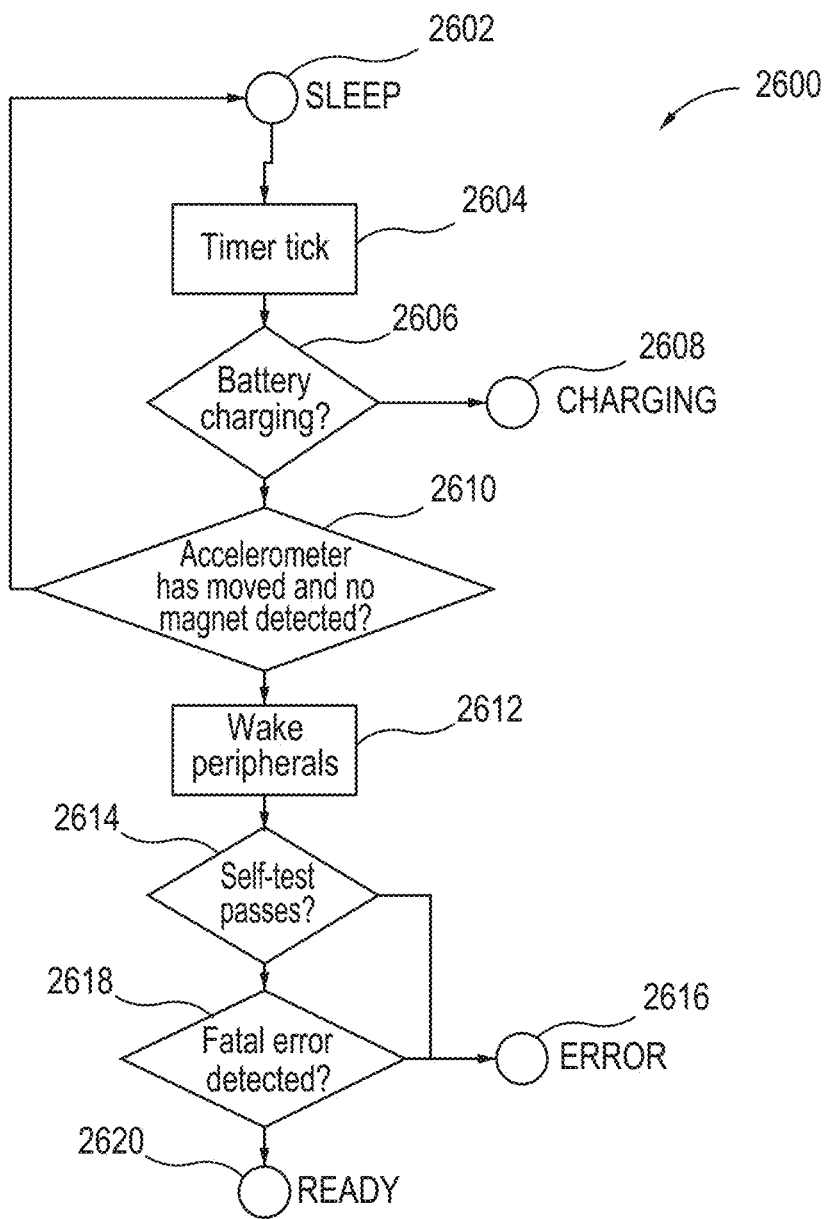
FIGS. 76-86 are logic flow charts representing code configured to be executed by the light therapy apparatus of FIG. 62, according to various embodiments.

The apparatus 2500 (e.g., via the microcontroller 2572) is configured to execute various algorithms, including executing various logic sequences, to control the state or status of the apparatus. For example, as schematically illustrated in FIG. 76, the apparatus 2500 is configured to execute an algorithm 2600 for determining whether the apparatus can move from the sleep state to the wake state. Although the following descriptions refer to particular portions of the light therapy device 2500, any of the methods described herein can be performed by any of the devices described herein. Referring to FIG. 76, in the sleep state 2602, the system clock operates to keep time 2604. At 2606, the algorithm 2600 queries whether the battery 2568 is charging. If the battery 2568 is being charged, the apparatus 2500 enters the charge status 2608. If the battery 2568 is not charging, the algorithm 2600 queries, at 2610, (1) whether the accelerometer has moved (or detected three-dimensional movement of the apparatus 2500), and (2) whether no magnet (e.g., in the external station 2580) is detected. If the answer to either of query (1) or (2) is negative, i.e., that either the accelerometer has not moved (or detected three-dimensional movement) or that the magnet is detected, the apparatus 2500 remains in the sleep state. If the answer to both query (1) and (2) is affirmative, i.e., that the accelerometer has moved (or detected three-dimensional movement) and that no magnet is detected, peripheral electronics of the apparatus 2500 are awoken, at 2612. When the peripheral electronics are awake, the apparatus 2500 is generally referred to as being in its wake state (not shown in FIG. 76). The apparatus 2500 is then configured to perform a self-test to confirm the functionality of the peripheral electronics. The algorithm 2600 queries, at 2614, whether the apparatus 2500 passes the self-test. If the apparatus 2500 fails the self-test, the apparatus 2500 moves to the error status 2616. If the apparatus 2500 passes the self-test, the algorithm 2600 queries, at 2618, whether a fatal error is detected. If the fatal error is detected, the apparatus 2500 moves to the error status 2616. If the fatal error is not detected, the apparatus 2500 moves to the ready status 2620.

Figure 77:
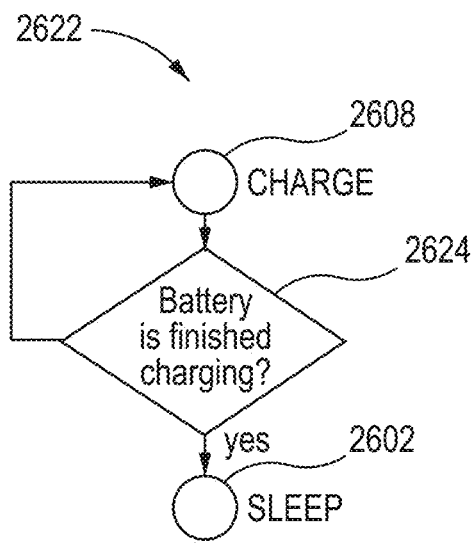

Referring to FIG. 77, in the charge status 2608, the apparatus 2500 (i.e., via the microcontroller 2572) is configured to execute an algorithm 2622 to query, at 2624, whether the battery 2568 has completed charging (e.g., is fully charged or is charged to at least a predetermined charge level). If charging the battery is incomplete, the apparatus 2500 remains in the charge status 2608. If the battery has completed charging, the apparatus 2500 returns to the (non-charging) sleep state 2602.

Figure 78:
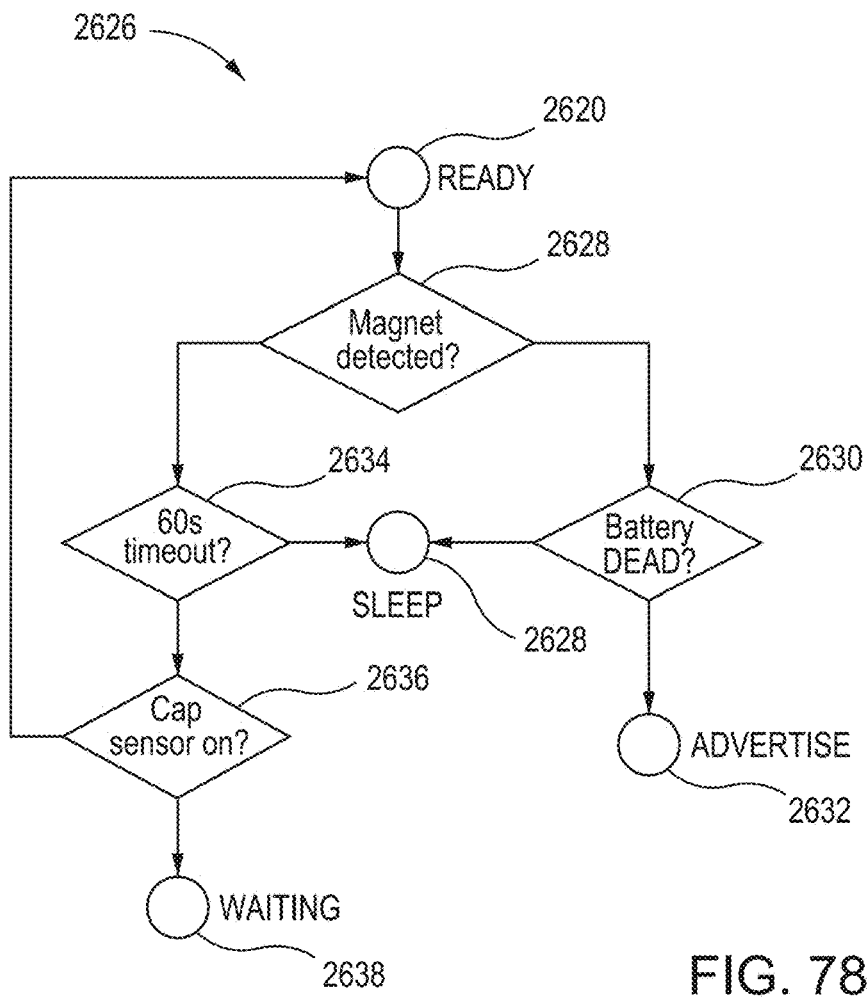

Referring to FIG. 78, in the ready status 2620, the apparatus 2500 is configured to execute an algorithm 2626 to query, at 2628, whether a magnet (e.g., in the external station 2580) is detected. The apparatus 2500 can determine if the magnet is detected based on whether the magnet switch in the bill 2560 is in its first position or its second position, as discussed herein. If the magnet switch is in its second position, the microcontroller 2572 can determine that the electronic circuitry within which the magnet switch is disposed is complete, and thereby determining that the magnet is detected. If the magnet is detected, the algorithm queries, at 2630 whether the battery 2568 is low or depleted, and in need of charging. If the battery 2568 is low or depleted, the apparatus 2500 enters the advertise status 2632. The apparatus 2500 can be configured to alert the patient or other user that the battery 2568 is low or depleted, and in need of charging, when the apparatus is in the advertise status 2632. For example, in the advertise status, the apparatus 2500 can be configured to provide one or more of an audible indicia or a visual indicia (e.g., via a light color and/or pattern emitted by the light indicator 2578), as described herein. If the battery 2568 is not low or depleted, and therefore not in need of charging, the apparatus 2500 enters the sleep state 2602.

Returning to operation 2628, if the apparatus 2500 determines that the magnet is not detected, the algorithm 2626 then queries, at 2634, whether a predetermined period of time has elapsed. The predetermined period of time is intended to be a sufficient duration during which a patient can remove the apparatus 2500 from the external station 2580 and dispose the apparatus in the patient's mouth to begin a light therapy treatment session. Generally, the predetermined period of time is on the order of seconds or minutes. For example, the predetermined period can be 20 seconds, 30 seconds, 40 seconds, 50 seconds, 60 seconds, 70 seconds, or more. In some embodiments, the predetermined period of time is 60 seconds. If the predetermined period of time has elapsed, the apparatus 2500 enters the sleep state 2602. In this manner, the apparatus 2500 is configured to help prevent depletion of the battery 2568 due to the apparatus maintaining itself the ready status 2620 beyond the predetermined period of time. If the predetermined period of time has not elapsed, the algorithm 2626 queries, at 2636, whether the capacitance sensor 2549 is on. Said another way, the algorithm 2626 queries whether the capacitance sensor 2549 indicates that the electrodes 2550, 2552 are, at the time of the query, detecting a capacitance change. If the capacitance sensor 2549 is on, the apparatus 2500 enters the waiting status 2638. If the capacitance sensor 2549 is not on (said another way, if at least one of the capacitance electrodes 2550, 2552 does not, at the time of the query, detect a capacitance change, i.e., the sensor 2549 is "off"), the apparatus 2500 remains in the ready status 2620. If the apparatus 2500 remains in the ready status 2620, the algorithm 2626 can be reexecuted until the apparatus enters a different status, such as one of the advertise 2632, sleep 2602, or waiting 2638 statuses.

Figure 79:
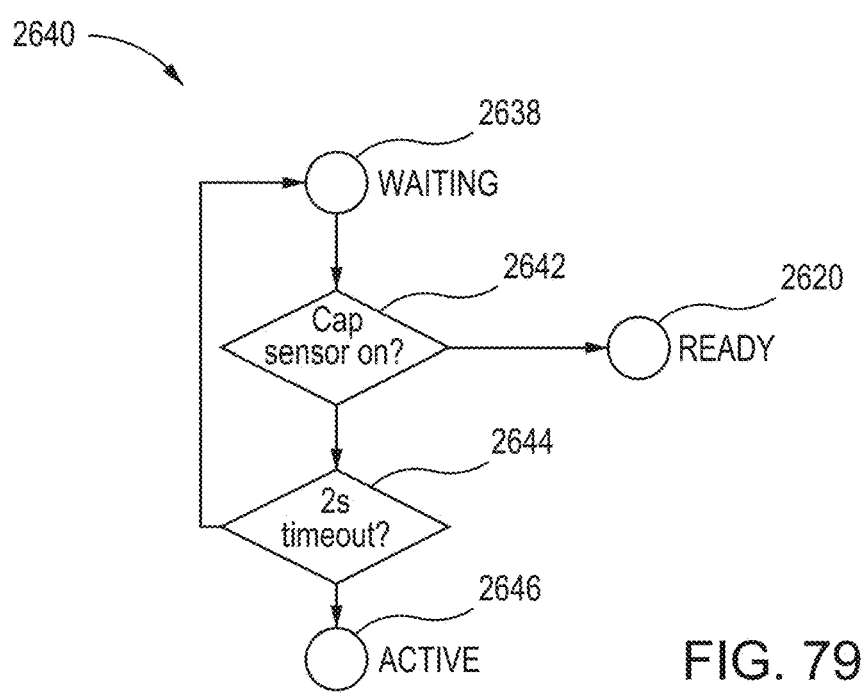

Referring to FIG. 79, in some embodiments, the apparatus 2500 is configured to execute an algorithm 2640 to determine whether the apparatus 2500 has been properly disposed within the patient's mouth. More specifically, when the apparatus 2500 is in the waiting status 2638, the apparatus is configured to execute an algorithm 2640 to query, at 2642, whether the capacitance sensor 2549 is on (e.g., whether the sensor 2549 has detected a capacitance change). In some embodiments, the capacitance sensor 2549 is configured to turn on when a capacitance change detected by each capacitance electrode 2550, 2552 is at or exceeds a predetermined threshold. The query, at 2642, is intended to determine whether the apparatus 2500 has been disposed within the patient's mouth in preparation for administration of the light therapy treatment session. If at least one of the capacitance electrodes 2550, 2552 has not detected a capacitance change at or exceeding the predetermined threshold, the capacitance sensor 2549 is off and the apparatus 2500 returns to the ready status 2620.

If it is determined that the capacitance sensor 2549 is on, the algorithm 2640 queries, at 2644, whether a predetermined period of time has elapsed subsequent to the determination that the capacitance sensor 2549 is on. The query, at 2642, is intended to determine whether the apparatus 2500 is properly positioned within the patient's mouth, thereby ensuring substantially balanced light administration to each side of the patient's mouth. Generally, the predetermined period of time is a duration on the order of seconds. For example, the predetermined period of time can be a duration within the range of 1 second to 5 seconds. In one embodiment, the predetermined period of time is a duration of 2 seconds. If the algorithm 2640 determines that the capacitance sensor 2549 was not on for the predetermined period of time, the apparatus 2500 remains in the waiting status 2638. If the capacitance sensor 2549 remained on for the predetermined period of time, the apparatus 2500 enters the active status 2646. In some embodiments, the microcontroller 2572 registers the bilateral detection of the capacitance change at or exceeding the predetermined threshold for the predetermined period of time.

Figure 80:
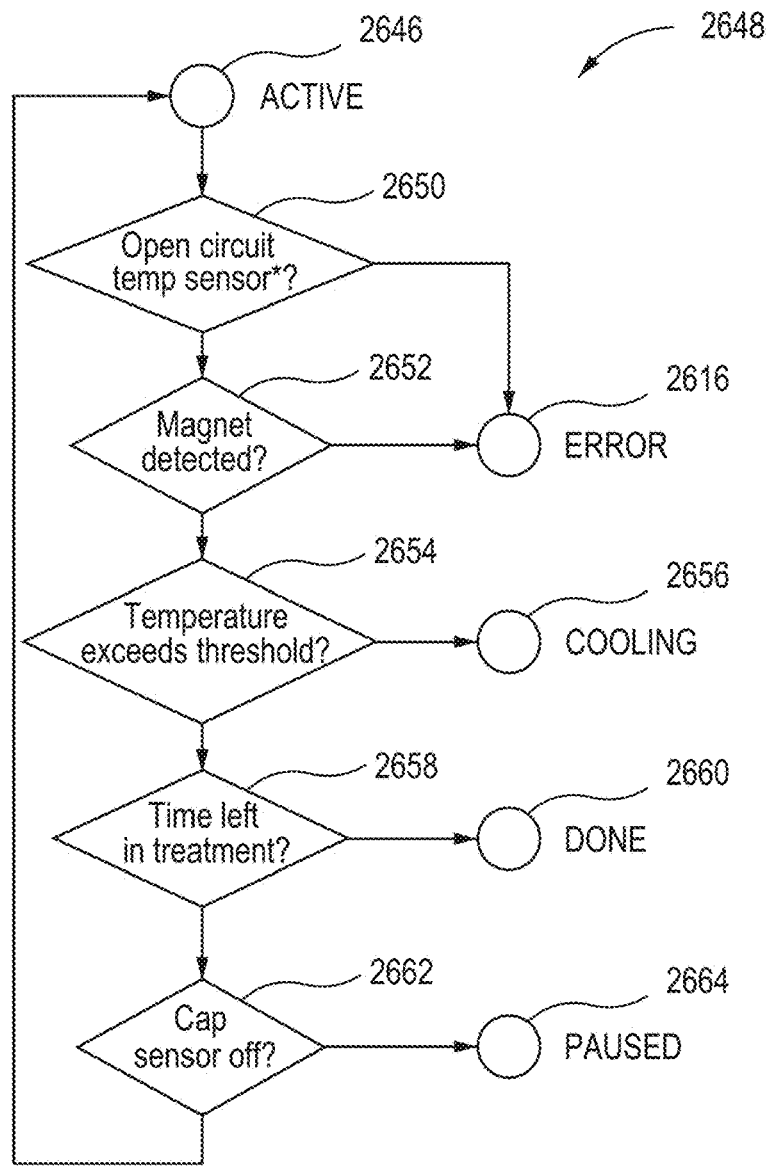

Referring to FIG. 80, when in the active status 2646, the apparatus 2500 is configured to execute an algorithm 2648 to query, at 2650, whether the temperature sensor 2577 (e.g., the thermocouple) is detected or functional. For example, the temperature sensor 2577 can indicate to the microcontroller 2572 that it is functional if the temperature sensor confirms it is able to determine a temperature based on information received from the one or more contacts 2545, 2547 on the flexible circuit board 2546. If the temperature sensor 2577 is not detected or is not functional, the apparatus 2500 enters the error status 2616. If it is determined that the temperature sensor 2577 is detected, or is functional, the algorithm 2648 is configured to query, at 2652, whether the magnet is detected. If it is determined that the magnet is detected, the apparatus 2500 enters the error status 2616. As can be understood in view of the description regarding apparatus 2500 herein, the apparatus 2500 is not intended to be in the active status (in which light can be emitted) and concurrently disposed on the external station 2580 such that the magnet can be detected.

If, at 2652, it is determined that the magnet is not detected, the algorithm 2648 is configured to query, at 2654, whether a temperature of the apparatus 2500 exceeds a predetermined temperature threshold. As discussed herein, in some embodiments, the temperature of the apparatus 2500 is the temperature measured by the temperature sensor 2577. In other embodiments, the temperature of the apparatus 2500 is the adjusted temperature calculated by the microcontroller 2572 based on the measured temperature. If it is determined that the temperature exceeds the predetermined temperature threshold, the apparatus 2500 enters the cooling status 2656.

If it is determined that the temperature does not exceed (i.e., is at or below) the first predetermined temperature threshold, the algorithm 2648 is configured to query, at 2658, whether any time remains for administering the treatment session. As discussed herein, for example, a treatment session can be about 3 minutes in duration. As such, the algorithm 2648 is configured to determine whether any of the 3 minutes for the treatment session remains, i.e., has not yet been completed. If it is determined that no time remains in the treatment session, the apparatus enters the done status 2660.

If it is determined that time remains in the treatment session, the algorithm 2648 is configured to query, at 2662, whether the capacitance sensor 2549 is off. If the capacitance sensor 2549 is off, the apparatus 2500 enters the paused status 2664. The capacitance sensor 2549 may have turned off, for example, because the patient removed the mouthpiece 2510 from the patient's mouth, or inadvertently shifted the mouthpiece 2510 within the patient's mouth such that at least one electrode 2550, 2552 does not have the threshold capacitance charge. If the capacitance sensor 2549 is on, the apparatus 2500 remains in the active status 2646, and the algorithm 2648 is reexecuted. The algorithm 2648 can be configured to be automatically reexecuted until the apparatus 2500 enters a status other than the active status 2646, such as one of the error status 2616, cooling status 2656, done status 2660, or paused status 2664.

Figure 81:
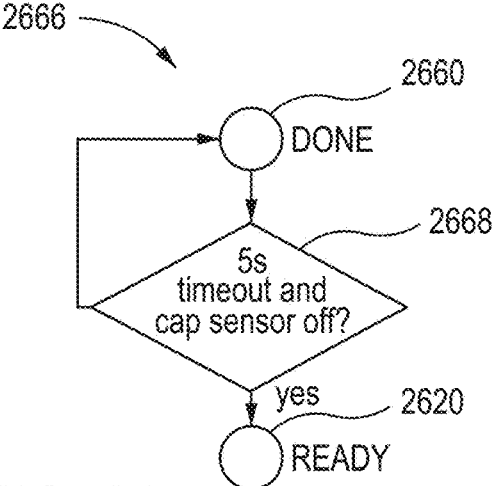

Referring to FIG. 81, when the apparatus 2500 is in the done status 2660, the apparatus 2500 is configured to execute an algorithm 2666 configured to determine if the apparatus should enter the ready status. Specifically, the algorithm 2666 is configured to query, at 2668, whether a predetermined period of time has elapsed since the apparatus 2500 entered the done status 2660. The predetermined period of time can be on the order of seconds, such as, for example, two seconds, three second, four seconds, five seconds, six seconds, or more. In some embodiments, the algorithm 2666 is configured to query whether 5 seconds have elapsed since the apparatus 2500 entered the done status. The algorithm 2666 is also configured to query whether the capacitance sensor 2549 is off. The algorithm can be configured to execute both queries, i.e., whether the predetermined period of time has elapsed and whether the capacitance sensor 2549 is off, concurrently. If it is determined that (1) the predetermined period of time has elapsed, and (2) the capacitance sensor 2549 is off, the apparatus 2500 enters the ready status 2620. If either the predetermined time period has not elapsed or the capacitance sensor 2549 is on, the apparatus 2500 remains in the done status 2660, and the apparatus 2500 can be configured to reexecute the algorithm 2666 until the apparatus enters a different status (e.g., the ready status 2620).

Figure 82:
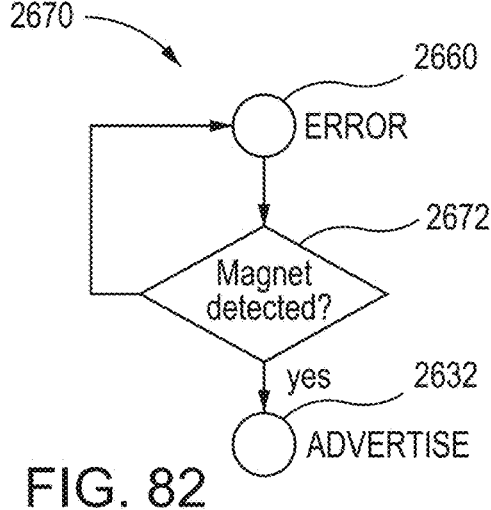

Referring to FIG. 82, when the apparatus 2500 is in the error status 2616, the apparatus 2500 is configured to execute an algorithm 2670 to determine if the apparatus should enter a different status, such as the advertise status 2632. The algorithm 2670 is configured to query, at 2672, whether the magnet is detected. If it is determined that the magnet is detected (e.g., if the apparatus 2500 is disposed on the external station 2580), the apparatus 2500 enters the advertise status 2632. If it is determined that the magnet is not detected, the apparatus 2500 remains in the error status 2616. The apparatus 2500 can be configured to reexecute the algorithm 2670 until the apparatus enters a different status (e.g., the advertise status 2632).

Figure 83:
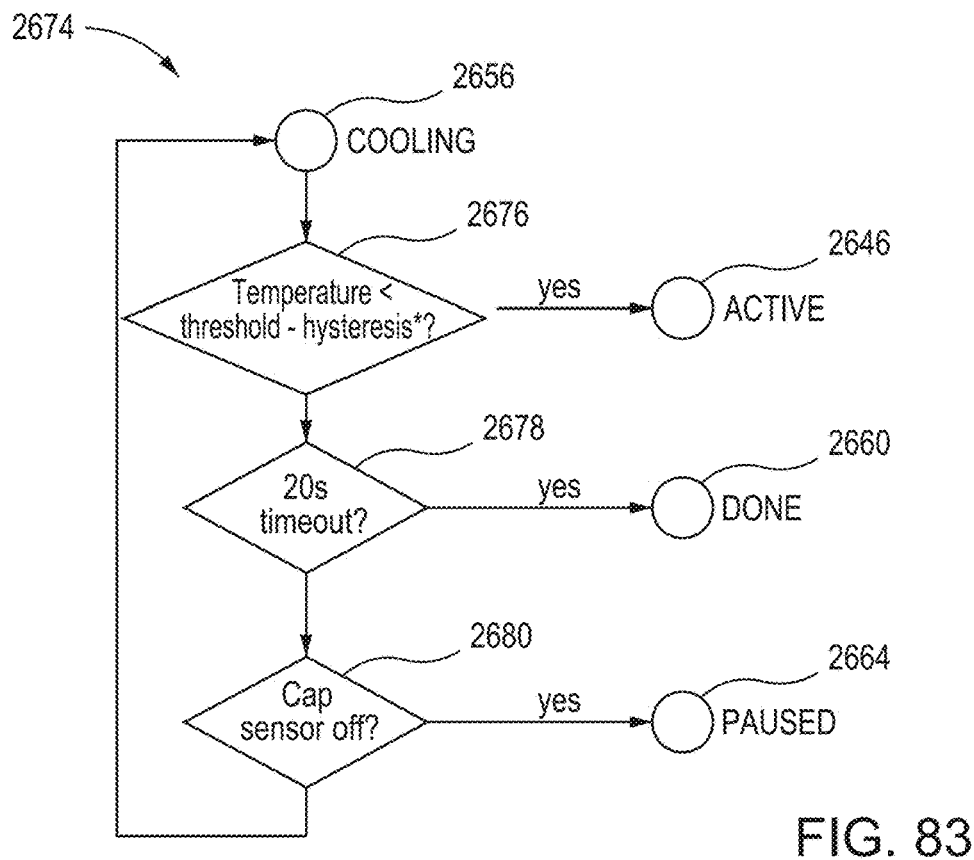

As discussed herein, when the apparatus 2500 is in the cooling status, light emission from the light array 2542 during a treatment session is, at least temporarily, ceased to permit the apparatus to cool down. The apparatus 2500 can be configured to execute an algorithm to determine if the apparatus should move from the cooling status 2656 to a different status, such as the active status 2646, done status 2660, or paused status 2664. Referring to FIG. 83, the apparatus 2500 is configured to execute an algorithm 2674 to query, at 2676, whether the temperature of the apparatus is less than the predetermined temperature threshold. More specifically, in some embodiments, the algorithm 2674 is configured to query, at 2676, whether the temperature of the apparatus 2500 is less than the predetermined temperature threshold value minus a hysteresis value. In the cooling status 2656, temperature of the apparatus 2500 should continue lowering until the apparatus 2500 reaches an ambient temperature of its environment. As such, a real-time temperature of the apparatus 2500 at the moment the apparatus determines an answer to the query, at 2676, may be less than the measured (or adjusted) temperature used to determine the answer to the query. The hysteresis value is a value used to adjust for the time lag between the temperature being measured (or adjusted) and the execution of the algorithm. If it is determined that the temperature of the apparatus 2500 is less than the predetermined temperature threshold, and in some embodiments less than the predetermined temperature threshold minus the hysteresis value, the apparatus enters (or returns) to the active status 2646.

If it is determined that the temperature of the apparatus 2500 is not less than the predetermined temperature threshold, and, in some embodiments is not less than the predetermined temperature threshold minus the hysteresis value, the algorithm 2674 is configured to query, at 2678, whether a predetermined time period has elapsed since the apparatus 2500 entered the cooling status 2656. The predetermined time period can be on the order of seconds, for example within the range of 5 seconds to 30 seconds. In some embodiments, the predetermined time period is 20 seconds. If it is determined that the predetermined time period has elapsed, the apparatus 2500 enters the done status 2660.

If it is determined that the predetermined time period has not elapsed, the algorithm 2674 is configured to query, at 2680, whether the capacitance sensor 2549 is off. If it is determined that the capacitance sensor 2549 is off, the apparatus 2500 enters the paused status. If it is determined that the capacitance sensor 2549 is on, the apparatus 2500 remains in the cooling status 2656. The apparatus 2500 can be configured to reexecute the algorithm 2674 until the apparatus enters a different status, such as the active status 2646, the done status 2660, or the paused status 2664.

Figure 84:
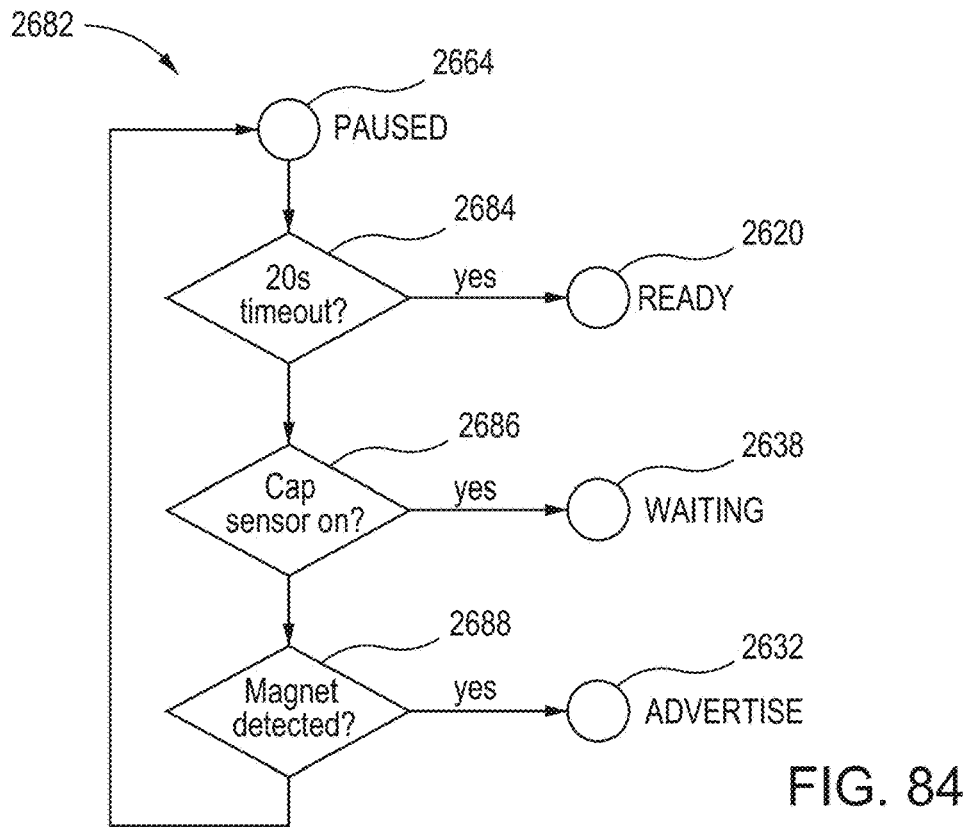

The apparatus 2500 can be configured to determine whether the apparatus, when in the paused status 2664, should enter a different status, such as one of the ready status 2620, the waiting status 2638, or the advertise status 2632. Referring to FIG. 84, the apparatus 2500 can be configured to execute an algorithm 2682, when the apparatus is in the paused status 2664, configured to query, at 2684, whether a predetermined period of time has elapsed since the apparatus 2500 entered the paused status. The predetermined time period can be on the order of seconds, for example within the range of 5 seconds to 30 seconds. In some embodiments, the predetermined time period is 20 seconds. If it is determined that the predetermined time period has elapsed, the apparatus 2500 enters the ready status 2620. If it is determined that the predetermined time period has not elapsed, the algorithm 2682 is configured to query, at 2686, whether the capacitance sensor 2549 is on. If it is determined that the capacitance sensor 2549 is on, the apparatus 2500 enters the waiting status 2638. If it is determined that the capacitance sensor 2549 is not on, the algorithm is configured to query, at 2688, whether the magnet is detected. If it is determined that the magnet is detected, the apparatus 2500 enters the advertise status 262. If it is determined that the magnet is not detected, the apparatus 2500 remains in the paused state 2664. The apparatus 2500 can be configured to reexecute the algorithm 2682 until the apparatus enters a different status, such as the ready status 2620, the waiting status 2638, or the advertise status 2632.

Figure 85:
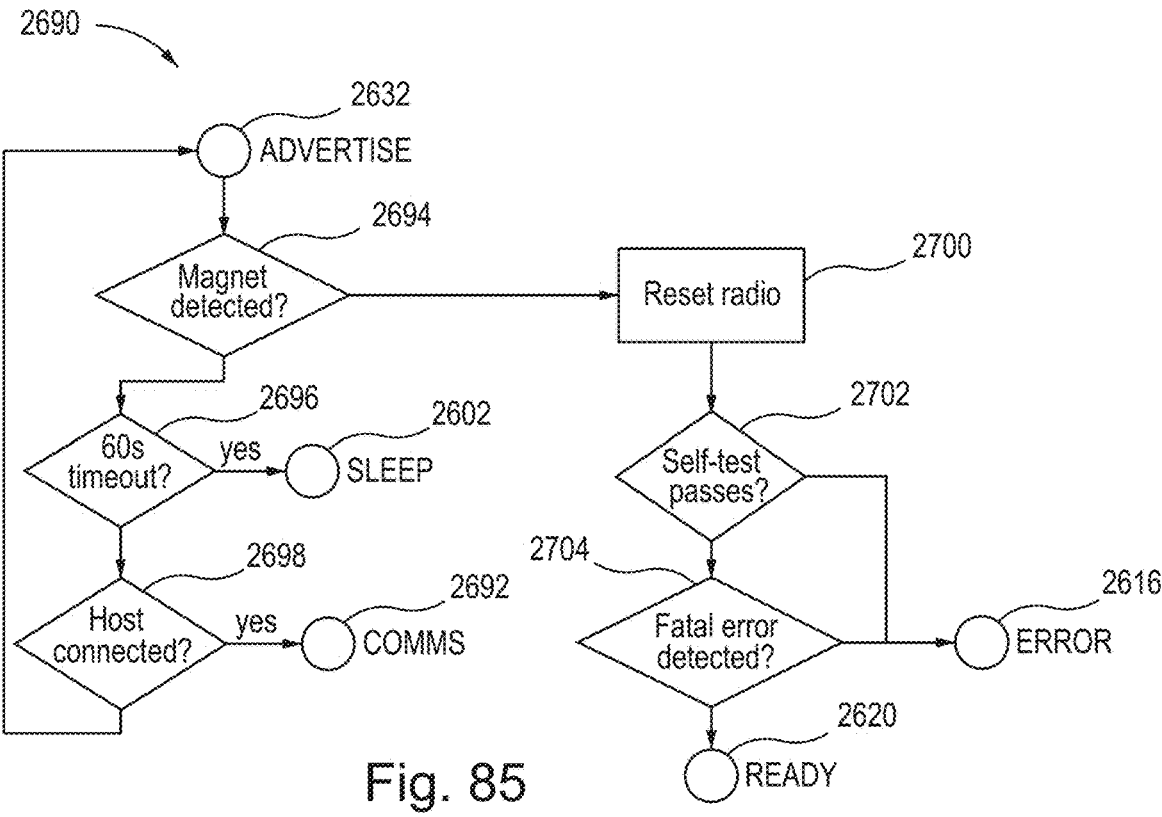

The apparatus 2500 can be configured to determine whether the apparatus, when in the advertise status 2632, should enter a different status, such as one of the sleep status 2602, communication status 2692, error status 2616, or ready status 2620. Referring to FIG. 85, the apparatus 2500 can be configured to execute an algorithm 2690, when the apparatus is in the advertise status 2632, configured to query, at 2694, whether the magnet is detected. As discussed herein, the magnet may be detected, for example, if the apparatus 2500 is disposed on the external station 2580. If it is determined that the magnet is detected, the algorithm 2690 is configured to query, at 2696 whether a predetermined period of time has elapsed since the apparatus 2500 entered the advertise status 2632. The predetermined time period can be on the order of seconds or minutes, for example within the range of 20 seconds to 2 minutes. In some embodiments, the predetermined time period is within the range of 45 seconds to 75 seconds. In some embodiments, the predetermined time period is 60 seconds. If it is determined that the predetermined time period has elapsed, the apparatus 2500 enters the sleep status 2602. If it is determined that the predetermined time period has not elapsed, the algorithm 2690 queries, at 2698, whether the external device (also referred to as a host device, e.g., a mobile phone, personal digital assistant, computer, portable electronic device, or the like) is connected to, or is in communication with, the apparatus 2500. If it is determined that the external device is connected to, or is in communication with, the apparatus 2500, the apparatus enters the communication status 2692. If it is determined that the external device is not connected to, or is not in communication with, the apparatus 2500, the apparatus remains in the advertise status 2632. The apparatus 2500 can then reexecute the algorithm 2690.

Returning to the algorithm's query, at 2694, of whether the magnet is detected, if the magnet is not detected, the apparatus 2500 is configured to reset its wireless transmitter, or other radio mechanism, as indicated at 2700. The algorithm 2690 is configured to query, at 2702, whether the apparatus 2500 passes a self-test. In some embodiments, as part of the query, the algorithm 2690 can be configured to execute the self-test. In other embodiments, the algorithm 2690 can be configured to cause the apparatus 2500 to execute a different algorithm (not shown) for performing the self-test. The self-test can be configured to determine whether the wireless transmitter 2576, or other radio mechanism, of the apparatus 2500 is functional. If it is determined that the apparatus 2500 did not pass the self-test, the apparatus enters the error status 2616. If it is determined that the apparatus 2500 passes the self-test, the algorithm 2690 is configured to query, at 2704, whether a fatal error is detected. If it is determined that a fatal error is detected, the apparatus 2500 enters the error status 2616. If it is determined that a fatal error is not detected, the apparatus 2500 enters the ready status 2620. The apparatus 2500 can be configured to reexecute at least a portion of the algorithm 2690 until the apparatus enters a different status, such as the sleep status 2602, communication status 2692, error status 2616, or ready status 2620.

Figure 86:
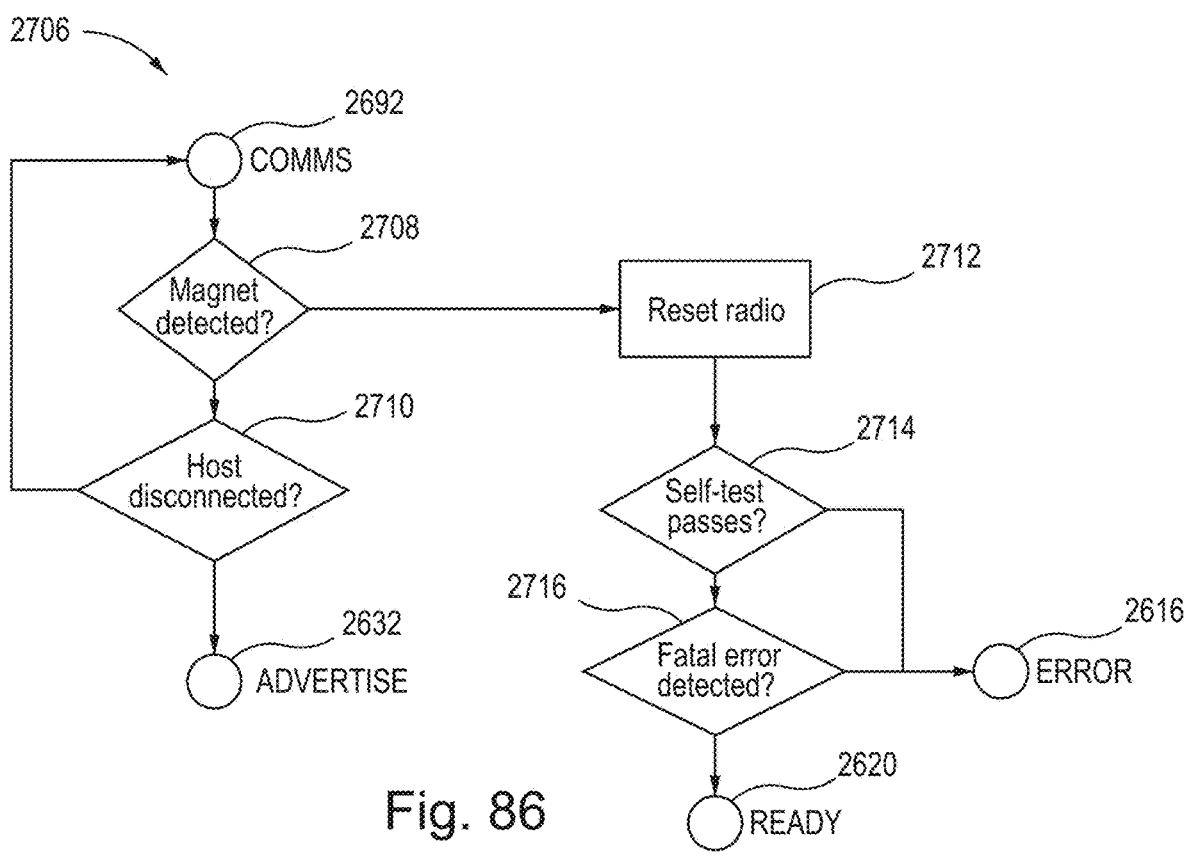

The apparatus 2500 can be configured to determine whether the apparatus, when in the communication status 2692, should enter a different status, such as one of the advertise status 2632, error status 2616, or ready status 2620. Referring to FIG. 86, the apparatus 2500 can be configured to execute an algorithm 2706, when the apparatus is in the communication status 2692, configured to query, at 2708, whether the magnet is detected. As discussed herein, the magnet may be detected, for example, if the apparatus 2500 is disposed on the external station 2580. If it is determined that the magnet is detected, the algorithm 2706 is configured to query, at 2710, whether the external device (also referred to as a host device, e.g., a mobile phone, personal digital assistant, computer, portable electronic device, or the like) is disconnected from, or is not in communication with, the apparatus 2500. If it is determined that the external device is disconnected from, or is not in communication with, the apparatus 2500, the apparatus enters the advertise status 2632. If it is determined that the external device is not disconnected from, or is in communication with, the apparatus 2500, the apparatus remains in the communication status 2692. The apparatus 2500 can then reexecute the algorithm 2706.

Returning to the algorithm's query, at 2708, of whether the magnet is detected, if the magnet is not detected, the apparatus 2500 is configured to reset its wireless transmitter, or other radio mechanism, as indicated at 2712. The algorithm 2706 is configured to query, at 2714, whether the apparatus 2500 passes the self-test. In some embodiments, the algorithm 2706 can be configured to execute the self-test. In other embodiments, the algorithm 2706 can be configured to cause the apparatus to execute a different algorithm (not shown) for performing the self-test. As described herein, the self-test can be configured to determine whether the wireless transmitter 2576, or other radio mechanism, of the apparatus 2500 is functional. If it is determined that the apparatus 2500 did not pass the self-test, the apparatus enters the error status 2616. If it is determined that the apparatus passes the self-test, the algorithm 2706 is configured to query, at 2716, whether a fatal error is detected. If it is determined that a fatal error is detected, the apparatus 2500 enters the error status 2616. If it is determined that a fatal error is not detected, the apparatus 2500 enters the ready status 2620. The apparatus 2500 can be configured to reexecute the algorithm 2706 until the apparatus enters a different status, such as the advertise status 2632, error status 2616, or ready status 2620.

Although the algorithms (e.g., algorithms 2600, 2622, 2626, 2640, 2648, 2666, 2670, 2674, 2682, 2690, 2706) have been illustrated and described herein as executing certain queries or steps in a certain order, in some embodiments, certain queries or steps can be differently ordered and/or certain queries or steps can be omitted. For example, in some embodiments, the algorithm query regarding whether the apparatus 2500 passes a self-test can be omitted. In another example, in some embodiments, the algorithm can query whether the capacitance sensor 2549 is on (or off, as applicable for a particular query), after (e.g., with respect to the waiting status algorithm) or before (e.g., with respect to the ready status algorithm) the query regarding whether a predetermined period of time has elapsed.

Furthermore, although the algorithms (e.g., algorithms 2600, 2622, 2626, 2640, 2648, 2666, 2670, 2674, 2682, 2690, 2706) have been illustrated and described herein as being distinct algorithms, in some embodiments, the executable code represented by the algorithms described herein can be included in a single algorithm. In other embodiments, the executable code represented by the algorithms described herein can be included in two or more algorithms. Moreover, the apparatus 2500 can be configured to execute algorithms in addition to those illustrated and described herein. For example, the apparatus 2500 can be configured to execute an algorithm configured to permit a maximum of two treatment sessions to be administered by the apparatus 2500 per day. In another embodiment, the apparatus 2500 can be configured to permit a maximum of four treatments sessions per day (e.g., two treatment sessions per upper and lower arch, per day).

In some embodiments, the light therapy apparatus 2500 is configured to provide indicia of a state or status of the apparatus. The term "indicia," is used herein as including the singular ("indicium") or the plural ("indicia"), unless the context clearly indicates otherwise. The indicia can include one or more of an audible indicia (e.g., a tone, beep, announcement, or the like), a tactile indicia (e.g., a vibration or the like), or a visual indicia (e.g., a light, a displayed message, or the like). The bill 2560 includes an indicator light 2578 configured to emit at least one of a pattern of light or a color of light, or both, indicative of the status of the light therapy apparatus 2500 or a treatment session being administered by the apparatus. More specifically, for example, the indicator light 2578 is configured to indicate, based on a combination of (1) the color of the light being emitted and (2) whether the light is being emitted in a solid pattern, a slow blink pattern or a fast blink pattern, a status of the device. The indicator light 2578 can be or include a light pipe.

For example, the indicator light 2578 can be configured to emit no light when the apparatus 2500 is turned off. In some embodiments, a patient may be instructed to return the apparatus 2500 to the external station 2580 when no light is emitted by the indicator light 2578. The indicator light 2578 can be configured to emit a green, solid light when the apparatus 2500 is ready to begin a treatment session. The indicator light 2578 can be configured to emit a green, fast blink light when the apparatus 2500 is ready to begin a treatment session and should be recharged after the treatment session. The indicator light 2578 can be configured to emit a green, slow blink light when the apparatus 2500 is being charged and/or when the apparatus 2500 is in wireless communication with an application of the external device.

The indicator light 2578 can be configured to emit a blue, solid light when the apparatus 2500 is activated and providing a treatment session. The indicator light 2578 can be configured to emit a blue, fast blink light when the treatment session is paused, but the treatment session may be continued. The indicator light 2578 can be configured to emit a blue, slow blink light when the treatment session is complete and the apparatus 2500 should be removed from the patient's mouth. The indicator light 2578 can be configured to emit a red, blinking light when the battery 2568 is low, indicating that the apparatus 2500 should be returned to the external station 2580 for recharging. The indicator light 2578 can be configured to emit a red, solid light when the apparatus 2500 is has detected an error, indicating that the reset protocol for the apparatus 2500 should be followed by the patient, which may including placing the apparatus 2500 on the external station 2580 and/or contacting customer support.

In some embodiments, the apparatus 2500 is configured to provide the audible indicia to the patient. For example, in some embodiments, the apparatus 2500 is configured to beep to alter the patient that at least one of (1) a treatment session has begun, (2) a treatment session has been paused, (3) the treatment session has ended.

Although the indicator light 2578 has been described as being configured to emit a specific color and pattern (e.g., green, solid) for a specific status (e.g., ready to begin treatment), in other embodiments, the apparatus 2500 can be programmed to cause the indicator light 2578 to emit light in any suitable combination of color and pattern for a variety of statuses.

The light therapy apparatus 2500 can be configured for use in an orthodontic treatment, including any treatment described herein.

In use, upon removal from its case, the light therapy apparatus 2500 is configured to automatically wake up from the sleep state, and go into a ready state (or pre-treatment mode), as described herein. In the ready state, the apparatus 2500 will periodically check for tissue contact. The patient places the mouthpiece 2510 into their mouth and positions the apparatus 2500 comfortably to begin treatment. Correct positioning is achieved by centering the mouthpiece 2510 in the mouth and setting the ridge 2518 in between the patient's central incisors. Once the apparatus 2500 is positioned correctly, the patient will bite down on the bite pad 2514. The light therapy apparatus 2500 detects when tissue contact has been achieved, and will automatically begin treatment, as described in more detail herein.

In some embodiments, for example, the light therapy apparatus 2500 is useful to irradiate at least a portion of the patient's upper jaw for about 3 minutes, the patient's lower jaw for about 3 minutes, or each of the patient's upper and lower jaws for about 3 minutes. More specifically, in one treatment program, the light therapy apparatus 2500 is useful to administer a light-therapy treatment session in which the oral tissue associated with each of the upper arch of the patient's mouth and the lower arch of the patient's mouth (or vice versa) are consecutively irradiated for 3 minutes per day, for a total treatment session of 6 minutes per day. During the treatment session, the light can be irradiated concurrently from all light emitters 2544 in the light array 2542. Also during treatment, the light emitters 2544 can include embedded LEDs configured to activate and directly illuminate the alveolar mucosa and alveolar bone. Administration of a first light therapy session of the treatment program can begin on the same date that the patient's orthodontic treatment begins (e.g., the day that brackets and wires are installed on the patient's teeth, e.g., $T_0$).

The light can be emitted at any suitable wavelength or combinations of wavelengths in accordance with the methods described herein. In some embodiments, the light is emitted at a wavelength of about 850 nm during the treatment session. In other embodiments, the light is emitted at a wavelength of 850 nm (±5 nm) during the treatment session. In some embodiments, the light emitters 2544 and/or LEDs can emit light at a blend of wavelengths, and not at a single wavelength like a laser. The peak light emission wavelength ($\lambda_{max}$) by the LEDs, can be, for example, 855 nm. T The treatment sessions can be administered for any suitable period, including, but not limited to, a period of four to twelve months. In some embodiments, use of the light therapy apparatus 2500 to administer light therapy treatment sessions according to a treatment program is continued until the patient's Little's Irregularity Index ("LII") score, described in more detail herein, is determined to be less than 1 (i.e., $T_1$). The patient's treatment program can continue until the patient's dental malocclusion is completely resolved (e.g. the patient's LII is about zero) and/or an acceptable clinical outcome has been achieved, which, in some embodiments, is determined at the patient's final orthodontic appointment during which the orthodontic appliance (e.g., brackets and wires) are uninstalled. In some embodiments, use of the light therapy apparatus 2500 to administer light therapy treatment sessions according to a treatment program is continued until the patient's orthodontic appliance is uninstalled from the patient's teeth (i.e., $T_2$). The light therapy apparatus 2500 can be configured to administer the treatment sessions in a clinical setting or in a home environment.

Such a treatment program can, for example, reduce the duration of an average period a patient is expected to need to use an orthodontic appliance (e.g., braces) to achieve a desired orthodontic result. For example, the apparatus 2500 can be used during the treatment program to reduce the duration of the treatment program from two years to six months. The foregoing treatment program and/or any treatment program described herein can reduce a duration of an orthodontic treatment administered without light therapy, as described herein, by about 50 percent to about 75 percent.

Referring to FIGS. 87-91, the light therapy apparatus 2500 can be configured to be disposed on, in or otherwise coupled to the external station 2580, for example, when the apparatus 2500 is not in use by the patient. The external station 2580 can be, for example a carrying case, charging caddy or station, or the like, or a combination of the foregoing.

Figure 87:
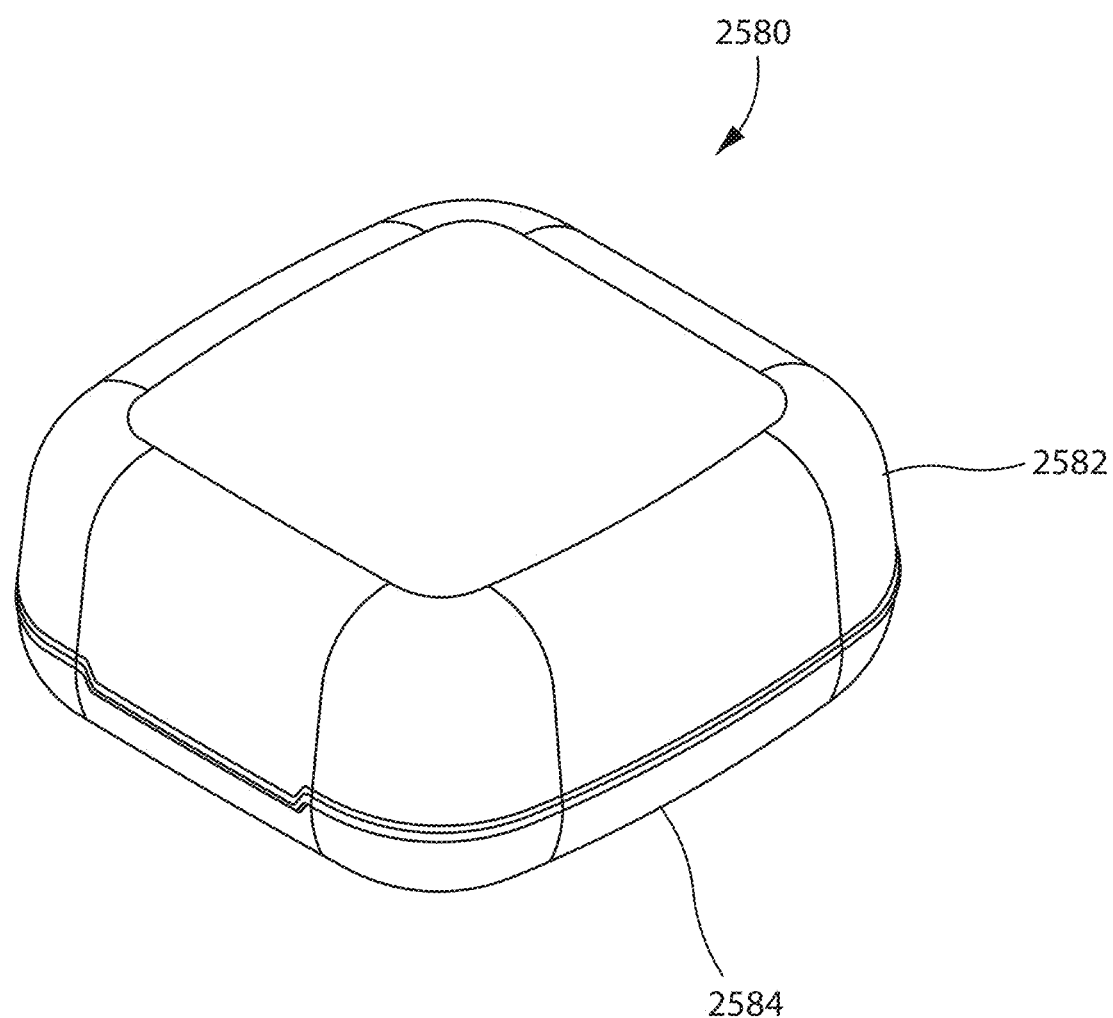
FIG. 87 is a perspective view of an external station according to an embodiment, within which the light therapy apparatus of FIG. 62 can be disposed.
Figure 88:
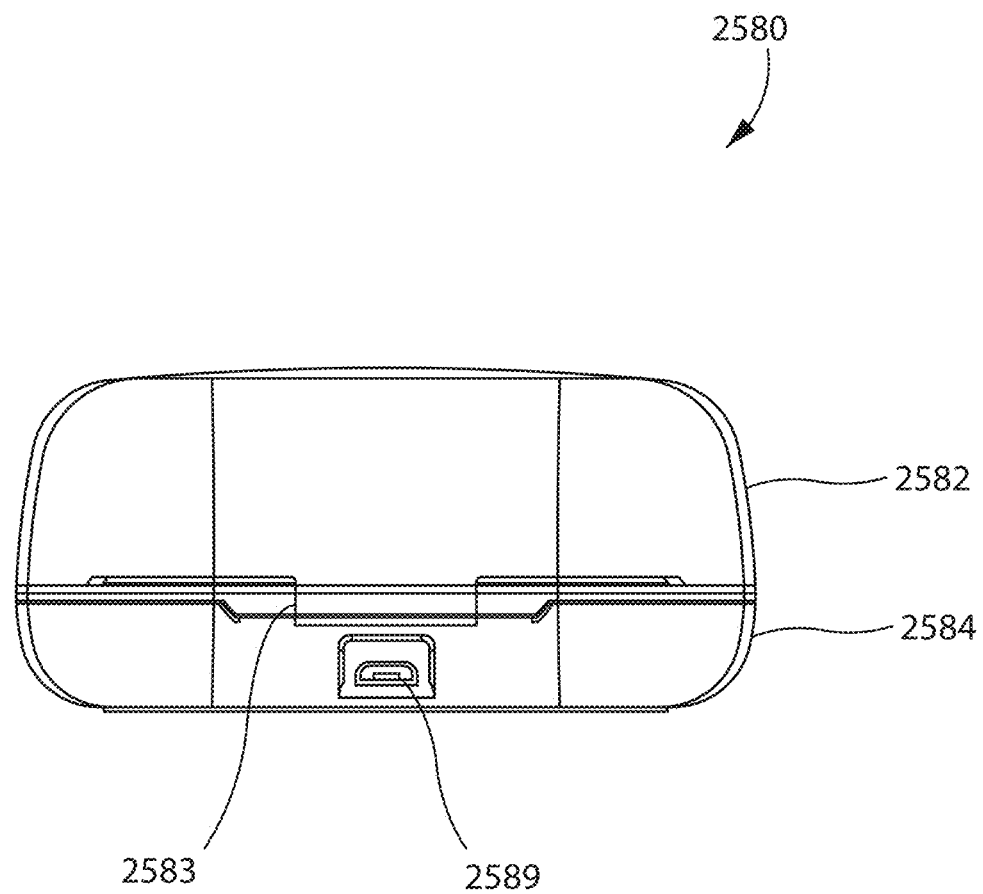
FIG. 88 is a rear view of the external station of FIG. 87.
Figure 89:
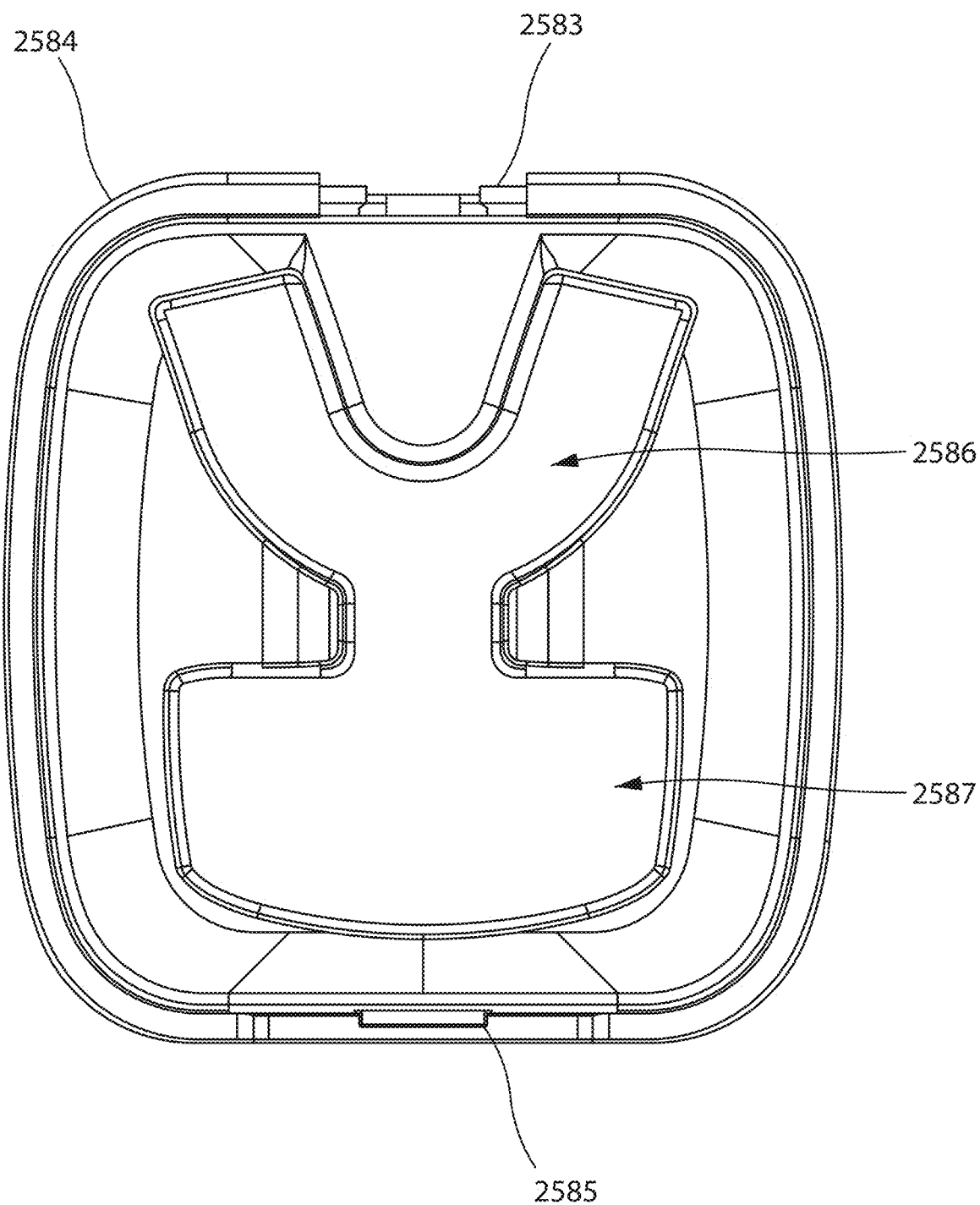
FIG. 89 is a top view of a bottom portion of the external station of FIG. 87.

The station 2580 includes a base 2584 and a lid 2582 and defines a cavity (not shown in FIGS. 87-91) formed by and between the base 2584 and the lid 2582 when the lid is in a closed position (as shown in FIG. 87). The lid 2582 can be coupled to the base 2584 using any suitable coupling mechanism, for example, using a hinge 2583 as shown in FIGS. 88 and 89. In this manner, the lid 2582 is conveniently moveable between its closed position and an open position (not shown).

The base 2584 can include a locking mechanism configured to secure the lid 2582 to the base 2584. For example, the base can include a latch 2585 configured to matingly engage a recess (not shown) in the lid 2582 to secure the lid in the closed position. The base 2584 and lid 2582 can be constructed of any suitable material, including, for example a plastic such as Bisphenol A-free polypropylene. In some embodiments, at least one of the base 2584 and lid 2582 is constructed of a material that is resistance to impact and/or scratches.

Figure 90:
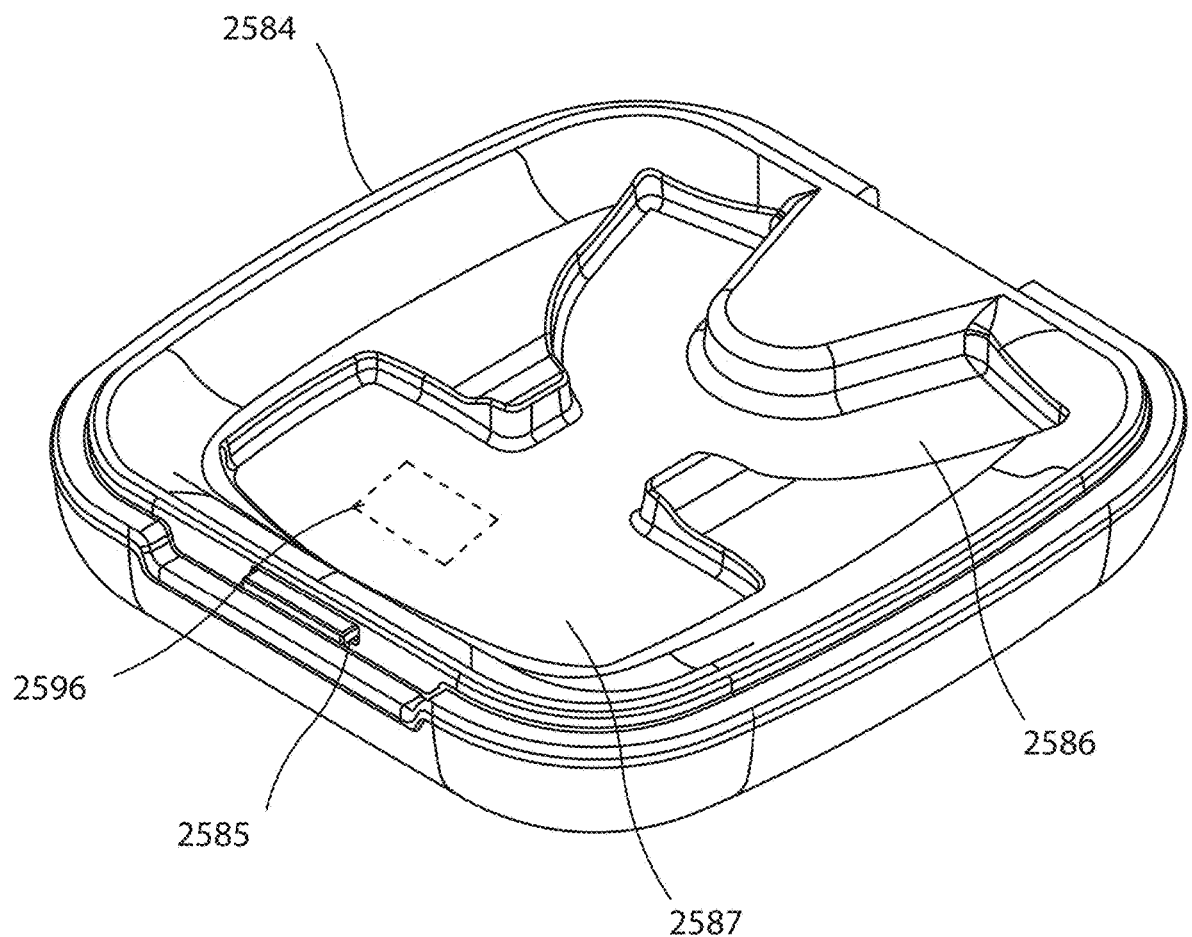
FIG. 90 is a perspective view of the bottom portion of the external station of FIG. 87.
Figure 91:
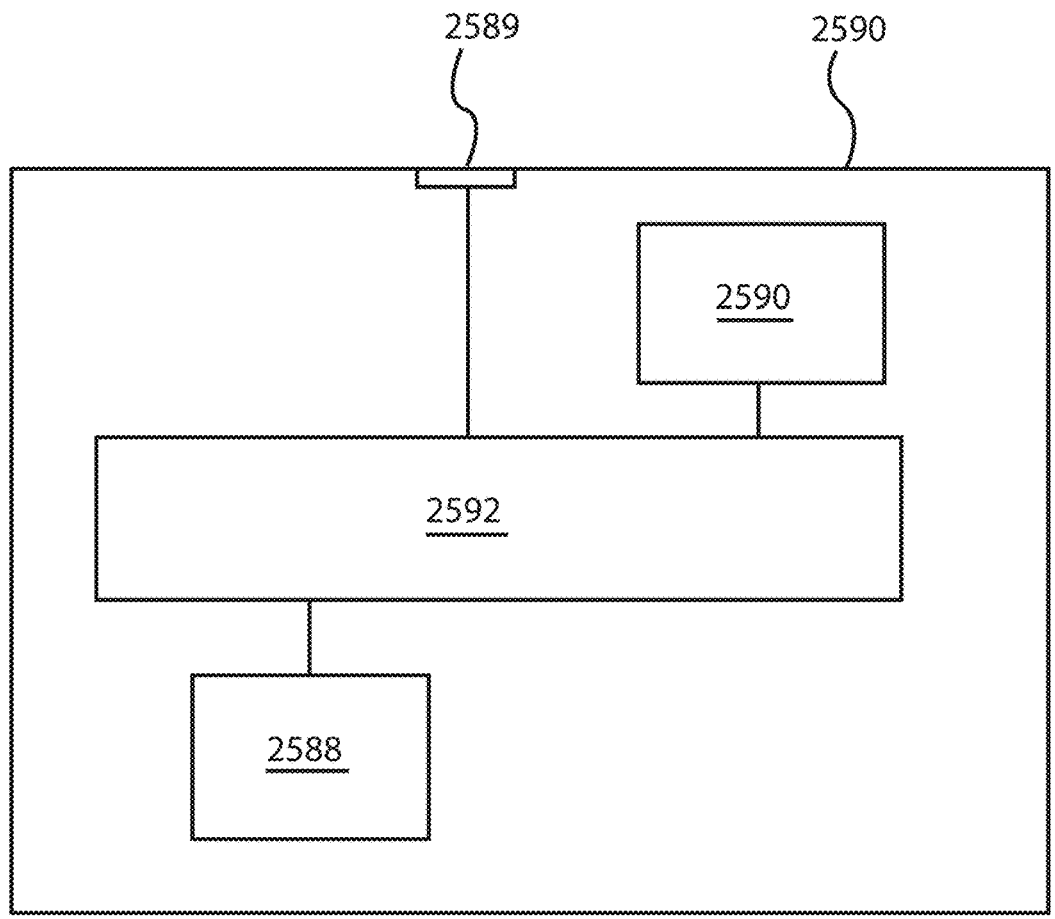
FIG. 91 is a schematic illustration of electronic components of the external station of FIG. 87.

The base 2584 can define a first recess 2586 configured to receive at least a portion of the mouthpiece 2510 and a second recess 2587 configured to receive at least a portion of the bill 2560. In some embodiments, as shown in FIGS. 89 and 90, the first recess 2586 is in continuous with the second recess 2587. A perimeter of the first recess 2586 can, for example, complement the contour of the mouthpiece 2510. A perimeter of the second recess 2587 can, for example, complement the contour of the bill 2560.

The external station 2580 can be configured to charge the apparatus 2500 when the apparatus 2500 is disposed on or otherwise coupled to the station. In this manner, the battery 2568 can be recharged when the bill 2560 is coupled to the charging station. In some embodiments, for example, the station 2580 is configured to inductively charge the apparatus 2500, e.g., by inductively charging the battery 2568 via the induction receiver coil 2569 of the mouthpiece 2510. More specifically, an electronics assembly 2590 (schematically illustrated in FIG. 91) includes a wireless charger (e.g., an induction transmitter coil) 2588 configured to induce an electromagnetic field in the induction receiver coil 2569, and the induction receiver coil is configured to convert the received energy into an electrical current for charging the battery 2568.

In some embodiments, the external station 2580 is configured to be coupled to a computer or other electronic device, such as via a USB, micro-USB or other suitable cable (not shown) received in a port 2589 of the external station 2580. For example, the USB cable can be configured for charging the external station 2580. In other embodiments, the external station 2580 can be configured to be charged by any conventional power supply. In some embodiments, external station 2580 is configured to be coupled to a medical grade power supply, such as a medical grade 6W power supply manufactured by TRUMPower. The power supply can be configured to comply with applicable regulatory standards and/or regulations. For example, the power supply can be configured to comply with IEC 60601-1 and/or other applicable standards. Electronic circuitry 2592 is configured to couple the port 2589 to the induction transmitter coil 2588, thus facilitating the inductive charging of the apparatus 2500 with no electrical connections between the apparatus 2500 and the external station 2580.

In some embodiments, the external station 2580 is configured to sanitize or otherwise disinfect at least a portion of the light therapy apparatus 2500. For example, the external station 2580 can include a light emitter 2594 configured to emit an ultraviolet light, or other suitable wavelength light, such as a blue light, to disinfect the mouthpiece 2510 when the apparatus 2500 is disposed in the external station 2580. In some embodiments, the lid 2582 of the external station 2580 must be in the closed position for the station to emit the disinfecting light. For example, in some embodiments, when the lid 2582 is in its closed position, a switch (not shown) is moved to a closed position, thereby completing an electrical circuit including the light emitter 2594 such that the light emitter 2594 can irradiate the light. In some embodiments, emission of the disinfecting light can be controlled via the electronics assembly 2590 of the external station 2580.

The external station 2580 includes a magnet 2596 (schematically illustrated with phantom lines in FIG. 90). As described above, the magnet 2596 is configured to cause the magnet switch 2575 of the bill 2560 to move from its first position to its second position when the apparatus 2500 is disposed on the base 2584 of the external station 2580.

Although the light therapy apparatus 2500 and external station 2580 have been described herein as being configured to comply with various industry standards, the apparatus 2500 and/or external station 2580 can be configured to comply with additional or alternative industry standards. For example, the apparatus 2500 and external station 2580 can be configured to be compliant with one or more of the following standards, or any combination thereof: IEC/EN 60601-1 Ed. 3.1: 2012—Medical Electrical Equipment Part 1: General requirements for basic safety and essential performance; IEC/EN 60601-1-2 Ed. 3: 2007—Collateral standard: Electromagnetic compatibility—Requirements and tests; EN 62471: 2009—Photobiological safety of lamps and lamp systems; IEC 60601-2-57: Ed. 1.0: 2011—Medical Electrical Equipment Part 2-57: Particular requirements for the basic safety and essential performance of non-laser light source equipment intended for therapeutic, diagnostic, monitoring and cosmetic/aesthetic use; EN 60529 Ed. 2.1: 2001—Degrees of protection provided by enclosures; IEC 60601-1-11—Collateral Standard: Requirements for medical electrical equipment and medical electrical systems used in the home healthcare environment; ISO 10993-1: 2009—Biological evaluation of medical devices—Part 1: Evaluation and testing within risk management process; ISO/BS/EN 14971: 2012—Medical Devices—Application of risk management to medical devices.

Figure 104:
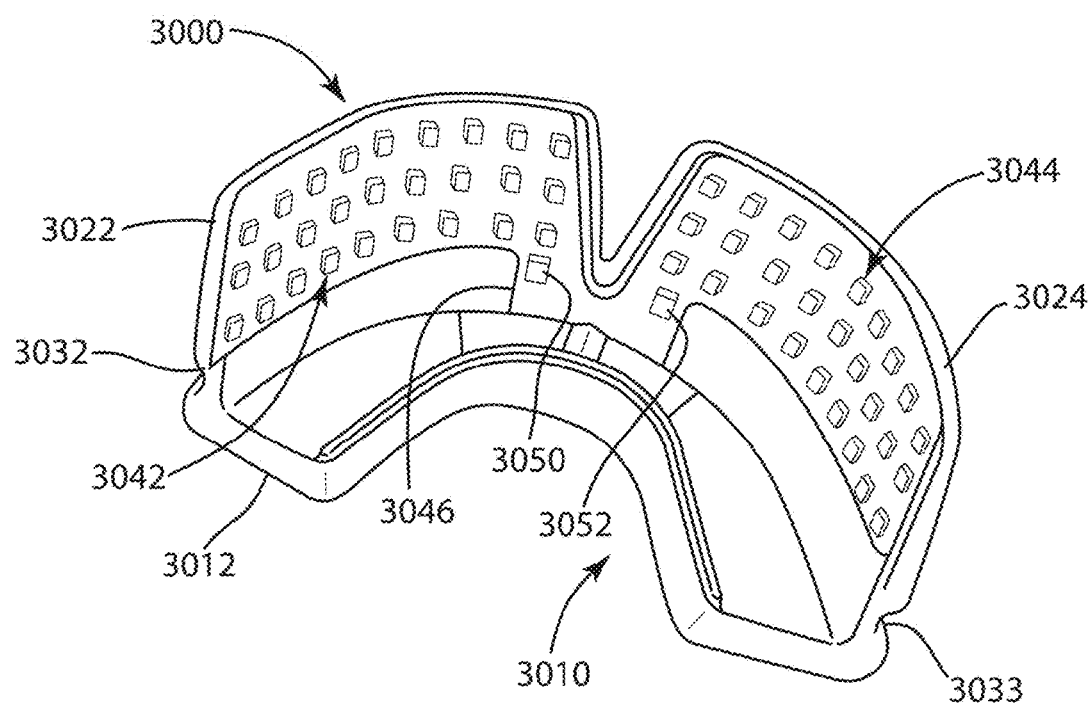
FIGS. 104-105 are rear perspective and rear views of a light therapy apparatus according to an embodiment.
Figure 105:
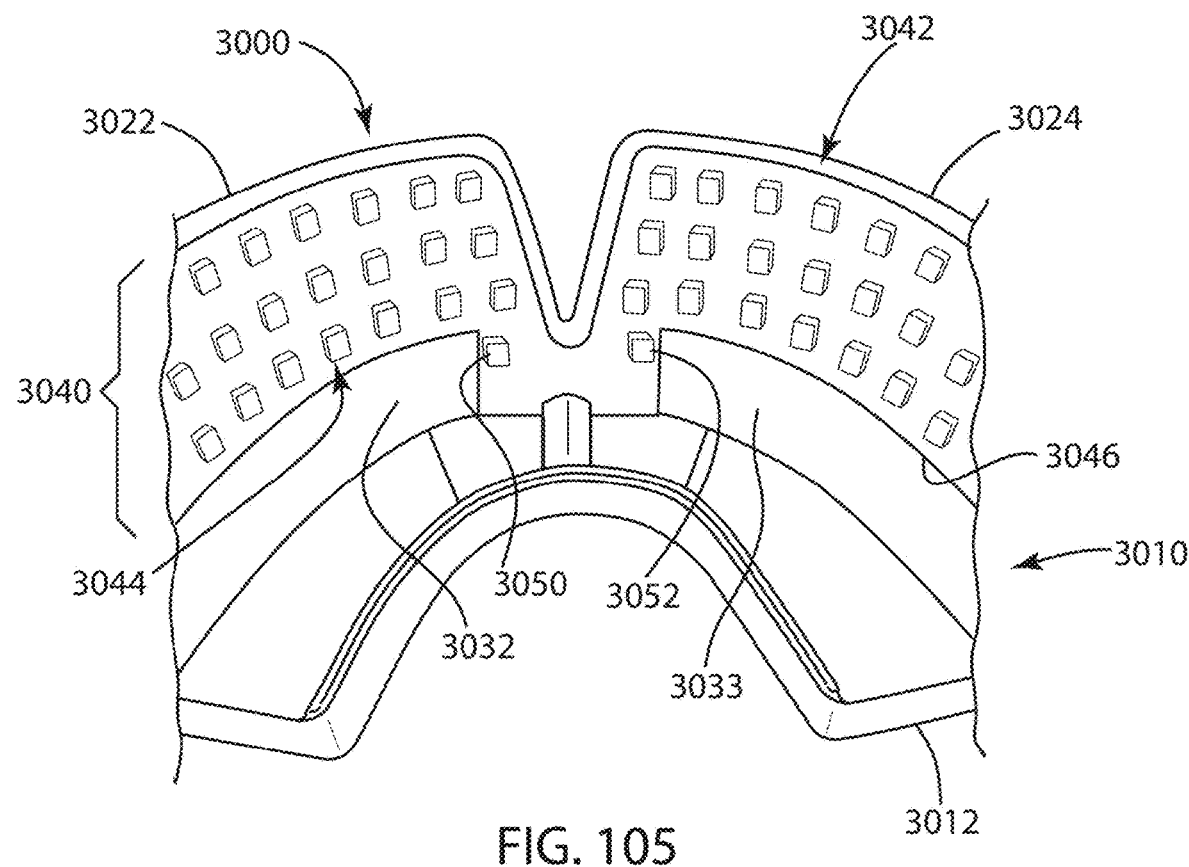

Although light therapy apparatus have been shown and described herein (e.g., light therapy apparatus 2500) as including a capacitance detection system to determine whether a mouthpiece (e.g., mouthpiece 2510) is disposed within the patient's mouth (i.e., in a manner suitable for the treatment session), in other embodiments, a light therapy apparatus can include a different mechanism to determine whether the mouthpiece is disposed within the patient's mouth. As shown in FIGS. 104-105, in some embodiments a light therapy apparatus 3000 includes a mouthpiece 3010 configured to be disposed within a mouth of a patient. The light therapy apparatus 3000 can be similar, or identical, to light therapy apparatus 2500, and mouthpiece 3010 can be similar to mouthpiece 2510, except as described herein. For example, mouthpiece 3010 includes a bite tray 3012, flanges 3022, 3024 transversely coupled to the bite tray, an electronics assembly 3040 including a light array 3042 and a flexible circuit board 3046, each of which is similar to a corresponding component of mouthpiece 2510, and thus is not described in detail with respect to mouthpiece 3010. In some embodiments, at least one or more portions of the mouthpiece 3010 are constructed from a substantially transparent material (e.g., silicone) such that one or more components embedded within the mouthpiece 3010 are visible through the mouthpiece 3010. Thus, for purposes of illustration, portions of the mouthpiece 3010, including portions of the first flange 3022, the second flange 3024 and the bite tray 3012 are shown as being transparent in FIGS. 104 and 105 to show portions of the electronics assembly 3040 and the structure disposed therein.

The light therapy apparatus 3000 is configured to determine whether the mouthpiece 3010 is disposed within the patient's mouth (i.e., in a manner suitable for a treatment session, as described herein). In this manner, the light therapy apparatus 3000 can be configured to only irradiate light for the treatment session when the apparatus 3000 has determined that the mouthpiece 3010 is disposed in the patient's mouth. The mouthpiece 3010 includes a first light emitter 3050 and a second light emitter 3052, each of which is configured and positioned to detect or measure an amount of light reflected by a portion of the patient's oral tissue. For example, the first and second light emitters 3050, 3052 can be configured to detect light emitted from the light emitters 3044 of the light array 3042 and reflected by the patient's oral soft tissue. In some embodiments, the light emitters 3044 can be configured to emit light, such as in a blinking or pulsing manner. The light emitters 3044 can be configured to blink or pulse at a predetermined rate. At least a portion of light emitted from the pulsing or blinking light emitters 3044 towards the oral soft tissue of the patient's mouth is reflected to the mouthpiece 3010 and is thereby detected by the first and second light emitters 3050, 3052. Suitable reflectance thresholds can be established to measure reflectance in order to determine that the light emitters 3044 of the light array 3042, and thus the mouthpiece 3010, is properly disposed in the patient's mouth for administering a treatment session. The apparatus 3000 can be configured to initiate irradiation of the oral tissue (i.e., begin the treatment session) when the first and second light emitters 3050, 3052 detect the light reflection from the oral soft tissue.

Each of the first and second light emitters 3050, 3052, can be coupled to the flexible circuit board 3046 in any suitable location. In some embodiments, the first and second light emitters 3050, 3052 are disposed on the flexible circuit board 3046 such that each of the first and second light emitters 3050, 3052 is positioned close to the patient's gum when the mouthpiece 3010 is disposed within the patient's mouth. As shown in FIGS. 104-105, the first and second light emitters 3050, 3052 are each disposed offset from parallel rows and/or columns of light emitters 3044 of the light array 3042. Each of the first and second light emitters 3050, 3052 can be disposed between a bottom row (in the orientation of the apparatus 3000 shown in FIG. 105) of light emitters 3044 and the bite tray 3012 of the mouthpiece 3010. In some embodiments, the first and second light emitters 3050, 3052 are substantially level with grooves 3032, 3033 defined by an outer face of the mouthpiece 3010. In use, when light is emitted from the light emitters 3044 of the light array 3042, the first and second light emitters 3050, 3052 each measure and/or produce a signal associated with an amount of light reflected by the patient's oral tissue (e.g., the gum). As such, the first and second light emitters 3050, 3052 act as a sensor configured to detect light reflectance. Each of the first and second light emitters 3050, 3052 includes a diode (not shown in FIGS. 104-105) configured to produce an electrical current associated with the amount of light detected or received. The first and second light emitters 3050, 3052, and their diodes, can be configured to send a signal associated with the measured light reflectance to a controller (e.g., in an extra-oral housing or bill) of the light therapy apparatus 3000. In some embodiments, the diodes of the first and second light emitters 3050, 3052 is configured to measure reflected light at about 855 nm.

At least a portion of the first and second light emitters 3050, 3052 can be embedded in the flanges 3022, 3024 of the mouthpiece 3010, for example, in a similar manner as discussed herein with respect to the light array 2542. The first and second light emitters 3050, 3052 are spaced apart on the flexible circuit board 3046. In some embodiments, the first and second light emitters 3050, 3052 are disposed at opposing locations with respect to the flexible circuit board 3046, as shown in FIG. 105, such that the first light emitter 3050 is beneath the portion of the light array 3042 embedded in the first flange 3022 and the second light emitter 3052 is beneath the portion of the light array 3042 embedded in the second flange 3024. In this manner, the apparatus 3000 is configured to detect light reflectance bilaterally.

As discussed herein, the first and second light emitters 3050, 3052 are configured to be disposed in close proximity to the patient's oral (e.g., gum) tissue when the mouthpiece 3010 is disposed within the patient's mouth in preparation for treatment. The apparatus 3000 is configured to irradiate light only after a predetermined light reflectance has been measured. Said another way, the apparatus 3000, and the controller more specifically, is configured to turn on the light emitters 3044 for a treatment session only after the predetermined light reflectance has been measured. The measured light reflectance is registered by the controller, which is configured to execute an algorithm to register the light reflectance, when (1) the predetermined amount of light reflectance is detected by each of the first and second light emitters 3050, 3052 (i.e., bilaterally), and/or (2) the predetermined amount of light reflectance is detected for a predetermined duration (e.g., for at least 2 seconds).

An intra-oral housing 3510 (also referred to herein as a "mouthpiece" of a light therapy apparatus 3500 according to an embodiment is illustrated in FIGS. 106-110. In some embodiments, at least one or more portions of the mouthpiece 3510 are constructed from a substantially transparent material (e.g., silicone) such that one or more components embedded within the mouthpiece 3510 are visible through the mouthpiece 3510. Thus, for purposes of illustration, portions of the mouthpiece 3510, including portions of the first flange 3522 and the second flange 3524 are shown as being transparent in FIGS. 106-110 to show portions of the electronics assembly 3540 and the structure disposed therein. The light therapy apparatus 3500 can be included in a light therapy system that is similar in many respects to the light therapy system described herein with respect to FIGS. 62-91. The light therapy apparatus 3500 is configured to irradiate light in any suitable manner described herein, including, for example, to irradiate the alveolus and/or tooth root area of the patient. Similarly stated, the light therapy apparatus 3500 is configured to administer light therapy to a patient's teeth and/or oral mucosa. More specifically, the light therapy apparatus 3500 is configured to administer light to the patient's teeth and/or oral mucosa sufficient to accelerate orthodontic movement of the patient's teeth and to reduce the overall treatment time for the patient when undergoing orthodontic treatment. The light therapy apparatus 3500 can be the same as or similar in many respects to, or include components the same as or similar in many respects to, the intra-oral apparatuses described herein, including, for example, apparatus 2100, apparatus 2500, and apparatus 3000.

The light therapy apparatus 3500 (and any light therapy apparatus described herein) is configured to be used in conjunction with traditional orthodontic treatment with an orthodontic appliance, such as brackets and wires, or aligners. Furthermore, in some embodiments, any light therapy apparatus shown and described herein can be used with any suitable orthodontic appliance, including, but not limited to, substantially transparent aligners. Such aligners are orthodontic appliances configured to move a patient's teeth and generally include a set of substantially transparent, removable trays that fit over one or more of the patient's teeth. Each tray of the set of trays is worn by the patient in a predetermined sequence or order, and sometimes for a specified amount or period of time. In certain instances, such aligners or trays generally conform to a patient's teeth but is slightly out of alignment with the starting (e.g., initial) tooth configuration. In this manner, the aligners or trays can exert a force on the teeth. In some embodiments, the orthodontic appliance (e.g., brackets and wires or an aligner) is configured to exert a force on one or more of the patient's teeth in an amount (or magnitude) effective to move the patient's teeth towards alignment. In some embodiments, the orthodontic appliance is configured to exert a force on one or more of the patient's teeth in an amount (or magnitude) effective to move the patient's teeth, for example, in one embodiment, for alignment. Similarly stated, the orthodontic appliance is configured to exert a force to minimize or close a gap or space between the patient's teeth. For example, the orthodontic appliance can be configured to exert an orthodontic force, a less-than-orthodontic force, or a heavy force, as described in detail herein, or a combination thereof, on one or more of the patient's teeth in an amount (or magnitude) effective for tooth movement (e.g., towards alignment or to minimize or close a gap between the patient's teeth).

The intra-oral housing 3510 of the light therapy apparatus 3500 is configured to be disposed in an oral cavity (e.g., in the mouth, not shown in FIGS. 106-110) of a patient. The intra-oral housing 3510 can be configured to be electronically and/or physically coupled to an external controller. In some embodiments, for example, the intra-oral housing 3510 is configured to be coupled to an extra-oral housing (or "bill," not shown in FIGS. 106-110) that is disposed externally to the patient's mouth when the intra-oral housing (or mouthpiece) 3510 is disposed within the patient's mouth. The extra-oral housing can be similar in many respects, or identical, to the extra-oral housing 2560 described herein with respect to FIGS. 62-91, and thus is not described in detail with respect to light therapy apparatus 3500. In other embodiments, the intra-oral housing 3510 is configured to be coupled to the controller via one or more wire or cable connectors (not shown in FIGS. 106-110).

Figure 108:
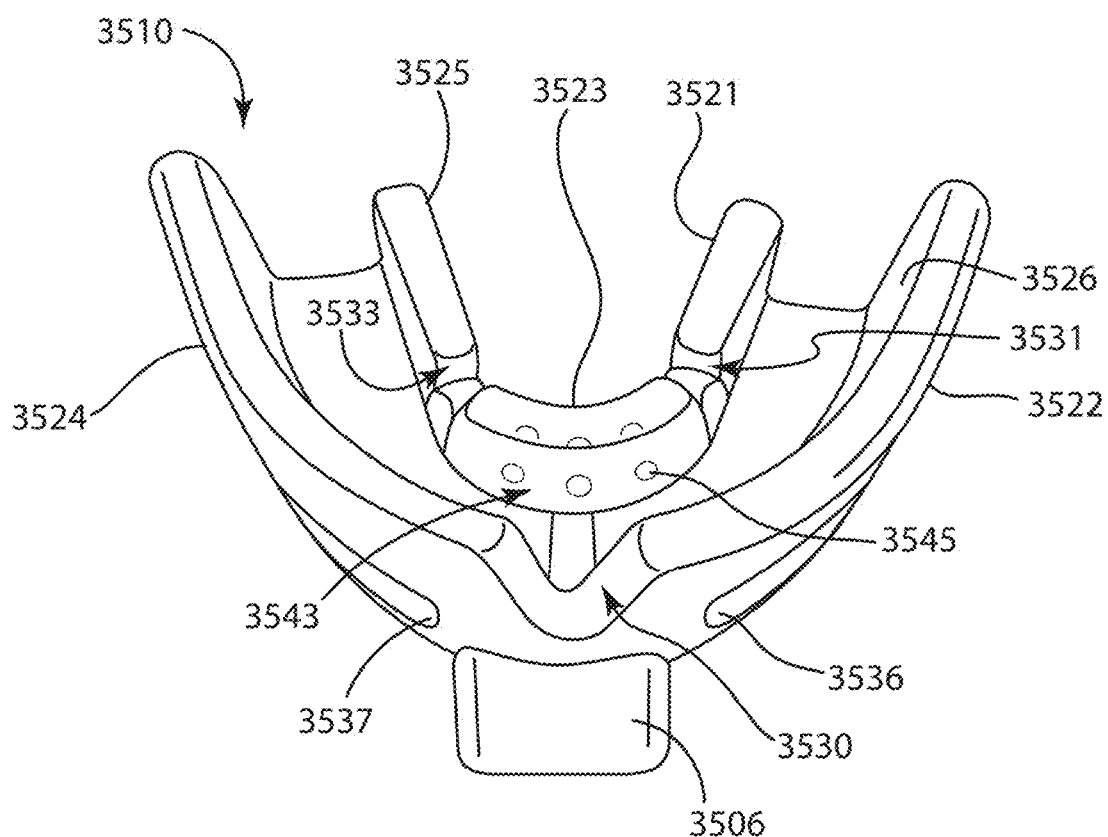
FIG. 108 is a top perspective view of the light therapy apparatus of FIG. 106.
Figure 109:
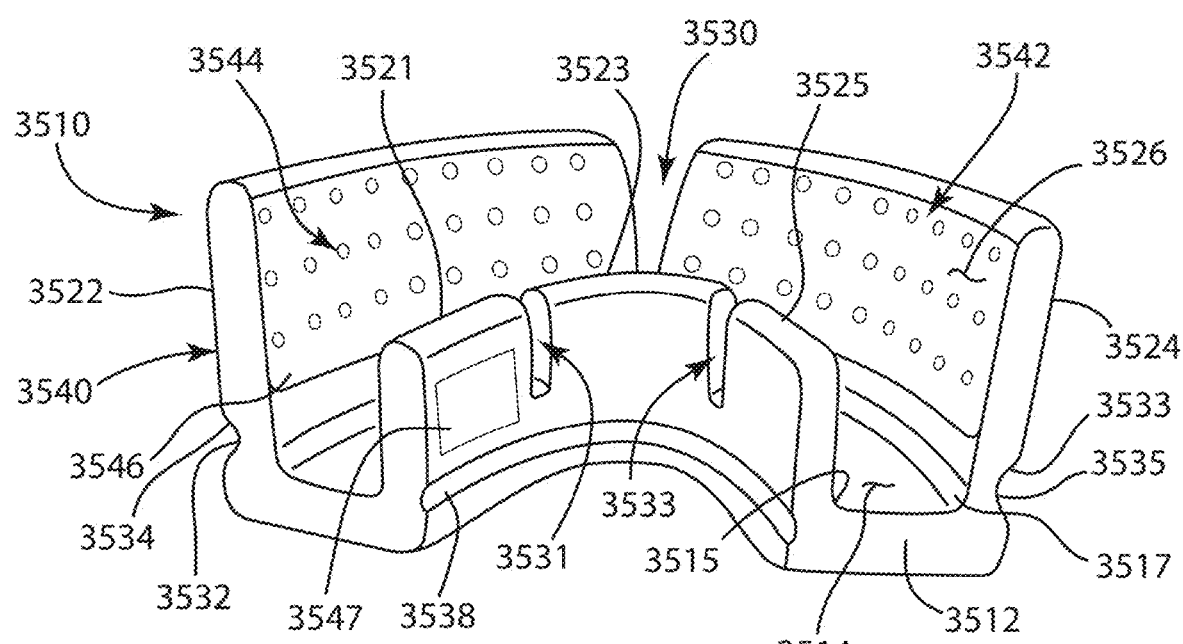
FIG. 109 is a rear view of the light therapy apparatus of FIG. 106.

The light therapy apparatus 3500 is configured to be useful for light therapy with the upper jaw and/or the lower jaw of the patient. In other words, the light therapy apparatus 3500 can be configured to administer light therapy with respect to the patient's upper jaw when the apparatus is in an upright position (e.g., as shown in FIG. 109), and can be configured to administer light therapy with respect to the patient's lower jaw when the apparatus is in an inverted position (e.g., not shown in FIGS. 106-110). As such, the mouthpiece 3510 is configured to be disposed within the patient's oral cavity with respect to each of the upper and lower jaws of the patient. Similarly stated, the mouthpiece 3510 is configured to matingly adapt to both the upper jaw and the lower jaw, as described herein, thus eliminating the need for a separate mouthpiece for each jaw. It should be noted that although the light therapy apparatus 3500 generally, and the mouthpiece 3510 specifically, may be described as being in the upright position when configured to be oriented with respect to the upper jaw and in the inverted position when configured to be oriented with respect to the lower jaw, in other embodiments, the light therapy apparatus 3500 and the mouthpiece 3510 are in the upright position when configured to be oriented with respect to the lower jaw of the patient, and in the inverted position when configured to be oriented with respect to the upper jaw of the patient.

The mouthpiece 3510 can be similar in one or more respects, and include components similar in one or more respects to the intra-oral housings described herein, including, for example, the intra-oral housings or mouthpieces described herein with reference to FIGS. 13-15, 30-37, 43-50, 62-91 and 104-105. The mouthpiece 3510 includes a bite tray 3512, flanges 3522, 3524, 3521, 3523, 3525, light arrays 3542, 3543 (see, e.g., FIG. 109). The mouthpiece 3510 can optionally include a support plate (not shown in FIGS. 106-110) similar or identical to the support plate 2554 of mouthpiece 2510. The bite tray 3512 is configured to receive at least a portion of the patient's teeth of the upper and/or lower jaw. As such, the bite tray 3512 is generally U-shaped, as shown in FIG. 109. The bite tray 3512 is configured to facilitate proper positioning of the mouthpiece 3510 within the patient's mouth. The bite tray 3512 generally includes the lower portion of the mouthpiece 3510. The bite tray 3512 includes a bite pad 3514 with an inner perimeter (or side wall) 3515 and an outer perimeter (or side wall) 3517 (see FIG. 109).

Flanges 3522, 3524, 3521, 3523, 3525, described in more detail herein, generally define an upper portion of the mouthpiece 3510. Outer flanges 3522, 3524 are coupled to the outer perimeter 3517 of the bite pad 3514. Inner flanges 3521, 3523, 3525 are coupled to the inner perimeter 3515 of the bite pad 3514. The flanges 3522, 3524, 3521, 3523, 3525 of the mouthpiece 3510 each extend and/or protrude from the bite pad 3514 in a first direction. As such, when the mouthpiece 3510 is disposed within the patient's mouth, the bite tray 3512 is positioned within the mouth such that the bite pad 3514 is adjacent the occlusal surface of one or more teeth, the outer flanges 3522, 3524 are disposed between the one or more teeth and buccal tissue, and the inner flanges 3521, 3523, 3525 are disposed between the one or more teeth and the tongue and/or palate. Similarly stated, the bite tray 3512 is configured such that when the mouthpiece 3510 is disposed within a mouth, a least a portion of one or more teeth are positioned between the outer flanges 3522, 3524 and the inner flanges 3521, 3523, 3525.

The bite tray 3512 can be similar in many respects, or identical, to the bite tray 2512 described with respect to FIGS. 62-91, and thus is not described in detail with respect to mouthpiece 3510. For example, the bite pad 3514 the bite tray 3512 can have any thickness suitable for receiving a bite force thereon, including a constant or spatially varied thickness as described with respect to bite pad 2514. In another example, the bite tray 3512 (and/or bite pad 3514) can be of any suitable dimensions, including those described herein with respect to bite tray 2512 (and/or bite pad 2514, respectively), and can be constructed of any suitable material, including those described herein with respect to bite tray 2512 (and/or bite pad 2514).

Figure 106:
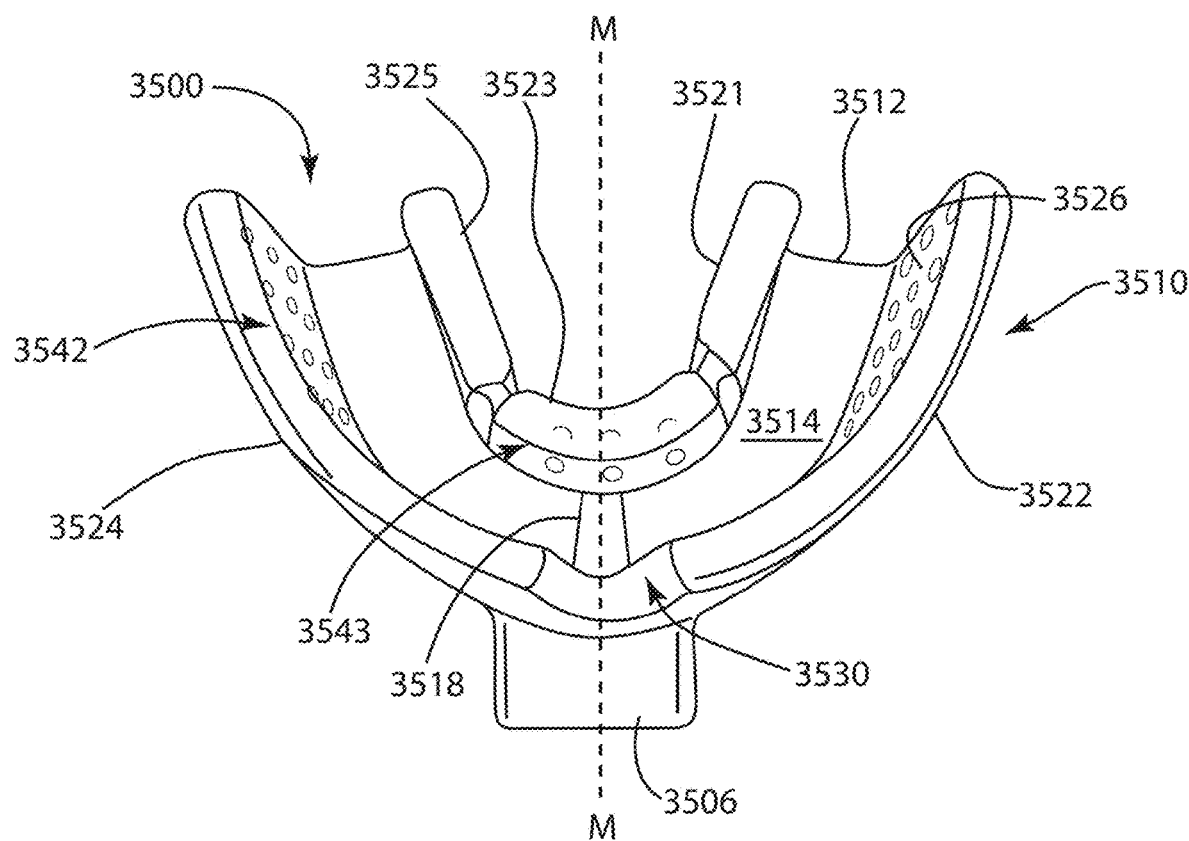
FIG. 106 is a top view of a light therapy apparatus according to an embodiment.

As shown in FIG. 106, an upper surface of the bite pad 3514 includes a ridge 3518. The ridge 3518 is disposed along a midline M of the mouthpiece 3510 and is elevated with respect to the upper surface of the bite tray 3512 and/or bite pad 3514. The ridge 3518 can extend between the inner perimeter 3515 of the bite pad 3514 and the outer perimeter 3517 of the bite pad 3514. The ridge 3518 facilitates positioning of the mouthpiece 3510 within the patient's oral cavity. For example, the mouthpiece 3510 is configured to be positioned within the patient's oral cavity such that the ridge 3518 is disposed between the patient's front central incisors (on either the upper jaw or the lower jaw). Proprioception of the patient related to the teeth and periodontium can produce sensory feedback to the patient regarding the position of the ridge 3518 of the mouthpiece 3510.

In this manner, the ridge 3518 facilitates centering of the mouthpiece 3510 within the oral cavity, thus promoting symmetry of a light therapy treatment on the alveolus, or other oral tissue, on both sides of the patient's mouth. In other words, in order to promote the symmetrical administration of light therapy to the root area, the mouthpiece 3510 can be positioned with the midline M of the mouthpiece 3510 seated along the sagittal plane or within (i.e., plus or minus) 5 degrees of the sagittal plane, and the ridge 3518 can facilitate such positioning in use. The ridge 3518 can have any suitable shape, including, for example, the shape of an inverted V, such that the point of the V can be disposed between the patient's front central incisors.

As noted above, the upper portion of the mouthpiece 3510 includes outer and inner flanges. The outer flanges include an outer first (or left) flange 3522 and an outer second (or right) flange 3524. The inner flanges include an inner first (or left) flange 3521, an inner second (or middle) flange 3523, and an inner third (or right) flange 3525. Although the outer and inner flanges are shown and described herein as including two and three flanges, respectively, in other embodiments, a mouthpiece can include a different number of outer and/or inner flanges.

The upper portion (i.e., the flanges 3522, 3524, 3521, 3523, 3525) of the mouthpiece 3510 is disposed transversely with respect to the bite plate 3514. The flanges 3522, 3524, 3521, 3523, 3525 are configured to be disposed, when the mouthpiece 3510 is disposed within the patient's mouth, such that the bite tray 3512 is adjacent an occlusal surface of the patient's teeth, adjacent a portion of a side of the patient's teeth and/or adjacent the alveolar mucosa. For example, the outer flanges 3522, 3524 can be disposed adjacent a portion of a buccal side of the patient's teeth and/or adjacent a buccal side of the alveolar mucosa. In this manner, a light array 3542 enclosed in the outer flanges 3522, 3524 (also referred to herein as "first light array"), as described in more detail herein, can be used to administer light to the patient's teeth and/or alveolar mucosa (e.g., towards the buccal side of the patient's teeth and/or alveolar mucosa). In another example, the inner flanges 3521, 3523, 3525 can be disposed adjacent a portion of a lingual or palatial side of the patient's teeth and/or adjacent a lingual or palatial side of the alveolar mucosa. In this manner, a light array 3543 enclosed in the inner flanges 3521, 3523, 3525 (also referred to herein as "second light array"), as described in more detail herein, can be used to administer light to the patient's teeth and/or alveolar mucosa (e.g., towards the lingual or palatial side of the patient's teeth and/or alveolar mucosa).

The outer flanges 3522, 3524 collectively contain the first light array 3542, and are each configured to be disposed between the buccal tissue and the alveolus. Thus, in use, the outer flanges 3522 and 3524 displace oral soft tissue to maintain the desired position of the light array 3542 relative to the anatomy of the patient. More specifically, the outer flanges 3522, 3524 are each configured to displace buccal tissue away from the patient's alveolus. In some embodiments, an inner face 3526 of the outer flanges 3522, 3524 can be spaced apart from the patient's alveolar tissue when the mouthpiece 3510 is disposed within the patient's mouth and the outer flanges 3522, 3524 are displacing the buccal tissue. In some embodiments, at least a portion of the inner face 3526 of the outer flanges 3522, 3524 can contact the patient's alveolar tissue when the mouthpiece 3510 is disposed within the patient's mouth and the outer flanges 3522, 3524 are displacing the buccal tissue.

The inner flanges 3521, 3523, 3525 collectively contain the second light array 3543, and are each configured to be disposed between the patient's tongue and/or palate and the alveolus. Thus, in use, the inner flanges 3521, 3523, 3525 can displace oral soft tissue to maintain the desired position of the second light array 3543 relative to the anatomy of the patient. More specifically, the inner flanges 3521, 3523, 3525 are each configured to displace lingual tissue away from, or otherwise prevent the lingual tissue from contacting, the patient's alveolus. In some embodiments, an inner face 3527 of the inner flanges 3521, 3523, 3525 (see FIG. 107) can be spaced apart from the patient's alveolar tissue when the mouthpiece 3510 is disposed within the patient's mouth and the inner flanges 3521, 3523, 3525 are displacing the lingual tissue. In some embodiments, at least a portion of the inner face 3527 of the inner flanges 3521, 3523, 3525 can contact the patient's alveolar tissue when the mouthpiece 3510 is disposed within the patient's mouth and the inner flanges 3521, 3523, 3525 are displacing the lingual tissue.

The flanges 3522, 3524, 3521, 3523, 3525 of the mouthpiece 3510 are configured to be flexible and/or deformable. Similarly stated, the flanges 3522, 3524, 3521, 3523, 3525 are constructed from a material and have geometrical dimensions and/or configurations to provide the desired flexibility, as described herein. Moreover, each of the outer first and second flanges 3522, 3524 and the inner first, second and third flanges 3521, 3523, 3525 is independently deflectable, movable and/or deformable with respect to the mouthpiece 3510 and/or each other. In this manner, the mouthpiece 3510 can be easily disposed within the oral cavity for a variety of different patients having a variety of different anatomical structures, as described herein.

For example, the mouthpiece 3510 includes certain geometric features (e.g., stress concentration risers, areas having a desired bending moment of inertia, etc.) to produce the desired flexibility, deformability and durability in connection with the material(s) from which the mouthpiece 3510 is constructed. As shown, the mouthpiece 3510 defines a notch 3530 and grooves 3532, 3533 configured to permit, or otherwise increase the ability of, the outer flanges 3522, 3524 to deflect inwardly towards the teeth, gums, jaw, or the like (as described above with respect to mouthpiece 3510 and FIG. 68). As shown in FIGS. 106-109, the mouthpiece 3510 defines the notch 3530 aligned with the midline M of the mouthpiece and between upper portions of the outer first flange 3522 and the outer second flange 3524. The notch 3530 is configured to permit the independent and/or inward deflection of each of the outer first flange 3522 and the outer second flange 3524, for example, in response to pressure from the patient's lip or inner cheek. In particular, the outer flanges 3522, 3524 are each configured to deflect inwardly with respect to the bite pad 3514. Similarly stated, when the mouthpiece 3510 is outside of the mouth in an undeformed state (i.e., a first configuration), the outer first flange 3522 and the outer second flange 3524 are each approximately perpendicular to the bite pad 3514. When the mouthpiece 3510 is disposed inside the mouth, the upper portion of the mouthpiece 3510 and/or the outer flanges 3522, 3524 are sufficiently flexible such that an angle formed between each outer flange 3522, 3524 and the bite pad 3514 (an "outer flange angle") is acute. This "tipping in" allows the outer flanges 3522, 3524 to conform to the interior surfaces of the mouth, thereby promoting the desired alignment of the light array 3542 relative to the bone and/or teeth.

The configuration of the notch 3530, including its shape and dimensions, can be similar in many respects, or identical, to notch 2530 described herein (e.g., with respect to FIG. 68), and thus is not described in detail with respect to mouthpiece 3510. For example, in one embodiment, an edge of each outer flange 3522, 3524 that forms a respective side of the notch 3530 tapers towards the point of a V-shape of the notch, which point can be substantially aligned with an upper edge of the grooves 3532, 3533. In another example, in other embodiments, the portion of the mouthpiece 3510 that defines a lower boundary of the notch 3530 can be in any suitable location relative to the grooves 3532, 3533 (e.g., either above or below the grooves).

The mouthpiece 3510 defines at least one groove 3532, 3533 defined by a lower outer (or front) surface of each of the outer first and second flanges 3522, 3524. For example, the mouthpiece 3510 includes the first groove 3532 and the second groove 3533, each defined by the outer or front surface 3528 of the mouthpiece 3510. The grooves 3532, 3533 can each be similar in many respects, or identical, to grooves 2532, 2533 described with respect to mouthpiece 2510 and FIGS. 62-91. The grooves 3532, 3533 are each disposed at a height between the bite pad 3514 and a lower edge of a flexible circuit board 3546 (see, e.g., FIGS. 107 and 109) of the mouthpiece 3510. Said another way, the grooves 3532, 3533 can be defined by a base portion of each of the outer first and second flanges 3522, 3524. The grooves 3532, 3533 each extend about the outer surface 3528 of the mouthpiece 3510 between the posterior end portion of the mouthpiece 3510 and an anterior end portion of the mouthpiece 3510, such that a first end 3534, 3535 of each groove 3532, 3533, respectively, is at or proximate to the posterior end portion of the mouthpiece 3510 and a second end 3536, 3537 of each groove 3532, 3533, respectively, is at or proximate to the anterior end of the mouthpiece 3510.

Figure 107:
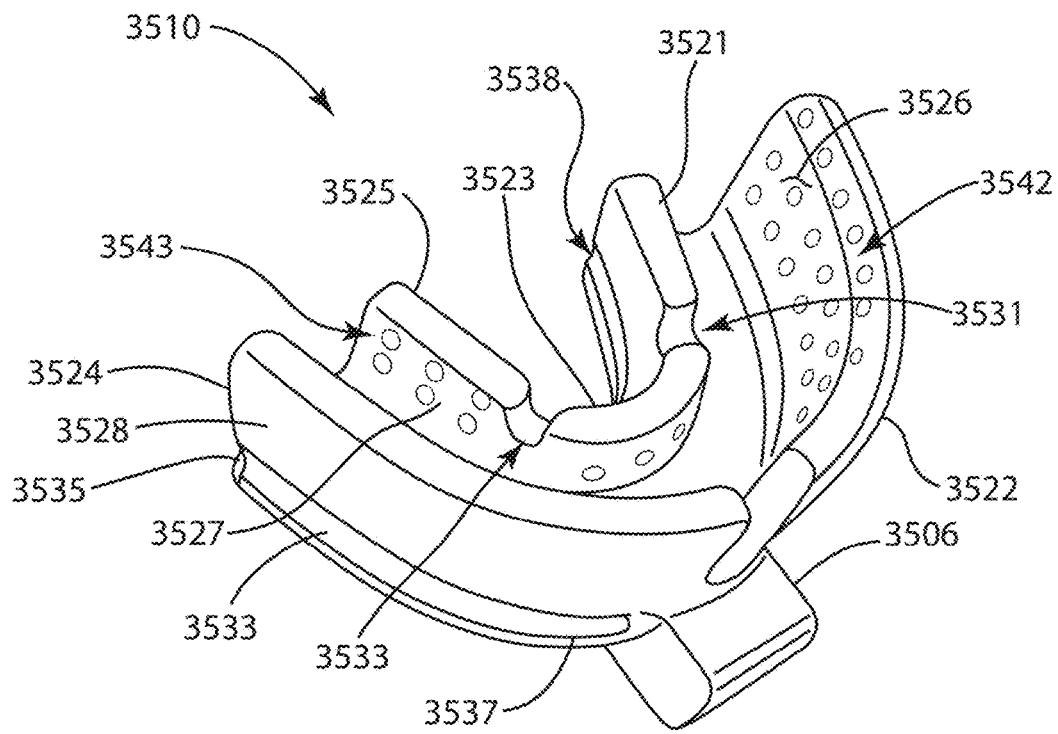
FIG. 107 is a perspective view of the light therapy apparatus of FIG. 106.
Figure 110:
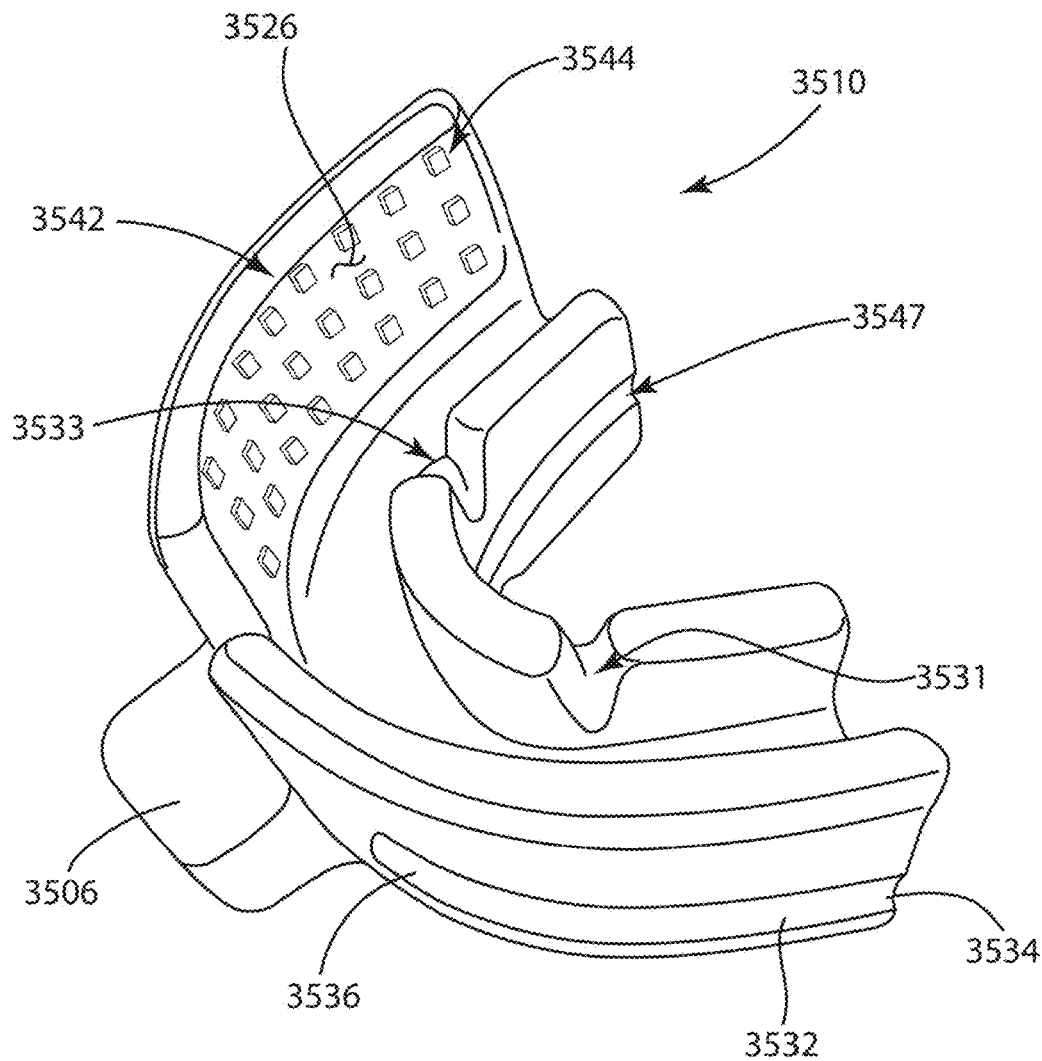
FIG. 110 is a perspective view of the light therapy apparatus of FIG. 106.

As shown in FIGS. 107 and 110, the second ends 3536, 3537 of the grooves 3532, 3533 can be spaced apart. In other words, the second ends 3536, 3537 of the grooves 3532, 3533 do not necessarily meet at the anterior end of the mouthpiece 3510. Similarly stated, the grooves 3532, 3533 are noncontiguous and/or do not share a common boundary. For example, the second ends 3536, 3537 of the grooves 3532, 3533 can be spaced apart by a width of a bridge 3506 extending from the front of the mouthpiece 3510. In another example, the second ends 3536, 3537 of the grooves 3532, 3533 can be spaced apart by a distance at least as great as a width of the notch 3530. The grooves 3532, 3533 can have any suitable shape, including, for example, that of a semi-circle or U-shape. The grooves 3532, 3533 produce a hinge-like structure (i.e., a "living hinge") about which the flanges 3522, 3524 can rotate, bend and/or deflect. In this manner, the grooves 3532, 3523 and the notch 3530 collectively permit the flanges 3522, 3524 to deflect inwardly, for example, in response to pressure from the patient's lip or inner cheek.

As such, the grooves 3532, 3533 and the notch 3530 collectively facilitate the transition of the mouthpiece 3510 between a first configuration and a second configuration. When the mouthpiece 3510 is in the first configuration, the angle formed between each flange 3522, 3524 and the bite pad 3514 (the "outer flange angle") has a first value. When the mouthpiece 3510 is in the second configuration, the outer flange angle has a second value that is different from the first value. In particular, the mouthpiece 3510 can be moved to the second configuration when disposed within the patient's mouth. In some embodiments, the second value is less than the first value (i.e., the outer flanges 3522, 3524 "tip" inwardly toward the bite plate 3512 when the mouthpiece 2510 is inserted into the mouth). In some embodiments, the outer flange angle is approximately 90 degrees when the mouthpiece is in the first configuration and is acute when the mouthpiece is in the second configuration. In some embodiments, the outer flange angle is about 80 degrees (e.g., the outer flanges 3522, 3524 tip inward toward the bite plate 3512 by about 10 degrees) when the mouthpiece is in the second configuration. In other embodiments, the outer flange angle is between about 75 degrees and about 80 degrees (e.g., the outer flanges 3522, 3524 tip inward toward the bite plate 3512 by between about 10 degrees and 15 degrees). In yet other embodiments, the outer flange angle is approximately 85 degrees, 75 degrees, 70 degrees, or 65 degrees (e.g., the outer flanges 3522, 3524 tip inward toward the bite plate by about 5 degrees, 15 degrees, about 20 degrees and about 25 degrees, respectively) when the mouthpiece is in the second configuration.

As shown, the mouthpiece 3510 also defines notches 3531, 3533 configured to permit, or otherwise increase the ability of, the inner flanges 3521, 3523, 3525 to deflect inwardly towards the bite plate 3512 (or outwardly towards the teeth, gums, jaw, or the like in a direction opposite to the inward deflection described above with respect to outer flanges 3522, 3524). As shown in FIGS. 107-109, the mouthpiece 3510 defines a first notch 3531 between upper portions of the first and second inner flanges 3521, 3523 of the mouthpiece, and a second notch 3533 between upper portions of the second and third inner flanges 3523, 3525 of the mouthpiece. Each notch 3531, 3533 of the inner flanges 3521, 3523, 3525 can be positioned on the mouthpiece 3510 equidistant from the midline M. An edge of the first and second inner flanges 3521, 3523 forms a respective side of the first notch 3531. An edge of the second inner flange 3523 (different from the edge forming a side of the first notch 3531) and an edge of the third inner flange 3523 form respective sides of the second notch 3533.

The first and second notches 3531, 3533 are configured to permit the independent and/or inward deflection of each of the inner first, second and third flanges 3521, 3523, 3525, for example, in response to pressure from the patient's tongue. In particular, the inner flanges 3521, 3523, 3525 are each configured to deflect inwardly with respect to the bite pad 3514. Similarly stated, when the mouthpiece 3510 is outside of the mouth in its first configuration, in an undeformed state, the inner first, second and third flanges 3521, 3523, 3525 are each approximately perpendicular to the bite pad 3514. When the mouthpiece 3510 is disposed inside the mouth, the upper portion of the mouthpiece 3510 and/or the inner flanges 3521, 3523, 3525 are sufficiently flexible such that an angle formed between each inner flange 3521, 3523, 3525 and the bite pad 3514 (an "inner flange angle") is acute. This "tipping in" allows the inner flanges 3522, 3524 to conform to the interior surfaces of the mouth, thereby promoting the desired alignment of the second light array 3543 relative to the bone and/or teeth.

The first and second notches 3531, 3533 of the inner flanges 3521, 3523, 3525 can have any suitable shape and/or dimension. As shown in FIGS. 107 and 110, an upper portion of the notches 3531, 3533 can be U-shaped. In some embodiments, a lower portion of the notches 3531, 3533 can be a vertically elongate opening or slit extended from the U-shaped upper portion of each notch 3531, 3533. In some embodiments, the lower portion of each notch 3531, 3533 can include an unbroken portion of material disposed adjacent a lower end of the U-shaped portion. The lower portion of each notch 3531, 3533 has a thickness less than a thickness of an adjacent inner flange (e.g., flange 3521, 3523, 3525) and is configured to separate, break, and/or otherwise tear, when a deflection force is applied to one or more of the inner flanges 3521, 3523, 3525. In this manner, the lower portion of each notch 3531, 3533 can be configured, to separate, break, and/or otherwise tear, when the mouthpiece is in its second configuration within the patient's mouth to form a vertically elongate opening or slit extended from the lower end of the U-shaped portion of the notch.

The mouthpiece 3510 can define a groove 3538 defined by a lower outer (or rear) surface of the inner flanges 3521, 3523, 3525. For example, as shown in FIG. 109, the mouthpiece 3510 includes the groove 3538 defined by an outer or rear surface of the mouthpiece 3510. The groove 3538 can be similar in many respects, or identical, to grooves 3532, 3533. The groove 3538 is disposed at a height between the bite pad 3514 and a lower edge of a flexible circuit board 3547 (see, e.g., FIG. 109) of the mouthpiece 3510. Said another way, the groove 3538 can be collectively defined by a base portion of each of the first, second and third inner flanges 3521, 3523, 3525, such that such that ends of the groove 3538 are each at or proximate to the posterior end portion of the mouthpiece 3510.

The groove 3538 can have any suitable shape, including, for example, that of a semi-circle or U-shape. The groove 3538 produces a hinge-like structure (i.e., a "living hinge") about which the inner flanges 3521, 3523, 3525 can rotate, bend and/or deflect. In this manner, the groove 3528 and the first and second notches 3531, 3533 collectively permit the inner flanges 3521, 3523, 3525 to deflect inwardly with respect to the bite plate (or outwardly with respect to the tongue and/or palate), for example, in response to pressure from the patient's tongue.

As such, the groove 3538 and the first and second notches 3531, 3533 collectively facilitate the transition of the mouthpiece 3510 between its first configuration and its second configuration. When the mouthpiece 3510 is in the first configuration, the angle formed between each inner flange 3521, 3523, 3525 and the bite pad 3514 (the "inner flange angle") has a first value. When the mouthpiece 3510 is in the second configuration, the inner flange angle has a second value that is different from the first value. In particular, the mouthpiece 3510 can be moved to the second configuration when disposed within the patient's mouth. In some embodiments, the second value is less than the first value (i.e., the inner flanges 3521, 3523, 3525 3524 "tip" inwardly towards the bite plate when the mouthpiece 2510 is inserted into the mouth). In some embodiments, the inner flange angle is approximately 90 degrees when the mouthpiece is in the first configuration and is acute when the mouthpiece is in the second configuration. In some embodiments, the inner flange angle is about 80 degrees (e.g., the inner flanges 3521, 3523, 3525 tip inward towards the bite plate by about 10 degrees) when the mouthpiece is in the second configuration. In other embodiments, the inner flange angle is between about 75 degrees and about 80 degrees (e.g., the inner flanges 3521, 3523, 3525 tip inward toward the bite plate by between about 10 degrees and 15 degrees). In yet other embodiments, the inner flange angle is approximately 85 degrees, 75 degrees, 70 degrees, or 65 degrees (e.g., the inner flanges 3521, 3523, 3525 tip inward towards the bite plate by about 5 degrees, 15 degrees, about 20 degrees and about 25 degrees, respectively) when the mouthpiece is in the second configuration.

The flexibility of the mouthpiece 3510, and of the flanges 3522, 3524, 3521, 3523, 3525 in particular, provides significant advantages. For example, in contrast to mouthpieces constructed of a hard plastic and/or with a permanent set (or shape), the current arrangement allows for easier insertion and better conformance to the oral tissue of the patient. The flexibility of the mouthpiece 3510 also accommodates variation in patient anatomy (whether between two different patients or for the same patient as that patient's anatomy changes over time). For example, some patients have a pronounced overbite and may need more or less than a 10 degree inward deflection (or "tip-in"). In such instances, the mouthpiece 3510 can conform to the internal structure and/or anatomy within the patient's mouth. As another example, as the orthodontia for a patient works over time, the patient's dental anatomy will change. Accordingly, the mouthpiece 3510 can conform to the internal structure and/or anatomy within the patient's mouth to accommodate such change without requiring new mouthpiece moldings or the like. Finally, the flexible design of the mouthpiece 3510 provides greater comfort for the patient than would be provided by mouthpieces constructed of a hard plastic.

Additionally, the flexible nature of the mouthpiece 3510 and/or the flanges 3522, 3524, 3521, 3523, 3525 provides manufacturing benefits. In particular, fabrication and/or molding of a mouthpiece having an acute angle between the bite surface and the side surface of the flange (i.e., the internal angle of the flange or the "flange angle") can be difficult. The design of the mouthpiece 3510, however, allows for the molding and/or fabrication to be performed with a flange angle of approximately ninety degrees (or greater), while allowing for an in-use flange angle that is acute (e.g., when the mouthpiece 3510 is in the second configuration, as described above).

The mouthpiece 3510 of the light therapy apparatus 3500 includes an electronics assembly 3540, generally shown in FIG. 109. The electronics assembly 3540 can be similar in many respects, or identical to, the electronics assembly 2540 of mouthpiece 2510 described herein (e.g., with respect to FIGS. 71-73). As shown, a first portion of the electronics assembly 3540 of the mouthpiece 3510 is disposed primarily in the flanges 3522, 3524. The first portion of the electronics assembly 3540 includes a light array 3542 and a flexible circuit board 3546. A second portion of the electronics assembly 3540 is disposed primarily in the inner flanges 3521, 3523, 3525. The second portion of the electronics assembly 3540 includes a light array 3543 and a flexible circuit board 3547. The light arrays 3542, 3543 each include one or more light emitters 3544, 3545, such as a plurality of LEDs. The light emitters 3544, 3545 are electrically and/or physically coupled to the flexible circuit boards 3546, 3547, respectively (only a portion of the flexible circuit board 3547 is shown in FIG. 109). The flexible circuit boards 3546, 3547, respectively, electrically couple the light emitters 3544, 3545, respectively, to electronic circuitry outside of the mouthpiece 3510 (e.g., in an extra-oral housing or via electrical connectors to an external controller, not shown). In this manner, the light emitters 3544, 3545, respectively, can receive power and/or a signal to produce the desired light, as described herein.

Referring to FIG. 109, the light emitters 3544 of the first portion of the electronics assembly 3540 are disposed on a first, palatial (or lingual) side of the flexible circuit board 3546 of the first portion of the electronics assembly. The light emitters 3545 of the second portion of the electronics assembly 3540 are disposed on a buccal side of the flexible circuit board 3547 of the second portion of the electronics assembly. In this manner, the light emitters 3544, 3545 are configured to emit light toward a patient's teeth and/or adjacent oral tissue when the mouthpiece 3510 is disposed within the patient's mouth. Said another way, the light emitters 3544 are configured to emit light towards the anterior root area of an upper and/or lower jaw and/or the buccal alveolar soft tissue and the light emitters 3545 are configured to emit light towards a posterior root area of an upper and/or lower jaw and/or the lingual alveolar soft tissue.

The light emitters 3544, 3545 can be configured to emit light at any suitable intensity, wavelength and/or frequency described herein. For example, in some embodiments, the light emitters 3544, 3545 can be configured to emit light in the infrared or near infrared wavelength range. For example, in some embodiments, the light emitters 3544, 3545 are configured to emit light at a wavelength of about 850 nm. In some embodiments, the light emitters 3544, 3545 are configured to emit light at a wavelength of 850 nm±5 nm. The light emitters 3544, 3545 can be configured to emit light sufficient deliver light energy to the patient's bone to facilitate and/or perform any of the methods described herein. The light emitters 3544, 3545 can be configured to emit light at less than 150 mW/cm$^2$.

The light emitters 3544, 3545 can be disposed on the flexible circuit boards 3546, 3547, respectively, and/or within the flanges 3522, 3524 and the inner flanges 3521, 3523, 3525, respectively, in any suitable configuration, including any configuration described herein. For example, in some embodiments, the light emitters 3544, 3545 are LEDs coupled to the flexible circuit boards 3546, 3547 in two or more parallel rows and/or columns. In one embodiment, the light emitters 3544 are coupled to the flexible circuit board 3546 of the first portion of the electronics assembly 3540 in three parallel rows, and the light emitters 3545 are coupled to the flexible circuit board of the second portion of the electronics assembly in two parallel rows.

The light array 3542 of the first portion of the electronics assembly 3540 can include about 54 light emitters 3544, or LEDs, with about 27 light emitters embedded in the first flange 3522 and about 27 light emitters 3544 embedded in the second flange 3524. The 27 light emitters 3544 can be arranged in any suitable configuration, including for example in nine evenly spaced columns with three spaced apart light emitters, or LEDs, per column. The light array 3543 of the second portion of the electronics assembly 3540 can include about 18 or 20 light emitters 3545, or LEDS, with about 6 light emitters embedded in each of the first and third inner flanges 3521, 3525, and 6 light emitters embedded in the second (or middle) panel 3523. The 6 light emitters 3545 can be arranged in any suitable configuration, including, for example, in three evenly spaced columns with two spaced apart light emitters, or LEDs, per column. The flexible circuit boards 3546, 3547 and light emitters 3544, 3545 can have any suitable dimensions for being coupled to, or embedded in, the outer flanges 3522, 3524 and the inner flanges 3521, 3523, 3525, respectively, of the mouthpiece 3510.

Figure 111:
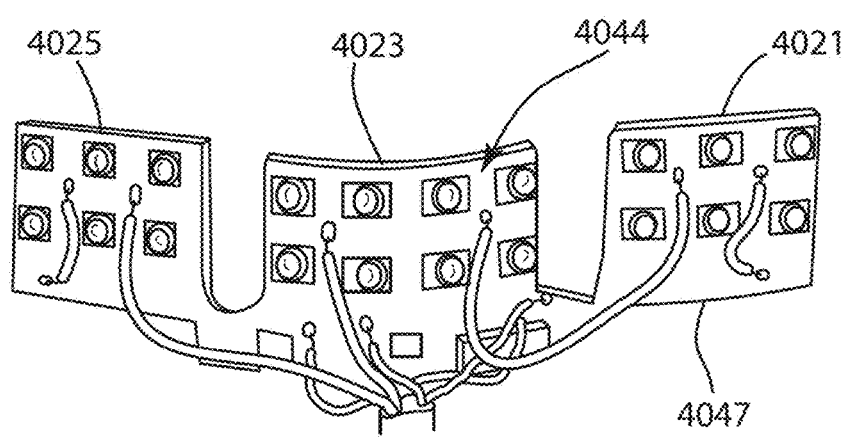
FIG. 111 is a front view of a portion of a light therapy apparatus according to an embodiment.

Although the mouthpiece 3510 has been shown as including 6 light emitters 3545 embedded in the inner flanges 3521, 3523, 3525, in other embodiments, the mouthpiece can include a different number of light emitters in the inner flanges, and each inner flange can include a different number of light emitters than another inner flange. For example, as shown in FIG. 111, a flexible circuit board 4047 includes first and third portions 4021, 4025, each having six (6) light emitters in two evenly spaced rows configured to be disposed in each of a first and third inner flange (not shown in FIG. 111) and a middle portion 4023 having eight (8) light emitters 4044 in two evenly spaced rows and configured to be disposed in a second (or middle) inner flange (not shown in FIG. 111). As also shown in FIG. 111, the flexible circuit board 4047 is configured such that its first portion 4021 is spaced apart from its second portion 4023, and its second portion is spaced apart from its third portion 4025, which facilitates the deflection (or "tipping in") of the inner flanges.

Returning to FIGS. 106-110, although the light emitters 3544 are shown as being evenly spaced within their respective flanges 3522, 3524 or inner flanges 3521, 3523, 3525, in other embodiments, the light emitters can be unevenly spaced within their respective flanges 3522, 3524 and/or inner flanges 3521, 3523, 3525. For example, in some embodiments, a mouthpiece can include a series of light emitters that are spaced apart by a first amount near the anterior portion of the mouthpiece and a second, different amount near the posterior portion of the mouthpiece.

The mouthpiece 3510 can be constructed of any suitable material, including, for example, any material described herein with respect to mouthpiece 2510, and thus such material is not described in detail with respect to mouthpiece 3510. For example, the mouthpiece 3510 can be constructed of an elastomeric material (e.g., a soft silicone). In another example, the mouthpiece 3510 can be fabricated from medical-grade injection-molded, highly flexible and very low durometer silicone. In another example, the silicone and/or portions of the mouthpiece 3510 are substantially transparent, such that one or more components embedded within the silicone are visible through the silicone. Moreover, in this manner, the mouthpiece 3510 can provide suitable optical properties for allowing the light produced and/or conveyed by the light emitters 3544, 3545 to pass through the mouthpiece 3510 to the desired target tissue. In some embodiments, the mouthpiece 3510, the flanges 3522, 3524, and/or the inner flanges 3521, 3523, 3525 can include one or more components configured to filter, focus and/or otherwise act upon the light produced by the light emitters 3544, 3545. In other embodiments, the mouthpiece 3510 can include air gaps between the light emitters 3544, 3545 and the surface of the flanges 3522, 3524 and inner flanges 3521, 3523, 3525, respectively, to facilitate focusing of the light. As shown in FIGS. 106-110, however, the mouthpiece 3510 is constructed such that the light emitters 3544, 3545 are fully encapsulated or embedded within the molded silicone such that no space or air gap exists between the silicone material and the first and second portions of the electronics assembly 3540. Similarly stated, the mouthpiece 3510 is devoid of an air gap between the light emitters 3544, 3545 and the material of the mouthpiece 3510, thus no air gap lensing is needed to produce the desired optical properties of the light produced by the light emitters 3544, 3545.

Methods for Regulating Tooth Movement

Methods for regulating tooth movement are provided herein. Such methods comprise administering an effective amount of light to a patient, wherein the effective amount of light is irradiated from the emitter of an apparatus of the invention. In some embodiments, at least a portion of the apparatus contacts the alveolar soft tissue (e.g., the alveolar mucosa) when the light is administered. In some embodiments, at least a portion of the apparatus does not contact, but is within a certain distance (e.g., within 0.1 cm to 3 cm), the alveolar soft tissue when the light is administered. As is described in more detail herein, the light is administered using any one of the intra-oral apparatuses of the invention. In some embodiments, the methods also comprise allowing a force, in one embodiment, a heavy force, to be exerted on one or more teeth of the patient in need thereof, wherein the light is administered before, during or after the force is exerted.

Other embodiments of the invention provide methods for reducing, minimizing or preventing tooth root resorption (e.g., apical root resorption), comprising administering an effective amount of light to a patient, wherein the effective amount of light is irradiated from the emitter of an apparatus of the invention. In some embodiments, at least a portion of the apparatus contacts the alveolar soft tissue when the light is administered. In some embodiments, the methods also comprise allowing a force, in one embodiment, a heavy force, to be exerted on one or more teeth of the patient in need thereof, wherein the light is administered before, during, or after the force is exerted. Methods for reducing bone resorption or inflammatory dentin or cementum resorption of the tooth root or periodontium are further provided in accordance with another aspect of the invention. Such methods comprise administering an effective amount of light to a patient, wherein the effective amount of light is irradiated from the emitter of an apparatus of the invention. In some embodiments, at least a portion of the apparatus contacts the alveolar soft tissue when the light is administered. In some embodiments, the methods also comprise allowing a force, in one embodiment, a heavy force, to be exerted on one or more teeth of the patient in need thereof, wherein the light is administered before, during, or after the force is exerted.

Another aspect of the invention provides methods for preventing or minimizing inflammation of tissue surrounding one or more teeth upon which forces, force, in one embodiment, heavy forces, are or were exerted, comprising administering an effective amount of light to a patient, wherein the effective amount of light is irradiated from the emitter of an apparatus of the invention. In some embodiments, at least a portion of the apparatus contacts the alveolar soft tissue when the light is administered. In some embodiments, the methods also comprise allowing a force, in one embodiment, a heavy force, to be exerted on one or more teeth of a patient in need thereof, wherein the light is administered before, during or after the force is exerted.

Another aspect of the invention provides methods for regenerating maxillary or mandibular alveolar bone, comprising administering an effective amount of light to a patient, wherein the effective amount of light is irradiated from the emitter of an apparatus of the invention. In some embodiments, at least a portion of the apparatus contacts the alveolar soft tissue when the light is administered. In some embodiments, the methods also comprise allowing a force, in one embodiment, a heavy force, to be exerted on one or more teeth of a patient in need thereof, wherein the light is administered before, during, or after the force is exerted.

In some embodiments, the methods further comprise allowing a functional appliance to exert a force on one or more teeth of the patient in need thereof; wherein the functional appliance exerts the force before, during or after the force, in one embodiment, the heavy force, is exerted and/or the light is administered. In this manner, the force can be exerted in conjunction with or in lieu of the force exerted by the functional appliance. In some embodiments, the methods comprise further administering an effective amount of vitamin D to the patient. The vitamin D can be administered before, during or after the force is exerted, the functional appliance exerts a force, and/or the light is administered. In this manner, the vitamin D can be administered to the patient in conjunction with or in lieu of the force being exerted or the functional appliance exerting a force.

Exerting Forces

As indicated herein, in some embodiments, a force is allowed to be exerted on one or more teeth of a patient in need thereof. In some embodiments, the force is allowed to be exerted on one or more teeth of the patient prior to, subsequent to or during administration of light from an apparatus of the invention. In some embodiments, the force can be an orthopedic force. For example, in some embodiments, the orthopedic force includes a force applied to one, two, or more teeth sufficient to cause movement in one or more bones underlying the tooth (or teeth). In some embodiments, an orthopedic force is a force having a magnitude of greater than about 300 grams of force. In other embodiments, an orthopedic force is a force having a magnitude of greater than or equal to about 350 grams of force, greater than or equal to about 400 grams of force, greater than or equal to about 450 grams of force, greater than or equal to about 500 grams of force, greater than or equal to about 550 grams of force, or greater than or equal to about 600 grams of force. In other embodiments, an orthopedic force is a force having a magnitude of less than or equal to about 500 grams of force, less than or equal to about 550 grams of force, less than or equal to about 600 grams of force, less than or equal to about 650 grams of force, less than or equal to about 700 grams of force, less than or equal to about 800 grams of force, less than or equal to about 900 grams of force, or less than or equal to about 1000 grams of force. In other embodiments, an orthopedic force ranges from about 300 grams of force to about 1000 grams of force. In other embodiments, an orthopedic force's lower range is about 300 grams of force, about 350 grams of force, about 400 grams of force, about 500 grams of force, about 600 grams of force or about 700 grams of force. In other embodiments the orthopedic force's upper range is about 500 grams of force, about 550 grams of force, about 600 grams of force, about 650 grams of force, about 700 grams of force, about 800 grams of force, about 900 grams of force, or about 1000 grams of force. In other embodiments, a force that is less than an orthopedic force is exerted on one or more of a patient's teeth. In this embodiment, the force has a magnitude of less than 100 grams of force, for example, a magnitude of about 200 grams of force or about 300 grams of force.

In some embodiments, the force is a less-than-orthopedic force. In some embodiments, a less-than-orthopedic force is a force having a magnitude of greater than about 30 grams of force. In other embodiments, a less-than-orthopedic force is a force having a magnitude of greater than or equal to about 50 grams of force, greater than or equal to about 75 grams of force, greater than or equal to about 100 grams of force, greater than or equal to about 150 grams of force, greater than or equal to about 200 grams of force, or greater than or equal to about 250 grams of force. In other embodiments, a less-than-orthopedic force is a force having a magnitude of less than or equal to about 50 grams of force, less than or equal to about 75 grams of force, less than or equal to about 100 grams of force, less than or equal to about 150 grams of force, less than or equal to about 200 grams of force, less than or equal to about 250 grams of force, or less than or equal to about 275 grams of force. In other embodiments, a less-than-orthopedic force ranges from about 30 grams of force to about 300 grams of force. In other embodiments, a less-than-orthopedic force's lower range is about 30 grams of force, about 50 grams of force, about 75 grams of force, about 100 grams of force, about 150 grams of force, about 200 grams of force, or about 250 grams of force. In other embodiments the less-than-orthopedic force's upper range is about 50 grams of force, about 75 grams of force, about 100 grams of force, about 150 grams of force, about 200 grams of force, about 250 grams of force, or about 275 grams of force.

In some embodiments, the force is a heavy force. The phrase "heavy force" as used herein refers to a force that ranges from about 150 grams of force to about 1000 grams of force, and that is exerted on a tooth. For example, in some embodiments, a heavy force is a force having a magnitude of greater than about 150 grams of force. In other embodiments, a heavy force is a force having a magnitude of greater than or equal to about 175 grams of force, greater than or equal to about 190 grams of force, greater than or equal to about 200 grams of force, greater than or equal to about 210 grams of force, greater than or equal to about 225 grams of force, or greater than or equal to about 250 grams of force. In other embodiments, a heavy force is a force having a magnitude of less than or equal to about 300 grams of force, less than or equal to about 350 grams of force, less than or equal to about 400 grams of force, less than or equal to about 450 grams of force, less than or equal to about 500 grams of force, less than or equal to about 550 grams of force, or less than or equal to about 600 grams of force, and so on up to less than or equal to about 1000 grams of force. In other embodiments, however, a heavy force ranges from about 150 grams of force to about 600 grams of force. In other embodiments, the heavy force's lower range is about 175 grams of force, about 190 grams of force, about 200 grams of force, about 210 grams of force, about 225 grams of force or about 250 grams of force. In other embodiments, the heavy force's upper range is about 300 grams of force, about 350 grams of force, about 400 grams of force, about 450 grams of force, about 500 grams of force, about 550 grams of force, or about 600 grams of force, and so on up to about 1000 grams of force. In some embodiments, the heavy force ranges from about 200 grams of force to about 500 grams of force. In other embodiments, the heavy force ranges from about 250 grams of force to about 450 grams of force. In one embodiment, the heavy force ranges from about 150 grams of force to about 300 grams of force.

In some embodiments, a heavy force is exerted on one or more teeth of the patient. For example, a heavy force can be exerted on one or more of the patient's teeth before, during, or after being administered with an effective amount of light to a region of the patient's gum (e.g., the alveolar soft tissue). In other embodiments, however, a force that is less than a heavy force is exerted on one or more of a patient's teeth. In this embodiment, the force has a magnitude of less than 150 grams of force, for example, a magnitude of about 100 grams of force or about 125 grams of force.

In some embodiments, the force exerted on one or more teeth of the patient can be a less-than-heavy force. Such a force can be exerted, for example, by a functional appliance or an orthodontic appliance. In some embodiments, a less-than-heavy force is a force having a magnitude of greater than about 10 grams of force. In other embodiments, a less-than-heavy force is a force having a magnitude of greater than or equal to about 20 grams of force, greater than or equal to about 30 grams of force, greater than or equal to about 40 grams of force, greater than or equal to about 50 grams of force, greater than or equal to about 75 grams of force, greater than or equal to about 100 grams of force, or greater than or equal to about 125 grams of force. In other embodiments, a less-than-heavy force is a force having a magnitude of less than or equal to about 30 grams of force, less than or equal to about 40 grams of force, less than or equal to about 50 grams of force, less than or equal to about 75 grams of force, less than or equal to about 100 grams of force, or less than or equal to about 150 grams of force. In other embodiments, a less-than-heavy force ranges from about 10 grams of force to about 150 grams of force. In other embodiments, a less-than-heavy force's lower range is about 10 grams of force, about 20 grams of force, about 30 grams of force, about 50 grams of force, about 75 grams of force, about 100 grams of force, or about 125 grams of force. In other embodiments the less-than-heavy force's upper range is about 30 grams of force, about 40 grams of force, about 50 grams of force, about 75 grams of force, about 100 grams of force, or less than about 150 grams of force.

The phrase "magnitude of force" as used herein refers to the amount of force exerted per tooth. Alternatively, the "magnitude of force" can refer to the amount of force exerted on a plurality of teeth. The magnitude of force exerted per tooth in the latter instance is the total magnitude of force divided by the number of teeth. For example, if about 300 grams of force are exerted on to two teeth, then the force exerted on each tooth is about 150 grams. The phrase "gram of force" as used herein refers to a unit of force equal to the magnitude of force exerted on one gram of mass by a force of 9.80665 m/s$^2$ (i.e., standard gravity). In some embodiments, the magnitude of force is a gram of force that is exerted on a tooth. In other embodiments, the magnitude of force is a gram of force that is exerted on a plurality of teeth.

In some embodiments, a force is a force of sufficient magnitude to cause at least some amount of tooth-root resorption. In some embodiments, an amount of tooth-root resorption caused by a force is correlated to the amount of force exerted such that an increase in the force exerted causes an increase in the amount of tooth-root resorption. In some embodiments, a force has sufficient magnitude to have pathophysiological effects, to create a hyalinized zone or tissue death, to cause cell death, or to cause tissue inflammation when the force is exerted without any other form of treatment, such as light treatment. The force can be an excessive pathophysiological force. A pathophysiological force may cause necrosis or root resorption. The force can also cause pressure on the periodontium that can result in ischemia, decreased blood flow, or cell death.

A force can be exerted on a tooth in any suitable manner. For example, in some embodiments, the force is exerted normal (e.g., orthogonal or at a 90 degree angle) relative to a side of one or more teeth. In some embodiments, the force is exerted at an angle relative to a side of one or more teeth. For example, the force can be exerted at an angle of about 45 degrees, about 60 degrees, about 70 degrees, about 75 degrees, about 80 degrees, about 85 degrees, about 90 degrees, about 95 degrees, about 100 degrees, about 105 degrees, about 110 degrees, about 120 degrees, or about 135 degrees relative to a side of one or more teeth. A force can be exerted normal (e.g., orthogonal or at a 90 degree angle) to, downwards to, or upwards to one or more teeth at any angle. In some embodiments, a proximal force is applied to one or more teeth. In some other embodiments, a distal force is applied to one or more tooth. In some embodiments, the force is coronal pressure, e.g., a pressure exerted in the direction of or on the crown of the tooth, which is useful to intrude teeth; in other embodiments, the force is apical pressure, e.g., a pressure exerted in the direction of or on the root, which is useful to extrude teeth. In some embodiments, a force is exerted on a mesial (e.g., side of tooth towards front of mouth) side of the tooth. In some embodiments, a force is exerted on a distal, e.g., side of tooth towards back of mouth) side of the tooth. A force can be exerted on a buccal, e.g., side of tooth towards cheek, side of the tooth, or a force can be exerted on a lingual, e.g., side of tooth towards tongue, side of the tooth. A force can be exerted on an occlusal surface of a tooth. A force can be exerted on an incisal surface of a tooth. A force can be exerted on a proximal surface of a tooth, e.g., mesial or distal surfaces in between teeth. A force can be exerted on an apical, e.g., toward a root end, surface of a tooth. In some embodiments, a force exerted on a tooth is translated to be exerted on the mandibular bone or maxillary bone. The force can be exerted by a functional appliance for regulating oral or maxillofacial bone remodeling. In some embodiments, the force can be exerted by an orthodontic appliance for regulating tooth movement.

A force can be directed to push one or more teeth toward one another. A force may be directed to push one or more teeth apart. A force may be directed to move one or more teeth toward a side. In some embodiments, a force may shift a tooth sideways along a maxilla or mandible. Alternatively, a force may move a tooth forwards or backwards relative to a maxilla or mandible. In some embodiments, a force can be directed to move a mandibular bone or maxillary bone forward in an anterior direction. A force can be directed to move a mandibular bone or maxillary bone backward in a posterior direction. A force can be directed to adjust an angle of a mandibular bone or maxillary bone. For example, the angle of a mandibular bone can be adjusted by moving a right side or a left side of a mandibular bone forward or backward. If a right side of a mandibular bone is moved forward or lengthened, while the left side of the mandibular bone maintains the same position or is moved backward or shortened, the mandibular bone can be angled more leftward (e.g., shifted sideways or to the left side). In other words, a force can be directed to move one or more teeth toward a side.

In some embodiments, a force is exerted at any point or region along a side of one or more teeth and/or along a side of an oral or maxillofacial bone, muscle, or soft tissue. In some embodiments, a force is exerted at or near the top of one or more teeth, i.e., the side of a tooth opposite its root or roots. In some embodiments, a force is exerted at or near the middle of the clinical crown, e.g., exposed to the air, above the gums, of one or more teeth. In other embodiments, a force is exerted at or near the bottom of the clinical crown of one or more teeth, i.e., the clinical crown of a tooth closer to its root. In some embodiments, the force is applied to the root of the one or more teeth. A force can be exerted on one or more of the points or regions described herein on one or more teeth. In some embodiments, a force is exerted along the side of the tooth. Depending on where or for how long the force is exerted, some or no tipped movement may occur to the tooth. Tipped movement is described in more detail herein.

In some embodiments, however, a force is exerted at or near a temporomandibular joint, condyle, or glenoid fossa. In some embodiments, a force is exerted on one or more of the right temporomandibular joint, right condyle, or right glenoid fossa; one or more of the left temporomandibular joint, left condyle, or left glenoid fossa; or one or more of both right and left temporomandibular joints, both right and left condyles, and both right and left glenoid fossa. In some embodiments, the force is exerted on the right temporomandibular joint without being exerted on the left temporomandibular joint, the right condyle without being exerted on the left condyle, the right glenoid fossa without being exerted on the left glenoid fossa, the left temporomandibular joint without being exerted on the right temporomandibular joint, the left condyle without being exerted on the right condyle, or the left glenoid fossa without being exerted on the right glenoid fossa. In some embodiments, the force is exerted on mandibular or maxillary alveolar bone. In some embodiments, the force is exerted on an anterior portion of the maxillary bone, mandibular bone, or temporal bone.

Depending on where or for how long the force is exerted, some or no tooth tipped movement may occur. In some embodiments, a force can increase the velocity of tooth movement as compared to where no force or a lighter force is exerted. In these embodiments, in other words, the force reduces the amount of time it takes for the tooth to move to its desired position within the gum. Exertion of a force on the maxillary bone, mandibular bone, temporal bone, or one or more of a patient's teeth, particularly where the patient is administered with an effective amount of light to his or her maxillary bone, mandibular bone, or one or more teeth, can further reduce the amount of time of orthodontic treatment that a patient might undergo.

In some embodiments, a force is exerted on one or more teeth of a patient by one or more orthodontic appliances. Accordingly, in one embodiment, an orthodontic appliance can exert a force on one or more of the patient's teeth to facilitate tooth movement. In some embodiments, a functional appliance exerts a force on oral or maxillofacial bone, muscle, soft tissue, or one or more teeth. The functional appliance can exert a force on only the mandibular bone of the patient. Alternatively, the functional appliance can exert a force only the maxillary bone of the patient. In some embodiments, the functional appliance exerts a force on only the temporal bone of the patient. The functional appliance can exert a force on both the mandibular bone and maxillary bone of the patient. The functional appliance can optionally exert a force on a maxillary bone, mandibular bone, or temporal bone by exerting a force on one or more tooth of the patient. The functional appliance can exert a force on only the jaw muscle. The functional appliance can exert a force on only the jaw soft tissue.

In some embodiments, the orthodontic appliance can be present on one or more of the patient's teeth, other oral regions of the patient, or the patient's head or face. In some embodiments, the patient wears two or more orthodontic appliances and less than all of these appliances exert a force on one or more of the patient's teeth. For example, the orthodontic appliance can exert a force on only one tooth of the patient or, alternatively, the orthodontic appliance can exert a force on a plurality of teeth of the patient. In another embodiment, the orthodontic appliance can selectively exert a force on less than all the teeth of the patient. Orthodontic appliances that exert forces can also include other intra-oral appliances and/or extra-oral appliances.

In some embodiments, the orthodontic appliance for exerting a force can be used for external anchorage, and can be the form of a temporary anchorage device or in the form of headgear. For example, a patient that uses the intra-oral apparatus can concurrently wear a second orthodontic appliance, e.g., in the form of headgear, for temporary period of time, e.g., at night. In some embodiments, the externally worn headgear can physically or electronically communicate with an intra-oral apparatus to facilitate tooth movement. External anchorage can be used to facilitate the exertion of forces to prevent untoward movement of anchorage teeth during use of forces.

As is described in more detail herein, the patient can wear an orthodontic appliance that exerts forces subsequent to initiating the administration of light. For example, the patient can wear an orthodontic appliance that exerts forces after one or more light treatment sessions are completed while using an intra-oral apparatus. In this manner, a force can be exerted on one or more teeth of the patient by the orthodontic appliance(s) subsequent to initiating the administration of light via an intra-oral apparatus. In some embodiments, however, a force is exerted on one or more teeth of the patient prior to or during the administration of light. In such an embodiment, the patient wears an orthodontic appliance and uses an intra-oral apparatus at the same time. In other embodiments, a force is exerted on one or more teeth of the patient prior to and during the administration of light. In some embodiments, a force is exerted on one or more teeth of the patient and the intra-oral apparatus emits light during the alignment phase of orthodontic treatment. In another embodiment, the patient uses a single intra-oral apparatus that both administers light and exerts a force. In other embodiments, a force is exerted on one or more teeth of the patient prior to initiating the administration of light. The patient, for example, could wear his or her orthodontic appliance for any length of time before beginning the light treatment.

In some instances, heavy forces can cause a periodontal ligament to compress, which can eventually lead to ischemia or cell death. To prevent ischemia or eventual cell death, the heavy force is exerted with the light treatment as described herein. In one embodiment, however, the heavy force is exerted after the light treatment has started. In some embodiments, the heavy force is exerted minutes, hours, or days after light treatment has started. In this manner, the light treatment can provide additional adenosine-5'-triphosphate (ATP) energy to tissue cells that will become stressed and could potentially become ischemic as a result of the heavy force. Illustrative frequencies of light treatment used by an intra-oral apparatus are described herein. In some embodiments, the heavy force is exerted concurrently with administration of light. In other embodiments, the heavy force is exerted subsequent to administration of light.

As described herein, a heavy force can be exerted on one of more teeth from any direction. More particularly, in some embodiments, the force pushes two or more teeth together or apart, or pushes one or more teeth to one side or area of a patient's mouth. For example, in some embodiments, the force can push two or more teeth toward the front of the patient's mouth, to the back of the patient's mouth, to the left of the patient's mouth, or to the right of the patient's mouth.

Regulating oral or maxillofacial bone remodeling can include changing the position of the mandibular bone or maxillary bone relative to one another or to the skull of the patient. Regulating oral or maxillofacial bone remodeling can also include controlling the position (e.g., forward, backward, sideways or angle) of the mandibular bone or maxillary bone, lengthening or shortening the mandibular bone or maxillary bone, lengthening or shortening a side of the mandibular bone or maxillary bone, altering the shape or dimensions of the mandibular bone or maxillary bone, or regulating (e.g., increasing, decreasing or maintaining) the velocity of the movement of the mandibular bone or maxillary bone relative to one another. For example, regulating oral or maxillofacial bone remodeling can include increasing the velocity of oral or maxillofacial bone remodeling.

By repositioning a mandibular bone forward or backwards, muscle tension can be caused on the joint area of the mandibular bone, or other parts of the mandibular bone. This tension can stimulate osteoblastic activity or bone remodeling, which can lengthen the mandibular bone through bone deposition on the condylar head and glenoid fossa of the temporal bone of the skull. Also, the tension can effect dental movement forward of the entire lower arch. In some cases, antagonistic force on the maxillary bone can retard the growth of the maxillary bone and cause remodeling and dental movement posteriorly. This can be desirable in situations where the oral or maxillofacial bone remodeling is regulated in order to remodel the maxillary bone posteriorly. Malocclusion can exist when there is a misalignment of teeth or the upper dental arch and the lower dental arch do not line up. The antagonist force on the maxillary bone can be more or less desirable depending on the severity of the malocclusion and whether the maxillary bone is protrusive. If the maxillary bone is protrusive, it can be desirable to retard maxillary forward growth or even retrude maxillary teeth and the jaw bone. A maxillary headgear can be used to retard or decrease the growth of the maxilla forward. In one example, a functional appliance can be used to reposition a mandibular bone forward while utilizing upper teeth or the maxillary bone as anchorage. An equal and opposite force can be exerted on the maxillary bone, which can lead to dental orthodontic movement and bone remodeling on the maxillary bone.

Some functional appliances (e.g., Bionator or Frankel), can prevent antagonist muscles from pushing on the bone and teeth. This can permit opposite agonist muscles to push on the bone and teeth. Thus, in some embodiments, allowing a force to be exerted on an oral or maxillofacial bone, muscle, or soft tissue, or one or more teeth, can include preventing a first group of muscles from exerting a force on the oral or maxillofacial bone, muscle, or soft tissue, or one or more teeth, thereby allowing a second group of muscles to exert the force. Some examples of muscles whose forces can be withheld, include cheek and lip (peri-oral) muscles. Examples of such muscles can include masseters, buccinators, mentalis muscle and orbicularis. This can allow other muscles, such as the tongue, to exert a force on the oral or maxillofacial bone, muscle, or soft tissue, or one or more teeth. In some cases, it can be desirable to prevent the tongue from interfering with and pushing on teeth, so a functional appliance or an orthodontic appliance can be inserted to prevent the tongue from pushing on the front teeth during swallowing. This could allow cheek and lip muscles to push on teeth and bone to retract and allow teeth to erupt into a normal position previously presented by an overactive and poorly positioned tongue. In one example, a Frankel appliance can hold the cheek and lip muscles away from the teeth to allow them room to grow into the correct position. While the cheek and lip muscles (opposing muscles) are held away from the teeth, the tongue (an agonist muscle pushing against the teeth from the inside) can push on the teeth, thereby allowing a lower arch, upper arch, or both lower and upper arch to expand without interference from the opposing cheek and lip muscles.

In some embodiments, the force exerted by a functional appliance can prevent muscles of a first group from exerting a first force, or can substantially reduce the amount of the first force, allowing muscles in a second group to exert a second force, which can result in bone remodeling caused by the second force. The muscles in the first group and the muscles in the second group can typically exert forces in different directions. For example, muscles can exert forces anteriorly, posteriorly, laterally to the left, laterally to the right, radially inward, radially outward, upward, or downward. In some embodiments, the muscles of the first group and the muscles of the second group can exert forces in a substantially opposite direction. The muscles in the first group and the muscles in the second group can exert forces in different directions. Alternatively, the force exerted by the functional appliance can alter the angle of the overall force applied to the region by increasing the relative effect of the second force, which can result in bone remodeling caused by the increased magnitude on the second force relative to the first force. Any number of muscle groups (e.g., 1, 2, 3, 4, 5, 6, or more) can exert force in any direction. The force exerted by the functional appliance can prevent one or more of the muscle groups from exerting a force or can reduce the amount of force exerted by one or more groups.

In some embodiments, a functional appliance can keep muscles away from the teeth so that the muscles that oppose those that are withdrawn via the functional appliance then can exert forces on the teeth to cause tooth movement and possible bone remodeling due to "imbalance" of previously balanced muscular pressure. In some embodiments, the functional appliance exerts a force on the oral or maxillofacial muscle or soft tissue in order to keep the muscles away.

The phrase "regulating tooth movement" as used herein refers to and includes one or more of the following functions and/or operations. For example, regulating tooth movement can include regulating, in one embodiment, aligning, the position of one or more teeth relative to a supporting tissue.

Regulating tooth movement can also include increasing, decreasing or maintaining the velocity of tooth movement relative to a supporting tissue. For example, regulating tooth movement can include increasing the velocity, or speed, of tooth movement. Regulating tooth movement can also include increasing, decreasing or maintaining the degree of bodily movement, e.g., relative to the degree of tipped movement, of one or more teeth. Regulating tooth movement can comprise moving one or more teeth bodily. "Bodily" movement means generally perpendicular tooth movement relative to the supporting tissue. "Tipped" movement means that the crown or coronal region of the tooth advances more quickly than the root or apical region of the tooth. Bodily tooth movement can occur without causing significant tipped movement of the tooth. By "significant tipped movement" is meant that about 20% of the tooth does not move in the same lateral direction as the remaining about 80%; in another embodiment about 10% of the tooth does not move in the same lateral direction as the remaining about 90%; in another embodiment about 5% of the tooth does not move in the same lateral direction as the remaining about 95%. Tooth movement can include lateral displacement, rotation, extrusion or intrusion of one or more teeth. Regulating tooth movement can include inducing the tilting or tipped movement of one or more teeth, minimizing or preventing the tilting or tipped movement one or more teeth, or maintaining or inducing alignment or orientation of the one or more teeth. Regulating tooth movement can also include stabilizing, retarding the rate of or preventing tooth movement. In some instances, regulating tooth movement can include causing one or more teeth to maintain their position. In some embodiments, regulating tooth movement can include causing one or both of (i) the displacement of one or more teeth and (ii) the maintenance of one or more other teeth in their position. In some embodiments, regulating tooth movement occurs prior to, subsequent to or during orthodontic treatment with an orthodontic appliance. In some embodiments, regulating tooth movement occurs prior to, subsequent to or during the alignment phase of orthodontic treatment. In some embodiments, tooth movement occurs during bone remodeling.

In some embodiments, regulating tooth movement occurs during an alignment phase of orthodontic treatment. Tooth movement during this phase can include the tipping movement of one or more teeth, the rotation of one or more teeth, and/or the extrusion or intrusion of one or more teeth. The extrusion or intrusion of one or more teeth can be a bodily movement that occurs during the alignment phase. In general, however, bodily movement does not usually occur during the alignment phase of orthodontic treatment. Rather, bodily movement typically occurs after the alignment phase of orthodontic treatment, when the teeth are aligned and crowding of the teeth is minimized. In some embodiments, regulating tooth movement occurs after the alignment phase of orthodontic treatment. In other embodiments, regulating tooth movement occurs prior to the alignment phase of orthodontic treatment.

In some embodiments, the type or shape of wire used in an orthodontic appliance can assist in regulating tooth movement. For example, an orthodontic appliance comprising a round wire worn by a patient during an alignment phase of orthodontic treatment can exert a force that increases the velocity of tipping movement, rotation, extrusion or intrusion of one or more teeth. An orthodontic appliance comprising a rectangular wire is generally worn after the alignment phase, e.g., during the finishing or detailing phase and/or the retention phase, or when the one or more teeth of the patient are aligned within the same horizontal plane such that crowding is minimal. A rectangular wire is generally stiffer than a round wire and can facilitate the bodily movement of one or more teeth.

In some embodiments, tooth movement is measured by a change in Little's Irregularity Index (LII). LII measures the degree of discrepancy between teeth and is the sum of the five (5) linear distances from one contact point to an adjacent contact point of the six (6) anterior teeth. An LII score of zero (0) indicates that the teeth are perfectly aligned. In some embodiments, one or more teeth of one or both of the upper arch or the lower arch are moved into alignment to the extent that the one or both of the upper-arch LII or the lower-arch LII ranges from zero (0) mm to less than 1 mm. An LII score of 1 mm or greater indicates that the teeth are misaligned and that tooth movement is needed for correction. A contact point measurement of 0 (zero) mm indicates perfect alignment of the two adjacent teeth. A contact point measure of, for example, 0.22 mm indicates that there is a discrepancy of 0.22 mm between the two adjacent teeth. In general, the higher the LII score, the less aligned are the teeth. For example, an LII score greater than 10 mm general indicates a severe misalignment. Additional details regarding LII and its calculations can be found in the following publication, which is incorporated by reference herein in its entirety: Little, R. M., "The irregularity index: a quantitative score of mandibular anterior alignment," Am. J. Orthod., 1975 November, 68(5): 554-63. The contact point measurements can be taken using a fine-tip digital caliper, such as a Tresna® Point Digital Caliper, Series SC02 commercially available from Guanglu Measuring Instrument Co., Ltd. of China. The caliper can be configured to measure the contact point to the nearest 0.1 mm. Contact point measurements can be taken using models of the patient's teeth.

Orthodontic Appliances

The present methods can be performed on a patient prior to being applied with one or more functional appliances and/or orthodontic appliances, during a time when the patient wears one or more functional appliances and/or orthodontic appliances, or after one or more functional appliances and/or orthodontic appliances has been removed from the patient. The one or more functional appliances and/or orthodontic appliances can be used in addition to the intra-oral apparatus (e.g., any light therapy apparatus described herein, including, but not limited to, light therapy apparatuses 2500 and 3500). A functional appliance or orthodontic appliance can be fixed or movable with respect to a patient's teeth and/or the intra-oral apparatus. As is disclosed herein, orthodontic appliances can include, for example, fixed active appliances such as pin and tube appliances, appliances using wires or brackets or springs, ribbon arch appliances, Begg lightwire appliances, edgewise appliances, pre-adjusted edgewise appliances, self-ligating edgewise appliances, bi-helix, tri-helix, quad-helix, rapid maxillary expansion appliance (RME); removable active appliances such as expansion and labial segment alignment appliance INVISALIGN™; substantially transparent aligners; orthodontic headgear including reverse headgear and conventional headgear; and other types of orthodontic apparatus. In one embodiment the orthodontic appliance comprises wires and brackets (examples of which are described herein, with respect to the section entitled "Examples").

In one embodiment, the orthodontic appliance is fixed. Examples of fixed orthodontic appliances include pin and tube appliances, ribbon arch appliances, Begg Lightwire appliances, edgewise appliances, pre-adjusted edgewise appliances, self-ligating edgewise appliances, hi-helix appliances, tri-helix appliances, quad helix appliances, rapid maxillary expansion appliances (RME), or pin stripe appliances. Fixed orthodontic appliances can be fixed to the patient's teeth during orthodontic treatment. In one embodiment, the orthodontic appliance is fixed and comprises wires and brackets. In another embodiment, the orthodontic appliance is removable. Examples of removable orthodontic appliances include Active Hawley appliances, Invisalign aligners, aligners, fan expanders, or sagittal appliances.

In some embodiments, the functional appliance is a mandibular repositioner or any other intra-oral apparatus that repositions the mandible to create tension on tissue to stimulate bone remodeling or tooth movement. Some examples of mandibular repositioners are Herbst, Twin Block, Fixed Twin Block, Bonded Twin Block, Biobloc, Forsus Fatigue (e.g., EZ2), Xbow (Crossbow), mandibular anterior repositioning appliance (Mara), Bass Dynamax, Bionator, Open Face Activator, Activator, Woodside Activator, Frankel (e.g., Frankel I, II, III, IV, V), Teuscher appliance, Andreson appliance, 3-Way Sagittal, Lower Schwartz, 3 Way Expander, jaw repositioning appliances, removable orthotic appliances, Series 2000®, BioPedic Appliance, Rick-A-Nator™, Ritto Appliance, Eureka Spring™, Twin Force Bite Corrector™, Alpern Class II Closers, Rapid palatal expander, Tandem™, facemask, reverse pull headgear, and conventional orthodontic headgear.

In one embodiment, the functional appliance is fixed. A fixed functional appliance can be cemented, for example, on one or more teeth. Some examples of fixed functional appliances include Herbst, Fixed Twin Block, Bonded Twin Block, Forsus Fatigue (e.g., EZ2), Xbow (Crossbow), Series 2000®, BioPedic Appliance, Rick-A-Nator™, Ritto Appliance, Eureka Spring™, Twin Force Bite Corrector™, Alpern Class II Closers, and Rapid palatal expander. In another embodiment, the functional appliance is removable. Some examples of removable functional appliances include Twin Block, Biobloc, mandibular anterior repositioning appliance (Mara), Bass Dynamax, Bionator, Open Face Activator, Activator, Woodside Activator, Frankel (e.g., Frankel I, II, III, IV, V), Teuscher appliance, Andreson appliance, 3-Way Sagittal, Lower Schwartz, 3 Way Expander, jaw repositioning appliances, and removable orthotic appliances. In some embodiments, the functional appliance is a combination fixed-removable functional appliance. A combination fixed-removable functional appliance can include one or more component that is fixed to a patient's teeth and one or more component that is removable from the fixed component. Some examples of combination fixed-removable functional appliances include Tandem™, a facemask, reverse pull headgear, and conventional orthodontic headgear.

In some embodiments, the functional appliance is a Class II corrector. Some examples of Class II correctors include Herbst, Twin Block, Forsus Fatigue, and Mara. In other embodiments, the functional appliance is a Class I corrector that is useful for creating and bony and dental expansion of crowded and lower arches. In other embodiments, the functional appliance is a Class III corrector that is useful for stimulating maxillary forward growth, or retruding or limiting mandibular growth.

In some embodiments, the functional appliances reposition a patient's mandibular bone anteriorly. The functional appliance can be a fixed functional mandibular repositioner. Examples of such functional appliances are a Herbst, Twin Block, Bonded Twin Block, Biobloc, and Bass Dynamax. In some embodiments, the functional appliances expand the jaw (e.g., using muscular pressure or lack of muscular forces to allow teeth to move and/or bone to remodel). Examples of such functional appliances can include Bionator, Open Face Activator, Activator, Woodside Activator, or Frankel. Light can be administered to the alveolar soft tissue and/or alveolar bones and teeth, as these appliances can cause orthodontic movement of teeth as well as bone remodeling. In some embodiments, the functional appliances control growth of the maxillary bone or mandibular bone. Examples of such functional appliances can include a facemask, or reverse pull headgear. Light can be administered to apical areas of the jaw, which can cause some orthodontic movement, but primarily remodels and provides anterior movement of maxillary bone. In some embodiments, the functional appliances exert a force on, or cause bone remodeling at, a temporomandibular joint, condyle, or glenoid fossa of a patient.

A functional appliance functions by exerting a force that causes muscle or tissue to exert a force directly on, for example, a tooth such that some aspect of the tooth changes as a result of said force from the muscle or tissue. In one specific example, a patient can wear a functional appliance to reposition his or her jaw, and the resultant position of the jaw exerts a force on surrounding tissue thereby allowing remodeling to occur. Functional changes can include changes in the maxillary bone, the mandibular bone, tooth position, bite and jaw function, and chewing. In contrast to functional appliances, orthodontic appliances function by exerting a force directly on, for example, a tooth to change some aspect of the tooth (e.g., to change the position of the tooth relative to another tooth).

Orthodontic appliances are commercially available and can include specifications (or other documentation) that specify the magnitude of force that the appliance is capable of exerting on one or more teeth. In some embodiments, an orthodontic appliance comprises steel wires, nickel titanium wires, or titanium molybdenum wires. In some embodiments, an orthodontic appliance comprises wires or springs that are of a high gauge. Some examples of wires that an orthodontic appliance can comprise are stainless steel or nickel-titanium wires having wire dimensions of one of the following:

| | |
|---|---|
| 0.0160" square | 0.406 mm square |
| 0.0160" × 0.0220" | 0.406 mm × 0.559 mm |
| 0.0170" square | 0.432 mm square |
| 0.0170" × 0.0220" | 0.432 mm × 0.559 mm |
| 0.0170" × 0.0250" | 0.432 mm × 0.635 mm |
| 0.0180" square | 0.457 mm square |
| 0.0180" × 0.0220" | 0.457 mm × 0.559 mm |
| 0.0180" × 0.0250" | 0.457 mm × 0.635 mm |
| 0.0190" square | 0.483 mm square |
| 0.0190" × 0.0250" | 0.483 mm × 0.635 mm |
| 0.0200" square | 0.508 mm square |
| 0.0210" × 0.0250" | 0.533 mm × 0.635 mm |

A practitioner installing the wires on a patient's teeth can select the appropriate wire(s) for the patient's orthodontic treatment program. In some embodiments, a first wire with a first dimension and/or first strength is installed at the time brackets are initially bonded to the patient's teeth, and a second wire with a second dimension and/or second strength is installed a time subsequent to bonding of the brackets, such as during a follow-up visit to the practitioner and, for example, after one or more light therapy treatment session have been administered to the patient's teeth with the orthodontic appliance installed thereon.

An orthodontic appliance can comprise brackets and wires. Commercially available brackets include those offered by SPEED System (www.speedsystem.com), DENTSPLY GAC International (www.gacinovation.com), brackets offered by Ormco Corporation (www.ormco.com) (e.g., Mini-Diamond® brackets), In-Ovation L Straightwire system brackets, or brackets offered by Orthodontic Design and Production, Inc. (e.g., Agility® self-ligating brackets). Wires can be nickel titanium and can have a diameter of 0.012 inch, 0.014 inch or 0.016 inch. In some embodiments, the wires are square or rectangular. In one embodiment, the wires are square and have a dimension of 0.015 inch×0.015 inch. In one embodiment, the wires have a dimension of 0.016 inch×0.016 inch. In another embodiment, the wire is rectangular and have a dimension of 0.017 inch×0.025 inch. In some embodiments, the wires are 0.016 inch Supercable nickel titanium wires.

Nickel-titanium closed or open-coil springs can be used. Some examples can include an elastomeric power chain, which can be capable of providing 100-800 grams of force, or intra-arch elastics. In some embodiments, the orthodontic appliance comprises an elastic material. An orthodontic appliance can exert a force on one or more teeth of the patient in addition to or in lieu of the intra-oral apparatus exerting a force on one or more teeth. For example, in some embodiments, the orthodontic appliance can exert or be configured to exert a heavy force on one or more teeth of the patient in addition to or in lieu of the intra-oral apparatus exerting a heavy force on one or more teeth. The orthodontic appliance can cause one or more teeth to move or maintain its position. In some embodiments, an orthodontic appliance causes bone remodeling of an oral or maxillofacial bone, or one or more tooth, such as a mandibular bone, maxillary bone, or temporal bone. In some embodiments, an apparatus of the invention does not exert a force on a patient's teeth. In some embodiments, an apparatus of the invention does not exert a heavy force on a patient's teeth.

A force, such as a heavy force, can be measured using a dynamometer or any similar device. For example, a dynamometer can measure the force that a wire, spring or similar mechanism from an orthodontic appliance exerts on one or more teeth or gums. In one example, the dynamometer (or similar device) can measure the force that the wires 12 from the intra-oral apparatus depicted in FIG. 3A exert on one or more teeth or gums. The measured force can depend on any number of parameters such as, for example, the gauge of the wire or the stiffness of the wire. In this manner, in some embodiments, a force can be calculated, in part, by measuring the tension or stiffness of the appliance's wire (or spring or similar mechanism), e.g., when such force is exerted on one or more teeth. Furthermore, in some embodiments, the appliance's wire (or spring or similar mechanism) is constructed from a material that is sensitive to temperature such that the stiffness of the wire, and therefore the heavy force exerted by that wire, can change based on the temperature of the wire. For example, in some embodiments, the stiffness of the wire (or spring or similar mechanism) increases when the wire temperature increases, and decreases when the wire temperature decreases. Thus, in some such embodiments, a force can be calculated, in part, by measuring the temperature of the wire (or spring or similar mechanism) or estimating its temperature when present in a patient's oral cavity. With respect to the gauge of the wire, it is generally well known in the art that increasing the gauge (or cross-section) of a wire can increase the stiffness of the wire which ultimately increases the heavy force that the wire exerts on one or more teeth.

Although the methods are described herein as being performable on a patient (1) prior to the patient being applied with one or more functional appliances and/or orthodontic appliances, (2) during a time when the patient wears one or more functional appliances and/or orthodontic appliances, or (3) after one or more functional appliances and/or orthodontic appliances has been removed from the patient, in some embodiments, the methods described herein can be performed on the patient independently of or without usage of a functional appliance and/or orthodontic appliance.

In one embodiment, a patient can use an intra-oral apparatus of the invention prior to, subsequent to or during a time that the patient wears an orthodontic appliance. In some embodiments, the patient begins use of the intra-oral apparatus on the same date the orthodontic appliance is installed on the patient's teeth. The orthodontic appliance installation can include bonding brackets to the patient's teeth and installing wire with the brackets. In other embodiments, the patient ends use of the intra-oral apparatus within one or more days (e.g., one, two, or three days) or one or more weeks (e.g., one or two weeks) before or after the orthodontic appliance is installed. In some embodiments, the patient ends use of the intra-oral apparatus on the same date that the orthodontic appliance is uninstalled from the patient's teeth. In other embodiments, the patient ends use of the intra-oral apparatus within one or more days (e.g., one, two, or three days) or one or more weeks (e.g., one or two weeks) before or after the orthodontic appliance is uninstalled.

In some embodiments the invention provides methods for regulating tooth movement, maintaining oral tissue health or improving oral tissue health, comprising administering to a patient in need thereof an effective amount of light from the emitter of an intra-oral apparatus of the invention. In some embodiments, at least a portion of the apparatus is configured to contact the patient's alveolar soft tissue. In some embodiments, the patient wears an orthodontic appliance that exerts a force on one or more teeth of the patient. In some embodiments, the light is administered during the alignment phase of orthodontic treatment. In some embodiments, the light is administered during only the alignment phase of orthodontic treatment. In some embodiments, the alveolar soft tissue is alveolar mucosa. In some embodiments, the force is a heavy force. In some embodiments, the patient wears the same or a different orthodontic appliance that exerts a force on one or more teeth of the patient during the retention phase of orthodontic treatment. In some embodiments, the force exerted during the retention phase is a heavy force.

In some embodiments the invention provides methods for orthodontic treatment, comprising administering to a patient in need thereof an effective amount of light from the emitter of an intra-oral apparatus of the invention. In some embodiments, at least a portion of the apparatus is configured to contact the patient's alveolar soft tissue. In some embodiments, the patient wears an orthodontic appliance that exerts a force on one or more teeth of the patient. In some embodiments, the light is administered during the space or gap closure phase of orthodontic treatment. In some embodiments, the light is administered during the alignment phase of orthodontic treatment. In some embodiments, the light is administered during only the alignment phase of orthodontic treatment. In some embodiments, the alveolar soft tissue is alveolar mucosa. In some embodiments, the force is effective for regulating tooth movement, maintaining oral tissue health or improving oral tissue health. In some embodiments, the force is a heavy force. In some embodiments, the patient wears the same or a different orthodontic appliance that exerts a force on one or more teeth of the patient during the retention phase of orthodontic treatment. In some embodiments, the force exerted during the retention phase is a heavy force.

In some embodiments the invention provides methods for orthodontic treatment, comprising administering to a patient who wears an orthodontic appliance or is in need of orthodontic treatment an effective amount of light from the emitter of an intra-oral apparatus of the invention (e.g., light therapy apparatus 2500 or 3500). In some embodiments, at least a portion of the apparatus is configured to contact the patient's alveolar soft tissue. In some embodiments, the patient wears an orthodontic appliance that exerts a force on one or more teeth of the patient. In some embodiments, the light is administered during the alignment phase of orthodontic treatment. In some embodiments, the light is administered during only the alignment phase of orthodontic treatment. In some embodiments, the alveolar soft tissue is alveolar mucosa. In some embodiments, the force is effective for regulating tooth movement, maintaining oral tissue health or improving oral tissue health. In some embodiments, the force is a heavy force. In some embodiments, the patient wears the same or a different orthodontic appliance that exerts a force on one or more teeth of the patient during the retention phase of orthodontic treatment. In some embodiments, the force exerted during the retention phase is a heavy force.

In some embodiments the invention provides methods for orthodontic treatment, comprising administering to a patient who wears an orthodontic appliance and is in need of orthodontic treatment an effective amount of light from the emitter of an intra-oral apparatus of the invention. In some embodiments, at least a portion of the apparatus is configured to contact the patient's alveolar soft tissue. In some embodiments, the orthodontic appliance exerts a force on one or more teeth of the patient. In some embodiments, the light is administered during the space or gap closure phase of orthodontic treatment. In some embodiments, the light is administered during the alignment phase of orthodontic treatment. In some embodiments, the light is administered during only the alignment phase of orthodontic treatment. In some embodiments, the alveolar soft tissue is alveolar mucosa. In some embodiments, the force is effective for regulating tooth movement, maintaining oral tissue health or improving oral tissue health. In some embodiments, the force is a heavy force. In some embodiments, the patient wears the same or a different orthodontic appliance that exerts a force on one or more teeth of the patient during the retention phase of orthodontic treatment. In some embodiments, the force exerted during the retention phase is a heavy force.

Vitamin D

As described herein, the present methods can further comprise administering vitamin D to the patient. Vitamin D is essential for normal bone metabolism—it promotes calcium absorption and bone resorption and maintains the necessary calcium and phosphate levels for bone formation. Patients deficient in vitamin D have an increased risk of bone loss and bone fracture, among many other risks. Insufficient vitamin D levels can also interfere with osteoclastic activity, which is essential to tooth movement, resulting in slower tooth movement. Thus, administering vitamin D can be an important part of orthodontic treatment.

The vitamin D can be, for example, vitamin D1, D2, D3, D4, D5, 1,25-dihydroxycholecalciferol, or mixtures thereof. In some embodiments, the vitamin D supplements other vitamin D sources for the patient.

The vitamin D can be administered in any suitable manner. For example, the vitamin D can be administered orally, via transdermal gel, by a patch, by a cream, by injection, by electrophoresis, or by insolation. Where the present methods further comprise administering vitamin D, in some embodiments, the vitamin D is not administered by insolation. In some embodiments, the vitamin D is administered via a vitamin D conveyance. For example, the vitamin D can be present in a composition suitable for oral administration, for example, a pill, capsule, tablet, chewable, gel, or liquid. In other embodiments, the vitamin D is administered transdermally. In one example, the vitamin D can be administered transdermally via a transdermal gel, cream, ointment, liquid, or paste that can be applied to the skin, gums, or any soft tissue. In another example, vitamin D can be administered transdermally via insolation, such as exposure to ultraviolet (UV) rays from the sun or artificially through tanning beds. The vitamin D can also be administered transdermally via a patch or microneedle on the skin, gums, or other soft tissue of the patient. In some embodiments, the vitamin D is be administered by injection using a syringe or needle at the skin, gums, or other soft tissue (such as, for example, oral tissue) of the patient. The injection can be intradermal, subcutaneous, intramuscular, intravenous, intraosseous, or intraperitoneal. In some embodiments, the vitamin D is administered electrophetically. The vitamin D can be applied, for example, to the surface of the skin, gums, or any other soft tissue, and a weak electrical current can drive the compound through the tissue.

Any combination of the various vitamin D administration techniques described herein can be employed. For example, a patient can be orally administered with vitamin D and also receive an injection of vitamin D as part of the administration process. In some embodiments, the administered vitamin D increases or maintains the vitamin D blood serum levels. In other embodiments, the administered vitamin D increases or maintains local vitamin D levels where the vitamin D is administered.

In some embodiments, the vitamin D is administered to a region, or in the proximity of a region. The region can be, for example, an oral region. The region can be, for example, on or in the proximity of oral or maxillofacial bone, muscle, or soft tissue. The region can be on or in the proximity of one or more tooth, the mandibular bone, the maxillary bone, or the temporal bone. In some embodiments, the vitamin D is orally administered, for example, via an oral composition that comprises vitamin D. In other embodiments, the vitamin D is administered locally to a region. The region can be on the skin of the patient overlying the patient's face, jawbone, lips, cheek, or chin. The region can be on the right side, the left side, a central region, or any combination thereof, of the patient's body such as, for example, the patient's face. The region can be within the patient's oral cavity. For example, the region can be the gums of the patient, or any other oral soft tissue. The region need not be an oral region; rather, the region can be, for example, on the neck, arm, leg, or torso of the patient. In some embodiments, the vitamin D can be administered systemically to the patient. For example, the vitamin D can be administered via insolation through a tanning bed that surrounds the patient's body. The region can include any area previously described.

In some embodiments, the vitamin D is administered to a region that is the same as or in the proximity of a region that is administered with light. In some embodiments, the vitamin D is administered to the same region that is administered with light. In some other embodiments, the vitamin D is administered to a region having the same, greater, or smaller size than the region administered with light. The vitamin D can be administered to a region adjacent to a region administered with light. In some embodiments, vitamin D is administered to a region within about 1 mm, about 2 mm, about 3 mm, about 5 mm, about 7 mm, about 10 mm, about 15 mm, about 20 mm, about 25 mm, about 30 mm, about 40 mm, about 50 mm, about 60 mm, about 70 mm, about 10 cm, about 15 cm, about 20 cm, about 30 cm, about 50 cm from a region that is administered with light. In other embodiments, the vitamin D is administered to a region that is different from the region that is administered with light. In some embodiments vitamin D is not administered to a region that is administered with light. In some embodiments, vitamin D is administered to a region other than the region that is administered with light. In some embodiments, vitamin D is administered systemically, which can encompass the region administered with light. In some instances, the vitamin D is administered systemically, raising overall vitamin D levels, which can include vitamin D levels in the region administered with light.

In some embodiments, the vitamin D is administered to a region that is proximate to a region upon which a force is exerted. The force can be, for example, a heavy force, a force exerted by an orthodontic appliance, or a force exerted by a functional appliance. In some embodiments, the vitamin D is administered to the same region upon which a force is exerted. In some embodiments, the region where the vitamin D is administered and the region upon which the force is exerted are the same size. In other embodiments, however, the size of the region where the vitamin D is administered is different from the size of the region upon which the force is exerted. The region where the vitamin D is administered can be, for example, smaller or larger than the region upon which the force is exerted. In some embodiments, the vitamin D is administered to a region adjacent to a region upon which a force is exerted. The vitamin D can be administered to a region, for example, within about 1 mm, about 2 mm, about 3 mm, about 5 mm, about 7 mm, about 10 mm, about 15 mm, about 20 mm, about 25 mm, about 30 mm, about 40 mm, about 50 mm, about 60 mm, about 70 mm, about 10 cm, about 15 cm, about 20 cm, about 30 cm, about 50 cm of a region upon which a force is exerted.

In some embodiments, the vitamin D is administered to a region that is different from the region upon which a force is exerted. In other words, the vitamin D is not administered to a region upon which a force is exerted. In some embodiments, vitamin D is administered systemically and can encompass the region upon which a force is exerted. For example, in some instances, the vitamin D is administered systemically and raises overall vitamin D levels, including the vitamin D levels in the region upon which a force is exerted.

The present methods can include administering an effective amount of vitamin D to a patient in need thereof, and administering an effective amount of light to, for example, the alveolar soft tissue, or any other oral or maxillofacial bone, muscle, or soft tissue, or one or more teeth of the patient. In some embodiments, the effective amount of vitamin D is administered to an oral region of the patient. Alternatively, the effective amount of vitamin D can be administered systemically to the patient. In some embodiments, the method further comprises testing the patient to determine his or her vitamin D level. For example, the patient can undergo blood testing to determine the patient's vitamin D level. If necessary, a patient can receive a vitamin D supplement or treatment. Light can be administered to the alveolar soft tissue and/or teeth in conjunction with orthodontic treatment and normal or higher vitamin D levels, which can accelerate orthodontic tooth movement.

The present methods can comprise administering an effective amount of vitamin D to a patient and providing any intra-oral light therapy apparatus described herein with reference to FIGS. 1-8. The method can optionally include determining whether the patient is vitamin D deficient. The method can optionally include measuring the patient's vitamin D blood serum level. In some embodiments, if the patient's vitamin D blood serum level is below a predetermined threshold, the patient can administer or be administered with a dosage of vitamin D. In some embodiments, the dosage of vitamin D is determined based on the patient's blood serum level and administered to the patient. The dosage of vitamin D to be administered to the patient can be determined, for example, based on the patient's blood serum level, so that the patient is administered with an effective amount of vitamin D. For example, if the patient is very deficient in vitamin D (i.e., has very low vitamin D blood serum levels), the patient can receive a greater dosage of vitamin D than if the patient is only slightly deficient in vitamin D (i.e., has higher vitamin D blood serum levels). In other embodiments, regardless of the vitamin D blood serum level, if the patient is vitamin D deficient, the patient receives the same vitamin D dosage. In yet other embodiments, a dosage of vitamin D is administered to the patient even if the patient is not vitamin D deficient. In embodiments where the patient is vitamin D deficient, the length of vitamin D treatment can vary depending on the degree of vitamin D deficiency.

The vitamin D can be administered in one or more dosages. In some embodiments, as described herein, a dosage of vitamin D is an effective amount of vitamin D. In other embodiments, a single dosage of vitamin D can be greater than or less than an effective amount of vitamin D. A dosage of vitamin D can be provided for a period of time. For example, the vitamin D can be administered daily. In some embodiments, the vitamin D is administered every hour, several times a day, once a day, once every several days, once a week, once every few weeks, once a month, once every few months, once a quarter, or with any other frequency. Vitamin D can be administered on a regular basis (e.g., every 6 hours, every day, every 10 days), or can be provided at irregular intervals (e.g., twice one day, skip a day, once the next day). In some embodiments, vitamin D is administered on an as-needed basis.

In some embodiments, the dosage is greater than about, is less than about, or is about 100 IU, about 200 IU, about 400 IU, about 500 IU, about 600 IU, about 800 IU, about 1,000 IU, about 1,200 IU, about 1,500 IU, about 1,600 IU, about 2,000 IU, about 2,500 IU, about 3,000 IU, about 4,000 IU, about 5,000 IU, about 6,000 IU, about 7,000 IU, about 8,000 IU, about 9,000 IU, about 10,000 IU, about 12,000 IU, about 15,000 IU, about 17,000 IU, about 20,000 IU, about 25,000 IU, about 30,000 IU, about 40,000 IU, about 50,000 IU, about 70,000 IU, about 100,000 IU, about 150,000 IU, about 200,000 IU, about 300,000 IU, about 400,000 IU, about 500,000 IU, about 600,000 IU, or about 800,000 IU. In some embodiments, the dosage amount varies each time the vitamin D is administered to the patient. In other embodiments, the dosage amount is a daily amount of vitamin D administered to the patient. In other embodiments, the dosage amount is the total vitamin D amount administered for a treatment regimen. For example, a daily oral dosage of vitamin D can range from 400 IU to 6,000 IU per day. In another example, a daily oral dosage of vitamin D can range from 2,000 IU to 6,000 IU per day. A daily oral supplement of 2,000 IU to 6,000 IU of vitamin D in adults has been shown to increase blood levels of vitamin D to 40 ng/mL within 3 months. In some regimens, higher initial dosages of vitamin D have shown increases in vitamin D blood levels. The dosage of vitamin D can be a single dose of 600,000 IU of oral vitamin D. Based on one clinical trial, a single dose of 600,000 IU of oral vitamin D was comparable to a dose of 20,000 IU per day of oral vitamin D for 30 days. In another embodiment, the dosage is 20,000 IU per day of oral vitamin D for 30 days.

The dosage of vitamin D can be sufficient to raise the vitamin D blood level from about 40 to about 60 ng/mL of venous blood. The dosage of vitamin D can be sufficient to raise vitamin D blood level to at least about, no more than about, or to about 20 ng/mL, about 30 ng/mL, about 35 ng/mL, about 40 ng/mL, about 45 ng/mL, about 50 ng/mL, about 55 ng/mL, about 60 ng/mL, about 65 ng/mL, about 70 ng/mL, about 75 ng/mL, or about 80 ng/mL. In some embodiments, the dosage of vitamin D is sufficient to raise the vitamin D blood level by any amount. For example, the dosage of vitamin D can be sufficient to raise the vitamin D blood level by about 5 ng/mL, about 10 ng/mL, about 15 ng/mL, about 20 ng/mL, about 25 ng/mL, about 30 ng/mL, about 35 ng/mL, about 40 ng/mL, about 45 ng/mL, about 50 ng/mL, about 55 ng/mL, or about 60 ng/mL. The vitamin D blood level can be raised to a desired level or by a desired amount within a period of time. For example, the period of time can be within one or more days, one or more weeks, one or more months, or one or more years. For example, a dosage of vitamin D administered daily can raise vitamin D blood serum levels to a desired level within 30 days, or within 3 months.

Vitamin D can be administered to the patient prior to, concurrently with, or subsequent to administering light therapy to the patient. Vitamin D can be administered to the patient prior to initiation of the light therapy administration, or prior to the completion of the light therapy administration. In some embodiments, a dosage of vitamin D is administered at a period of time (e.g., seconds, minutes, hours, days, weeks, months) prior to initiation of the light therapy administration or prior to completion of the light therapy administration. In some embodiments, a dosage of vitamin D is administered at a period of time (e.g., seconds, minutes, hours, days, weeks, months) subsequent to initiation of the light therapy administration or subsequent to completion of the light therapy administration. In some embodiments, a vitamin D treatment regimen (which can span one or more doses of vitamin D) is initiated or completed prior to initiation of light therapy administration or prior to completion of light therapy administration. In other embodiments, the vitamin D treatment regimen is initiated or completed subsequent to the initiation of light therapy administration or subsequent to completion of light therapy administration. The vitamin D treatment regimen can be in progress during light therapy administration.

Vitamin D can be administered to the patient prior to, currently with, or subsequent to engaging an intra-oral light therapy apparatus with the patient. The intra-oral light therapy apparatus can be any of the apparatus depicted in FIGS. 1-8. Vitamin D can also be administered to the patient prior to removing the intra-oral light therapy apparatus from the patient. In some embodiments, a dosage of vitamin D can be administered at a period of time (e.g., seconds, minutes, hours, days, weeks, months) prior to engaging the intra-oral light therapy apparatus with the patient or prior to removing the intra-oral light therapy apparatus from the patient. In some embodiments, a dosage of vitamin D is administered at a period of time (e.g., seconds, minutes, hours, days, weeks, months) subsequent to engaging the intra-oral light therapy apparatus with the patient or subsequent to removing the intra-oral light therapy apparatus from the patient. In some embodiments, a vitamin D treatment regimen (which can span one or more doses of vitamin D) is initiated or completed prior to engaging the intra-oral light therapy apparatus with the patient or prior to removing the intra-oral light therapy apparatus from the patient. In other embodiments, the vitamin D treatment regimen is initiated or completed subsequent to engaging the intra-oral light therapy apparatus with the patient or subsequent to removing the intra-oral light therapy apparatus from the patient. The vitamin D treatment regimen can be in progress during light therapy administration.

Vitamin D can be administered to the patient prior to, currently with, or subsequent to exerting a force on one or more teeth of the patient. The force can be, for example, a heavy force, a force exerted by an orthodontic appliance, or a force exerted by a functional appliance. In some embodiments, the force can be less than a heavy force. In some embodiments, the vitamin D is administered to the patient prior to initiation of exerting a force on one or more teeth of the patient, or prior to the completion of exerting a force on one or more teeth of the patient. In some embodiments, a dosage of vitamin D is administered at a period of time (e.g., seconds, minutes, hours, days, weeks, months) prior to initiation of exerting a force on one or more teeth of the patient or prior to completion of exerting a force on one or more teeth of the patient. In other embodiments, a dosage of vitamin D is administered at a period of time (e.g., seconds, minutes, hours, days, weeks, months) subsequent to initiation of exerting a force on one or more teeth of the patient or subsequent to completion of exerting a force on one or more teeth of the patient. In some embodiments, a vitamin D treatment regimen (which can span one or more doses of vitamin D) is initiated or completed prior to initiation of exerting a force on one or more teeth of the patient or prior to completion of exerting a force on one or more teeth of the patient. In other embodiments, the vitamin D treatment regimen is initiated or completed subsequent to the initiation of exerting a force on one or more teeth of the patient or subsequent to completion of exerting a force on one or more teeth of the patient. The vitamin D treatment regimen can be in progress while exerting a force on one or more teeth of the patient.

Vitamin D can be administered to the patient prior to, concurrently with, or subsequent to installing one or more orthodontic appliances on the patient's teeth or functional appliances in the patient's oral cavity. In some embodiments, the vitamin D is administered to the patient prior to removing one or more orthodontic appliances from the patient's teeth. In some embodiments, a dosage of vitamin D is administered at a period of time (e.g., seconds, minutes, hours, days, weeks, months) prior to installing one or more orthodontic appliances on the patient's teeth or prior to removing one or more orthodontic appliances from the patient's teeth. In other embodiments, a dosage of vitamin D is administered at a period of time (e.g., seconds, minutes, hours, days, weeks, months) subsequent to installing one or more orthodontic appliances on the patient's teeth or subsequent to removing one or more orthodontic appliances from the patient's teeth. In some embodiments, a vitamin D treatment regimen (which can span one or more doses of vitamin D) is initiated or completed prior to installing one or more orthodontic appliances on the patient's teeth or prior to removing one or more orthodontic appliances from the patient's teeth. In other embodiments, the vitamin D treatment regimen is initiated or completed subsequent to the installing one or more orthodontic appliances on the patient's teeth or subsequent to removing one or more orthodontic appliances from the patient's teeth. The vitamin D treatment regimen can be in progress while an orthodontic appliance is installed on the patient's teeth.

The administration of vitamin D can increase the amount of tooth movement compared to treatment methods where vitamin D is not administered. The administration of vitamin D can also increase the rate of tooth movement compared to treatment methods where vitamin D is not administered. In some embodiments, the administration of vitamin D increases the velocity of tooth movement by about 5%, about 10%, about 15%, about 20%, about 25%, about 30%, about 40%, about 50%, about 60%, about 70%, about 80%, about 90%, or by any percentage falling within about 1% to about 90%, relative to treatment methods for regulating tooth movement that do not comprise administering vitamin D. In some embodiments, the administration of vitamin D increases the rate of bone remodeling compared to treatment methods where vitamin D is not administered. In some embodiments, the administration of vitamin D increases the velocity of bone remodeling by about 5%, about 10%, about 15%, about 20%, about 25%, about 30%, about 40%, about 50%, about 60%, about 70%, about 80%, about 90%, or by any percentage falling within about 1% to about 90%, relative to treatment methods for regulating bone remodeling that do not comprise administering vitamin D.

The administration of vitamin D can reduce the amount of time that the patient undergoes orthodontic treatment. The administration of vitamin D can also reduce the amount of time that a force is exerted on one or more teeth of the patient. In some embodiments, the administration of vitamin D reduces the amount of time that a patient undergoes orthodontic treatment or that a force is exerted on one or more teeth of the patient by about 5%, about 10%, about 15%, about 20%, about 25%, about 30%, about 40%, about 50%, about 60%, about 70%, about 80%, about 90%, or by any percentage falling within about 1% to about 90%, relative to treatment methods that do not comprise administering vitamin D.

The administration of vitamin D can increase the rate of bone remodeling compared to treatment methods where vitamin D is not administered. The administration of vitamin D can also increase the rate of one or both of bone deposition and resorption compared to treatment methods where vitamin D is not administered. In some embodiments, the administration of vitamin D increases the rate of one or both of bone deposition or resorption by about 5%, about 10%, about 15%, about 20%, about 25%, about 30%, about 40%, about 50%, about 60%, about 70%, about 80%, about 90%, or by any percentage falling within about 1% to about 90%, relative to treatment methods that do not comprise administering vitamin D.

In one example, an adult patient's Vitamin D3 blood-serum level is measured during his routine orthodontic-examination and -records appointment. Laboratory results can indicate that the patient's vitamin D3 serum levels are at 20 ng/ml, which is considered to be deficient and abnormal. In this example, the patient's orthodontic diagnosis is Class I mild crowding with 4 mm of crowding on the upper arch and 4 mm on the lower arch. An orthodontic treatment plan can be formulated to include the installation of a fixed orthodontic appliance with some mild expansion of the upper and lower arches.

In this example, the patient self-administers oral oil-based vitamin D3 capsules at an amount of 6000 IU per day for 3 months to increase and normalize his vitamin D3 serum levels. Laboratory serum testing can optionally be performed again after 3 months of vitamin D3 supplementation. The patient can maintains or adjusts his oral dose of vitamin D3 based on his subsequent lab results. It should be understood that there are a number of alternative oral and/or systemic dosing protocols for vitamin D administration that could be followed to achieve similar results. The dosing protocol outlined above is merely one of many approaches.

In this example, orthodontic treatment can start either after the 3 month period or within three months prior. The orthodontic treatment can include conventional fixed orthodontic brackets and bands placed on the patient's teeth. Light can be administered to the patient on a daily basis, for example, for 20 minutes at an intensity of 50 mW/cm2 at wavelength of about 850 nm using an intra-oral light therapy apparatus, such as the one shown in FIG. 1. The orthodontic treatment can continue with the finishing of teeth once the arches have been expanded. In this example, it is believed that the active orthodontic treatment would be completed in 50% to 75% less time than orthodontic treatment without light therapy due to the combination of daily administration of light and vitamin D3 supplementation.

At a passive stage of orthodontic treatment, i.e., retention phase, a fixed retention orthodontic appliance can be installed on the patient's teeth. In one embodiment, a Hawley retainer, which is a removable appliance that is designed to maintain tooth position of the anterior teeth, is installed on a patient's anterior teeth. In some embodiments, a fixed retainer appliance, such as one including orthodontic brackets, is bonded to the upper 6, lower 6, or upper 6 and lower 6, anterior teeth. The patient can continue with vitamin D3 supplementation. In some examples, the patient self-administers 2000 IU per day to 12,000 IU orally per day. The dosage can be determined based on vitamin D blood serum levels which can be measured periodically to determine dosing. As a result, alveolar bone density around the teeth can be increased during the passive stage. During the passive stage, the patient can be administered once per week with light having a wavelength of about 625 nm using an intra-oral light therapy apparatus, such as the light therapy apparatus shown in FIG. 1 and/or FIG. 6, in areas of the upper and lower arch.

Administering Light Treatment

Light can be administered to the patient using an intra-oral apparatus (including, but not limited to, any intra-oral apparatus or light therapy apparatus, such as apparatus 2500, 3500, described herein) in any of the following ways.

Light can be administered to a region of the patient's mouth. Some examples of these regions include, but are not limited to, one or more teeth (e.g., incisor, canine, premolar, or molar, such as a maxillary central incisor, maxillary lateral incisor, maxillary canine, maxillary first premolar, maxillary second premolar, maxillary first molar, maxillary second molar, maxillary third molar, mandibular central incisor, mandibular lateral incisor, mandibular canine, mandibular first premolar, mandibular second premolar, mandibular first molar, mandibular second molar, or mandibular third molar), a root of one or more teeth (e.g., wherein a root of a tooth may include a portion of one or more roots supporting the tooth, one root supporting the tooth, a plurality of roots supporting the tooth, or all of the roots supporting the tooth), tissue supporting one or more teeth, a portion of the maxilla (e.g., portion of the patient's maxillary alveolar bone), a portion of the mandible (e.g., portion of the patient's mandibular alveolar bone), alveolus, basal tissue, gingiva (e.g., alveolar soft tissue), periodontal ligaments, cementum, periodontium, a region of a jaw bone or tissue, or at least a portion of the patient's other oral soft tissue or bone tissue. The region can be located on a left side or right side of the patient's mouth. In some embodiments, one or more regions are located on both the left and right side of the patient's mouth. In some embodiments, the region can be located in the front of the patient's mouth. The region can include one, two, three, four, five, six, seven, eight, or more teeth, or tissue surrounding or supporting the teeth. The region can include one or more roots of one, two, three, four, five, six, seven, eight, or more teeth, or periodontium of teeth. Regions can include tissue (e.g., alveolar or basal tissue) surrounding or supporting any of the teeth specifically described with or without including the tooth itself. Regions can include teeth or tissue supported by the maxilla or teeth supported by the mandible. One or more regions can be adjacent to one another, continuous with one another, or separate from one another. Any description herein of regions or examples of regions can apply to any other region or examples of treatment regions provided herein.

In some embodiments, light irradiates a region that can include a portion of tissue (e.g., bone tissue, or soft tissue) or other regions within the patient's oral cavity without irradiating one or more other portions of the patient's oral cavity. For example, light can irradiate the mandibular first molar on the right side of the patient's oral cavity without irradiating the mandibular third molar that is also located on the right side of the patient's oral cavity. In some embodiments, light is administered to one or more roots of only one tooth root and to only one periodontium. Alternatively, light is administered to one or more roots of a plurality of teeth and to a plurality of periodontia. Light can be administered to one or more roots of all or less than all the teeth and periodontia in the patient's oral cavity. One or more selected teeth, roots or periodontia can be irradiated with light. For example, the mandibular first molar and the mandibular third molar on the right side of the patient's oral cavity can be irradiated without the mandibular second molar being irradiated.

In some embodiments, light is administered to a patient's alveolar soft tissue, wherein an effective amount of light is irradiated from one or more emitters of an apparatus of the invention. In one embodiment, the alveolar soft tissue is alveolar mucosa.

Figure 19:
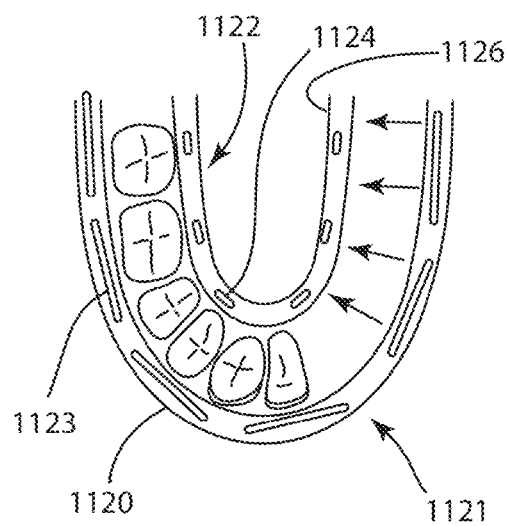
FIG. 19 is a top view of a portion of an intra-oral light-therapy apparatus according to an embodiment of the invention.

In some embodiments, light from an intra-oral apparatus can irradiate a region that includes a portion of tissue (e.g., bone tissue, or soft tissue) at a much greater intensity than it irradiates other portions of the patient's tissue within the mouth. For example, light can irradiate a first tissue region (e.g., the region of tissue covered by panel 2 shown in FIG. 1) at an intensity that is 3×, 5×, 10×, 20×, 50×, or 100× greater than the intensity that irradiates any other region or portion of the patient's tissue (e.g., the regions of tissue covered by remaining panels 1 and 3-6 shown in FIG. 1). In one embodiment, light can irradiate a portion of a patient's alveolar soft tissue at a greater intensity than that of light that irradiates any of the patient's teeth. In another embodiment, light can irradiate or be focused with a greater intensity on the one or more teeth upon which heavy forces are optionally applied (that are desired to be moved), relative to the one or more teeth on which heavy forces are not exerted. Teeth with lower forces or anchorage teeth can be selectively shielded from light or irradiated at lower light intensity so that they can move less and the anchorage effect can be enhanced. In some embodiments, this is achieved by applying to the intra-oral apparatus, or adjusting within the intra-oral apparatus, one or more masks that shield from light one or more non-regions, as described with respect to FIG. 5. In some embodiments, light reaching a region can have an intensity that is greater than a threshold value. In some embodiments, this is achieved by applying to the intra-oral apparatus, or adjusting within the intra-oral apparatus, the density of emitters adjacent one or more regions, as described with respect to FIG. 19. In some embodiments, the threshold value can have an intensity as described elsewhere herein.

In some embodiments, the region can be close to a surface within the patient's mouth, or within a soft tissue or bone tissue. The region can be at a depth from the surface within the patient's mouth. For example, the region can be about 1 µm, about 1 µm, about 10 µm, about 50µ, about 100 µm, about 200 µm, about 300 µm, about 500 µm, about 750 µm, about 1 mm, about 2 mm, about 3 mm, about 4 mm, about 5 mm, about 7 mm, about 10 mm, about 15 mm, about 20 mm, about 25 mm, about 30 mm, about 40 mm, about 50 mm, about 60 mm, or about 70 mm from the surface within the patient's mouth. Light can irradiate a region, which can have an area greater than, less than, or about 1 nm$^2$, about 1 µm$^2$, about 0.1 mm$^2$, about 0.2 mm$^2$, about 0.3 mm$^2$, about 0.4 mm$^2$, about 0.5 mm$^2$, about 0.7 mm$^2$, about 1 mm$^2$, about 10 mm$^2$, about 0.2 cm$^2$, about 0.5 cm$^2$, about 1 cm$^2$, about 2 cm$^2$, about 3 cm$^2$, about 5 cm$^2$, about 7 cm$^2$, about 10 cm$^2$, about 15 cm$^2$, about 20 cm$^2$, about 25 cm$^2$, about 30 cm$^2$, about 35 cm$^2$, about 40 cm$^2$, about 50 cm$^2$, about 60 cm$^2$, about 80 cm$^2$, about 100 cm$^2$, about 120 cm$^2$, about 140 cm$^2$, about 160 cm$^2$, about 180 cm$^2$ or about 200 cm$^2$. Light can irradiate one area, a plurality of areas, a point, or a plurality of points. In some embodiments, light irradiates a particular area without irradiating with significant intensity surrounding areas. For example, light can irradiate a particular tooth or set of teeth without significant amounts of light irradiating adjacent teeth. In one embodiment, irradiating a tooth includes irradiating an exposed surface of the tooth, a tooth root, or a periodontium of the tooth (see, for example, FIG. 4 and associated description).

The light administered by an intra-oral apparatus can be emitted from multiple light sources (e.g., emitters 32 shown in FIG. 3A). Light can irradiate a continuous region or one or more discrete regions based on the location of the light sources or emitters within the intra-oral apparatus, as described herein. Light can irradiate various regions from different directions. For example, light can be administered from a right side of a patient's mouth (e.g., from panel 1 shown in FIG. 1) and from a left side of a patient's mouth (e.g., from panel 3 shown in FIG. 1). The light sources or emitters can be adjusted within an intra-oral apparatus such that the administered light is angled upward toward a region, or angled downward to toward a region. The light source or emitters can be displaced, can be angled, can be rotated, or any combination thereof within the intra-oral apparatus.

As described herein, an effective amount of light can be administered via the intra-oral apparatus. An effective amount of light is an amount of light that is effective for regulating tooth-movement; reducing, preventing or minimizing tooth-root resorption; reducing bone resorption, inflammatory dentin resorption or cementum resorption; preventing or minimizing inflammation, or remodeling of tissue surrounding one or more teeth upon which heavy forces are or were exerted; regenerating maxillary or mandibular alveolar bone; or for other methods disclosed herein. The light's properties can include, but are not limited to: its intensity, wavelength, coherency, range, peak wavelength of emission, energy density, continuity, pulsing, duty cycle, frequency or duration.

In some embodiments, a method for regulating tooth movement can further comprise determining an effective amount of light. The determination can be based on an intended tooth movement regulation effect. The method can further comprise selecting one or more light properties to provide the effective amount of light. The method can further comprise receiving instructions from a controller, and emitting light having particular properties. The controller can be, for example, controller 430 shown in FIG. 7, the external electronic device described with respect to FIG. 17, or any other controller described herein. The controller can implement any of the steps described herein.

Light can be administered from one or more light source within an intra-oral apparatus capable of irradiating light having intended properties. As described herein, the intra-oral apparatus can emit light from one or more light emitters, such as emitters 32, 132, 232, and/or 332. In some embodiments, the intra-oral apparatus comprises about 10 to about 15 emitters, about 15 to about 20 emitters, about 20 to about 30 emitters, about 30 to about 40 emitters, about 40 to about 50 emitters, about 50 to about 70 emitters, or about 70 emitters to about 100 emitters. For example, light can be administered from one or more of the following emitters: a light-emitting diode (LED), which can be present in an array; and a laser, for example, a vertical cavity surface emitting laser (VCSEL) or other suitable light emitter such as an Indium-Gallium-Aluminum-Phosphide (InGaAlP) laser, a Gallium-Arsenic Phosphide/Gallium Phosphide (GaAsP/GaP) laser, or a Gallium-Aluminum-Arsenide/Gallium-Aluminum-Arsenide (GaAlAs/GaAs) laser. In one embodiment, the intra-oral apparatus comprises a plurality of lasers. A plurality of light emitters can emit light at one or more different wavelengths. Alternatively, one or more light emitters can emit light at the same wavelength. The one or more light emitters can be arranged on or within the intra-oral apparatus in any manner, such as a linear array or another arrangement described herein.

An effective amount of light can have an intensity that is effective for regulating tooth movement. In one embodiment, the light intensity is at least about 10 mW/cm$^2$. In other embodiments, the light intensity is about 1 mW/cm$^2$ or greater, about 3 mW/cm$^2$ or greater, about 5 mW/cm$^2$ or greater, about 7 mW/cm$^2$ or greater, about 12 mW/cm$^2$ or greater, about 15 mW/cm$^2$ or greater, about 20 mW/cm$^2$ or greater, about 30 mW/cm$^2$ or greater, about 50 mW/cm$^2$ or greater, about 75 mW/cm$^2$ or greater, about 100 mW/cm$^2$ or greater, about 200 mW/cm$^2$ or greater, about 500 mW/cm$^2$ or greater, or about 1 W/cm$^2$ or greater. In other embodiments, the light intensity is about 20 mW/cm$^2$ or less, about 30 mW/cm$^2$ or less, about 50 mW/cm$^2$ or less, about 75 mW/cm$^2$ or less, about 100 mW/cm$^2$ or less, about 200 mW/cm$^2$ or less, about 500 mW/cm$^2$ or less, about 1 W/cm$^2$ or less, about 2 W/cm$^2$ or less, about 5 W/cm$^2$ or less, or about 10 W/cm$^2$ or less. In one embodiment the light intensity ranges from about 1 mW/cm$^2$ to about 10 W/cm$^2$. In another embodiment, the light intensity's lower range is about 3 mW/cm$^2$, about 5 mW/cm$^2$, about 7 mW/cm$^2$, about 12 mW/cm$^2$, about 15 mW/cm$^2$, about 20 mW/cm$^2$, about 30 mW/cm$^2$, about 50 mW/cm$^2$, about 75 mW/cm$^2$, about 100 mW/cm$^2$, about 200 mW/cm$^2$, about 500 mW/cm$^2$, or about 1 W/cm$^2$. In another embodiment, the light intensity's upper range is about 20 mW/cm$^2$, about 30 mW/cm$^2$, about 50 mW/cm$^2$, about 75 mW/cm$^2$, about 100 mW/cm$^2$, about 200 mW/cm$^2$, about 500 mW/cm$^2$, about 1 W/cm$^2$, about 2 W/cm$^2$, about 5 W/cm$^2$, or about 10 W/cm$^2$. In yet another embodiment, the light intensity is at 15 mW/cm$^2$. Light can be administered having an intensity falling within a range determined by any of the intensities described herein. In some embodiments, the intensity is an average intensity. In some embodiments, the light has an intensity in the range of about 10 mW/cm$^2$ to about 60 mW/cm$^2$, or about 20 mW/cm$^2$ to about 60 mW/cm$^2$. In such embodiments, the peak light intensity can about 50 mW/cm$^2$ or greater. A peak wavelength is the wavelength at which the highest intensity of light is emitted. In some embodiments, light can be pulsed. In other embodiments, the output of light is continuous. In some embodiments, the light intensity can vary over time in a cyclical or non-cyclical fashion. The light intensity can vary with or without pulsing. In some embodiments, pulse width modulation can be used to affect a desired light intensity. If one or more wavelengths of light are administered, then each wavelength can be administered at its own intensity. In some embodiments, an effective amount or dosage of light can include administering light having an intensity of about 15 mW/cm$^2$ for less than or up to three minutes duration. Additional details regarding effective amounts or dosages of light are described herein.

In some embodiments, an effective amount of light can include light having a wavelength that is within in a particular range, or light of a range of wavelengths. The light is not necessarily visible light. For example, the light can include infrared light or near-infrared light. The light can also be provided in the visible light region. Light can be administered having one or more wavelengths ranging from about 620 nm to about 1000 nm. In some embodiments, administered light has one or more wavelengths ranging from about 585 nm to about 665 nm, about 815 nm to about 895 nm, about 640 nm to about 680 nm, or about 740 nm to about 780 nm, or any given wavelength or range of wavelengths within those ranges, such as, for example, about 625 nm or about 855 nm, or about 605 nm to about 645 nm, or about 835 nm to about 875 nm. In some embodiments, the administered light has one or more wavelengths from about 605 nm to about 645 nm, or from about 835 nm to about 875 nm. In some embodiments, the administered light has one or more wavelengths from about 615 nm to about 635 nm, or from about 845 nm to about 865 nm. In some embodiments, the wavelengths of the administered light are about 625 nm or about 855 nm. In additional embodiments, the administered light has one or more wavelengths ranging from about 400 nm to about 1200 nm. In particular embodiments, the administered light has one or more wavelengths ranging from about 500 nm to about 700 nm, about 585 nm to about 665 nm, about 605 nm to about 630 nm, about 620 nm to about 680 nm, about 815 nm to about 895 nm, about 820 nm to about 890 nm, about 640 nm to about 680 nm, or about 740 nm to about 780 nm. In some embodiments the administered light has one or more wavelengths in one or both of the following wavelength ranges: about 820 to about 890 nm and about 620 to about 680 nm. In some embodiments, the administered light has one or more wavelengths in the ranges of about 820 to about 890 nm and about 620 nm to about 680 nm. In some embodiments, the administered light has one or more wavelengths in the ranges of about 815 to about 895 nm and about 585 to about 665 nm. The administered light can alternatively have one or more wavelengths in one or more of the following ranges: about 613 nm to about 624 nm, about 667 nm to about 684 nm, about 750 nm to about 773 nm, about 812 nm to about 846 nm. In one embodiment, the light wavelength's lower range is about 400 nm, about 450 nm, about 500 nm, about 550 nm, about 585 nm, about 595 nm, about 605 nm, about 613 nm, about 615 nm, about 620 nm, about 624 nm, about 625 nm, about 640 nm, about 650 nm, about 667 nm, about 680 nm, about 710 nm, about 740 nm, about 750 nm, about 770 nm, about 812 nm, about 815 nm, about 820 nm, about 835 nm, about 845 nm, or about 860 nm. In another embodiment, the light wavelength's upper range is about 585 nm, about 605 nm, about 624 nm, about 630 nm, about 635 nm, about 645 nm, about 655 nm, about 660 nm, about 665 nm, about 680 nm, about 684 nm, about 700 nm, about 725 nm, about 755 nm, about 773 nm, about 780 nm, about 795 nm, about 815 nm, about 830 nm, about 846 nm, about 855 nm, about 865 nm, about 875 nm, about 890 nm, about 895 nm, about 935 nm, about 975 nm, about 1000 nm, about 1050 nm, about 1100 nm, or about 1200 nm.

The wavelengths of light administered comprise or consist of the wavelength values described herein.

For example, in some embodiments, light administered to a region does not comprise one or more wavelengths exceeding one or more of the following: about 585 nm, about 605 nm, about 624 nm, about 630 nm, about 635 nm, about 645 nm, about 655 nm, about 660 nm, about 665 nm, about 680 nm, about 684 nm, about 700 nm, about 725 nm, about 755 nm, about 773 nm, about 780 nm, about 795 nm, about 815 nm, about 830 nm, about 846 nm, about 855 nm, about 865 nm, about 875 nm, about 890 nm, about 895 nm, about 905 nm, about 910 nm, about 915 nm, about 920 nm, about 935 nm, about 975 nm, about 1000 nm, about 1050 nm, about 1100 nm, or about 1200 nm. For example, in some embodiments, no light exceeding about 585 nm, about 605 nm, about 624 nm, about 630 nm, about 635 nm, about 645 nm, about 655 nm, about 660 nm, about 665 nm, about 680 nm, about 684 nm, about 700 nm, about 725 nm, about 755 nm, about 773 nm, about 780 nm, about 795 nm, about 815 nm, about 830 nm, about 846 nm, about 855 nm, about 865 nm, about 875 nm, about 890 nm, about 895 nm, about 905 nm, about 910 nm, about 915 nm, about 920 nm, about 935 nm, about 975 nm, about 1000 nm, about 1050 nm, about 1100 nm, or about 1200 nm is administered to a selected region. In some embodiments, light administered to a region does not comprise one or more wavelengths below one or more of the following: about 400 nm, about 450 nm, about 500 nm, about 550 nm, about 585 nm, about 595 nm, about 605 nm, about 613 nm, about 615 nm, about 620 nm, about 624 nm, about 625 nm, about 640 nm, about 650 nm, about 667 nm, about 680 nm, about 710 nm, about 740 nm, about 750 nm, about 770 nm, about 812 nm, about 815 nm, about 820 nm, about 835 nm, about 845 nm, or about 860 nm. For example, in some embodiments, no light below about 400 nm, about 450 nm, about 500 nm, about 550 nm, about 585 nm, about 595 nm, about 605 nm, about 613 nm, about 615 nm, about 620 nm, about 624 nm, about 625 nm, about 640 nm, about 650 nm, about 667 nm, about 680 nm, about 710 nm, about 740 nm, about 750 nm, about 770 nm, about 812 nm, about 815 nm, about 820 nm, about 835 nm, about 845 nm, or about 860 nm is administered to a selected region. In some embodiments, the light administered does not comprise a wavelength of about 600 nm or less. In some embodiments, the light administered does not comprise a wavelength of about 1000 nm or greater. In some embodiments, the light administered does not comprise a wavelength of about 600 nm or less and does not comprise a wavelength of about 1000 nm or greater.

In some embodiments, light administered to a region with a sufficient intensity to be an effective amount in the present methods does not comprise one or more wavelengths exceeding one or more of the following: about 585 nm, about 605 nm, about 624 nm, about 630 nm, about 635 nm, about 645 nm, about 655 nm, about 660 nm, about 665 nm, about 680 nm, about 684 nm, about 700 nm, about 725 nm, about 755 nm, about 773 nm, about 780 nm, about 795 nm, about 815 nm, about 830 nm, about 846 nm, about 855 nm, about 865 nm, about 875 nm, about 890 nm, about 895 nm, about 905 nm, about 910 nm, about 915 nm, about 920 nm, about 935 nm, about 975 nm, about 1000 nm, about 1050 nm, about 1100 nm, or about 1200 nm. For example, in some embodiments, no light having a sufficient intensity to be an effective amount for oral or maxillofacial bone remodeling and exceeding about 585 nm, about 605 nm, about 624 nm, about 630 nm, about 635 nm, about 645 nm, about 655 nm, about 660 nm, about 665 nm, about 680 nm, about 684 nm, about 700 nm, about 725 nm, about 755 nm, about 773 nm, about 780 nm, about 795 nm, about 815 nm, about 830 nm, about 846 nm, about 855 nm, about 865 nm, about 875 nm, about 890 nm, about 895 nm, about 905 nm, about 910 nm, about 915 nm, about 920 nm, about 935 nm, about 975 nm, about 1000 nm, about 1050 nm, about 1100 nm, or about 1200 nm is administered to a selected region. In some embodiments, light administered to a region with a sufficient intensity to be an effective amount in the present methods does not comprise one or more wavelengths exceeding one or more of the following: about 400 nm, about 450 nm, about 500 nm, about 550 nm, about 585 nm, about 595 nm, about 605 nm, about 613 nm, about 615 nm, about 620 nm, about 624 nm, about 625 nm, about 640 nm, about 650 nm, about 667 nm, about 680 nm, about 710 nm, about 740 nm, about 750 nm, about 770 nm, about 812 nm, about 815 nm, about 820 nm, about 835 nm, about 845 nm, or about 860 nm. For example, in some embodiments, no light having a sufficient intensity to be an effective amount in the present methods and below about 400 nm, about 450 nm, about 500 nm, about 550 nm, about 585 nm, about 595 nm, about 605 nm, about 613 nm, about 615 nm, about 620 nm, about 624 nm, about 625 nm, about 640 nm, about 650 nm, about 667 nm, about 680 nm, about 710 nm, about 740 nm, about 750 nm, about 770 nm, about 812 nm, about 815 nm, about 820 nm, about 835 nm, about 845 nm, or about 860 nm is administered to a selected region. In some embodiments, the light administered does not comprise a wavelength of about 600 nm or less having a sufficient intensity to be an effective amount for the present methods. In some embodiments, the light administered does not comprise a wavelength of about 1000 nm or greater having a sufficient intensity to be an effective amount for the present methods. In some embodiments, the light administered does not comprise a wavelength of about 600 nm or less having a sufficient intensity to be an effective amount for the present methods and does not comprise a wavelength of about 1000 nm or greater having a sufficient intensity to be an effective amount for the present methods.

In some embodiments, certain treatments respond better to specific wavelength ranges. For example, in some embodiments, tooth movement (or, more particularly, rapid tooth movement) is more effective when the amount of light administered has a wavelength from about 700 nm to about 900 nm. For example, the effective amount of light can have a wavelength of about 850 nm. In one embodiment, the intra-oral apparatus irradiates light having a wavelength of about 850 nm and with an intensity of less than 100 mW/cm$^2$ continuous wave. In some embodiments, bone healing or bone grafting is more effective when the amount of light administered has a wavelength from about 600 nm to about 700 nm.

In some embodiments, light is administered at a wavelength sufficient to produce a bactericidal and/or bacteriostatic effect on the patient's teeth and/or oral mucosa. In other words, light can be administered at a wavelength sufficient to kill and/or prevent reproduction of bacteria on the patient's teeth and/or oral mucosa. For example, the light can be administered at a blue or similar wavelength, such as a wavelength of from about 450 nm to about 495 nm. In some embodiments, the bactericidal- and/or bacteriostatic-effective light can be administered concurrently with administration of light effective to accelerate tooth movement. For example, in some embodiments, light can concurrently be administered to the patient at a blue wavelength, for the resulting bactericidal and/or bacteriostatic effect, and at a red to infrared wavelength to accelerate tooth movement (e.g., towards alignment). In some embodiments, the bactericidal-and/or bacteriostatic-effective light can be administered prior to administration of light effective to accelerate tooth movement. In some embodiments, the bactericidal- and/or bacteriostatic-effective light can be administered subsequent to administration of light effective to accelerate tooth movement.

In some embodiments, light is administered at one, two, or more of the light ranges described. In some instances, light is not administered outside of one, two, or more of the light ranges described. In other embodiments, administered light has other wavelengths, as desired for a particular application. In some embodiments, light having a first set of characteristics (e.g., wavelength, intensity, pulsing, timing) can be administered to a first region (e.g., the region at the panel 1 shown in FIG. 1), and light with a second set of characteristics can be administered to a second region (e.g., the region at panel 3 shown in FIG. 1). The first region and the second region can be the same region, can partially overlap, or can not overlap. The first set of characteristics can be the same as the second set of characteristics, can partially overlap with the second set, or can all be different from the second set. In one embodiment, one region of a jaw can receive light within a first wavelength range, while another region of the jaw can receive light within a second wavelength range. The first and second wavelengths can overlap. Alternatively, in other embodiments, the first and second wavelengths do not overlap.

In some embodiments, one or more wavelengths of light can be sequentially or simultaneously administered to the patient. For example, an intra-oral apparatus of the invention can include a first emitter that emits light having a wavelength of about 850 nm and a second emitter that sequentially or simultaneously emits light having a wavelength of about 620 nm. In some embodiments, the first emitter can be configured to emit light during a first period of time and the second emitter can be configured to emit light during a second period of time following the first period of time. Stated another way, the second emitter emits light having a wavelength of about 850 nm after the first emitter begins emitting light having a wavelength of about 620 nm, or the second emitter emits light having a wavelength of about 620 nm after the first emitter begins emitting light having a wavelength of about 850 nm. In some embodiments, light having a wavelength of about 850 nm is administered daily to a patient until one or more of the following orthodontic treatment phases are complete or almost complete: the alignment phase, the space-closure phase, the finishing-or-detailing phase or the retention phase. Once one or more of these phases are complete or almost complete, the patient can begin receiving a blended light treatment, which comprises administering light having a wavelength of, e.g., about 850 nm and about 620 nm. The about 850 nm wavelength of light can be administered to the patient sequentially or simultaneously with the about 620 nm wavelength of light. Once the teeth have moved into their final position, the passive stage of orthodontic treatment can begin and the patient can begin receiving light having a wavelength of about 620 nm only.

Although examples of light wavelength ranges are provided below for different applications, light having any other light wavelength value, which can include those described herein, can be administered for those applications.

In some embodiments, administering light having a wavelength in the range of about 815 nm to about 895 nm, such as about 835 nm to about 875 nm, or about 855 nm, is useful in the present methods, in one embodiment, for increasing the rate of movement of teeth. In one embodiment, increasing the rate of tooth movement does not increase the tipping motion of teeth beyond that which is experienced by orthodontic patients who are not provided with light via the intra-oral apparatus. In some embodiments, administering light having a wavelength in the range of about 585 nm to about 665 nm, such as about 605 nm to about 645 nm, or about 625 nm, is likewise useful in the present methods, in one embodiment, for increasing the rate of movement of teeth. In some embodiments, administering light having any of the aforementioned wavelengths, in conjunction with using a functional appliance, exerting a heavy force and/or administering vitamin D, is useful in the present methods, in one embodiment, for increasing the rate of movement of teeth.

In one embodiment, administration of light having a wavelength in the range of about 585 nm to about 665 nm increases the amount or extent of bodily tooth movement to a greater degree than administration with light having a wavelength in the range of about 815 nm to about 895 nm. In such embodiments, administering light having a wavelength in the aforementioned ranges, in conjunction with a using functional appliance, exerting a heavy force and/or administering vitamin D can further increase the amount or extent of bodily tooth movement to a greater degree than administering light alone. Administering light having a wavelength in the range of about 585 nm to about 665 nm (e.g., about 625 nm) can result in about 10% to about 50% less tipped movement than the administration of light having a wavelength in the range of about 815 nm to about 895 nm (e.g., about 855 nm). For example, about 10%, about 15%, about 20%, about 25%, about 30%, about 35%, about 40%, about 45%, or about 50% less tipped movement can occur. Particular wavelengths of light can minimize tipped movement. In some embodiments, particular wavelengths administered in conjunction with using a functional appliance, exerting a heavy force and/or administering vitamin D can further minimize tipped movement of teeth.

Thus, in one embodiment, administration of light having a wavelength in the range of about 605 nm to about 645 nm, such as about 625 nm, is useful in the present methods, in one embodiment, for facilitating the bodily movement of teeth in orthodontic treatment and optionally increasing bone regeneration. In some embodiments, the methods further comprise increasing bone regeneration. In another embodiment, administration of light having a wavelength in the range of about 835 to about 875 nm, such as about 855 nm, is useful in the present methods, in one embodiment, for increasing the rate of movement of teeth for which some degree of tipped movement is desirable or acceptable and optionally increasing bone regeneration. In the aforementioned embodiments, administering light of these respective ranges, in conjunction with using a functional appliance, exerting a heavy force and/or administering vitamin D, can be useful, for example, for facilitating the bodily movement of teeth in orthodontic treatment and optionally increasing bone regeneration.

In other embodiments, administration of light having a wavelength as described herein, in one embodiment in the range of about 605 nm to about 645 nm, such as about 625 nm, is useful for increasing the quality or degree of bone remodeling. Accordingly the present invention further relates to methods for increasing the quality or degree of bone remodeling, comprising administering an effective amount of light to a patient, wherein the effective amount of light is irradiated from the emitter of an apparatus of the invention. In some embodiments, at least a portion of the apparatus contacts the alveolar soft tissue when the light is administered. In some embodiments, the methods for increasing the quality or degree of bone remodeling further comprise allowing a heavy force to be exerted on one or more teeth of a patient in need thereof and/or administering vitamin D to a patient.

Bone remodeling can include changes in any bone characteristic, such as, but not limited to, bone shape, bone volume, bone density, or bone mineral content. In some embodiments, bone remodeling can include bone growth or resorption. Effecting bone growth or bone resorption can result in altering bone shape or position (i.e., tooth movement). Increasing the quality or degree of bone remodeling can aid in adjusting the shape or position of bone (such as a mandibular bone or maxillary bone), or can aid in increasing the retention of teeth in a particular position, for example, in a position resulting from orthodontic treatment, such as an appliance of one or more orthodontic appliances, decreasing the potential for teeth to move back to a previous position, for example, a position prior to orthodontic treatment, such as any appliance of one or more orthodontic appliances. Thus, administration of light having a wavelength in the range of about 585 nm to about 665 nm, or about 605 nm to about 645 nm, or about 615 nm to about 635 nm, or about 625 nm, optionally also with light in the range of 815 nm to 895 nm, can be useful in the present methods, for example, for stabilizing the movement of teeth prior to, subsequent to or concurrently with orthodontic treatment. Accordingly, in other embodiments, the present methods further comprise performing orthodontic treatment, such as installing one or more orthodontic appliances on the patient, prior to, subsequent to or concurrently with the administration of light via the intra-oral apparatus. The intra-oral apparatus can be configured to be worn over the orthodontic appliance, or at least a portion of the orthodontic appliance, during the administration of light. In one embodiment the orthodontic appliance is a retainer device or a passive orthodontic appliance. Other suitable orthodontic appliances can include, for example, removable retainers such as a Hawley retainer or a vacuum formed retainer, or fixed retainers such as a bonded lingual retainer. These appliances can assist in maintaining tooth position prior to, subsequent to or concurrently with the administration of light, for example, by stimulating bone regeneration or remodeling. In some embodiments, the present methods further comprise regulating oral or maxillofacial bone remodeling, such as installing one or more functional appliances to a patient prior to, subsequent to or concurrently with the administration of light. Administration with light having a wavelength in the range of about 815 nm to about 895 nm, or about 835 nm to about 875 nm, or about 845 nm to about 865 nm, or about 855 nm, can also be useful for stabilizing tooth movement, in one embodiment prior to, subsequent to or concurrently with orthodontic treatment. In one embodiment administration of light having wavelengths in the range of about 585 nm to about 665 nm increases bone regeneration or remodeling to a greater degree or extent that does administration of light having wavelengths in the range of about 815 nm to about 895 nm.

Tooth-root resorption can include breakdown or destruction, or subsequent loss, of the root structure of a tooth. Tooth-root resorption can be caused by differentiation of macrophages into osteoclasts in surrounding tissue which, if in close proximity to the root surface can resorb the root surface cementum and underlying root dentine. Tooth-root resorption can be exacerbated by heavy or supra-physiologic orthodontic forces that exert on periodontal tissue pressure that is higher than the normal physiologic capillary and interstitial pressure. This prevents normal blood flow, which can cause schema (lack of blood supply) and ultimately cell death of soft tissue and bone in the periodontium. These dead tissues, also known as a "hyalinized zone," are removed through multi-nucleated cells and undermining respiration process and in many cases healthy bone, cementum and dentin are resorbed through this process.

Accordingly, administering light having a particular wavelength, is useful for modulating the speed, quality and type of tooth movement, e.g., bodily versus tipped, and for increasing or stabilizing tooth movement. In some embodiments, stabilizing tooth movement can comprise moving one or more teeth with less tipped movement. Stabilizing tooth movement can also include retarding or arresting tooth movements in particular ways. For example, this can include minimizing the amount of, or eliminating, slanting (or tipped movement). Administration of light can also be useful for increasing (or inducing) bone regeneration or remodeling. Administration of light can also be useful for reducing, minimizing, or preventing tooth root resorption, bone resorption, inflammatory dentin or cementum resorption, or inflammation of tissue. Administering light, in conjunction with using a functional appliance, exerting a heavy force, and/or administering vitamin D, can further be useful for these purposes.

In some embodiments, the light can be administered to at least a portion of a patient's alveolar soft tissue or other oral tissue, or to it entirely. Alternatively, using an intra-oral apparatus, light of one or more particular wavelengths can be administered to different selected regions of a patient's alveolar soft tissue in order to effect movement of teeth (e.g. anchor (no movement), bodily, or tipped) in one or more regions of a patient's mouth. For example, one or more regions in which it is desired that the teeth not be moved, or that the teeth serve as an anchor to facilitate movement of teeth in other selected regions of a patient's jaw, can be optionally screened or masked such that they receive no light, as described herein with reference to FIG. 5. Alternatively, the one or more regions in which it is desired that the teeth not be moved, or that the teeth serve as an anchor to facilitate movement of teeth in other selected regions of a patient's jaw, do not receive light as the light emitters over such regions are turned off. Regions in which it is desired that the teeth be moved bodily can be administered with light having a wavelength in the range of about 585 nm to about 665 nm, in the range of about 605 nm to about 645 nm, about 615 nm to about 635 nm, or about 625 nm. Regions in which it is desired to increase tooth movement but permit some tipped movement of the teeth can be administered with light having a wavelength in the range of about 815 nm to about 895 nm, about 835 nm to about 875 nm, about 845 nm to about 865 nm, or about 855 nm. Tooth movement can be selectively regulated by administering an effective amount of light having one wavelength to one or more selected regions of a patient's alveolar soft tissue, and by administering an effective amount of light having a different wavelength to one or more different selected regions of the mucosa.

In some embodiments, light can be administered within a narrow range of wavelengths (e.g., 50 nm or less, 30 nm or less, 20 nm or less, 10 nm or less, 5 nm or less), or at a single wavelength. In some embodiments, light is administered at a limited wavelength range (e.g., 1000 nm or less, 700 nm or less, 600 nm or less, 500 nm or less, 400 nm or less, 300 nm or less, 250 nm or less, 200 nm or less, 150 nm or less, 100 nm or less, or 75 nm or less). In some embodiments, the light administered does not include wavelengths beyond the narrow or limited range of wavelengths. The narrow or limited range of wavelengths can have any of the upper or lower limits of wavelength as described previously. In some embodiments, however, the light administered does not include light having a sufficient intensity to constitute an effective amount having wavelengths beyond the narrow or limited range of wavelengths.

In some embodiments, light can be emitted at one, two, or more peak wavelengths of emission. A peak wavelength is the wavelength at which the highest intensity of light is emitted. In some embodiments, light can be administered at a range of wavelengths that includes a peak wavelength having the highest intensity within the range. In some embodiments, a peak wavelength can be at about 620 nm, about 640 nm, about 650 nm, about 655 nm, about 660 nm, about 665 nm, about 670 nm, about 680 nm, about 690 nm, about 800 nm, about 820 nm, about 830 nm, about 835 nm, about 840 nm, about 845 nm, about 850 nm, about 860 nm, about 870 nm, about 890 nm, about 910 or about 930 nm. In some embodiments, the administered light does not have wavelengths that vary from the peak wavelength by more than about 1 nm, about 2 nm, about 3 nm, about 5 nm, about 10 nm, about 15 nm, about 20 nm, about 30 nm, about 40 nm, about 50 nm, about 75 nm, about 100 nm, about 150 nm, about 200 nm, about 250 nm, about 300 nm, about 400 nm, or about 500 nm.

Where two or more light wavelengths are administered, the light can be administered at any ratio of each wavelength's intensity. For example, light administered at a first wavelength can have an intensity that is about 1.1×, 1.2×, 1.3×, 1.5×, 1.7×, 2.0×, 2.5×, 3.0×, 3.5×, 4.0×, 5.0×, 10×, 12×, 15×, 20×, 30×, 50×, 100× that of light administered at a second wavelength. In some embodiments, the administered light is emitted from one or more light emitters, in another embodiment, from one or more light emitters having a first set of properties and, optionally, from a second set of light emitters having a second set of properties. In other embodiments, the number of light emitters having a first set of characteristics exceeds that of the light emitters having a second set of characteristics. For example, the number of light emitters having the first set of characteristics can be about 1.1×, 1.2×, 1.3×, 1.5×, 1.7×, 2.0×, 2.5×, 3.0×, 3.5×, 4.0×, 5.0×, 10×, 12×, 15×, 20×, 30×, 50×, 100× the number of light emitters having the second set of characteristics, or vice versa.

The light can optionally be monochrome or substantially monochrome, e.g., having a wavelength from about 10 nm less than to about 10 nm greater than a specific wavelength. When light is "substantially monochrome" it consists of a single wavelength or comprises other wavelengths that are emitted at an intensity that is ineffective in the present methods, including for regulating oral or maxillofacial bone remodeling when administered to the oral or maxillofacial bone, muscle, or soft tissue, or one or more teeth of a patient, with or without allowing a functional appliance to exert a force on oral or maxillofacial bone, muscle, or soft tissue, or one or more teeth of the patient. In some embodiments, substantially monochrome light is emitted at a narrow range of wavelengths without being emitted at other wavelengths outside the range or without an effective intensity of light being emitted at other wavelengths outside the range. In some embodiments, substantially monochrome light is emitted within an about 5 nm or less, about 10 nm or less, or about 20 nm or less wavelength range without being emitted at other wavelengths outside the range or without an effective intensity of light being emitted at other wavelengths outside the range. Administering light from light emitters that emit at multiple wavelengths can allow for irradiation over multiple wavelengths or greater selectivity and precision in administration. The light can optionally comprise incoherent light. In some embodiments, light can be administered at a single frequency, light can have a phase that drifts relatively quickly, a pulse of light waves can have an amplitude that changes quickly, or a light wave can encompass a broad range of frequencies.

Light can be administered directly from a light emitter to a region in the patient's mouth. In some embodiments, light can be modified by optics before reaching or traveling through the surface within the patient's mouth (e.g., the alveolar soft tissue). For example, light can be diffused, focused, parallel, reflected, redirected, or filtered after it is emitted and before it reaches or travels through the surface within the patient's mouth. Such modification can be achieved, for example, by using a foil or other suitable material with the intra-oral apparatus, such as the reflective backing 20 depicted in FIG. 3A. In one embodiment, light of one or more wavelengths can be selectively blocked or partially filtered before reaching the surface within the patient's mouth. In some embodiments, light can diverge or converge from an emission source before reaching the region. For example, light can diverge in a beam having an included angle θ in the range of about 45-60°. The emitted light diverge to have an included angle θ of 0 to about 15°, 0 to about 30°, 0 to about 45°, 0 to about 60°, 0 to about 75°, 0 to about 90°, or 0 to about 120°.

In some embodiments, industry standard LEDs are used to produce the light. The LEDs can include one or more emitter arrays arranged on a series of treatment arrays to cover the target area of the alveolus of both the maxilla and mandible.

Light that irradiates the region can optionally have the same or about the same characteristics as light that is emitted. In some embodiments, light that reaches the region does not have the same characteristics as the light that is emitted. One or more of the light characteristics can optionally be altered prior to administration or when it passes through the oral tissue of the patient. One or more of the light characteristics can optionally be altered when it passes through optics, such as one or more lenses or mirrors that are coupled to or disposed within the intra-oral apparatus. For example, one or more of the light characteristics can be altered in the range of about ±20% or less, about ±15% or less, about ±10% or less, about ±5% or less, about ±3% or less, about ±1% or less, about ±0.5% or less, or about ±0.1% or less.

The dosage or effective amount of light that irradiates from, for example, the light emitters, can range from about 24 J/cm$^2$ to about 200 J/cm$^2$. The effective dosage of light can be administered once or repetitively. In some embodiments, the effective amount can have an irradiated light energy density that is from about 30 J/cm² to about 100 J/cm². In other embodiments, the effective amount can be about 5 J/cm² or less, about 10 J/cm² or less, about 20 J/cm² or less, about 30 J/cm² or less, about 50 J/cm² or less, about 75 J/cm² or less, about 100 J/cm² or less, about 125 J/cm² or less, about 150 J/cm² or less, about 175 J/cm² or less, or about 200 J/cm² or less. The effective amount of irradiated light can be about 1 J/cm² or more, about 5 J/cm² or more, about 10 J/cm² or more, about 20 J/cm² or more, about 25 J/cm² or more, about 30 J/cm² or more, about 40 J/cm² or more, about 50 J/cm² or more, about 60 J/cm² or more, about 75 J/cm² or more, about 100 J/cm² or less, about 125 J/cm² or more, about 150 J/cm² or more, or about 175 J/cm² or more. The effective amount of irradiated light can be in a range bounded by any of the energy density values described herein. The effective amount of irradiated light can be increased, for example, by using a light source that emits light having a relatively higher average intensity, or by increasing the duration of administration of light.

An effective amount of light can have an energy density that reaches a region, such as the mandibular bone or maxillary bone. For example, an effective amount of light that reaches a region can be from about 0.5 J/cm² to about 100 J/cm². The effective amount of light that reaches the region can be administered once or repetitively. In some other embodiments, the effective amount has an irradiated light energy density that is from about 1 J/cm² to about 50 J/cm². In other embodiments, the effective amount of light is about 0.5 J/cm² or less, about 1 J/cm² or less, about 2 J/cm² or less, about 5 J/cm² or less, about 10 J/cm² or less, about 15 J/cm² or less, about 20 J/cm² or less, about 30 J/cm² or less, about 40 J/cm² or less, about 50 J/cm² or less, about 70 J/cm² or less, about 80 J/cm² or less, about 90 J/cm² or less, or about 100 J/cm² or less. The effective amount of light can be about 0.5 J/cm² or more, about 1 J/cm² or more, about 2 J/cm² or more, about 3 J/cm² or more, about 5 J/cm² or more, about 10 J/cm² or more, about 15 J/cm² or more, about 20 J/cm² or more, about 30 J/cm² or more, about 40 J/cm² or more, about 50 J/cm² or less, about 60 J/cm² or more, about 70 J/cm² or more, or about 80 J/cm² or more. The effective amount of light that reaches the region can be in a range bounded by any of the energy density values described herein.

The duration over which the effective amount, which is optionally repetitive, is administered via the intra-oral apparatus can range from about 10 to about 40 minutes. In other embodiments, dosage can be administered in a period of time of about 30 seconds or more, about 1 minute or more, about 2 minutes or more, about 3 minutes or more, about 5 minutes or more, about 7 minutes or more, about 10 minutes or more, about 15 minutes or more, about 20 minutes or more, about 25 minutes or more, about 30 minutes or more, about 40 minutes or more, about 50 minutes or more, about 1 hour or more, about 1 hour 15 minutes or more, about 1 hour 30 minutes or more, or about 2 hours or more. The effective amount can be administered in a period of time of about 3 minutes or less, about 5 minutes or less, about 10 minutes or less, about 15 minutes or less, about 20 minutes or less, about 25 minutes or less, about 30 minutes or less, about 35 minutes or less, about 40 minutes or less, about 50 minutes or less, about 1 hour or less, about 1 hour 15 minutes or less, about 1 hour 30 minutes or less, about 2 hours or less, or about 4 hours or less. The effective amount can be administered in a range of time within any of the time values described herein. In some embodiments, one or more light blocking masks or shades can be used with the intra-oral apparatus. An oral mask can block one or more wavelengths of light, or can reduce the intensity of one or more wavelengths of light, from reaching a region covered by the oral mask. This can include an upper arch (e.g., maxillary teeth), or lower arch (e.g., mandibular teeth). In some embodiments, the oral mask contacts oral tissue or one or more teeth of a patient.

Any time period can be provided between dosages of light. For example, the time period between dosages can be on the order of seconds, minutes, hours, days, weeks, months, quarter of a year, or years.

The effective amount, which in some embodiments is repetitive, can be administered with any desired frequency, e.g., four times daily, three times daily, twice daily, daily, every second day, weekly, biweekly, monthly, or quarterly. In some embodiments, dosage can be administered at regular intervals (e.g., daily), while in other embodiments, the dosage is not administered at regular intervals (e.g., administration can occur 2 times a week at any time during the week). In one embodiment, light can be administered in the morning and at night. Light can be administered throughout the time period that a patient is undergoing bone remodeling or tooth movement. In some embodiments, a patient undergoes orthodontic treatment in addition to undergoing bone remodeling or tooth movement. Orthodontic treatment can occur prior to, subsequent to, or concurrently with oral or maxillofacial bone remodeling. Light can be administered throughout the time period that a patient is undergoing orthodontic treatment, or following treatment to stabilize tooth movement. For example, light can be administered after a functional appliance or an orthodontic appliance is applied, removed, adjusted, after an appointment, or after an active stage, as described herein. It can be desirable to administer light with greater frequency, e.g. four times daily, three times daily, twice daily, daily or every second day, while a patient is undergoing orthodontic treatment. Where light is being administered, for example, to stabilize tooth movement or reduce tooth-root resorption, treatments of reduced frequency, e.g. weekly, biweekly, monthly, or quarterly, can be used to minimize inconvenience to patients. In some embodiments, the effective amount of light maintains the ATP energy levels of tissue cells, e.g., ischemic tissue cells, to prevent cell death, as described herein. In some embodiments, light is administered no less than about every second day. In some embodiments, a patient receives light treatment at least three or four times a week.

Light can be administered for any length of time. In some embodiments, light can be administered on the order of seconds, minutes, hours, days, weeks, months, quarters, or years. For example, light can be administered while an orthodontic appliance or a functional appliance exerts a force. One or more dosages of light can be administered over a period of time during which a patient is undergoing oral or maxillofacial bone remodeling during which an orthodontic appliance or a functional appliance exerts a force. In some embodiments, one or more dosages of light can be administered over a period of time during which a force is exerted on one or more teeth, during which a patient is wearing an orthodontic appliance that itself can exert a force, such as a heavy force, or during which a patient is undergoing orthodontic treatment during which a force, such as a heavy force may be applied. In some embodiments, while a patient is undergoing orthodontic treatment or is wearing a secondary appliance, the patient is administered with light via the intra-oral apparatus. For example, a portion of the intra-oral apparatus (e.g., a mouthpiece) can be configured to be disposed over the orthodontic appliance, such as an orthodontic appliance that can exert a force effective to move one or more teeth, during the light administration. In other embodiments, the intra-oral apparatus exerts a heavy force on one or more teeth such that no secondary appliance is necessary. Administration of light, which can include regular, irregular, continuous or discontinuous administration of light, can be on the order of days, weeks, months, quarters, or years. In some embodiments, light is administered over a plurality of days, weeks, months, quarters, or years. In some embodiments, light is administered over a plurality of sessions. In some embodiments, one or more hours, days, weeks, months, quarters, or years occur between sessions.

If the light emitters are pulsed, then their duty cycle can be adjusted as desired; e.g., light can be administered with a duty cycle of about 10%, about 20%, about 30%, about 40%, about 50%, about 60%, about 70%, about 80%, or about 90%. The pulsing can occur with any frequency. For example, light can be pulsed every picosecond, nanosecond, microsecond, millisecond, second, multiple seconds, or minutes. Frequencies can include, but are not limited to, about 1 mHz, about 10 mHz, about 50 mHz, about 100 mHz, about 500 mHz, about 1 Hz, about 2 Hz, about 5 Hz, about 10 Hz, about 15 Hz, about 20 Hz, about 25 Hz, about 30 Hz, about 35 Hz, about 40 Hz, about 50 Hz, about 70 Hz, about 100 Hz, about 200 Hz, about 500 Hz, or about 1 kHz. Any of the aforementioned characteristics of light emission (e.g., whether the light is on or off, continuous or pulsed, duty cycle, frequency, intensity, wavelength) can be varied or maintained. Where the light is emitted from a source having a controller, any characteristics of light emission can be varied or maintained in accordance with instructions from its controller.

In some embodiments, the emitters of the intra-oral apparatus can be controlled so that the number of lights that are on or off at a given period can be individually controllable. For example, a light source or emitter can be turned on or off relative to other light sources or emitters (such as, e.g., the apparatus depicted in FIG. 18C). Various light sources can be modulated individually (e.g., one or more properties of a particular light source can be varied) or otherwise individually controlled, to expose individual sections of a patient's alveolar soft tissue or other regions to a desired energy density. This can be desirable when it is desirable to administer light to different regions (e.g., via the various panels of the intra-oral apparatus). Thus, the position of light being administered can be varied. In another embodiment, different types of light sources can be turned on or off relative to other light emitters. For example, at some times, light emitted in a first wavelength range can be turned on while light emitted in a second wavelength range can be turned off, vice versa, or both types of light emitters can be turned on or off Thus, the wavelength of light being administered can be varied. In some embodiments, the intensity of light being administered can be varied (e.g., by turning some light sources on or off, or varying the intensity emitted by the light sources). Administering light selectively can enable an increased anchorage effect (by reason of lower tooth mobility) of teeth which are not exposed to any light, which can thereby permit for more precise bone remodeling or movement of teeth to which light is administered.

In some embodiments, particularly where infrared light is administered to a patient, the present methods further comprise providing emission of a visible light. In one embodiment the visible light is bright enough to aid in the apparatus's positioning if performed by a person other than the patient. The visible light can be, but is not necessarily, of a wavelength or wavelength range that is beneficial for light treatment or regulation of tooth movement. In some embodiments, the ratio of the intensities of the visible and infrared components of the light is 1 part or less visible light to 5 parts or more infrared light. In other embodiments, the ratio of the intensities of visible and infrared components is about 1 part or more visible light to 5 parts or more infrared light, 1 part or more visible light to 3 parts infrared light, 1 part or more visible light to 2 parts infrared light, 1 part or more visible light to 1 part infra-red light, 2 parts or more visible light to 1 part infrared light, 3 parts or more visible light to 1 part infrared light, 5 parts or more visible light to 1 part infrared light, 10 parts or more visible light to 1 part infrared light, or substantially no infrared light. In some embodiments, light can be emitted within a range can include wavelengths less than an order of magnitude relative to one another. Alternatively, the range can include wavelengths emitted at one, two, three or more orders of magnitude relative to one another.

The region and desired light characteristics can vary from patient to patient. A physician, dentist, other health-care provider or patient can determine a light treatment regimen for a patient wearing an intra-oral apparatus.

In some instances, it can be desirable to administer light to less than all regions of the patient's alveolar soft tissue, for example, if it is desired that teeth in other regions do not need to be moved (e.g. it can be desired to regulate the movement of only the upper teeth of a patient, or only the lower teeth, or to use certain teeth as an anchor when regulating the movement of other teeth by administering no light to, e.g., blocking light from, the anchor teeth). Administering light to selected regions of the patient's alveolar soft tissue can comprise causing light to irradiate one or more selected tooth roots through the tissue or mucosa.

In one embodiment, light is selectively administered to less than all regions of the patient's alveolar soft tissue before, during, or after the exertion of heavy forces. In one embodiment, light is not administered to an anchor tooth. In this embodiment, a secondary appliance, such as a functional appliance, is located between the anchor region or tooth and one or more selected bone region sought to be remodeled. The secondary appliance can exert a force on the selected bone region, for example, on another tooth. In some embodiments, the force is a heavy force. In some embodiments, an effective amount of light is administered to the selected bone region or other tooth and not to the anchor region or anchored tooth via the intra-oral apparatus. The administration of light can increase the rate of the selected bone remodeling region or velocity (or rate of movement) of the other tooth and reduce, minimize, or prevent root resorption of the other tooth, while not increasing the rate of bone remodeling of the non-selected regions or velocity of the anchor tooth.

It can also be desirable to administer light of different wavelengths to different regions of the patient's alveolar soft tissue, if it is desired to differentially manipulate the movement of a patient's teeth, as described herein. For example, light of a first wavelength can be administered to a first region and light of a second wavelength can be administered to a second region. The first and second wavelengths can include any wavelengths described elsewhere herein, such as for example, about 585 nm to about 665 nm, or about 815 nm to about 895 nm.

Light can be administered over an area (also referred to herein as a "light irradiation area"). For example, light can be administered to a region with an area. In some embodiments, light characteristics (e.g., light intensity) can remain uniform over the area. In other embodiments, light characteristics can vary over the area. For example, light intensity can be uniform or can vary over an area of a region. The area of light administration can have any shape or size.

Light can be administered to a light irradiation area of any size and shape. For example, a region, such as a specified region of the patient's alveolar soft tissue, can have any size or shape. The light irradiation area can have one or more dimensions (e.g., length, width, diameter) that range from about 1 to about 80 mm or from about 1 to about 70 mm. In some embodiments, one or more dimensions (e.g., length, width, diameter) of a light irradiation area can range from about 1 to about 3 mm, about 3 to about 5 mm, about 5 to about 7 mm, about 7 to about 10 mm, about 10 to about 15 mm, about 15 to about 20 mm, about 20 to about 25 mm, about 25 to about 30 mm, about 30 to about 35 mm, about 35 to about 40 mm, about 40 to about 50 mm, about 50 to about 60 mm, or about 60 to about 80 mm.

A light-irradiation area can have any shape, which can include, but is not limited to, a substantially rectangular shape, square shape, triangular shape, hexagonal shape, octagonal shape, trapezoidal shape, circular shape, elliptical shape, crescent shape, cylindrical shape or half-circle. In some embodiments, the dimensions of a light emitter can be about the same as dimensions for a light irradiation area. In other embodiments, the dimensions of a light source can be greater than the dimensions of a light irradiation area. Alternatively, the dimensions of a light source can be less than the dimensions of the light irradiation area. The relative areas of a light source and light irradiation area can depend on any angle, which can be a parallel, convergence, or divergence angle, at which light is emitted.

In some embodiments, an effective amount of light can be provided in a treatment regimen using the intra-oral apparatus. The treatment regimen can be used in the present methods.

In one embodiment, a typical treatment regimen provides a dose of light daily. Each of the daily doses of light can be administered over a period lasting from a few minutes to about an hour when the patient is using the intra-oral apparatus. For example, daily ½ hour doses of light can be effective and are not unduly inconvenient for patients. A single daily dose can be as effective as dividing the same dose into multiple sessions administered at different times during the day. Some treatment regimens can comprise administering light in 5 treatments per week for 12 weeks. Each treatment can last ½ hour and irradiate the patient's oral tissue with light having wavelengths of 660 nm and 840 nm. The 660 nm light can have an intensity of about 20 mW/cm$^2$ at the skin's surface. The 840 nm light can have an intensity of about 10 mW/cm$^2$ at the skin's surface. These treatment regimens can enhance bone density.

Other treatment regimens can comprise administering light in daily treatments for 21 days. Each treatment lasts from about 20 minutes to about one hour and illuminates the tissues of a patient's mouth with light having a wavelength of 618 nm and an intensity of 20 mW/cm$^2$ at the skin's surface. These treatment regimens can accelerate healing of bone grafts.

Another treatment regimen can include a twice-daily administration of light for six months. Light can be administered, via the intra-oral apparatus, at a wavelength of about 660 nm or about 840 nm, or at both wavelengths. The intensity of the light can be about 20 mW/cm$^2$ at the target surface within the patient's mouth. An orthodontic appliance or a functional appliance can be present in the patient's mouth while the light is administered. Subsequent to the first 6 month period, a second 6 month period can be provided where light is administered once every other day. The same functional appliance or one or more orthodontic appliances can be present in the patient's mouth at this time. The administration of light can optionally become less frequent or be administered at a lower intensity as treatment progresses. In some embodiments, the same intra-oral apparatus is used throughout the treatment regimen. In other embodiments, however, one or more different intra-oral apparatus are used throughout the treatment regimen.

Another treatment regimen can include administering light to a patient having an orthodontic appliance or a functional appliance, and then subsequently adjusting the appliance. In one such embodiment, the patient uses both the intra-oral apparatus and the appliance (e.g., braces). The intra-oral apparatus can, for example, fit over the secondary appliance such that the intra-oral apparatus and orthodontic appliance can be used simultaneously. In some embodiments, two or more other orthodontic appliances can be used with the intra-oral apparatus. In other embodiments, an orthodontic appliance and a functional appliance are used with the intra-oral apparatus. The orthodontic appliance can be installed on the patient's teeth prior to, subsequent to, or concurrently with the installation of a functional appliance. In some embodiments, the orthodontic appliance worn and adjusted is the intra-oral apparatus, which also administers the light. In some embodiments, adjusting an orthodontic appliance may increase or alter the magnitude of a force applied on one or more teeth. Adjusting an orthodontic appliance may alter the direction of a force applied on one or more teeth. Light can be administered to one or more selected teeth for up to an hour prior to adjusting an orthodontic appliance. Adjusting the orthodontic appliance can cause a heavy force to be exerted on the one or more teeth. Adjusting the appliance can change the magnitude or direction, or both, of the force exerted. Adjusting the appliance can comprise tightening, loosening or replacing one or more of the appliance's wires, springs or elastic devices. Different sizes, materials, or shapes of such components can be used. Light can then be administered daily to the one or more selected teeth, until the next adjustment of the appliance. This administration of light can reduce, minimize, or prevent tooth-root resorption, bone resorption, tissue inflammation, periodontium resorption or cementum resorption.

Another treatment regimen can include administering vitamin D to a patient; administering light to a region of the alveolar soft tissue, or the mandibular bone, maxillary bone, or one or more teeth; installing a functional appliance or an orthodontic appliance; and subsequently adjusting the orthodontic appliance or functional appliance. In some embodiments, adjusting a functional appliance or an orthodontic appliance increases or decreases the magnitude of a force exerted on one or more teeth, mandibular bone, maxillary bone, or temporal bone. Adjusting a functional appliance also can alter the direction of a force exerted. Light can be administered to one or more selected regions for up to an hour prior to adjusting a functional appliance or an orthodontic appliance. Adjusting the functional appliance or orthodontic appliance can cause a force to be exerted on the one or more teeth, mandibular bone, maxillary bone, or temporal bone. Adjusting the functional appliance or orthodontic appliance can change the magnitude or direction, or both, of the force exerted. Adjusting the functional appliance or orthodontic appliance can comprise tightening, loosening or replacing one or more of the appliance's wires, springs or elastic devices. Different sizes, materials, or shapes of such components can be used. Light can then be administered, for example, daily, to the one or more selected regions, until the next adjustment of the functional appliance or orthodontic appliance. This administration of light can regulate oral or maxillofacial bone remodeling. In some embodiments, the administration of light regulates tooth movement. For example, the administration of vitamin D and administration of light can increase the rate of bone remodeling or tooth movement. This can decrease the amount of time that a functional appliance or an orthodontic appliance is worn or needs to be worn by a patient.

The present methods can further comprise controlling temperature of the apparatus of the invention, the patient's mouth, the patient's alveolar soft tissue or of any light source that is directed at or that contacts the patient's mouth or region thereof. As described herein, the intra-oral apparatus can include a temperature sensor (or other like sensor) that monitors the temperature of the patient's mouth, the patient's alveolar soft tissue and/or light emitters. The method can comprise cooling, heating, or maintaining the temperature at a patient's mouth. A patient's mouth, for example, the patient's alveolar soft tissue, can be contacted with a temperature control mechanism, which can cause the removal or provision of heat. In some embodiments, such a temperature control mechanism is coupled to or disposed within the intra-oral apparatus. In some embodiments, the temperature of the light source can be controlled. The temperature control mechanism can communicate with the light source. Heat can be removed from or provided to the light source. Any embodiments for temperature regulation described herein can be used within the method. The method can further comprise measuring a temperature of the patient's mouth, measuring a temperature at a particular surface region within the patient's mouth, e.g., the alveolar soft tissue, or measuring a temperature at one or more of the light emitters. Temperature regulation can optionally occur in response to one or more temperature measurements made.

In one embodiment the present methods are performed prior to, subsequent to or concurrently with orthodontic treatment of a patient. In one embodiment the administration of light is repetitive.

Oral or maxillofacial bone remodeling can occur at the mandibular bone, maxillary bone, or temporal bone. In some embodiments, oral or maxillofacial bone remodeling can occur at a joint, such as the temporomandibular joint. The some embodiments, oral or maxillofacial bone remodeling can occur at a condyle or glenoid fossa. The regulation of oral or maxillofacial bone remodeling can result in the repositioning of the mandibular bone or maxillary bone, the lengthening or shortening of the mandibular bone or maxillary bone, or altering the angle, shape, or dimensions of the mandibular bone or maxillary bone.

Oral or maxillofacial bone remodeling can include the installation of a functional appliance in a patient. A functional appliance can be present on one or more teeth of a patient. The methods can comprise installing a functional appliance in a patient, such as installing the appliance on one or more teeth, the patient's gums, the patient's maxillary or mandibular bone, or other oral or maxillofacial features of the patient, adjusting a functional appliance of the patient, or can comprise removing a functional appliance from the patient. A treatment for oral or maxillofacial bone remodeling can include a period of time during which the functional appliance is installed in the patient. In some embodiments, treatment for oral or maxillofacial bone remodeling can include a period of time after the functional appliance has been installed in or removed from the patient. In some embodiments, treatment for oral or maxillofacial bone remodeling can include a period of time preceding the installation of a functional appliance. In other embodiments treatment for oral or maxillofacial bone remodeling includes a period of time prior to, during, or subsequent to the exertion of a force on oral or maxillofacial bone, muscle, soft tissue, or one or more teeth, such as mandibular bone, maxillary bone, temporal bone, or on one or more oral muscles that can prevent the oral muscles from exerting a force on the one or more teeth, mandibular bone, maxillary bone, temporal bone. Treatment for oral or maxillofacial bone remodeling can include a period of time while a patient is seeing or consulting with an orthodontist or other dental specialist.

Treatment for oral or maxillofacial bone remodeling, including methods for regulating such remodeling, can include an active stage and a passive stage. An active stage can include some time during which a functional appliance is installed in and/or on the patient. In some embodiments, an active stage includes a time during which a force is exerted on a tooth, mandibular bone, maxillary bone, temporal bone. An active stage can include a period during which the patient is undergoing one or more adjustments to the patient's functional appliance. In some embodiments, the active stage includes the alignment phase of orthodontic treatment. A passive stage can include a period after a functional appliance has been removed from the patient. In some embodiments, a passive stage includes a period during which a functional appliance is installed, but is no longer undergoing adjustments. In some embodiments, a passive stage includes a period during which there is no further muscular tension on the jaw or teeth when the functional appliance is in position, which typically occurs after a period of treatment and bone remodeling. In some embodiments, a passive stage includes a period during which a functional appliance is not providing force to effect bone remodeling. Instead, the passive stage can include a period during which a functional appliance is installed in a patient and that maintains the maxillary bone or mandibular bone in its position. Any stage of oral or maxillofacial bone remodeling can last on the order of days, weeks, months, quarters, or years.

An orthodontic treatment can cause one or more teeth to move or maintain its position relative to a supporting maxilla or mandible, or can include regulation of tooth movement. In some embodiments, orthodontic treatment can include reducing or closing the space or gap between teeth, for example, that resulting from an injury, extraction or the like. In some instances, orthodontic treatment can include aligning teeth. Orthodontic treatment can include treating malocclusion, which can occur when teeth fit together improperly, for example, as a result of their individual positions or positions of underlying jaw bone as they relate to one another. Malocclusion can be treated using light treatment or tooth movement regulation according to the methods described herein. Accordingly, the present invention further relates to methods for treating or preventing malocclusion, comprising administering an effective amount of light to a patient, wherein the effective amount of light is irradiated from the emitter of an apparatus of the invention. In some embodiments, at least a portion of the apparatus contacts the alveolar soft tissue when the light is administered. In some embodiments, the methods further comprise allowing a heavy force to be exerted on one or more teeth of a patient in need thereof. In some embodiments, the light is administered before, during or after the heavy force is exerted.

An orthodontic treatment can include the installation of an orthodontic appliance in a patient. An orthodontic appliance can be present on one or more teeth of a patient. The methods can comprise installing an orthodontic appliance in a patient, such as installing the appliance to one or more teeth of the patient, adjusting an orthodontic appliance of the patient, or can comprise removing an orthodontic appliance from the patient. In some embodiments, an orthodontic appliance can be installed or removed prior to, subsequent to, or concurrently with the installation or removal of a functional appliance. Orthodontic treatment can include a period of time during which the orthodontic appliance is applied to the patient. In some embodiments, orthodontic treatment can include a period of time after the orthodontic appliance has been applied or removed from the patient. In some embodiments, orthodontic treatment can include a period of time preceding the application of an orthodontic appliance. In other embodiments orthodontic treatment includes a period of time prior to, during, or subsequent to the exertion of a heavy force on one or more teeth. Orthodontic treatment can include a period of time while a patient is seeing or consulting with an orthodontist.

In some embodiments, orthodontic treatment can include an active stage and a passive stage. An active stage can include time during which an orthodontic appliance is installed in the patient. In some instances, an active stage can include time during which a force is applied to one or more teeth to effect tooth movement. In some embodiments, the force applied to one or more teeth during an active stage is a heavy force. An active stage can include a period during which the patient is undergoing one or more adjustments to the patient's appliance. In some embodiments, the active stage includes one or more of the following phases of orthodontic treatment: the alignment phase, a space-closure phase, and a finishing-or-detailing phase. The alignment phase is described herein. The space-closure phase typically occurs after the alignment phase, if the alignment phase is needed. In general, during the space-closure phase, one or more teeth are moved so that any gaps between the teeth are minimized. The finishing-or-detailing phase typically occurs after the space-closure phase, if the space-closure phase is needed. In general, during the finishing-or-detailing phase, square or rectangular wires are installed on one or more teeth of the patient, in some embodiments, as part of an orthodontic appliance that comprises brackets, and used to torque one or more of the teeth so that the teeth are set to a final, corrected position. Bodily movement of one or more teeth typically occurs during one or both of the space-closure phase and the finishing-or-detailing phase. Light treatment can be administered to the patient during any one or more of the phases of the active stage or during the passive stage.

A passive stage, which comprises the retention phase, can include a period after an appliance has been removed from the patient. In some instances, a passive stage can include a period during which an appliance is installed but is no longer undergoing adjustments. In some instances a passive stage can include a period during which an orthodontic appliance no longer exerts a force on the teeth. In some embodiments, a passive stage can include a period during which, for example, an orthodontic appliance is not providing force to effect movement of a tooth. Instead, the passive stage can include a period during which an appliance is installed in a patient and that maintains one or more teeth in its position. In some embodiments, any stage of orthodontic treatment can last on the order of days, weeks, months, quarters, or years.

In some embodiments, orthodontic treatment can result in bone remodeling. In some embodiments, orthodontic treatment and bone remodeling or tooth movement occurs concurrently. In some embodiments, in addition to light treatment, force can be exerted on one or more tooth, any region of the jaw, or any other region of the mouth or head. Force can be exerted by the intra-oral apparatus and/or an orthodontic appliance. In some embodiments, the force is a heavy force. Bone remodeling can involve altering the position or morphology of bone, including the jaw bone. For example, a jaw bone can be moved forward, or can be lengthened. Other examples of bone remodeling, as disclosed herein, can also be applicable. In some embodiments, bone remodeling can occur in conjunction with regulating tooth movement. Accordingly, the present methods are useful for and, in one embodiment, result in bone remodeling. Light can be administered to a region, such as any oral bone or tissue, and is useful for bone remodeling. Accordingly, the invention further provides methods for inducing bone remodeling, comprising administering an effective amount of light to a patient, wherein the effective amount of light is irradiated from the emitter of an apparatus of the invention. In some embodiments, at least a portion of the apparatus contacts the alveolar soft tissue when the light is administered. In some embodiments, the methods further comprise allowing a heavy force to be exerted on one or more teeth of a patient in need thereof. In some embodiments, the light is administered before, during or after the heavy force is exerted. Light treatment can increase the rate of bone remodeling, and can be provided in conjunction with forces for bone remodeling. For example, administering an effective amount of light as described in the present methods can reduce the amount of time to achieve the same degree of bone remodeling without light by about 10%, about 20%, about 30%, about 40%, about 50%, about 60%, about 70%, about 80%, or about 90%. Light treatment can promote bone remodeling which can increase the rate of teeth movement. This can allow heavier forces to be used, which could accelerate tooth movement even more than with lighter forces. Such forces can be exerted by one or more orthodontic appliances.

Installing, adjusting, or removing of an orthodontic appliance can occur before or after administering an effective amount of light via the intra-oral apparatus. In some embodiments, the effective amount of light can aid in regulating or accelerating the movement of teeth during orthodontic treatment with an orthodontic appliance, or regulating or accelerating bone remodeling during oral or maxillofacial bone remodeling with a functional appliance. The effective amount of light can be useful for reducing the amount of time an orthodontic appliance is worn during an orthodontic treatment, or that a functional appliance is worn during treatment for oral or maxillofacial bone remodeling. In other words, the effective amount of light can be useful for reducing a patient's orthodontic treatment time, in comparison to the orthodontic treatment time without administration of the effective amount of light. For example, according to the methods of the present invention, the application of light can reduce treatment time (e.g., wearing a functional appliance or an orthodontic appliance) by up to about 10%, about 20%, about 30%, about 40%, about 50%, about 60%, about 70%, about 75%, about 80%, about 85%, or about 90% of the treatment time. For example, administering light having a wavelength in the range of about 585 nm to about 665 nm (e.g., about 625 nm) can reduce the amount of time that a patient wears an orthodontic appliance or a functional appliance by about 5% to about 90%, for example, by about 5%, about 10%, about 20%, about 30%, about 40%, about 50%, about 60%, about 70%, about 75%, about 80%, about 85%, or about 90%. Administering light having a wavelength in the range of about 815 nm to about 895 nm (e.g., about 855 nm) can reduce the amount of time that a patient wears an orthodontic appliance or a functional appliance by about 5% to about 90%, for example, by about 5%, about 10%, about 20%, about 30%, about 40%, about 50%, about 60%, about 70%, about 75%, about 80%, about 85%, or about 90%.

In some embodiments, administering an effective amount of light with desired light characteristics results in an overall reduction in the amount of time necessary for treatment. For example, a treatment can include the installation of a functional appliance, the removal of the functional appliance, and the installation or removal of an orthodontic appliance. By combining the use of a functional appliance and an orthodontic appliance, the overall treatment time can be reduced. Furthermore, increased control on the bone remodeling and tooth movement can be delivered. This can be particularly advantageous during a patient's adolescent growth phase.

Administering light having a wavelength in the range of about 585 nm to about 665 nm (e.g., about 625 nm) can result in a rate of tooth movement that is about 5% to about 90% faster than the rate of tooth movement without the administration of light. For example, the rate of tooth movement can be about 5%, about 10%, about 20%, about 30%, about 40%, about 50%, about 60%, about 70%, about 75%, about 80%, about 85%, or about 90% faster than the rate of tooth movement without the administration of light.

Administering light having a wavelength in the range of about 815 nm to about 895 nm (e.g., about 855 nm) can result in a rate of tooth movement that is about 5% to about 60% faster than the rate of tooth movement resulting from the administration of light having a wavelength in the range of 585 nm to about 665 nm (e.g., about 625 nm). For example, the rate of tooth movement can be about 5%, about 10%, about 20%, about 30%, about 40%, about 50%, about 55%, or about 60% faster than the rate of tooth movement resulting from the administration of light having a wavelength in the range of 585 nm to about 665 nm (e.g., about 625 nm).

Administering light having a wavelength in the range of about 815 nm to about 895 nm (e.g., about 855 nm) can result in a rate of tooth movement that is about 5% to about 95% faster than the rate of tooth movement without the administration of light. For example, the rate of tooth movement can be about 5%, about 10%, about 20%, about 30%, about 40%, about 50%, about 60%, about 70%, about 75%, about 80%, about 85%, about 90%, or about 95% faster than the rate of tooth movement without the administration of light.

In some embodiments, in addition to light treatment, orthodontic treatments, particularly those that comprise the use of an orthodontic appliance, can exert forces, such as heavy forces, on one or more teeth. This can result in a rate of tooth movement that is about 5% to about 80% faster than the rate of tooth movement without the exertion of heavy forces. For example, the exertion of heavy forces in one or more teeth can increase the rate of tooth movement by about 5%, about 10%, about 20%, about 30%, about 40%, about 50%, about 60%, about 70%, about 75%, or about 80%. Heavy forces can result in tooth-root resorption, bone resorption, inflammatory resorption of dentin, cementum resorption, or tissue inflammation.

In some embodiments, the administration of an effective amount of light can aid in reducing, preventing or minimizing tooth-root resorption when a heavy force is allowed to be exerted on one or more tooth. The effective amount of light can be useful for reducing the amount of tooth-root resorption as compared to when a heavy force is allowed to be exerted on one or more tooth without administering the effective amount of light. For example, according to the methods of the present invention, the administration of light can reduce tooth-root resorption (e.g., apical root resorption) by up to about 1%, about 2%, about 3%, about 5%, about 7%, about 10%, about 15%, about 20%, about 25%, about 30%, about 40%, about 50%, about 60%, about 70%, about 80%, or about 90%. Reducing tooth-root resorption, particularly while applying heavy forces, may allow for a reduction of the amount of time for orthodontic treatment, or the amount of time that a patient wears an orthodontic appliance. Administering an effective amount of light can reduce the amount of time that a patient wears orthodontic appliances by about 5% to about 90%, for example, by about 5%, about 10%, about 20%, about 30%, about 40%, about 50%, about 60%, about 70%, about 75%, about 80%, about 85%, or about 90%.

In some embodiments, administration of an effective amount of light can aid in reducing, preventing or minimizing bone resorption or inflammatory dentin or cementum resorption of the tooth root or periodontium. The effective amount of light can be useful for reducing bone resorption or inflammatory dentin or cementum resorption of the tooth root and periodontium, as compared to when a heavy force is allowed to be exerted on one or more teeth without administering the effective amount of light. For example, according to the methods of the present invention, the administration of light can reduce bone resorption or inflammatory dentin or cementum resorption of the tooth root or periodontium by up to about 1%, about 2%, about 3%, about 5%, about 7%, about 10%, about 15%, about 20%, about 25%, about 30%, about 40%, about 50%, about 60%, about 70%, about 80%, or about 90%. Reducing bone resorption or inflammatory resorption of dentin or cementum resorption of the tooth root or periodontium while exerting heavy forces can reduce the amount of time for orthodontic treatment, or amount of time that a patient wears an orthodontic appliance. Administering an effective amount of light can reduce the amount of time that a patient wears orthodontic appliances by about 5% to about 90%, for example, by about 5%, about 10%, about 20%, about 30%, about 40%, about 50%, about 60%, about 70%, about 75%, about 80%, about 85%, or about 90%.

In some embodiments, administration of the effective amount of light can aid in reducing, preventing or minimizing inflammation of tissue surrounding one or more teeth upon which heavy forces are or were exerted. The effective amount of light can be useful for reducing the amount of inflammation of tissue surrounding one or more teeth upon which heavy forces are or were exerted, as compared to when a heavy force is allowed to be exerted on one or more tooth without administering the effective amount of light. In one embodiment, according to the methods of the present invention, the administration of light can reduce inflammation of tissue surrounding one or more teeth upon which heavy forces are or were exerted by up to about 1%, about 2%, about 3%, about 5%, about 7%, about 10%, about 15%, about 20%, about 25%, about 30%, about 40%, about 50%, about 60%, about 70%, about 80%, or about 90%. Reducing inflammation of tissue surrounding one or more teeth upon which heavy forces are or were exerted while applying heavy forces can reduce the amount of time for orthodontic treatment, or amount of time that a patient wears an orthodontic appliance. Administering an effective amount of light can reduce the amount of time that a patient wears an orthodontic appliance by about 5% to about 90%, for example, by about 5%, about 10%, about 20%, about 30%, about 40%, about 50%, about 60%, about 70%, about 75%, about 80%, about 85%, or about 90%.

The light can be administered via the intra-oral apparatus in accordance with a treatment regimen. In some embodiments, when a functional appliance or an orthodontic appliance is used in conjunction with the intra-oral apparatus, the functional appliance or orthodontic appliance can be installed prior to administering the light via the intra-oral apparatus, the functional appliance or orthodontic appliance can be installed concurrently with administering the light via the intra-oral apparatus, the functional appliance or orthodontic appliance can be installed subsequent to administering the light via the intra-oral apparatus, or any combination thereof. In some embodiments, a functional appliance or an orthodontic appliance can be removed prior to administering the light via the intra-oral apparatus, the functional appliance or orthodontic appliance can be removed concurrently with administering the light via the intra-oral apparatus, the functional or orthodontic appliance can be removed subsequent to administering the light via the intra-oral apparatus, or any combination thereof. In some embodiments, a functional appliance or orthodontic appliance can be adjusted prior to administering the light via the intra-oral apparatus, the functional appliance or orthodontic appliance can be adjusted concurrently with administering the light via the intra-oral apparatus, the functional appliance or orthodontic appliance can be adjusted subsequent to administering the light via the intra-oral apparatus, or any combination thereof.

The functional appliance or orthodontic appliance can exert a force on one or more teeth of the patient in addition to or in lieu of the intra-oral apparatus exerting a force on one or more teeth. A force can be exerted (e.g., by the functional appliance and/or the orthodontic appliance subsequent to, concurrently with, or prior to the administration of light via the intra-oral apparatus. A force may be exerted subsequent to, concurrently with, or prior to initiation of the administration of light. A force can be exerted subsequent to, concurrently with, or prior to the initiation of a light treatment regimen involving the intra-oral apparatus. A force can be exerted subsequent to, concurrently with, or prior to the initiation of a light treatment session involving the intra-oral apparatus. In some embodiments, a force can be exerted one or more seconds, one or more minutes, one or more hours, one or more days or one or more weeks subsequent to administering the light and/or one or fewer days, one or fewer weeks, or one or fewer weeks subsequent to administering the light. The light can be administered by the intra-oral apparatus for any length of time. In some embodiments, a force is exerted one or more seconds, one or more minutes, one or more hours, one or more days or one or more weeks subsequent to initiating light administration and/or one or fewer days, one or fewer weeks, or one or fewer weeks subsequent to initiating light administration. In some embodiments, a force can be exerted one or more seconds, one or more minutes, one or more hours, one or more days or one or more weeks subsequent to ending light administration and/or one or fewer days, one or fewer weeks, or one or fewer weeks subsequent to ending light administration. The force can be, for example, a heavy force.

Light can be administered for any period of time before, during, or after the exertion of a heavy force. For example, light can be administered for about 1 minute, about 2 minutes, about 3 minutes, about 5 minutes, about 10 minutes, about 15 minutes, about 20 minutes, about 30 minutes, about 45 minutes, about 1 hour, about 90 minutes, about 2 hours, about 3 hours, about 4 hours, or about 6 hours prior to, during, or after the exertion of a force, such as a heavy force. In some embodiments, light is administered for about 5 minutes to about 10 minutes. In some embodiments, light is administered at any amount of time prior to, during, or after the initiation of the exertion of a force. For example, light can be administered about 1 minute, about 2 minutes, about 3 minutes, about 5 minutes, about 10 minutes, about 15 minutes, about 20 minutes, about 30 minutes, about 45 minutes, about 1 hour, about 90 minutes, about 2 hours, about 3 hours, about 4 hours, about 6 hours, about 12 hours, about 1 day, about 36 hours, about 2 days, about 3 days, about 4 days, about 1 week, about 2 weeks, or about 1 month prior to, during, or after the initiation of the exertion of a force. In some embodiments, light is administered for about 5 minutes to about 10 minutes.

Administering light prior to initiating or exerting a force, as described herein, can be part of a pretreatment regimen. In some embodiments, however, no such pretreatment occurs and the functional appliance or orthodontic appliance exerts a force prior to any light being administered. The functional appliance or orthodontic appliance can exert a force, for example, at one or more seconds, one or more minutes, one or more hours, one or more days or one or more weeks prior to administering the light and/or one or fewer days, one or fewer weeks, or one or fewer weeks prior to administering the light. Thus, a follow-up treatment of light can be provided after the exertion of the force. In some embodiments, a force is exerted during the administration of light, or at one or more stages of the administration of light.

In some embodiments, the functional appliance or orthodontic appliance exerts the force at the same region as the region that is administered with light. In other embodiments, the functional appliance or orthodontic appliance exerts the force on a region that is different from the region that is administered with light. In some embodiments, allowing the functional appliance or orthodontic to exert a force on a region other than the region administered with light can result in allowing a force to be exerted to a region that is administered with light.

In one embodiment, the dosage or effective amount of light has a density that ranges from about 24 J/cm$^2$ to about 200 J/cm$^2$, and has a wavelength in the range of about 585 nm to about 665 nm, or about 815 nm to about 895 nm. Administration of light having a wavelength in the range of about 585 nm to about 665 nm can be useful in the present methods, in one embodiment, for promoting bodily movement of teeth or minimize tipped movement of teeth, or both. Administration of light having a wavelength in the range of 815 nm to about 895 nm, can also be useful in the present methods, for example, for increasing the velocity of teeth through the patient's bone. In some other embodiments, an effective dosage of light can have any of the light characteristics as described anywhere herein. Teeth in a region of the patient's maxillary or mandibular alveolar bone to which light is not administered can be used as an anchor to facilitate movement of teeth in the selected region. Light is administered directly to a specific region of the patient's mouth, e.g., the patient's alveolar soft tissue, using the intra-oral apparatus, as described herein.

In some embodiments, the present methods comprise administering to a patient in need thereof, via an intra-oral apparatus, an effective amount of light having a first wavelength to a selected first region of the patient's mouth (e.g., a first region of the alveolar soft tissue), and further comprise administering, via the intra-oral apparatus, an effective amount of light having a second wavelength to a selected second region of the patient's mouth (e.g., a second region of the alveolar soft tissue). In one embodiment the effective amount of light having a first wavelength is a repetitive dosage. In another embodiment the effective amount of light having a second wavelength is a repetitive dosage. Regions other than alveolar soft tissue can receive the first or second wavelength of light. In one embodiment, the effective amount of light can be in the range of 24 J/cm$^2$ to 200 J/cm$^2$. The first wavelength can be in the range of about 585 nm to about 665 nm, and the second wavelength can be in the range of about 815 nm to about 895 nm. In other embodiments, an effective amount of light can have any light characteristics as described anywhere herein.

In some embodiments, the methods further comprise installing the intra-oral apparatus and/or a secondary appliance (such as, for example, a functional appliance or an orthodontic appliance), removing the intra-oral apparatus and/or a secondary appliance, or adjusting the intra-oral apparatus and/or a secondary appliance. In other embodiments, the methods comprise administering light via the intra-oral apparatus until orthodontic treatment is complete. Orthodontic treatment can be deemed complete after appointments with an orthodontic specialist are completed, after the movement of one or more teeth has been stabilized to remain in the substantially same position, e.g., within about 1 to about 3 millimeters of a specific position, without the aid of any type of orthodontic appliance, or during a passive stage of orthodontic treatment as described in greater detail herein. Light can be administered to the region before, during, after, or any combination thereof, a secondary appliance is installed, adjusted, or removed. The secondary appliance can be applied, adjusted, or removed before, during, after, or any combination thereof, the application of light via the intra-oral apparatus. In some embodiments, a force, such as a heavy force, can be exerted when the orthodontic appliance is installed or adjusted, or for a period of time following such installation or adjustment.

As described herein, the speed of tooth movement, e.g., through the bone, or the quality of that movement (e.g., "bodily" or "tipped" movement) can be regulated by administration of light. In one embodiment the present methods are useful for effecting bone regeneration, which can occur concurrently with the present methods. Bone regeneration can be enhanced by administering light according to the present methods. Where orthodontic treatment is performed, light can be administered before, during or after orthodontic treatment using the intra-oral apparatus. The light can be emitted from the intra-oral light-therapy apparatus in any manner described herein. Bone regeneration can include bone growth or bone resorption. This can include osteoblast or osteoclast activation. Tooth movement can require osteoclastic and osteoblastic activity. In one embodiment, the administration of light according to the present methods stimulates osteoclasts or osteoblasts and, accordingly, stimulates osteoclastic and osteoblastic activity. The administration of light can increase the rate of tooth movement that can accompany bone remodeling.

For example, the present methods, in one embodiment for regulating tooth movement, can also comprise applying, adjusting or removing a tooth mask or other oral mask. The mask can be coupled to, disposed within, or otherwise part of the intra-oral apparatus. In some embodiments, one or more of the panels of the intra-oral apparatus can include a mask. In other embodiments, the mask is separate from the intra-oral apparatus but is configured to contact the intra-oral apparatus when the patient is wearing the intra-oral apparatus. A tooth mask can be applied or removed prior to, during, or after the administration of light. Light can be administered to a region before, during, after, or any combination thereof, an oral mask or tooth mask is applied, adjusted, or removed. In some embodiments, one or more of a patient's teeth, or other region of the patient's mouth, can be at least partially covered with a mask that can block at least some of the light. A mask can block one or more wavelengths of light. In some embodiments, the mask can completely block one or more wavelength of light, and in other embodiments, the mask can reduce the amount or intensity of light reaching the teeth, or other region of the patient's mouth. In some embodiments, the intensity of the light administered to the teeth, or other region of the patient's mouth, can be zero, or can be less than the intensity of the light emitted from a light source.

In accordance with another aspect of the invention, the present methods, in one embodiment for tooth-movement regulation, can regulate the bone regeneration. For example, the present methods can increase the rate of bone regeneration. In some embodiments, bone regeneration can facilitate tooth-movement regulation, for example, can increase the velocity or quality of movement, or can stabilize tooth movement. For example, bone regeneration can occur prior to, during or following tooth movement. Bone regeneration can include bone growth, bone strengthening or bone resorption. For example, during bone regeneration, bone mineral density (BMD) can increase, bone volume (BV) can increase, bone mineral content (BMC) can increase, and the ratio of bone volume to total volume (BV/TV) or bone density can increase. Higher BV/TV can indicate denser bone, where less bone regeneration can occur, which is desirable after tooth movement has occurred to enhance the stability of teeth. Specifically, teeth move more slowly through denser and more mineralized bone, and maintain their position longer than in less dense bone. Teeth are therefore less likely to relapse and move back to their original, misaligned state. In this manner, light treatment can increase the quality of the bone or, more specifically, increase the mineral density of the bone to prevent relapse after orthodontic treatment. In some such embodiments, the light treatment occurs after force is applied to the one or more teeth of the patient (i.e., when force is no longer being applied to the patient's teeth). In one embodiment, the patient wears an orthodontic appliance during such light treatment. In another embodiment, the patient does not wear an orthodontic appliance during such light treatment.

Other examples of parameters that can be affected during bone regeneration can include trabecular bone surface, bone quality, osteoclastic activity (e.g., osteoclast and preosteoclast counts), and bone resorption. Light treatment can enhance existing cellular processes. Bone regeneration can occur in any bone tissue or oral region. For example, bone regeneration can occur in a portion or all of a maxillary alveolar bone, in mandibular alveolar bone, or around one or more teeth. In some embodiments, bone regeneration can occur around one or more teeth, which can include a periodontium. In some embodiments, the region around one or more teeth can be within about 1 mm, about 2 mm, or about 3 mm from the surface of the teeth.

In some embodiments, light treatment according to the present methods can also result in treating or preventing jaw osteonecrosis. Accordingly, the present methods are useful for treating or preventing jaw osteonecrosis. Accordingly, the invention further provides methods for treating or preventing jaw osteonecrosis, comprising administering an effective amount of light to a patient, wherein the effective amount of light is irradiated from the emitter of an apparatus of the present invention. In some embodiments, at least a portion of the apparatus contacts the alveolar soft tissue when the light is administered. The methods optionally include allowing a heavy force to be exerted on one or more teeth of the patient, who is in need thereof. When applicable, light can be administered before, during or after the heavy force is exerted. Treating or preventing jaw osteonecrosis can comprise reversing osteonecrosis through the use of light treatment according to the methods described herein. Jaw osteonecrosis can occur with respect to any bone tissue. For example, jaw osteonecrosis, can occur with respect to a portion or all of a maxillary alveolar bone, mandibular alveolar bone, or one or more teeth. In some embodiments, methods for treating or preventing jaw osteonecrosis further comprise administering to the patient an effective amount of vitamin D.

In some embodiments, light treatment according to the present methods can also result in reducing, minimizing, or preventing tooth-root resorption, bone resorption, inflammatory resorption of dentin or cementum resorption, or inflammation of tissue. Accordingly, the present methods are useful for reducing, minimizing, or preventing tooth-root resorption, bone resorption, inflammatory dentin or cementum resorption, or inflammation of tissue. Accordingly, the invention further provides methods for reducing, minimizing, or preventing tooth-root resorption (e.g., apical root resorption), bone resorption, inflammatory dentin or cementum resorption, or inflammation of tissue, comprising administering an effective amount of light to a patient, wherein the effective amount of light is irradiated from the emitter of an apparatus of the invention, and, optionally, allowing a heavy force to be exerted on one or more teeth of the patient, who is in need thereof. In some embodiments, at least a portion of the apparatus contacts the alveolar soft tissue when the light is administered. When applicable, light can be administered before, during, or after the heavy force is exerted. Such light-treatment methods may be used or useful in conjunction with heavy forces applied to one or more teeth.

In some embodiments, light treatment regulates tooth movement during an alignment phase of orthodontic treatment. In another embodiment, light treatment regulates tooth movement during a phase other than the alignment phase of orthodontic treatment, including, but not limited to, a gap or space closure phase or orthodontic treatment. In yet another embodiment, light therapy regulates tooth movement following the alignment phase of orthodontic treatment.

In some embodiments, the region to which light is administered is any oral tissue, such as soft tissue or bone tissue, including the alveolar soft tissue and, in some embodiments, the alveolar mucosa. In some embodiments, the oral tissue is that on which oral surgery was performed. In some embodiments, the oral tissue includes one or both of hard and soft tissue at the site of oral surgery within the patient's oral cavity. The present methods are useful for at least one of treating tissue and promoting soft tissue healing after one or more of oral surgery, maxillofacial surgery, craniofacial surgery and orthognathic surgery. The oral surgery can include periodontal surgery; surgery for orthodontic purposes; surgery for non-orthodontic purposes; placement of one or more dental implants; surgery relating to bone grafts; surgery relating to oral cancer; abnormal cell growth, or a tumor; surgery for tooth removal; gingival surgery; and surgery relating to connective tissue grafts, gingival grafts, or other soft tissue grafts. More specifically, the oral surgery can include surgery for tooth removal for orthodontic reasons and surgery to remove one or more teeth for non-orthodontic reasons, including, but not limited to, tooth removal because of one or more of the following conditions: supernumerary teeth, ectopic teeth (e.g., in which the canine tooth is impacted in the patient's palate), impacted wisdom teeth, periodontal disease, fractured or otherwise traumatized teeth, failing infected root canal treated teeth, unrestorable teeth, or infected teeth. The oral tissue can include one or more of: a portion or all of tissue supporting one or more teeth, the gums (i.e., gingiva), the alveolar soft tissue, a maxillary alveolar bone, mandibular alveolar bone, or one or more teeth. Accordingly, the invention further provides methods for treating oral tissue after oral surgery, comprising administering an effective amount of light to a patient, wherein the effective amount of light is irradiated from the emitter of an apparatus of the invention. In some embodiments, the treating comprises healing.

In some embodiments, light administration to the oral tissue begins within about 24 hours of performance of the oral surgery (including, for example, placement of a dental implant). In some embodiments, light administration to the oral tissue begins within about 6 hours of performance of the oral surgery (including, for example, placement of the dental implant). In some embodiments, light administration to the oral tissue begins within about 1 hour of performance of the oral surgery (including, for example, placement of the dental implant). In some embodiments, light is administered to the oral tissue in one or more treatment sessions. In some embodiments, the light is administered to the oral tissue for about 1 minute to about 10 minutes during the treatment session. In some embodiments, the light is administered for about 6 minutes during the treatment session. In some embodiments, the light is administered for about 3 minutes during the treatment session. In some embodiments, the light is administered to the patient during one treatment session per day. In some embodiments, the light is administered to the patient during two treatment sessions per day.

In some embodiments, at least a portion of the apparatus contacts, when the light is administered, a region of the patient's alveolar soft tissue on which surgery was performed. In some embodiments, the method also includes allowing a heavy force to be exerted on one or more teeth of the patient, who is in need thereof. When applicable, light can be administered before, during or after the heavy force is exerted. The present methods are also useful for increasing the rate of oral-tissue healing following oral surgery. Accordingly the invention further provides methods for increasing the rate of oral-tissue healing following oral surgery, comprising administering an effective amount of light to a patient, wherein the effective amount of light is irradiated from the emitter of an apparatus of the invention. In some embodiments, at least a portion of the apparatus contacts, when the light is administered, a region of the patient's alveolar soft tissue on which surgery is intended to be performed. In some embodiments, the method also includes allowing a heavy force to be exerted on one or more teeth of the patient, who is in need thereof. When applicable, light can be administered before, during or after the heavy force is exerted.

In some embodiments, the methods further comprise performing oral surgery on the oral tissue. The oral surgery can be performed prior to or subsequent to the administration of light treatment according to the present methods. In some embodiments, the region of light administration can be the alveolar bone or the alveolar soft tissue. In some embodiments, the administration occurs for about 20 minutes. In some embodiments, the wavelength of administered light is about 625 nm. In some embodiments, the wavelength of administered light is about 850 nm. In some embodiments, light is administered at an intensity of about 100 mW/cm$^2$. In some embodiments, the light may be administered following oral surgery, prior to oral surgery, or during oral surgery. In some embodiments, the light is administered to tissue on which oral surgery was performed, prior to oral surgery or during oral surgery. In some embodiments, the tissue will be or is in need of healing, e.g., as a result of the oral surgery. In some embodiments, the invention relates to methods for treating nerve damage or numbness, which may occur as a result of oral surgery (e.g., on a patient's jaw). In some embodiments, the invention relates to methods for treating or preventing periodontitis, comprising administering an effective amount of light to a patient, wherein the effective amount of light is irradiated from the emitter of an apparatus of the invention.

In some embodiments, the invention relates to methods for treating a site of oral surgery, comprising administering an effective amount of light to a patient, wherein the effective amount of light is irradiated from the emitter of an apparatus of the invention. In some embodiments, the treating comprises healing. In some embodiments, the invention relates to methods for healing oral tissue adjacent to one or more dental implants, for example, endosseous dental implants. More specifically, the methods can include healing oral tissue at a site of surgical placement of one or more dental implants, in which the site includes one or both of hard tissue and soft tissue. Healing of the oral tissue can include one or both of accelerating the growth of bone between a bore drilled into the jaw for placement of the dental implant and the surface of the dental implant and accelerating osseo-integration of endosseous dental implants. The method for healing surgical site oral tissue comprises administering an effective amount of light to a patient, wherein the effective amount of light is irradiated from the emitter of an apparatus of the invention. In some embodiments, at least a portion of the apparatus contacts the alveolar soft tissue when the light is administered. In some embodiments, the methods further comprise allowing a heavy force to be exerted on one or more teeth of the patient who is in need thereof. When applicable, light can be administered before, during or after the heavy force is exerted. In one embodiment, these methods can be performed according to the teachings disclosed herein for the methods for regulating tooth movement.

In some embodiments, the present methods can further comprise applying a substance to a region, such as an oral region, e.g., the alveolar soft tissue, or in the proximity of a region, before, during, or after the administration of light. The substance can be applied before, during, or after the intra-oral apparatus is within the mouth of the patient. In some embodiments the methods do not comprise applying a substance to a region, or in the proximity of a region, before, during, or after the administration of light, or before, during, or after the exertion of heavy forces. In some instances, a substance can already occur at a region naturally. The substance can enhance or inhibit the effects of the light administration. In one embodiment, the substance can be a visible-light- or infrared-light-absorbing substance, such as a dye. One or more light characteristics, such as wavelength, can be selected in response to the presence or application of the substance.

Figure 92:
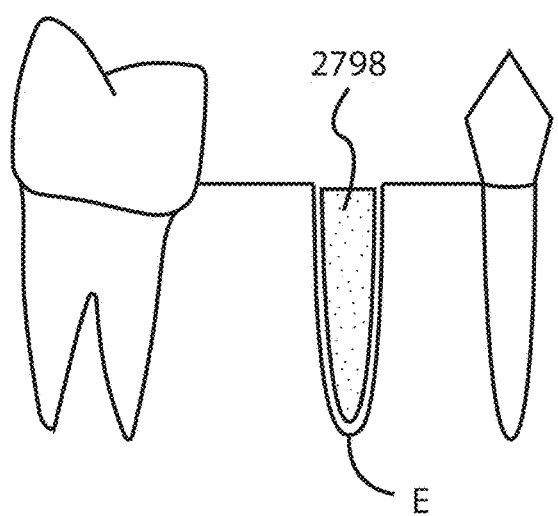
FIG. 92 is a side view of a barrier implant implanted at an extraction site according to an embodiment.

Although methods for treating a site of oral surgery have been described herein, in some embodiments, as increasing or accelerating a rate of oral tissue healing following the oral surgery, in other embodiments, it may be desirable to delay healing of the oral tissue at the site of the oral surgery. For example, an orthodontic treatment program can include a first phase, during which a patient's teeth are aligned and leveled, and a second phase in which gaps or spaces between teeth are closed (e.g., through retraction of one or more anterior teeth and/or mesial movement of one or more posterior teeth). In some treatment programs, one or more of the patient's teeth (e.g., one or more premolars in a crowded dental arch) are extracted before an orthodontic appliance is installed and before the first phase of the orthodontic treatment. Light therapy treatment, as described in various embodiments herein, may, in some cases, stimulate and accelerate healing of oral tissue at the site of extraction. The accelerated healing can include an increased rate of bone growth as the extraction site (e.g., tooth socket) is healed. The higher bone density at the extraction site (compared to the expected bone density of a normal rate of healing in the absence of light therapy), however, may not be preferable for patients whose orthodontic treatment program includes the second phase for gap or space closure, because the higher bone density can slow down movement of tooth roots that is needed for the gap or space closure. In other words, the tooth socket at the extraction site may include denser and more mature bone, than would otherwise occur in the absence of the light therapy for tooth movement during the first, alignment, phase, and thus slow the resorption of bone and movement of tooth roots during the gap closure phase of orthodontic treatment. Accordingly, in a method according to an embodiment, a barrier implant 2798 (see, e.g., FIG. 92) is implanted at an extraction site E following extraction of the tooth. In some embodiments, the barrier implant 2798 is implanted immediately after the tooth is extracted, such as during the same oral surgery session. As such, the barrier implant 2798 is also implanted before light therapy is administered. The barrier implant 2798 is configured to prevent accelerated healing at the extraction site E as a result of the light therapy administration during an alignment phase of orthodontic treatment. The barrier implant 2798 can be, for example, a resorbable collagen plug. The collagen plug 2798 can be configured to resorb as new bone is formed at the extraction site E, and such that the new bone is formed more slowly than the accelerated healing that would otherwise occur because of the light therapy administration.

One aspect of the invention provides for a light treatment kit comprising an intra-oral light-therapy apparatus as described herein and instructions for use in the present methods. The kit can further comprise a light source that is separate from the intra-oral light-therapy apparatus. The separate light source and/or the light sources of the intra-oral light-therapy apparatus can be removable and disposable, so that they can be easily replaced after a given amount of use. In some embodiments, a light-therapy apparatus and separate light sources can be individually packaged or can be packaged together. The separate light source can operate in conjunction with the light sources of the intra-oral light-therapy apparatus to aid in light administration. The separate light sources can emit light in any manner described herein and can further have any wavelength of characteristic described herein.

The kit can also comprise a programmable controller as described herein. The kit can further comprise any components useful for the controller to operate. For example, the kit can comprise a component to power the controller or the intra-oral light-therapy apparatus. The kit can also comprise a component that allows the controller to operably connect with an intra-oral light-therapy apparatus.

The kit can also comprise software, an algorithm, or a set of computer readable media that can provide instructions to a controller. The software, algorithm, or set of computer readable media can be provided on a memory medium. The memory medium can be a removable or portable, such as a CD, USB flash drive, or external hard drive The kit can be conveniently packaged and can be commercially available. The kit can also include written instructions for use or maintenance of items therein.

As described herein, a light therapy apparatus according to embodiments of the invention can be electronically linked, or paired, with an external device, such as a mobile phone, including smartphones (e.g., an iPhone® or an Android™ based device), personal digital assistance, computer, tablet, portable electronic device, or the like. In this manner, the apparatus can be configured for at least one of wireless uni-directional or wireless bi-directional communication with the external device, such as via a Bluetooth® or other wireless connection. In some embodiments, the apparatus (e.g., apparatus 2500) is configured to transmit data associated with a patient's compliance with a prescribed treatment program, during which the patient is to use the apparatus to administer light therapy to the patient's teeth, to the external device. As such, in some embodiments, a light therapy system includes the external device. The external device can be used, for example, by a dental practitioner to receive, store, and analyze the patient compliance data, in addition to other patient information, as described herein.

Referring to FIGS. 93-102, the external device can be configured to execute code to at least one of receive, store, or process the patient compliance data transmitted by the light therapy apparatus. For example, an application including the executable code can be loaded onto the external device. The executable code can be configured to display one or more screens on the external device to enable the dental practitioner to enter information associated with one or more patients and access the patient compliance data.

Figure 93:
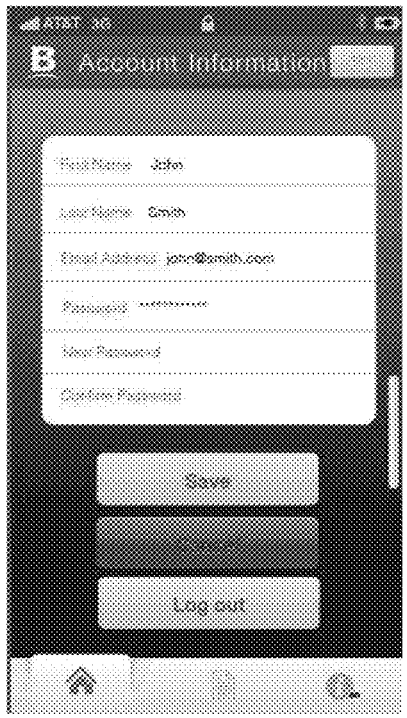
FIGS. 93-103 are images of sample display screens of an external electronic device according to an embodiment.
Figure 94:
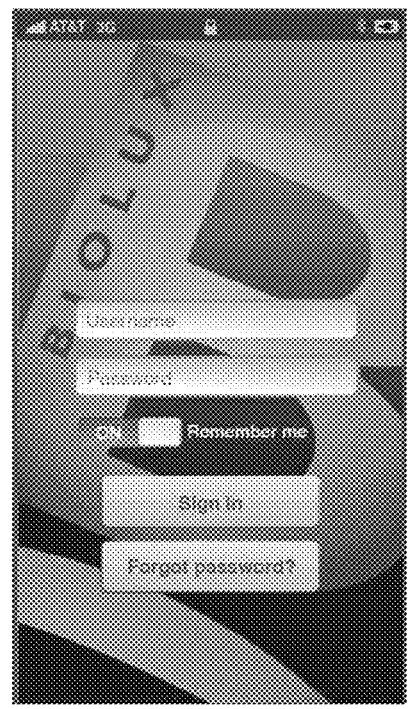
Figure 95:
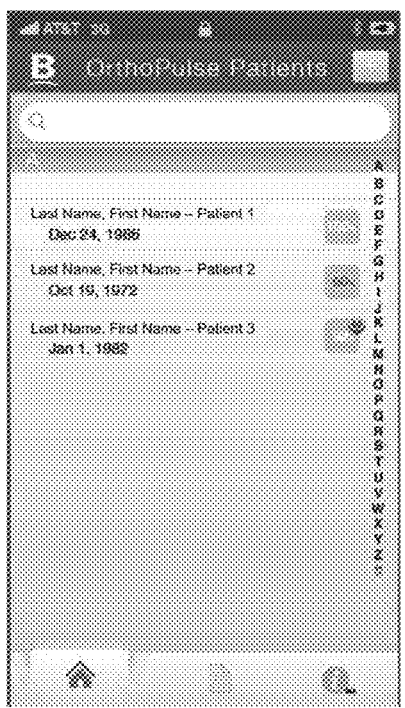

The external device can be configured for the practitioner (or a designated compliance administrator) to create a new account. For example, as shown in FIG. 93, the external device can require entry of the practitioner's name, an email address, and a password (and can include password reset capabilities). As shown in FIG. 94, the external device can be configured to require entry of log-in credentials to access the application, such as via a long-in screen, to maintain security of the patient information. As shown in FIG. 95, the external device can be configured to display a list of patients for whom patient information has been entered onto the external device.

Figure 96:
Figure 97:
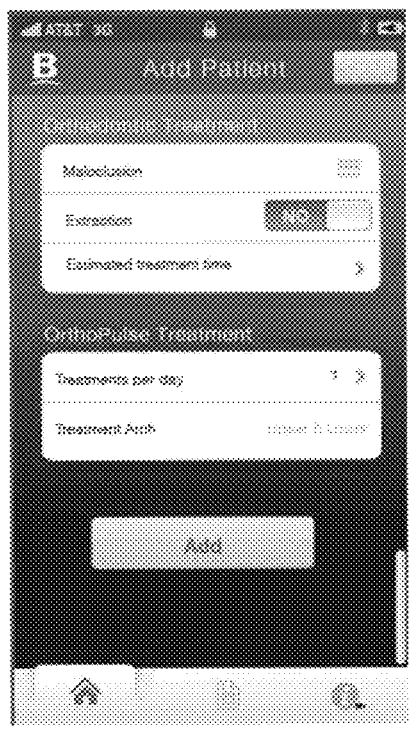
Figure 98:
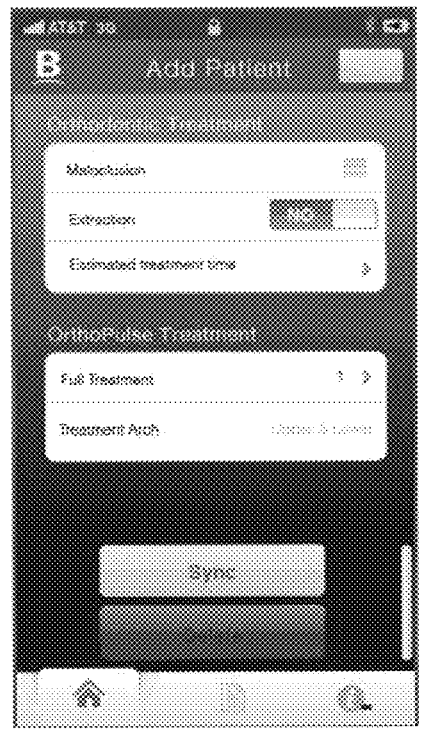

As shown in FIGS. 96-98, the external device can be configured to display a screen via which information associated with a new patient can be added to the external device. For example, external device can be configured to receive patient information such as the patient's name, date of birth, gender, contact information (e.g., an email address). The external device can also be configured to receive information associated with an orthodontic treatment program for the patient. For example, the external device can be configured to receive information about the patient's malocclusion, whether the patient's orthodontic treatment includes tooth extraction, and the patient's estimated treatment time. The external device can also be configured to receive information about the patient's light therapy treatment program, including the number of treatment sessions to be administered per day, and the arch or arches (i.e., upper, lower, or upper and lower arches) to which light therapy is to be administered during the treatment session.

Figure 99:
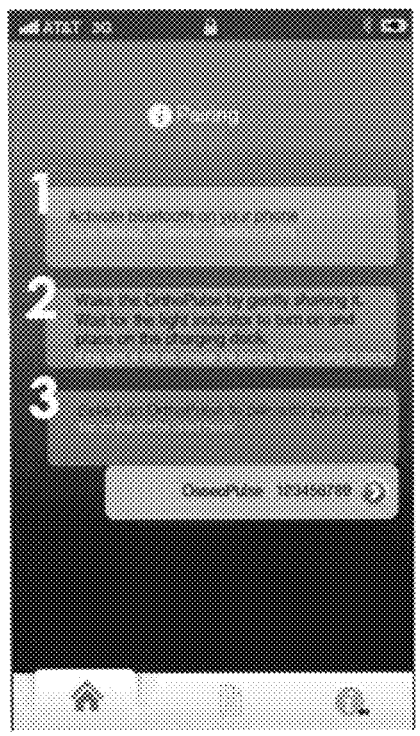
Figure 100:

As shown in FIG. 99, the external device is configured to be paired with a light therapy apparatus, e.g., a light therapy apparatus according to an embodiment described herein. In some embodiments, the external device is configured to display instructions on a pairing screen for pairing the external device and the light therapy apparatus. The external device can be configured to display a confirmation indicating whether or not the external device and the light therapy apparatus were successfully paired, as shown in FIG. 100. The external device can also be configured to provide a tutorial, for example, to assist the practitioner with entering the patient information as shown in FIGS. 96-98. The external device can be configured to be paired with the light therapy apparatus before or after the patient information is entered into the external device. After the external device and light therapy apparatus are paired, the external device can receive the patient compliance data from the light therapy apparatus.

Figure 101:
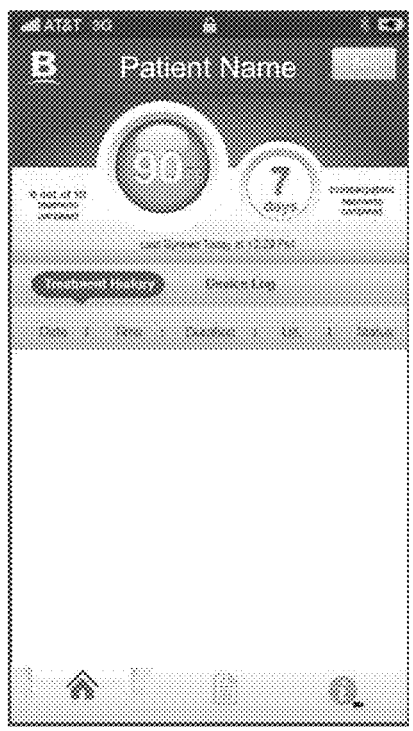
Figure 102:
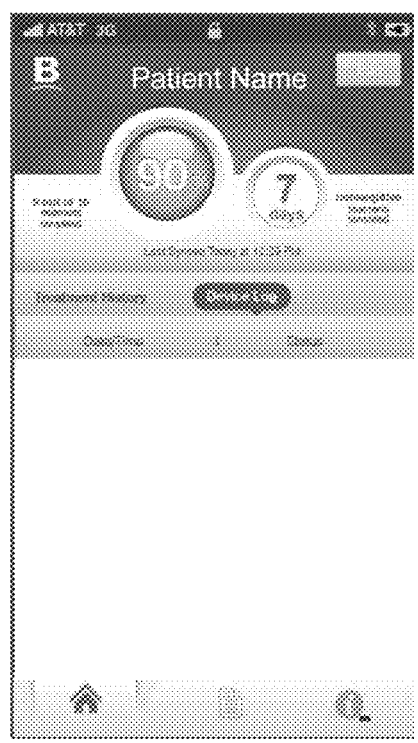

The external device can be configured to display at least a portion of the patient compliance data. For example, as shown in FIGS. 101 and 102, the external device can be configured to display a number of treatments sessions completed by and prescribed for the patient (e.g., "9 out of 10") and/or a percentage of the total number of prescribed treatments sessions completed by the patient (e.g., 90%). The external device can be configured to display a number of consecutive treatment sessions completed by the patient (e.g., "7 days of consecutive treatments completed"). The external device can be configured to display the last incidence (e.g., date and time) patient compliance data was received from the light therapy apparatus. In other words, the external device can display when the patient compliance data stored on the external device was last synced with the patient compliance data stored on the light therapy apparatus. As shown in FIG. 98, the external device can be configured to synchronize patient compliance data with the light therapy apparatus, if, for example, such synchronization was not already initiated by the light therapy apparatus itself.

Figure 103:
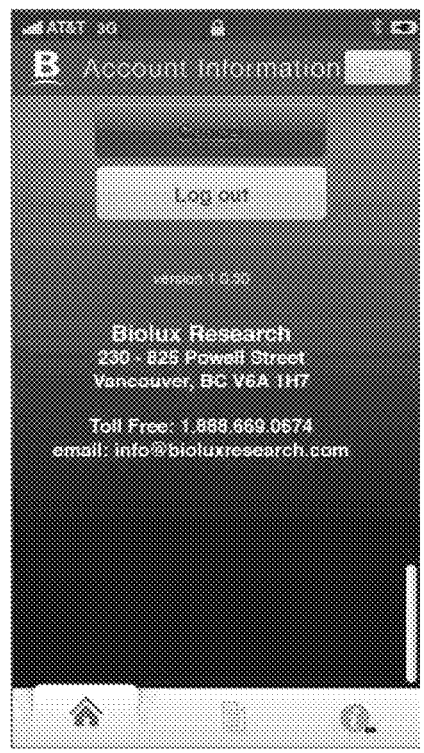

The external device can also be configured to display a log of the patient's usage of the light therapy apparatus, including a listing of one or more of the date a treatment session was administered using the light therapy apparatus, the time of the treatment session, the duration of the treatment session, whether the treatment session was administered with respect to the patient's upper or lower arch, and a status of the treatment session or light therapy device. As shown in FIG. 102, the external device can also be configured to display a log associated with the light therapy apparatus itself, including a status of the device and a date and time of the status. The status log can, for example, list the light therapy apparatus' status history indicating each time the apparatus was in one or more of the device statuses (or states), such as sleep, ready, charge, communication, or error statuses, described herein. Finally, as shown in FIG. 103, the external device can be configured to provide a log out option to exit the application. The external device can also be configured to display contact information, such as for a manufacturer of the light therapy apparatus, as shown in FIG. 103.

As shown in FIG. 112, a method 4100 according to an embodiment can include determining a rate by which a patient should transition from use of one orthodontic appliance applied to one or more teeth of the patient to use of another orthodontic appliance applied to one or more teeth of the patient. For example, an orthodontic treatment regimen for the patient can include using a plurality of orthodontic appliances, one at a time and in a predetermined or orthodontic-prescribed sequence. Said another way, the regimen can provide for sequentially removably coupling each orthodontic appliance from the plurality of orthodontic appliances to one or more teeth of the patient. More specifically, in some embodiments, each orthodontic appliance can be an aligner from a plurality, or set, of aligners configured to be removably coupled to the teeth of the patient in a predetermined order or sequence. The plurality of aligners can include at least one substantially transparent aligner. Each aligner of the plurality of aligners can be substantially transparent. In other embodiments, the plurality of orthodontic appliances can include any other suitable orthodontic appliance described herein. The time period during which the orthodontic appliance (e.g., a first aligner) is coupled to the patient's teeth is referred to with respect to this method as a treatment "period" during the treatment regimen. The patient need not wear the orthodontic appliance and/or have the orthodontic appliance installed on the patient's teeth continuously during the period. For example, for removable orthodontic appliances, the period could span several days or weeks, during which the patient can remove the appliance for periods (e.g., to brush their teeth, etc.).

Generally, a first phase of the method 4100 includes assessing a patient's individual rate of tooth movement during a period at which a portion of the orthodontic appliances from the plurality of orthodontic appliances are sequentially applied to the patient's teeth based on a predetermined schedule of when the orthodontic appliance is to be removed and replaced by the next orthodontic appliance in the sequence (also referred to herein as "switching" appliances), and a second phase of the method 4100 includes determining a modified or accelerated rate (compared to the predetermined schedule) of orthodontic appliance switching for the remaining orthodontic appliances from the plurality of orthodontic appliances in the sequence. The modified or accelerated rate of orthodontic appliance switching can be based on the patient's natural rate of tooth movement and/or a rate of tooth movement during use of the portion of orthodontic appliances from the plurality of orthodontic appliances. As such, the modified or accelerated rate of orthodontic appliance switching (i.e., the period determined for the patient) is specific to the patient and can optimize the patient's tooth movement during the orthodontic treatment and reduce the patient's overall orthodontic treatment time.

At 4110, the method 4100 includes receiving an indication associated with a contact between the orthodontic appliance and a tissue within an oral cavity of the patient. More specifically, the indication can be associated with one or more sensations caused by at least one of a pressure exerted by the orthodontic appliance removably within the oral cavity of the patient and/or a perceived pain associated with the orthodontic appliance that is or was coupled to the patient's teeth or can include an assessment of the indication by the patient. For example, in one embodiment, the indication includes the number of air gaps present between the teeth and orthodontic appliance, when the orthodontic appliance is coupled to the patient's teeth, and are perceived by the patient through visual assessment. In a further embodiment, the indication includes the aforementioned assessment of air gaps and one or more additional sensations. The sensation can include one or both of pressure and pain, and in one embodiment the one or more sensations (e.g., pressure and pain) are self-assessed by the patient. The self-assessment in one embodiment includes the assessment of pain on a scale of 1 to 3, where "1" indicates no pain or almost no pain, "2" indicates some pain and "3" indicates much pain. In another embodiment, the self-assessment includes the assessment of pressure exerted by the orthodontic appliance on a scale of 1 to 3, where "1" indicates no pressure or almost no pressure, "2" indicates moderate pressure and "3" indicates a high level of pressure (see, e.g., FIG. 113). In some embodiments, the receiving includes receiving a pressure indication associated with the pressure exerted by the orthodontic appliance on the tissue within the oral cavity and a pain indication associated with the orthodontic appliance being coupled to the teeth of the patient. In other embodiments, the receiving includes receiving an indication associated with a reduction in and/or absence of a pressure exerted by the orthodontic appliance and/or a reduction in and/or absence of a pain indication associated with the orthodontic appliance being coupled to the teeth of the patient.

The indication can be received, for example, at device external to the orthodontic appliance (also referred to herein as the "external device"), such as a mobile phone, including smartphones (e.g., an iPhone® or an Android™ based device), personal digital assistance, computer, tablet, portable electronic device, or the like. In this manner, for example, an orthodontist (or dental practitioner) can, remotely from the patient, access data associated with the received indication(s). As such, the orthodontist can review and/or evaluate the data and prescribe an accelerated or otherwise modified rate of orthodontic appliance switching for a remainder of the orthodontic treatment program including the remainder of the plurality of orthodontic appliances. Such remote access to the indication data allows the patient and orthodontist to avoid having multiple office visits. In some embodiments, as described in more detail below, the orthodontist and/or the patient can execute code to perform at least a portion of the evaluation of the received indication (s) data and/or determining a modified or accelerated orthodontic appliance switching based on the evaluation.

The indication can be received daily, or at another suitable interval. For example, pain, pressure and/or fit in one embodiment, is assessed on a daily basis by the patient and/or orthodontist. In one embodiment, the indication is received each day during the course of treatment with the orthodontic appliance or plurality thereof. In some embodiments, the indication is received each day for a predetermined number of days. For example, in some embodiments, the predetermined number of days is from about four days to about ten days. In another example, in some embodiments, the predetermined number of days is six days. Although the indication is received each day for the predetermined number of days, data included in the indication may vary over the course of the predetermined number of days. In other words, and as an example only, an indication received on day one of the predetermined number of days may include an indication of a sensation of pressure but no pain, while an indication received on day two of the predetermined number of days may include an indication of a sensation of pressure and a sensation of pain. However, in other embodiments, the indication does not vary over the course of predetermined number of days (e.g., pain, pressure and fit are assessed on each day).

Figure 113:
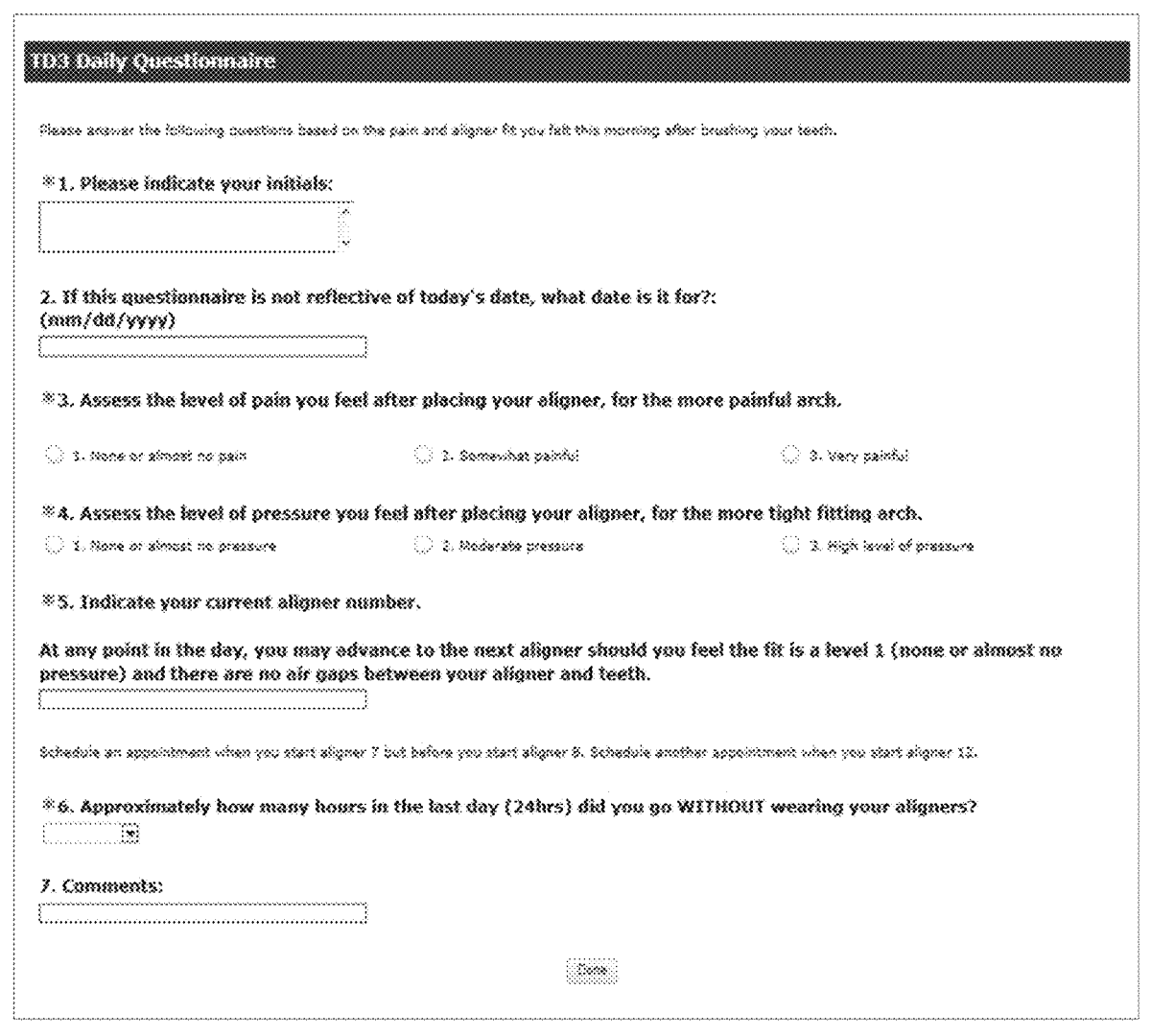

In some embodiments, the indication is input by the patient, as described in more detail herein. For example, a patient can input into an electronic device his or her answers to a series of questions related to the patient's use of the orthodontic appliance. Stated another way, the external device can be configured to receive data associated with one or more patient inputs into the patient's electronic device, including patient responses to an electronic questionnaire, such as the questionnaire shown in FIG. 113 (e.g., to assess pain, pressure and/or fit as described above). Referring to FIG. 113, the patient can input his or her initials (or other identifying information) and, optionally, indicate the date of orthodontic appliance usage for which the questionnaire is being completed. The patient can indicate a level of pain felt by the patient after applying the orthodontic appliance to one or more of the patient's teeth. For example, the indication can be a level of pain and/or pressure felt by the patient after applying an aligner to one or more of the patient's teeth. In some embodiments, the indication is based on the more painful arch of the upper or lower arches. Example pain indications include (1) none or almost no pain, (2) some pain, and (3) much pain. The patient can indicate a level of pressure felt by the patient after applying the orthodontic appliance to one or more of the patient's teeth. For example, the indication can be a level of pressure felt by the patient after applying the aligner to one or more of the patient's teeth. In some embodiments, the indication is based on the tighter fitting arch of the upper or lower arches. Example pressure indications include (1) none or almost no pressure, (2) moderate pressure, and (3) high level of pressure. In some embodiments, the indication relates to the number of air gaps present between the teeth and the aligner, scored on a scale of 1-3, where 1 indicates no air gaps. The patient can indicate the orthodontic appliance that is currently being applied to one or more of the patient's teeth, or that was applied to the one or more of the patient's teeth for the date of orthodontic appliance usage for which the questionnaire is being completed. For example, the patient can indicate an aligner number for a particular aligner from a plurality, or set, of aligners. The patient can indicate approximately how many hours in the last day (or 24 hour period) that the patient did not wear any orthodontic appliance from the plurality of orthodontic appliances. The external device can also optionally be configured to receive, via patient inputs to the questionnaire using the electronic device, additional comments from the patient.

In some embodiments, the orthodontic appliance is a first orthodontic appliance (e.g., an aligner) of the plurality of orthodontic appliances, the predetermined number of days is a first predetermined number of days, and/or the indication is a first indication. In such embodiments, the method 4100 optionally includes, at 4120, receiving a second indication associated with a sensation experienced by the patient and caused by a second orthodontic device from the plurality of orthodontic appliances. The indication can be the number of air gaps present between the patient's teeth and aligner, a sensation such as pressure or pain caused be the aligner, or a combination of the three. More specifically, the second indication can be associated with at least one of a pressure exerted by the second orthodontic appliance removably applied to the patient's teeth and/or within an oral cavity of the patient or a perceived pain associated with the second orthodontic appliance applied to the patient's teeth. In some embodiments, the receiving includes receiving a pressure indication associated with the pressure exerted by the second orthodontic appliance and a pain indication associated with the second orthodontic appliance. In other embodiments, the receiving includes receiving an indication associated with a reduction in and/or absence of a pressure exerted by the orthodontic appliance and/or a reduction in and/or absence of a pain indication associated with the orthodontic appliance being coupled to the teeth of the patient. The second indication can be received each day for a second predetermined number of days.

At 4130, the method 4100 includes determining a treatment period associated with each orthodontic appliance from the plurality of orthodontic appliances based on the indication (e.g., the first indication and/or the second indication). In some embodiments, the treatment period is determined based on the first indication, the second indication or both the first and second indication. For example, where the first indication is associated with one or more air gaps between an aligner and a patient's teeth or one or more sensations, e.g., pain or fit (pressure), the treatment period for the first orthodontic appliance of the plurality of orthodontic appliances is the number of days until pain is assessed as no pain or almost no pain, pressure is assessed as no pressure or almost no pressure, and no air gaps are present. In a further embodiment, where a plurality of orthodontic appliances are used in a treatment method, the treatment period for each of the respective plurality of orthodontic appliances is the number of days until pain is assessed as no pain or almost no pain, pressure is assessed as no pressure or almost no pressure, and no air gaps are present. In some embodiments, a weighted transition factor can be determined based on the indication for each day and the number of hours during which the orthodontic appliance has or had been within the oral cavity of the patient (e.g., applied to the one or more teeth of the patient). For example, the indication received by the external device can include an indication of the number of hours during which the orthodontic appliance was applied to the one or more teeth of the patient. Such information can be input by the patient, as described in more detail herein. In some embodiments, a tooth movement factor is determined based on the indication for each day. The tooth movement factor is associated, at least in part, with an amount of movement of one or more of the patient's teeth. In some embodiments, a weighted light factor is determined based on the indication for each day and a light indication associated with whether the patient has received a light therapy during the period when the orthodontic appliance has or had been within the oral cavity of the patient. The weighted light factor can include and/or be associated with any other parameter associated with the light therapy, such as the duration of the light therapy per day, the wavelength of the light therapy, the power of the light used during the light therapy or the like.

At 4140, the method 4100 includes producing a signal associated with the treatment period. For example, the signal (e.g., a first signal) can be produced after the treatment period is determined. In some embodiments, the signal is produced by the external device. The signal can include an electronic signal, including, but not limited to, a text message, a visual indicator, a graphical depiction. In some embodiments, the signal is sent to an electronic device associated with the patient, including, for example, a mobile phone, including smartphones (e.g., an iPhone®, a Google® device, or an Android™ based device), personal digital assistant, computer, tablet, portable electronic device, or the like.

At 4150, the method 4100 optionally includes determining a total treatment duration associated with the plurality of orthodontic appliances based on the indication. The total treatment duration is the total duration of the treatment regimen during which the plurality of orthodontic appliances is removably coupled to the patient's teeth.

At 4160, the method 4100 also optionally includes producing a second signal associated with a total treatment duration. For example, the second signal can include an electronic signal configured to be sent to the patient's device. The second signal can be configured to indicate to the patient the total period of time (duration) during which the patient sequentially has or will use the plurality of orthodontic appliances for their prescribed orthodontic treatment. As such, the second signal can also be configured to indicate when the patient's orthodontic treatment, or at least the portion of the orthodontic treatment including use of the sequence of orthodontic appliances, will end or has ended.

In some embodiments, the external device can be configured to execute code to at least one of receive the indication (s), determine the treatment period, and produce the signal (s). For example, an application including the executable code can be loaded onto the external device. The executable code can be configured to perform the following algorithm:

$$T=(N \times D)-(A \times D)$$

$$T2=(N \times M)-(A \times M)$$

where:
N=the total number of orthodontic appliances in the plurality of orthodontic appliances for the patient's arch with the highest number of prescribed orthodontic appliances;
D=in number of days, the frequency of orthodontic appliance switching pursuant to the predetermined schedule;
M=in number of days, a natural rate of orthodontic appliance switching after an evaluation period during the predetermined number of days;
A=the number of the orthodontic appliance in use by the patient with respect to the orthodontic appliance's placement in the sequence of the plurality of orthodontic appliances (e.g., orthodontic appliance number n in a sequence of 1 . . . n . . . 12 orthodontic appliances);
T=a time remaining for orthodontic appliance switching based on the predetermined schedule of orthodontic appliance switching;
T2=a time remaining for orthodontic appliance switching based on the modified or accelerated rate of orthodontic appliance switching.

The executable code can be configured to determine a percentage reduction in orthodontic treatment time for the patient using the modified or accelerated rate of orthodontic appliance switching based on the following algorithm: (T−T2)/T.

The method optionally includes administering light therapy when one or more orthodontic appliances of the plurality of orthodontic appliances are sequentially coupled to the one or more teeth of the patient. For example, the first orthodontic appliance can be applied to one or more of the patient's teeth, at a first time and for a first time period. Light is administered to one or more of the patient's teeth when the first orthodontic appliance is applied to the one or more of the patient's teeth during at least a portion of the first time period. For example, light can be administered according to any suitable method described herein, including at any suitable wavelength, intensity, or for any suitable duration, as described herein. In some embodiments, a light therapy apparatus is disposed about or over a portion of the first orthodontic appliance when the light is administered. In some embodiments, the light therapy apparatus is configured to detect a number, within the sequence of the plurality of orthodontic appliances, of an orthodontic appliance applied to one or more of the patient's teeth. For example, the light therapy apparatus can be configured to detect the orthodontic appliance's number using radio frequency identification ("RFID"). In such embodiments, for example, the light therapy apparatus can include an RFID reader in at least one of an intra-oral housing or an extra-oral housing of the light therapy apparatus. In another example, the light therapy apparatus includes an optical bar code reader configured to read an optical bar code of the orthodontic appliance, which can indicate the orthodontic appliance's number.

A method according to an embodiment for aligning one or more of a patient's teeth. The methods include disposing a first orthodontic appliance within an oral cavity of a patient such that the orthodontic appliance is removably coupled to the teeth of the patient. The first orthodontic appliance can be any suitable orthodontic appliance described herein, including, but not limited to, an aligner. The methods include determining a time period specific to the patient. The time period during which an orthodontic appliance (e.g., the first orthodontic appliance, such as a first aligner) is coupled to the patient's teeth is referred to with respect to this method as a "period" during a treatment regimen. The method includes maintaining the first orthodontic appliance within the oral cavity for the period. Although the orthodontic appliance is described herein as being maintained within the oral cavity during the period, in some embodiments, the patient need not wear the orthodontic appliance and/or have the orthodontic appliance installed on the patient's teeth absolutely continuously during the period. For example, for removable orthodontic appliances, the period could span several days or weeks, during which the patient can remove the appliance for brief periods (e.g., to brush their teeth, etc.) and then reinstall the appliance within the oral cavity. After the period, a second orthodontic appliance is disposed within the oral cavity such that the second orthodontic appliance is removably coupled to the teeth of the patient.

The method can include coupling orthodontic appliances from the plurality of orthodontic appliances, in sequence, until alignment of one or more of the patient's teeth is achieved. For example, in some embodiments, the patient may sequentially dispose a first, a second, a third . . . up to an $n^{th}$ orthodontic appliance (where n is any suitable integer, for example, from four to thirty) from the plurality of orthodontic until alignment is achieved. In use, for example, the patient can wear the first orthodontic appliance for a period of time, then replace the first orthodontic appliance with the second orthodontic appliance, which is worn for a subsequent period of time, then replace the second orthodontic appliance with a third orthodontic appliance, which is worn for a subsequent period of time, and so on with repeatedly replacing (e.g., removing the most recently worn appliance and installing the next appliance in the sequence) orthodontic appliances until alignment is achieved. In some embodiments, alignment of one or more teeth of one or both of the upper or lower arches is achieved when the one or both of the upper arch LII score or the lower arch LII score is within the range of zero (0) mm to less than one (1) mm. In other words, the patient's teeth can be determined to be in alignment when the patient's LII score for the arch being measured is less than 1 mm. An LII score of zero (0) can indicate that the teeth are perfectly aligned.

In some embodiments, each orthodontic appliance from the plurality of orthodontic appliances is disposed within the oral cavity of the patient such that each orthodontic appliance is removably coupled to the patient's teeth (also referred to herein as being "worn") by the patient, in order, for a period of time. The period of time can be, for example, a few days (e.g., 2, 3, 4, 5, or 6 days) or one or more weeks (e.g., 1, 2, or 3 weeks). The period of time that one orthodontic appliance from the plurality of orthodontic appliances is worn by the patient can be different than a period of time that another orthodontic appliance from the plurality of orthodontic appliances is worn by the patient. In other words, each orthodontic appliance from the plurality of orthodontic appliances can be worn by the patient for a period time that is independent or irrespective of a period of time for which another orthodontic appliance from the plurality of orthodontic appliances is worn by the patient. For example, the first orthodontic appliance can be worn for a first period of time, the second orthodontic appliance can be subsequently worn for a second period of time that is less than or greater than the first period of time in duration. In some embodiments, a third orthodontic appliance is worn subsequent to the second orthodontic appliance for a third period of time that is less or greater in duration than at least one of the first period of time or the second period of time. In other embodiments, the third orthodontic appliance is worn subsequent to the second orthodontic appliance for a third period of time that is substantially equal in duration to the first period of time or the second period of time. Additionally, a first portion or subset of the plurality of orthodontic appliances can be worn for a substantially equal period of time, and second portion or subset of the plurality of orthodontic appliances can be worn for one or more periods of time different than the period of time the first portion of plurality of orthodontic appliances is worn.

In some embodiments, a method of coupling orthodontic appliances from a plurality of orthodontic appliances can include administering a light therapy using any of the light therapy devices shown and described herein. Similarly stated, in some embodiments, a method of changing orthodontic appliances (replacing a first orthodontic appliance with a second, unused orthodontic appliance) can include a light therapy using any of the light therapy devices shown and described herein. For example, in some embodiments, a method can include disposing a first orthodontic appliance within an oral cavity of a patient such that the first orthodontic appliance is removably coupled to the teeth of the patient. The first orthodontic appliance can be any suitable orthodontic appliance from a set of removable orthodontic appliances as described herein. The method further includes administering a light therapy when the first orthodontic appliance from the set of orthodontic appliance is within the oral cavity of the patient. The light therapy can be administered using any of the light therapy devices shown and described herein.

A period specific to the patient is determined. As described herein, the period is the time period during which an orthodontic appliance from the set of orthodontic appliances is to be worn according to a treatment regimen. The period can be determined using any of the methods described herein. For example, in some embodiments, the period can be determined based on a light indication associated with the light therapy administered. In other embodiments, as described herein, the period can be determined based on an indication associated with the reduction of the pain, a reduction of a sensation, an assessment of whether air gaps between the teeth and orthodontic appliance exist and/or the reduction the pressure associated with the first orthodontic appliance. The first orthodontic appliance is maintained within the oral cavity for the period.

The method further includes disposing a second orthodontic appliance within the oral cavity of the patient after the period such that the second orthodontic appliance is removably coupled to the teeth of the patient.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code or algorithm) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

Some embodiments and/or methods described herein can be performed by software (executed on hardware), hardware, or a combination thereof. Hardware modules may include, for example, a general-purpose processor (or microprocessor or microcontroller), a field programmable gate array (FPGA), and/or an application specific integrated circuit (ASIC). Software modules (executed on hardware) can be expressed in a variety of software languages (e.g., computer code), including C, C++, Java®, Ruby, Visual Basic®, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

The invention further provides methods for regulating tooth movement, maintaining oral tissue health or improving oral tissue health. The method includes administering to a patient in need thereof an effective amount of light from the emitter of the apparatus.

The apparatus is useful for increasing the rate of oral-tissue healing following oral surgery.

The invention further provides methods for increasing the rate of oral-tissue healing following oral surgery. The method includes administering to a patient's tissue on which oral surgery was performed and which is in need of healing an effective amount of light from the emitter of the apparatus.

In some embodiments, an apparatus includes a housing, an emitter and an electronic circuit. The housing is configured to fit within a patient's mouth. The emitter is optically coupled to the housing, and is configured to emit an effective amount of a light to the alveolar soft tissue when the housing is disposed within the mouth. The electronic circuit is operatively coupled to the emitter, and is configured to control the emitter when the housing is disposed within the mouth and the apparatus is in use during orthodontic treatment.

The apparatus is useful for regulating tooth movement or for maintaining or improving oral tissue health.

The invention further provides methods for regulating tooth movement, maintaining oral tissue health or improving oral tissue health. The method includes administering to a patient in need thereof an effective amount of light from the emitter of the apparatus.

The invention provides systems, including a first portion and a second portion. The first portion is configured to be disposed within a patient's mouth. A first emitter coupled to the first portion is configured to emit an effective amount of a light at a first wavelength to the alveolar soft tissue when the first portion is disposed within the mouth. An electronic circuit is operatively coupled to the first emitter, and is configured to control the first emitter when the first portion is disposed within the mouth and the apparatus is in use during a first stage of an orthodontic treatment. The first stage begins at a time $T_0$. The second portion is different from the first portion, and is configured to be disposed within the patient's mouth. A second emitter is coupled to the second portion and is configured to emit an effective amount of a light at a second wavelength, different than the first wavelength, to the alveolar soft tissue when the second portion is disposed within the mouth. The electronic circuit is operatively coupled to the second emitter, the electronic circuit configured to control the second emitter when the second portion is disposed within the mouth and the apparatus is in use during a second stage of the orthodontic treatment. The second stage is subsequent to the first stage, and begins at a time $T_{>0}$.

In some embodiments, a method includes receiving, each day for a predetermined number of days, an indication associated with contact between an orthodontic appliance and a tissue within an oral cavity of a patient. The orthodontic appliance is one of a set of orthodontic appliances that is removably coupled to the teeth of the patient. A treatment period associated with each orthodontic appliance from the plurality of orthodontic appliances is determined based on the indication. The method further includes producing a signal associated with the treatment period.

In some embodiments, a method includes disposing a first orthodontic appliance within an oral cavity of a patient such that the first orthodontic appliance is removably coupled to the teeth of the patient. A period specific to the patient is determined. The first orthodontic appliance is maintained within the oral cavity for the period. The method further includes disposing a second orthodontic appliance within the oral cavity of the patient after the period such that the second orthodontic appliance is removably coupled to the teeth of the patient.

EXAMPLE 1

A male adult patient's Vitamin D3 blood-serum level is measured during his routine orthodontic-examination and -records appointment. Laboratory results indicate that the patient's vitamin D3 serum levels are at 20 ng/ml, which is considered to be deficient and abnormal. The patient's orthodontic diagnosis is Class I mild crowding with 4 mm of crowding on the upper arch and 4 mm on the lower arch. An orthodontic treatment plan is formulated to include the installation of a fixed orthodontic appliance with some mild expansion of the upper and lower arches.

The patient self-administers oral oil-based vitamin D3 capsules at an amount of 6000 IU per day for 3 months to increase and normalize his vitamin D3 serum levels. Laboratory serum testing is optionally performed again after 3 months of vitamin D3 supplementation. The patient maintains or adjusts his oral dose of vitamin D3 based on his subsequent lab results.

Orthodontic treatment is started either after the 3 month period or within three months prior. The orthodontic treatment includes conventional fixed orthodontic brackets and bands placed on the patient's teeth using an initial 0.016 inch NiTi wire tied in place with silicone ligatures. Light is administered to the patient on a daily basis for 20 minutes at an intensity of 50 mW/cm2 at wavelength of about 850 nm using an intra-oral light therapy apparatus, such as the one shown in FIG. 1. The orthodontic treatment continues with the finishing of teeth once the arches have been expanded. It is believed that the active orthodontic treatment would be completed in 50% to 75% less time than orthodontic treatment without light therapy due to the combination of daily administration of light and vitamin D3 supplementation.

At a passive stage of orthodontic treatment, i.e., retention phase, a fixed retention orthodontic appliance can be installed on the patient's teeth. In one embodiment, a Hawley retainer, which is a removable appliance that is designed to maintain tooth position of the anterior teeth, is installed on a patient's anterior teeth. In some embodiments, a fixed retainer appliance, such as one including orthodontic brackets, is bonded to the lower 6 anterior teeth. The patient continues with vitamin D3 supplementation. In some examples, the patient self-administers 2000 IU per day to 12,000 IU orally per day. The dosage can be determined based on vitamin D blood serum levels which can be measured periodically to determine dosing. As a result, alveolar bone density around the teeth can be increased during the passive stage. During the passive stage, the patient is administered once per week with light having a wavelength of about 625 nm using an intra-oral light therapy apparatus, such as the light therapy apparatus shown in FIG. 1 and/or FIG. 6, in areas of the upper and lower arch.

EXAMPLE 2

Figure 38:
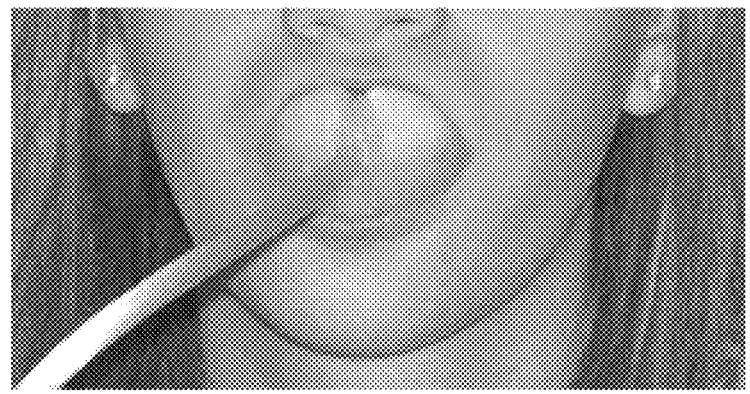
FIG. 38 is an image of an intra-oral light-therapy apparatus according to an embodiment of the invention disposed in the oral cavity of and in use by a patient.

In one study, an illustrative intra-oral light-therapy device of the invention, depicted in FIG. 38, was used during the alignment phase of orthodontic treatment to irradiate the maxillary anterior teeth of three (3) patients. The intra-oral light-therapy device included an intra-oral housing with a light-emitting fabric panel embedded in each of a silicone buccal flange and a silicone lingual or palatial flange of the intra-oral housing, and a LED light source disposed exterior to the mouth of the patient. The fabric of the light-emitting panel was made by weaving acrylic optical fibers into a mat. Each patient was provided with his or her own intra-oral light-therapy device, which was used in conjunction with a conventional buccal fixed orthodontic bracket treatment protocol. The treatment and results of three of the patients—Patient A, Patient B, and Patient C—are described in detail herein.

During the study, the intra-oral light-therapy device was used by each patient every day until he or she achieved an LII value of 1 mm or less. When in use, the intra-oral light-therapy device contacted each patient's maxillary alveolar soft tissue and irradiated the tissue with light having a wavelength of about 850 nm for about six minutes per day.

During the study, the patients visited a clinician every two (2) weeks. At each visit, the clinician performed regular orthodontic procedures, collected data that included intra-oral photographs and study models, recorded patient compliance and checked the functionality of the intra-oral light-therapy device. To assess the effectiveness of the treatment, the clinician used the LII grading system to score the models produced at each appointment. Maxillary anterior intra-oral light therapy continued every day until the clinician determined that the patient's LII score decreased to 1 mm or less.

Patients were selected for participation in this study based on, at least, the following criteria: (1) the patient was eligible for full mouth fixed orthodontic treatment of the upper arch to correct crowding, misalignment and rotated teeth; (2) a presence of permanent dentition (i.e., permanent, or adult, teeth); (3) the upper-arch teeth had an LII from 5 mm to 12 mm, provided that no tooth was blocked out of alignment; and (4) the patient was from 12 to 45 years old. The following types of individuals were excluded from this study: (1) pregnant women; (2) individuals enrolled in another study with periodontally involved teeth; (3) individuals who use bisphosphonates; or (4) individuals with any compromised dental or medical conditions.

Patient A

Figure 39:
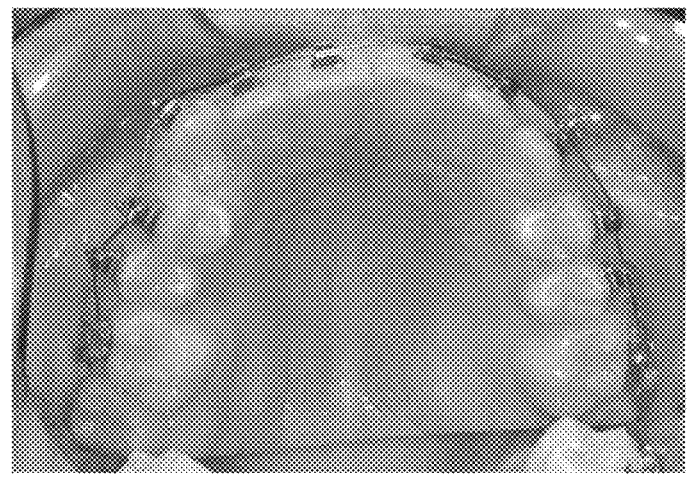
FIG. 39 is an image of an upper arch of a patient prior to light therapy treatment using the intra-oral light-therapy apparatus of FIG. 38.
Figure 40:
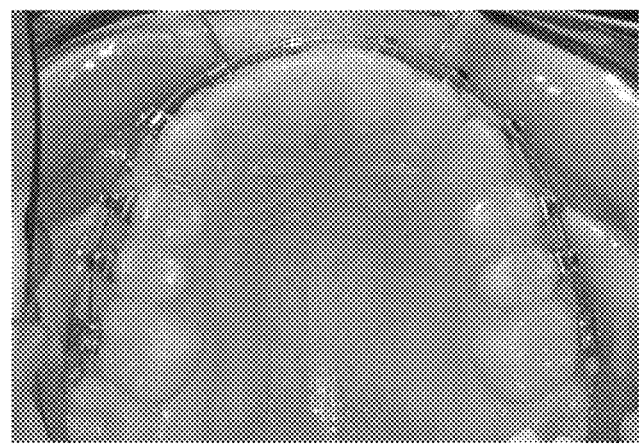
FIG. 40 is an image of the patient's upper arch of FIG. 39 after light therapy treatment using the intra-oral light-therapy apparatus of FIG. 38.

Patient A is a thirteen (13)-year-old female who wore SPEED System™ brackets and 0.016 inch Supercable nickel titanium wires during the alignment phase of her orthodontic treatment. On day 1 of the study, Patient A's upper-arch LII was about 5.1 mm. FIG. 39 is a photograph of Patient A's upper arch on day 1 of the study. After only 30 days of using the intra-oral light-therapy device for light treatment in combination with the SPEED System™ brackets and the wires, Patient A's LII was reduced to 0.5 mm. The rate of Patient A's tooth movement during that period was about 1.07 mm/week. FIG. 40 is a photograph showing the corrected orientation of the teeth in Patient A's upper arch on day 30 of the study.

Comparison to Control

The results for Patient A were compared to those from a 13-year-old control patient who also wore SPEED System™ brackets and 0.016 inch Supercable nickel titanium wires during the alignment phase of her orthodontic treatment, but who did not receive light therapy. The control patient had an upper-arch LII of about 5.2 mm on day 1. In contrast to the tooth-movement time for Patient A, it took 78 days for the control patient's upper-arch LII to reduce to 1 mm or less. The rate of the control patient's tooth movement during that period was only about 0.42 mm/week.

Patient B

Figure 41:
FIG. 41 is an image of the upper arch of a patient prior to light therapy treatment using the intra-oral light-therapy apparatus of FIG. 38.
Figure 42:
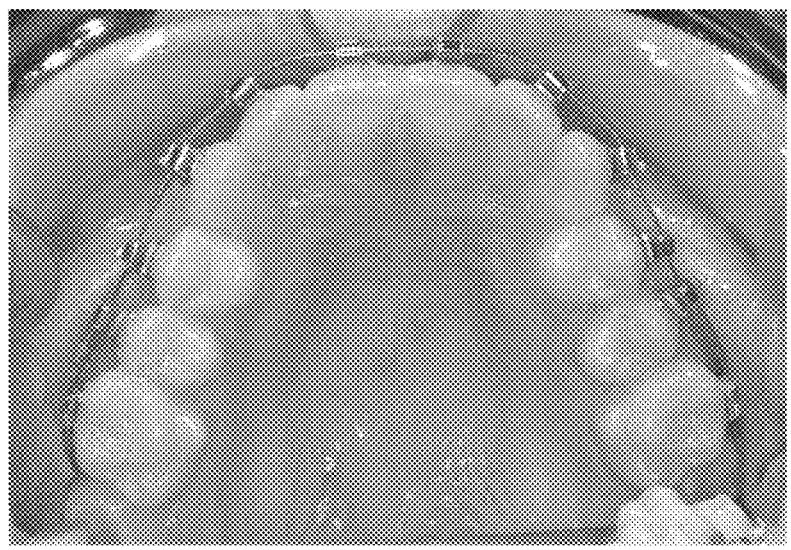
FIG. 42 is an image of the patient's upper arch of FIG. 41 after light therapy treatment using the intra-oral light-therapy apparatus of FIG. 38.

Patient B is also a thirteen (13)-year-old female who wore SPEED System™ brackets and 0.016 inch Supercable nickel titanium wires during the alignment phase of her orthodontic treatment. On day 1 of the study, Patient B's upper-arch LII was about 9.3 mm. FIG. 41 is a photograph of Patient B's upper arch on day 1 of the study. After only 41 days of using the intra-oral light-therapy device for light treatment in combination with the SPEED System™ brackets and the wires, Patient B's LII was reduced to 0.8 mm. The rate of Patient B's tooth movement during that period was about 1.45 mm/week. FIG. 42 is a photograph showing the corrected orientation of the teeth in Patient B's upper arch on day 41 of the study.

Comparison to Control

The results for Patient B were compared to those from a similar-age, control patient who also wore SPEED System™ brackets and 0.016 inch Supercable nickel titanium wires during the alignment phase of orthodontic treatment, but who did not receive light therapy. The control patient had an upper-arch LII of about 8.8 mm on day 1. In contrast to the tooth-movement time for Patient B, it took 129 days for the control patient's upper-arch LII to reduce to 0.3 mm. The rate of the control patient's tooth movement during that period was only about 0.46 mm/week.

Patient C

Patient C is an eighteen (18)-year-old male who wore In-Ovation L Straightwire system brackets and both 0.012 inch and 0.016 inch nickel titanium wires during the alignment phase of his orthodontic treatment. On day 1 of the study, Patient C's upper-arch LII was about 5.02 mm. After only 42 days of using the intra-oral light-therapy device for light treatment in combination with the In-Ovation L Straightwire system and the wires, Patient C's LII was reduced to zero. The rate of Patient C's tooth movement during that period was about 0.84 mm/week.

EXAMPLE 3

In one study, an intra-oral light therapy device of the invention, depicted in FIGS. 43-44, was used during the alignment phase of orthodontic treatment to irradiate one or both of the maxillary and mandibular anterior teeth of nine (9) patients (Intra-Oral Group). The intra-oral light therapy device included a flexible intra-oral housing with LEDs mounted on a flexible circuit and embedded in soft flexible buccal flanges of the intra-oral housing. Each patient was provided with his or her own intra-oral light therapy device, which was used in conjunction with a conventional buccal fixed orthodontic bracket treatment protocol.

During the study, each patient wore 0.018 slot Mini-Diamond® brackets (obtained commercially from Ormco Corporation, Orange, CA) aligned with 0.014 or 0.016 inch nickel titanium wire, initially, and then progressed to using 0.016 inch by 0.016 inch (also referred to as "16×16") nickel titanium wire.

During the study, the intra-oral light therapy device was used by each patient every day until he or she achieved an LII value of 1 mm or less, with no single LII contact point greater than 0.25 mm. When in use, the intra-oral light therapy device irradiated the tissue with light having a wavelength of about 850 nm (±5 nm). Unless otherwise noted herein, light therapy was administered to one or both of the maxillary arch or the mandibular arch of each patient for about three minutes per day, and at a light output intensity from about 60 mW/cm$^2$ to about 100 mW/cm$^2$. The mean intensity of the irradiated light for the Intra-Oral Group was about 70 mW/cm$^2$.

During the study, the patients visited a clinician every two (2) to three (3) weeks. At each visit, the clinician performed regular orthodontic procedures, collected data that included intra-oral photographs and study models, recorded patient compliance and checked the functionality of the intra-oral light therapy device. To assess the effectiveness of the treatment, the clinician used the LII grading system to score the models produced at each appointment. The light therapy continued every day until the clinician determined that the patient's LII score decreased to 1 mm or less, with no single LII contact point greater than 0.25 mm. The clinician also collected dental impressions and models at $T_0$ (i.e., day 1), which represents the day of maxillary bonding, start of orthodontic treatment (e.g., date brackets and/or wires are installed on the patient's teeth), date of patient assignment of the intra-oral light therapy device, and start of the patient's daily usage of the intra-oral light therapy device, and at $T_1$, which represents the day at which the clinician determined the patient achieved an LII value of 1 mm or less, with no single contact point greater than 0.25 mm.

Patients were selected for participation in this study based on, at least, the following criteria: (1) the patient was eligible for full mouth fixed orthodontic treatment of the upper arch (and/or the lower arch) to correct crowding, misalignment and rotated teeth; (2) a presence of permanent dentition (i.e., permanent, or adult, teeth); (3) the upper-arch (and/or the lower-arch) teeth had an LII from 3 mm to 12 mm, provided that no tooth was blocked out of alignment; and (4) the patient was from 11-27 years old. The following types of individuals were excluded from this study: (1) pregnant women; (2) individuals enrolled in another study with periodontally involved teeth; (3) individuals who use bisphosphonates; or (4) individuals with any compromised dental or medical conditions.

Figure 59:
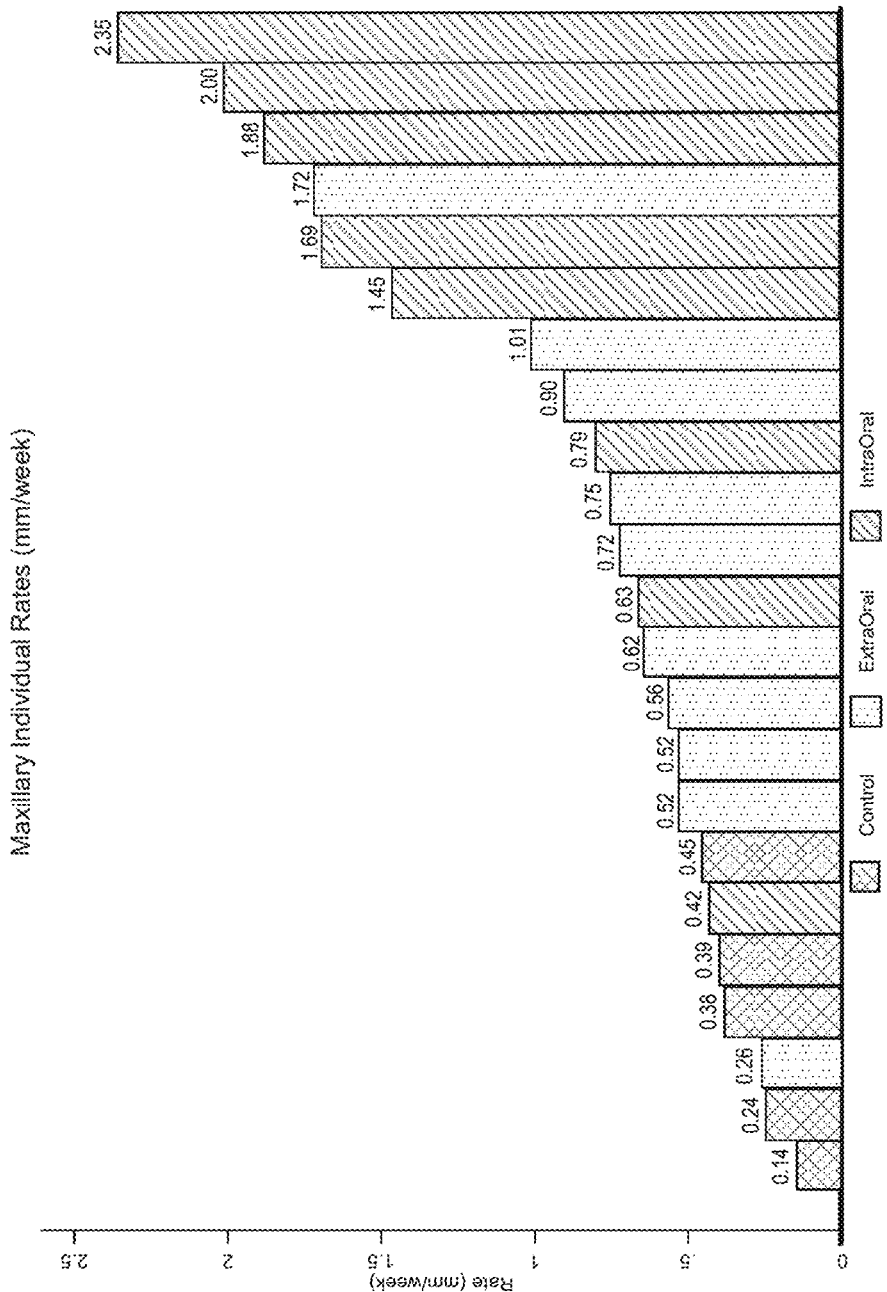
FIG. 59 is a graphical illustration of individual rates of maxillary tooth movement for study group participants.
Figure 60:
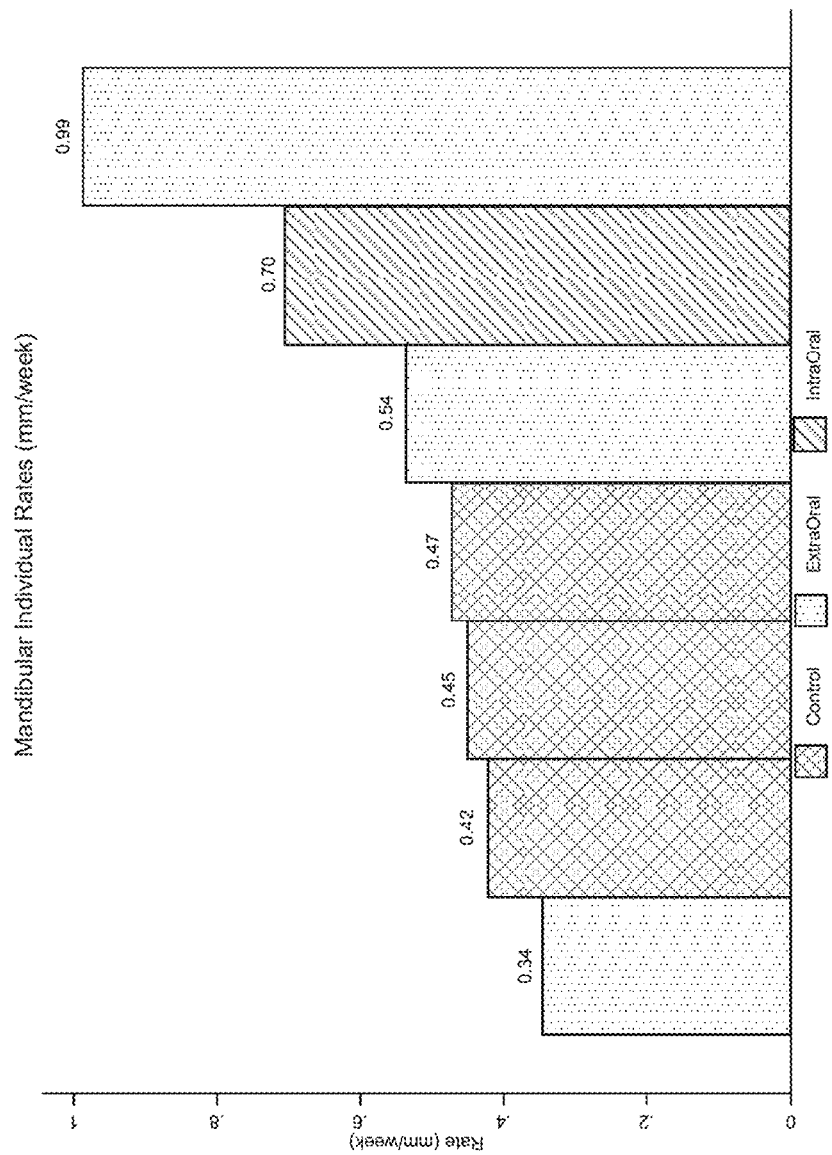
FIG. 60 is a graphical illustration of individual rates of mandibular tooth movement for study group participants.

The mean rate of tooth movement during the study period for the nine patients using the intra-oral light therapy device in combination with the conventional buccal fixed orthodontic bracket treatment protocol, as described herein, was about 1.32 mm per week. The mean time to alignment for the nine patients was 41 days. The rates of tooth movement among the nine patients during the study period ranged from 0.42 mm per week to 2.35 mm per week, as shown in FIGS. 59 and 60. The treatment and results of the nine patients— Patient D, Patient E, Patient F, Patient G, Patient H, Patient I, Patient J, Patient K, and Patient L—are described in detail herein.

For any age herein that is represented to the nearest tenth, the age indicates the age in years and fraction of the year.

Patient D

Patient D is a 12.8-year-old male. On day 1 (i.e., $T_0$) of the study, Patient D's upper-arch LII was about 5.7 mm. Light therapy was administered to Patient D's maxillary arch for about three minutes per day, and at a light output intensity of about 67 mW/cm$^2$. The patient received a light therapy dose of 12.1 J/cm$^2$ per day. After only 17 days of using the intra-oral light therapy device for light treatment in combination with the Mini-Diamond® brackets and wires, Patient D's LII was reduced to 0 mm. The rate of Patient D's tooth movement during the study period was about 2.35 mm/week.

Patient E

Patient E is a 12.6-year-old female. On day 1 (i.e., $T_0$) of the study, Patient E's upper-arch LII was about 6.0 mm. Light therapy was administered to Patient E's maxillary arch for about three minutes per day, and at a light output intensity of about 78 mW/cm$^2$. The patient received a light therapy dose of 14.0 J/cm$^2$ per day. After only 21 days of using the intra-oral light therapy device for light treatment in combination with the Mini-Diamond® brackets and the wires, Patient E's LII was reduced to 0 mm. The rate of Patient E's tooth movement during the study period was about 2.0 mm/week.

Patient F

Patient F is a 13.2-year-old female. On day 1 (i.e., $T_0$) of the study, Patient F's upper-arch LII was about 3.6 mm. Light therapy was administered for about three minutes per dental arch two times per day, and at a light output intensity of about 61 mW/cm$^2$. The patient received a light therapy dose of 22.0 J/cm$^2$ per day. After only 40 days of using the intra-oral light therapy device for light treatment in combination with the Mini-Diamond® brackets and the wires, Patient F's LII was reduced to 0 mm. The rate of Patient F's tooth movement during the study period was about 0.63 mm/week. It is noted that Patient F missed a scheduled visit with the clinician on day 21, which may have resulted in the foregoing alignment rate being significantly underestimated.

Patient G

Patient G is a 14.3-year-old male. On day 1 (i.e., $T_0$) of the study, Patient G's upper-arch LII was about 12.1 mm. Light therapy was administered for about three minutes per day, and at a light output intensity of about 78 mW/cm$^2$. The patient received a light therapy dose of 14.1 J/cm$^2$ per day. After only 50 days of using the intra-oral light therapy device for light treatment in combination with the Mini-Diamond® brackets and the wires, Patient G's LII was reduced to 0 mm. The rate of Patient G's tooth movement during the study period was about 1.69 mm/week.

Patient H

Patient H is a 16.5-year-old female. On day 1 (i.e., $T_0$) of the study, Patient H's upper-arch LII was about 5.5 mm. Light therapy was administered to Patient H's maxillary arch for about three minutes per day, and at a light output intensity of about 63 mW/cm$^2$. The patient received a light therapy dose of 11.3 J/cm$^2$ per day. After 92 days of using the intra-oral light therapy device for light treatment in combination with the Mini-Diamond® brackets and wires, Patient H's LII was reduced to 0 mm. The rate of Patient H's tooth movement during the study period was about 0.42 mm/week. It is noted that Patient H missed a scheduled visit with the clinician on day 74, which may have resulted in the foregoing alignment rate being significantly underestimated.

Patient I

Patient I is a 14.2-year-old female. On day 1 (i.e., $T_0$) of the study, Patient I's upper-arch LII was about 11.0 mm. Light therapy was administered to Patient I's maxillary arch for about three minutes per day, and at a light output intensity of about 78 mW/cm$^2$. The patient received a light therapy dose of 14.0 J/cm$^2$ per day. After 53 days of using the intra-oral light therapy device for light treatment in combination with the Mini-Diamond® brackets and wires, Patient I's LII was reduced to less than 1 mm. The rate of Patient I's tooth movement during the study period was about 1.45 mm/week. It is noted that Patient I missed a scheduled visit with the clinician on day 21, which may have resulted in the foregoing alignment rate being significantly underestimated.

Patient J

Patient J is a 12.4-year-old female. On day 1 (i.e., $T_0$) of the study, Patient J's upper-arch LII was about 5.5 mm. Light therapy was administered to Patient J's maxillary arch for about three minutes twice per day, and at a light output intensity of about 57 mW/cm$^2$. The patient received a light therapy dose of 20.4 J/cm$^2$ per day. After 49 days of using the intra-oral light therapy device for light treatment in combination with the Mini-Diamond® brackets and wires, Patient J's LII was reduced to 0 mm. The rate of Patient J's tooth movement during the study period was about 0.79 mm/week.

Patient K

Patient K is a 13.9-year-old male. On day 1 (i.e., $T_0$) of the study, Patient K's upper-arch LII was about 14.2 mm. Light therapy was administered to Patient K's maxillary arch for about three minutes twice per day, and at a light output intensity of about 58 mW/cm$^2$. The patient received a light therapy dose of 20.7 J/cm$^2$ per day. After 50 days of using the intra-oral light therapy device for light treatment in combination with SPEED System™ brackets and wires, Patient K's LII was reduced to 0.8 mm. The rate of Patient K's tooth movement during the study period was about 1.88 mm/week.

Patient L 17.7-year-old female. On day 1 (i.e., $T_0$) of the study, Patient L's lower-arch LII was about 3.0 mm. Light therapy was administered to Patient L's mandibular arch for about three minutes per day, and at a light output intensity of about 80 mW/cm$^2$. The patient received a light therapy dose of 14.4 J/cm$^2$ per day. After 22 days of using the intra-oral light therapy device for light treatment in combination with the Mini-Diamond® brackets and wires, Patient L's LII was reduced to 0.8 mm. The rate of Patient L's tooth movement during the study period was about 0.70 mm/week.

Comparison to Controls

The results for Patients D-J were compared to those from two control patients, identified here as Control A and Control B. Controls A and B were selected, in part, for having a similar age and initial LII of the upper-arch as Patients D-J. The same clinician evaluated Patients D-J and Controls A and B.

Control A is a 14-year-old female control patient who wore SPEED System™ brackets, and wires as described for Patients D-J, during the alignment phase of her orthodontic treatment, but who did not receive light therapy. Control A had an upper-arch LII of about 5.9 mm on day 1. In contrast to the tooth-movement time for Patients D-L, it took 92 days for Control A's upper-arch LII to reduce to 0 mm. The rate of the Control A's tooth movement during that the study period was only about 0.45 mm/week.

Control B is an 11-year-old female who also wore one of SPEED System™ brackets, and wires as described for Patients D-J, during the alignment phase of her orthodontic treatment, but who did not receive light therapy. Control B had an upper-arch LII of about 6.6 mm on day 1. In contrast to the tooth movement time for Patients D-L, it took 105 days for Control B's upper-arch LII to reduce to 1 mm or less (i.e., Control B's LII reduced to 0.7 mm). The rate of Control B's tooth movement during the study period was only about 0.39 mm/week.

It is noted that one or more patients may have achieved an LII value of 1 mm or less before the patient progressed to using the 16×16 nickel titanium wire.

EXAMPLE 4

The results of the Intra-Oral Group of Example 3 were compared to the results of an Extra-Oral Group and a Control Group. Specifically, data regarding the rate of tooth movement (also referred to as "alignment rate") for the Intra-Oral Group were compared to the rate of tooth movement for the Control Group, which included eight (8) patients who also wore conventional buccal fixed orthodontic brackets, i.e., one of SPEED System™ brackets or Agility® self-ligating brackets (commercially available from Orthodontic Design and Production, Inc.), and wires, as described in Example 3 herein, during the alignment phase of his or her orthodontic treatment, but did not receive light therapy. Two of the eight Control Group patients were Controls A and B of Example 3. The Control Group is a subset of a control group of patients from a multi-site, multi-investigator study. The pooled control group patients had a mean rate of tooth movement of about 0.50 mm per week. In comparison, the mean rate of tooth movement during the study period for Patients D-L was about 1.32 mm per week, which is about 2.64 times greater than expected based on the rate of tooth movement of the pooled control group patient data. The eight Control Group patients had a mean rate of tooth movement of 0.32 mm per week. In comparison, the mean rate of tooth movement during the study period for the Intra-Oral Group was about 3.6 times greater than expected based on the rate of tooth movement of the Control Group patient data. Additionally, while the mean time to alignment for the Intra-Oral Group was 41 days, the Control Group had a mean time to alignment of 115 days, thus demonstrating significant improvement with the intra-oral device.

Data regarding the rate of tooth movement for the Intra-Oral Group and the Control Group were also compared to the rate of tooth movement for the Extra-Oral Group, which included thirteen (13) patients receiving extra-oral light therapy in combination with orthodontic treatment.

Figure 61:
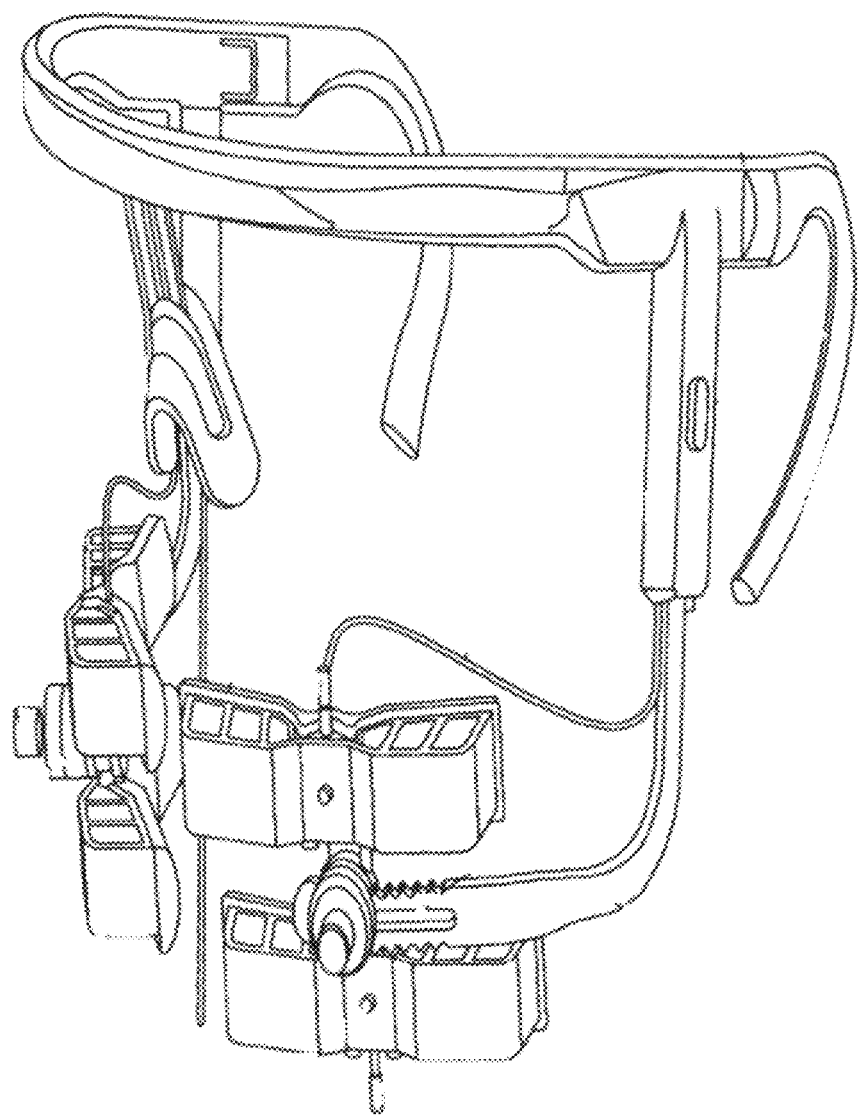
FIG. 61 is a perspective view of a comparative extra-oral light therapy device.

Specifically, in the Extra-Oral Group, each of the thirteen patients used an extra-oral device (depicted in FIG. 21A of International Patent Publication No. WO 2012/0075584, which is incorporated by reference herein in its entirety, and reproduced here as FIG. 61) for light treatment and wore conventional fixed brackets, i.e., one of SPEED System™ brackets or Agility® self-ligating brackets that were aligned with 0.014 or 0.016 inch nickel titanium wire and final rectangular alignment wire of at least 0.017 inch by 0.025 inch (also referred to as "17×25") nickel titanium wire. The extra-oral device used by each patient included a set of four extra-oral light arrays, each of which includes a flexible printed circuit board and a set of LEDs. The light arrays were positioned extra-orally in contact with each patient's face. The light arrays were coupled to a handheld controller via conductive cables. A headset of the device included attachment and adjustment mechanisms for positioning on the patient's face such that the light arrays were directed to a target oral tissue.

Light was administered to the Extra-Oral Group using the extra-oral device which irradiated light at a near infrared wavelength of about 850 nm (±5 nm) and an intensity of ranging from about 60 mW/cm$^2$ to about 100 mW/cm$^2$. The mean intensity of the irradiated light for the Extra-Oral Group was about 70 mW/cm$^2$. Patients in the Extra-Oral Group were randomized into one of three groups receiving light treatment of 20 minutes/day, 30 minutes/day, or 1 hour/week, respectively. During the study, patients in the Extra-oral Group and the Control Group) visited a clinician every two weeks for a six week period from the beginning of the study period and then every four weeks until alignment (as defined in Example 3 herein) was achieved. At each visit, the clinician performed regular orthodontic procedures, collected data that included photographs representing the occlusal and buccal views of the patient's dentition and recorded patient compliance, which was monitored by a microprocessor in the controller of the extra-oral device. The effectiveness of the treatment was assessed using the LII grading system, in a manner similar to that described in Example 3.

It should be noted that the patients in the Extra-Oral Group and the Control Group are a subset of a larger group of patients of a multi-site and multi-investigator study; however, the subset was selected for comparison with the Intra-Oral Group because its patients were from the same single site and assigned to the same investigator as the patients described in Example 3.

In total, the comparison of data from the Intra-Oral Group, the Extra-Oral Group and the Control Group included data for twenty-three (23) maxillary arches and seven (7) mandibular arches. Of the thirty (30) total arches, eighteen (18) are arches of female patients and twelve (12) are arches of male patients, and twenty-three (23) are arches of Caucasian patients and seven (7) are arches of non-Caucasian patients of various other ethnicities. The patients ranged in age from 11 years old to 27 years old, with a mean age of 14 years. Each patient had an initial LII (i.e., on day 1 of the study period for each patient) ranging from 3 mm to 12 mm.

The rate of individual patient's maxillary tooth movement is represented in the bar graph in FIG. 59, in which individual patients are shown on the x-axis and the rate of tooth movement in mm per week is shown on the y-axis. As illustrated, the individual rates of maxillary tooth movement for the Intra-Oral Group ranged from 0.42 mm per week to 2.35 mm per week, for the Extra-Oral Group ranged from 0.26 mm per week to 1.72 mm per week, and for the Control Group ranged from 0.14 mm per week to 0.45 mm per week.

The rate of individual patient's mandibular tooth movement is represented in the bar graph shown in FIG. 60, in which individual patients are shown on the x-axis and the rate of tooth movement in mm per week is shown on the y-axis. As illustrated, the individual rate of mandibular tooth movement for the Intra-Oral Group was 0.79 mm, for the Extra-Oral Group ranged from 0.34 mm per week to 0.99 mm per week, and for the Control Group ranged from 0.42 mm per week to 0.47 mm per week.

As noted above, the mean rate of tooth movement during the study period for the Intra-Oral Group was about 1.32 mm per week. The Extra-Oral Group had a mean rate of tooth movement of about 0.73 mm per week, with a standard deviation of 0.37 mm. The Control Group had a mean rate of tooth movement of about 0.37 mm per week, with a standard deviation of 0.12 mm.

Analysis of the data in the comparative study showed that the alignment rate results achieved in the Intra-Oral Group, i.e., resulting from the patient's combined usage of the intra-oral light therapy device to administer light therapy and conventional orthodontic brackets, are statistically significant (at $p<0.01$) when compared to the alignment rate results of the Control Group, in which no patient received light therapy during the study period. Analysis of the data in the comparative study showed that the alignment results achieved in the Extra-Oral Group, i.e., resulting from the patient's combined usage of the extra-oral device to administer light therapy and conventional orthodontic brackets, are statistically significant (at $p<0.1$), albeit less so than in the Intra-Oral Group, when compared to the alignment rate results of the Control Group, in which no patient received light therapy during the study period.

EXAMPLE 5

In one study, a mandibular anterior intra-oral light therapy device of the invention, depicted in FIG. 44, was used during a post-operative period to irradiate the root area of the lower jaw of a patient. The intra-oral light therapy device included an intra-oral housing with LEDs mounted on flexible printed circuit boards, which were disposed in an interior region of soft flexible buccal flanges of the intra-oral housing. The interior region of the buccal flanges is formed between opposing outer surfaces, in which the first outer surface is disposed on the buccal side of the flange and the second outer surface is disposed on the lingual or palatial side of the flange. Specifically, during the manufacturing process, the printed circuit boards were inserted into the interior region of each of left side and a right side buccal flange from the bottom of the buccal flanges, and then the bottoms of the buccal flanges were coupled using adhesive to a bite plane portion, thereby sealing the LEDs mounted on the flexible printed circuit boards within the buccal flanges.

On day 1 of the study, six (6) dental implants were placed in the anterior portion of the patient's lower jaw. On day 2 of the study, a temporary crown was loaded on each of the six implants. The intra-oral light therapy device was used by the patient every day for seven (7) days post-operatively, beginning on day 1, and on that day, within about 1 hour of placement of the dental implants. When in use, the intra-oral light therapy device irradiated the root tissue of the lower jaw with light having a wavelength of about 850 nm (±5 nm). Light therapy was administered to the patient's root tissue of the lower jaw for about six minutes per day, and at a light output intensity of about 100 mW/cm$^2$.

An Osstell™ Mentor device (commercially available from Osstell AB) was used to measure stability of the implants at the time of surgery (i.e., on day 1), and again on day 7 to measure any relative change in the implants' stability. The Mentor device uses resonance frequency analysis to measure stability, presented as an implant stability quotient (ISQ). The stability measured on day 7 showed no net decrease in stability of the six implants from their stability measured on day 1. More specifically, the average ISQ value measured on day 7 was unchanged from the average ISQ value measured on day 1. Such a result stands in stark contrast to the typical decrease in stability of dental implants that follows their placement and that can occur for up to 90 days thereafter, before the implants regain stability comparable to that of the implants on the day of their placement. Without being bound by theory, the typical decrease in stability is believed to be due to inflammatory resorption of bone supporting the dental implants and believed to result from the surgical process of drilling into the bone. It is noted that the patient had a history of very poor post-operative soft-tissue healing, including unwanted exposure of underlying bone, from previous implant surgeries on the right and left posterior quadrants of the patient's lower jaw. In this case, however, the patient's soft tissue healing at day 7 was optimal compared to what the patient experienced from the previous implant surgeries with the two lower posterior dental quadrants.

EXAMPLE 6

In one study, an illustrative intra-oral light-therapy device of the invention was used during the space closure phase of orthodontic treatment to irradiate the maxillary and/or mandibular arches of twenty-three (23) patients with a total of sixty-seven (67) extraction quadrants (the "Intra-Oral Group"). The intra-oral light-therapy device included an intra-oral housing including a flexible circuit of light arrays of LED light emitters embedded in medical-grade silicone buccal flanges of the intra-oral housing, similar to the intra-oral housing shown in FIG. 72. The intra-oral housing was electronically coupled via a connector to a hand-held controller disposed external to the intra-oral housing. The controller included a microprocessor, an LCD screen and processor-executable code. The controller coupled the intra-oral housing with a power source. Each patient was provided with his or her own intra-oral light-therapy device, which was used in conjunction with a conventional fixed orthodontic appliance, as described herein. The treatment and results of the patients in the Intra-Oral Group were compared to the treatment and results of patients in a Control Group, which included twenty-two (22) patients with fifty-six (56) extraction quadrants who wore conventional fixed appliances, as described herein, during the space closure phase of his or her orthodontic treatment, but did not receive light therapy. The treatment and results of the patients from the Intra-Oral Group and Control Group are described in detail herein.

During the study and prior to the start of treatment, each patient was provided full mouth scaling and polishing and was given appropriate oral hygiene instructions. Routine orthodontic records including study casts, photos, a panoramic radiograph (OPG) and lateral cephalogram were taken. When each patient reached the active space closure phase of his or her orthodontic treatment, impressions were taken to construct new models (T1).

All patients were treated with conventional fixed appliances with a slot size of 0.022×0.028, MBT prescription. Bonding methods were standardized in all patients using bonding adhesive composite Transbond XT (available from 3M Unitek). Extraction spaces were closed by sliding mechanics with the posterior anchorage segment held together by figure 8 steel ligature to ensure a single anchorage unit. Extraction spaces were closed using nitinol (NiTi) closed-coil springs (available from G&H Wire Co.) from the hook of the first molar to the hook of the working wire (19×25 stainless steel). One hundred and fifty (150) grams of force was applied throughout the space closure duration. This level of force was maintained, regardless of the amount of extraction spaces, by using a dynamometer and manufacturer guidelines. Active space closure was done on 0.019×0.025 inch stainless steel wires with hooks. Miniscrews were utilized for space closure in some patients, however randomization was carried out that such that the same number of patients in which miniscrews were utilized were in each group.

During the study, the intra-oral light-therapy device was used by each patient in the Intra-Oral Group every day until space closure was achieved. When in use, the intra-oral light-therapy device irradiated the patient's oral tissue with light having a wavelength of about 850 nm and a power output of about 33 mW/cm$^2$ for about three minutes per day per treated arch to yield a gum-line dose of about 6 J/cm$^2$. The microprocessor of the controller tracked usage of the intra-oral light therapy device. Patients were expected to maintain 75% compliance or greater throughout the duration of space closure. If one or two sessions were missed, patients were advised to make up for the few lost sessions spread throughout the following day.

During the study, the patients visited a clinician every two (2) weeks for the first three visits, and then every two (2) to four (4) weeks based on the patient's compliance level and any complication regarding orthodontic appliance breakage. At each visit, the clinician performed regular space closure recall procedures, retrieved patient compliance data, checked the functionality of the intra-oral light-therapy device, and visually inspected the patient for space closure. Active spaced closure was considered complete (T2) when the space that remained was 2 mm or less, as determined clinically by visual inspection, or when molar anchorage was lost in the judgment of the clinician. When T2 was reached, impressions were taken of each patient to construct a T2 model, intra-oral photographs were taken, the light therapy apparatus was returned to the clinician, and the patient was exited from the study.

The amount of extraction spaces before active space closure was measured on the T1 models (minimum of 3 mm) using a digital caliper with accuracy up to 0.01. Reference points were the free gingival margin of each end of the extraction space. Spaces present mesial to the patient's canine tooth (or teeth) were measured and added to the extraction space to be closed on both sides. Each measurement was taken by an examiner who was blind as to whether the model was for a patient in the Intra-Oral Group or Control Group. Where possible, the examiner was also blind as to whether the model was a T1 model or a T2 model. The study models were measured randomly so that T1 and T2 models of the same patient were not measured consecutively. Measurements were taken twice, at spaced intervals, for each model, and the average of the two measurements was used as the final value.

Patients were selected for participation in this study based on, at least, the following criteria: (1) a presence of permanent dentition (i.e., permanent, or adult, teeth); (2) the patient was engaged in comprehensive orthodontic therapy, which therapy included an extraction treatment plan for extraction of the patient's first or second premolar in at least one of the upper arch or lower arch, or both arches; (3) the patient had a minimum of a 3 mm extraction space to be closed in at least one quadrant of the patient's upper and/or lower arches; (4) the patient demonstrated good oral hygiene; (5) the patient was not undergoing adjunct orthodontic treatment, such as that involving extra- or intra-oral appliances; and (6) the patient was from 12 to 40 years old. The following types of individuals were excluded from this study: (1) individuals with primary or mixed dentition; (2) individuals with active periodontal disease or evidence of horizontal bone loss; (3) individuals who could not maintain a minimum compliance rate of 75% in using the intraoral light therapy apparatus; or (4) individuals with any systemic disease or using any medication that may affect bone metabolism, such as long term use of NSAIDs or bisphosphonates, among others.

Patients in the Intra-Oral Group had space closure rates within the range of 0.41 mm/month to 2.80 mm/month, with a standard deviation of 0.49 mm/month. The Intra-Oral Group had a mean space closure rate of 1.07 mm per month. Patients in the Control Group had space closure rates within the range of 0.12 mm/month to 1.79 mm/month, with a standard deviation of 0.37 mm/month. Individual patient data for each of the Control and Intra-Oral Groups is shown in FIGS. 114A, 114B, 115A and 115B, respectively. In FIGS. 114A-B and 115A-B, data for each patient in the study includes the tooth number extracted, the total extraction space in the T1 model in millimeters, the total extraction space in the T2 model in millimeters, and the time in days to achieve space closure for the identified tooth number and patient. The tooth numbering shown in FIGS. 114A-B and 115A-B is based on the ISO and FDI World Dental Federation numbering systems. The Control Group had a mean space closure rate of 0.85 mm per month. The mean space closure rate of the Intra-Oral Group is statistically significantly faster (p-value<0.05, i.e., 0.0047) than the mean space closure rate of the Control Group.

The results regarding the patient's velocity of space closure were also analyzed by age per group. Specifically, within each group, the space closure rate data was separated by youth (11-19 years old) and adults (20-42 years old). Youth patients in the Intra-Oral Group had space closure rates in the range of 0.53 mm/month to 2.80 mm/month, with a standard deviation of 0.49 mm/month. Youth patients in the Control Group had space closure rates in the range of 0.44 mm/month to 1.79 mm/month, with a standard deviation of 0.36 mm/month. The mean space closure rate of the youth patients in the Control Group was 0.93 mm/month, and the mean space closure rate of the youth patients in the Intra-Oral Group was 1.20 mm/month. The mean space closure rate of the youth patients in the Intra-Oral Group is statistically significantly faster (p-value<0.05, i.e., 0.0068) than the mean space closure rate of youth patients in the Control Group. The youth patients in the Intra-Oral Group demonstrated a 28% improvement in the rate of space closure when compared to the youth patients in the Control Group.

Adult patients in the Intra-Oral Group had space closure rates in the range of 0.56 mm/month to 1.67 mm/month. Adult patients in the Control Group had space closure rates in the range of 0.12 mm/month to 0.87 mm/month. The mean space closure rate of the adult patients in the Control Group was 0.52 mm/month, and the mean space closure rate of the adult patients in the Intra-Oral Group was 0.77 mm/month. The mean space closure rate of the adult patients in the Intra-Oral Group is statistically significantly faster (p-value<0.05, i.e., 0.0426) than the mean space closure rate of adult patients in the Control Group. The adult patients in the Intra-Oral Group demonstrated a 48% improvement in the rate of space closure when compared to the adult patients in the Control Group.

In conclusion, the results of the study demonstrate that use of light therapy in conjunction with conventional orthodontic treatment is statistically significantly effective at accelerating the rate of space closure for extraction cases in both the maxilla and mandible arches in both the adult and youth population.

EXAMPLE 7

This example provides results from a prospective, crossover, single center pilot study aimed at observing the clinical efficacy of a light therapy device described herein or of AcceleDent® on the rate of patient progression through Invisalign® (Align Technology, Inc.) aligners and thus, the rate of tooth movement during aligner treatment.

By utilizing a crossover design, the patient becomes his or her own control, allowing comparison of the patient's natural rate of tooth movement and aligner switching with the patient's rate of aligner switching when using an interventional light therapy device. In this study, interventions are conducted with a light therapy device described herein or an AcceleDent device. When comparing the aligner switching rate for a patient during the non-intervention (control) period with the aligner switching rate during the intervention period (crossover design), the effect of the intervention device on the rate of switching aligners can be determined.

Invisalign® aligners are designed to move the teeth by a predetermined fixed amount per aligner, and their manufacturer instructs replacing these aligners on a fixed schedule, typically every 7 or 14 days. However, individual biological variation contributes to the rate at which teeth move—some patients' teeth move fast, while other patients' teeth move slower. Accordingly, each patient has his or her own unique rate of tooth movement, which translates into a unique rate of when aligners should be switched.

This example provides a method for determining a customized rate of aligner switching for each individual patient. The study utilized a daily self-evaluation for aligner fit, pressure and pain, which allows patients to switch aligners based on their natural tooth movement rate.

Patients were included or excluded from the study based on the following criteria:
Inclusion
  Presence of permanent dentition
  Eligible and scheduled for full mouth fixed orthodontic treatment.
  Good oral hygiene, as determined by the Qualified Investigator orthodontist.
  Age 12-60
  Non-smoker
Exclusion:
  Pregnant females
  Patients currently enrolled in another clinical study
  Non-steroidal Anti-Inflammatory drug (NSAID) use during study (Acetaminophen acceptable)
  Periodontally involved teeth
  Use of bisphosphonates The two Invisalign® study groups were as follows:
Study Group 1: Patients were prescribed a series of conventional Invisalign® aligners, each of which is programmed to laterally translate a tooth ¼ mm during a 14 day period, at which point it is replaced.

Study Group 2: Patients were prescribed a series of conventional Invisalign® aligners, each of which is programmed to laterally translate a tooth ⅛ mm during a 7 day period, at which point it is replaced. Accordingly, the "⅛ mm" aligner is the same aligner as the "¼ mm" aligner, but is prescribed to be replaced every 7 days instead of every 14 days. A patient in the ¼ mm group uses half as many aligners as a patient in the ⅛ mm study group, if both patients cycle through aligners for the same amount of total time and both patients follow the orthodontist's prescription to replace the aligners every 7 days or every 14 days, respectively. The aligner replacement is made by the patient and assumes his or her compliance with an orthodontist's instructions.

The 3 Intervention Groups were as follows:
Intervention Group 1 (OPx1): light therapy device of FIG. 110, (OrthoPulse™) 5 min/arch=10 min daily.
Intervention Group 2 (OPx2): light therapy device of FIG. 110, (OrthoPulse™) 10 min/arch=20 min daily
Intervention Group 3 (AD): AcceleDent 20 min daily, both arches.

Each patient served as his or her own control by progressing through aligners with no intervention, establishing a control period. Patients progressed through at least 6 aligners in each control period (±1 aligner). During the control period, the patient self-assessed aligner fit on a daily basis, based on pressure, pain, and number of air bubbles present (see below discussion on method of self-assessment). This established a baseline aligner-change interval for each individual patient. After the control period, an intervention device was used on a daily basis while the patient continued progressing through aligners, establishing an intervention period (see above for the three intervention groups). Patients progressed through at least 6 aligners in each intervention period (±1 aligner). After a light therapy device patient completed a first invention period (e.g., either OPx1 or OPx2), the patient was given the opportunity to complete a subsequent light therapy intervention period. The light therapy patient was given the option regarding the intervention treatment protocol (i.e., either OPx1 or OPx2) for the subsequent intervention period, although OPx1 patients were recommended to complete an OPx2 intervention period as the subsequent period. Similarly, OPx2 patients were recommended to complete an OPx1 intervention period as the subsequent period. The baseline aligner change interval for each individual patient (control period) was compared to his or her aligner change interval during intervention. Aligners were changed by a method of self-assessment, as described below.

Each patient progressed through each aligner by a method of self-assessment, via an online daily questionnaire. Every day, the patients assessed: (A) pain levels: 1 (no pain or almost no pain), 2 (some pain), 3 (much pain); (B) aligner fit/pressure on teeth: 1 (no pressure or almost no pressure), 2 (moderate pressure), 3 (high level of pressure); (C) air gaps present between aligner and teeth: rated 1-3, where 1 indicates no air gaps. Each patient progressed into the subsequent aligner when pain score was 1, aligner fit score was 1and no air gaps were present.

The average number of days that aligners were used during the control (no intervention) period was compared to the average number of days that aligners were used during the intervention period. The percent reduction of the average number of days that aligners were used was compared to conventional Invisalign aligner change frequency for each of the control, OPx1, OPx2 and AcceleDent periods.

Results

Thirteen patients have completed a control period and at least one intervention period (6 patients were treated with ¼ mm Invisalign aligners and 7 patients were treated with ⅛ mm Invisalign aligners).

Figure 116:
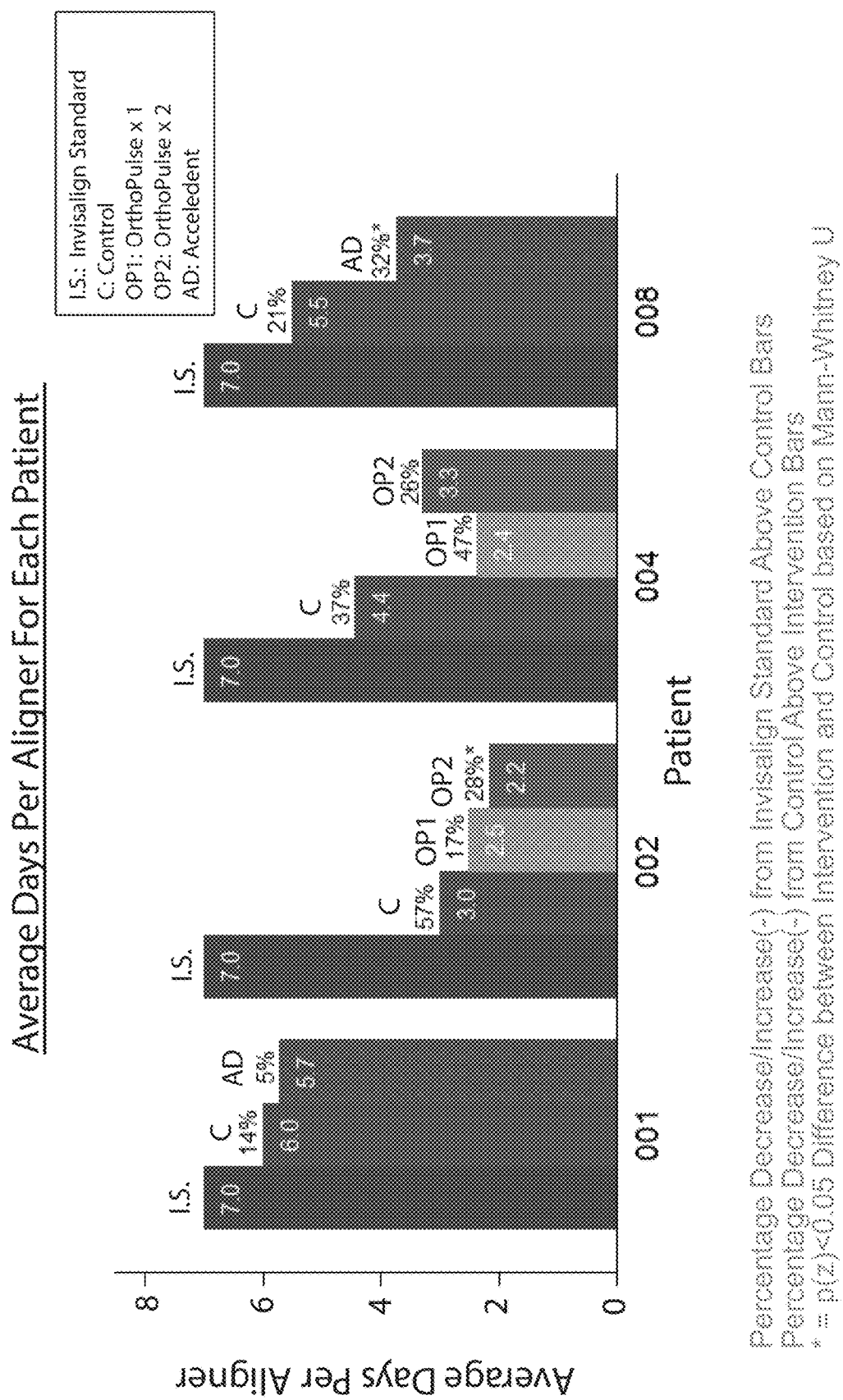
FIGS. 116-118 are bar graphs showing an average number of days per aligner for individual patients in the study described in Example 7.
Figure 117:
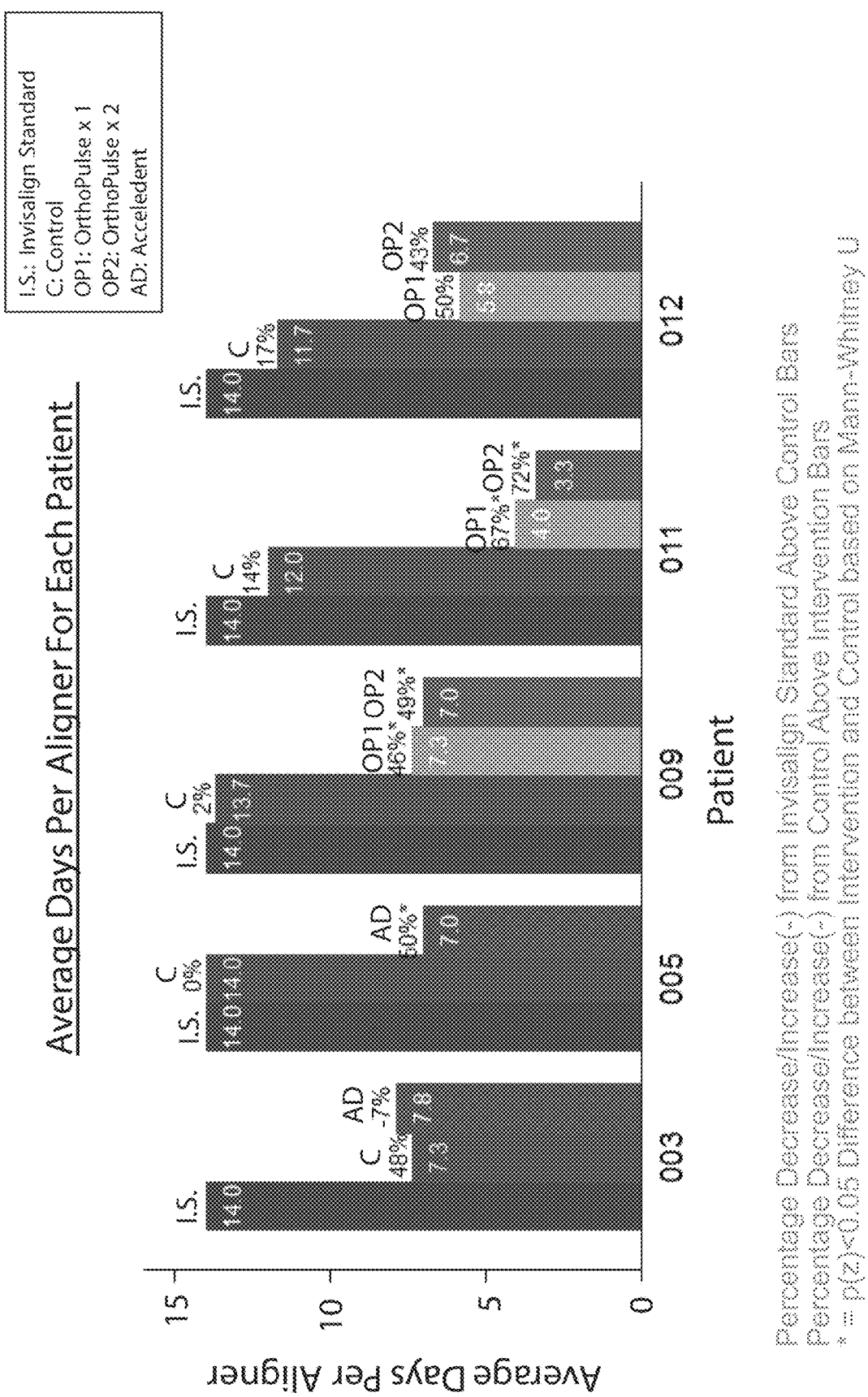
Figure 118:
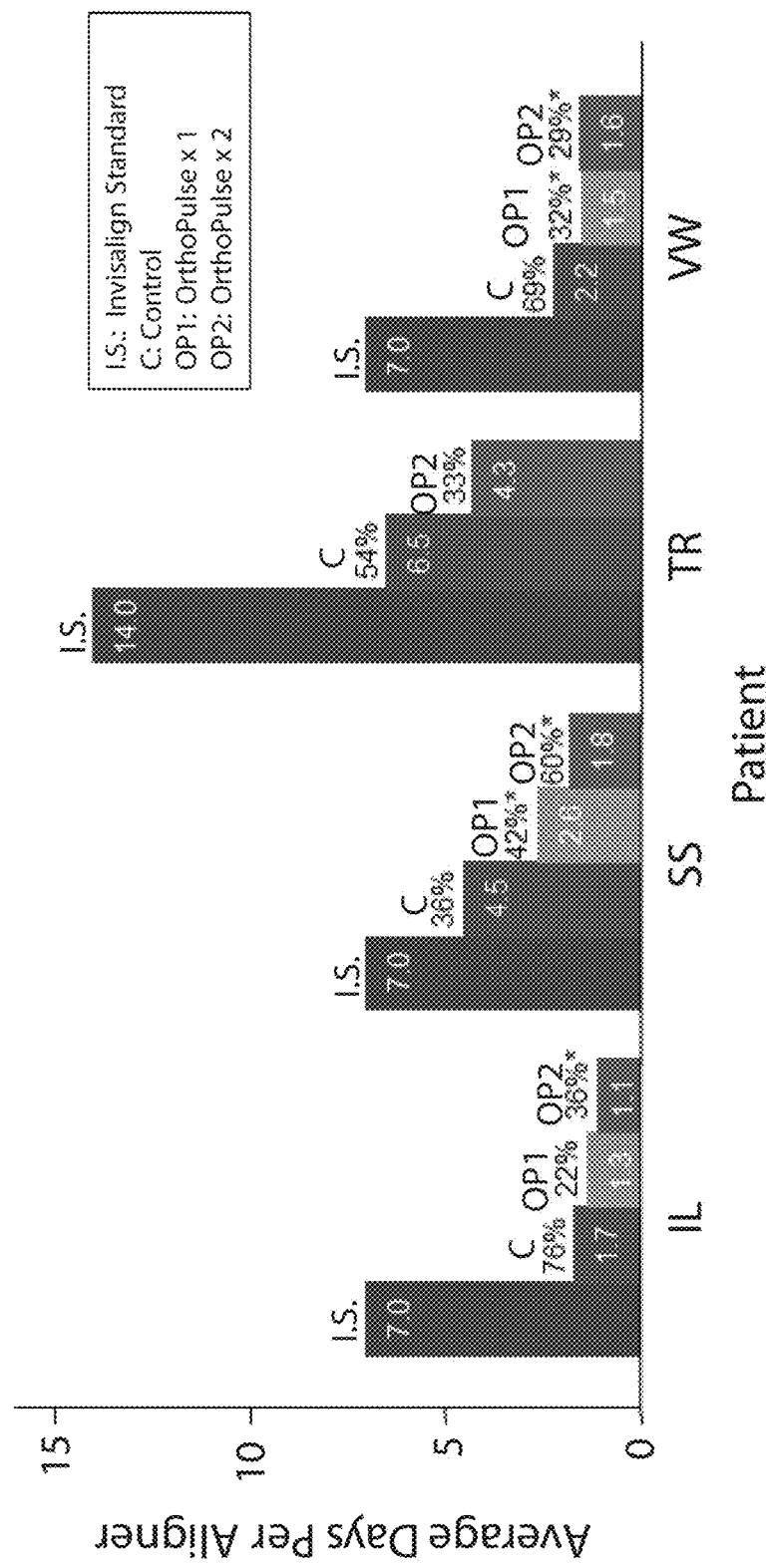

The results of the study are provided in FIGS. 116-118. In each of these figures, the percent value above each control bar represents improvement over conventional Invisalign switching frequency. The percent value above each intervention bar (OP1, OP2, AD) represents improvement over the same patient's control period. Mann-Whitney U test results are reported above intervention bars comparing intervention to control within each patient (*=p<0.05).

Days per aligners for all AcceleDent patients were compared to their control, and light therapy patients were also compared to their own control for each individual patient (FIGS. 116-118). Percentage reductions of aligner switching rate for each of the Invisalign® study groups (i.e., (i) ¼ mm group and (ii) ⅛ mm aligner group) were pooled, and are presented in Table 1. Two-tailed T-tests were used to compare the significance levels of comparisons.

the patient's mouth for administration of light to one of the upper jaw and the lower jaw at a time, in other embodiments, an apparatus includes an intra-oral housing with upper and lower flanges, each including an LED array coupled to or embedded therein. In this manner, the apparatus is configured to concurrently administer light therapy with respect to each of the upper and lower jaws.

Although the bite pad 2514 is described above as having a thickness that varies from the anterior portion (thinner) to the posterior portion (thicker), in other embodiments, the anterior portion of the bite pads shown and described herein can be thicker than that of the posterior portion. Moreover, in some embodiments, a thickness of any of the bite pads shown herein can vary along any direction, for example, from a lingual (or inside portion) to the buccal (or cheek-side) portion.

Although the mouthpiece 2510 is shown as including a notch 2530, a first groove 2532 and a second groove 2534, in other embodiments, any of the mouthpieces shown and described herein can include any suitable geometric features and/or combinations of materials to produce the desired flexibility for placement of the light array. For example, in some embodiments, the mouthpiece 2510 and any of the mouthpieces shown and described herein can include a series of notches along the upper portion of the flanges 2522,

TABLE 1

Percent reduction for pooled ¼ mm and ⅛ mm Invisalign aligner.

| | | | Percentage Reductions (%) | | | | | |
|---|---|---|---|---|---|---|---|---|
| Intervention | Patient N | Aligner N | From prescribed | p-value | From control* | p-value | From AcceleDent** | p-value |
| Control (AD) | 4 | 19 | 21% | 0.00 | — | — | — | — |
| AcceleDent | 4 | 41 | 43% | 0.00 | 17 | 0.00 | — | — |
| Control (OP) | 9 | 46 | 46% | 0.00 | — | — | — | — |
| OrthoPulse OPx1 | 8 | 70 | 66% | 0.00 | 51% | 0.00 | 41% | 0.00 |
| OrthoPulse OPx2 | 9 | 107 | 70% | 0.00 | 56% | 0.00 | 48% | 0.00 |

*two-tailed t-tests used for comparing within patient aligner spells, i.e., the duration of time for each individual aligner (i.e., either ⅛ or ¼ mm aligner) compared to Control
**two-tailed t-tests used for comparing full pooled aligner spell groups (i.e., the duration of time for patients treated with ⅛ and ¼ mm aligners, pooled, not just within patient groups) to AcceleDent The results indicate that by using patient self-evaluation of aligner fit and pressure, each patient's natural rate of switching aligners was able to be determined. OrthoPulse OPx1 and OPx2 treatments resulted in a significant reduction in the number of days required per aligner as compared to each patient's own control: 51% reduction for OPx1 and 56% reduction for OPx2. A greater reduction in number of days required per aligner was observed for OPx1 and OPx2 patients, as compared to the AcceleDent patients.

While various embodiments of the invention have been described herein, it should be understood that they have been presented by way of example only, and not limitation. For example, although apparatus (e.g., apparatus 2100) have been described herein as including a gyroscope, in other embodiments, an apparatus can include any suitable mechanism for detecting tilt and/or spatial orientation of the apparatus such that the mechanism can help determine whether the apparatus is in an upright or inverted position.

In another example, although apparatus (e.g., apparatus 2100) have been illustrated and described herein as including an intra-oral housing configured to be positioned within

2524, a series of circumferential perforations about the buccal portion (i.e., the cheek-side) and/or the lingual (i.e., inside) portion, or the like.

Where schematics and/or embodiments described herein indicate certain components arranged in certain orientations or positions, the arrangement of components may be modified, unless the context clearly indicates otherwise. Similarly, where methods and/or events described above indicate certain events and/or procedures occurring in certain order, the ordering of certain events and/or procedures may be modified, unless the context clearly indicates otherwise. Although various embodiments have been described as having particular features and/or combinations of components, other embodiments are possible having a combination of any features and/or components from any of embodiments where appropriate.

What is claimed is:
1. A light therapy apparatus comprising:
a mouthpiece defining a first surface and which is disposable within a mouth of a subject, the mouthpiece comprising:

a bite tray;
an inner flange coupled to a first side of the bite tray, the inner flange comprising a plurality of light emitters;
an outer flange coupled to a second side of the bite tray, the outer flange comprising a plurality of light emitters and forming a first angle relative to the bite tray and a second angle relative to the bite tray when the mouthpiece is disposed within the mouth of the subject;
a light-sensitive agent which is configured to be applied within the mouth of the subject;
an extra-oral housing defining a second surface and which is coupled to the mouthpiece such that the extra-oral housing is positioned to extend externally of the mouth when the mouthpiece is disposed within the mouth, wherein the first surface of the mouthpiece and the second surface of the extra-oral housing present a common bottom surface opposite to the inner flange and the outer flange; a rechargeable battery configured to be wireless charged through the common bottom surface and contained within the extra-oral housing; and
a controller contained within the extra-oral housing and in communication with the plurality of light emitters which are programmed to administer light upon the light-sensitive agent within the mouth of the subject, wherein the controller is configured to emit the light which is targeted for interaction with the light-sensitive agent.

2. The light therapy apparatus of claim 1, wherein the mouthpiece is rotatable between an upright position and an inverted position, wherein the mouthpiece is configured to administer light to an upper jaw of the subject when disposed in the upright position in the mouth and to administer light to a lower jaw of the subject when the mouthpiece is disposed in the inverted position in the mouth.

3. The light therapy apparatus of claim 1, wherein the mouthpiece further comprises an additional inner flange coupled to the first side of the bite tray, wherein the inner flange and the additional inner flange are independently deflectable.

4. The light therapy apparatus of claim 1, wherein the outer flange comprises a first outer flange and a second outer flange each coupled to the second side of the bite tray.

5. The light therapy apparatus of claim 1 further comprising a first flexible circuit board, wherein the plurality of light emitters of the outer flange are coupled to the first flexible circuit board.

6. The light therapy apparatus of claim 5 wherein the first flexible circuit board communicatively couples the plurality of light emitters of the outer flange to the extra-oral housing.

7. The light therapy apparatus of claim 5 further comprising a second flexible circuit board, wherein the plurality of light emitters of the inner flange are coupled to the second flexible circuit board.

8. The light therapy apparatus of claim 7 wherein the second flexible circuit board communicatively couples the plurality of light emitters of the inner flange to the extra-oral housing.

9. The light therapy apparatus of claim 1, wherein the plurality of light emitters of the inner flange, and the plurality of light emitters of the outer flange, are configured to emit light having a wavelength from about 400 nm to about 1200 nm.

10. The light therapy apparatus of claim 9, wherein the plurality of light emitters of the inner flange, and the plurality of light emitters of the outer flange, are configured to emit light having a wavelength from about 845 nm to about 865 nm.

11. The light therapy apparatus of claim 1 wherein the extra-oral housing is coupled to the mouthpiece via a bridge.

12. The light therapy apparatus of claim 11, wherein the controller comprises instructions to administer pulsed light from the mouthpiece.

13. The light therapy apparatus of claim 12, wherein the pulsed light has a duty cycle of about 20%.

14. The light therapy apparatus of claim 11, wherein the controller comprises instructions to administer light having an intensity from about 200 mW/cm2 to about 500 mW/cm2.

15. The light therapy apparatus of claim 11, wherein the controller comprises instructions to administer light having an energy density from about 1 J/cm2 to about 5 J/cm2.

16. The light therapy apparatus of claim 1 wherein the light is configured for treating or preventing periodontitis.

17. The light therapy apparatus of claim 1, wherein the inner flange is configured for placement adjacent to lingual alveolar soft tissue of the subject.

18. The light therapy apparatus of claim 17, wherein the outer flange is configured for placement adjacent to buccal alveolar soft tissue of the subject.

19. The light therapy apparatus of claim 1, wherein the inner flange is configured as a continuous flange.

20. The light therapy apparatus of claim 1, wherein the outer flange is configured as a continuous flange.

21. The light therapy apparatus of claim 1, wherein the outer flange is comprised of one or more individual flanges.

22. The light therapy apparatus of claim 1, wherein the plurality of light emitters of the inner flange, and the plurality of light emitters of the outer flange, are configured to emit light having a wavelength from about 620 nm to 1000 nm.

23. The light therapy apparatus of claim 1, wherein the plurality of light emitters of the inner flange, and the plurality of light emitters of the outer flange, are configured to emit light having a wavelength from about 605 nm to 700 nm.

24. The light therapy apparatus of claim 1, wherein the plurality of light emitters of the inner flange, and the plurality of light emitters of the outer flange, are configured to emit light having a wavelength from about 750 nm to 855 nm.

25. The light therapy apparatus of claim 1, whereby at least a portion of the extra-oral housing is visible to the patient when the mouthpiece is disposed within the mouth.

26. The light therapy apparatus of claim 25, further comprising a visual indicia positioned along the portion of the extra-oral housing such that the visual indicia is positioned to be in a line of light of the patient when the mouthpiece is disposed within the mouth.

27. The light therapy apparatus of claim 1, where the mouthpiece defines at least one groove along a base portion of the outer flange extending between a posterior end portion and an anterior end portion of the mouthpiece such that the at least one groove permits the outer flange to deflect in response to pressure from within the mouth of the subject.

* * * * *